(12) United States Patent
Wang et al.

(10) Patent No.: US 8,691,184 B2
(45) Date of Patent: Apr. 8, 2014

(54) BCL-2/BCL-XL INHIBITORS AND THERAPEUTIC METHODS USING THE SAME

(75) Inventors: Shaomeng Wang, Saline, MI (US);
Haibin Zhou, Ann Arbor, MI (US);
Jianfang Chen, Ann Arbor, MI (US);
Angelo Aguilar, Ann Arbor, MI (US);
Jennifer L. Meagher, Plymouth, MI (US); Duxin Sun, Ann Arbor, MI (US);
Chao-Yie Yang, Ann Arbor, MI (US);
Liu Liu, Ann Arbor, MI (US);
Longchuan Bai, Ann Arbor, MI (US);
Donna McEachem, Ann Arbor, MI (US); Jeanne Stuckey, Fenton, MI (US);
Xiaoqin Li, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/356,763

(22) Filed: Jan. 24, 2012

(65) Prior Publication Data
US 2012/0189539 A1    Jul. 26, 2012

Related U.S. Application Data

(60) Provisional application No. 61/436,077, filed on Jan. 25, 2011.

(51) Int. Cl.
*A61K 51/00* (2006.01)
*A61K 31/5377* (2006.01)
*A61K 31/496* (2006.01)
*C07D 413/14* (2006.01)
*C07D 403/12* (2006.01)
*C07D 401/14* (2006.01)
*C07D 403/10* (2006.01)
*C07D 405/10* (2006.01)
*A61P 35/00* (2006.01)
*A61K 31/5513* (2006.01)
*C07D 471/04* (2006.01)

(52) U.S. Cl.
USPC ............... 424/1.11; 514/210.18; 514/210.2; 514/218; 514/236.5; 514/252.11; 514/253.04; 514/253.09; 514/254.01; 514/254.1; 540/575; 544/121; 544/357; 544/362; 544/364; 544/372; 544/379

(58) Field of Classification Search
None
See application file for complete search history.

(56) References Cited

U.S. PATENT DOCUMENTS

2006/0084647 A1   4/2006   Wang et al.
2007/0197532 A1   8/2007   Cao et al.

FOREIGN PATENT DOCUMENTS

WO   WO-2010/010154 A1   1/2010

OTHER PUBLICATIONS

Vippagunta et al. "Crystalline Solids," Advanced Drug Delivery Reviews, 2001, 48, pp. 18.*
Müller, Inorganic Chemistry, p. 14-15, 1993.*
International Search Report in counterpart international application No. PCT/US2012/022315, dated Aug. 27, 2012.

* cited by examiner

*Primary Examiner* — Ernst Arnold
*Assistant Examiner* — Jianfeng Song
(74) *Attorney, Agent, or Firm* — Marshall, Gerstein & Borun LLP

(57) ABSTRACT

Inhibitors of Bcl-2/Bcl-xL and compositions containing the same are disclosed. Methods of using the Bcl-2/Bcl-xL inhibitors in the treatment of diseases and conditions wherein inhibition of Bcl-2/Bcl-xL provides a benefit, like cancers, also are disclosed.

15 Claims, No Drawings

BCL-2/BCL-XL INHIBITORS AND THERAPEUTIC METHODS USING THE SAME

CROSS REFERENCE TO RELATED APPLICATIONS

This application claims the benefit of U.S. provisional patent application No. 61/436,077, filed Jan. 25, 2011, incorporated herein by reference in its entirety.

GOVERNMENT FUNDING

This invention was made with government support under Grant No. NIH/NCI 5U19CA113317 awarded by National Institutes of Health. The government has certain rights in the invention.

FIELD OF THE INVENTION

The present invention relates to Bcl-2/Bcl-xL inhibitors and to therapeutic methods of treating conditions and diseases wherein inhibition of Bcl-2/Bcl-xL provides a benefit.

BACKGROUND OF THE INVENTION

Apoptosis resistance is a hallmark of human cancer (1-3). Cancer cells must overcome a continual bombardment by cellular stresses, such as DNA damage, oncogene activation, aberrant cell cycle progression, and harsh microenvironments, that would cause normal cells to undergo apoptosis. One of the primary means by which cancer cells evade apoptosis is by up-regulation of anti-apoptotic proteins of the Bcl-2 family. Targeting key apoptosis regulators to overcome apoptosis-resistance and promote apoptosis of tumor cells is a new cancer therapeutic strategy (4,5).

Bcl-2 proteins function as critical regulators of apoptosis in both cancer and normal cells (6-10). Bcl-2 proteins serve as a check on apoptosis allowing healthy and useful cells to survive. This protein family includes anti-apoptotic proteins, such as Bcl-2, Bcl-xL, and Mcl-1, and pro-apoptotic molecules, including Bid, Bim, Bad, Bak and Bax (6-10). While normal cells have low expression levels of the anti-apoptotic Bcl-2 and Bcl-xL proteins, these proteins are found to be highly overexpressed in many different types of human tumors.[6-10] This overexpression has been linked to poor prognosis in several types of cancer, and to clinical resistance to chemotherapeutic agents and radiation (6-10). Consistent with clinical observations, laboratory studies have established that overexpression of Bcl-2 or Bcl-xL causes cancer cells to become more resistant to chemotherapeutic agents in vitro and in vivo (6-10). Inhibition of apoptosis by Bcl-2 contributes to cancer by inhibiting cell death. Therefore, targeting Bcl-2 and/or Bcl-xL has been pursued as a cancer therapeutic strategy (11-34). Inhibiting Bcl-2 activity in cancer cells can reduce chemotherapeutic resistance and increase the killing of cancer cells.

Bcl-2 and Bcl-xL proteins inhibit apoptosis by heterodimerization with pro-apoptotic Bcl-2 family proteins, such as Bak, Bax, Bim, Bid, Puma, and Bad (6-10). Experimentally determined three-dimensional structures of Bcl-xL and Bcl-2 have shown that these proteins possess a well-defined groove, which interacts with the BH3 (Bcl-2 Homology 3) domain of the pro-apoptotic Bcl-2 proteins (38-42). It has been proposed that non-peptide small molecules designed to block the heterodimerization of Bcl-2/Bcl-xL proteins with their pro-death binding partners may be effective as antagonists of Bcl-2/Bcl-xL, and that such small molecule inhibitors may have a great therapeutic potential for the treatment of human cancers in which Bcl-2 and/or Bcl-xL are highly expressed (18-37).

Although non-peptide, small molecule inhibitors of Bcl-2/Bcl-xL have been reported, most of the inhibitors have weak to modest affinities for these proteins and lack a well-defined mode of action for their cellular activity (18-37). The exceptions are ABT-737, ABT-263, and their analogues (26-34). ABT-737 and ABT-263 bind to Bcl-2, Bcl-xL, and Bcl-w with very high affinities ($K_i$<1 nM) and have high specificity over Mcl-1 and A1, two other anti-apoptotic Bcl-2 proteins (26, 32, 34). ABT-263 has advanced into Phase I/II clinical trials and shows promising antitumor activity in the clinic (45).

Despite the discovery of ABT-737 and ABT-263, the design of potent, non-peptide inhibitors of Bcl-2/Bcl-xL remains a significant challenge in modern drug discovery. Accordingly, a need still exists in the art for Bcl-2/Bcl-xL inhibitors having physical and pharmacological properties that permit use of the inhibitors in therapeutic applications. The present invention provides compounds designed to bind to Bcl-2/Bcl-xL and inhibit Bcl-2/Bcl-xL activity.

SUMMARY OF THE INVENTION

The present invention is directed to inhibitors of Bcl-2/Bcl-xL, to compositions comprising the inhibitors, and to methods of using the inhibitors in a therapeutic treatment of conditions and diseases wherein inhibition of Bcl-2/Bcl-xL activity provides a benefit. The present compounds are potent inhibitors of Bcl-2/Bcl-xL activation, and induce apoptosis of cancer cells that express Bcl-2 and/or Bcl-xL.

More particularly, the present invention is directed to compounds having a structural formula (I):

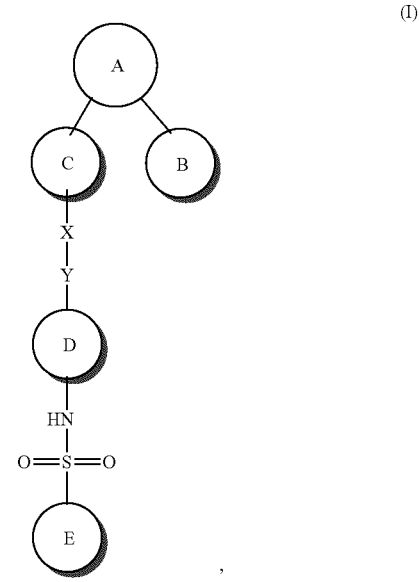

wherein A is null, optionally substituted phenyl, or an optionally substituted five or six-membered aromatic ring in which 1 to 4 carbon atoms individually are replaced by nitrogen, oxygen, or sulfur;

B, C, D, and E individually are optionally substituted phenyl or an optionally substituted five or six-membered aromatic ring in which 1 to 4 carbon atoms individually are replaced by nitrogen, oxygen, or sulfur;

X and Y, independently, are null, O, S, CO, $SO_2$, SO, $PO_3H$, NR', BR', PR', POR', alkylene, cycloalkylene, alkenylene, cycloalkenylene, alkynylene, or arylene; or X and Y can be taken together to form a 5-7 membered ring, or X and Y can be Z—$(CH_2)_{1-3}$—Z', wherein Z and Z', independently, are O, S, NR', CO, SO, $SO_2$, $PO_3H$, PR', or POR; and R' is H, alkyl, cycloalkyl, alkenyl, cycloalkenyl, alkynyl, aryl, heteroaryl, or heterocycloalkyl, or a pharmaceutically acceptable salt, hydrate, or solvate thereof.

In various embodiments, rings A, B, C, D, and E contain one to four substituents independently selected from the group consisting of CN, $NO_2$, halo, alkyl, cycloalkyl, alkenyl, cycloalkenyl, alkynyl, aryl, heteroaryl, heterocycloalkyl, OR', SR', NR'R", $CO_2R'$, COR', OCOR', CONR'R", CONR'$SO_2R"$, NR'COR", NR'$SO_2R"$, $C_{1-3}$alkyleneCH(OH) $CH_2OH$, $SO_2R'$, and $SO_2NR'R"$, wherein each R' and R", independently, is H, alkyl, cycloalkyl, alkenyl, cycloalkenyl, alkynyl, $CF_3$, aryl, heteroaryl, $C_{1-3}$alkyleneheterocycloalkyl, or heterocycloalkyl;

In some embodiments, two substituents on the same A, B, C, D, or E ring can be taken together to form a ring. In other embodiments, R' and R" can be taken together with the atoms to which they are bound to form a 3 to 7 membered ring.

In one embodiment, the present invention provides a method of treating a condition or disease by administering a therapeutically effective amount of a compound of structural formula (I) to an individual in need thereof. The disease or condition of interest is treatable by inhibition of Bcl-2 and/or Bcl-xL, for example, a cancer.

Another embodiment of the present invention is to provide a composition comprising (a) a Bcl-2/Bcl-xL inhibitor of structural formula (I) and (b) an excipient and/or pharmaceutically acceptable carrier useful in treating diseases or conditions wherein inhibition of Bcl-2/Bcl-xL provides a benefit.

Another embodiment of the present invention is to utilize a composition comprising a compound of structural formula (I) and a second therapeutically active agent in a method of treating an individual for a disease or condition wherein inhibition of Bcl-2/Bcl-xL provides a benefit.

In a further embodiment, the invention provides for use of a composition comprising a Bcl-2/Bcl-xL inhibitor of structural formula (I) and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising a Bcl-2/Bcl-xL inhibitor of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

The Bcl-2/Bcl-xL inhibitor of structural formula (I) and the second therapeutic agent can be administered together as a single-unit dose or separately as multi-unit doses, wherein the Bcl-2/Bcl-xL inhibitor of structural formula (I) is administered before the second therapeutic agent or vice versa. It is envisioned that one or more dose of a Bcl-2/Bcl-xL inhibitor of structural formula (I) and/or one or more dose of a second therapeutic agent can be administered.

In one embodiment, a Bcl-2/Bcl-xL inhibitor of structural formula (I) and a second therapeutic agent are administered simultaneously. In related embodiments, a Bcl-2/Bcl-xL inhibitor of structural formula (I) and second therapeutic agent are administered from a single composition or from separate compositions. In a further embodiment, the Bcl-2/Bcl-xL inhibitor of structural formula (I) and second therapeutic agent are administered sequentially. A Bcl-2/Bcl-xL inhibitor of structural formula (I), as used in the present invention, can be administered in an amount of about 0.005 to about 500 milligrams per dose, about 0.05 to about 250 milligrams per dose, or about 0.5 to about 100 milligrams per dose.

These and other embodiments and features of the present invention will become apparent from the following detailed description of the preferred embodiments.

DETAILED DESCRIPTION OF THE PREFERRED EMBODIMENTS

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "Bcl-2/Bcl-xL" as used herein means Bcl-2, Bcl-xL, or Bcl-2 and Bcl-xL, i.e., Bcl-2 and/or Bcl-xL.

The term "a disease or condition wherein inhibition of Bcl-2 and/or Bcl-xL provides a benefit" pertains to a condition in which Bcl-2 and/or Bcl-xL, and/or an action of Bcl-2 and/or Bcl-xL, is important or necessary, e.g., for the onset, progress, expression of that disease or condition, or a disease or a condition which is known to be treated by a Bcl-2/Bcl-xL inhibitor (such as ABT-737 or ABT-263). An example of such a condition includes, but is not limited to, a cancer. One of ordinary skill in the art is readily able to determine whether a compound treats a disease or condition mediated by Bcl-2/Bcl-xL for any particular cell type, for example, by assays which conveniently can be used to assess the activity of particular compounds.

The term "second therapeutic agent" refers to a therapeutic agent different from a Bcl-2 and/or Bcl-xL inhibitor of structural formula (I) and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, a compound of structural formula (I) is a potent inhibitor of Bcl-2/Bcl-xL and can be used in treating diseases and conditions wherein inhibition of Bcl-2/Bcl-xL provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce Bcl-2/Bcl-xL signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Bcl-2/Bcl-xL inhibitor of structural formula (I) can be administered at the same time or sequentially in any order at different points in time as a second therapeutic agent. A present Bcl-2/Bcl-xL inhibitor and the second therapeutic agent can be administered separately, in any appropriate form and by any suitable route. When a present Bcl-2/Bcl-xL inhibitor and the second therapeutic agent are not administered concurrently, it is understood that they can be administered in any order to a subject in need thereof. For example, a present Bcl-2/Bcl-xL inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Bcl-2/Bcl-xL inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

Over the past decade, research into apoptosis has established that targeting Bcl-2 and/or Bcl-xL using small molecule inhibitors is a viable cancer therapeutic strategy (35-37). The discovery of ABT-737 and ABT-263, and the early clinical data on ABT-263, have demonstrated that non-peptide, small molecule inhibitors of Bcl-2 and/or Bcl-xL have great therapeutic potential for the treatment of many types of human cancer in which Bcl-2 and/or Bcl-xL are overexpressed and for which current anticancer agents are largely ineffective (26-36).

Despite the discovery of ABT-737 and ABT-263, few new classes of highly potent, small molecule inhibitors of Bcl-2/Bcl-xL with affinities to Bcl-2/Bcl-xL and cellular potencies approaching that achieved by ABT-737/ABT-263 have been reported. This is because the design of small molecule inhibitors of Bcl-2/Bcl-xL involves targeting and blocking the interactions of the Bcl-2/Bcl-xL proteins with their pro-apoptotic binding partners, a task which has been proven to be very challenging for at least three main reasons. First, compared to typical binding sites in enzymes and receptors, the interfaces between Bcl-2 or Bcl-xL and their binding partners are very large (38-42). The interaction of Bcl-2/Bcl-xL with its binding partners, such as BAD and Bim proteins, is mediated by a 20-25 residue BH3 domain in BAD and Bim and a large binding groove in Bcl-2/Bcl-xL. Second, the binding grooves in Bcl-2/Bcl-xL are very hydrophobic in nature, making it difficult to design druglike small molecules (26, 38-42). Third, Bcl-2 and Bcl-xL are extremely conformationally flexible and can adopt quite distinct conformations in the ligand-free structure and when bound to different ligands (26, 38-42). Some of the binding pockets observed for Bcl-xL in the crystal structures of its complexes with BAD (41), Bim (43), and ABT-737(44) are induced by ligand binding and are not presented in a ligand-free crystal structure (38). These three factors make the design of potent and druglike small molecule inhibitors of Bcl-2/Bcl-xL a paramount challenge in modern drug discovery.

The present invention is directed to new class of potent and specific inhibitors of Bcl-2/Bcl-xL. The present compounds can bind to Bcl-2 and/or Bcl-xL with $K_i$ values <1 nM and function as potent antagonists of Bcl-2 and Bcl-xL in cell-free functional assays. The compounds potently induce apoptosis in cancer cells and have a mechanism of action that is highly consistent with targeting Bcl-2 and Bcl-xL. A tested compound demonstrates robust apoptosis induction in vivo in tumor tissues and shows strong antitumor activity against the H146 xenograft tumors.

The Bcl-2/Bcl-xL inhibitors of the present invention therefore are useful in the treatment of unwanted proliferating cells, including cancers and precancers, in subjects in need of such treatment. Also provided are methods of treating a subject having unwanted proliferating cells comprising administering a therapeutically effective amount of a present compound to a subject in need of such treatment. Also provided are methods of preventing the proliferation of unwanted proliferating cells, such as cancers and precancers, in a subject comprising the step of administering a therapeutically effective amount of a compound of structural formula (I) to a subject at risk of developing a condition characterized by unwanted proliferating cells. In some embodiments, the compounds of structural formula (I) reduced the proliferation of unwanted cells by inducing apotosis in those cells.

The present invention is directed to Bcl-2/Bcl-xL inhibitors having a structural formula (I):

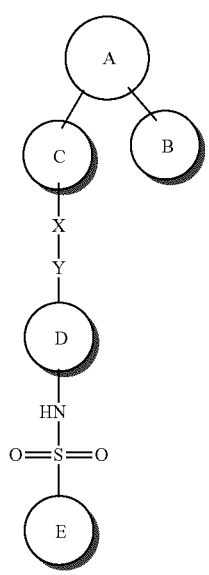

(I)

wherein A is null, optionally substituted phenyl, or an optionally substituted five or six-membered aromatic ring in which 1 to 4 carbon atoms individually are replaced by nitrogen, oxygen, or sulfur;

B, C, D, and E individually are optionally substituted phenyl or an optionally substituted five or six-membered aromatic ring in which 1 to 4 carbon atoms individually are replaced by nitrogen, oxygen, or sulfur;

X and Y, independently, are null, O, S, CO, $SO_2$, SO, $PO_3H$, NR', BR', PR', POR', alkylene, cycloalkylene, alkenylene, cycloalkenylene, alkynylene, or arylene; or X and Y can be taken together to form a 5-7 membered ring, or X and Y can be Z—$(CH_2)_{1-3}$-E, wherein Z and Z', independently, are O, S, NR', CO, SO, $SO_2$, $PO_3H$, PR', or POR; and R' is H, alkyl, cycloalkyl, alkenyl, cycloalkenyl, alkynyl, aryl, heteroaryl, or heterocycloalkyl, or a pharmaceutically acceptable salt, hydrate, or solvate thereof.

Examples of rings A, B, C, D, and E include, but are not limited to,

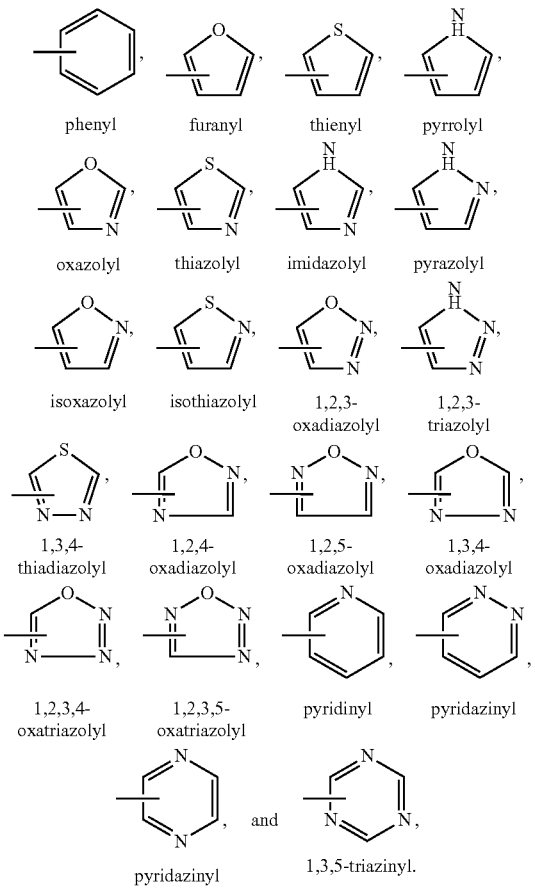

The compounds of structural formula (I) inhibit Bcl-2/Bcl-xL and are useful in the treatment of a variety of diseases and conditions. In particular, the compounds of structural formula (I) are used in methods of treating a disease or condition wherein inhibition of Bcl-2/Bcl-xL provides a benefit, for example, cancers. The method comprises administering a therapeutically effective amount of a compound of structural formula (I) to an individual in need thereof. The present methods also encompass administering a second therapeutic agent to the individual in addition to the compound of structural formula (I). The second therapeutic agent is selected from drugs known as useful in treating the disease or condition afflicting the individual in need thereof, e.g., a chemotherapeutic agent and/or radiation known as useful in treating a particular cancer.

As used herein, the term "alkyl" refers to straight chained and branched saturated $C_{1-10}$ hydrocarbon groups, nonlimiting examples of which include methyl, ethyl, and straight chain and branched propyl, butyl, pentyl, hexyl, heptyl, octyl, nonyl, and decyl groups. The term $C_n$ means the alkyl group has "n" carbon atoms. The term "alkylene" refers to an alkyl group having a substituent. An alkyl, e.g., methyl, or alkylene, e.g., —CH₂—, group can be substituted with halo, trifluoromethyl, trifluoromethoxy, hydroxy, alkoxy, nitro, cyano, alkylamino, or amino groups, for example.

The term "alkenyl" is defined identically as "alkyl," except for containing a carbon-carbon double bond, e.g., ethenyl, propenyl, and butenyl. The term "alkenylene" is defined identically to "alkylene" except for containing a carbon-carbon double bond. The term "alkynyl" and "alkynylene" are defined identically as "alkyl" and "alkylene" except the group contains a carbon-carbon triple bond.

As used herein, the term "halo" is defined as fluoro, chloro, bromo, and iodo.

The term "hydroxy" is defined as —OH.

The term "alkoxy" is defined as —OR, wherein R is alkyl.

The term "amino" is defined as —NH₂, and the term "alkylamino" is defined as —NR₂, wherein at least one R is alkyl and the second R is alkyl or hydrogen.

The term "nitro" is defined as —NO₂.

The term "cyano" is defined as —CN.

The term "trifluoromethyl" is defined as CF₃.

The term "trifluoromethoxy" is defined as —OCF₃.

As used herein, groups such as

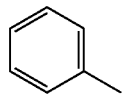

is an abbreviation for

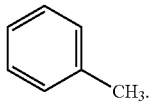

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four, groups independently selected from, for example, halo, alkyl, alkenyl, OCF₃, NO₂, CN, NC, —OH, alkoxy, amino, alkylamino, CO₂H, —CO₂alkyl, aryl, and heteroaryl.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —OCF₃, —NO₂, —CN, —NC, —OH, alkoxy, amino, alkylamino, CO₂H, —CO₂alkyl, aryl, and heteroaryl.

As used herein, the term "cycloalkyl" means a monocyclic aliphatic ring containing three to eight carbon atoms.

As used herein, the term "heterocycloalkyl" means a monocyclic or a bicyclic aliphatic ring containing 5 to 10 total atoms, of which one to five of the atoms are independently selected from nitrogen, oxygen, and sulfur and the remaining atoms are carbon.

In accordance with the present invention, ring B is phenyl or a five- or six-membered aromatic ring in which one to four of the carbon atoms, independently, are replaced by nitrogen, oxygen, or sulfur. In one preferred embodiment, ring B is phenyl. In other preferred embodiments, ring B is phenyl substituted with one or more halo group.

Specific non-limiting examples of ring B include:

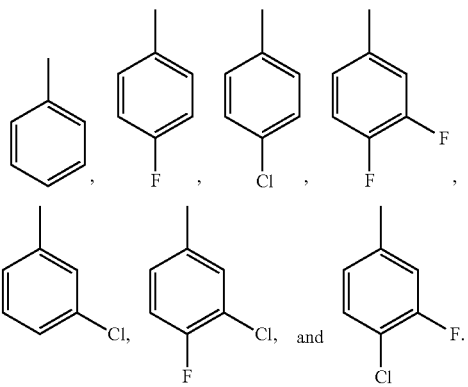

Ring A of the compound of structural formula (I) also is phenyl or a five- or six-membered aromatic ring in which one to four, and preferably one to three, of the carbon atoms, independently, are replaced by nitrogen, oxygen, or sulfur. In some preferred embodiments, ring A is selected form the group consisting of

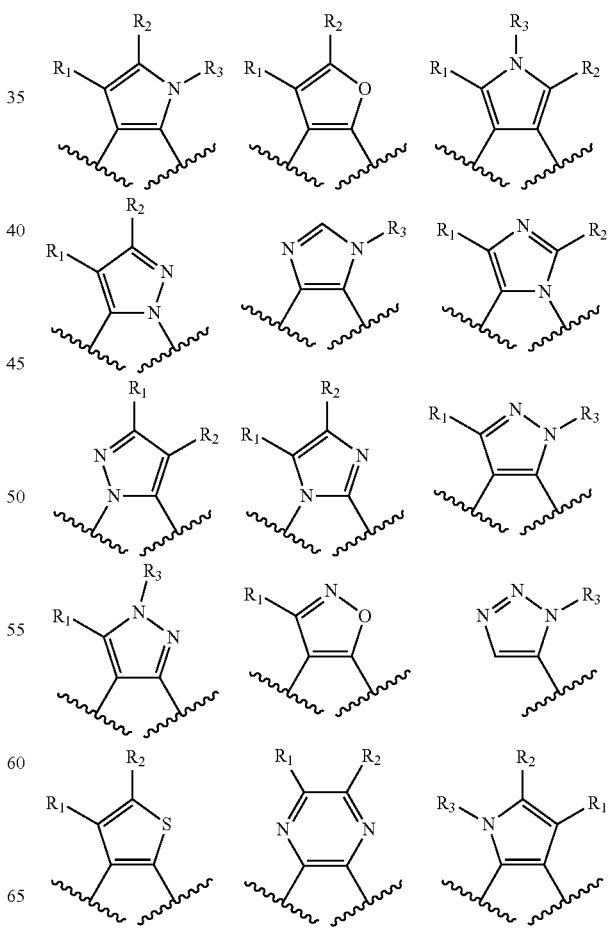

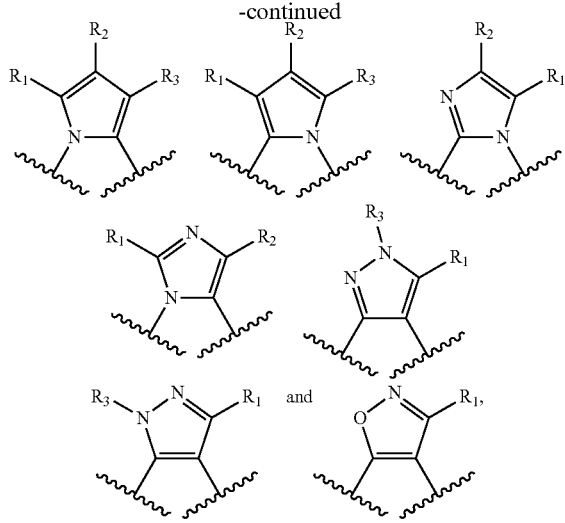

wherein $R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R'', COR', $CO_2$R', OCOR', CONR'R'', CONR'SO$_2$R'', NR'COR'', NR'CONR''R''', NR'C=SNR''R''', NR'SO$_2$R'', SO$_2$R', and SO$_2$NR'R'';

$R_3$ is selected from a group consisting of H, alkyl, cycloalkyl, alkenyl, cycloalkenyl, alkynyl, aryl, heteroaryl, heterocycloalkyl, OR', NR'R'', $CO_2$R', COR', CONR'R'', CONR'SO$_2$R'', $C_{1-3}$alkyleneCH(OH)CH$_2$OH, SO$_2$R', and SO$_2$NR'R'';

R', R'', and R''', independently, are H, alkyl, cycloalkyl, alkenyl, cycloalkenyl, alkynyl, aryl, heteroaryl, $C_{1-3}$alkyleneheterocycloalkyl, or heterocycloalkyl;

R' and R'', or R'' and R''', can be taken together with the atom to which they are bound to form a 3 to 7 membered ring.

In some preferred embodiments, the A ring is

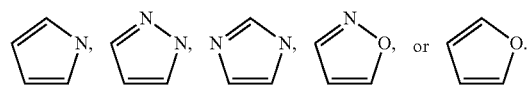

In other preferred embodiments, a non-aromatic nitrogen atom of the A ring is substituted with $C_{1-6}$alkyl, e.g., methyl, ethyl, n-propyl, isopropyl, or n-butyl; cycloalkyl, e.g., cyclopropyl; —(CH$_2$)$_{1-3}$N(CH$_3$)$_2$, or —(CH$_2$)$_{1-3}$CH(OH)CH$_2$OH. In another preferred embodiment, a non-aromatic nitrogen atom of the A ring and an adjacent carbon of the A ring are taken together to form a five or six membered ring, e.g.,

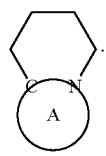

In still other preferred embodiments, one to three carbon atoms, and preferably one or two carbon atoms, of the A ring are substituted, independently, with $CH_3$, $C_2H_5$, $C_3H_7$, $CF_3$, $NH_2$, Cl, CN, $CO_2H$, C(=O)CH$_3$, C(=O)C$_2$H$_5$, C(=O)CF$_3$, SO$_2$CH$_3$, SO$_2$C$_2$H$_5$, SO$_2$C$_3$H$_7$, SO$_2$CF$_3$, SO$_2$N(CH$_3$)$_2$, C(=O)NHSO$_2$CH$_3$, C(=O)NH$_2$, C(=O)NHCH$_3$, C(=O)NH(CH$_2$)$^{1-3}$N(CH$_3$)$_2$, C(=O)NHSO$_2$CH$_3$,

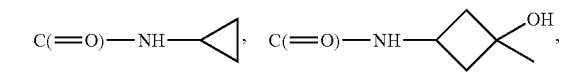

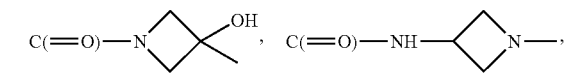

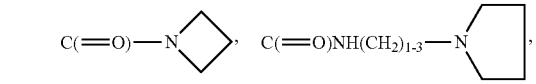

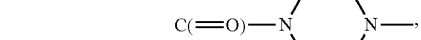

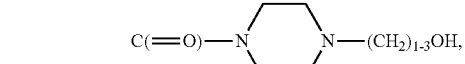

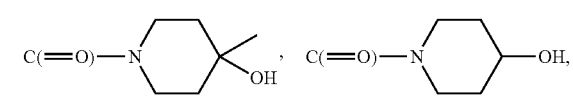

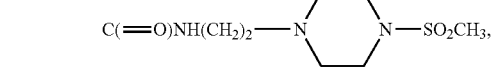

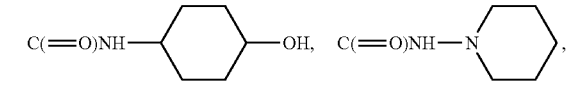

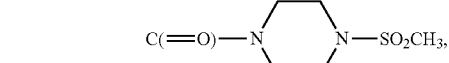

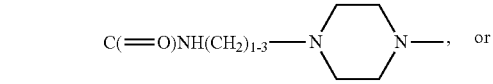

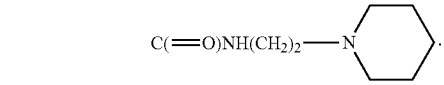

In some preferred embodiments, the C ring is phenyl, optionally substituted with one or two substituents selected from halo and $C_{1-3}$alkyl. Specific embodiments include a phenyl ring substituted with one or two fluoro, bromo, chloro, or methyl.

In other preferred embodiments, the moiety —X—Y— is selected from the group consisting of —C≡C—, —CH$_2$CH$_2$—, —NHCH$_2$CH$_2$NH—, —OCH$_2$CH$_2$—O—,

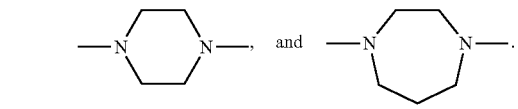

In yet another preferred embodiment, the D ring is phenyl, either unsubstituted or substituted. For example, an inhibitor of structural formula (I) wherein the D ring is phenyl has a structure

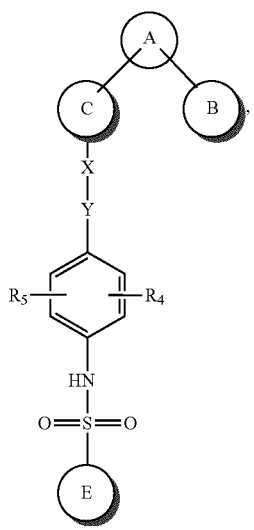

wherein $R_4$ and $R_5$, independently, are selected from a group consisting of H, CN, $NO_2$, halo, alkyl, cycloalkyl, alkenyl, cycloalkenyl, alkynyl, aryl, heteroaryl, heterocycloalkyl, OR', SR', NR'R'', $CO_2R'$, OCOR', CONR'R'', CONR'SO_2R'', NR'COR'', NR'CONR''R''', NR'C=SNR''R''', NR'SO_2R'', $SO_2R'$, and $SO_2NR'R''$. All other rings and R groups are defined as above.

One preferred $R_4$ or $R_5$ group is halo, e.g., fluoro.

In still another preferred embodiment, the E ring is phenyl, preferably containing one to five, and more preferably one or two, substituents. For example, an inhibitor of structural formula (I), wherein D and E are both phenyl, has a structure:

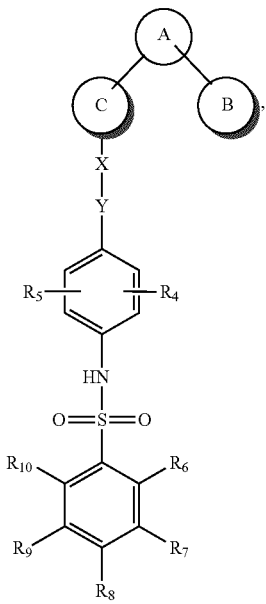

wherein $R_6$, $R_7$, $R_8$, $R_9$ and $R_{10}$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R'', $CO_2R'$, OCOR', CONR'R'', CONR'SO_2R'', NR'COR'', NR'CONR''R''', NR'C=SNR''R''', NR'SO_2R'', $SO_2R'$, and $SO_2NR'R''$. All other rings and R groups are defined as above.

In some preferred embodiments, a substituent on a phenyl ring E at a position meta to the $SO_2$ group of compound (I) is $NO_2$ or $SO_2CF_3$. In other preferred embodiments, a substituent on a phenyl ring E at a position para to the $SO_2$ group of compound (I) is

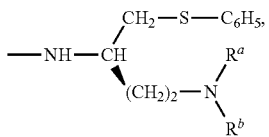

wherein $R^a$ and $R^b$, individually, are H, methyl, and

or $R^a$ and $R^b$ are taken together to form

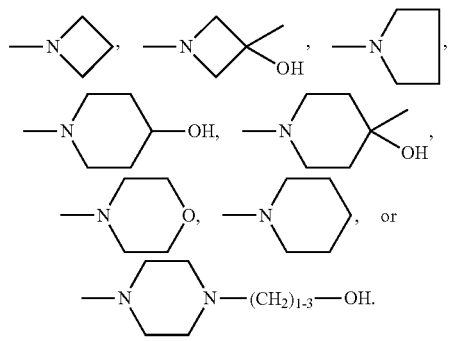

A preferred inhibitor of the present invention has a structural (II):

(II)

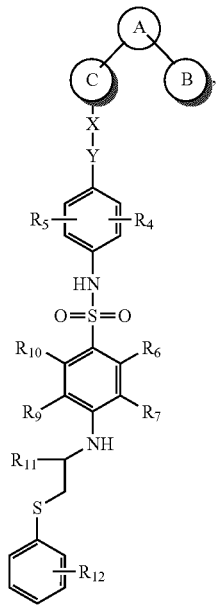

wherein the A ring is selected from the group consisting of

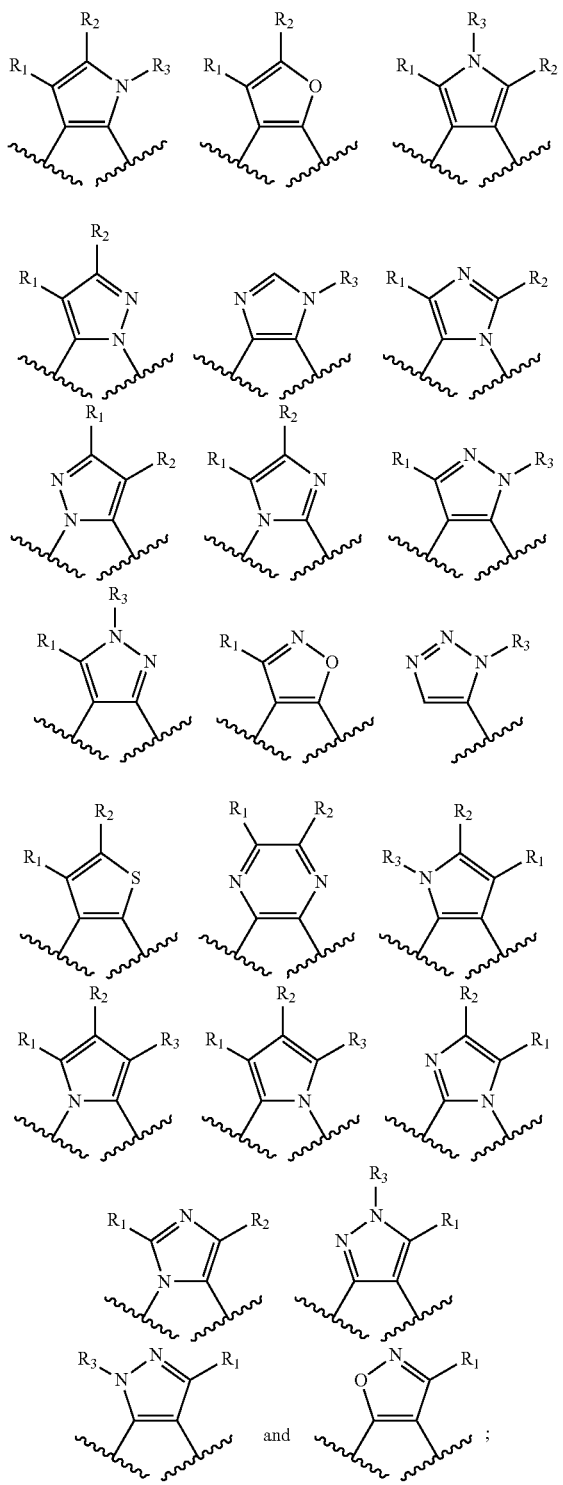

rings B and C are optionally substituted phenyl;

X, Y, $R_1$, $R_2$, $R_3$, $R_4$, $R_5$, $R_6$, $R_7$, $R_8$, $R_9$, $R_{10}$, R', R", R'" are defined as above; and $R_{11}$ and $R_{12}$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", CONR'$SO_2$R", NR'COR", NR'CONR"R'", NR'$SO_2$R", $SO_2$R', and $SO_2$NR'R";

or a pharmaceutically acceptable salt, hydrate, or solvate thereof.

Additionally, salts, hydrates, and solvates of the present compounds also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Compounds of the invention can exist as salts. Pharmaceutically acceptable salts of the compounds of the invention often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I) as well as pharmaceutically acceptable salts, hydrates, or solvates thereof.

Specific compounds of the present invention include, but are not limited to, compounds having the structure set forth below.

| Compound No. | |
|---|---|
| 1 | 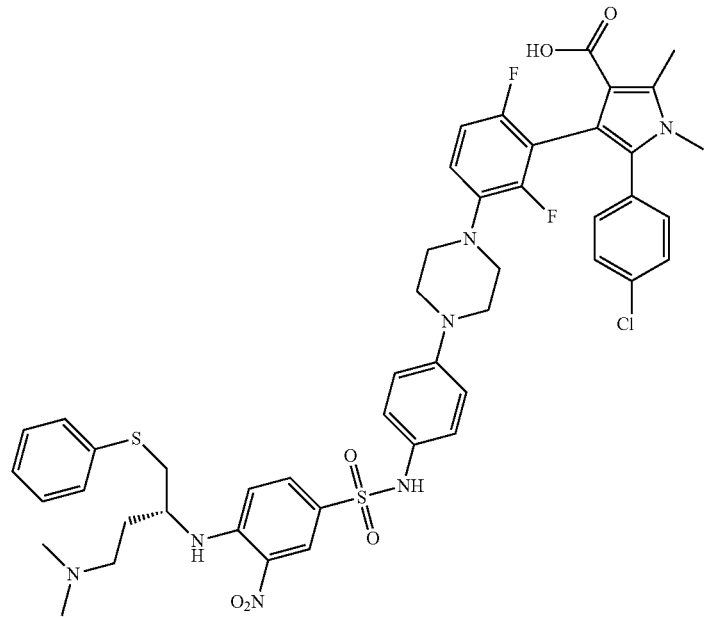 [SMILES: Cc1c(C(=O)O)c(-c2c(F)ccc(N3CCN(c4ccc(NS(=O)(=O)c5ccc(N[C@H](CCN(C)C)CSc6ccccc6)c([N+](=O)[O-])c5)cc4)CC3)c2F)c(-c2ccc(Cl)cc2)n1C] |
| 2 | 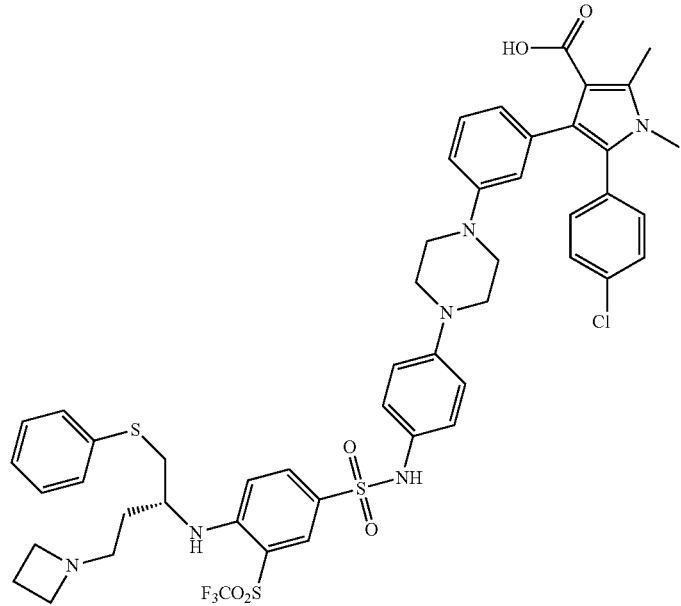 |

-continued
| Compound No. | |
|---|---|
| 3 | 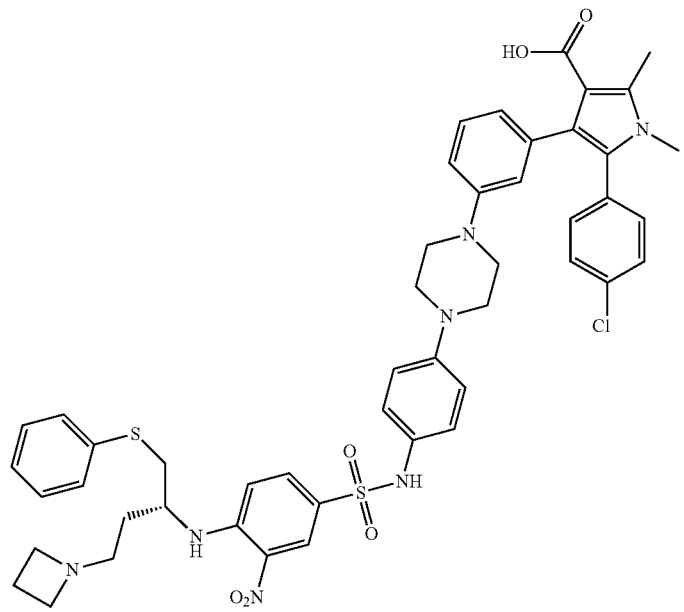 [SMILES: Cc1c(C(=O)O)c(-c2cccc(N3CCN(c4ccc(NS(=O)(=O)c5ccc(N[C@H](CCN6CCC6)CSc6ccccc6)c([N+](=O)[O-])c5)cc4)CC3)c2)c(-c2ccc(Cl)cc2)n1C] |
| 4 | 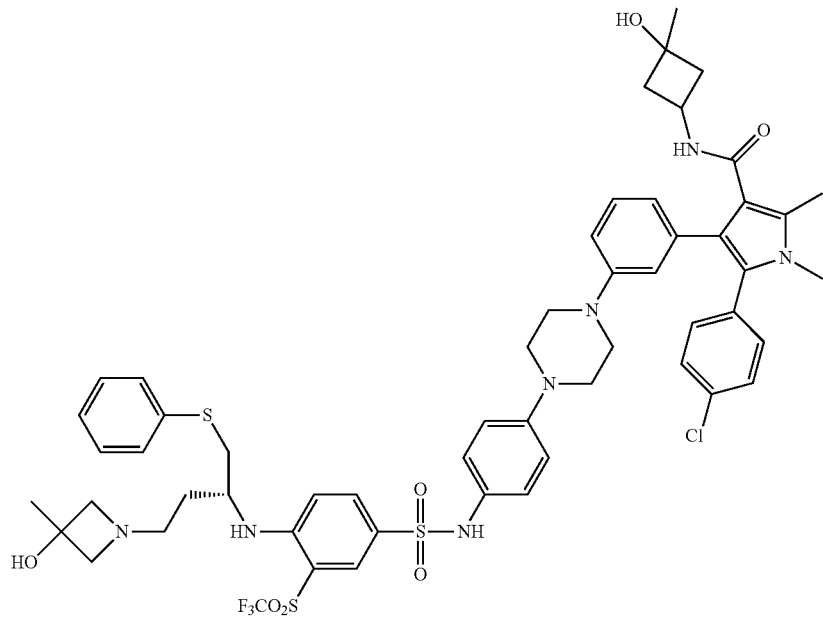 |

-continued
| Compound No. | |
|---|---|
| 5 | 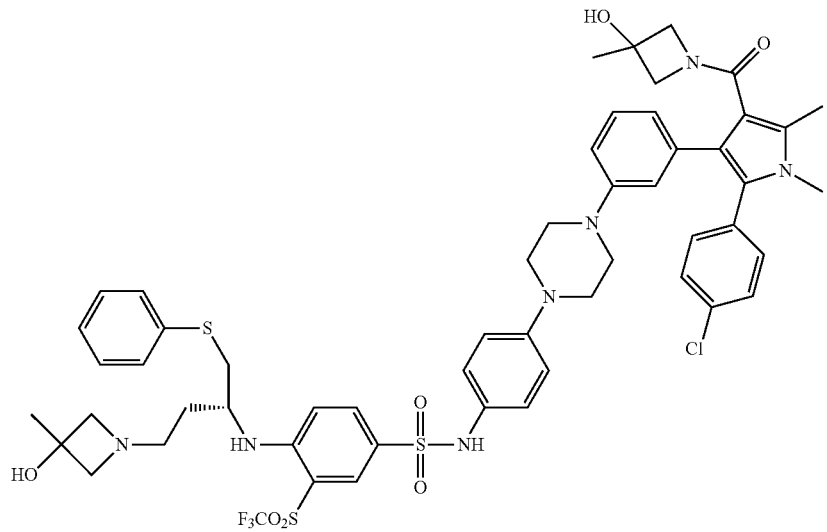 |
| 6 | 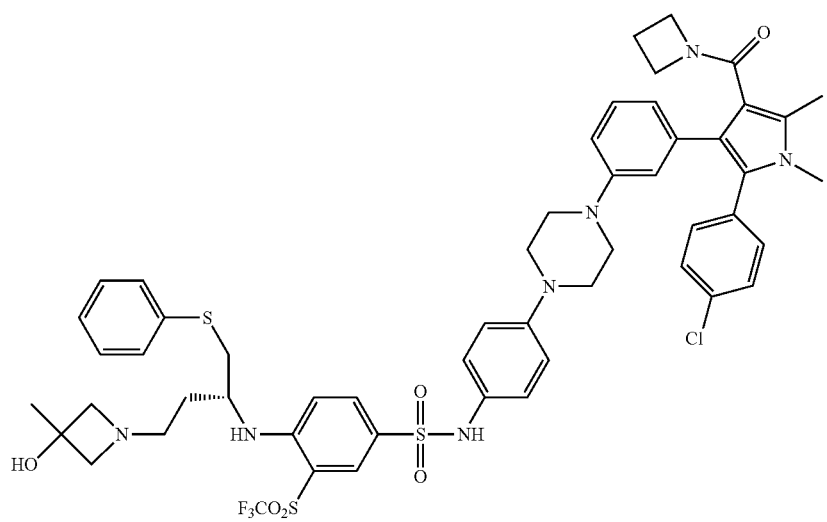 |
| 7 | 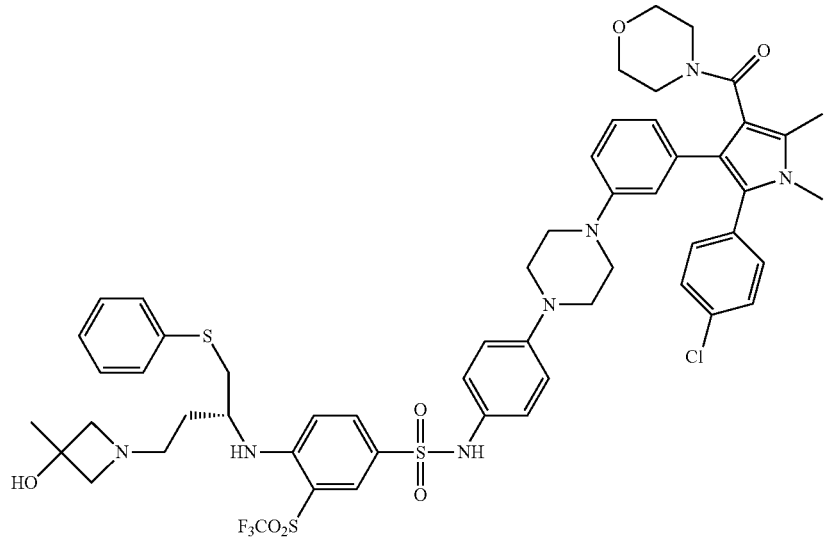 |

| Compound No. | |
|---|---|
| 8 | 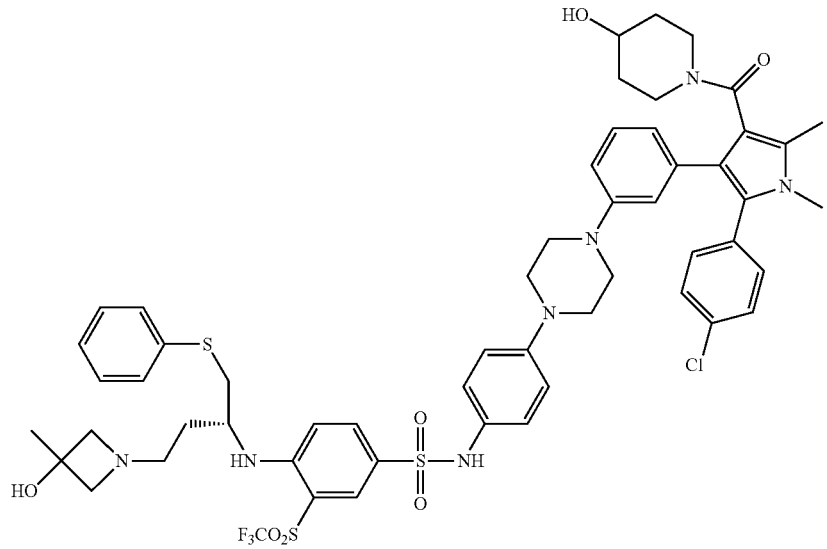 |
| 9 | 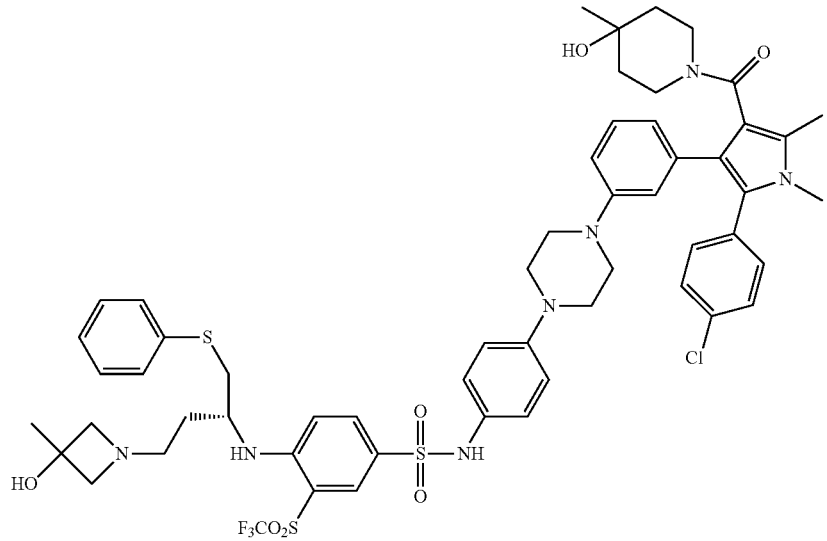 |

| Compound No. | |
|---|---|
| 10 | 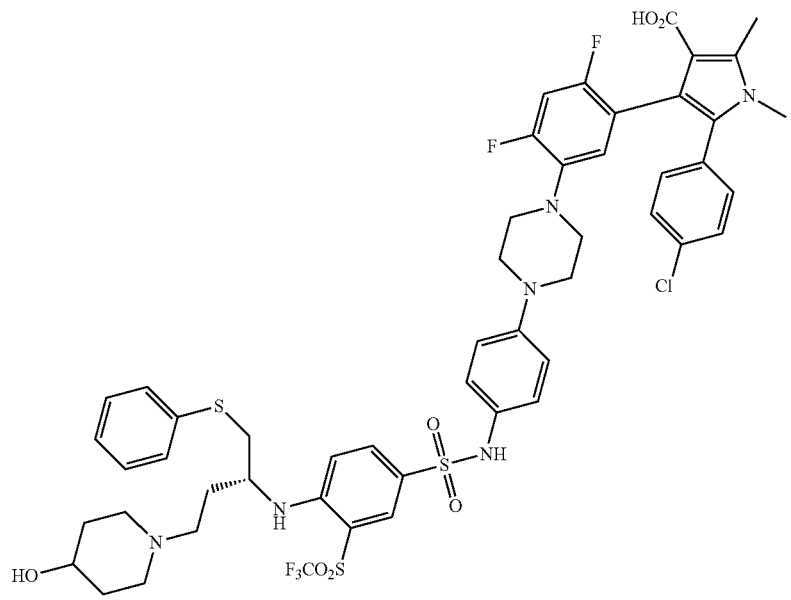 |
| 11 | 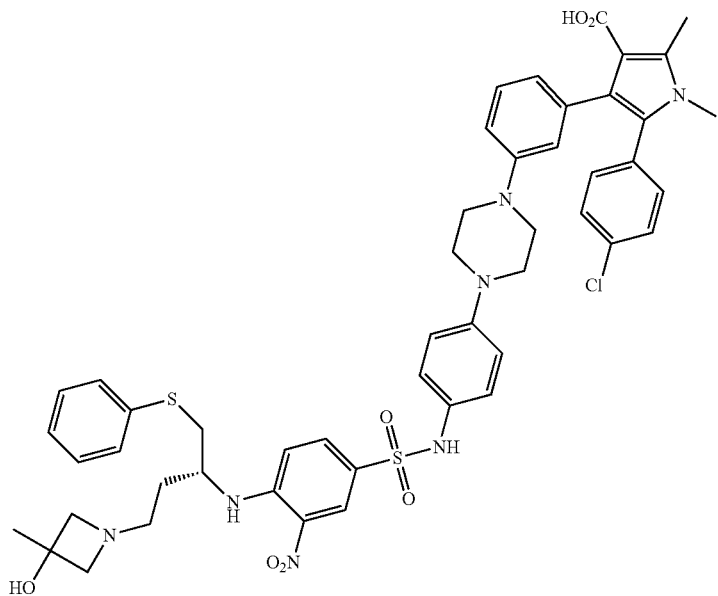 |

| Compound No. | |
|---|---|
| 12 | 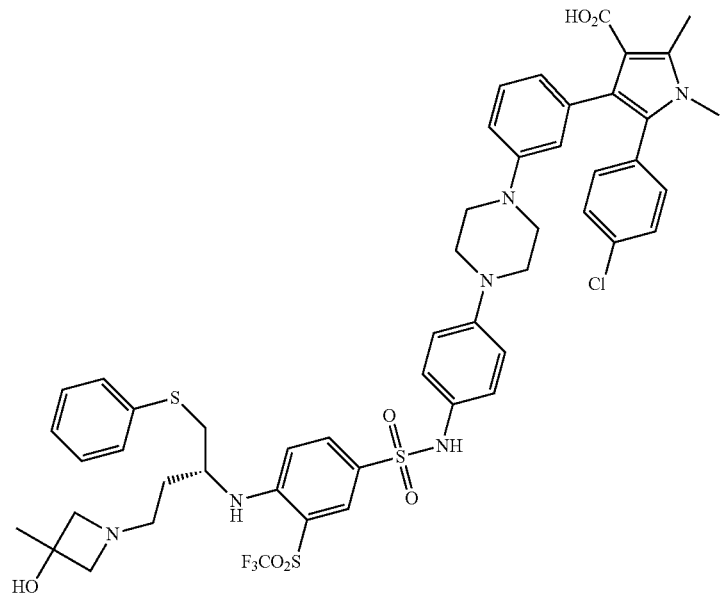 |
| 13 | 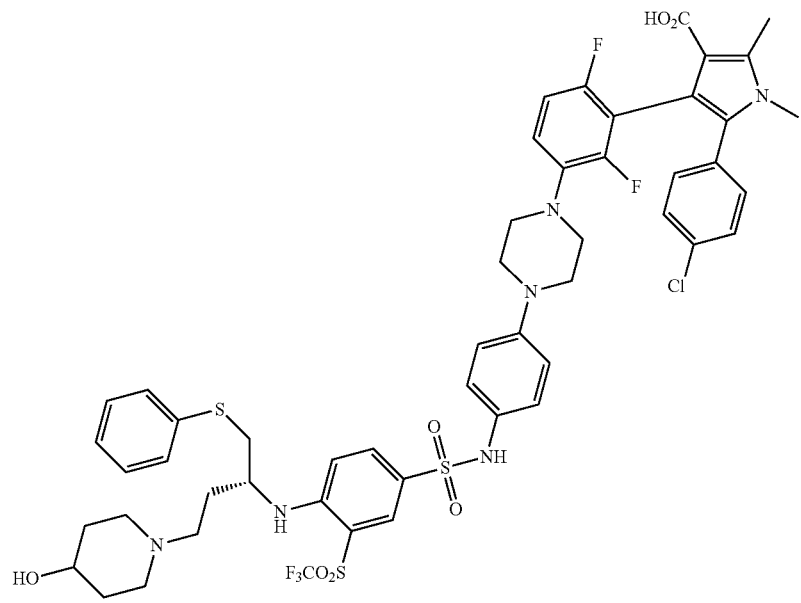 |

| Compound No. | |
|---|---|
| 14 | 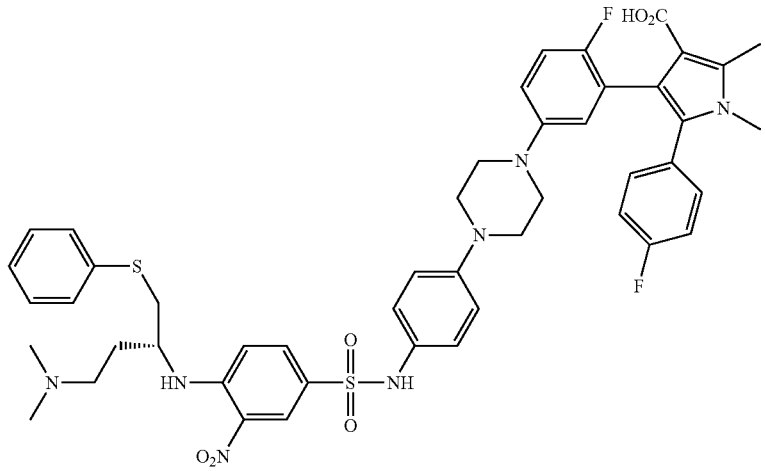 [SMILES: Cc1c(C(=O)O)c(-c2cc(N3CCN(c4ccc(NS(=O)(=O)c5ccc(N[C@H](CCN(C)C)CSc6ccccc6)c([N+](=O)[O-])c5)cc4)CC3)ccc2F)c(-c2ccc(F)cc2)n1C] |
| 15 | 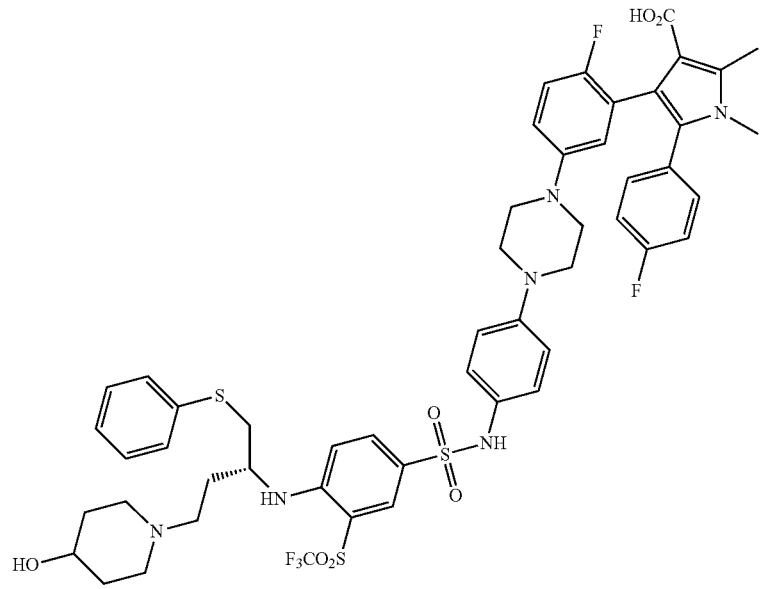 |
| 16 | 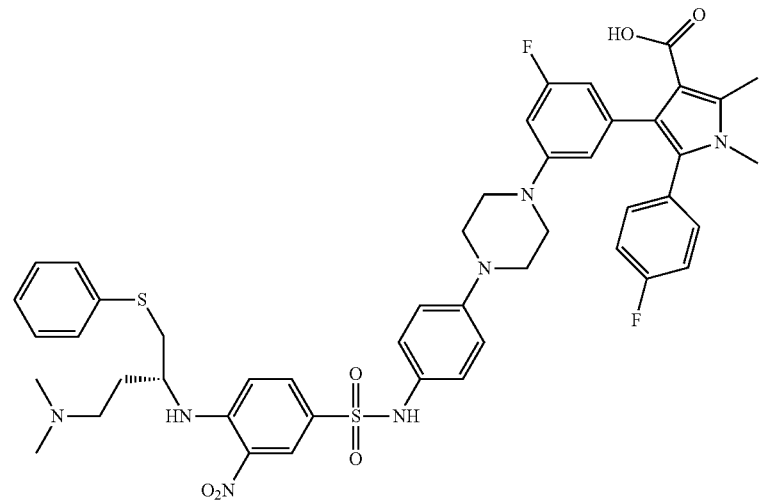 [SMILES: Cc1c(C(=O)O)c(-c2cc(F)cc(N3CCN(c4ccc(NS(=O)(=O)c5ccc(N[C@H](CCN(C)C)CSc6ccccc6)c([N+](=O)[O-])c5)cc4)CC3)c2)c(-c2ccc(F)cc2)n1C] |

| Compound No. | |
|---|---|
| 17 | 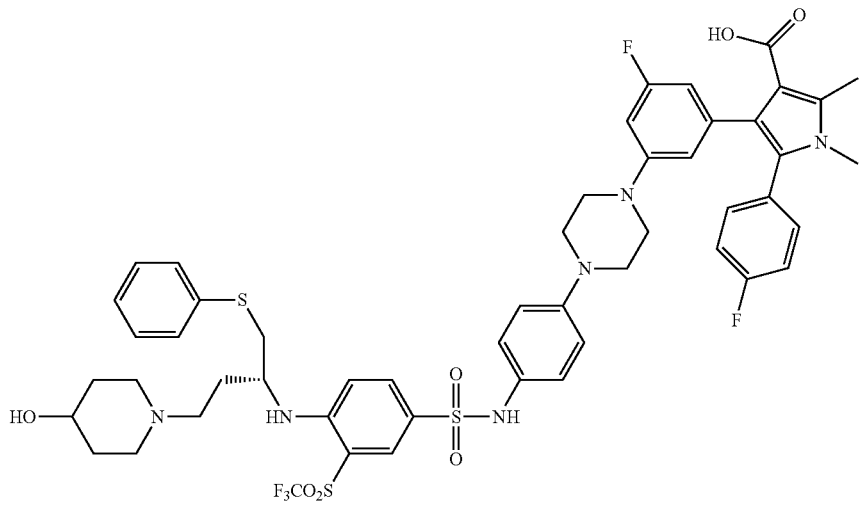 |
| 18 | 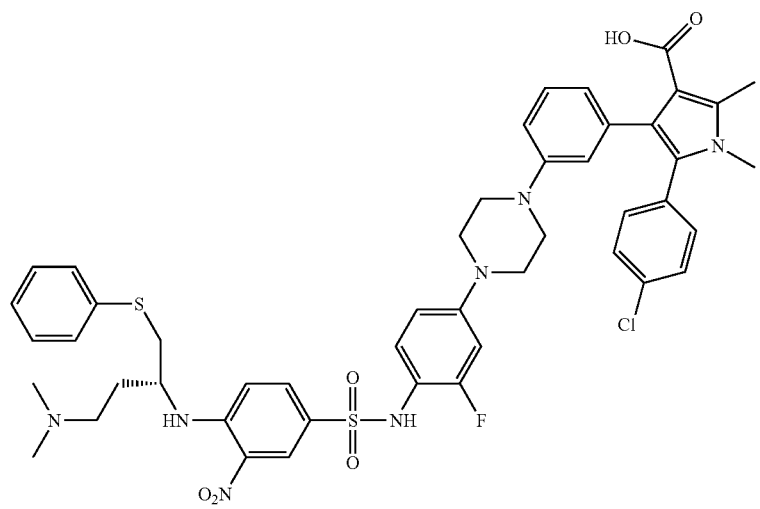 [SMILES: Cc1c(C(=O)O)c(-c2cccc(N3CCN(c4ccc(NS(=O)(=O)c5ccc(N[C@H](CCN(C)C)CSc6ccccc6)c([N+](=O)[O-])c5)c(F)c4)CC3)c2)c(-c2ccc(Cl)cc2)n1C] |
| 19 | 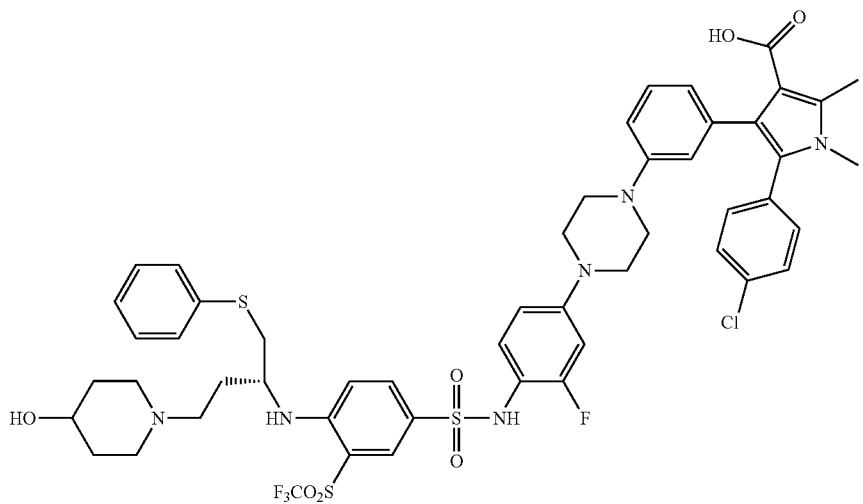 |

-continued
Compound No.
20
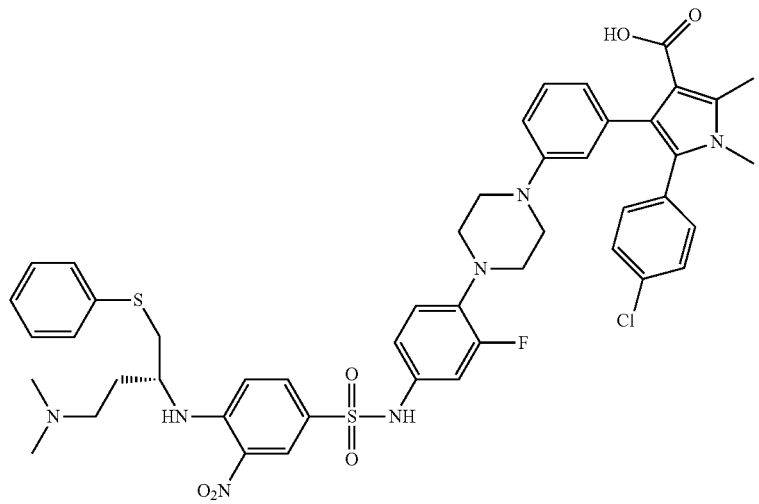 [SMILES: Cc1c(C(=O)O)c(-c2cccc(N3CCN(c4ccc(NS(=O)(=O)c5ccc(N[C@H](CCN(C)C)CSc6ccccc6)c([N+](=O)[O-])c5)cc4F)CC3)c2)c(-c2ccc(Cl)cc2)n1C]
21
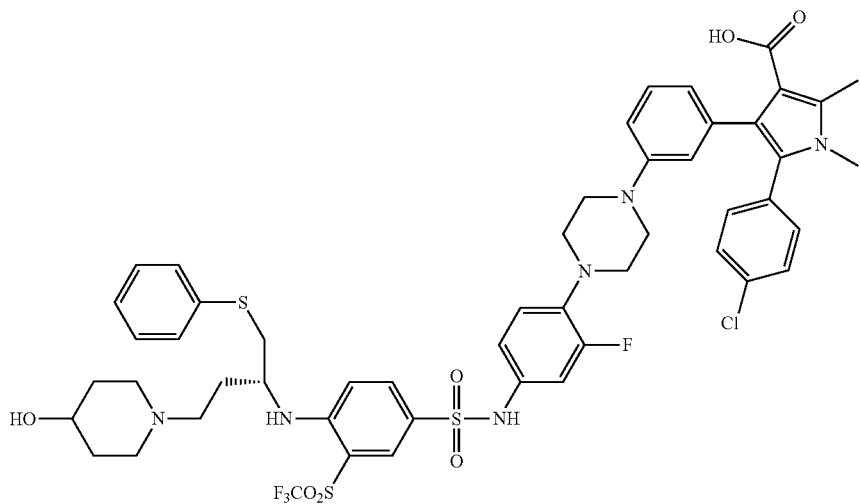
22
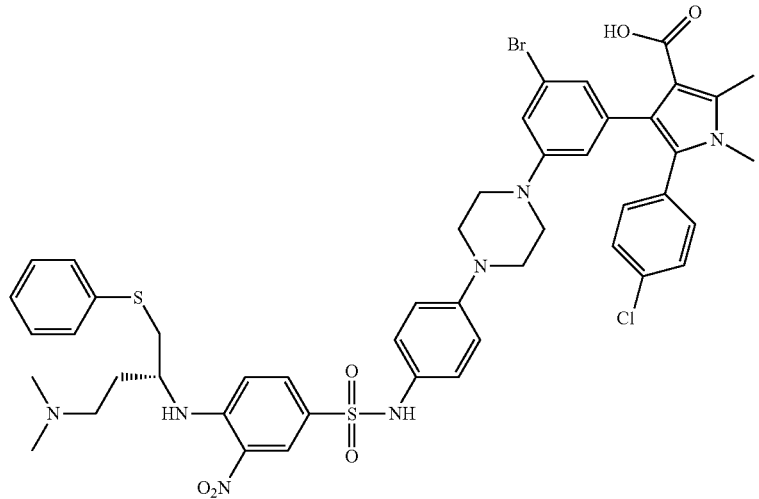

| Compound No. | |
|---|---|
| 23 | 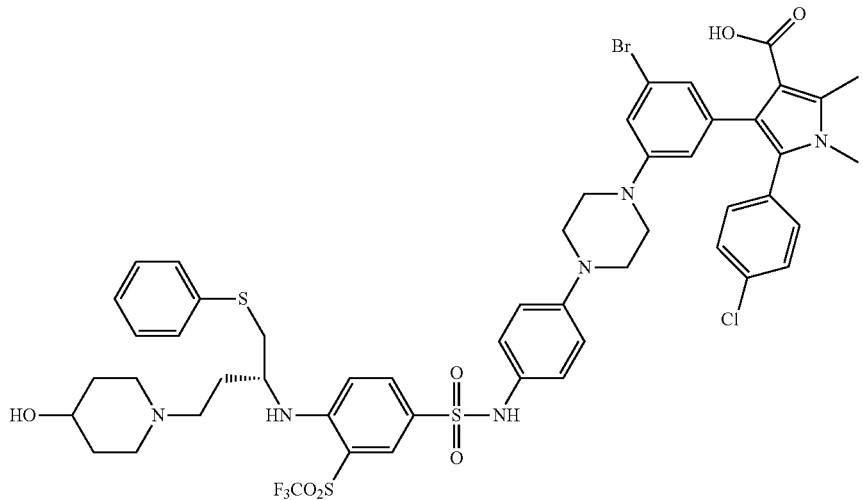 |
| 24 | 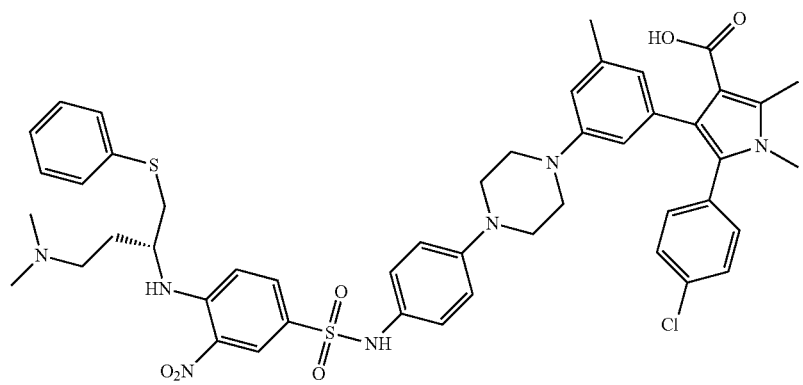 |
| 25 | 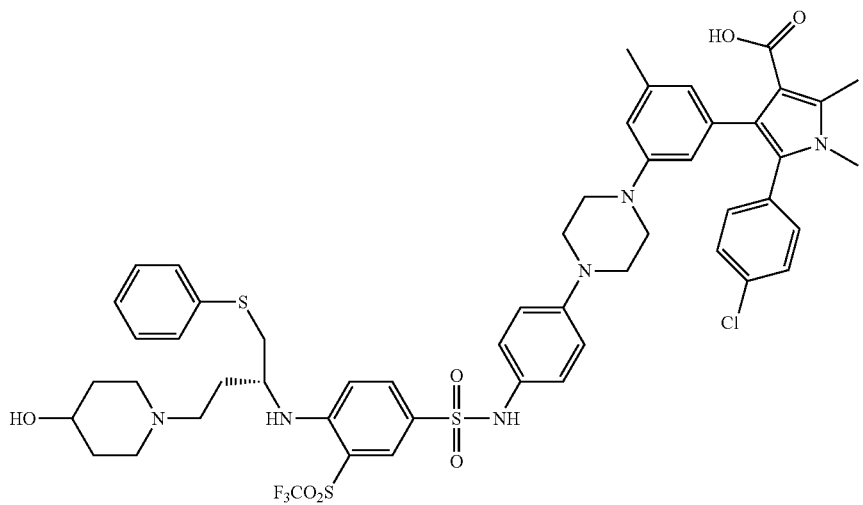 |

-continued
| Compound No. | |
|---|---|
| 26 | 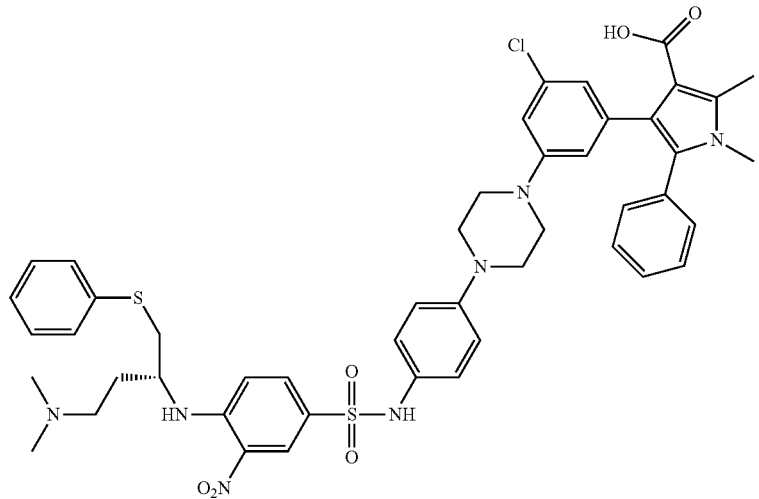 [SMILES: Cc1c(C(=O)O)c(-c2cc(Cl)cc(N3CCN(c4ccc(NS(=O)(=O)c5ccc(N[C@H](CCN(C)C)CSc6ccccc6)c([N+](=O)[O-])c5)cc4)CC3)c2)c(-c2ccccc2)n1C] |
| 27 | 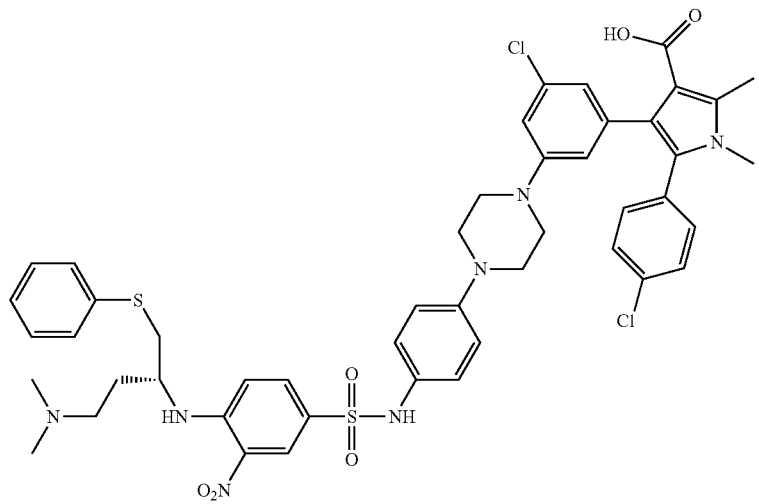 |
| 28 | 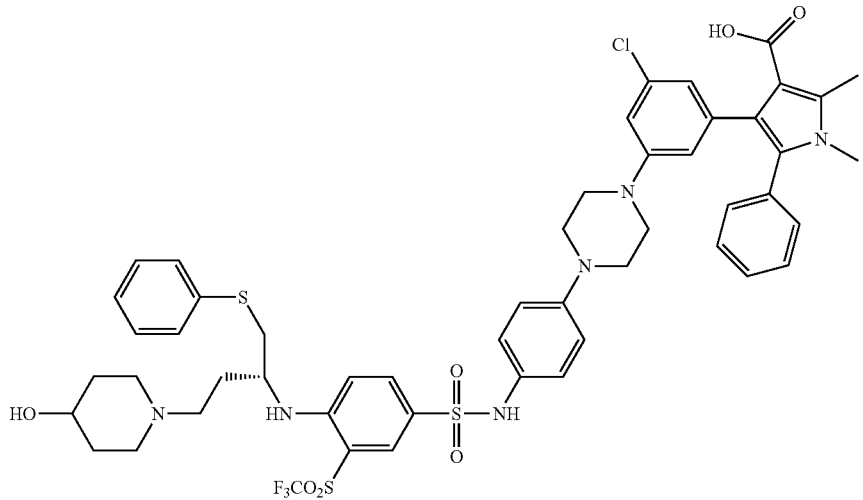 |

| Compound No. | |
|---|---|
| 29 | 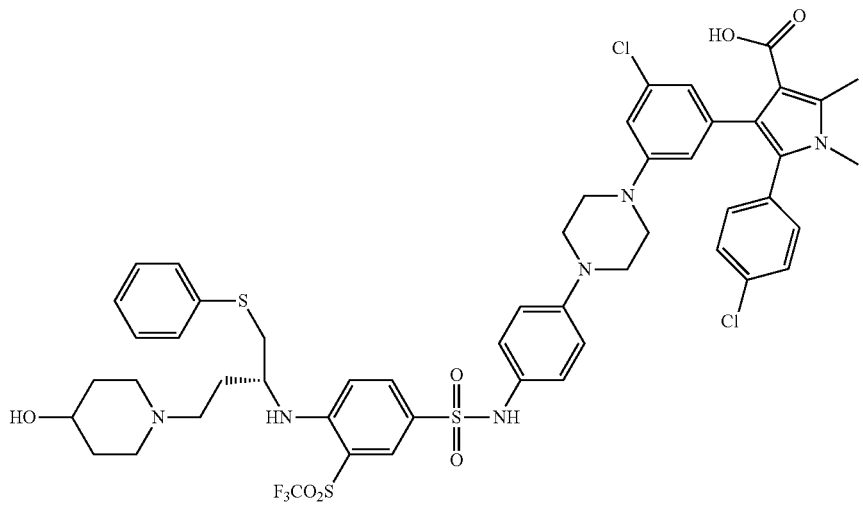 |
| 30 | 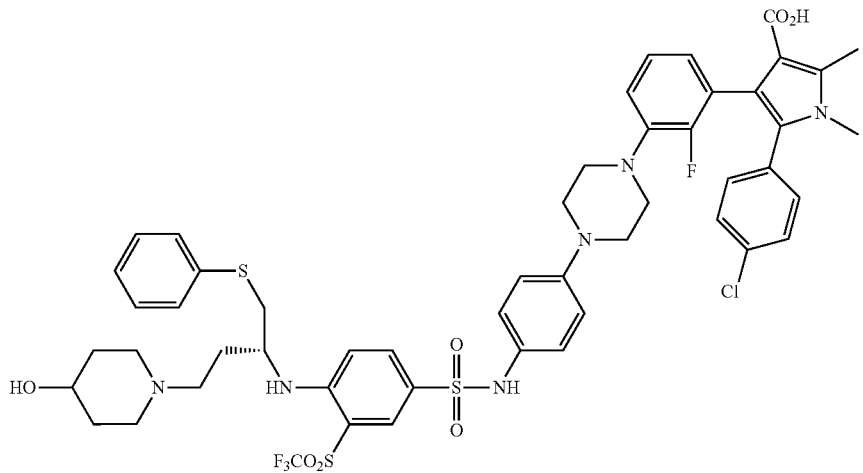 |
| 31 | 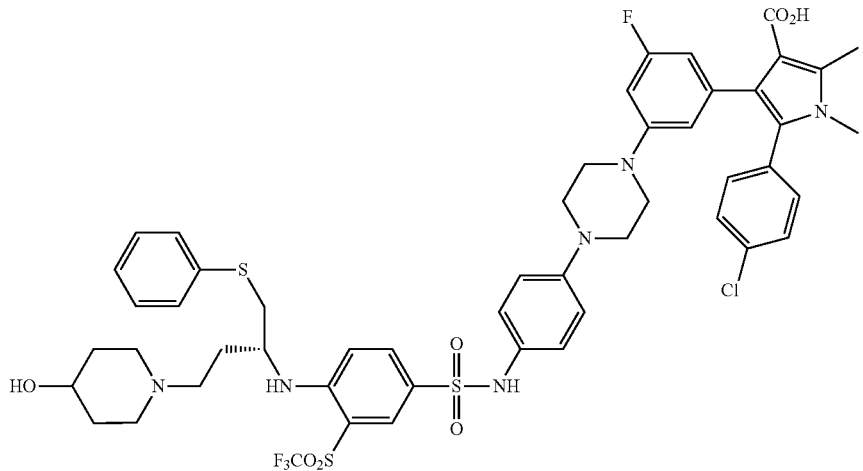 |

| Compound No. | |
|---|---|
| 32 | 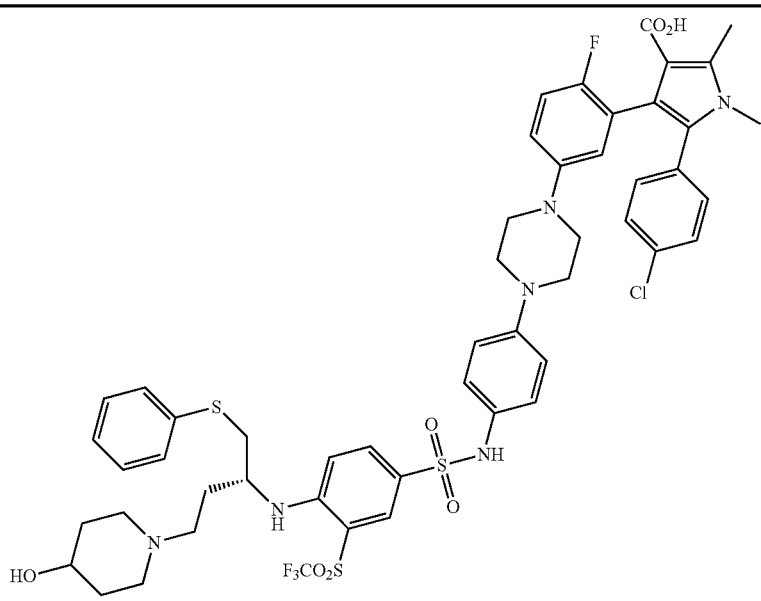 |
| 33 | 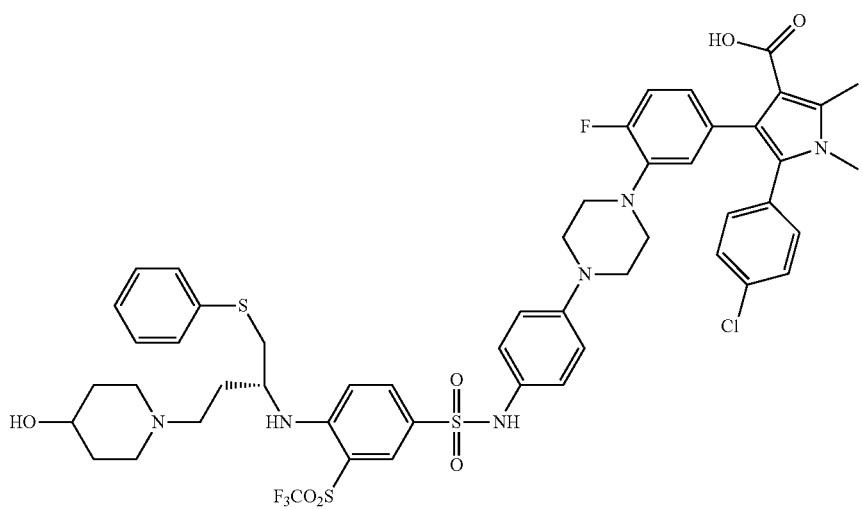 |
| 34 | 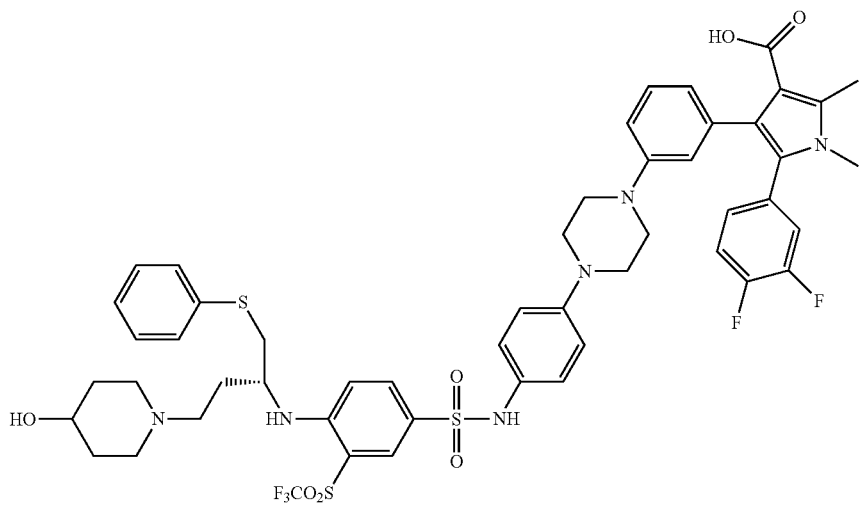 |

| Compound No. |
| --- |
| 35 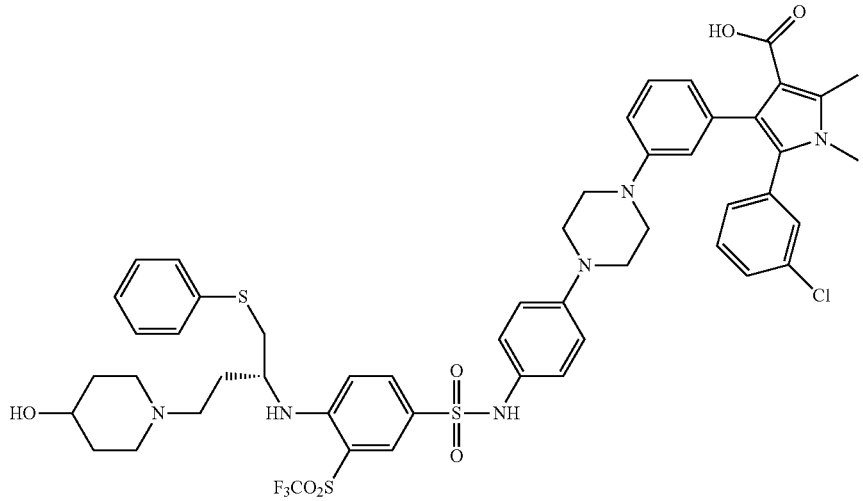 |
| 36 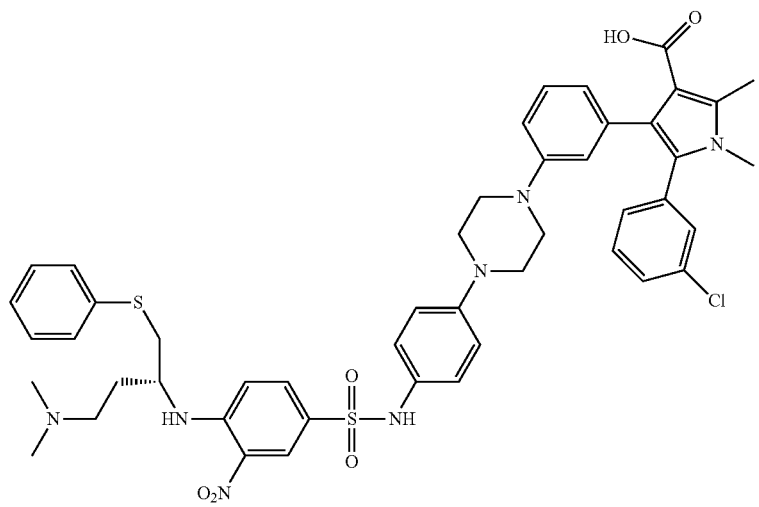 [SMILES: Cc1c(C(=O)O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2cccc(Cl)c2)n1C] |
| 37 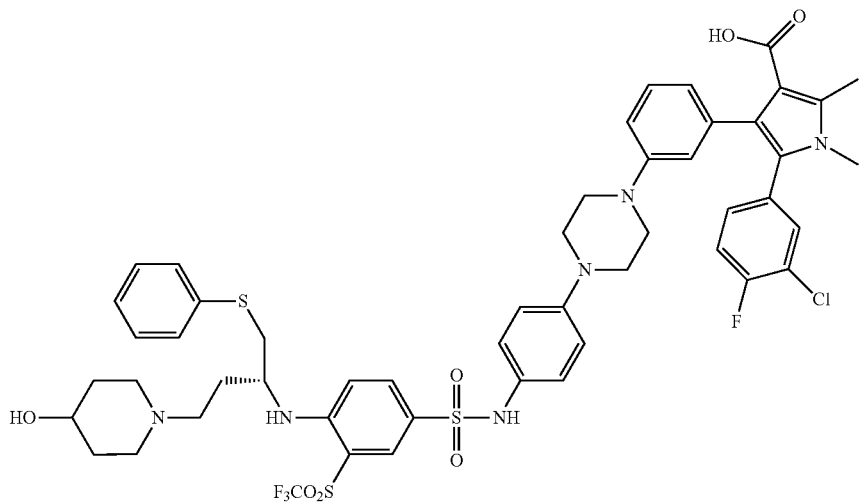 |

| Compound No. | |
|---|---|
| 38 | 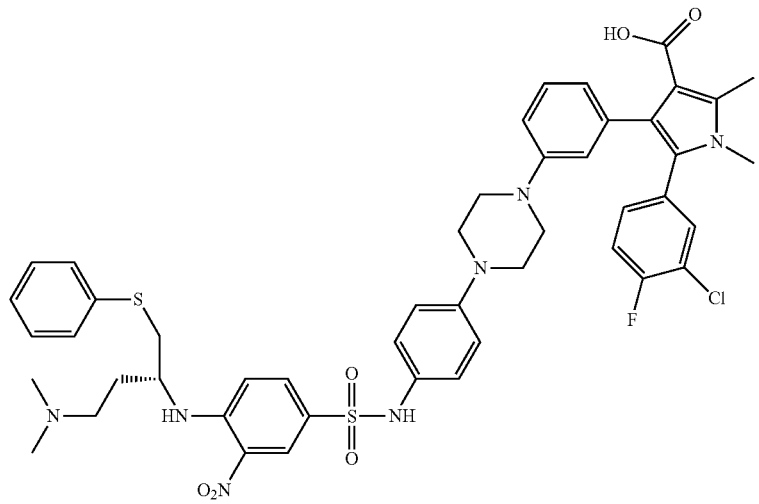 [SMILES: Cc1c(C(=O)O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(F)c(Cl)c2)n1C] |
| 39 | 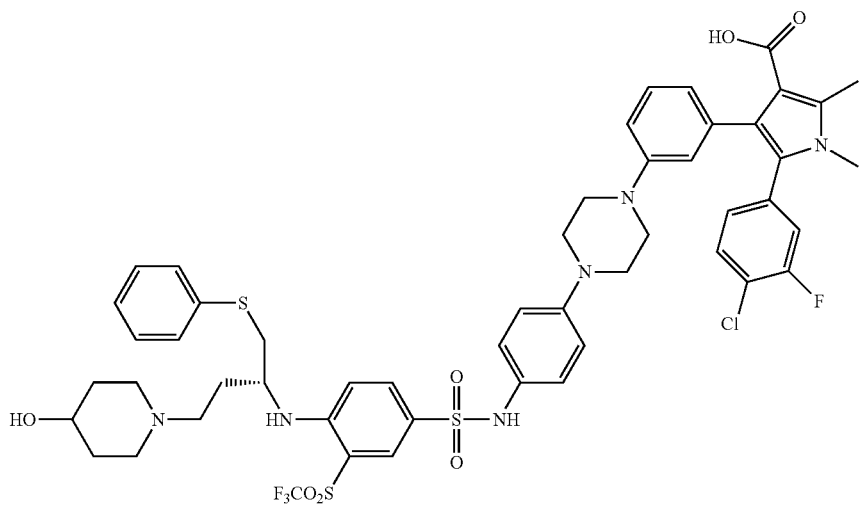 |
| 40 | 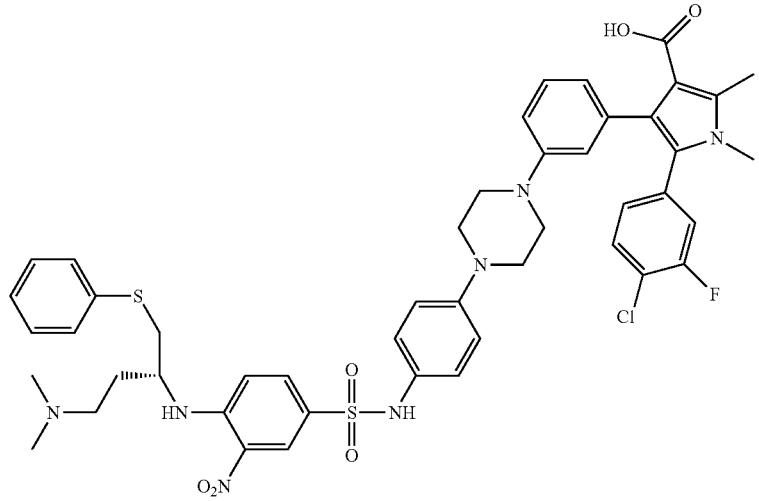 [SMILES: Cc1c(C(=O)O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)c(F)c2)n1C] |

-continued
| Compound No. | |
|---|---|
| 41 | 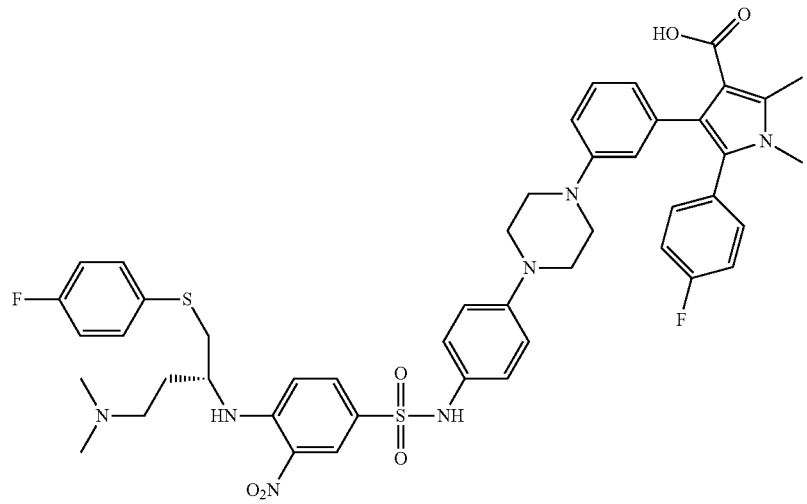 [SMILES: Cc1c(C(=O)O)c(-c2cccc(N3CCN(c4ccc(NS(=O)(=O)c5ccc(N[C@H](CCN(C)C)CSc6ccc(F)cc6)c([N+](=O)[O-])c5)cc4)CC3)c2)c(-c2ccc(F)cc2)n1C] |
| 42 | 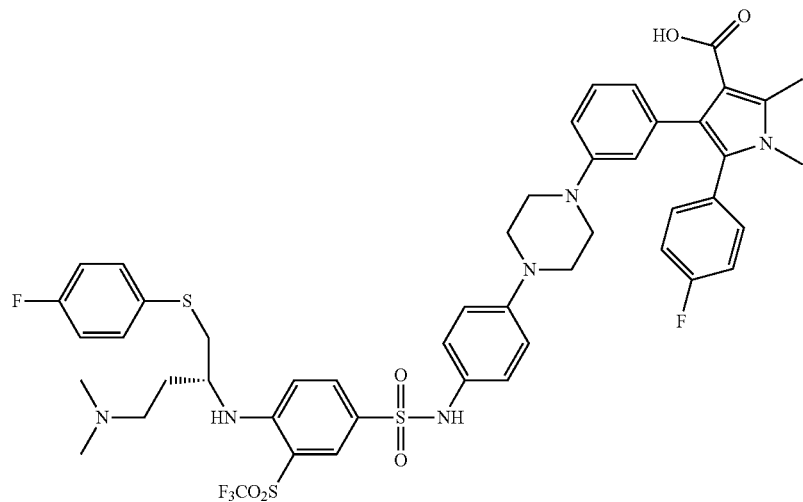 |
| 43 | 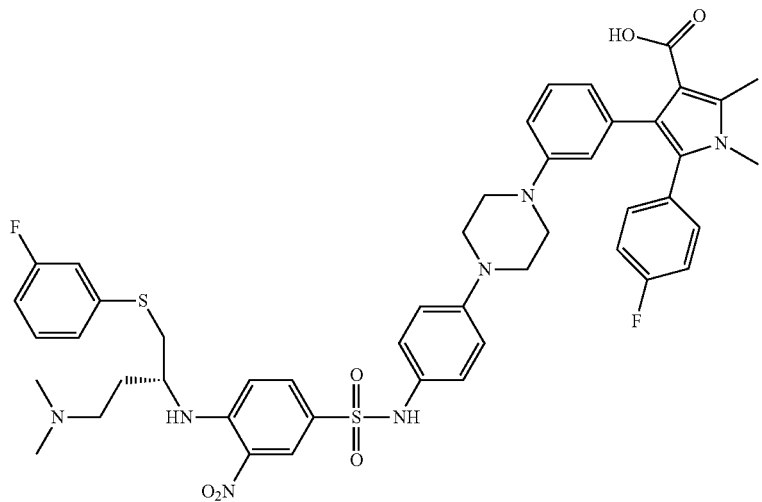 [SMILES: Cc1c(C(=O)O)c(-c2cccc(N3CCN(c4ccc(NS(=O)(=O)c5ccc(N[C@H](CCN(C)C)CSc6cccc(F)c6)c([N+](=O)[O-])c5)cc4)CC3)c2)c(-c2ccc(F)cc2)n1C] |

| Compound No. | |
|---|---|
| 44 | 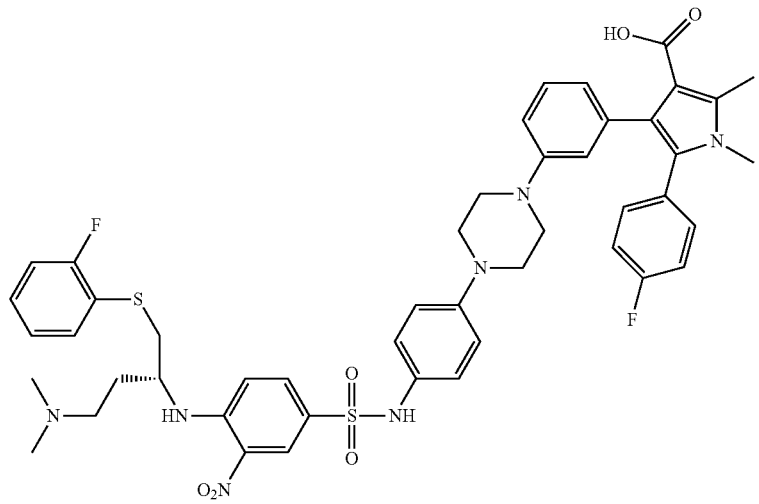 [SMILES: Cc1c(C(=O)O)c(-c2cccc(N3CCN(c4ccc(NS(=O)(=O)c5ccc(N[C@H](CCN(C)C)CSc6ccccc6F)c([N+](=O)[O-])c5)cc4)CC3)c2)c(-c2ccc(F)cc2)n1C] |
| 45 | 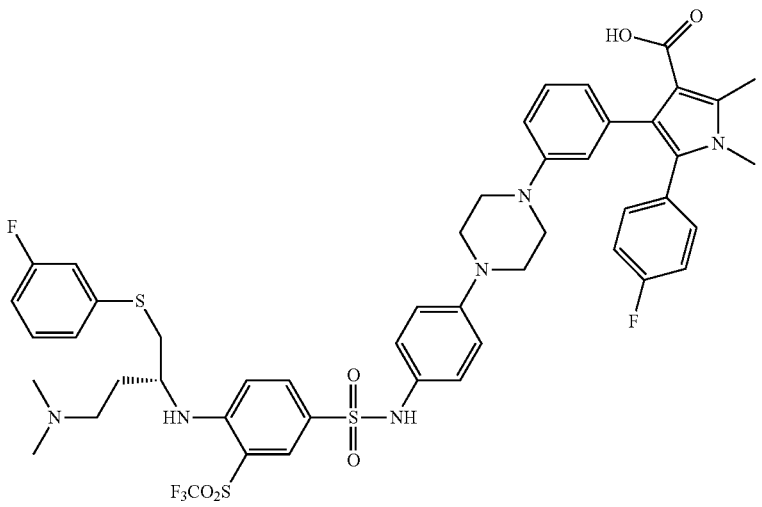 |
| 46 | 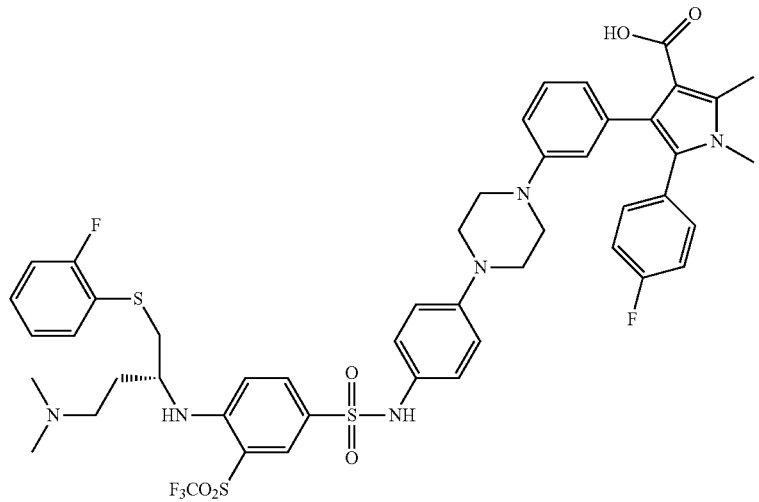 |

| Compound No. | |
|---|---|
| 47 | 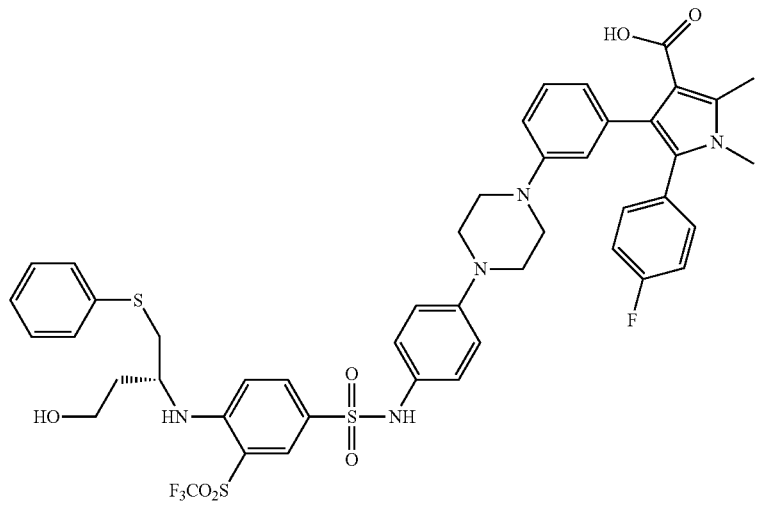 |
| 48 | 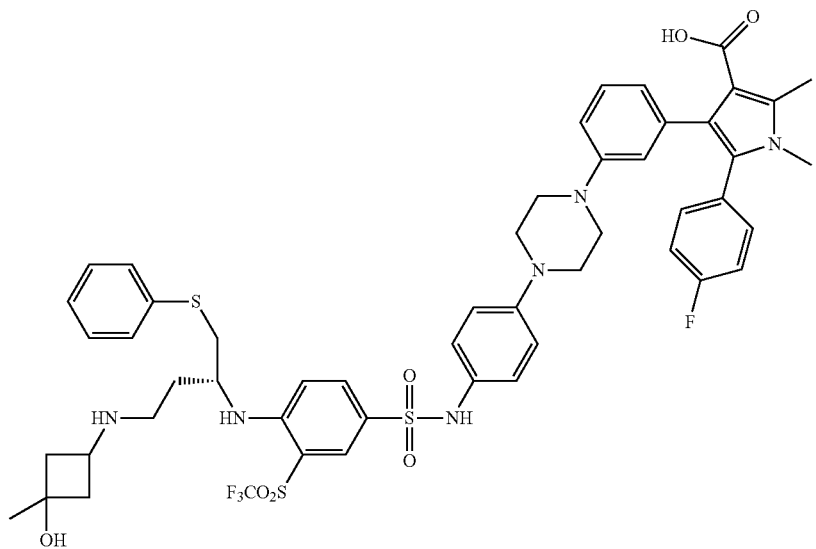 |
| 49 | 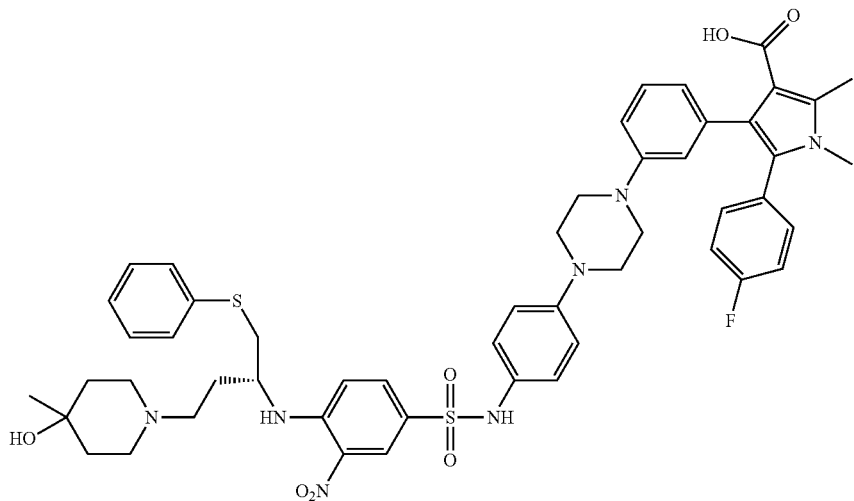 |

| Compound No. | |
|---|---|
| 50 | 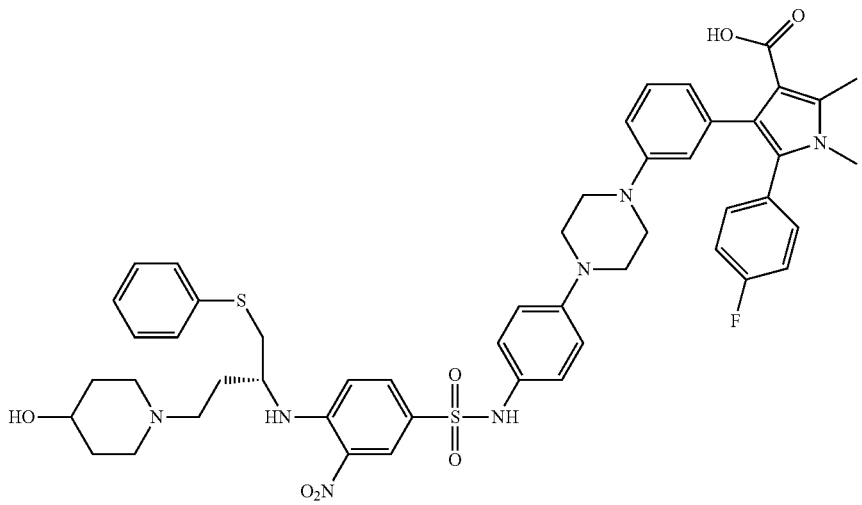 |
| 51 | 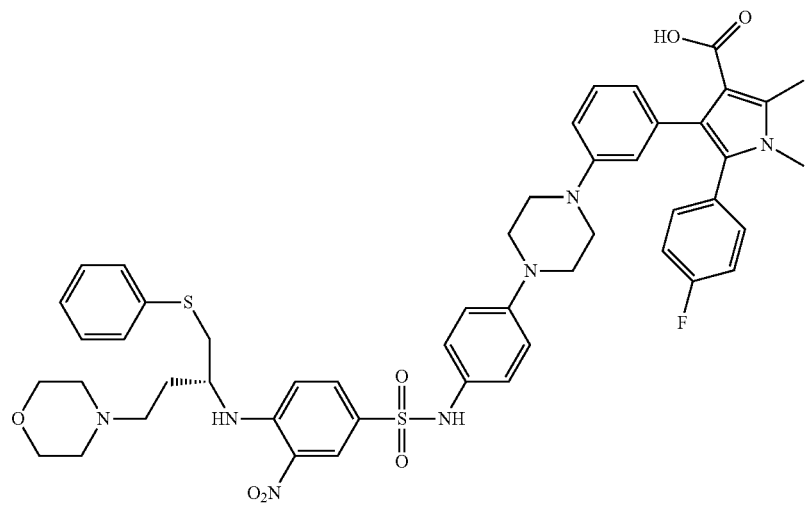 [SMILES: Cc1c(C(=O)O)c(-c2cccc(N3CCN(c4ccc(NS(=O)(=O)c5ccc(N[C@H](CCN6CCOCC6)CSc6ccccc6)c([N+](=O)[O-])c5)cc4)CC3)c2)c(-c2ccc(F)cc2)n1C] |
| 52 | 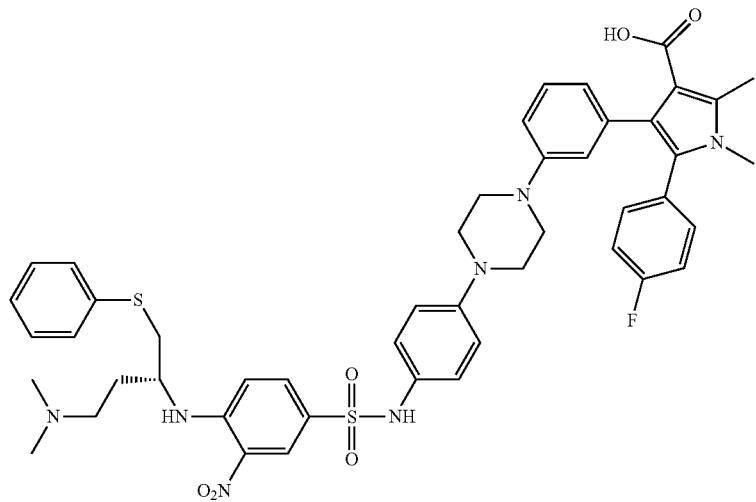 |

| Compound No. | |
|---|---|
| 53 | 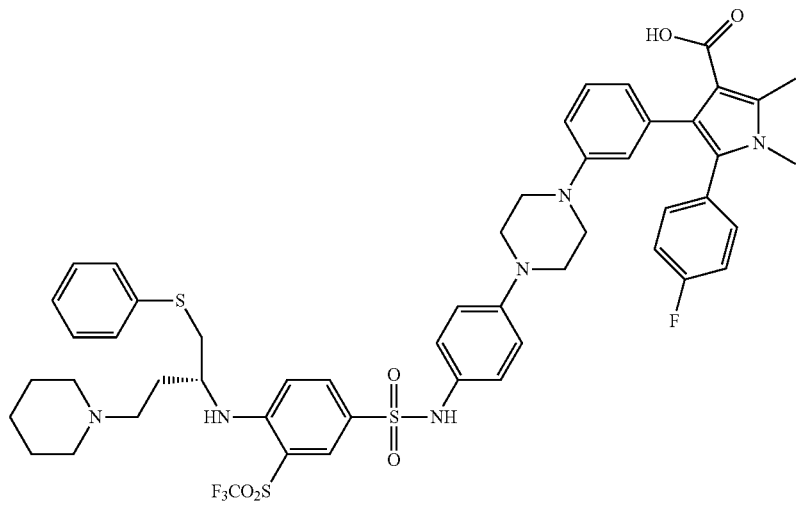 |
| 54 | 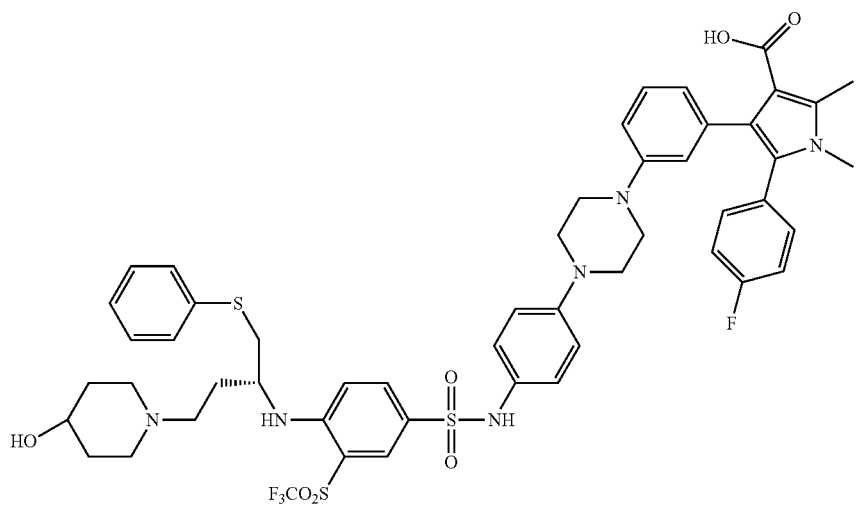 |
| 55 | 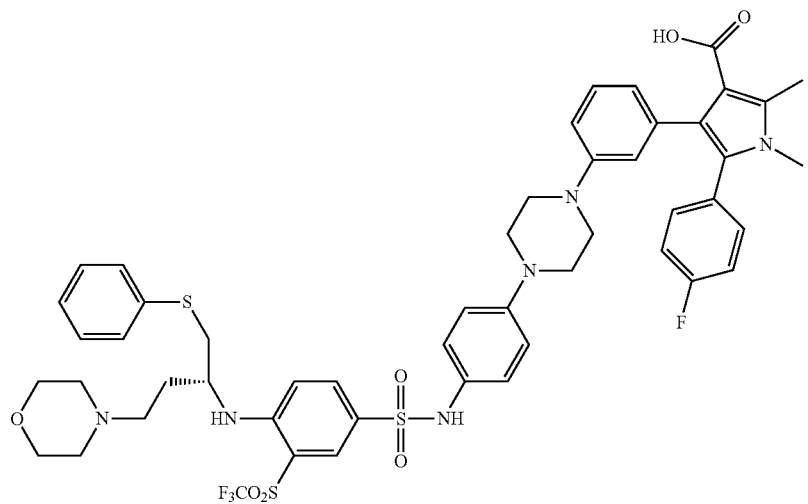 |

| Compound No. | |
|---|---|
| 56 | 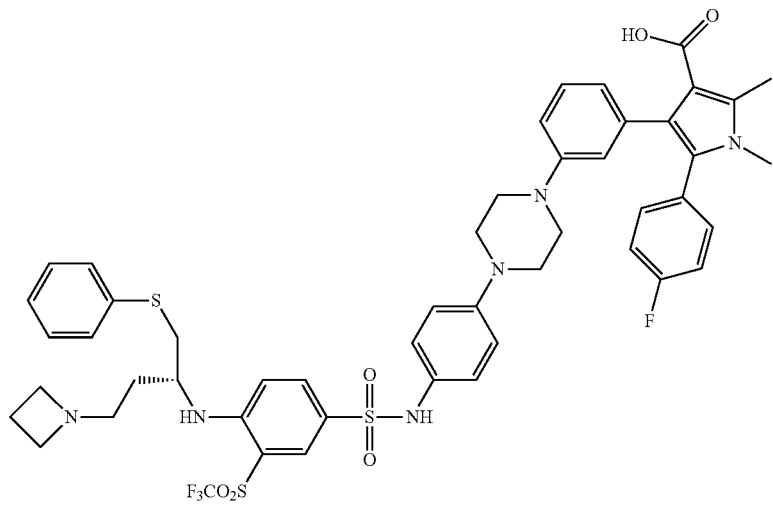 |
| 57 | 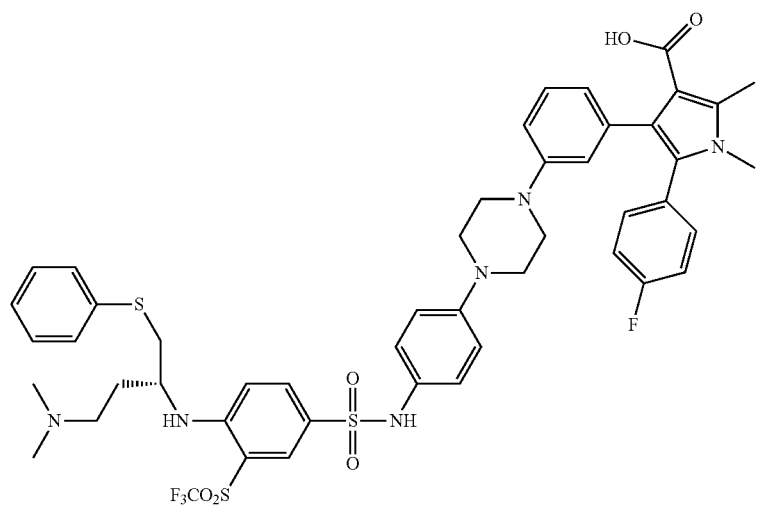 |
| 58 | 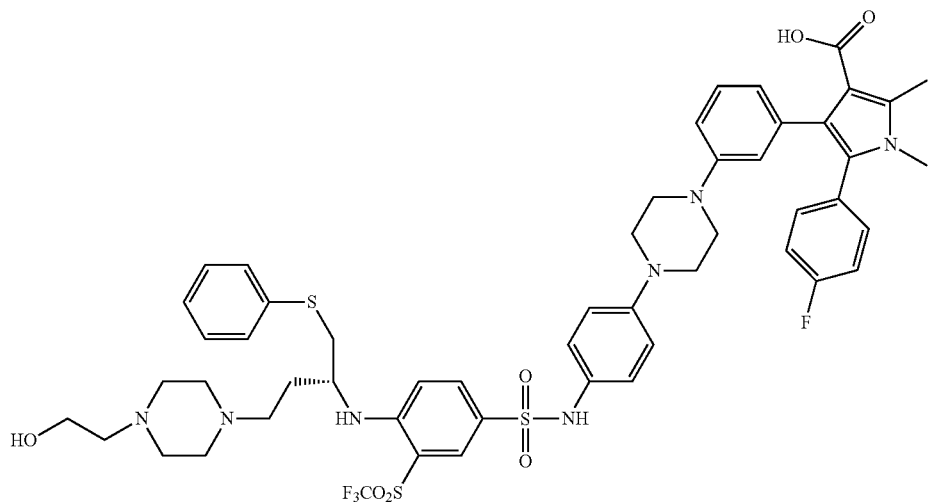 |

| Compound No. | |
|---|---|
| 59 | 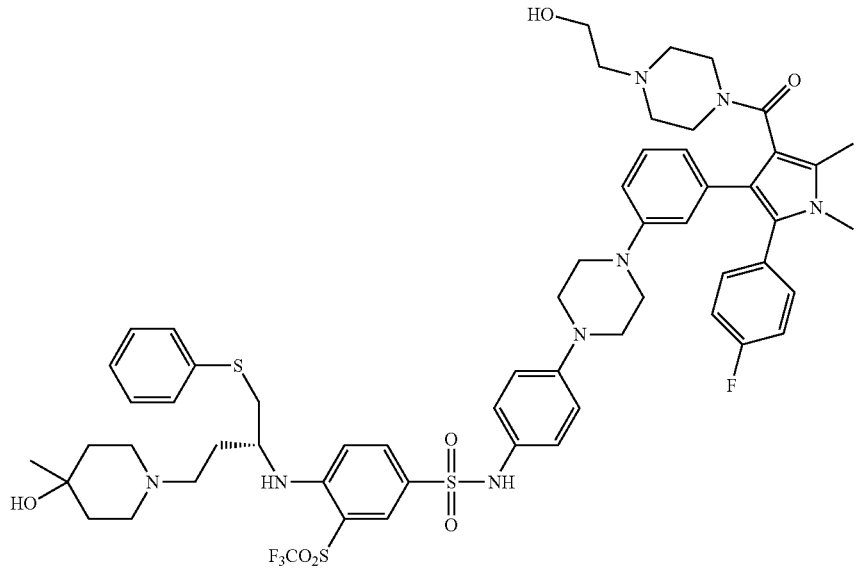 |
| 60 | 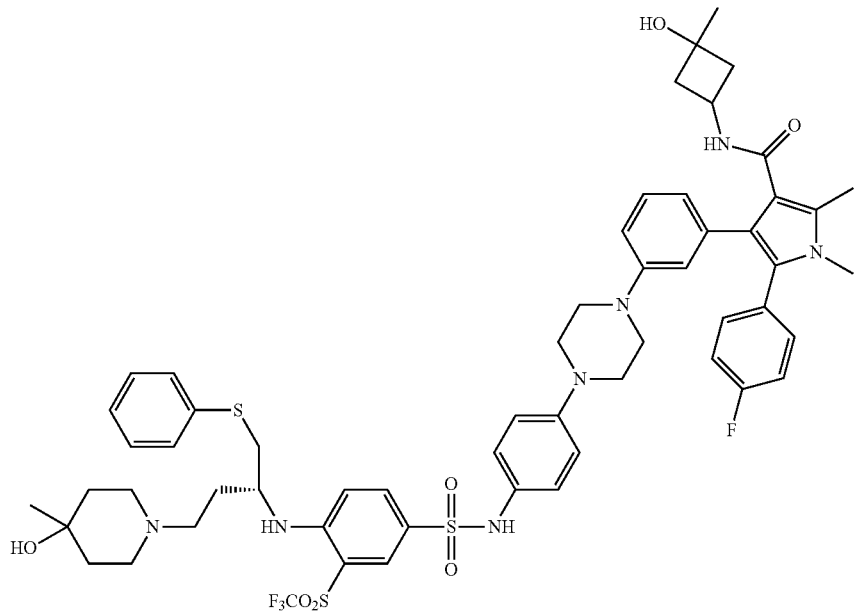 |

| Compound No. | |
|---|---|
| 61 | 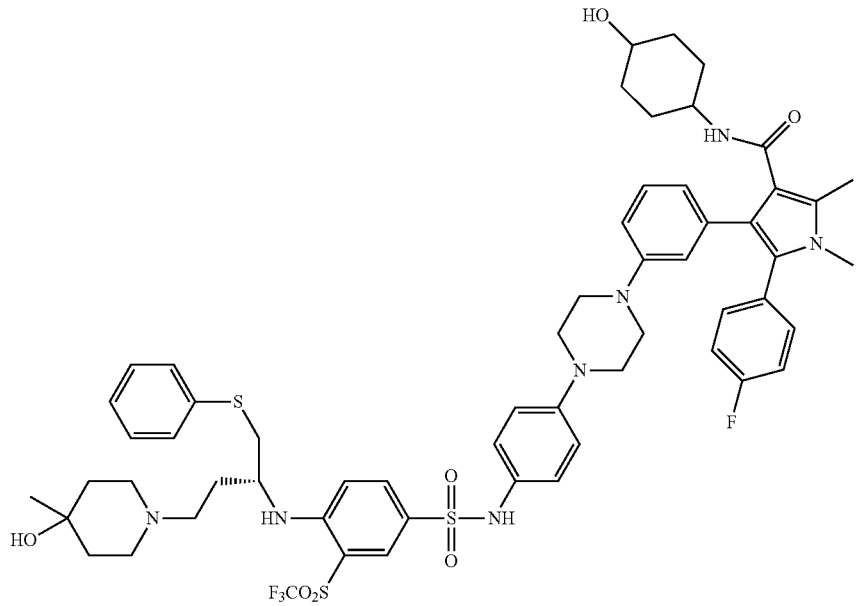 |
| 62 | 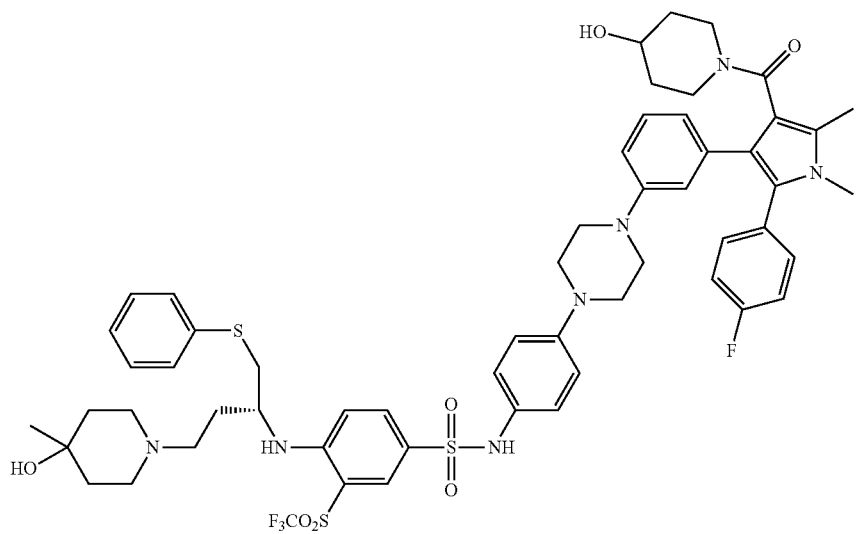 |

-continued
| Compound No. |
| --- |
63
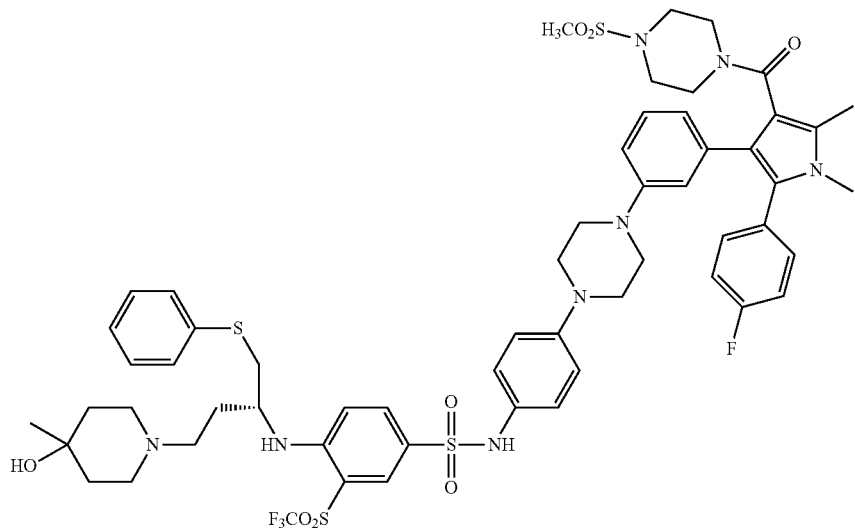
64
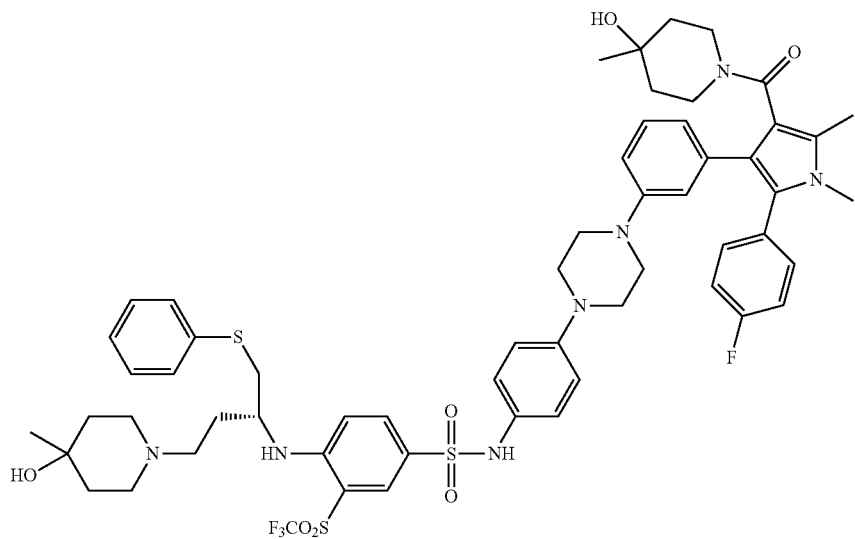
65
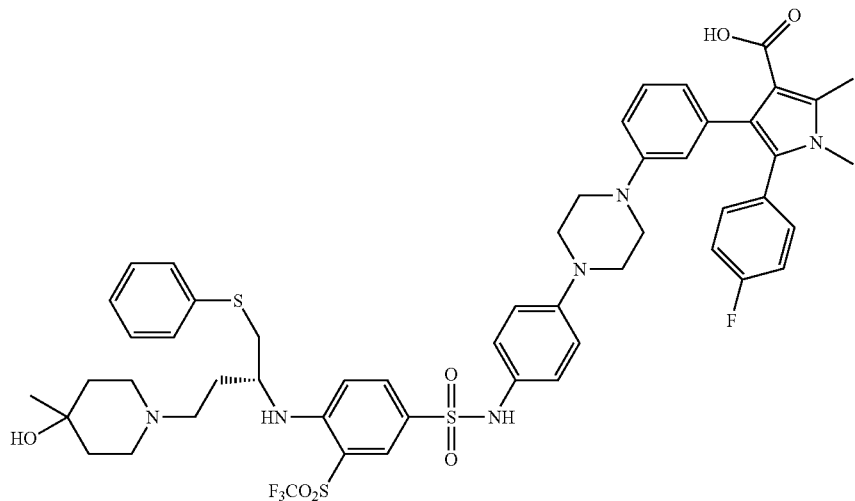

| Compound No. | |
|---|---|
| 66 | 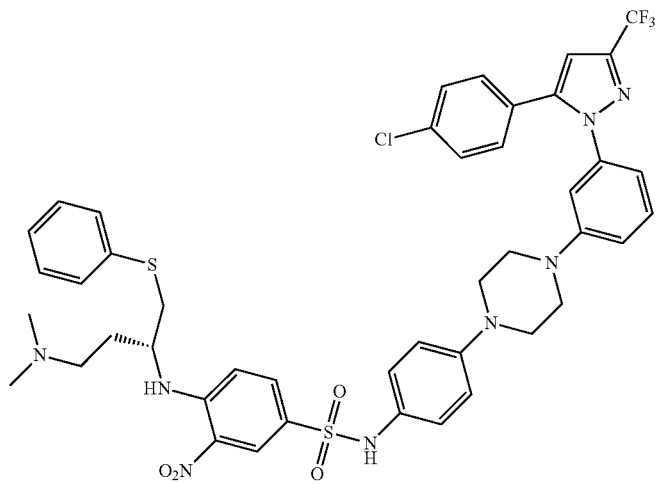 [SMILES: CN(C)CC[C@H](CSc1ccccc1)Nc1ccc(S(=O)(=O)Nc2ccc(N3CCN(c4cccc(-n5nc(C(F)(F)F)cc5-c5ccc(Cl)cc5)c4)CC3)cc2)cc1[N+](=O)[O-]] |
| 67 | 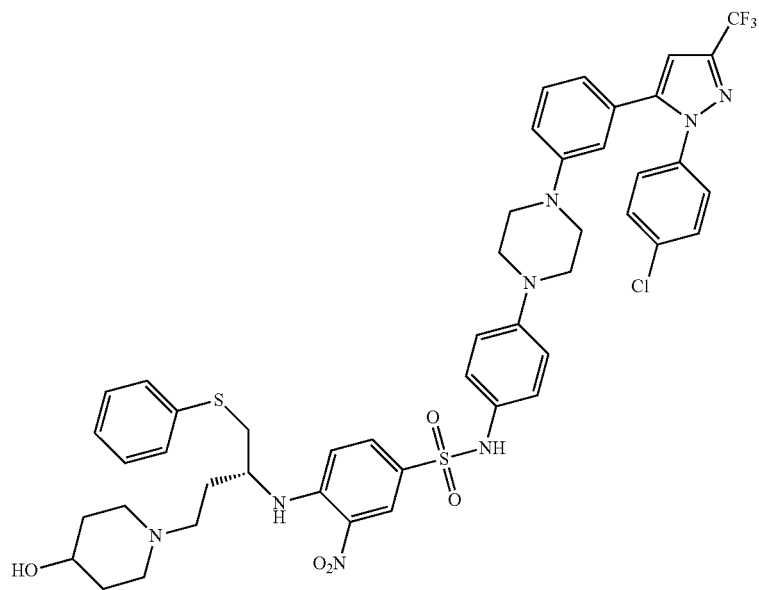 [SMILES: O=[N+]([O-])c1cc(S(=O)(=O)Nc2ccc(N3CCN(c4cccc(-c5cc(C(F)(F)F)nn5-c5ccc(Cl)cc5)c4)CC3)cc2)ccc1N[C@H](CCN1CCC(O)CC1)CSc1ccccc1] |

-continued
| Compound No. | |
|---|---|
| 68 | 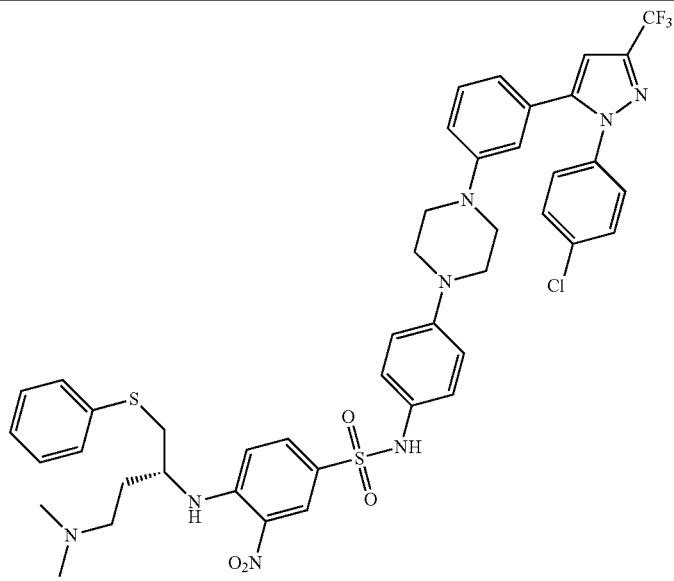 |
| 69 | 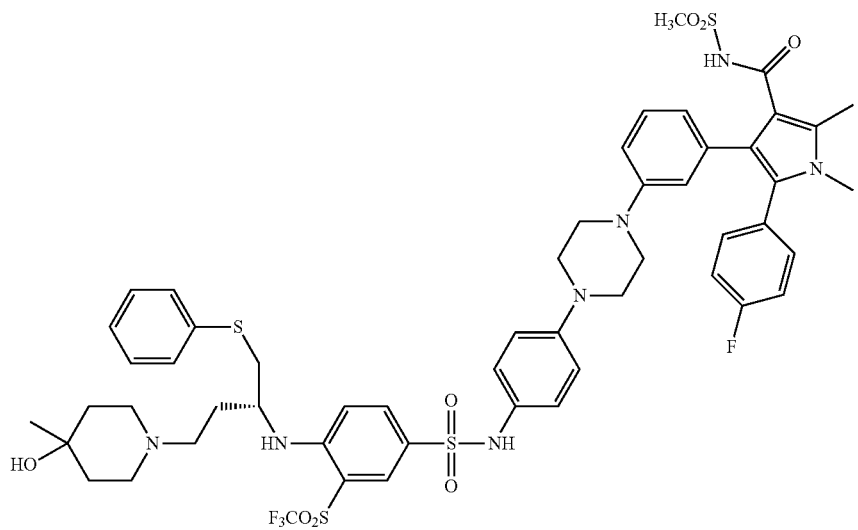 |
| 70 | 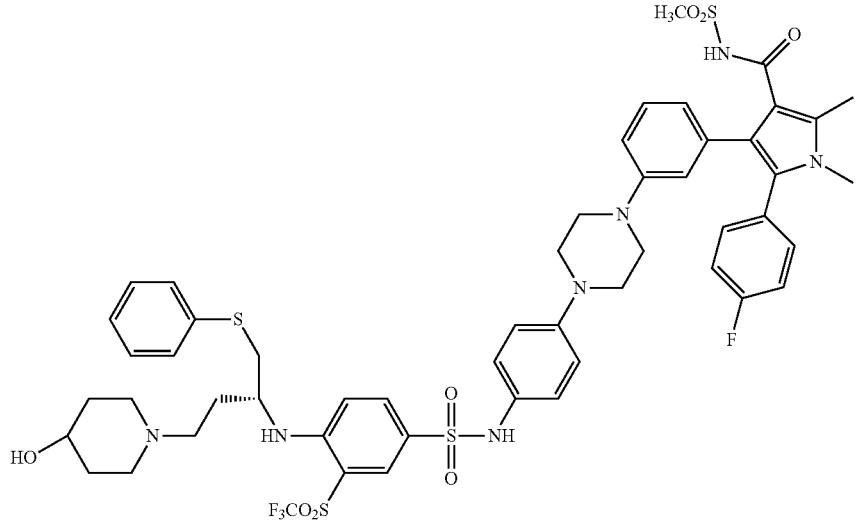 |

| Compound No. | |
|---|---|
| 71 | 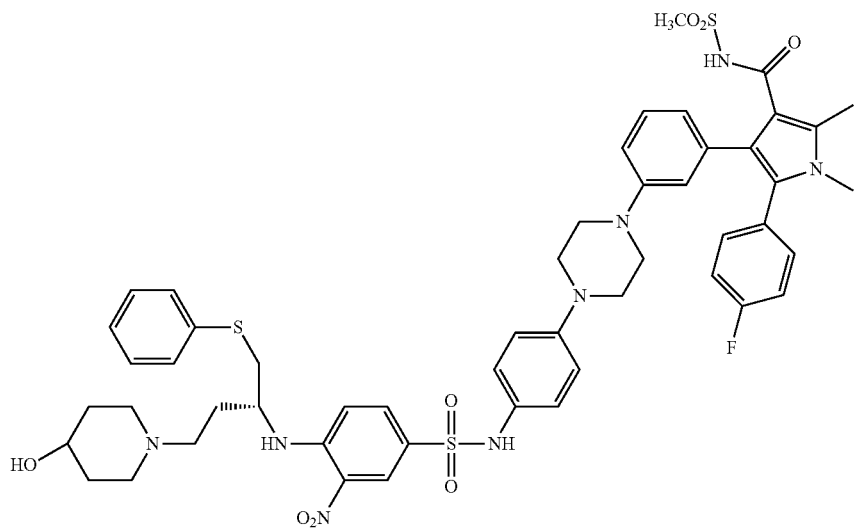 |
| 72 | 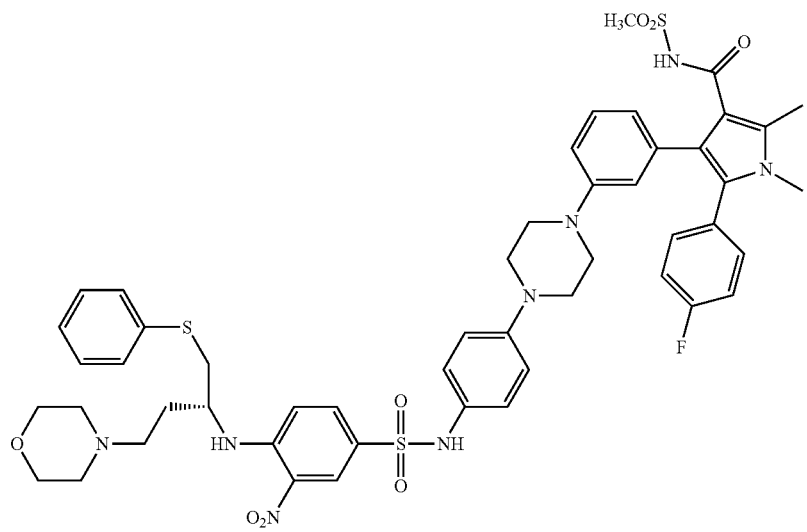 |
| 73 | 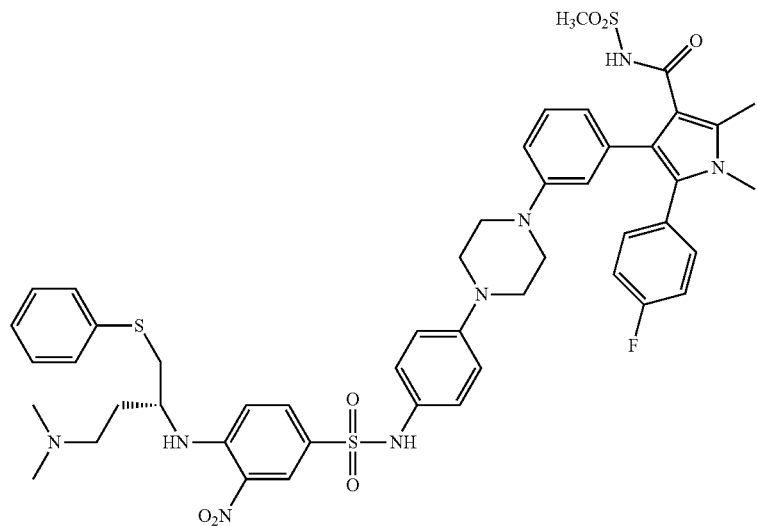 |

| Compound No. | |
|---|---|
| 74 | 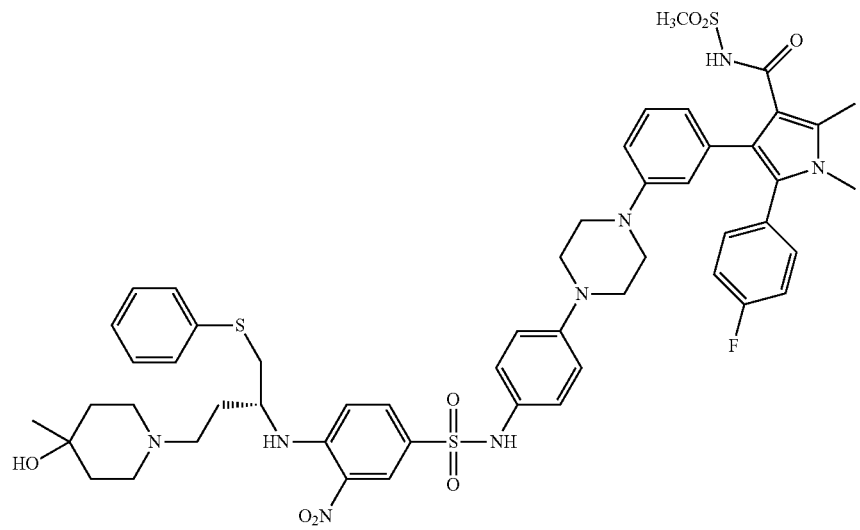 |
| 75 | 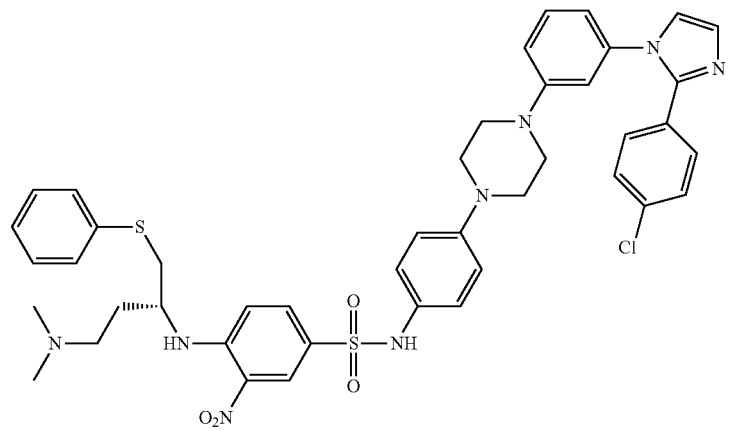 [SMILES: CN(C)CC[C@H](CSc1ccccc1)Nc1ccc(S(=O)(=O)Nc2ccc(N3CCN(c4cccc(-n5ccnc5-c5ccc(Cl)cc5)c4)CC3)cc2)cc1[N+](=O)[O-]] |
| 76 | 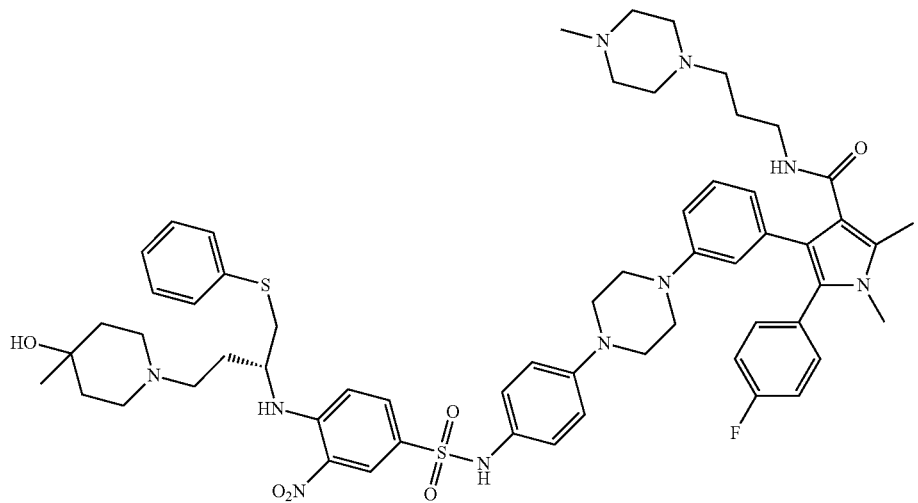 [SMILES: Cc1c(C(=O)NCCCN2CCN(C)CC2)c(-c2cccc(N3CCN(c4ccc(NS(=O)(=O)c5ccc(N[C@H](CCN6CCC(C)(O)CC6)CSc6ccccc6)c([N+](=O)[O-])c5)cc4)CC3)c2)c(-c2ccc(F)cc2)n1C] |

US 8,691,184 B2
| Compound No. |
| --- |
| 77 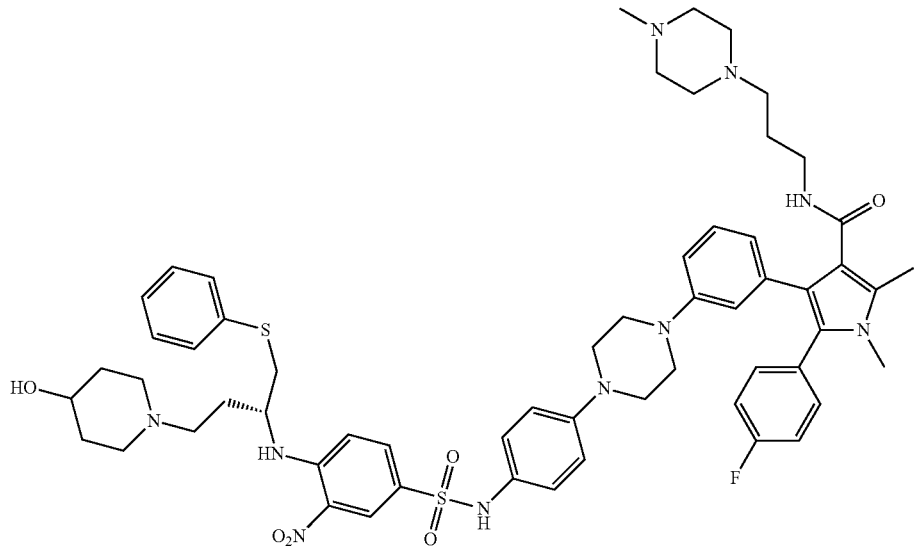 [SMILES: Cc1c(C(=O)NCCCN2CCN(C)CC2)c(-c2cccc(N3CCN(c4ccc(NS(=O)(=O)c5ccc(N[C@H](CCN6CCC(O)CC6)CSc6ccccc6)c([N+](=O)[O-])c5)cc4)CC3)c2)c(-c2ccc(F)cc2)n1C] |
| 78 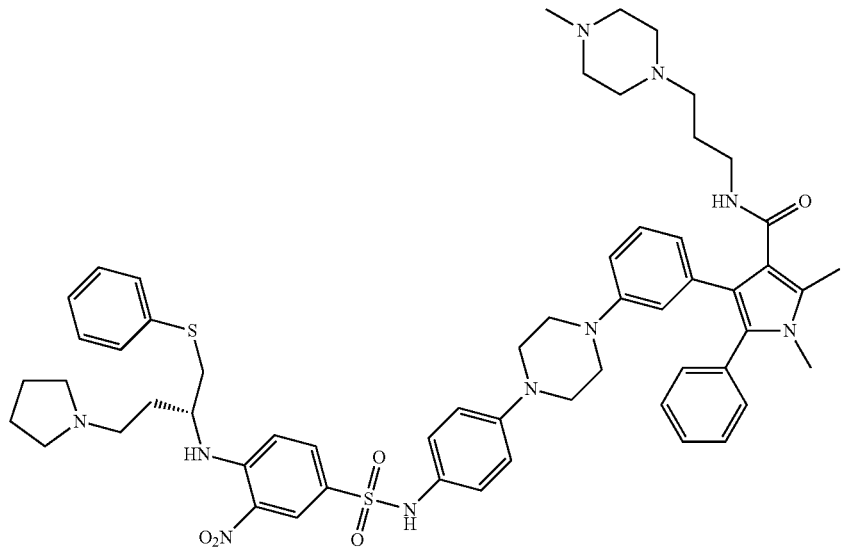 [SMILES: Cc1c(C(=O)NCCCN2CCN(C)CC2)c(-c2cccc(N3CCN(c4ccc(NS(=O)(=O)c5ccc(N[C@H](CCN6CCCC6)CSc6ccccc6)c([N+](=O)[O-])c5)cc4)CC3)c2)c(-c2ccccc2)n1C] |

| Compound No. | |
|---|---|
| 79 | 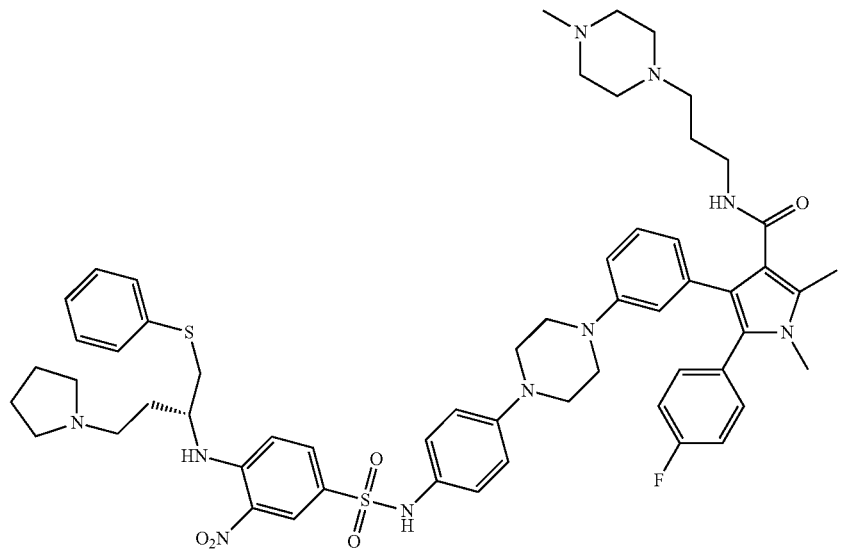 [SMILES: Cc1c(C(=O)NCCCN2CCN(C)CC2)c(-c2cccc(N3CCN(c4ccc(NS(=O)(=O)c5ccc(N[C@H](CCN6CCCC6)CSc6ccccc6)c([N+](=O)[O-])c5)cc4)CC3)c2)c(-c2ccc(F)cc2)n1C] |
| 80 | 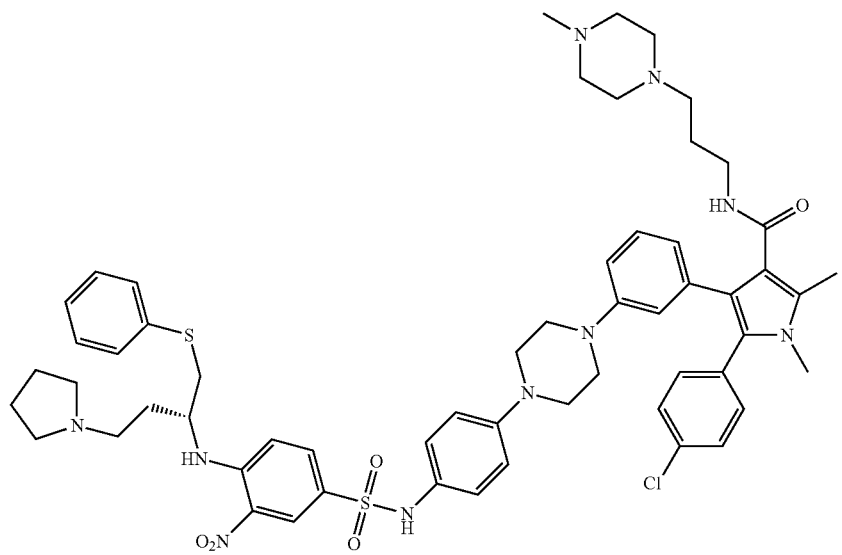 |
| 81 | 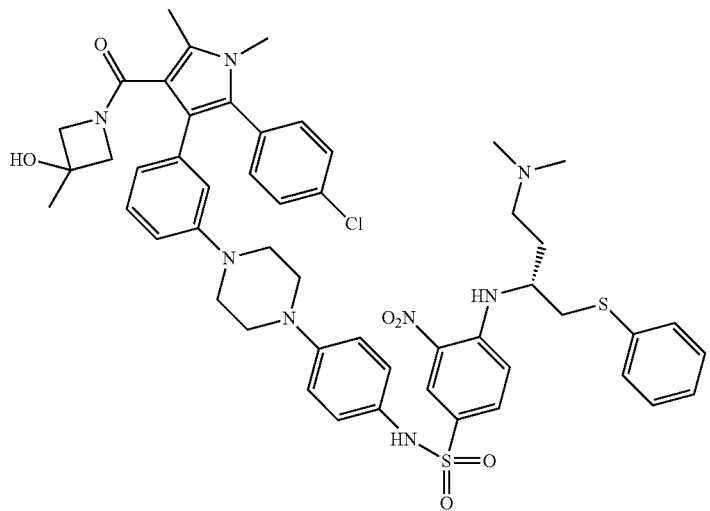 [SMILES: Cc1c(C(=O)N2CC(C)(O)C2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |

| Compound No. | |
|---|---|
| 82 | 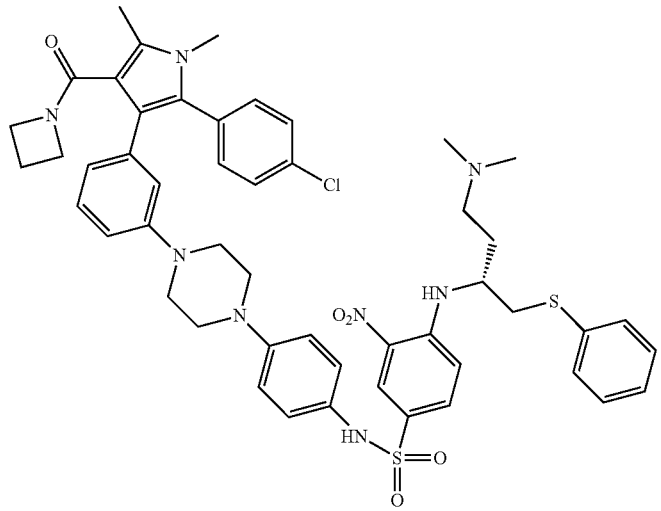 [SMILES: Cc1c(C(=O)N2CCC2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |
| 83 | 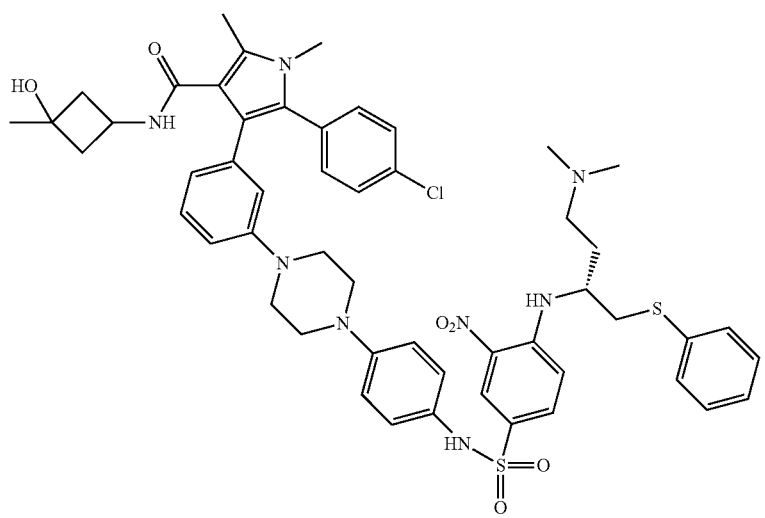 [SMILES: Cc1c(C(=O)NC2CC(C)(O)C2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |
| 84 | 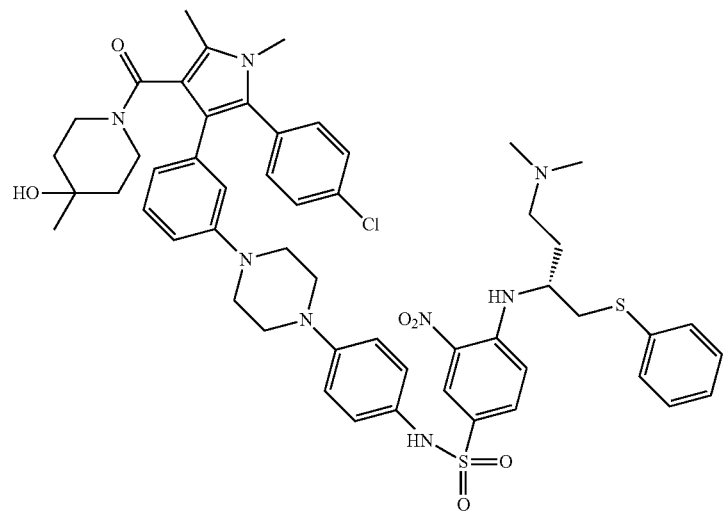 [SMILES: Cc1c(C(=O)N2CCC(C)(O)CC2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |

| Compound No. | |
|---|---|
| 85 | 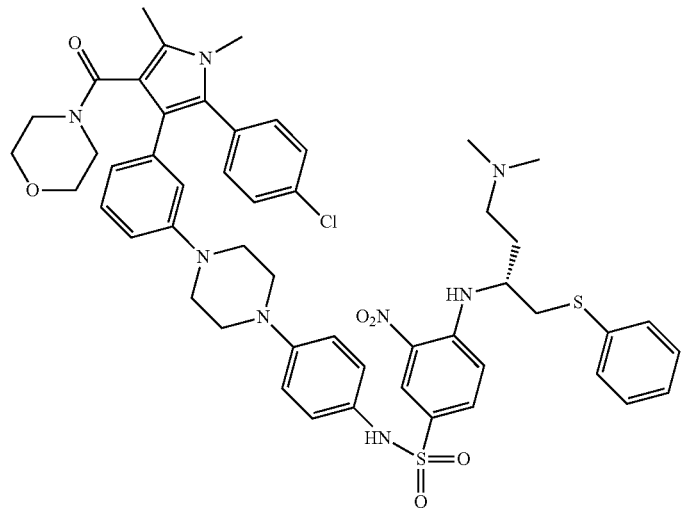 [SMILES: Cc1c(C(=O)N2CCOCC2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |
| 86 | 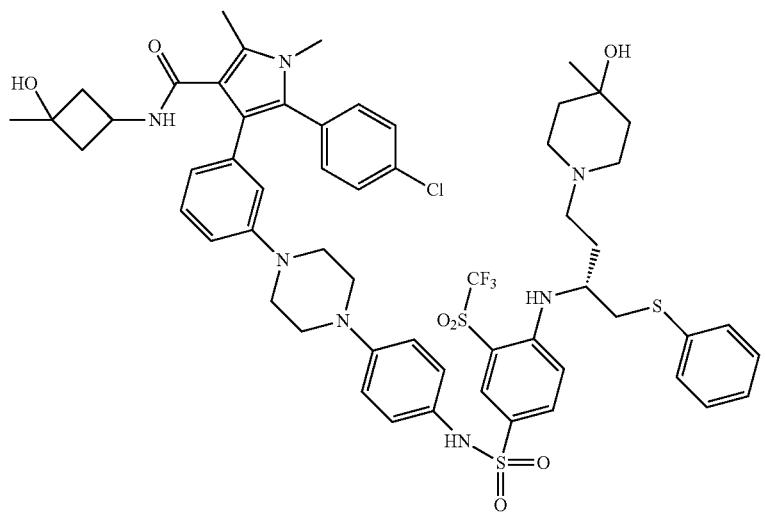 [SMILES: Cc1c(C(=O)NC2CC(C)(O)C2)c(-c2cccc(N3CCN(c4ccc(NS(=O)(=O)c5ccc(N[C@H](CCN6CCC(C)(O)CC6)CSc6ccccc6)c(S(=O)(=O)C(F)(F)F)c5)cc4)CC3)c2)c(-c2ccc(Cl)cc2)n1C] |
| 87 | 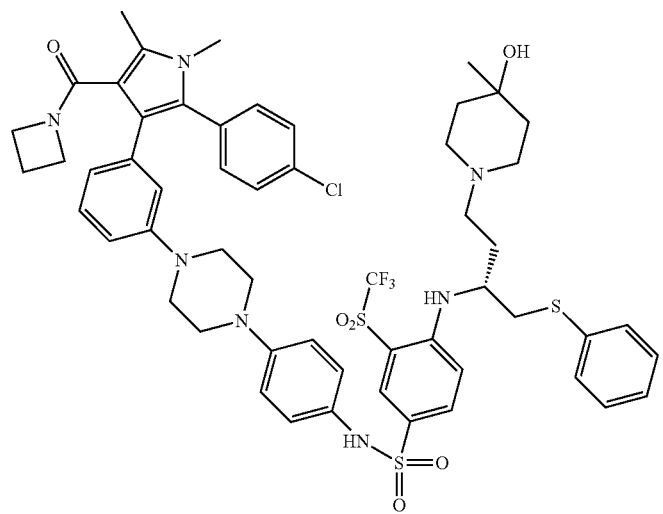 [SMILES: Cc1c(C(=O)N2CCC2)c(-c2cccc(N3CCN(c4ccc(NS(=O)(=O)c5ccc(N[C@H](CCN6CCC(C)(O)CC6)CSc6ccccc6)c(S(=O)(=O)C(F)(F)F)c5)cc4)CC3)c2)c(-c2ccc(Cl)cc2)n1C] |

| Compound No. | |
|---|---|
| 88 | 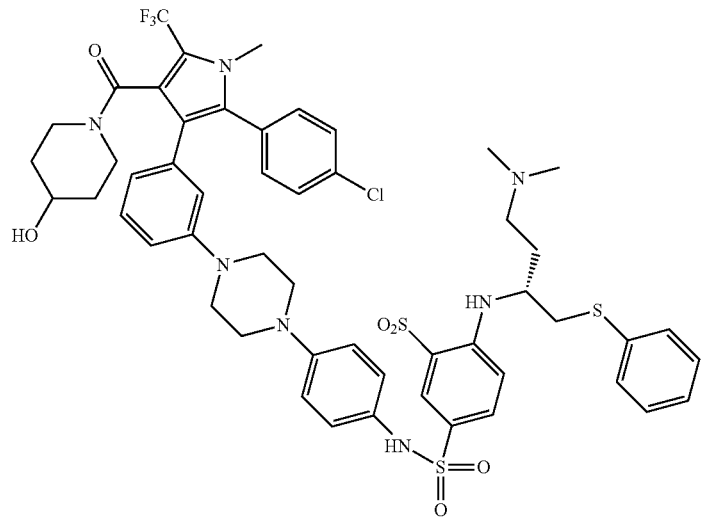 |
| 89 | 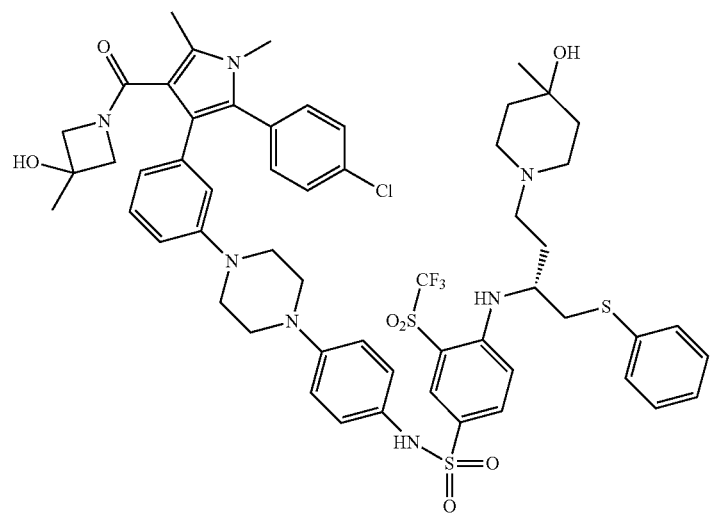 [SMILES: Cc1c(C(=O)N2CC(C)(O)C2)c(-c2cccc(N3CCN(c4ccc(NS(=O)(=O)c5ccc(N[C@H](CCN6CCC(C)(O)CC6)CSc6ccccc6)c(S(=O)(=O)C(F)(F)F)c5)cc4)CC3)c2)c(-c2ccc(Cl)cc2)n1C] |
| 90 | 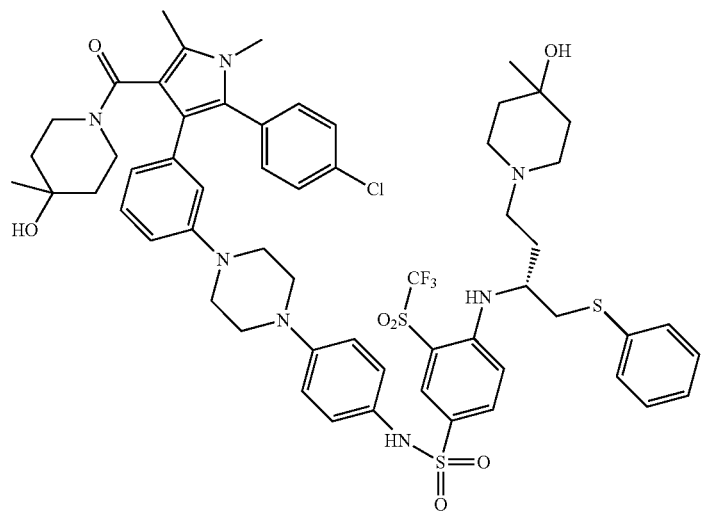 [SMILES: Cc1c(C(=O)N2CCC(C)(O)CC2)c(-c2cccc(N3CCN(c4ccc(NS(=O)(=O)c5ccc(N[C@H](CCN6CCC(C)(O)CC6)CSc6ccccc6)c(S(=O)(=O)C(F)(F)F)c5)cc4)CC3)c2)c(-c2ccc(Cl)cc2)n1C] |

| Compound No. | |
|---|---|
| 91 | 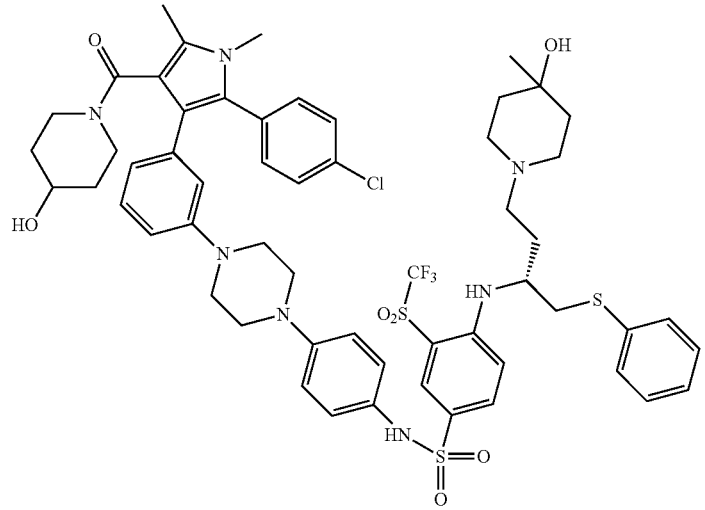 [SMILES: Cc1c(C(=O)N2CCC(O)CC2)c(-c2cccc(N3CCN(c4ccc(NS(=O)(=O)c5ccc(N[C@H](CCN6CCC(C)(O)CC6)CSc6ccccc6)c(S(=O)(=O)C(F)(F)F)c5)cc4)CC3)c2)c(-c2ccc(Cl)cc2)n1C] |
| 92 | 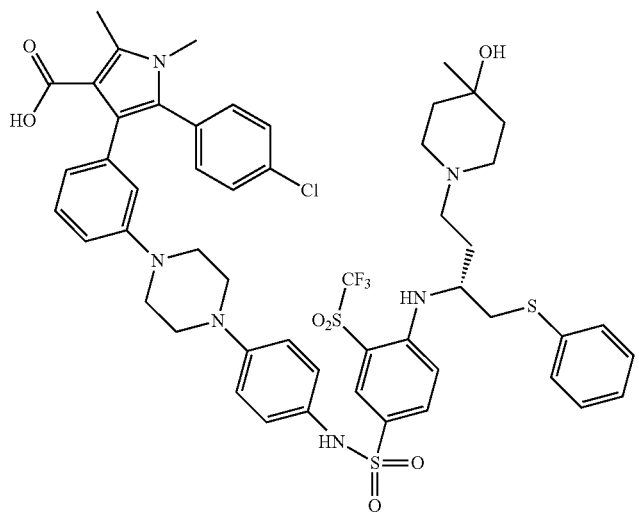 [SMILES: Cc1c(C(=O)O)c(-c2cccc(N3CCN(c4ccc(NS(=O)(=O)c5ccc(N[C@H](CCN6CCC(C)(O)CC6)CSc6ccccc6)c(S(=O)(=O)C(F)(F)F)c5)cc4)CC3)c2)c(-c2ccc(Cl)cc2)n1C] |
| 93 | 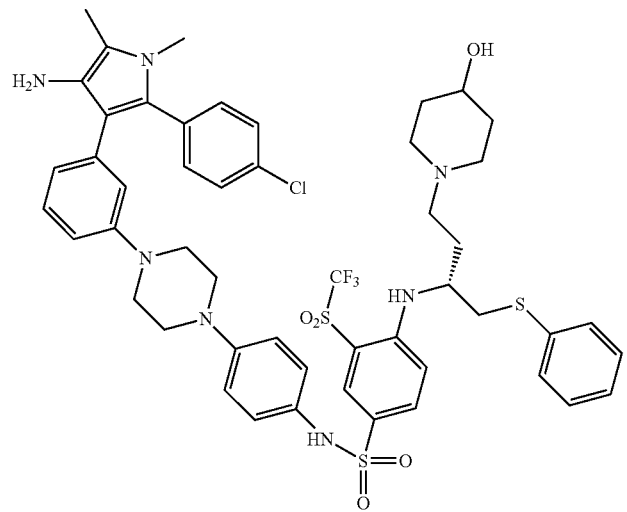 [SMILES: Cc1c(N)c(-c2cccc(N3CCN(c4ccc(NS(=O)(=O)c5ccc(N[C@H](CCN6CCC(O)CC6)CSc6ccccc6)c(S(=O)(=O)C(F)(F)F)c5)cc4)CC3)c2)c(-c2ccc(Cl)cc2)n1C] |

| Compound No. | |
|---|---|
| 94 | 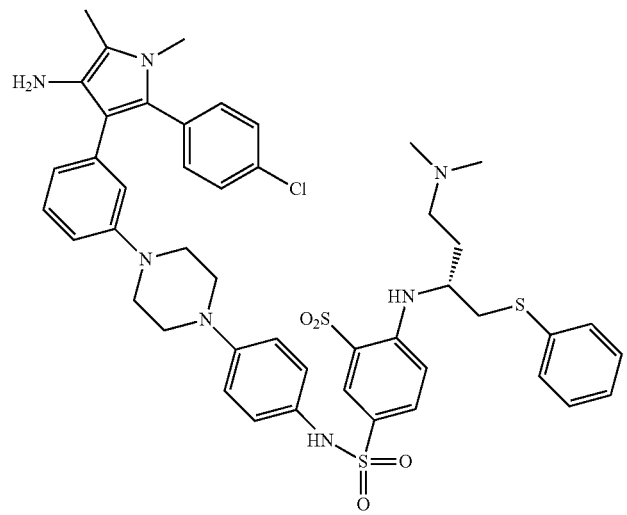 |
| 95 | 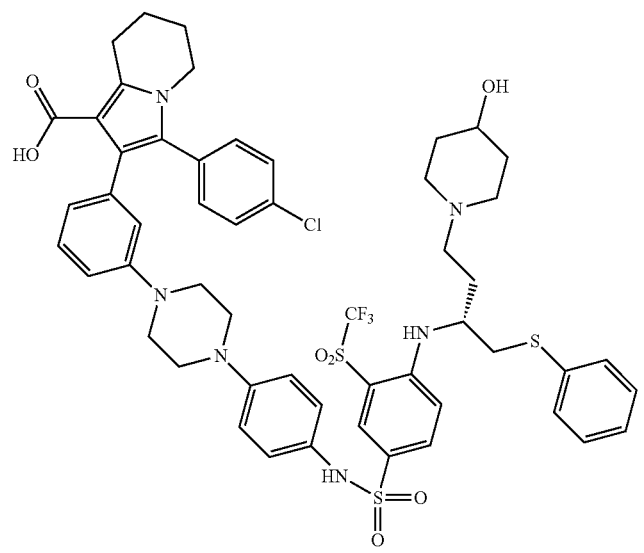 [SMILES: O=C(O)c1c(-c2cccc(N3CCN(c4ccc(NS(=O)(=O)c5ccc(N[C@H](CCN6CCC(O)CC6)CSc6ccccc6)c(S(=O)(=O)C(F)(F)F)c5)cc4)CC3)c2)c(-c2ccc(Cl)cc2)n2c1CCCC2] |
| 96 | 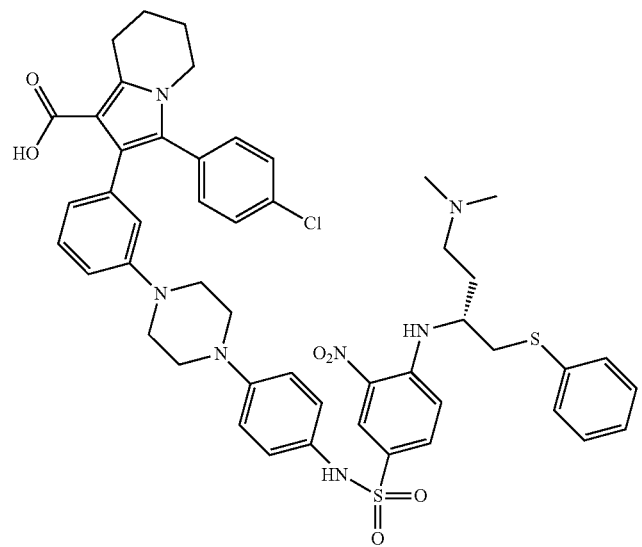 [SMILES: CN(C)CC[C@H](CSc1ccccc1)Nc1ccc(S(=O)(=O)Nc2ccc(N3CCN(c4cccc(-c5c(C(=O)O)c6n(c5-c5ccc(Cl)cc5)CCCC6)c4)CC3)cc2)cc1[N+](=O)[O-]] |

| Compound No. | |
|---|---|
| 97 | 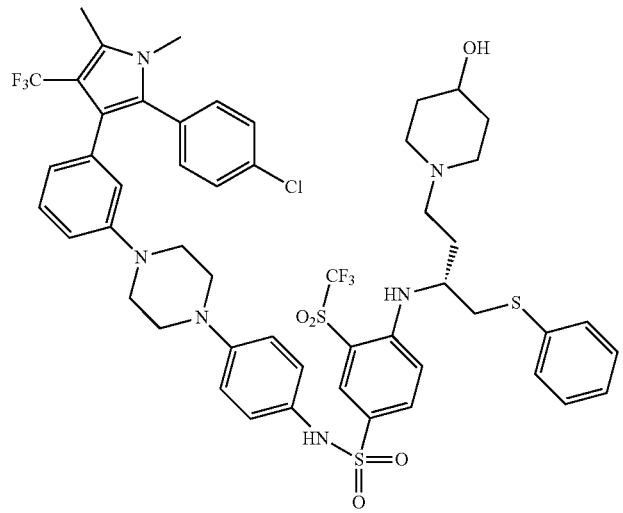 [SMILES: Cc1c(C(F)(F)F)c(-c2cccc(N3CCN(c4ccc(NS(=O)(=O)c5ccc(N[C@H](CCN6CCC(O)CC6)CSc6ccccc6)c(S(=O)(=O)C(F)(F)F)c5)cc4)CC3)c2)c(-c2ccc(Cl)cc2)n1C] |
| 98 | 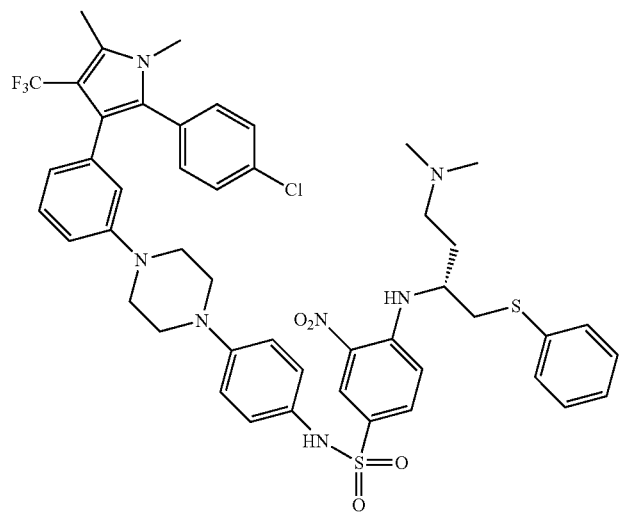 [SMILES: Cc1c(C(F)(F)F)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |
| 99 | 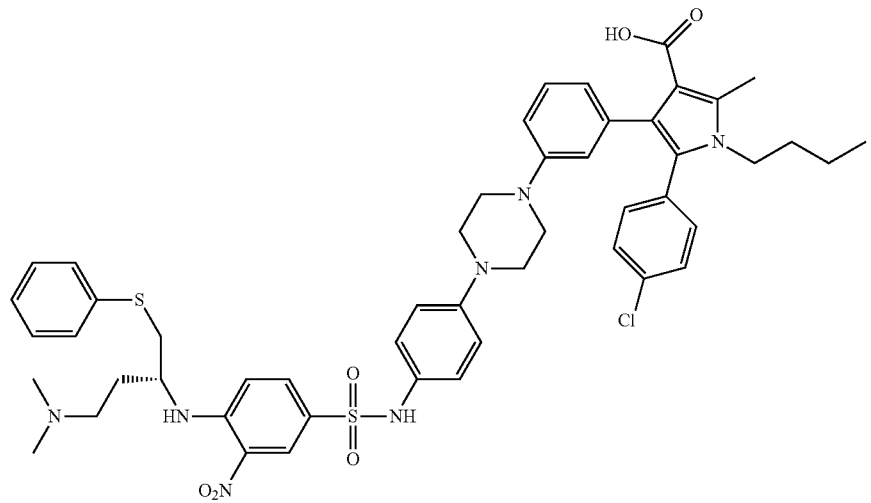 [SMILES: CCCCn1c(C)c(C(=O)O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c1-c1ccc(Cl)cc1] |

| Compound No. | |
|---|---|
| 100 | 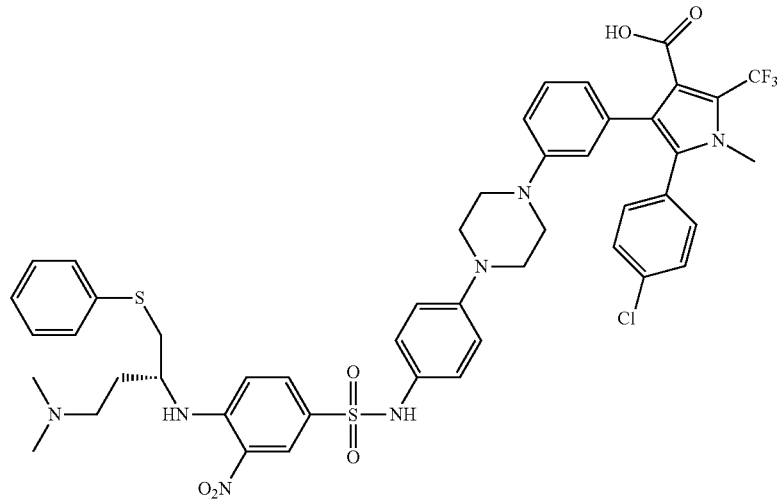 [SMILES: CN(C)CC[C@H](CSc1ccccc1)Nc1ccc(S(=O)(=O)Nc2ccc(N3CCN(c4cccc(-c5c(C(=O)O)c(C(F)(F)F)n(C)c5-c5ccc(Cl)cc5)c4)CC3)cc2)cc1[N+](=O)[O-]] |
| 101 | 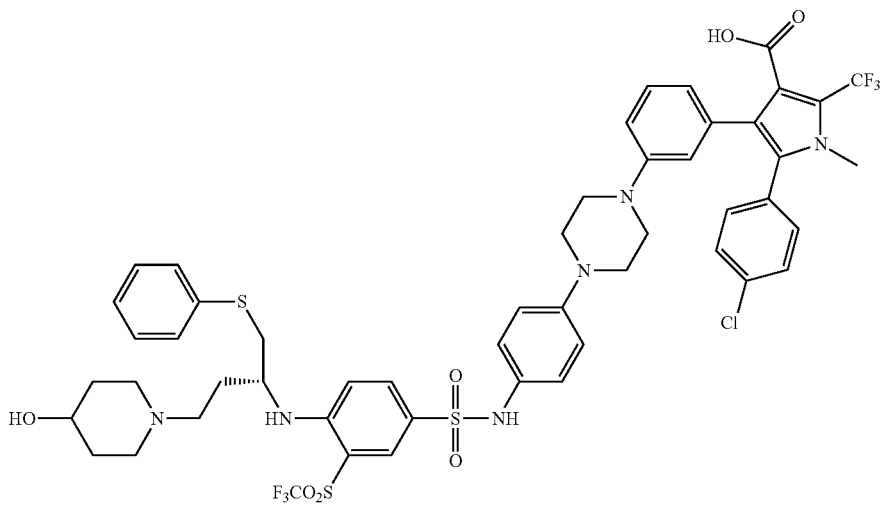 |
| 102 | 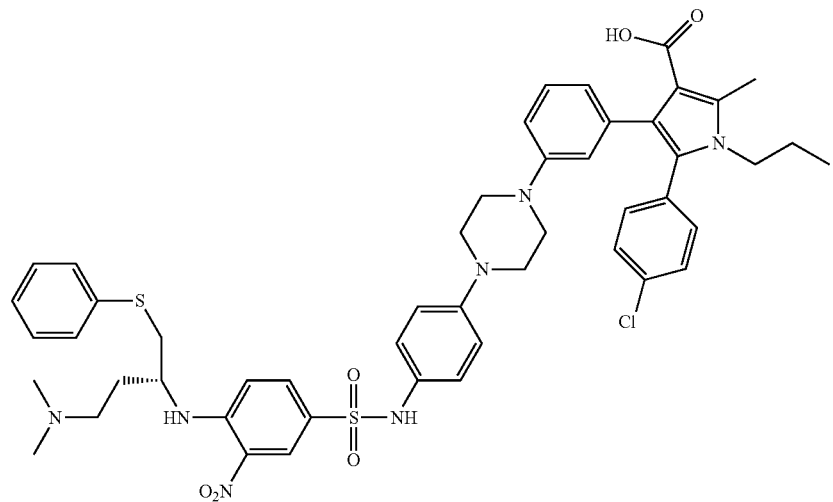 [SMILES: CCCn1c(C)c(C(=O)O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c1-c1ccc(Cl)cc1] |

| Compound No. | |
|---|---|
| 103 | 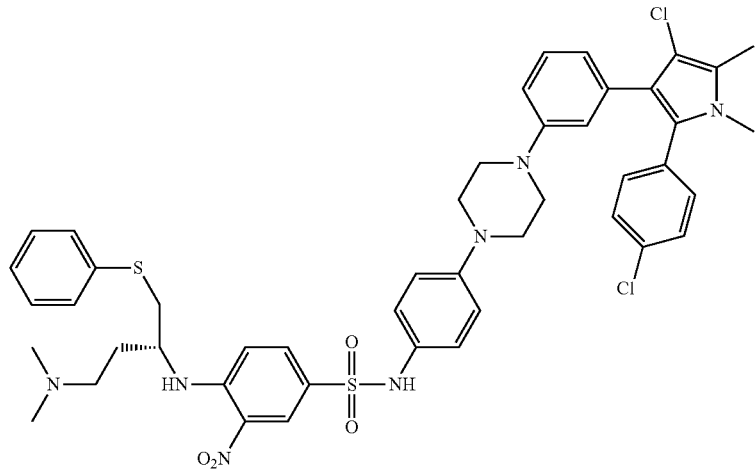 [SMILES: Cc1c(Cl)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |
| 104 | 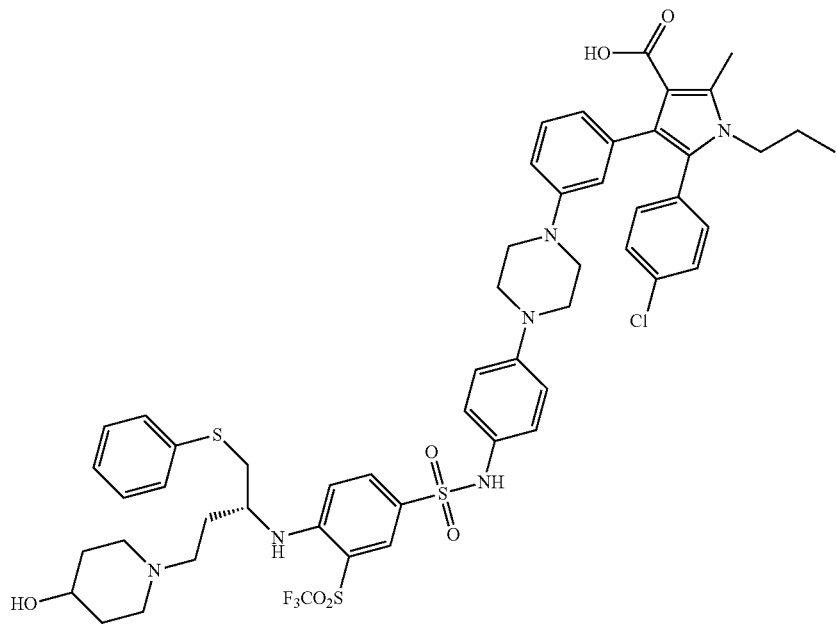 |

| Compound No. | |
|---|---|
| 105 | 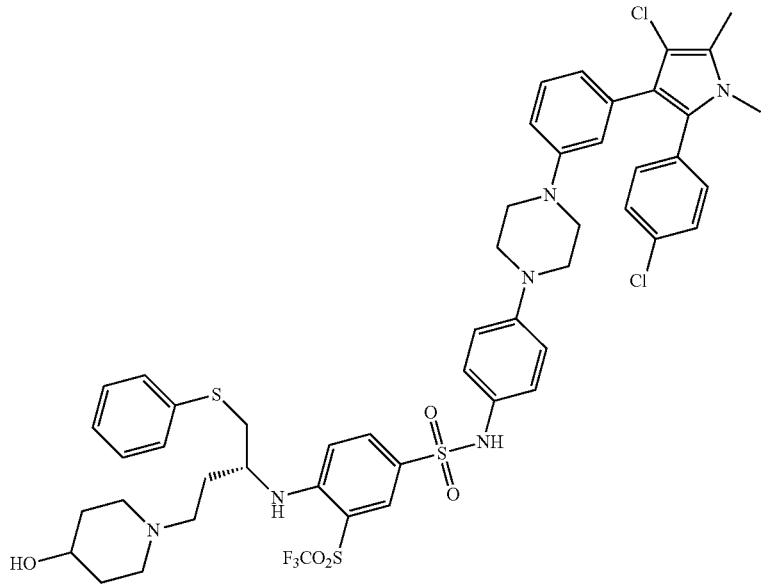 |
| 106 | 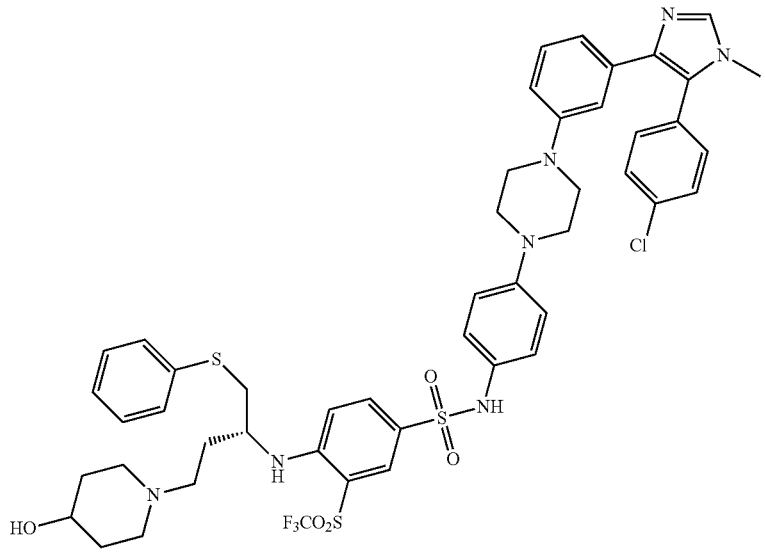 |

| Compound No. | |
|---|---|
| 107 | 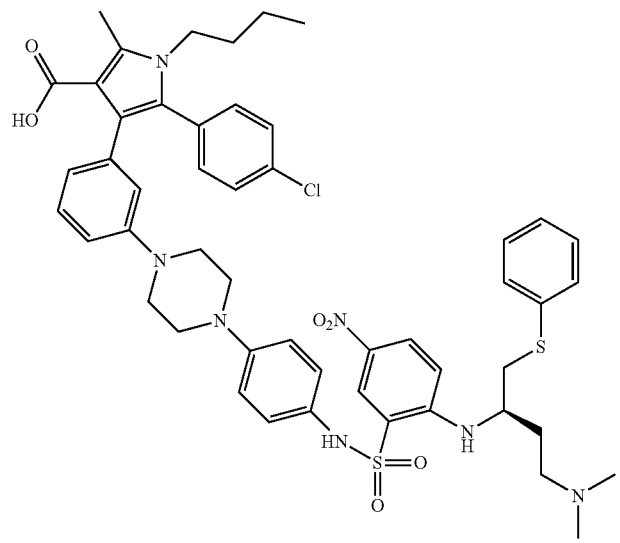 [SMILES: CCCCn1c(C)c(C(=O)O)c(-c2cccc(N3CCN(c4ccc(NS(=O)(=O)c5cc([N+](=O)[O-])ccc5N[C@H](CCN(C)C)CSc5ccccc5)cc4)CC3)c2)c1-c1ccc(Cl)cc1] |
| 108 | 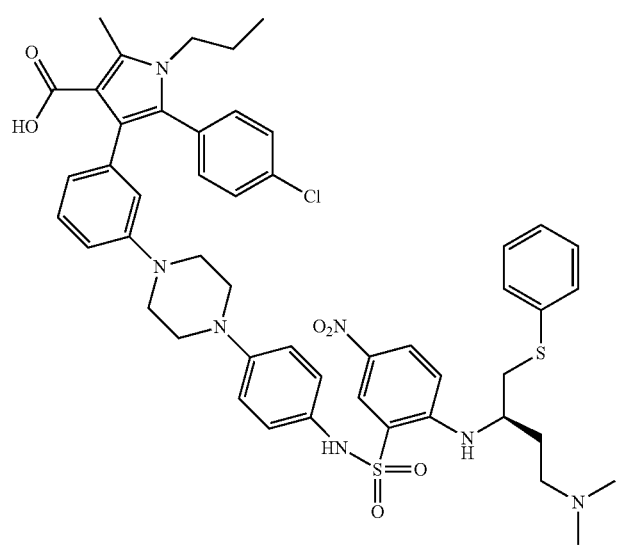 [SMILES: CCCn1c(C)c(C(=O)O)c(-c2cccc(N3CCN(c4ccc(NS(=O)(=O)c5cc([N+](=O)[O-])ccc5N[C@H](CCN(C)C)CSc5ccccc5)cc4)CC3)c2)c1-c1ccc(Cl)cc1] |
| 109 | 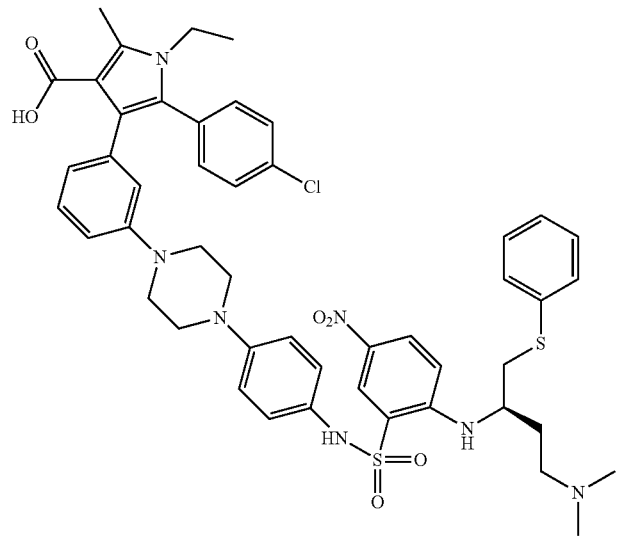 [SMILES: CCn1c(C)c(C(=O)O)c(-c2cccc(N3CCN(c4ccc(NS(=O)(=O)c5cc([N+](=O)[O-])ccc5N[C@H](CCN(C)C)CSc5ccccc5)cc4)CC3)c2)c1-c1ccc(Cl)cc1] |

| Compound No. | |
|---|---|
| 110 | 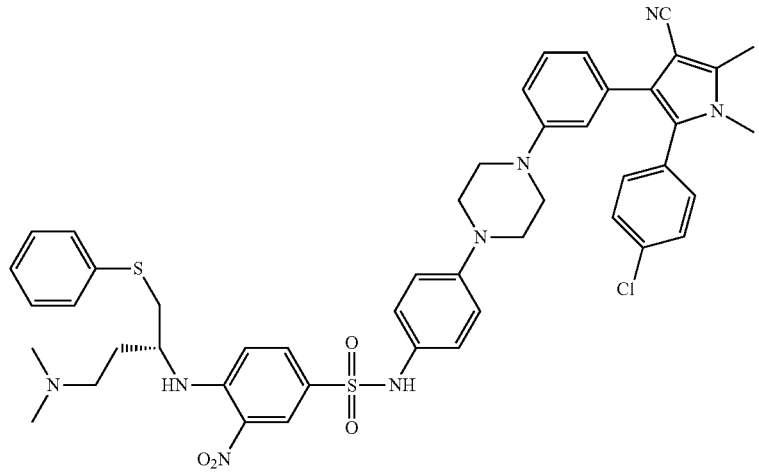 |
| 111 | 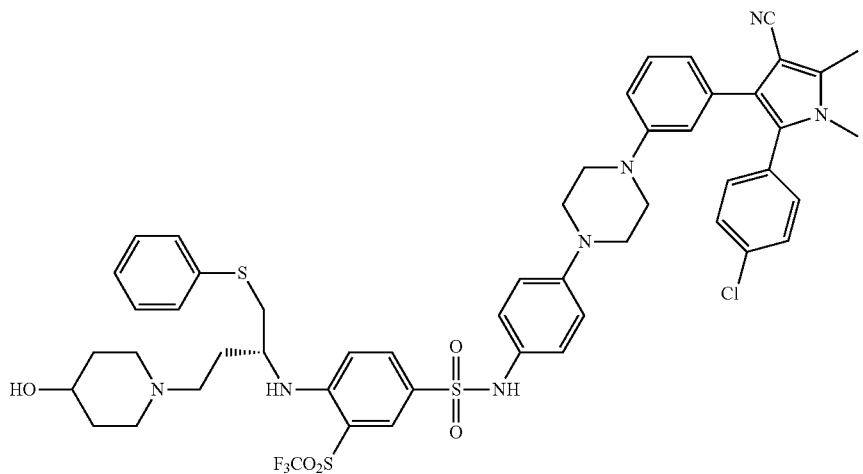 |
| 112 | 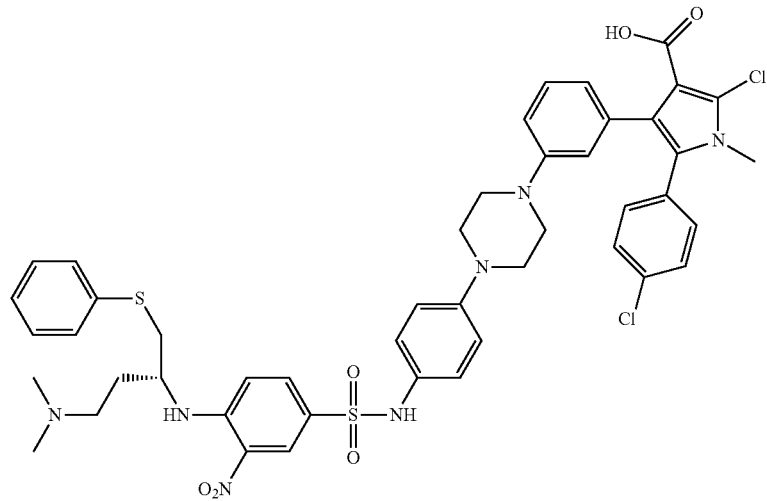 [SMILES: CN(C)CC[C@H](CSc1ccccc1)Nc1ccc(S(=O)(=O)Nc2ccc(N3CCN(c4cccc(-c5c(C(=O)O)c(Cl)n(C)c5-c5ccc(Cl)cc5)c4)CC3)cc2)cc1[N+](=O)[O-]] |

| Compound No. | |
|---|---|
| 113 | 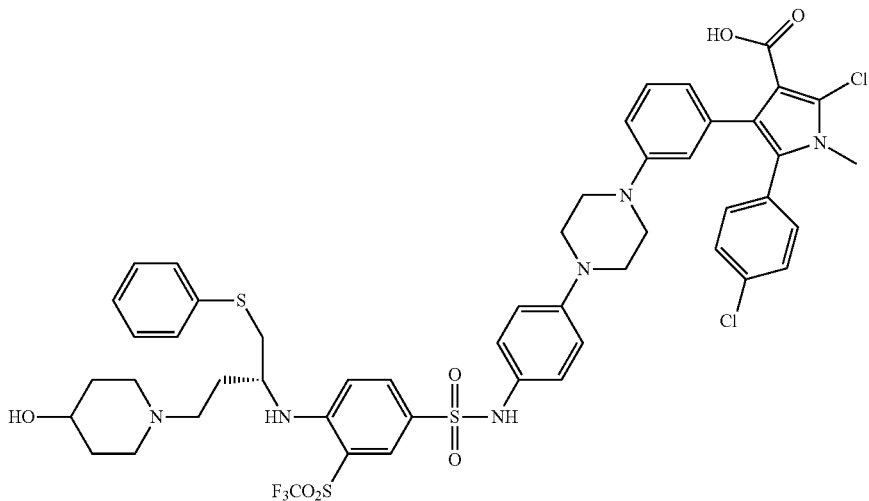 |
| 114 | 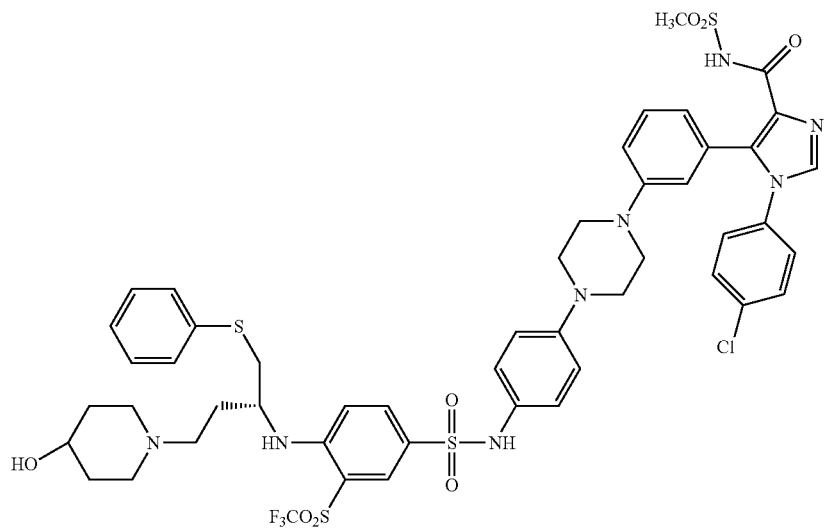 |
| 115 | 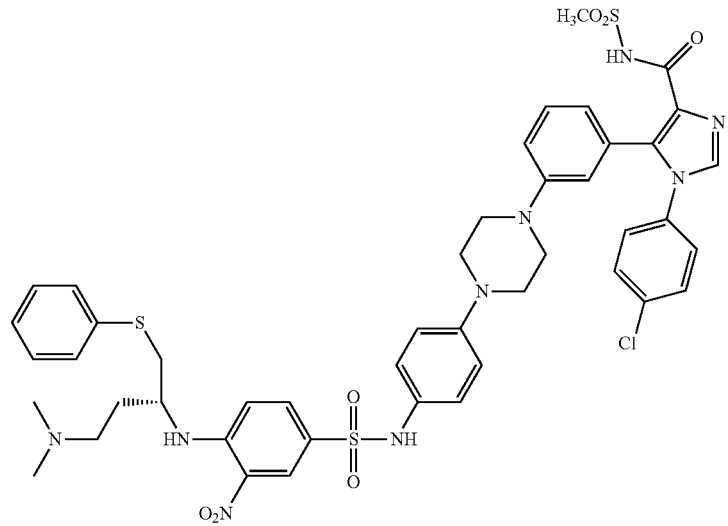 |

| Compound No. | |
|---|---|
| 116 | 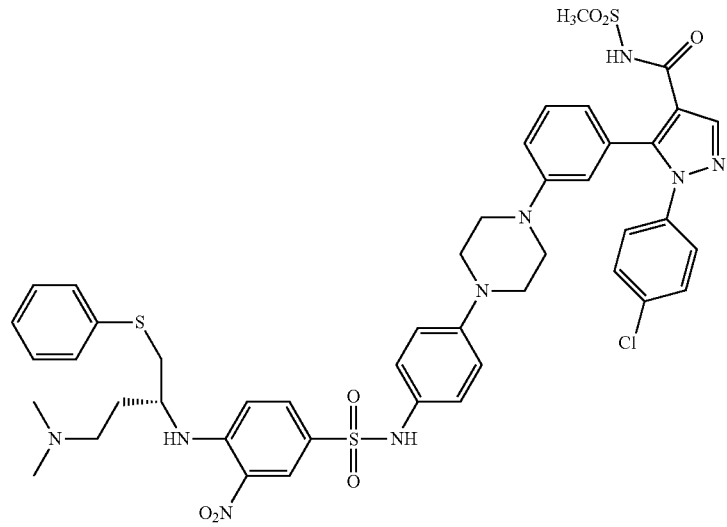 |
| 117 | 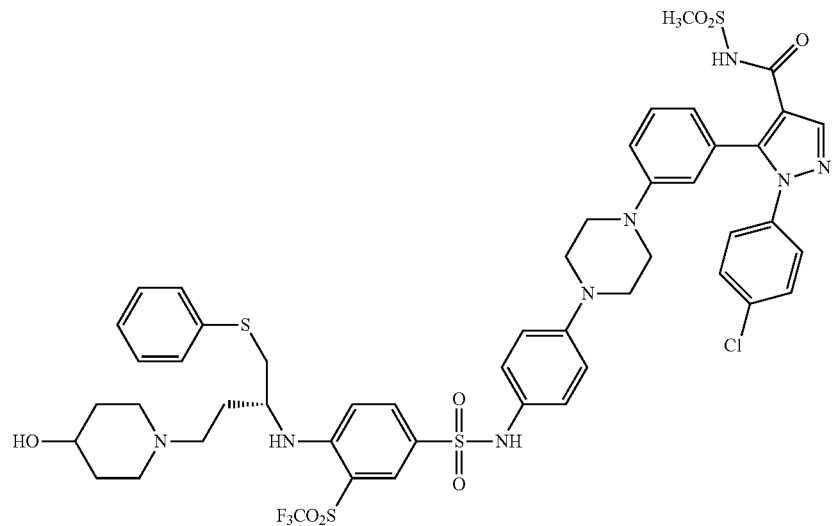 |
| 118 | 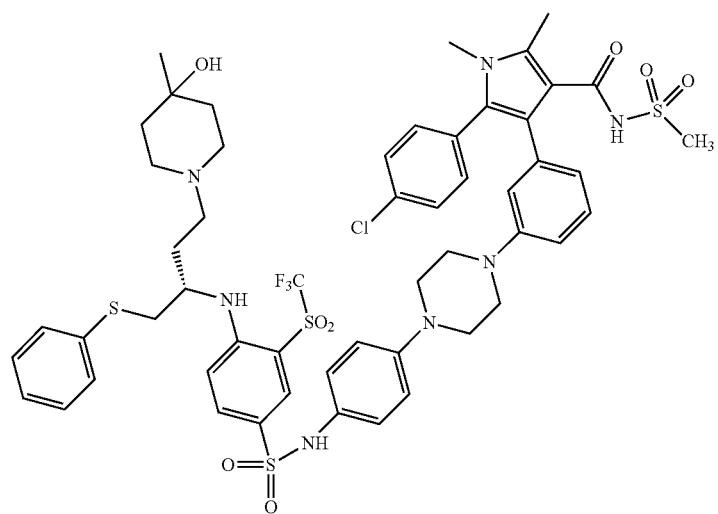 [SMILES: Cc1c(C(=O)NS(C)(=O)=O)c(-c2cccc(N3CCN(c4ccc(NS(=O)(=O)c5ccc(N[C@@H](CCN6CCC(C)(O)CC6)CSc6ccccc6)c(S(=O)(=O)C(F)(F)F)c5)cc4)CC3)c2)c(-c2ccc(Cl)cc2)n1C] |

| Compound No. | |
|---|---|
| 119 | 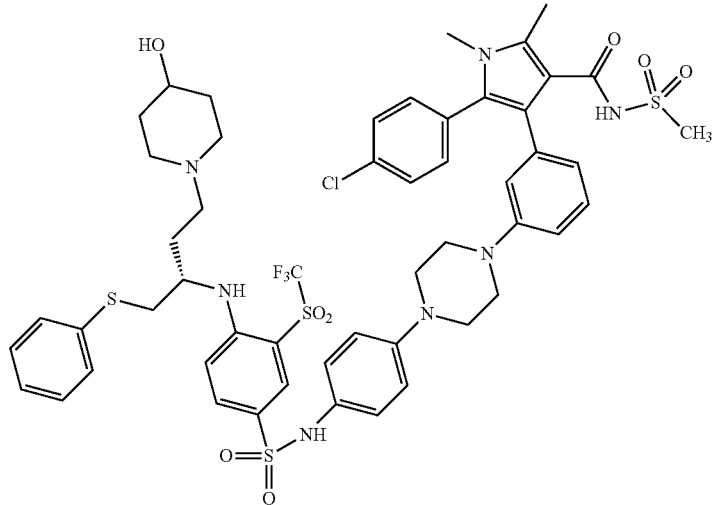 [SMILES: Cc1c(C(=O)NS(C)(=O)=O)c(-c2cccc(N3CCN(c4ccc(NS(=O)(=O)c5ccc(N[C@@H](CCN6CCC(O)CC6)CSc6ccccc6)c(S(=O)(=O)C(F)(F)F)c5)cc4)CC3)c2)c(-c2ccc(Cl)cc2)n1C] |
| 120 | 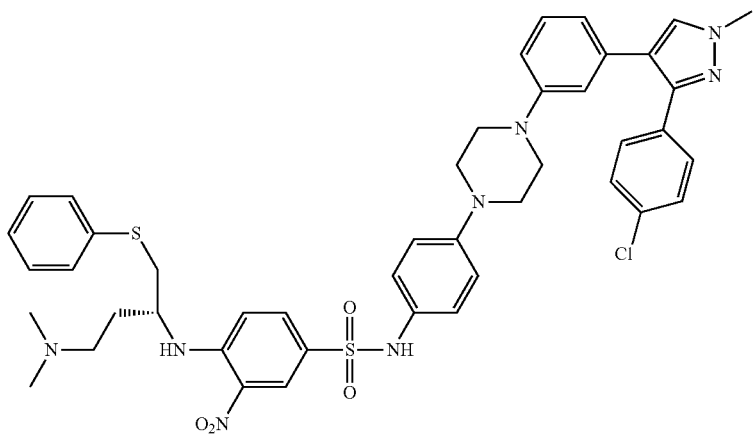 [SMILES: CN(C)CC[C@H](CSc1ccccc1)Nc1ccc(S(=O)(=O)Nc2ccc(N3CCN(c4cccc(-c5cn(C)nc5-c5ccc(Cl)cc5)c4)CC3)cc2)cc1[N+](=O)[O-]] |
| 121 | 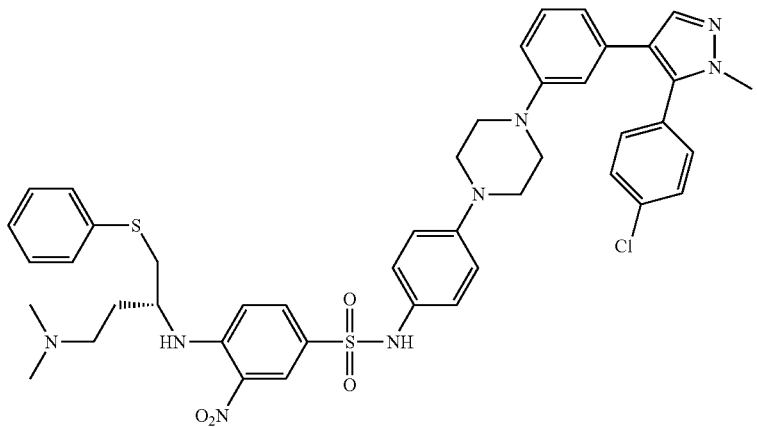 [SMILES: CN(C)CC[C@H](CSc1ccccc1)Nc1ccc(S(=O)(=O)Nc2ccc(N3CCN(c4cccc(-c5cnn(C)c5-c5ccc(Cl)cc5)c4)CC3)cc2)cc1[N+](=O)[O-]] |

| Compound No. | |
|---|---|
| 122 | 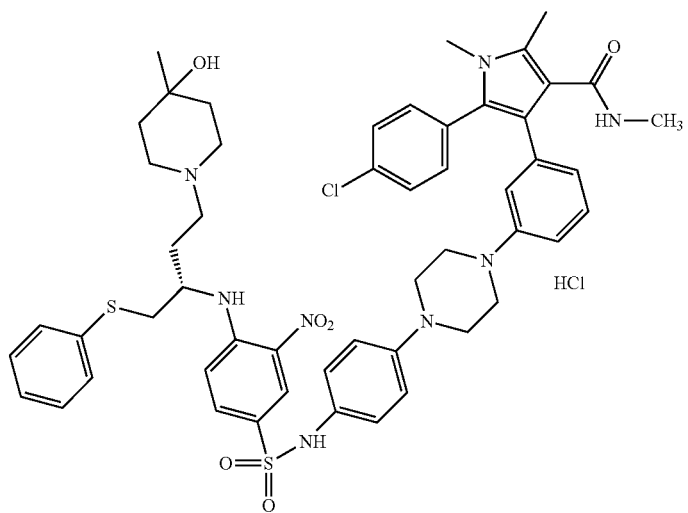 [SMILES: CNC(=O)c1c(-c2cccc(N3CCN(c4ccc(NS(=O)(=O)c5ccc(N[C@@H](CCN6CCC(C)(O)CC6)CSc6ccccc6)c([N+](=O)[O-])c5)cc4)CC3)c2)c(-c2ccc(Cl)cc2)n(C)c1C ; Cl] |
| 123 | 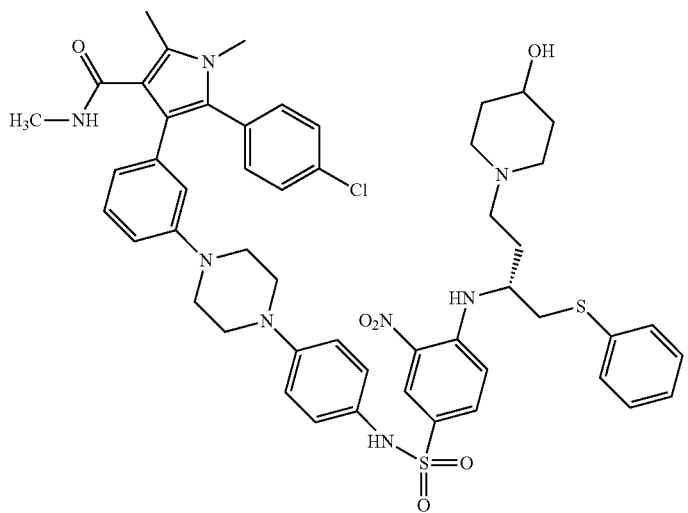 [SMILES: CNC(=O)c1c(-c2cccc(N3CCN(c4ccc(NS(=O)(=O)c5ccc(N[C@H](CCN6CCC(O)CC6)CSc6ccccc6)c([N+](=O)[O-])c5)cc4)CC3)c2)c(-c2ccc(Cl)cc2)n(C)c1C] |
| 124 | 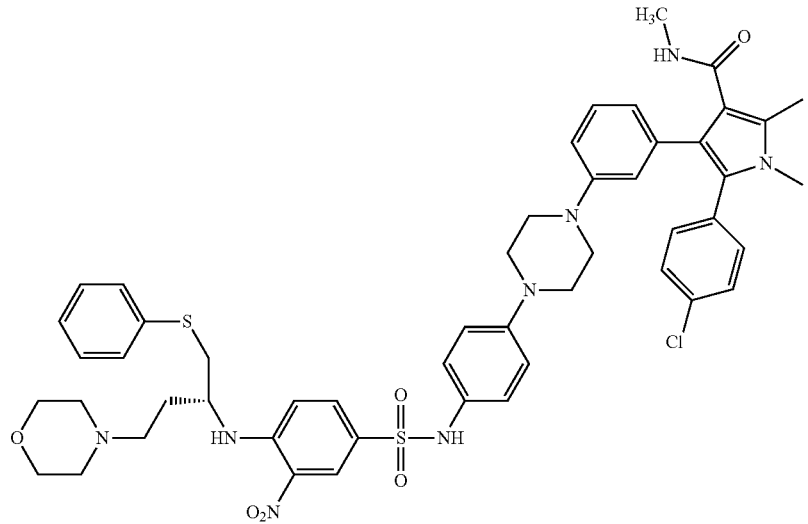 [SMILES: CNC(=O)c1c(-c2cccc(N3CCN(c4ccc(NS(=O)(=O)c5ccc(N[C@H](CCN6CCOCC6)CSc6ccccc6)c([N+](=O)[O-])c5)cc4)CC3)c2)c(-c2ccc(Cl)cc2)n(C)c1C] |

| Compound No. |
|---|
| 125 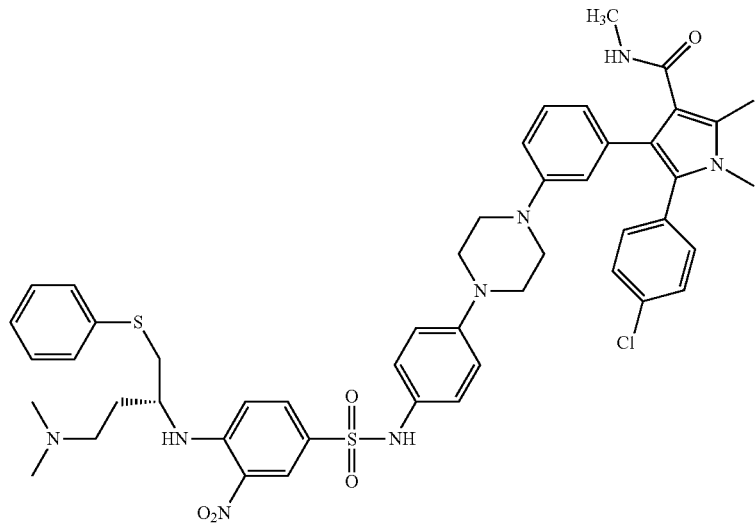 [SMILES: CNC(=O)c1c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n(C)c1C] |
| 126 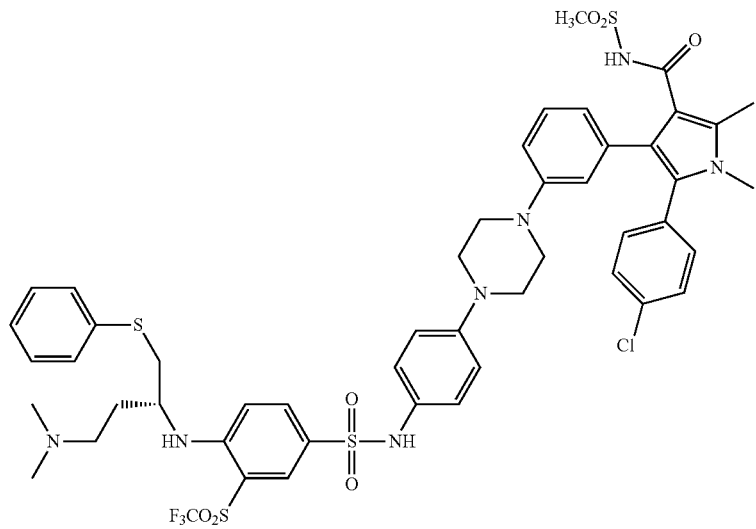 |
| 127 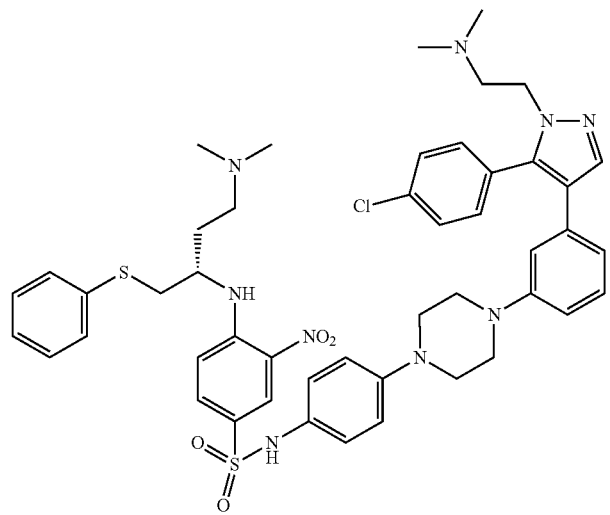 [SMILES: CN(C)CC[C@@H](CSc1ccccc1)Nc1ccc(S(=O)(=O)Nc2ccc(N3CCN(c4cccc(-c5cnn(CCN(C)C)c5-c5ccc(Cl)cc5)c4)CC3)cc2)cc1[N+](=O)[O-]] |

| Compound No. | |
|---|---|
| 128 | 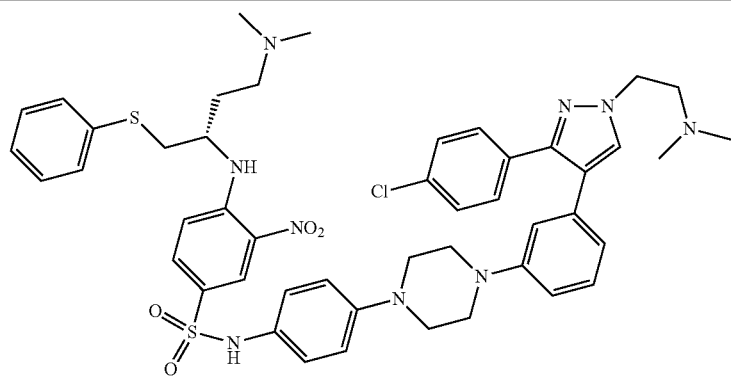 [SMILES: CN(C)CC[C@@H](CSc1ccccc1)Nc1ccc(S(=O)(=O)Nc2ccc(N3CCN(c4cccc(-c5cn(CCN(C)C)nc5-c5ccc(Cl)cc5)c4)CC3)cc2)cc1[N+](=O)[O-]] |
| 129 | 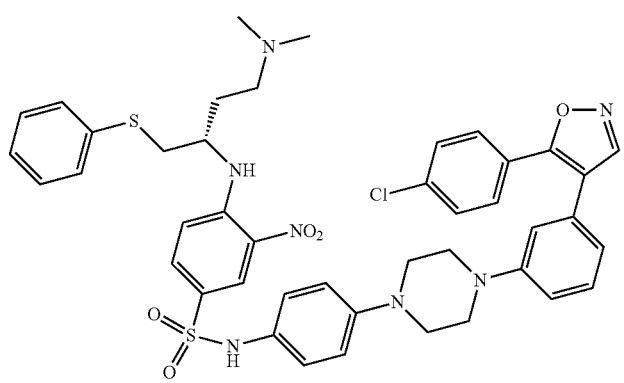 [SMILES: CN(C)CC[C@@H](CSc1ccccc1)Nc1ccc(S(=O)(=O)Nc2ccc(N3CCN(c4cccc(-c5cnoc5-c5ccc(Cl)cc5)c4)CC3)cc2)cc1[N+](=O)[O-]] |
| 130 | 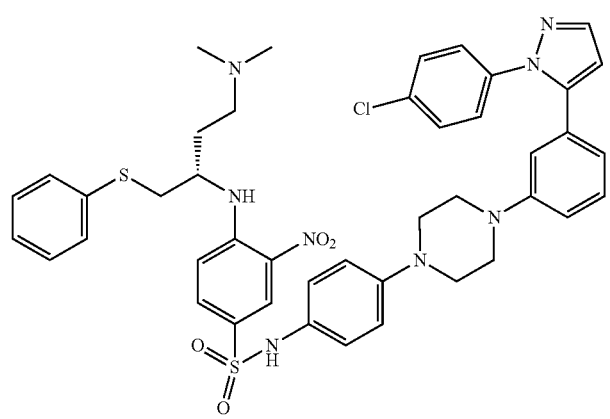 [SMILES: CN(C)CC[C@@H](CSc1ccccc1)Nc1ccc(S(=O)(=O)Nc2ccc(N3CCN(c4cccc(-c5ccnn5-c5ccc(Cl)cc5)c4)CC3)cc2)cc1[N+](=O)[O-]] |
| 131 | 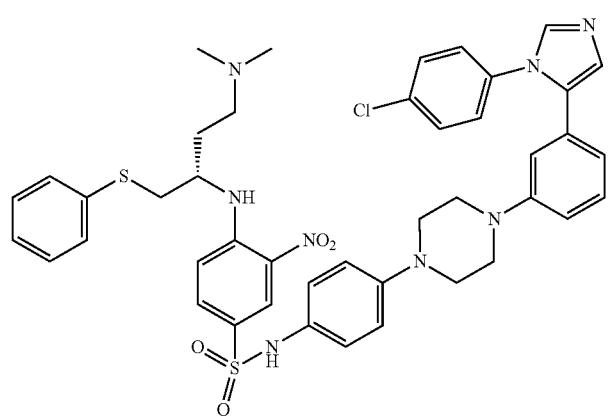 [SMILES: CN(C)CC[C@@H](CSc1ccccc1)Nc1ccc(S(=O)(=O)Nc2ccc(N3CCN(c4cccc(-c5cncn5-c5ccc(Cl)cc5)c4)CC3)cc2)cc1[N+](=O)[O-]] |

| Compound No. |
| --- |
| 132 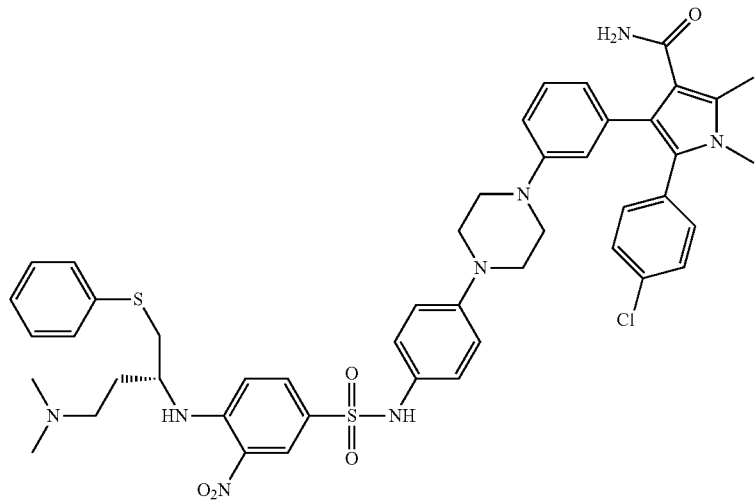 |
| 133 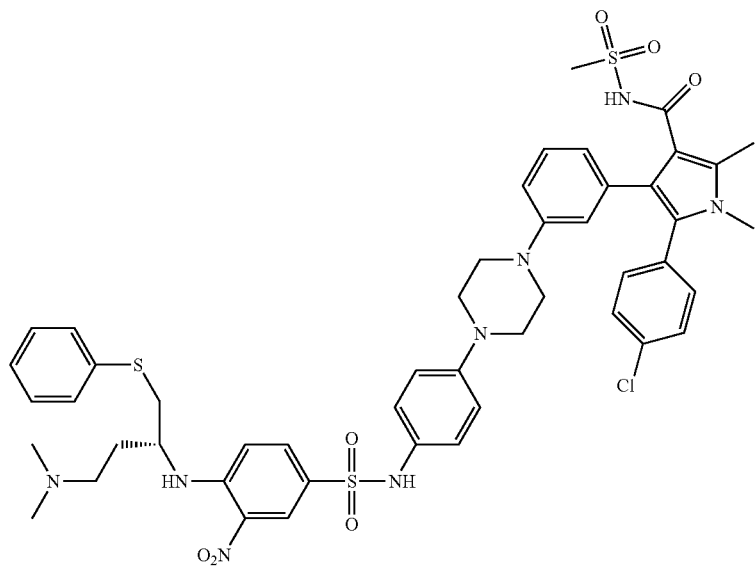 [SMILES: Cc1c(C(=O)NS(C)(=O)=O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |

| Compound No. | |
|---|---|
| 134 | 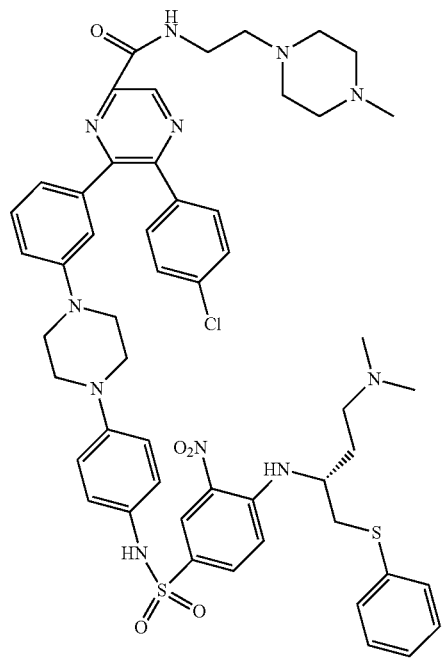 [SMILES: CN(C)CC[C@H](CSc1ccccc1)Nc1ccc(S(=O)(=O)Nc2ccc(N3CCN(c4cccc(-c5nc(C(=O)NCCN6CCN(C)CC6)cnc5-c5ccc(Cl)cc5)c4)CC3)cc2)cc1[N+](=O)[O-]] |
| 135 | 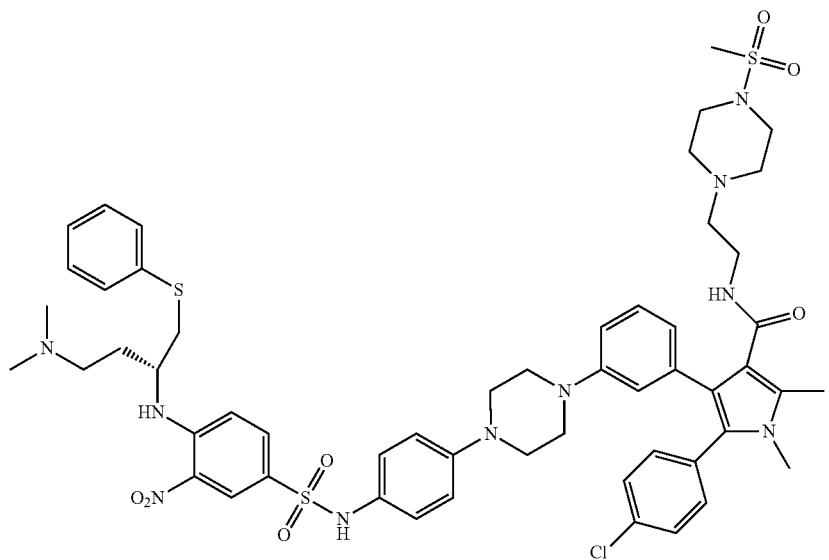 |

| Compound No. | |
|---|---|
| 136 | 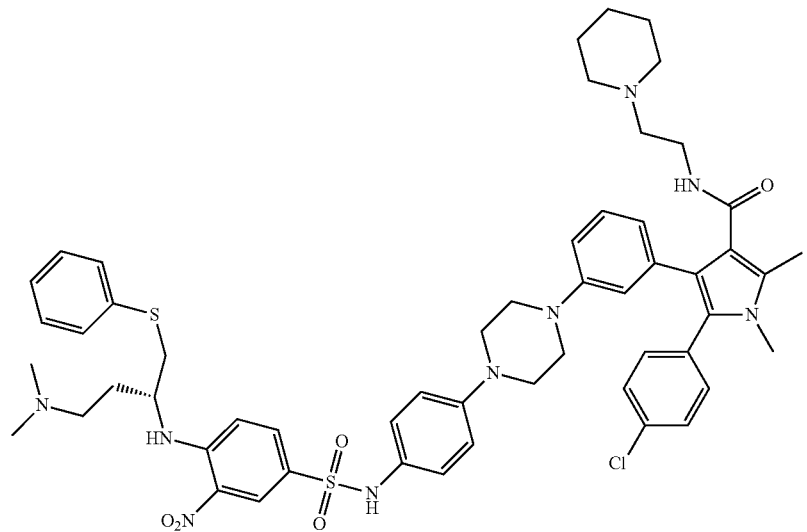 |
| 137 | 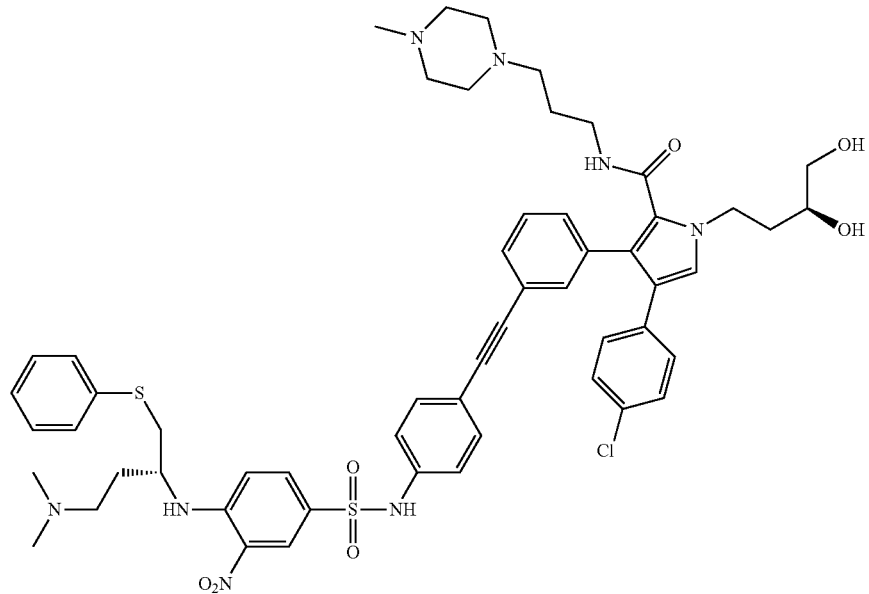 [SMILES: CN(C)CC[C@H](CSc1ccccc1)Nc1ccc(S(=O)(=O)Nc2ccc(C#Cc3cccc(-c4c(-c5ccc(Cl)cc5)cn(CC[C@H](O)CO)c4C(=O)NCCCN4CCN(C)CC4)c3)cc2)cc1[N+](=O)[O-]] |

| Compound No. |
|---|
| 138 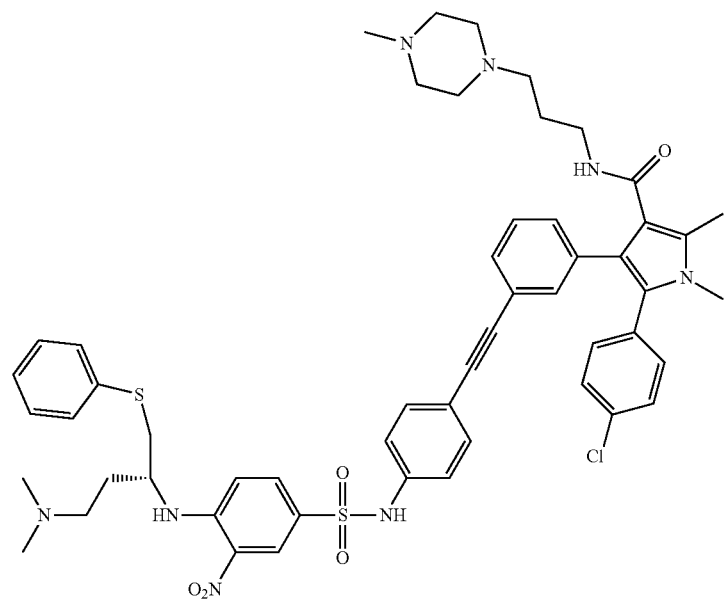 [SMILES: Cc1c(C(=O)NCCCN2CCN(C)CC2)c(-c2cccc(C#Cc3ccc(NS(=O)(=O)c4ccc(N[C@H](CCN(C)C)CSc5ccccc5)c([N+](=O)[O-])c4)cc3)c2)c(-c2ccc(Cl)cc2)n1C] |
| 139 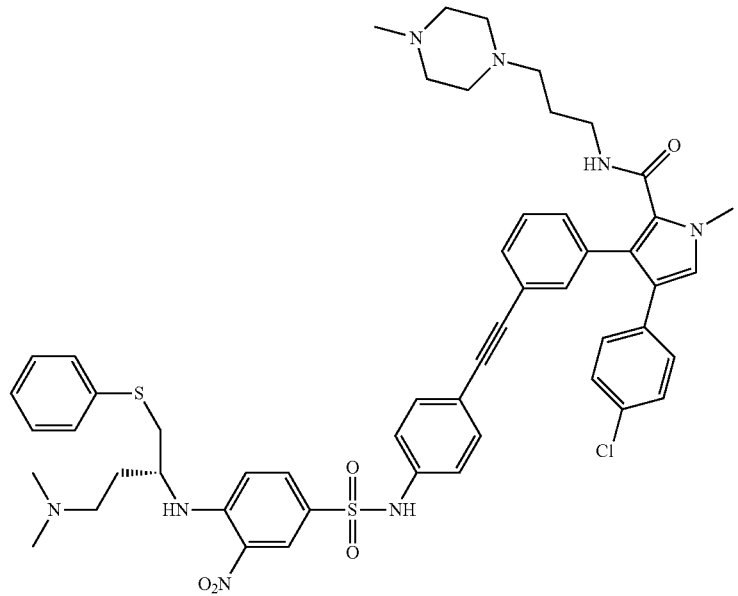 [SMILES: CN(C)CC[C@H](CSc1ccccc1)Nc1ccc(S(=O)(=O)Nc2ccc(C#Cc3cccc(-c4c(-c5ccc(Cl)cc5)cn(C)c4C(=O)NCCCN4CCN(C)CC4)c3)cc2)cc1[N+](=O)[O-]] |

-continued
| Compound No. |
|---|
| 140 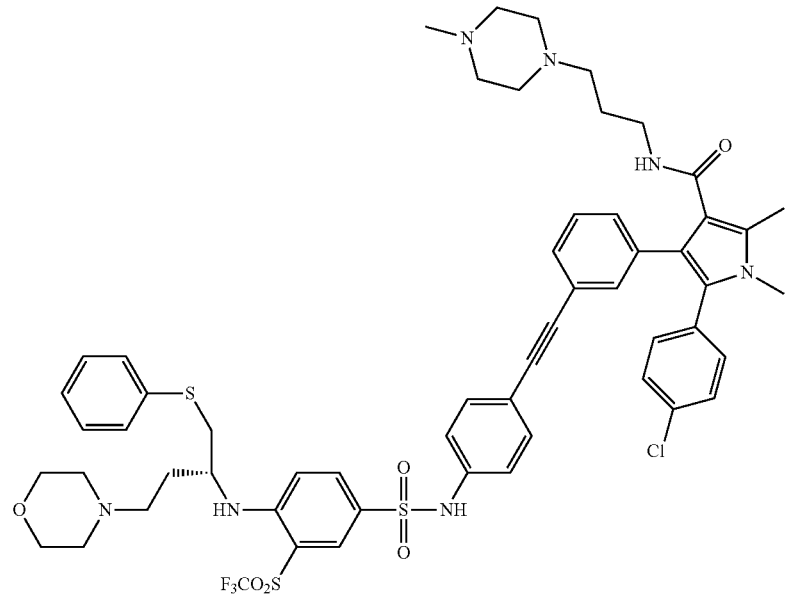 |
| 141 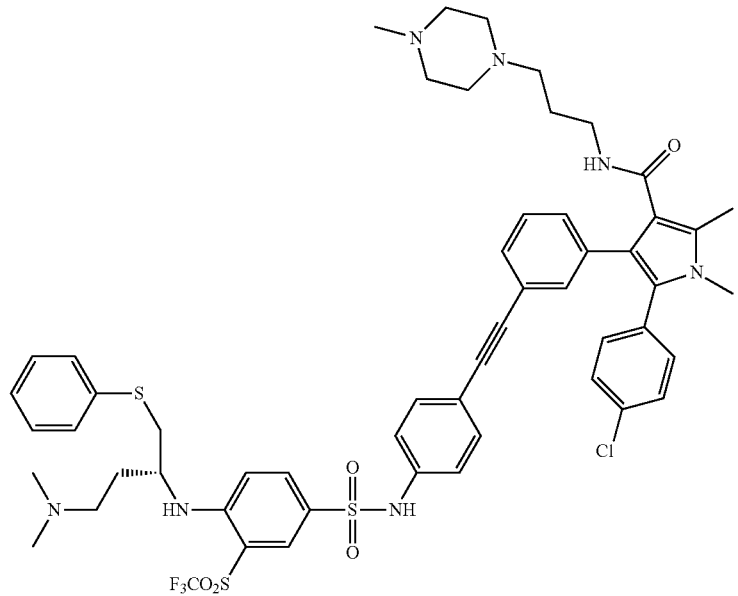 |

-continued
| Compound No. |
|---|
| 142 |
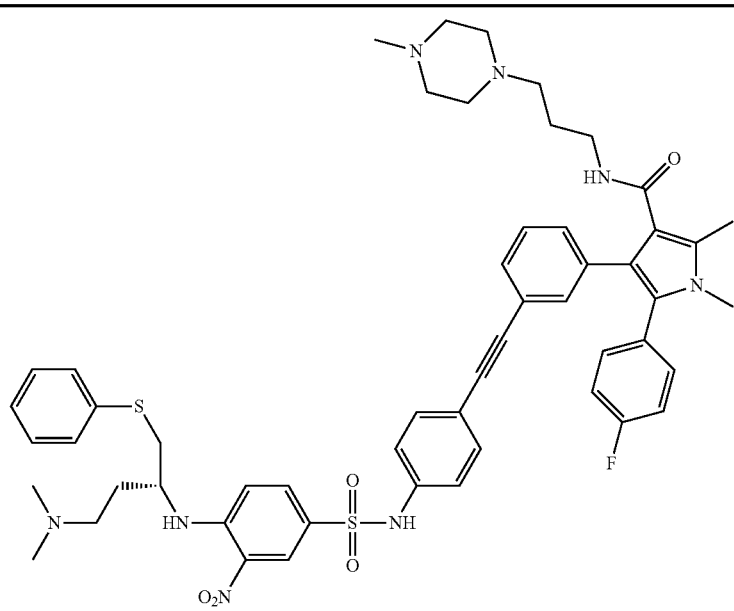
| 143 |
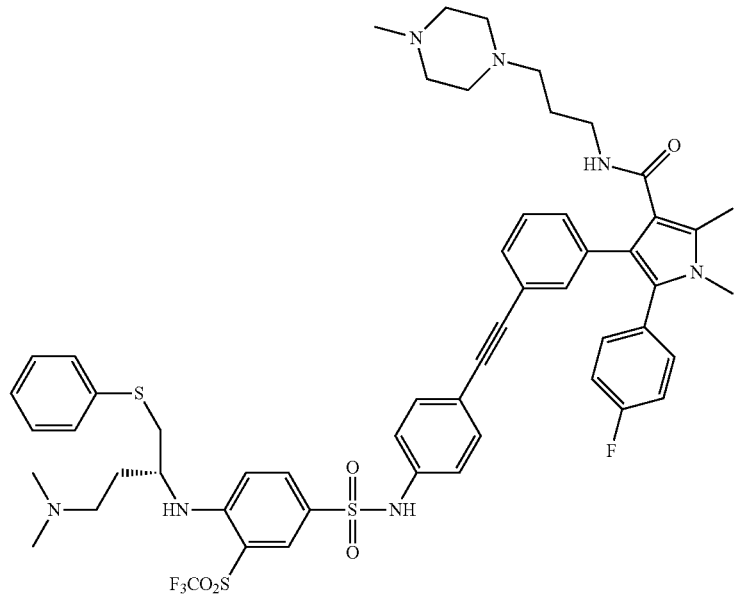 [SMILES: Cc1c(C(=O)NCCCN2CCN(C)CC2)c(-c2cccc(C#Cc3ccc(NS(=O)(=O)c4ccc(N[C@H](CCN(C)C)CSc5ccccc5)c([N+](=O)[O-])c4)cc3)c2)c(-c2ccc(F)cc2)n1C]

US 8,691,184 B2
123                                                                                                      124
-continued
| Compound No. |
|---|
| 144 |
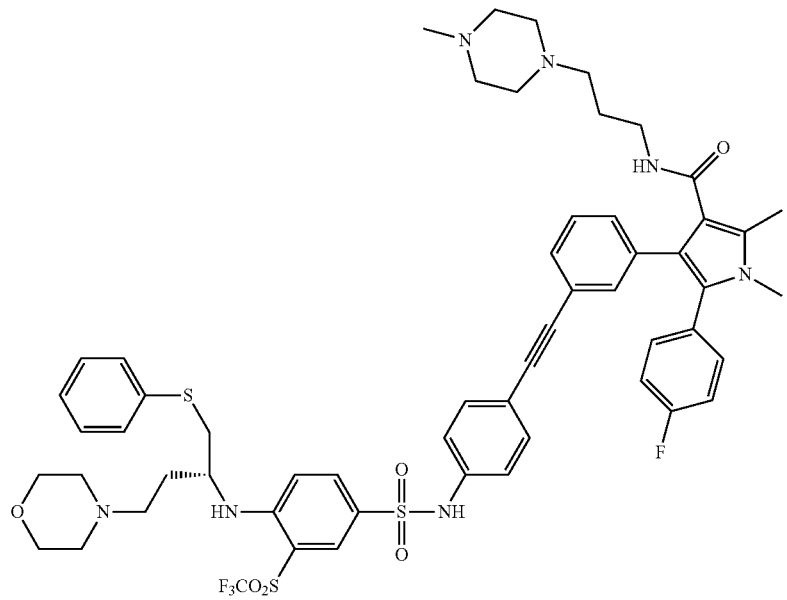
| 145 |
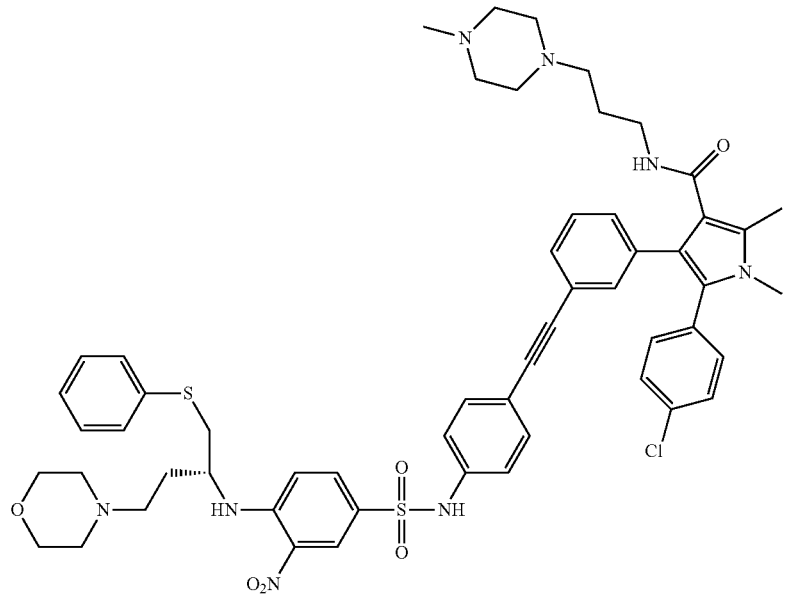 [SMILES: Cc1c(C(=O)NCCCN2CCN(C)CC2)c(-c2cccc(C#Cc3ccc(NS(=O)(=O)c4ccc(N[C@H](CCN5CCOCC5)CSc5ccccc5)c([N+](=O)[O-])c4)cc3)c2)c(-c2ccc(Cl)cc2)n1C]

-continued
| Compound No. |
|---|
| 146 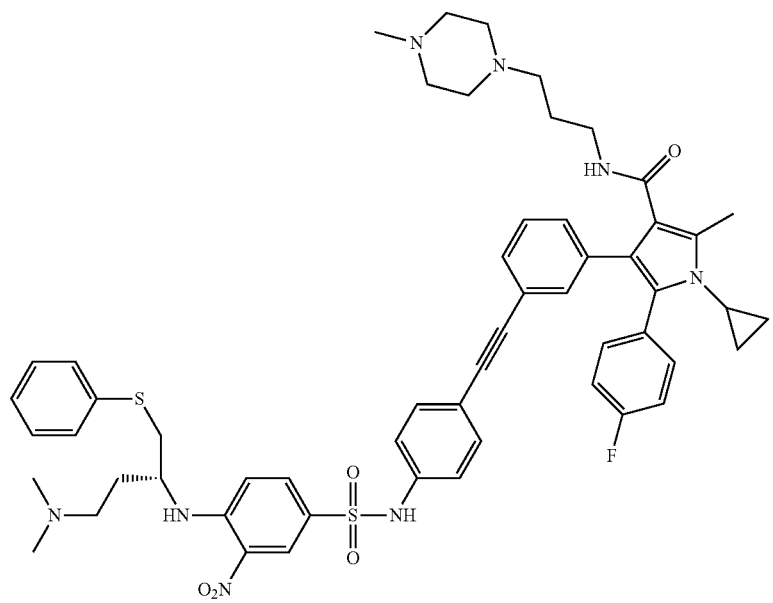 [SMILES: Cc1c(C(=O)NCCCN2CCN(C)CC2)c(-c2cccc(C#Cc3ccc(NS(=O)(=O)c4ccc(N[C@H](CCN(C)C)CSc5ccccc5)c([N+](=O)[O-])c4)cc3)c2)c(-c2ccc(F)cc2)n1C1CC1] |
| 147 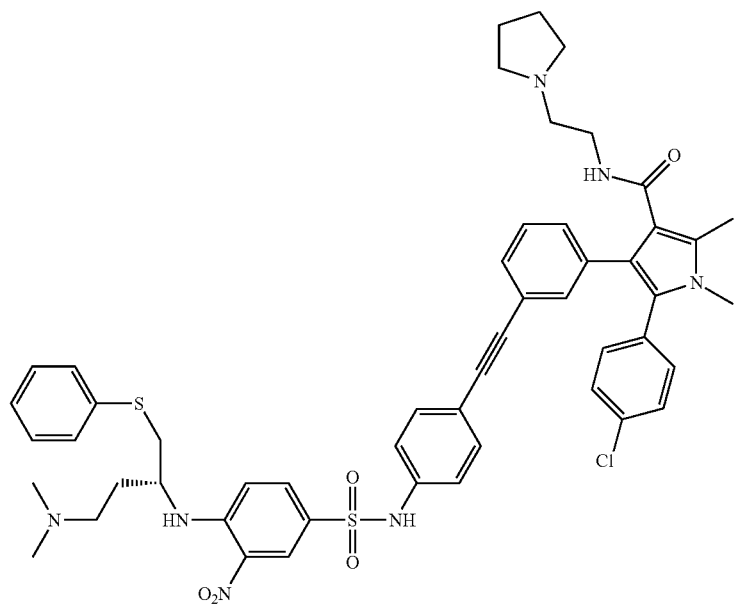 [SMILES: Cc1c(C(=O)NCCN2CCCC2)c(-c2cccc(C#Cc3ccc(NS(=O)(=O)c4ccc(N[C@H](CCN(C)C)CSc5ccccc5)c([N+](=O)[O-])c4)cc3)c2)c(-c2ccc(Cl)cc2)n1C] |

-continued
| Compound No. | |
|---|---|
| 148 | 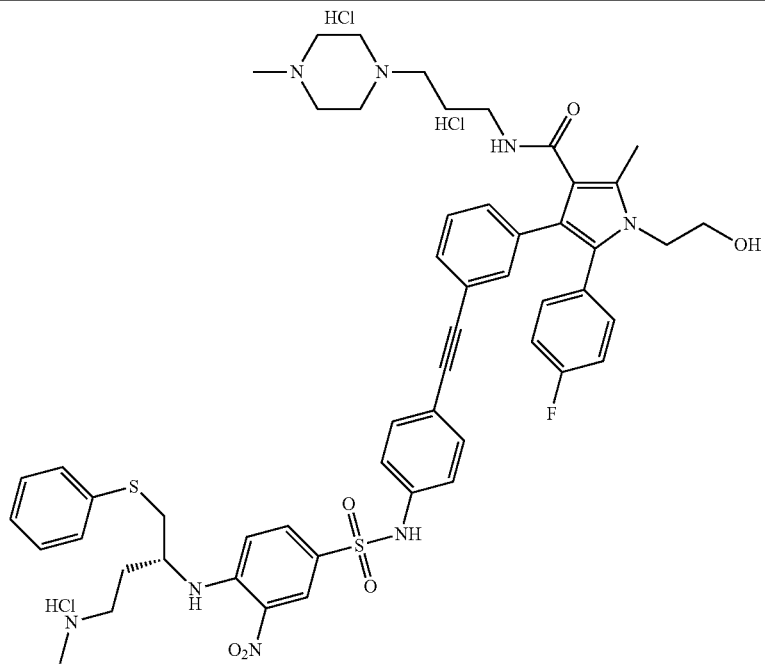 |
| 149 | 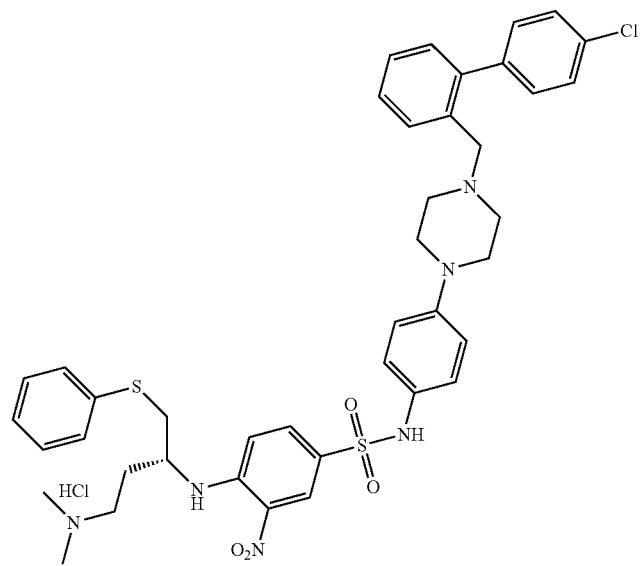 [SMILES: CN(C)CC[C@H](CSc1ccccc1)Nc1ccc(S(=O)(=O)Nc2ccc(N3CCN(Cc4ccccc4-c4ccc(Cl)cc4)CC3)cc2)cc1[N+](=O)[O-] ; Cl] |

| Compound No. |
|---|
| 150 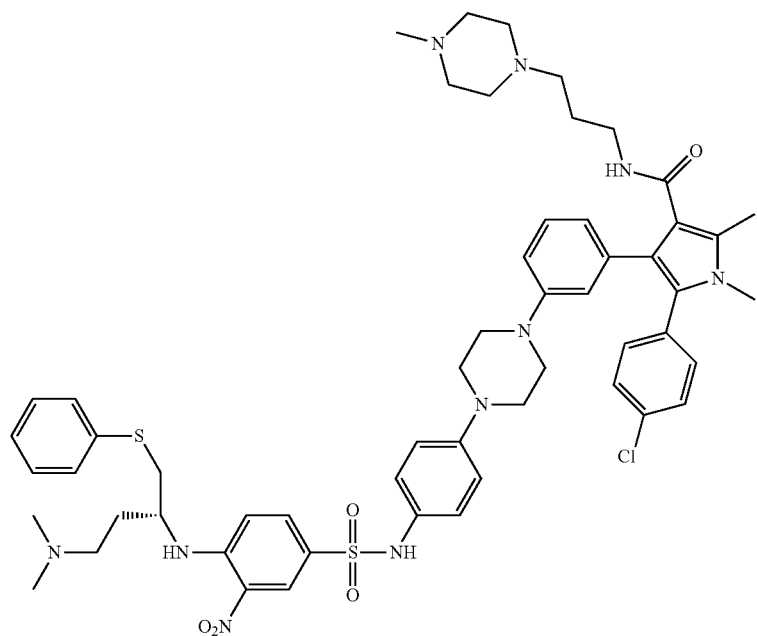 |
| 151 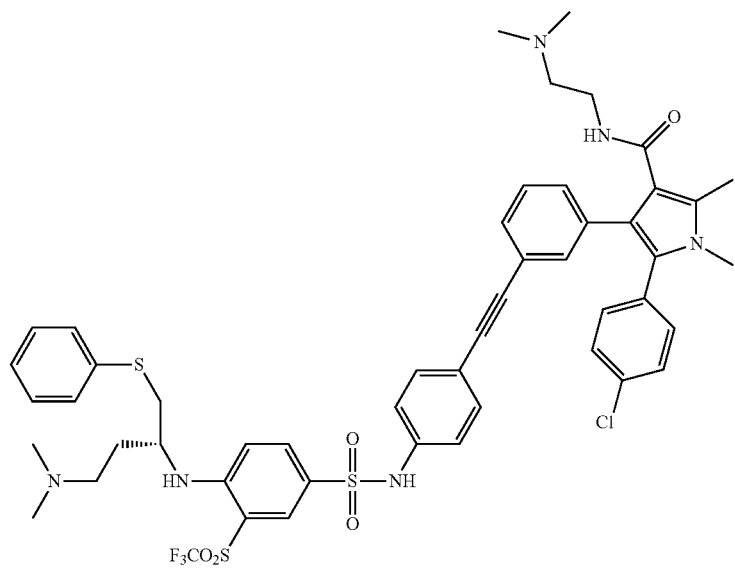 |

-continued
| Compound No. |
|---|
| 152 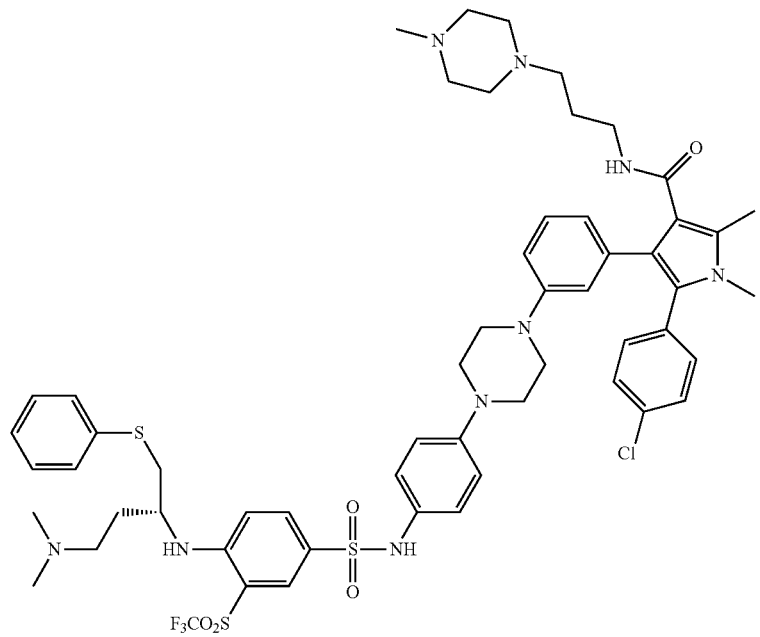 |
| 153 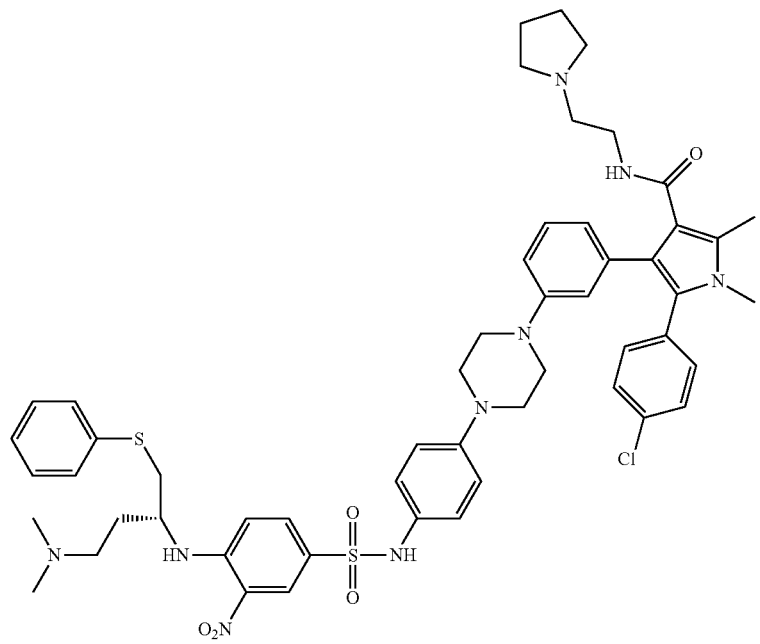 [SMILES: Cc1c(C(=O)NCCN2CCCC2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |

-continued
| Compound No. | |
|---|---|
| 154 | 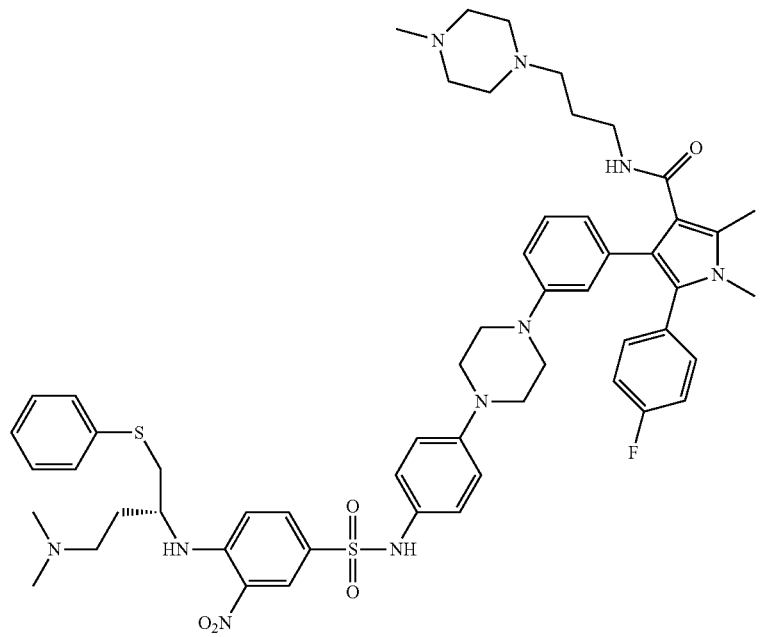 |
| 155 | 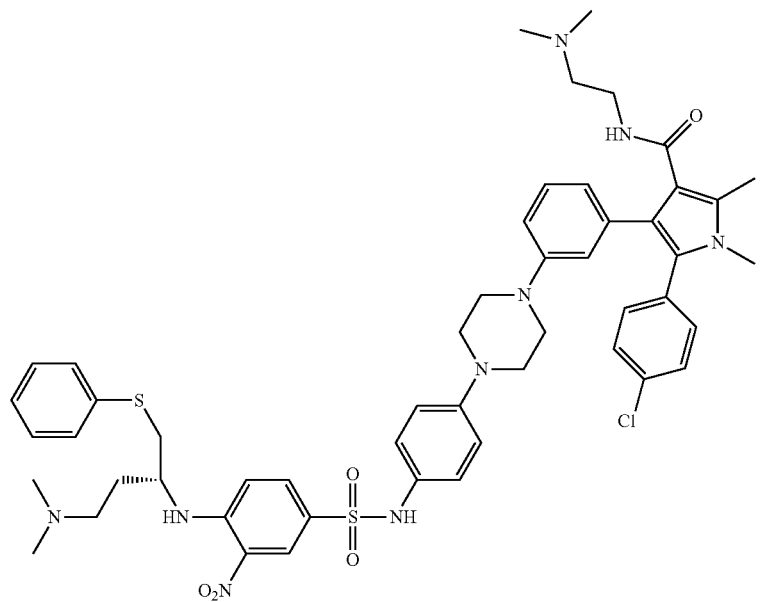 [SMILES: Cc1c(C(=O)NCCN(C)C)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C] |

-continued
| Compound No. |
| --- |
156
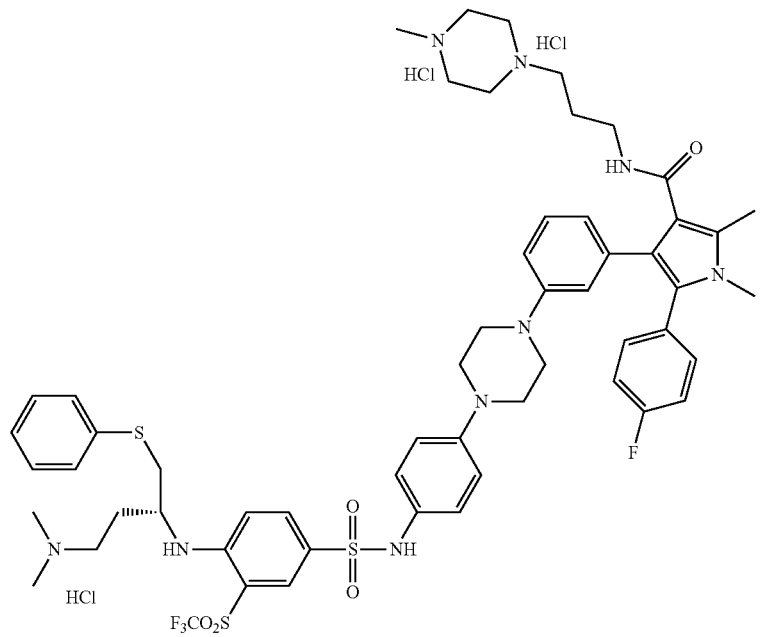
157
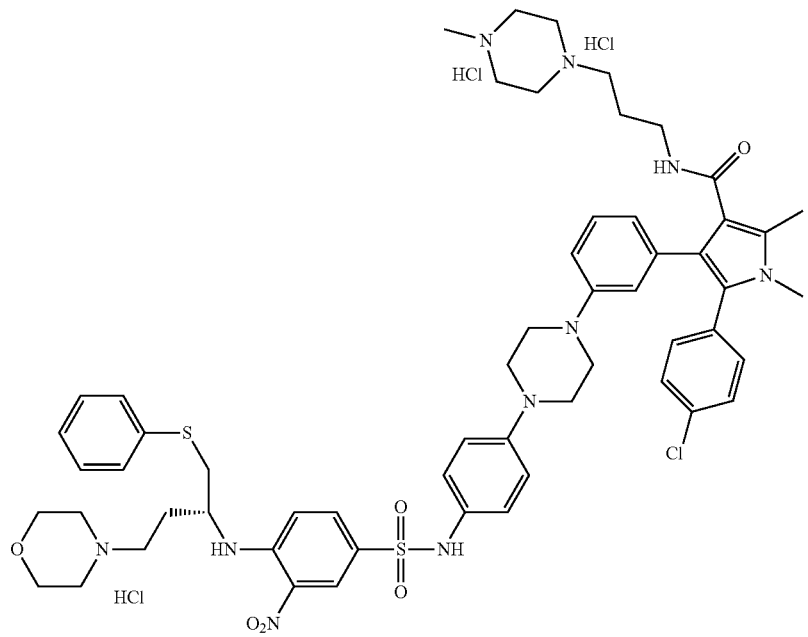 [SMILES: Cc1c(C(=O)NCCCN2CCN(C)CC2)c(-c2cccc(N3CCN(c4ccc(NS(=O)(=O)c5ccc(N[C@H](CCN6CCOCC6)CSc6ccccc6)c([N+](=O)[O-])c5)cc4)CC3)c2)c(-c2ccc(Cl)cc2)n1C ; Cl ; Cl ; Cl]

| Compound No. | |
|---|---|
| 158 | 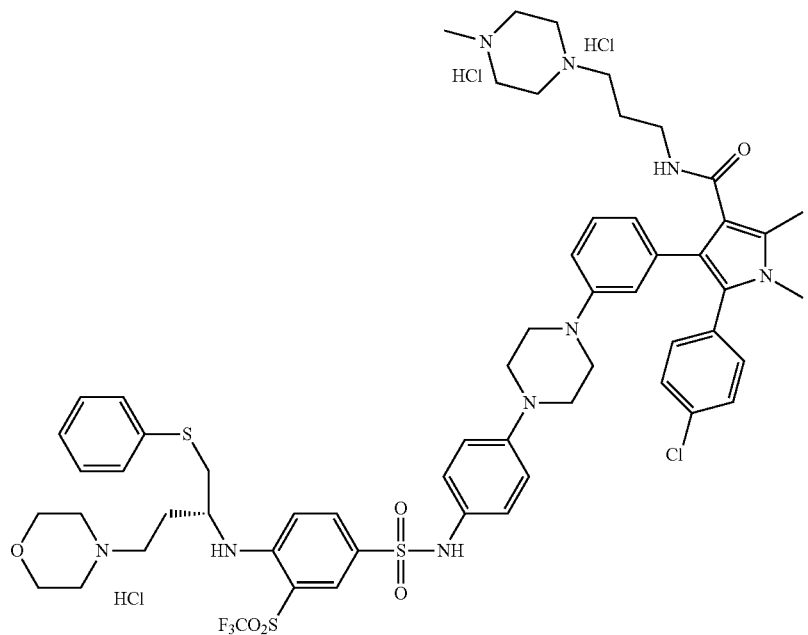 |
| 159 | 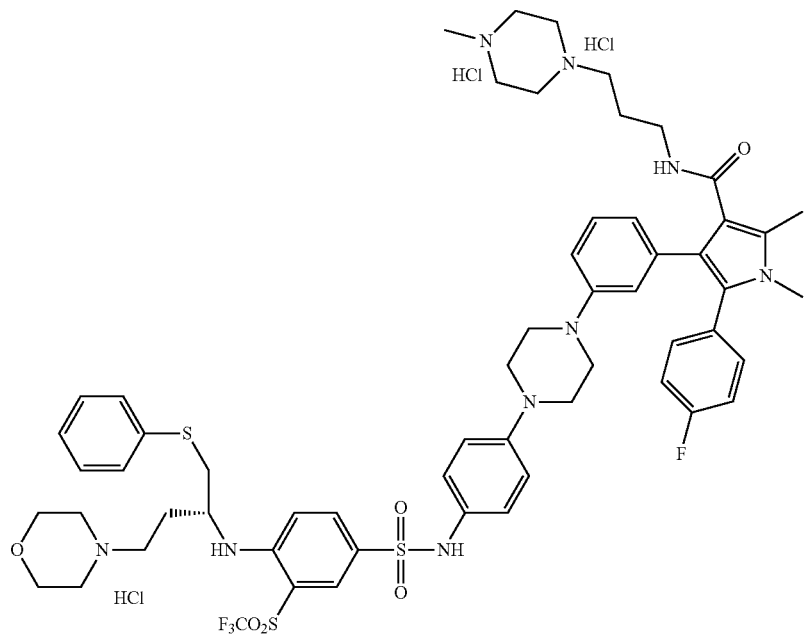 |

-continued
| Compound No. | |
|---|---|
| 160 | 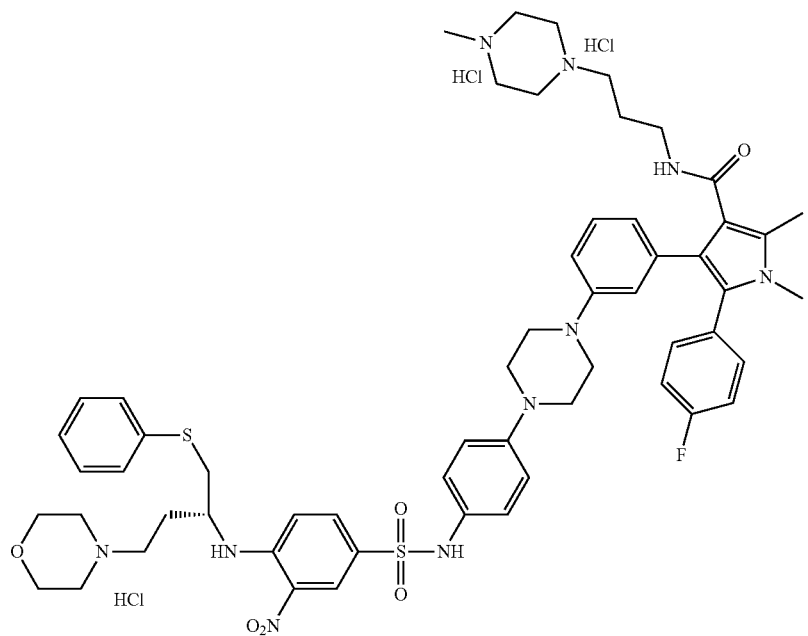 [SMILES: Cc1c(C(=O)NCCCN2CCN(C)CC2)c(-c2cccc(N3CCN(c4ccc(NS(=O)(=O)c5ccc(N[C@H](CCN6CCOCC6)CSc6ccccc6)c([N+](=O)[O-])c5)cc4)CC3)c2)c(-c2ccc(F)cc2)n1C ; Cl ; Cl ; Cl] |
| 161 | 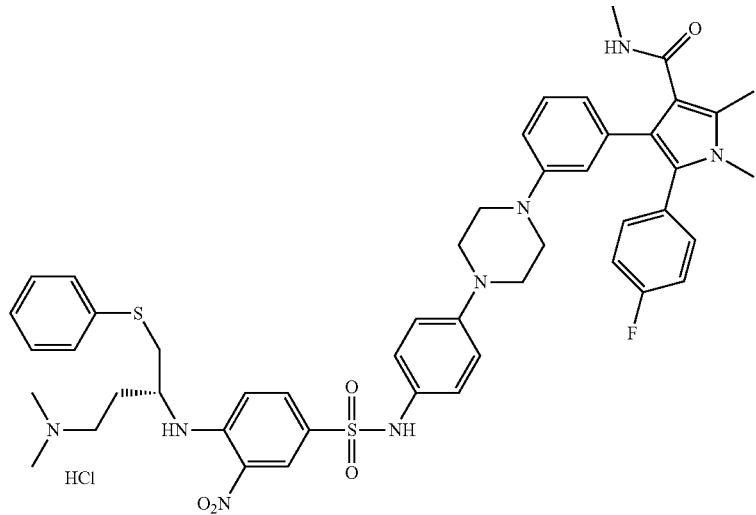 [SMILES: CNC(=O)c1c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(F)cc2)n(C)c1C ; Cl] |

| Compound No. | |
|---|---|
| 162 | 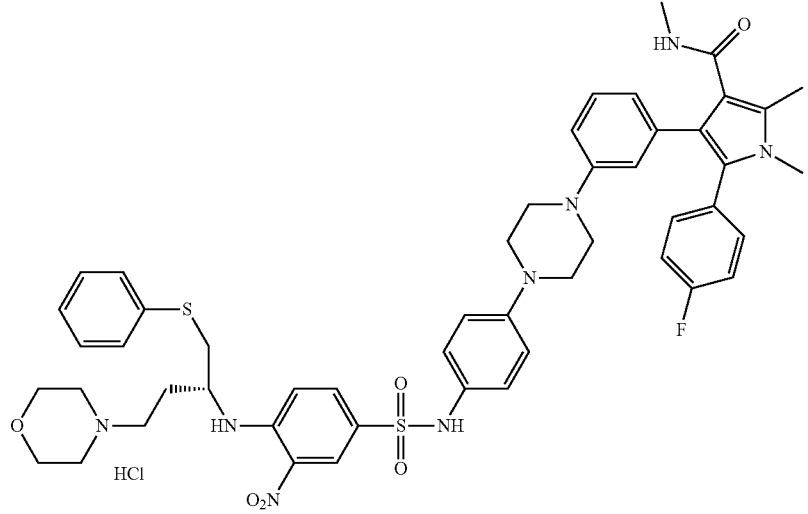 [SMILES: CNC(=O)c1c(-c2cccc(N3CCN(c4ccc(NS(=O)(=O)c5ccc(N[C@H](CCN6CCOCC6)CSc6ccccc6)c([N+](=O)[O-])c5)cc4)CC3)c2)c(-c2ccc(F)cc2)n(C)c1C ; Cl] |
| 163 | 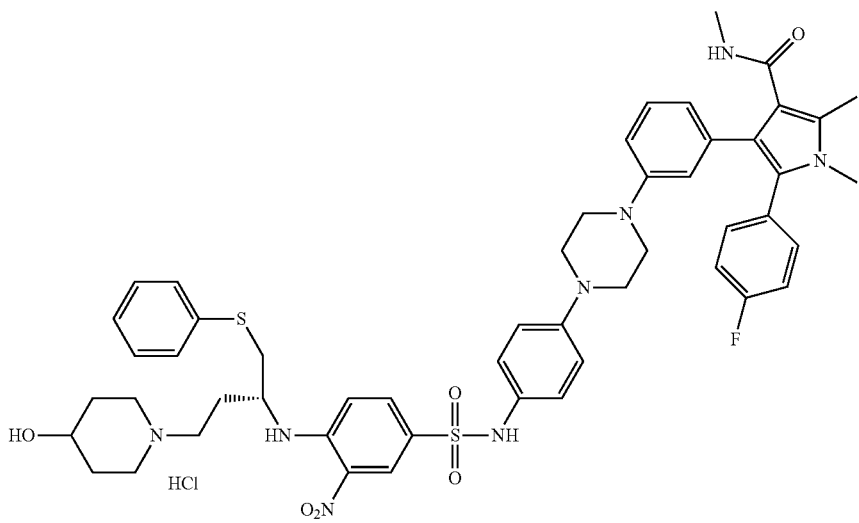 [SMILES: CNC(=O)c1c(-c2cccc(N3CCN(c4ccc(NS(=O)(=O)c5ccc(N[C@H](CCN6CCC(O)CC6)CSc6ccccc6)c([N+](=O)[O-])c5)cc4)CC3)c2)c(-c2ccc(F)cc2)n(C)c1C ; Cl] |
| 164 | 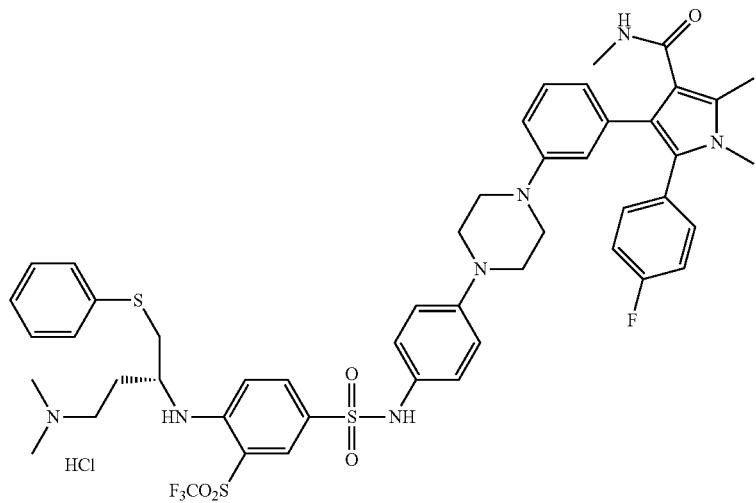 |

| Compound No. |
|---|
| 165 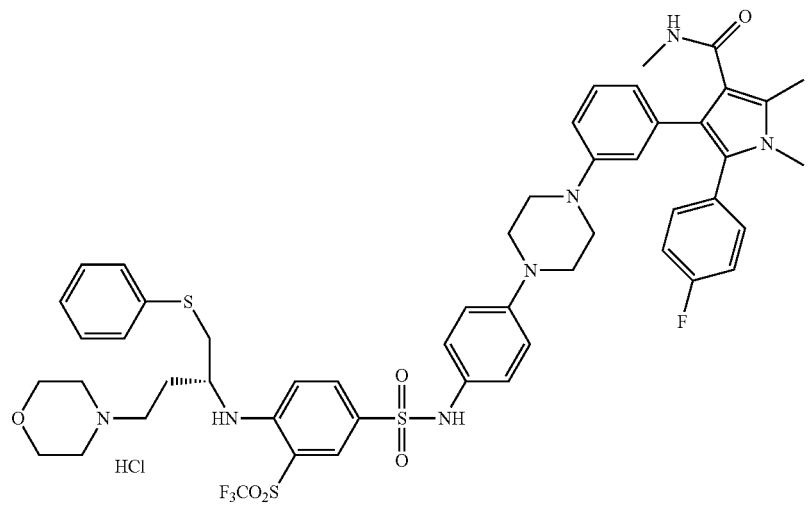 |
| 166 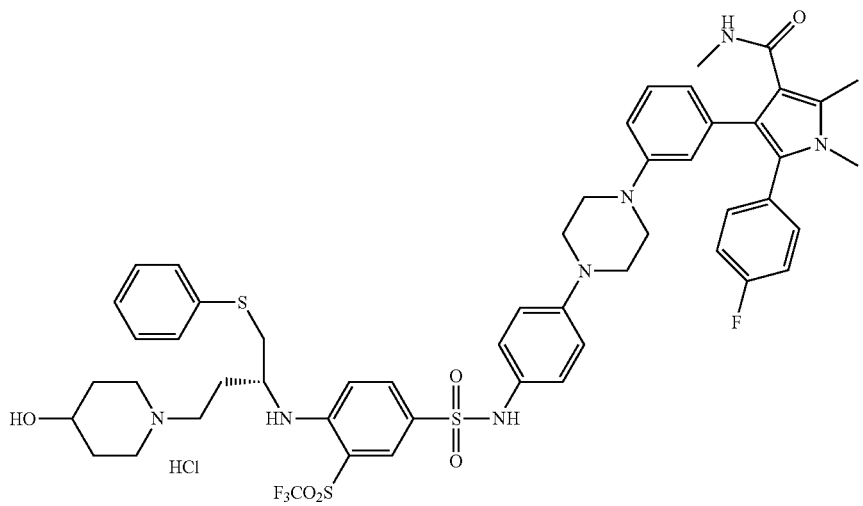 |
| 167 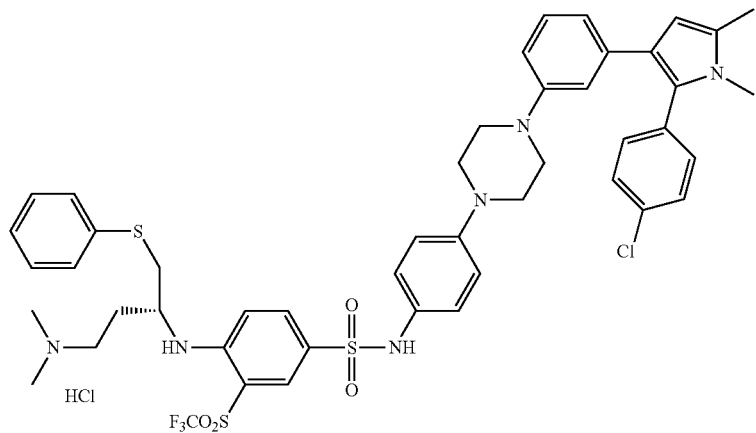 [SMILES: Cc1cc(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C ; Cl] |

| Compound No. | |
|---|---|
| 168 | 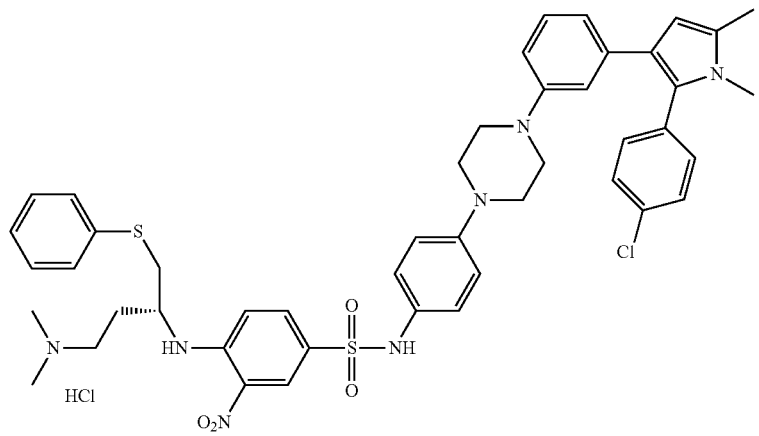 |
| 169 | 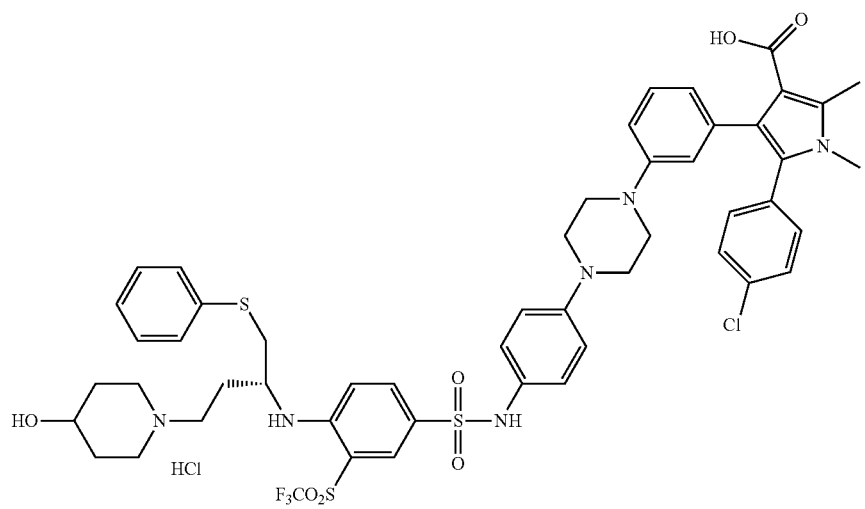 |
| 170 | 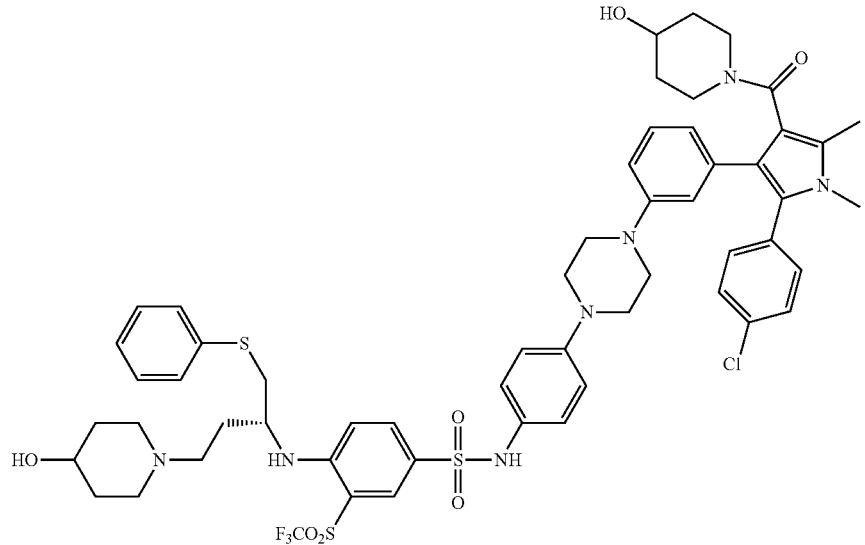 |

| Compound No. | |
|---|---|
| 171 | 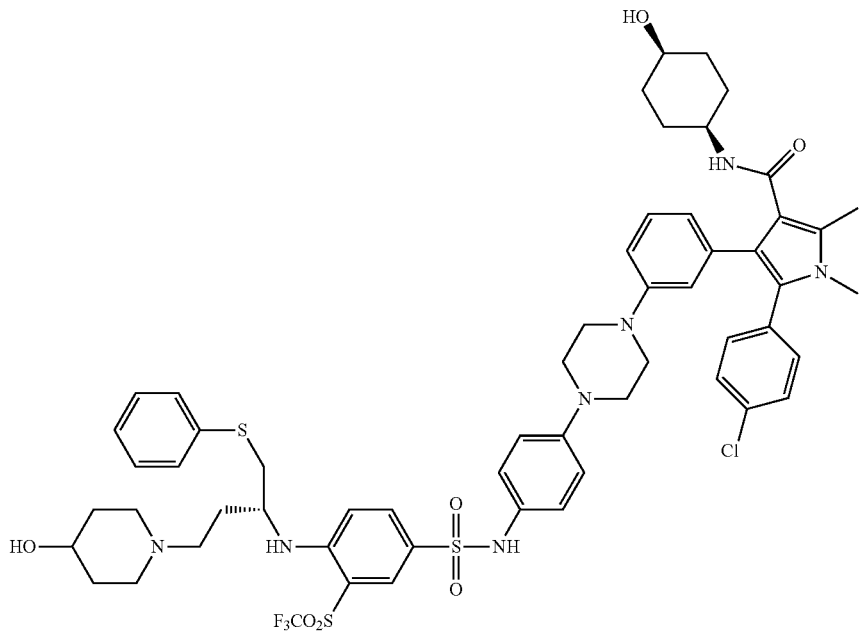 |
| 172 | 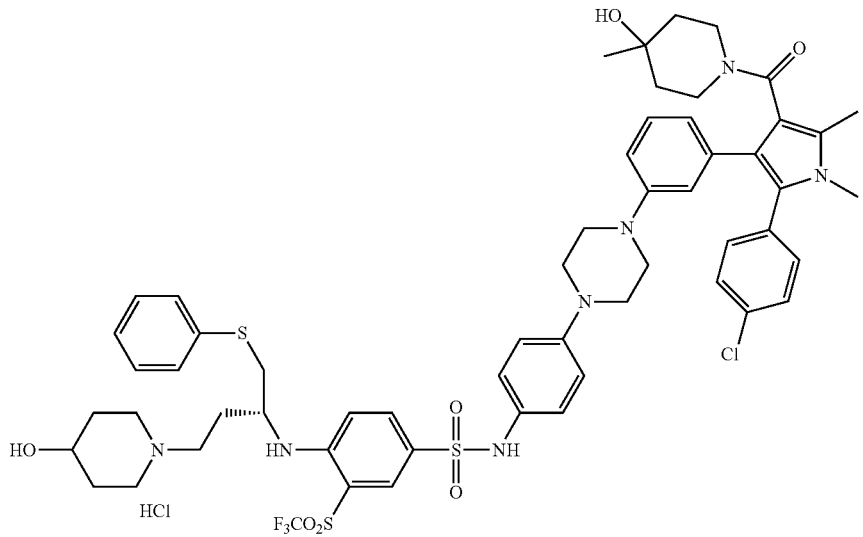 |

| Compound No. | |
|---|---|
| 173 | 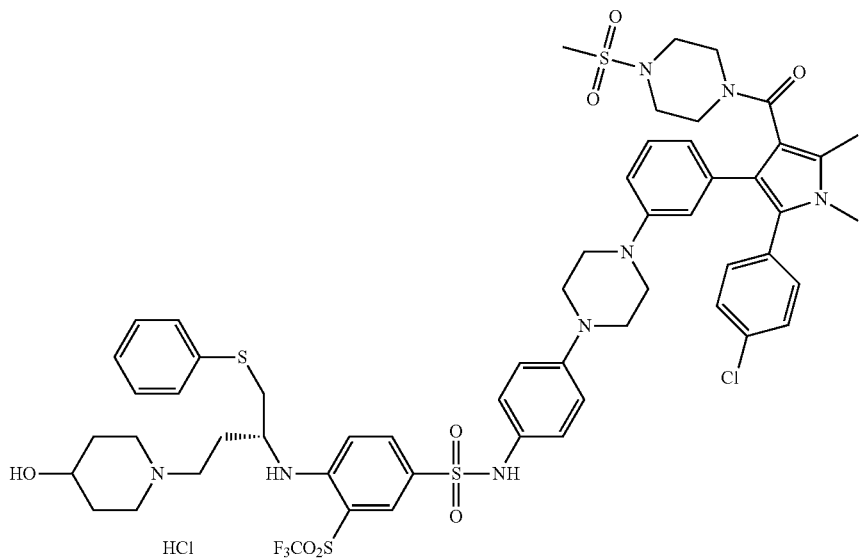 |
| 174 | 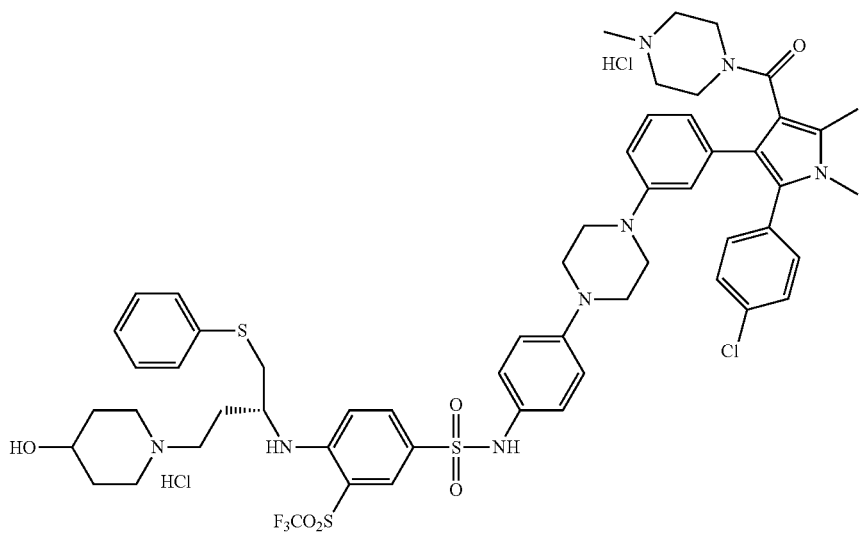 |
| 175 | 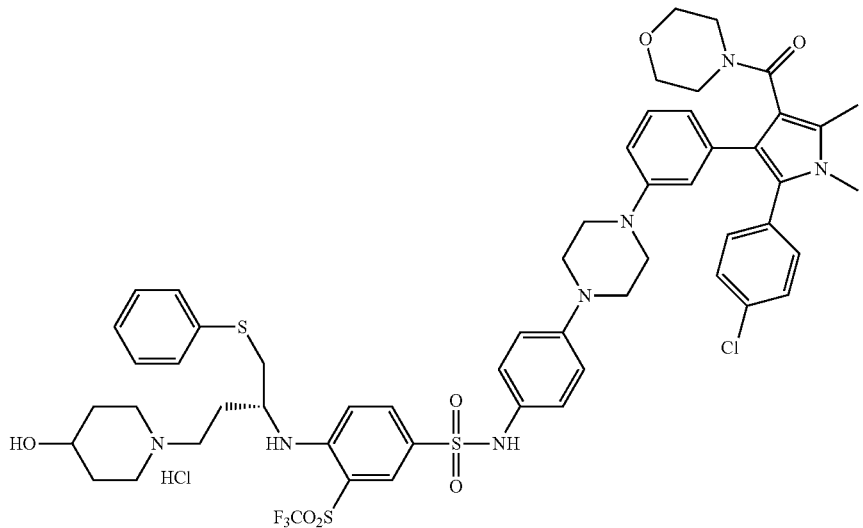 |

| Compound No. | |
|---|---|
| 176 | 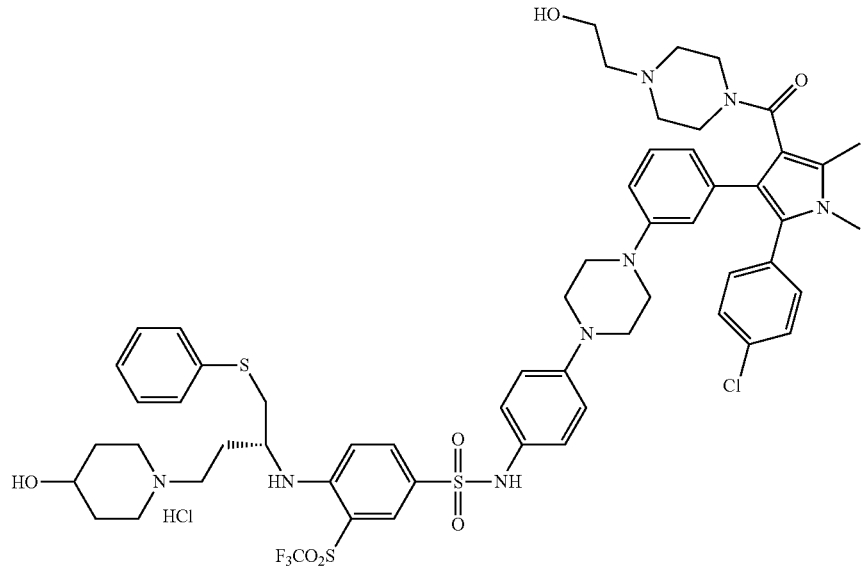 |
| 177 | 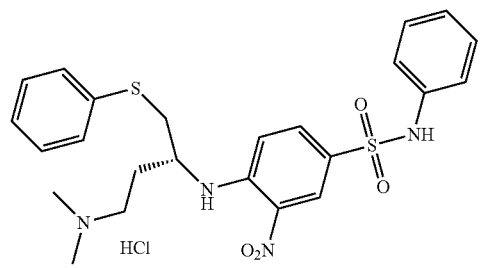 [SMILES: CN(C)CC[C@H](CSc1ccccc1)Nc1ccc(S(=O)(=O)Nc2ccccc2)cc1[N+](=O)[O-] ; Cl] |
| 178 | 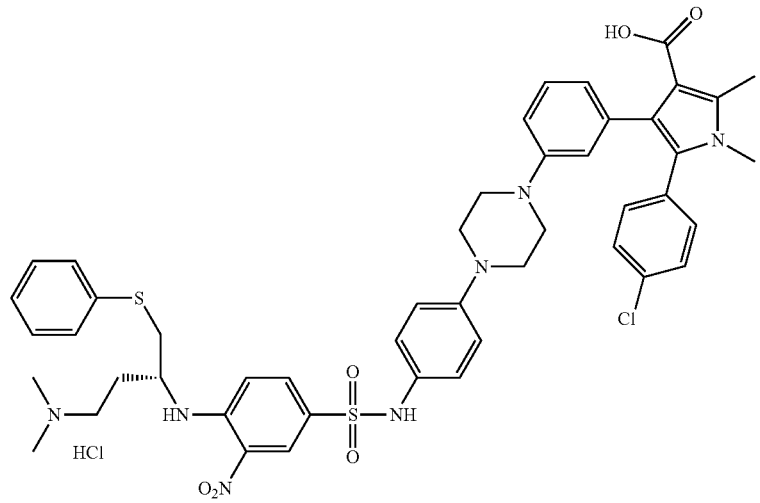 |

-continued
| Compound No. |
|---|
| 179 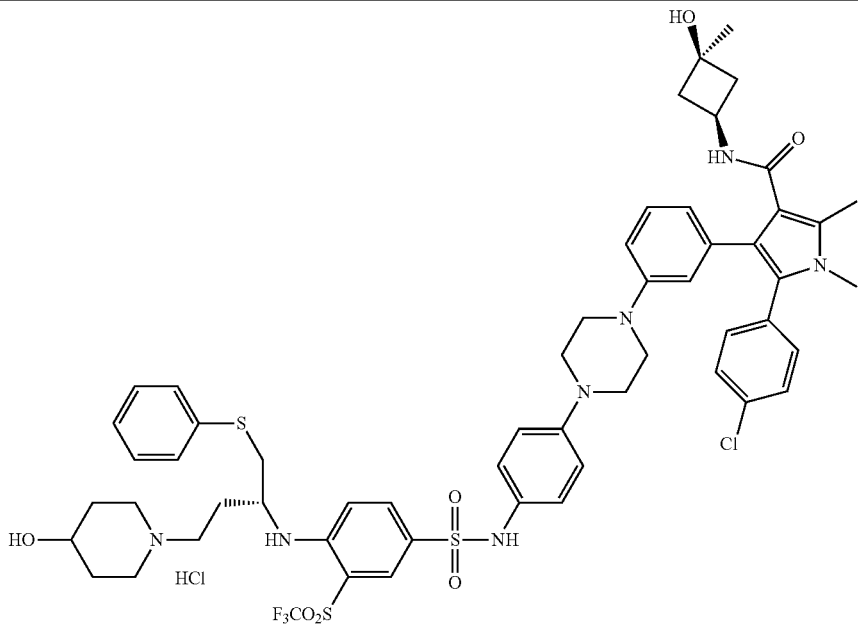 |
| 180 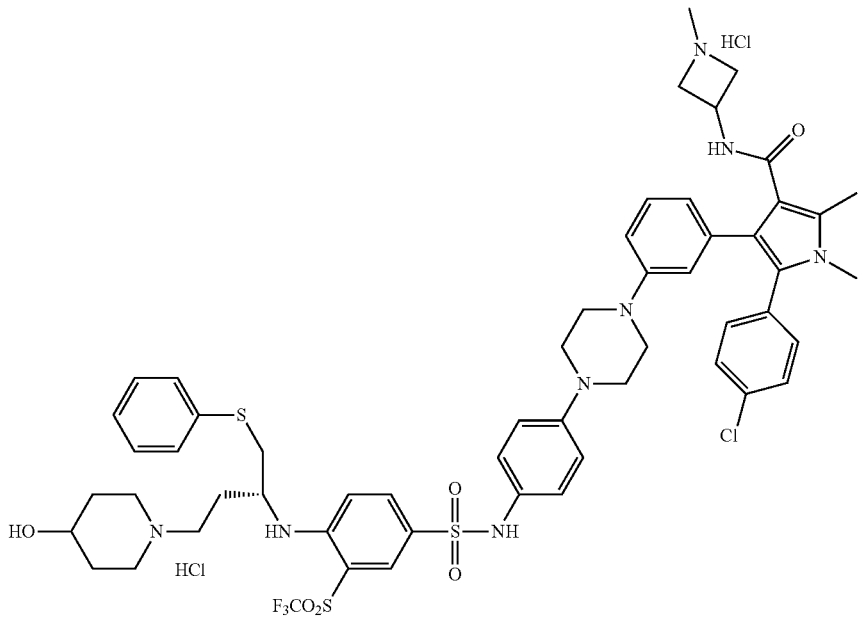 |

-continued
| Compound No. | |
|---|---|
| 181 | 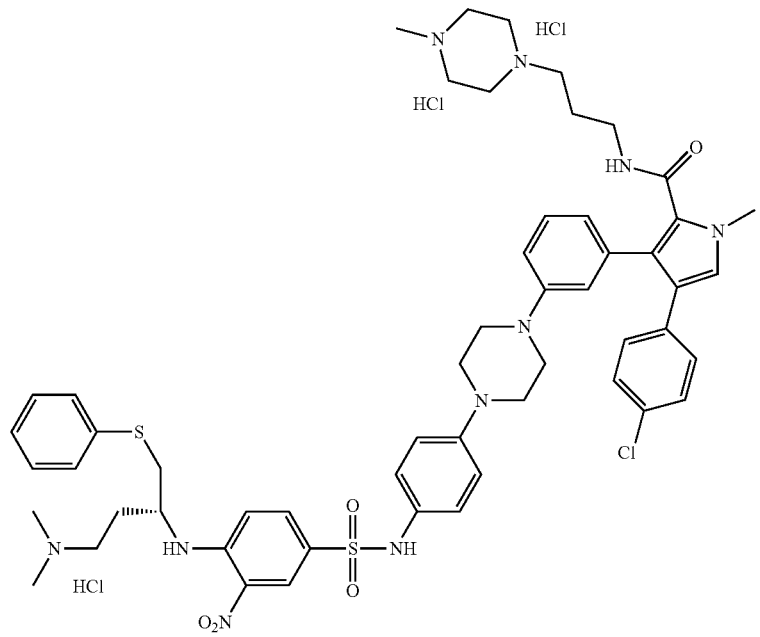 [SMILES: CN(C)CC[C@H](CSc1ccccc1)Nc1ccc(S(=O)(=O)Nc2ccc(N3CCN(c4cccc(-c5c(-c6ccc(Cl)cc6)cn(C)c5C(=O)NCCCN5CCN(C)CC5)c4)CC3)cc2)cc1[N+](=O)[O-] ; Cl ; Cl ; Cl] |
| 182 | 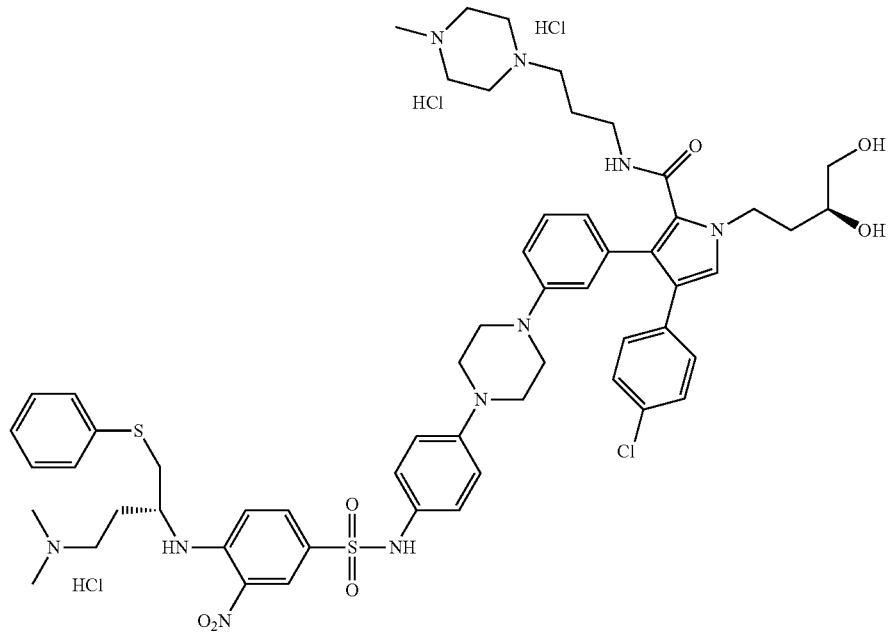 [SMILES: CN(C)CC[C@H](CSc1ccccc1)Nc1ccc(S(=O)(=O)Nc2ccc(N3CCN(c4cccc(-c5c(-c6ccc(Cl)cc6)cn(CC[C@H](O)CO)c5C(=O)NCCCN5CCN(C)CC5)c4)CC3)cc2)cc1[N+](=O)[O-] ; Cl ; Cl ; Cl] |

-continued
| Compound No. |
|---|
| 183 |
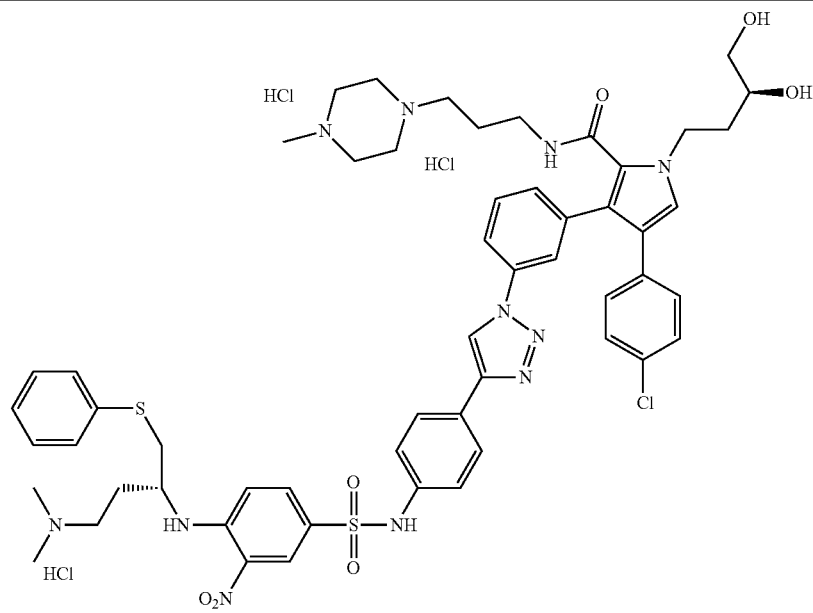
184
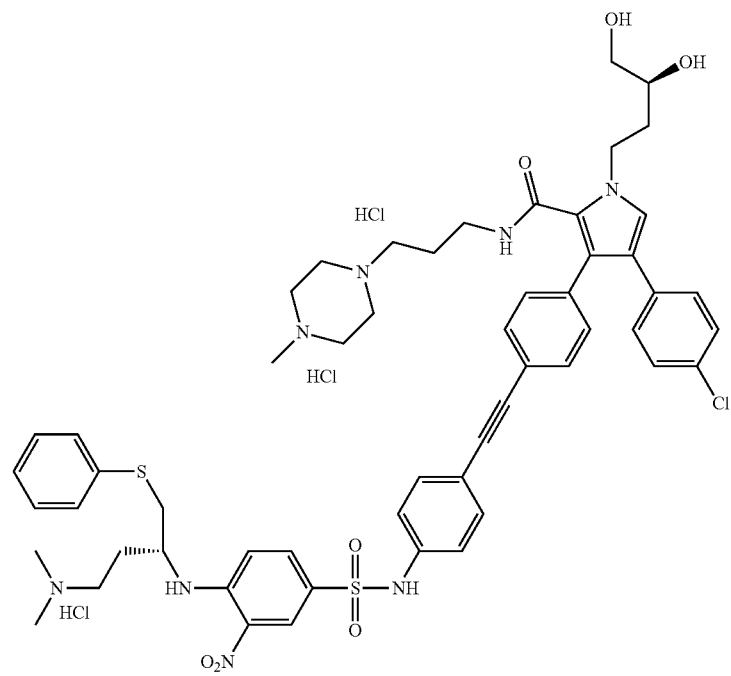 [SMILES: CN(C)CC[C@H](CSc1ccccc1)Nc1ccc(S(=O)(=O)Nc2ccc(C#Cc3ccc(-c4c(-c5ccc(Cl)cc5)cn(CC[C@H](O)CO)c4C(=O)NCCCN4CCN(C)CC4)cc3)cc2)cc1[N+](=O)[O-] ; Cl ; Cl ; Cl]

| Compound No. | |
|---|---|
| 185 | 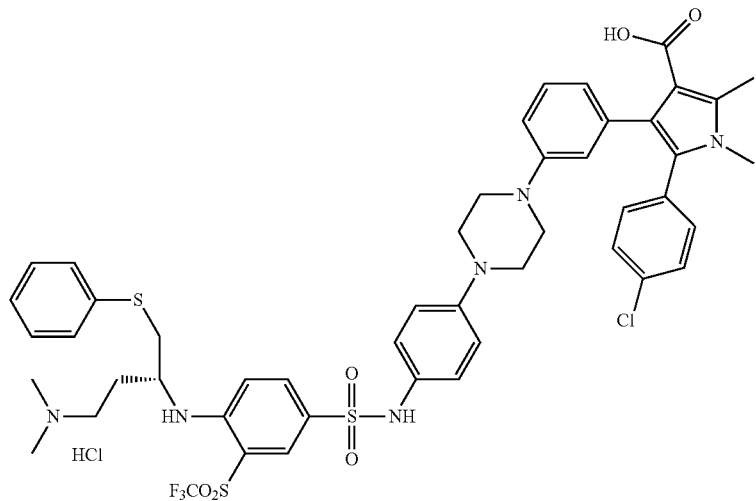 |
| 186 | 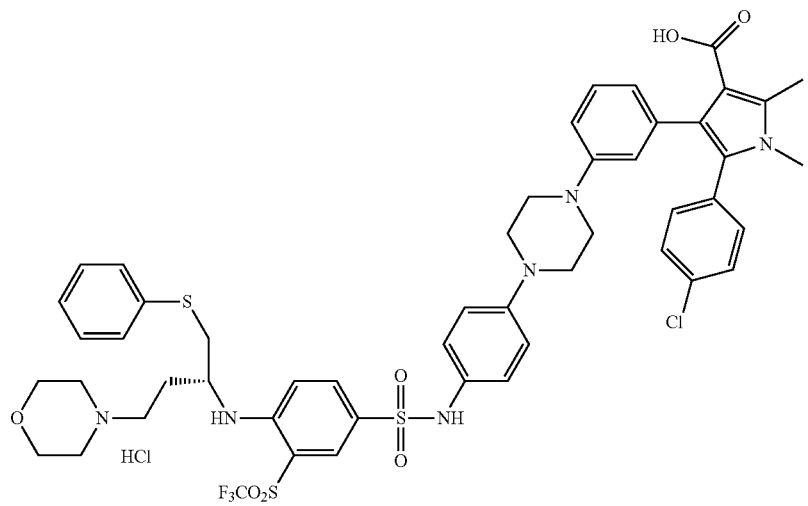 |
| 187 | 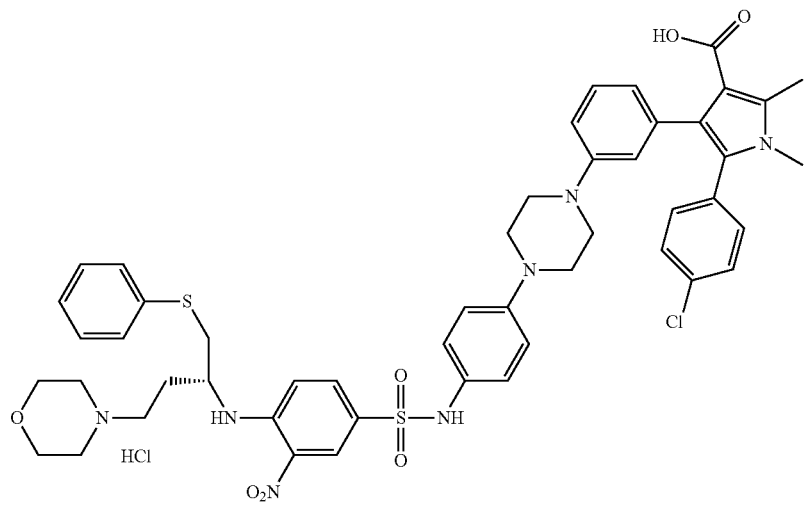 [SMILES: Cc1c(C(=O)O)c(-c2cccc(N3CCN(c4ccc(NS(=O)(=O)c5ccc(N[C@H](CCN6CCOCC6)CSc6ccccc6)c([N+](=O)[O-])c5)cc4)CC3)c2)c(-c2ccc(Cl)cc2)n1C ; Cl] |

| Compound No. | |
|---|---|
| 188 | 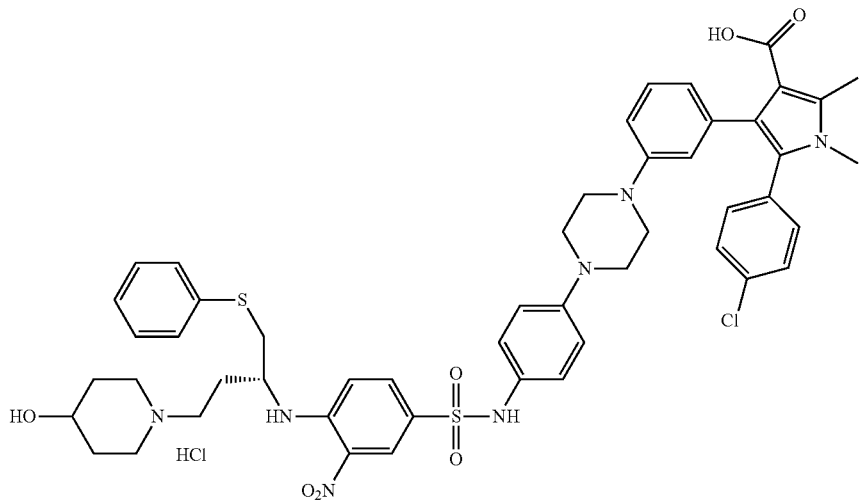 [SMILES: Cc1c(C(=O)O)c(-c2cccc(N3CCN(c4ccc(NS(=O)(=O)c5ccc(N[C@H](CCN6CCC(O)CC6)CSc6ccccc6)c([N+](=O)[O-])c5)cc4)CC3)c2)c(-c2ccc(Cl)cc2)n1C ; Cl] |
| 189 | 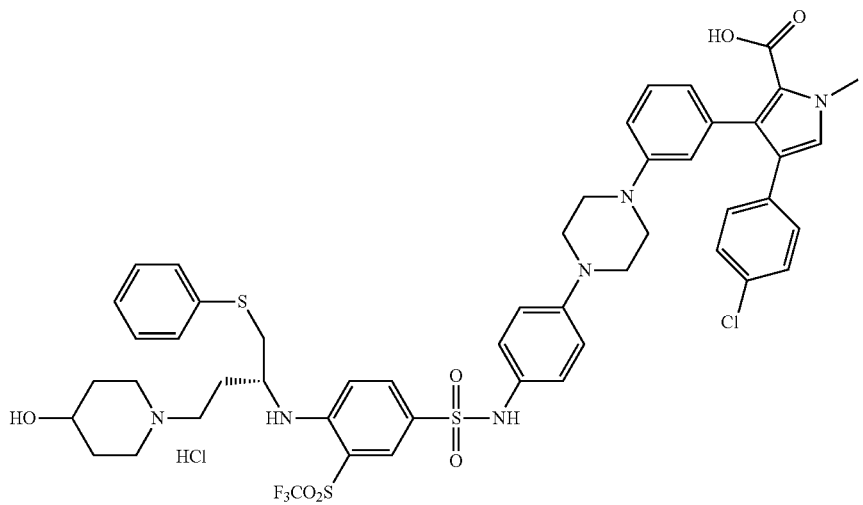 |
| 190 | 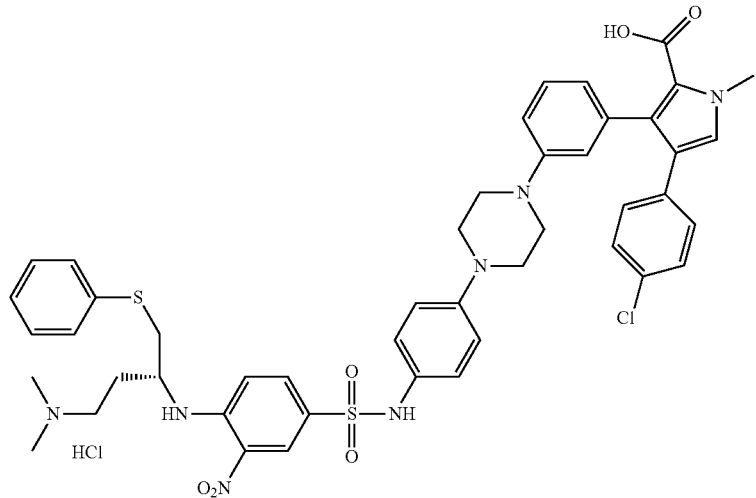 [SMILES: CN(C)CC[C@H](CSc1ccccc1)Nc1ccc(S(=O)(=O)Nc2ccc(N3CCN(c4cccc(-c5c(-c6ccc(Cl)cc6)cn(C)c5C(=O)O)c4)CC3)cc2)cc1[N+](=O)[O-] ; Cl] |

| Compound No. | |
|---|---|
| 191 | 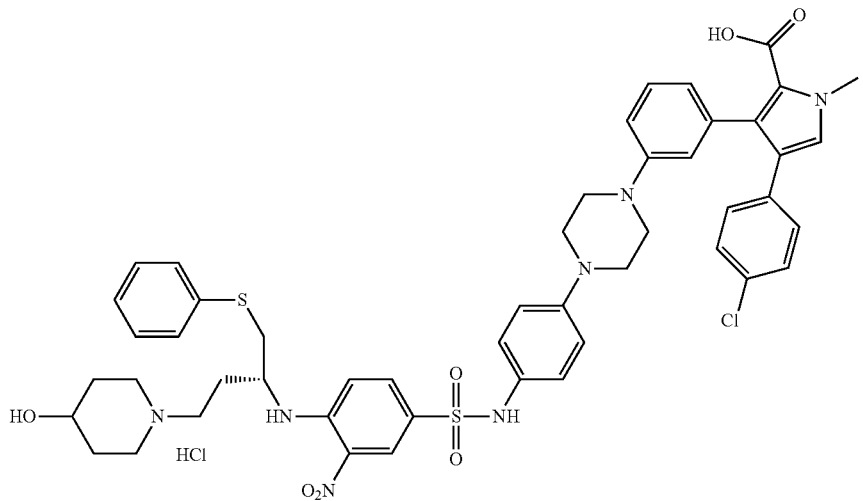 [SMILES: Cn1cc(-c2ccc(Cl)cc2)c(-c2cccc(N3CCN(c4ccc(NS(=O)(=O)c5ccc(N[C@H](CCN6CCC(O)CC6)CSc6ccccc6)c([N+](=O)[O-])c5)cc4)CC3)c2)c1C(=O)O ; Cl] |
| 192 | 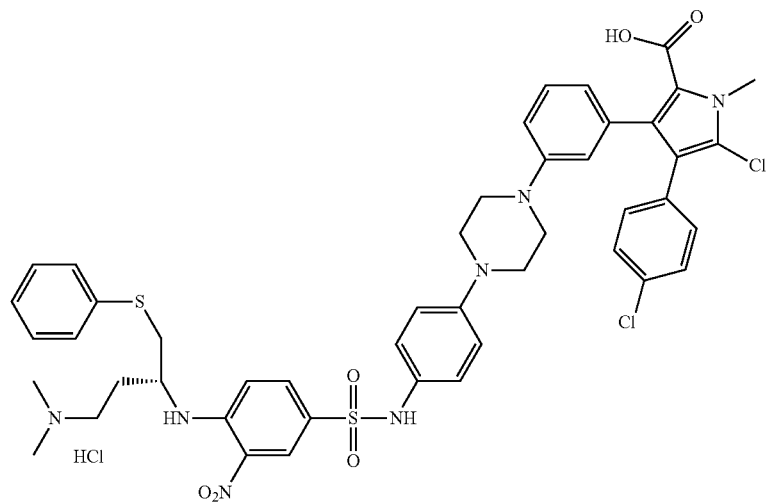 [SMILES: CN(C)CC[C@H](CSc1ccccc1)Nc1ccc(S(=O)(=O)Nc2ccc(N3CCN(c4cccc(-c5c(-c6ccc(Cl)cc6)c(Cl)n(C)c5C(=O)O)c4)CC3)cc2)cc1[N+](=O)[O-] ; Cl] |
| 193 | 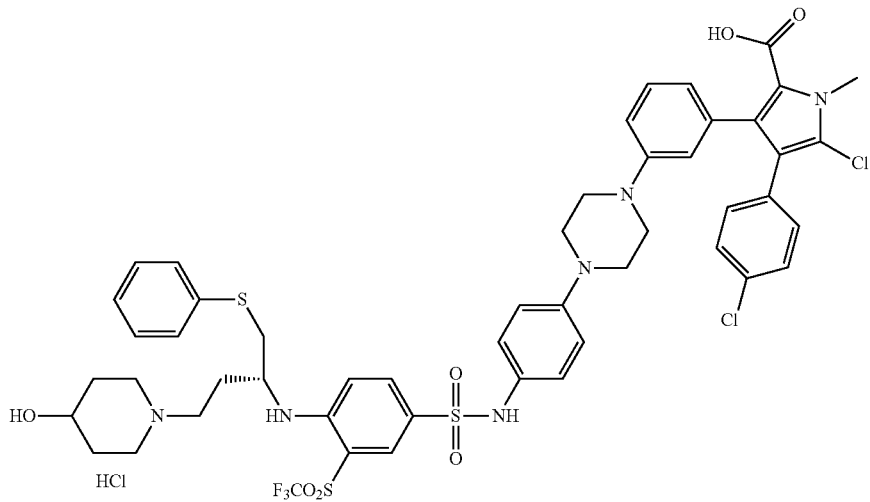 |

| Compound No. |
|---|
| 194 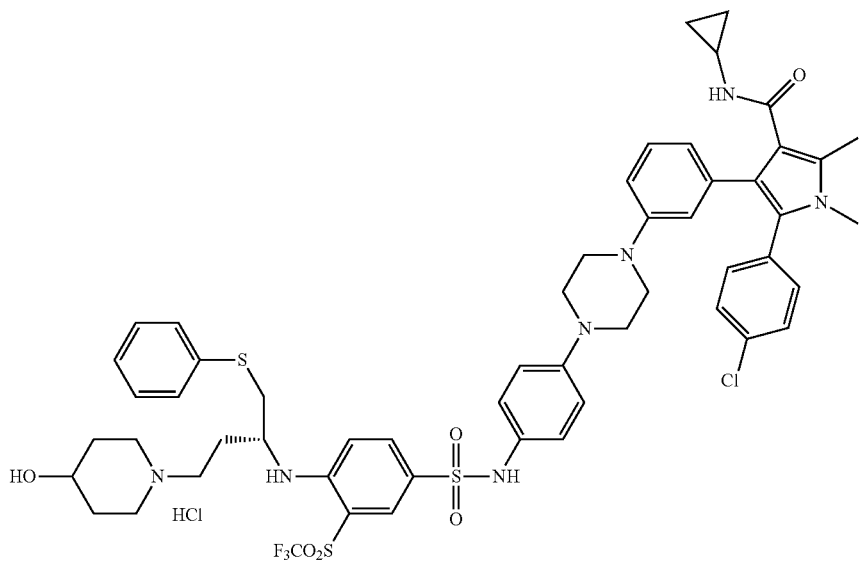 |
| 195 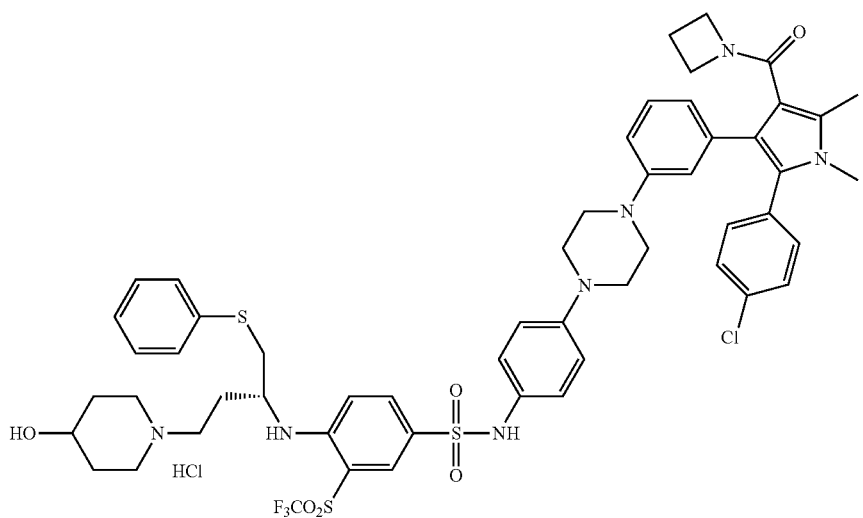 |
| 196 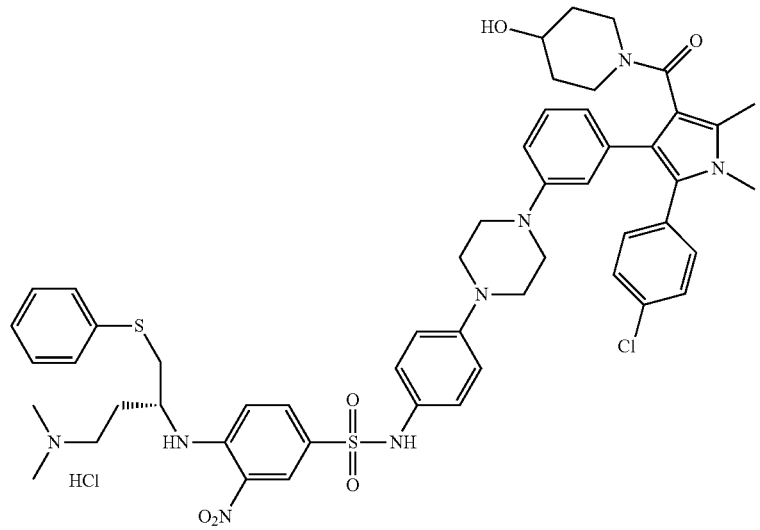 [SMILES: Cc1c(C(=O)N2CCC(O)CC2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C ; Cl] |

| Compound No. |
| --- |
197
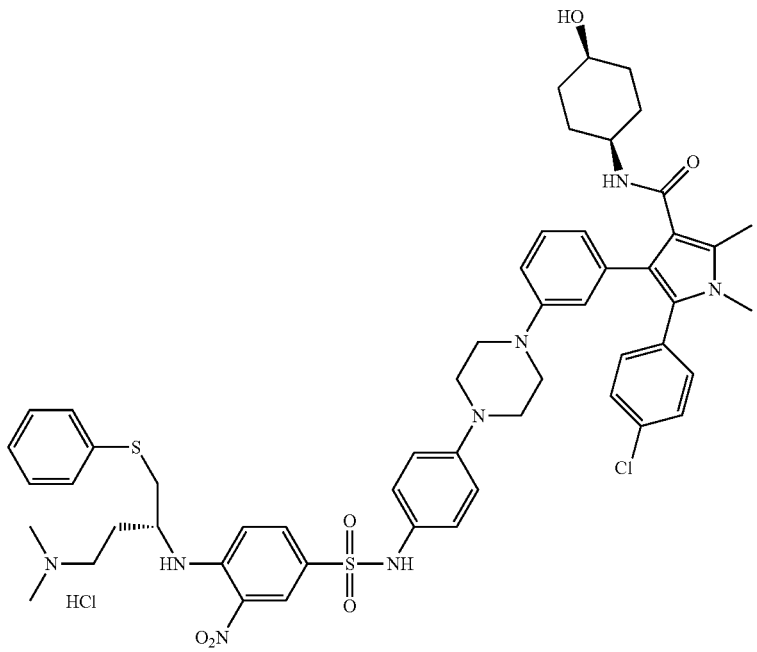 [SMILES: Cc1c(C(=O)N[C@H]2CC[C@@H](O)CC2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C ; Cl]
198
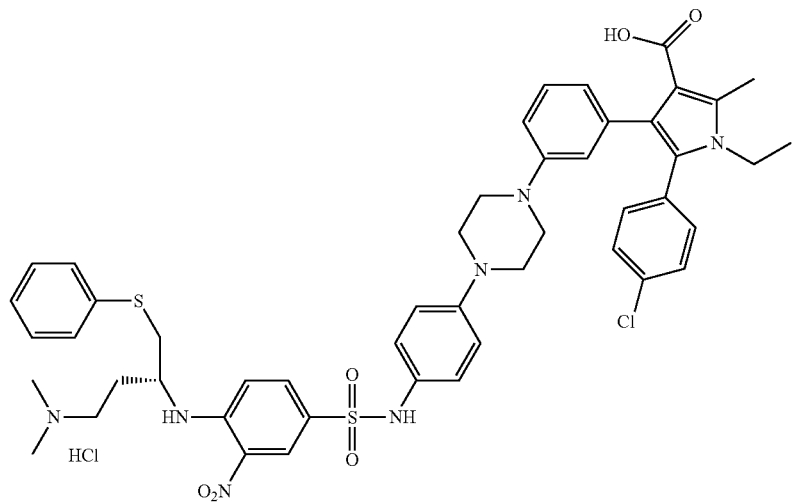 [SMILES: CCn1c(C)c(C(=O)O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c1-c1ccc(Cl)cc1 ; Cl]

| Compound No. | |
|---|---|
| 199 | 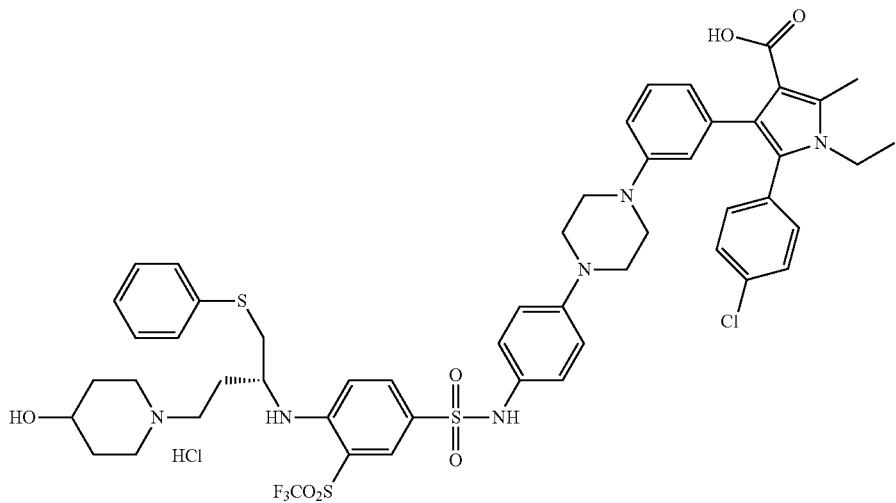 |
| 200 | 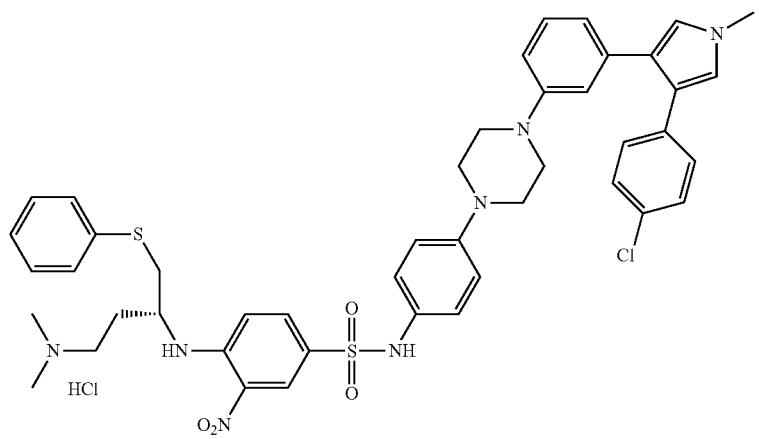 [SMILES: CN(C)CC[C@H](CSc1ccccc1)Nc1ccc(S(=O)(=O)Nc2ccc(N3CCN(c4cccc(-c5cn(C)cc5-c5ccc(Cl)cc5)c4)CC3)cc2)cc1[N+](=O)[O-] ; Cl] |
| 201 | 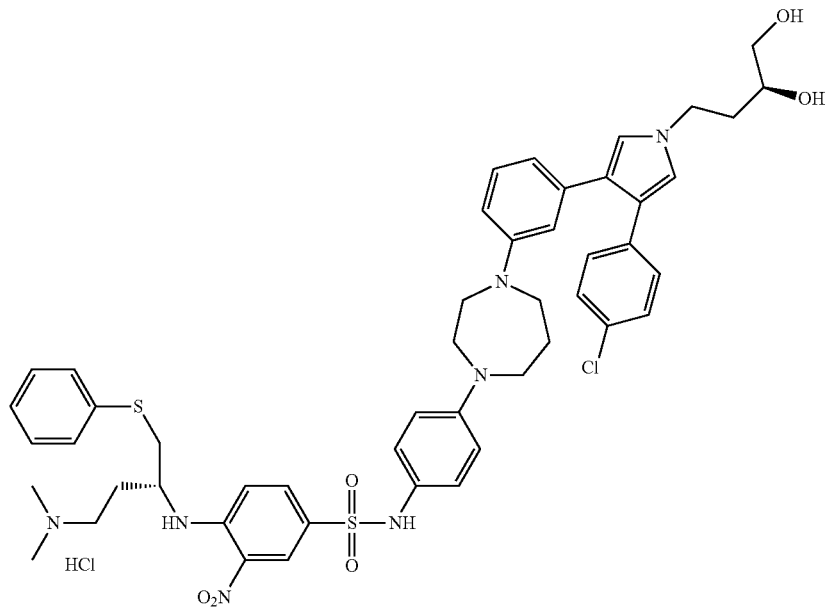 [SMILES: CN(C)CC[C@H](CSc1ccccc1)Nc1ccc(S(=O)(=O)Nc2ccc(N3CCCN(c4cccc(-c5cn(CC[C@H](O)CO)cc5-c5ccc(Cl)cc5)c4)CC3)cc2)cc1[N+](=O)[O-] ; Cl] |

-continued
| Compound No. |
| --- |
202
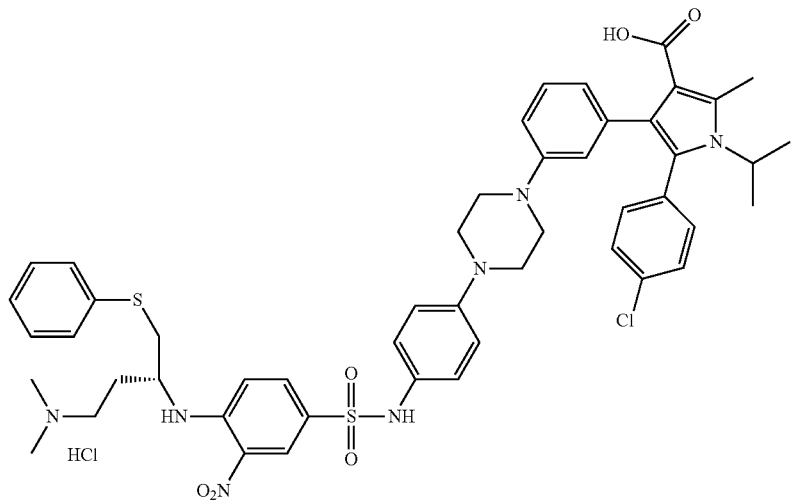 [SMILES: Cc1c(C(=O)O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C(C)C ; Cl]
203
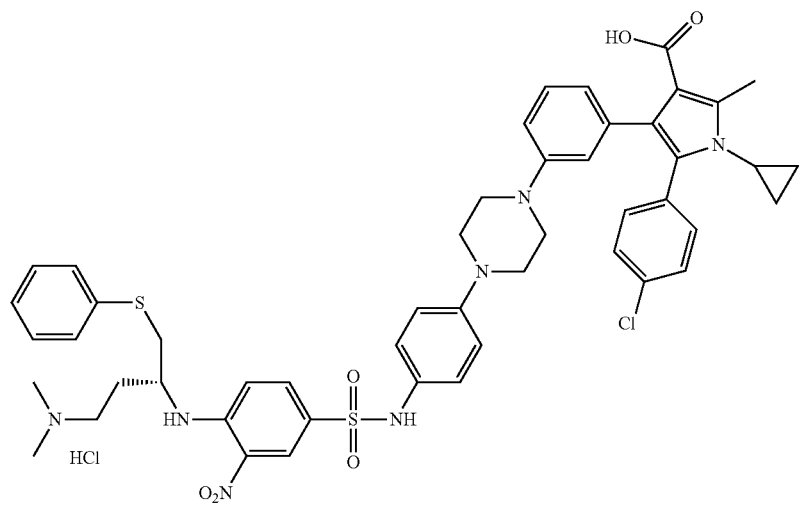 [SMILES: Cc1c(C(=O)O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C1CC1 ; Cl]
204
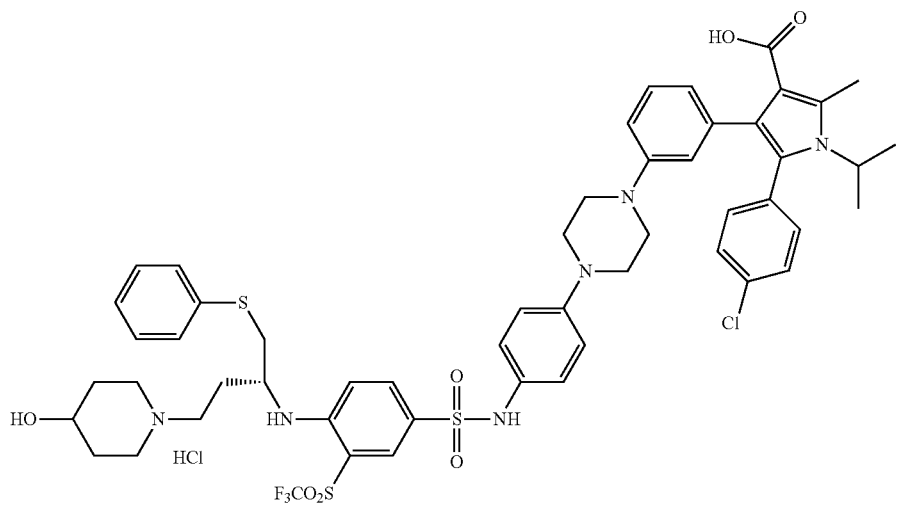

-continued
| Compound No. | |
|---|---|
| 205 | 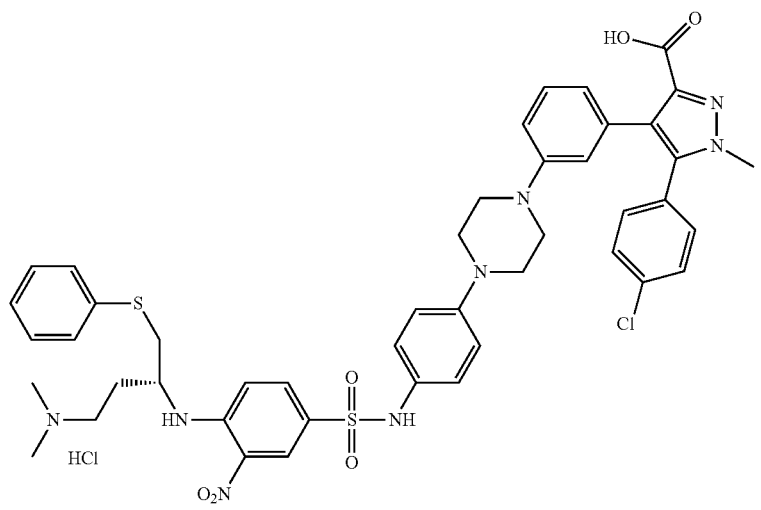 [SMILES: CN(C)CC[C@H](CSc1ccccc1)Nc1ccc(S(=O)(=O)Nc2ccc(N3CCN(c4cccc(-c5c(C(=O)O)nn(C)c5-c5ccc(Cl)cc5)c4)CC3)cc2)cc1[N+](=O)[O-] ; Cl] |
| 206 | 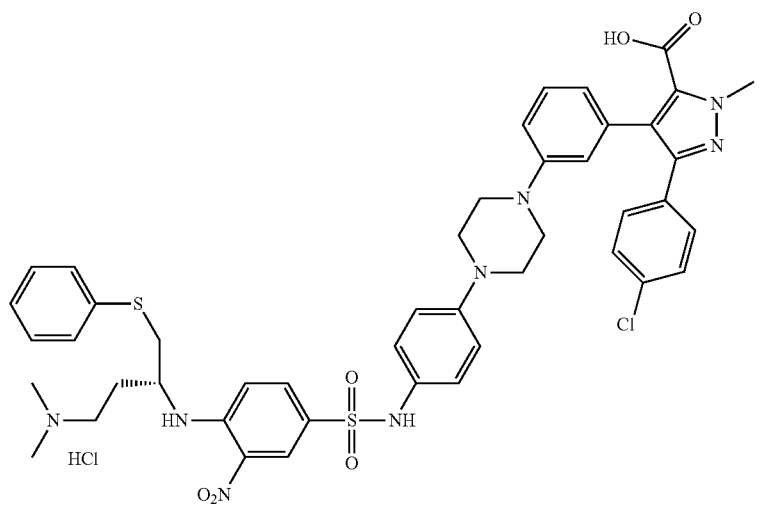 [SMILES: CN(C)CC[C@H](CSc1ccccc1)Nc1ccc(S(=O)(=O)Nc2ccc(N3CCN(c4cccc(-c5c(-c6ccc(Cl)cc6)nn(C)c5C(=O)O)c4)CC3)cc2)cc1[N+](=O)[O-] ; Cl] |
| 207 | 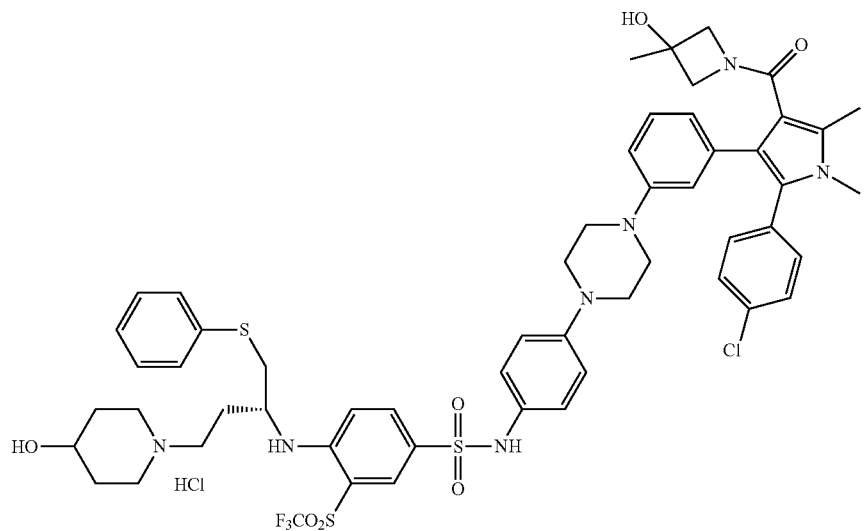 |

| Compound No. | |
|---|---|
| 208 | 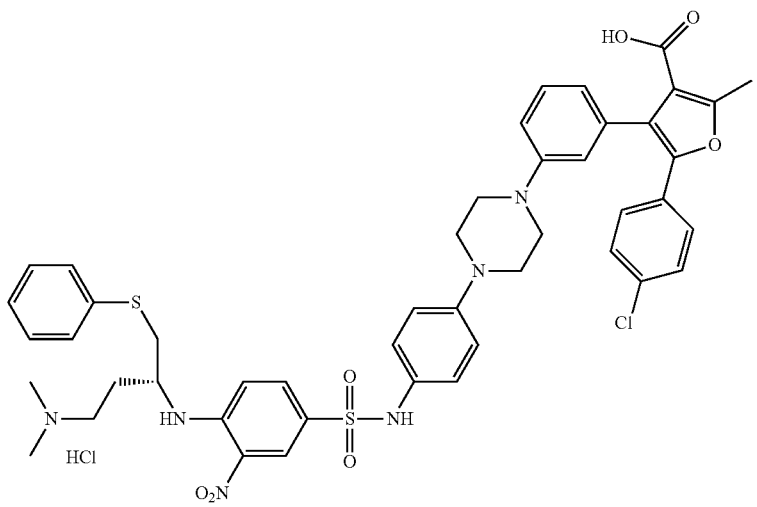 [SMILES: Cc1oc(-c2ccc(Cl)cc2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c1C(=O)O ; Cl] |
| 209 | 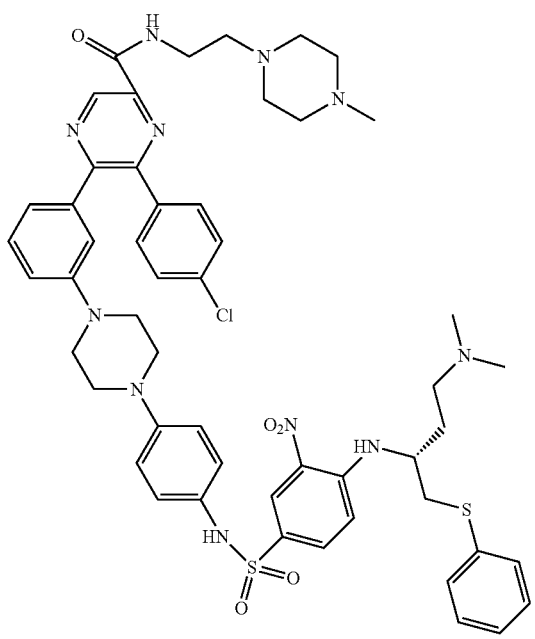 [SMILES: CN(C)CC[C@H](CSc1ccccc1)Nc1ccc(S(=O)(=O)Nc2ccc(N3CCN(c4cccc(-c5ncc(C(=O)NCCN6CCN(C)CC6)nc5-c5ccc(Cl)cc5)c4)CC3)cc2)cc1[N+](=O)[O-]] |

The present invention provides Bcl-2/Bcl-xL inhibitors, as exemplified by compounds of structural formula (I), for the treatment of a variety of diseases and conditions wherein inhibition of Bcl-2 and/or Bcl-xL has a beneficial effect. In one embodiment, the present invention relates to a method of treating an individual suffering from a disease or condition wherein inhibition of the Bcl-2/Bcl-xL provides a benefit comprising administering a therapeutically effective amount of a compound of structural formula (I) to an individual in need thereof.

The method of the present invention can be accomplished by administering a compound of structural formula (I) as the neat compound or as a pharmaceutical composition. Administration of a pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) and, optionally, a second therapeutic agent useful in the treatment of diseases and conditions wherein inhibition of Bcl-2/Bcl-xL provides a benefit, packaged separately or together, and an insert having instructions for using these active agents.

In many embodiments, a compound of structural formula (I) is administered in conjunction with a second therapeutic agent useful in the treatment of a disease or condition wherein inhibition of Bcl-2/Bcl-xL provides a benefit. The second therapeutic agent is different from the compound of structural formula (I). A compound of structural formula (I) and the second therapeutic agent can be administered simultaneously or sequentially to achieve the desired effect. In addition, the compound of structural formula (I) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agents, for example, but not limited to, anticancer agents.

The diseases and conditions that can be treated in accordance to the invention include, for example, cancers. A variety of cancers can be treated including, but not limited to: carcinomas, including bladder (including accelerated and metastic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyoscarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Additional forms of cancer treatable by the Bcl-2/Bcl-xL inhibitors of the present invention include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

Additional diseases and conditions, including cancers, that can be treated by administration of a present Bcl-2/Bcl-xL inhibitor are disclosed in U.S. Patent Publication No. 2007/0027135; U.S. Pat. No. 7,432,304; and U.S. Patent Publication No. 2010/0278921, each incorporated herein in its entirety.

In the present method, a therapeutically effective amount of one or more compound (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A compound of structural formula (I) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) is administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the Bcl-2/Bcl-xL inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present Bcl-2/Bcl-xL inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A compound of structural formula (I) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Bcl-2/Bcl-xL inhibitor of structural formula (I), or a composition containing the same, can be from about 1 ng/kg to about 200 g/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 g/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

In the treatment of a cancer, a compound of structural formula (I) can be administered with a chemotherapeutic agent and/or radiation.

Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present Bcl-2/Bcl-xL inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a Bcl-2/Bcl-xL inhibitor of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the invention include hormones and antagonists thereof, radioisotopes, antibodies, natural products, and combinations thereof.

Examples of chemotherapeutic agents useful in a method of the present invention are listed in the following table.

TABLE 1

Alkylating agents
Nitrogen mustards mechlorethamine
cyclophosphamide
ifosfamide
melphalan
chlorambucil
uracil mustard
temozolomide TABLE 1-continued Nitrosoureas carmustine (BCNU)
lomustine (CCNU)
semustine (methyl-CCNU)
chlormethine
streptozocin
Ethylenimine/Methyl-melamine triethylenemelamine (TEM)
triethylene thiophosphoramide
(thiotepa)
hexamethylmelamine
(HMM, altretamine)
Alkyl sulfonates busulfan
pipobroman
Triazines dacarbazine (DTIC)
Antimetabolites
Folic Acid analogs methotrexate
trimetrexate
pemetrexed
(Multi-targeted antifolate)
Natural products
Antimitotic drugs
Taxanes paclitaxel
Vinca alkaloids
vinblastine (VLB)
vincristine
vinorelbine
vindesine
Taxotere ® (docetaxel)
estramustine
estramustine phosphate
Epipodophylotoxins etoposide
teniposide
Antibiotics actimomycin D
daunomycin (rubidomycin)
doxorubicin (adriamycin)
mitoxantroneidarubicin
bleomycin
splicamycin (mithramycin)
mitromycin-C
dactinomycin
aphidicolin
epirubicin
idarubicin
daunorubicin
mithramycin
deoxy co-formycin
Enzymes L-asparaginase
L-arginase
Pyrimidine analogs 5-fluorouracil
fluorodeoxyuridine
gemcitabine
cytosine arabinoside
(AraC, cytarabine)
5-azacytidine
2,2'-difluorodeoxy-cytidine
floxuridine
pentostatine
Purine analogs 6-mercaptopurine
6-thioguanine
azathioprine
2'-deoxycoformycin
(pentostatin)
erythrohydroxynonyl-adenine (EHNA)
fludarabine phosphate
2-chlorodeoxyadenosine
(cladribine, 2-CdA)
Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equivalents
dexamethasone
Radiosensitizers metronidazole
misonidazole
desmethylmisonidazole
pimonidazole
etanidazole
nimorazole
RSU 1069
EO9
RB 6145
Nonsteroidal antiandrogens SR4233
flutamide
nicotinamide
5-bromodeozyuridine
5-iododeoxyuridine
bromodeoxycytidine
Miscellaneous agents
Platinium coordination complexes cisplatin
carboplatin
oxaliplatin
anthracenedione
mitoxantrone
Substituted urea hydroxyurea
Methylhydrazine derivatives N-methylhydrazine (MIH)
procarbazine
Adrenocortical suppressant mitotane (o,p'-DDD)
ainoglutethimide
ainoglutethimide
Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents TABLE 1-continued

| Antiandrogens |
| --- |
| flutamide |
| gonadotropin-releasing hormone analogs |
| leuprolide |

| Cytokines |
| --- |
| interferon (α, β, γ) |
| interleukin-2 |

| Photosensitizers |
| --- |
| hematoporphyrin derivatives |
| PHOTOFRIN® |
| benzoporphyrin derivatives |
| Npe6 |
| tin etioporphyrin (SnET2) |
| pheoboride-a |
| bacteriochlorophyll-a |
| naphthalocyanines |
| phthalocyanines |
| zinc phthalocyanines |

| Radiation |
| --- |
| X-ray |
| ultraviolet light |
| gamma radiation |
| visible light |
| infrared radiation |
| microwave radiation |

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792, trityl cysteine (NSC 83265), vinblastine sulfate (NSC 49842), vincristine sulfate (NSC 67574), natural and synthetic epothilones including but not limited to epothilone A, eopthilone B, and discodermolide (see Service, (1996) Science, 274: 2009) estramustine, nocodazole, MAP4, and the like. Examples of such agents are also described in Bulinski (1997) *J. Cell Sci.* 110:3055 3064; Panda (1997) *Proc. Natl. Acad. Sci. USA* 94:10560-10564; Muhlradt (1997) *Cancer Res.* 57:3344-3346; Nicolaou (1997) *Nature* 397:268-272; Vasquez (1997) *Mol. Biol. Cell.* 8:973-985; and Panda (1996) *J. Biol. Chem.* 271:29807-29812.

Cytostatic agents that may be used include, but are not limited to, hormones and steroids (including synthetic analogs): 17-α-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminogluthimide, estramustine, medroxyprogesteroneacetate, leuprolide, flutamide, toremifene, zoladex.

Other cytostatic agents are antiangiogenics, such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX® (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

Additional second therapeutic agents that can be administered with a Bcl-2/Bcl-xL inhibitor of the present invention are disclosed in U.S. Patent Publication 2007/0027135; U.S. Pat. No. 7,432,304; and U.S. Patent Publication No. 2010/0278921, each incorporated herein by reference.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I).

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, the compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the Bcl-2/Bcl-xL inhibitors are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

Prior Bcl-2/Bcl-xL inhibitors possessed properties that hindered their development as therapeutic agents. In accordance with an important feature of the present invention, compounds of structural formula (I) were synthesized and evaluated as inhibitors for Bcl-2/Bcl-xL. For example, compounds of the present invention typically have a bonding affinity ($IC_{50}$) to Bcl-2/Bcl-xL of less than 100 less than 50 µM, less than 25 µM, and less than 5 µM.

Synthesis of Compounds

Compounds of the present invention and were prepared as follows. The following synthetic schemes are representative of the reactions used to synthesize compounds of structural formula (I). Modifications and alternate schemes to prepare Bcl-2/Bcl-xL inhibitors of the invention are readily within the capabilities of persons skilled in the art.

Solvents and reagents were obtained commercially and used without further purification. Chemical shifts (δ) of NMR spectra are reported as δ values (ppm) downfield relative to an internal standard, with multiplicities reported in the usual manner.

Unless otherwise stated all temperatures are in degrees Celsius.

In the synthetic methods, the examples, and throughout the specification, the abbreviations have the following meanings:

| | |
|---|---|
| DMF | dimethylformamide |
| min | minutes |
| $CH_2Cl_2$/DCM | methylene chloride |
| MeOH | methanol |
| $Na_2SO_4$ | sodium sulfate |
| AcOH | acetic acid |
| MS | mass spectrometry |
| $Na_2CO_3$ | sodium carbonate |
| h | hours |
| $NaHCO_3$ | sodium bicarbonate |
| HCl | hydrochloric acid |
| g | gram |
| mol | mole |
| mmol | millimole |
| mL | milliliter |
| TMS | tetramethylsilane |
| TFA | trifluoroacetic acid |
| KOH | potassium hydroxide |
| $NH_2OH \cdot HCl$ | hydroxylamine hydrochloride |
| NaOMe | sodium methoxide |
| $CD_3OD$ | deuterated methanol |
| M | molar |
| KOtBu | potassium tert-butoxide |
| DMSO | dimethyl sulfoxide |
| N | normal |
| $SOCl_2$ | thionyl chloride |
| $CD_3CN$ | deuterated acetonitrile |
| RT | room temperature |
| DME | dimethyl ether |
| CuI | copper iodide |
| NMR | nuclear magnetic resonance spectrometry |
| THF | tetrahydrofuran |
| NaOH | sodium hydroxide |
| $PdCl_2(PPh)_3$ | dichloro-triphenylphosphino-palladium (II) |
| $NEt_3$ | triethylamine |
| $CDCl_3$ | deuterated chloroform |
| Hz | Hertz |
| Ar | aryl |
| $H_2O$ | water |
| EtOH | ethanol |
| EDC | 1-ethyl-3-(3-dimethylaminopropyl)carbodiimide hydrochloride |
| HOBt | 1-hydroxybenzotriazole |
| DIPEA | N,N-diisopropylethylamine |
| DMAP | 4-dimethylaminopyridine |
| $K_2CO_3$ | potassium carbonate |
| NCS | N-chlorosuccinimide |
| NIS | N-iodosuccinimide |
| NBS | N-bromosuccinimide |
| $NaIO_4$ | sodium periodate |
| $NH_4OAc$ | ammonium acetate |
| CAN | cerium(IV)ammonium nitrate |
| $CH_3CN$/MeCN | acetonitrile |
| $CsCO_3$ | cesium carbonate |

-continued

| Pd(OAc)$_2$ | palladium(II) diacetate |
| ClPO(OEt)$_2$ | diethyl chlorophosphate |
| NaOH | sodium hydroxide |
| AlCl$_3$ | aluminum chloride |
| (PhO)$_2$PON$_3$ | diphenyl phosphorazidate |
| t-BuOH | t-butyl alcohol |
| NH$_3$ | ammonia |
| MeI | methyl iodide |
| LDA | lithium diisopropylamide |
| BOC | di-tert-buyl dicarbonate |
| AcCl | acetyl chloride |
| MnO$_2$ | manganese dioxide |
| MTBE | methyl tet-butyl ether |
| NaNO$_2$ | sodium nitrite |
| SnCl$_2$ | tin(II)chloride |
| Pd/C | palladium on carbon |
| Et$_2$NH | diethylamine |
| (PPh$_3$)$_4$Pd | tetrakis(triphenylphosphine)palladium(0) |
| NaN$_3$ | sodium azide |
| n-BuLi | n-butyl lithium |
| mCPBA | m-chloroperoxybenzoic acid |
| Ac$_2$O | acetic anhydride |
| Pd(dba)$_2$ | bis(dibenzylidene acetone)palladium(0) |
| PBu$_3$ | tributyl phosphine |
| NaOtBu | sodium tert-butoxide |

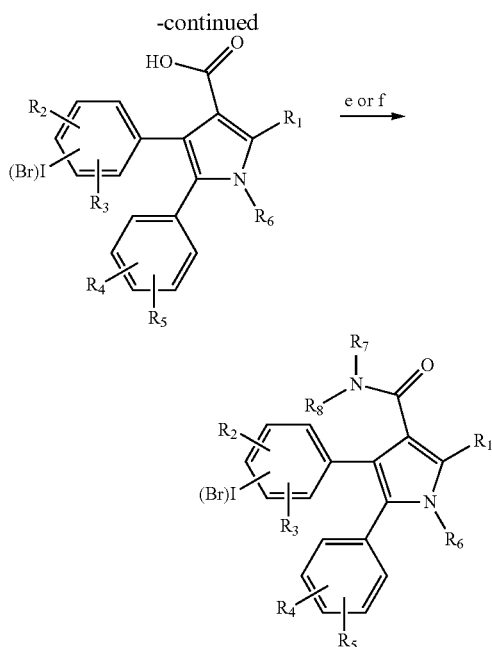

a) ArCHO, cat. piperidine, cat. AcOH, toluene, reflux; b) ArCHO, Et$_3$N, thiazolium catalyst, 70° C.; c) i. R$_6$NH$_2$, MeOH, room temp; ii. 1M HCl, H$_2$O; d) NaOH, Dioxane/EtOH/H$_2$O, reflux; e) R$_7$NHR$_8$, EDC, HOBt, DCM, DIPEA, room temp; f) i. SOCl$_2$ reflux 2 h ii. R$_7$NHR$_8$, DMAP, 1,2-dichloroethane, reflux Scheme, core-1

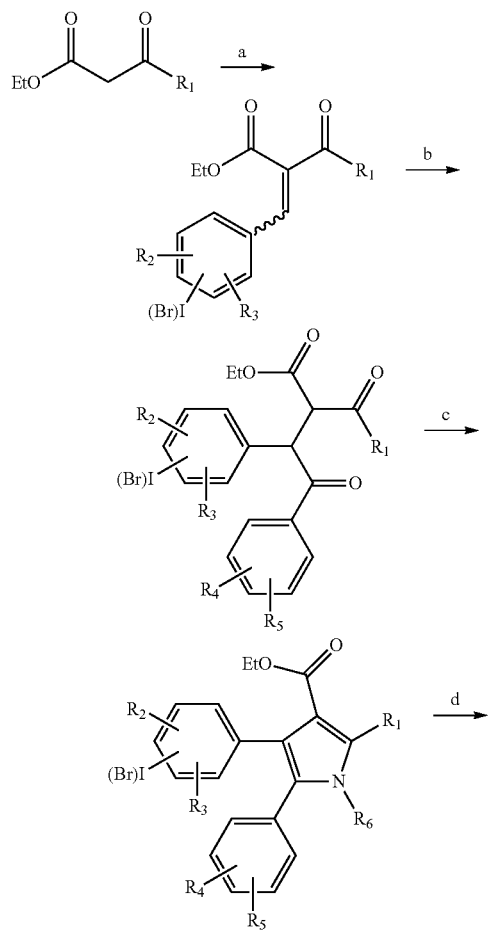

Scheme, core-2

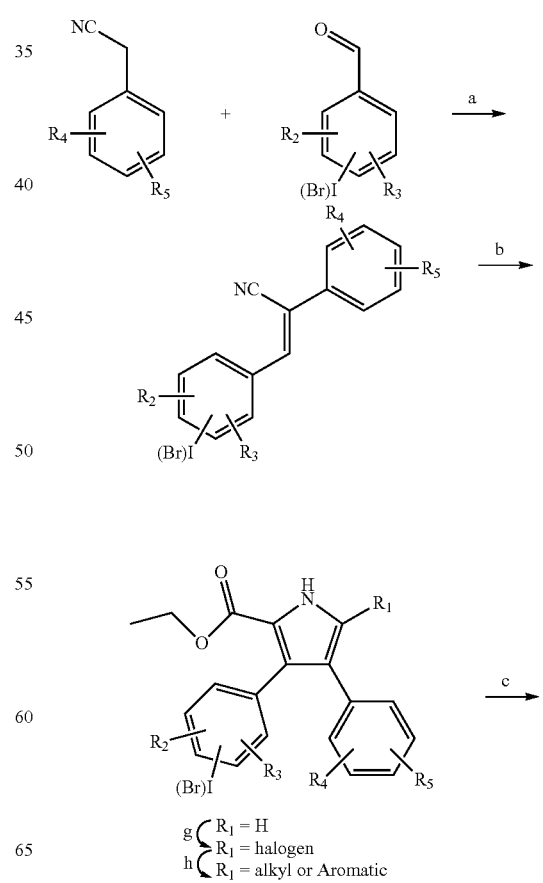

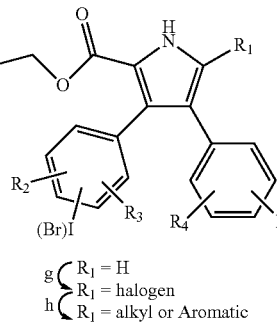

189
-continued
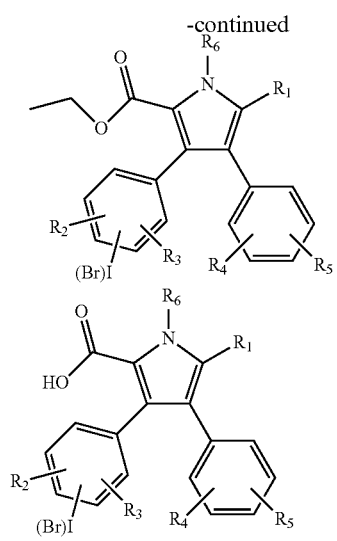
190
-continued
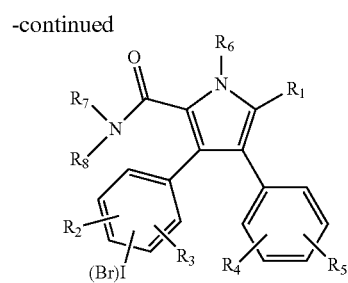
a) K$_2$CO$_3$, MeOH, reflux; b) CNCH$_2$COOEt, t-BuOK; c) R$_6$—I, K$_2$CO$_3$; d) KOH, H$_2$O/THF/MeOH; e) R$_7$NHR$_8$, EDCl, HOBt, DIEA, DCM; f) i. SOCl$_2$ reflux 2 h ii. R$_7$NHR$_8$, DMAP, 1,2-dichloroethane, reflux; g) NCS or NIS or NBS, DMF RT; h) sonogashira coupling or suzuki coupling

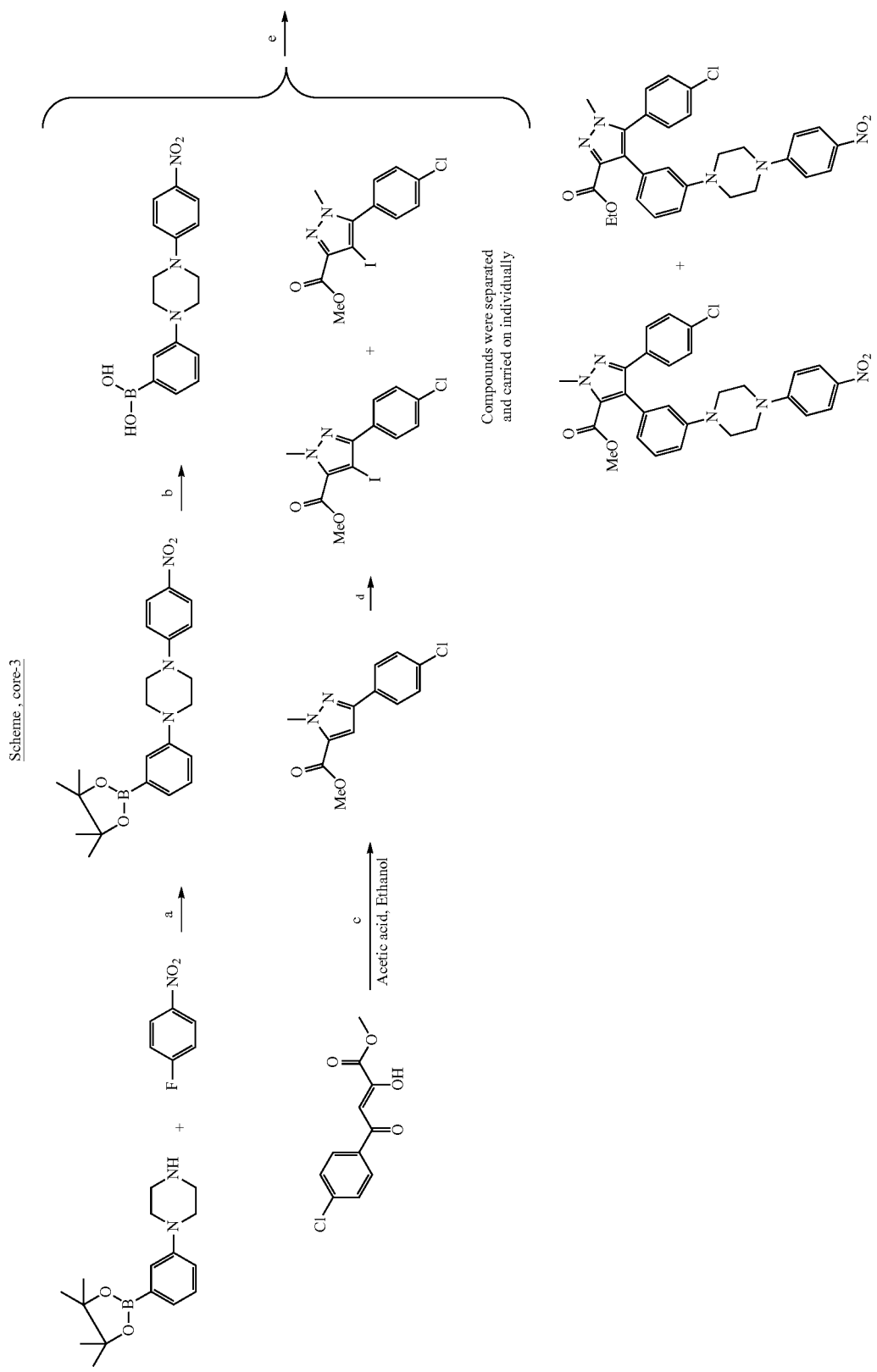

Scheme, core-4
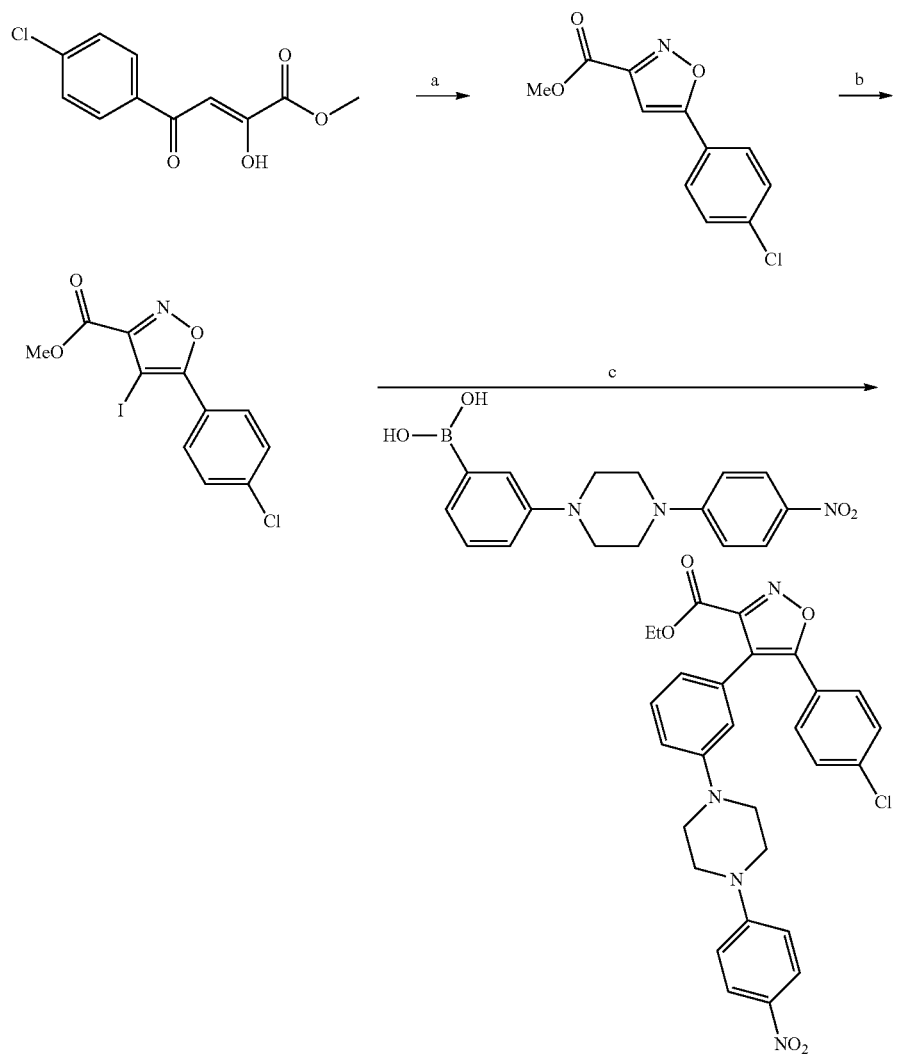
a) HO—NH$_2$, Acetic acid, Ethanol, b) NIS, CAN, MeCN, c) Pd(OAc)$_2$, CsCO$_3$
Scheme, core-5
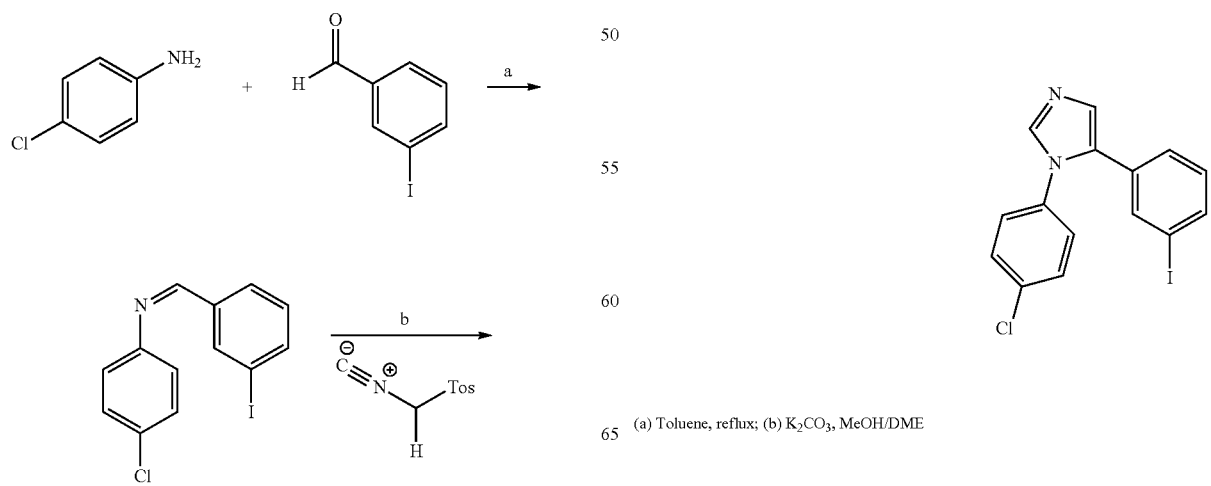
(a) Toluene, reflux; (b) K$_2$CO$_3$, MeOH/DME

Scheme, core-6
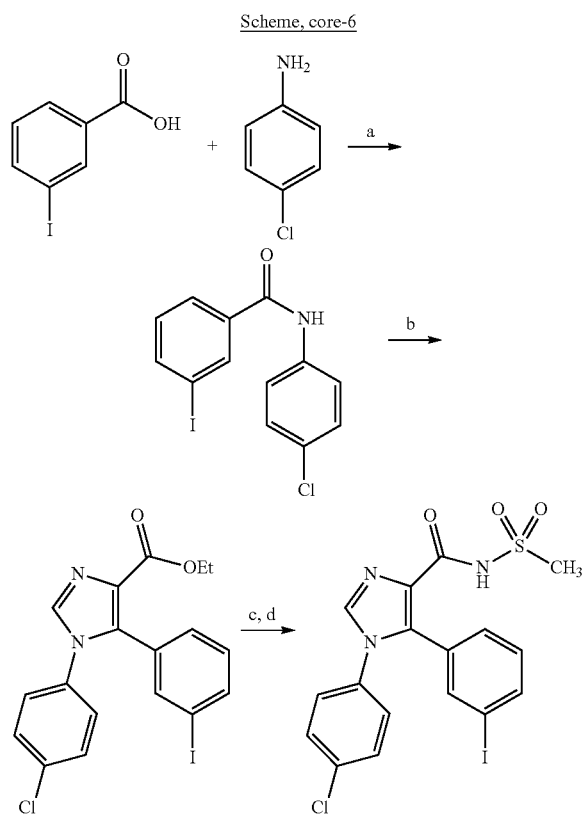
(a) EDCl, HOBt, $CH_2Cl_2$, DIEA; (b) (i) KOtBu, THF, $ClPO(OEt)_2$ (ii) ethyl isocyanoacetate; (c) NaOH, dioxane:EtOH:$H_2O$ (1:1:1) reflux 2 h; (d) (i) $SOCl_2$, reflux 2 h (ii) 1,2-dichloroethane, methylsulfonamide reflux overnight
Scheme, core-7
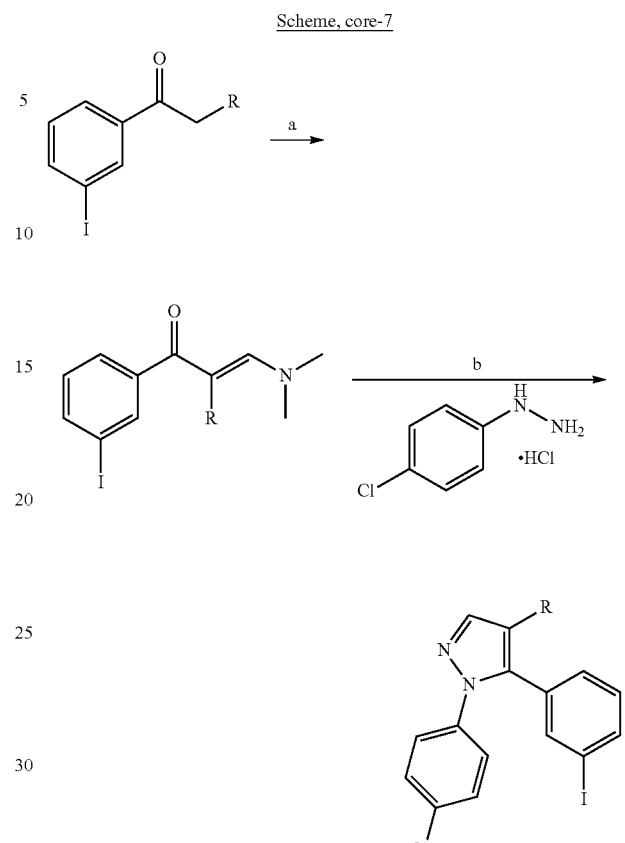
R = H or —$CO_2Et$
(a) N,N-Dimethylformamide dimethyl acetal, Toluene, reflux; (b) Ethanol, reflux

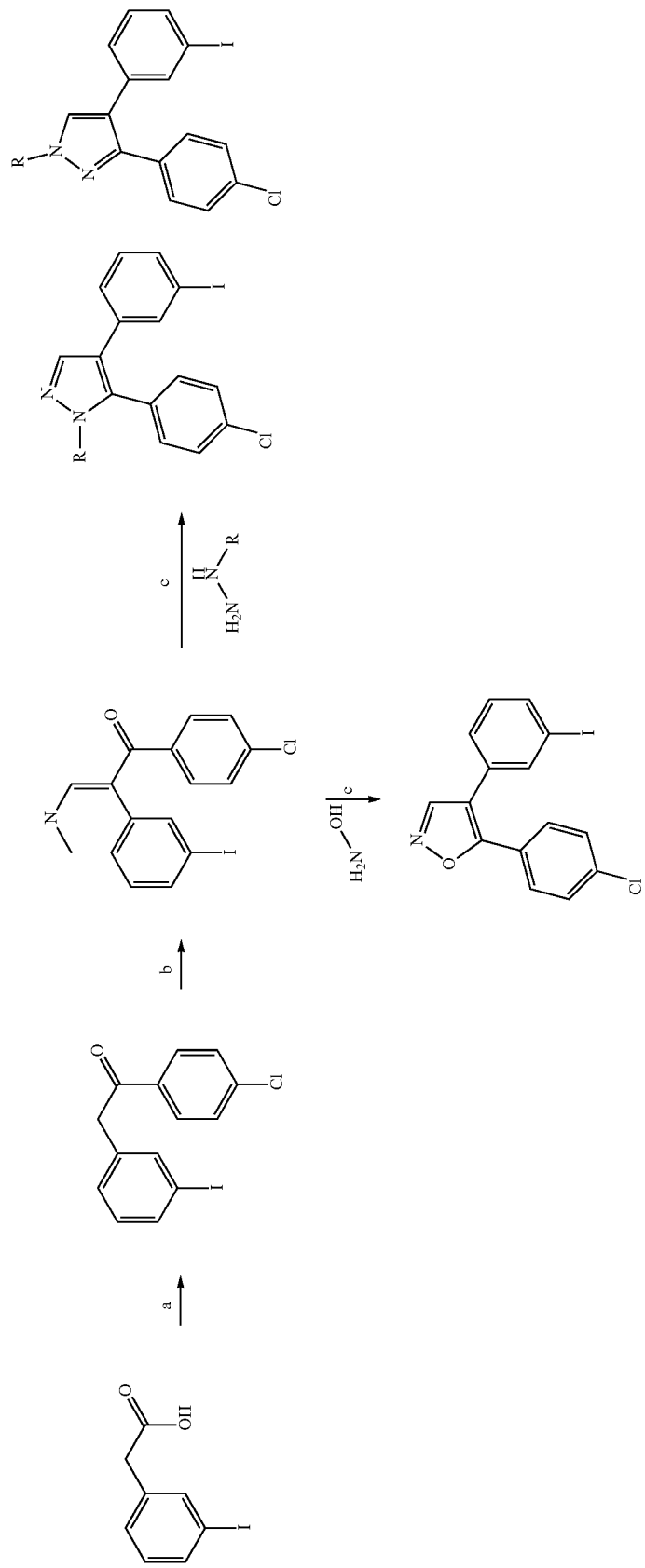

Scheme, core-10
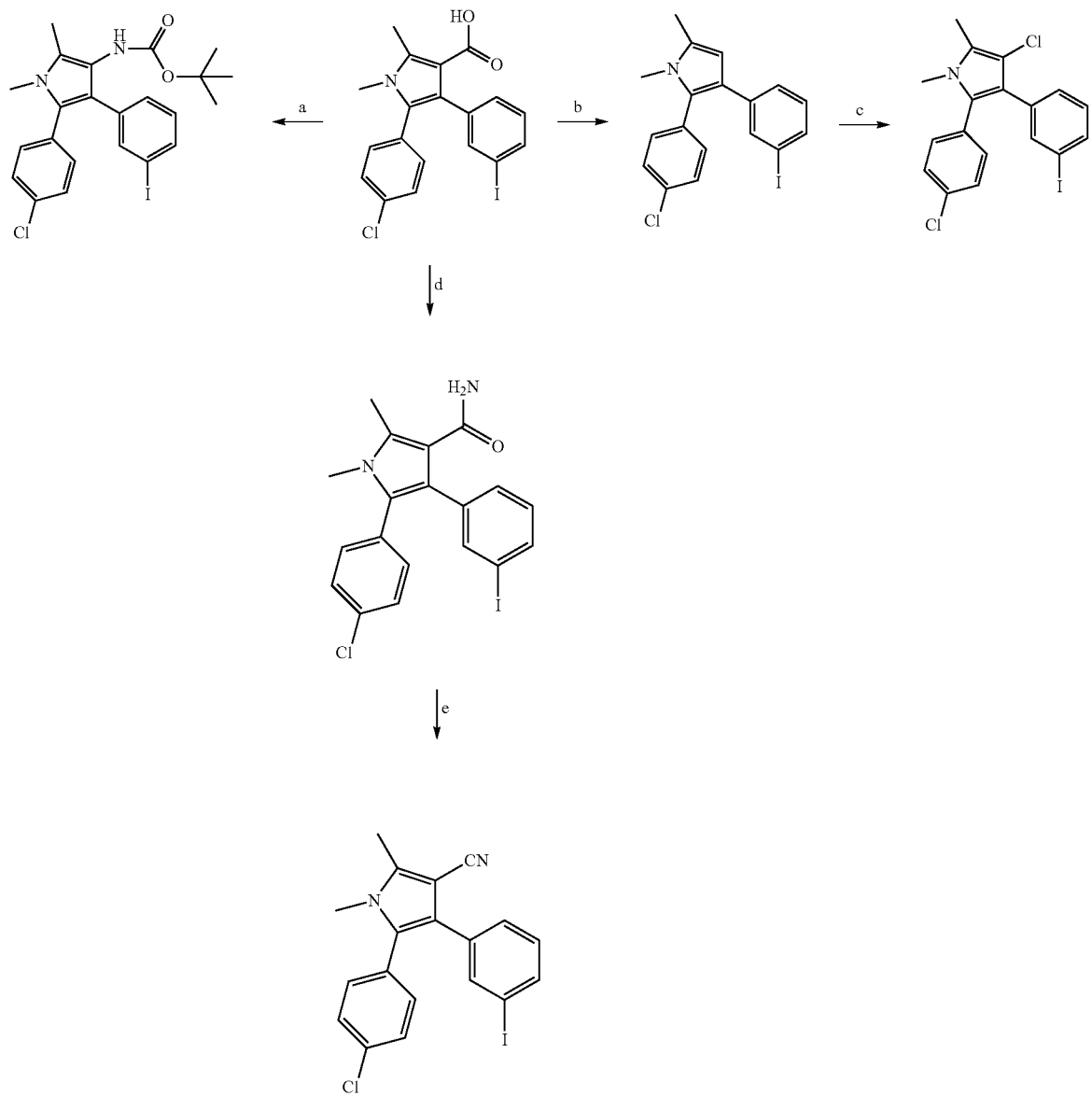
(a) (i) (PhO)₂PON₃, THF, RT overnight (ii) t-BuOH, Toluene, reflux overnight; (b) CH₂Cl₂, TFA, RT 30 min; (c) NCS, DMF, RT 2 h;
(d) EDCl, HOBt, DIEA, CH₂Cl₂, 0.5M NH₃ in dioxane; (e) trifluoroacetic anhydride, pyridine, dioxane 0° C. to RT
Scheme, core-11
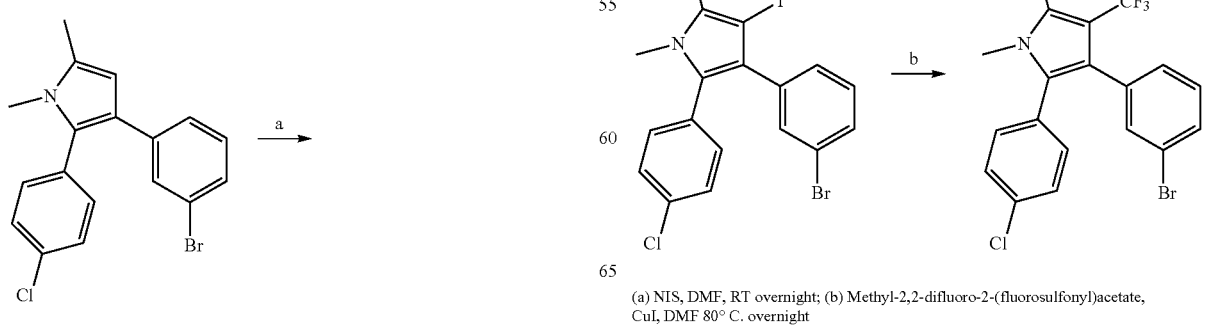
(a) NIS, DMF, RT overnight; (b) Methyl-2,2-difluoro-2-(fluorosulfonyl)acetate,
CuI, DMF 80° C. overnight

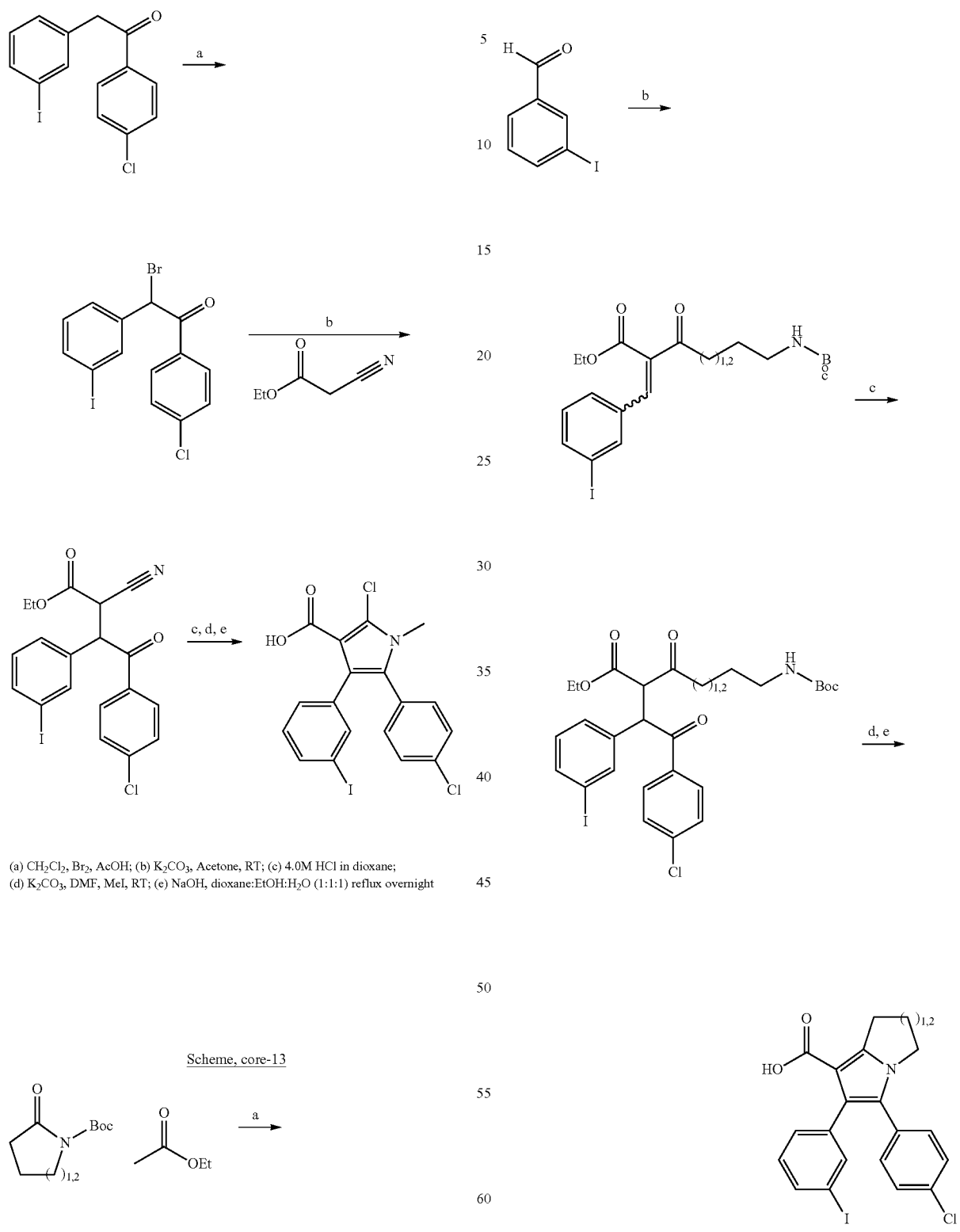

Scheme, core-14
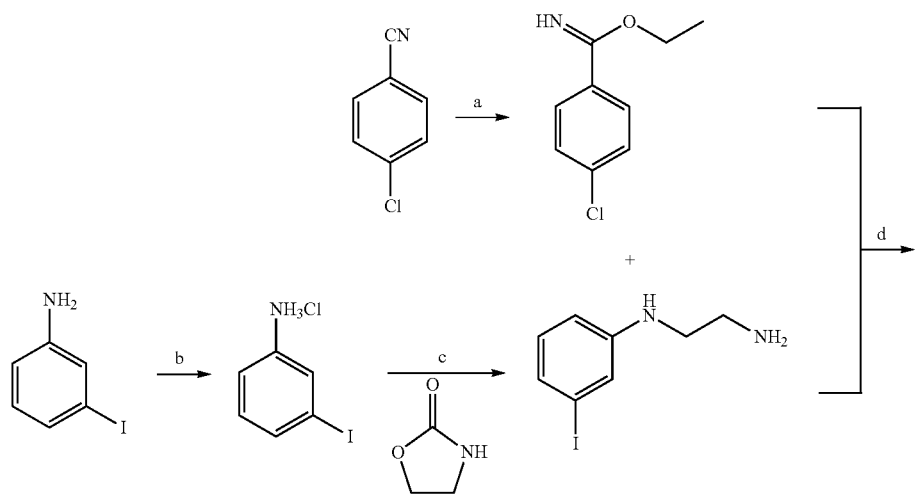
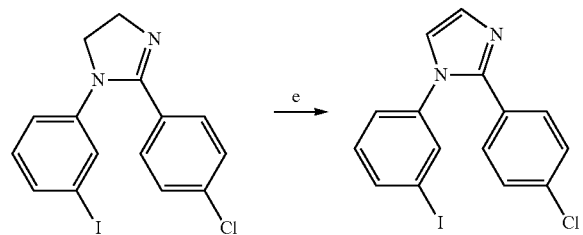
a) AcCl, EtOH; b) HCl; c) heat, 16 h; d) i. AcOH, ii. NaHCO3; e) MnO2
Scheme, core-15
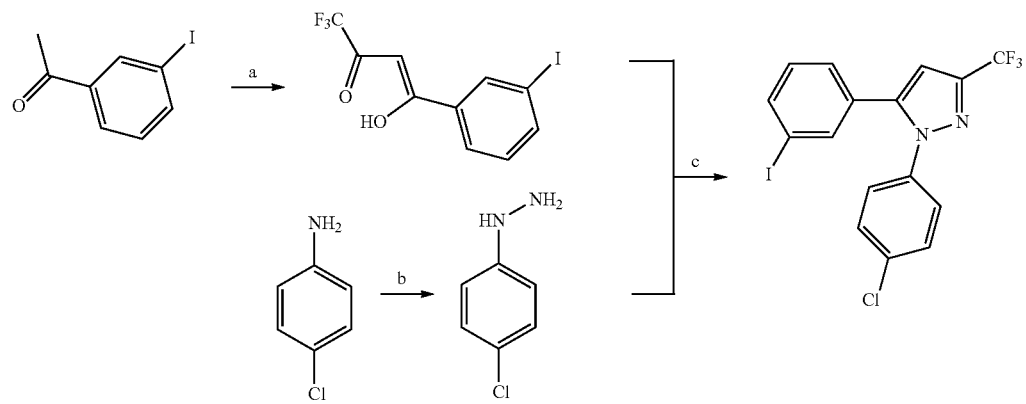
a) NaOMe, MTBE; b) NaNO2, SnCl2, HCl; c) EtOH, reflux

205
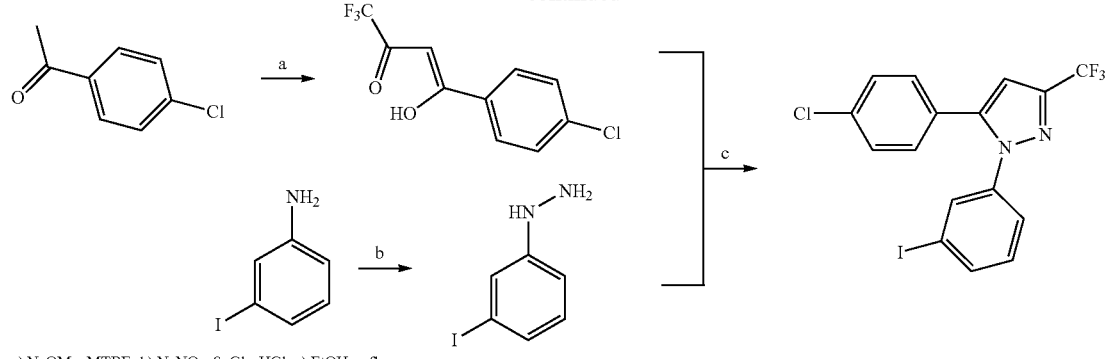
a) NaOMe, MTBE; b) NaNO₂, SnCl₂, HCl; c) EtOH, reflux
206
General scheme 1
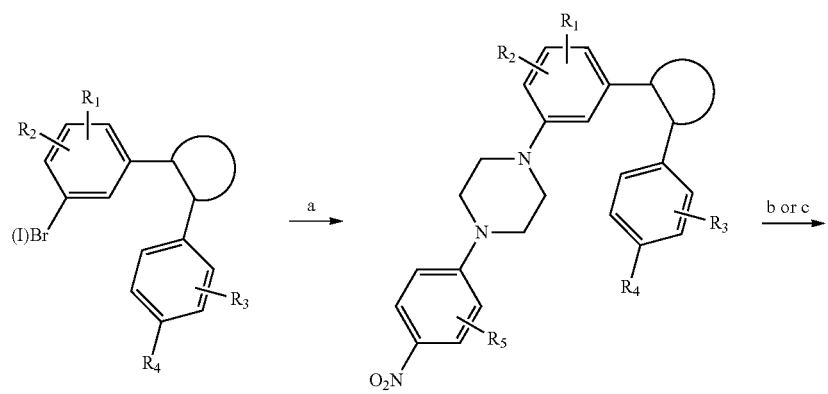
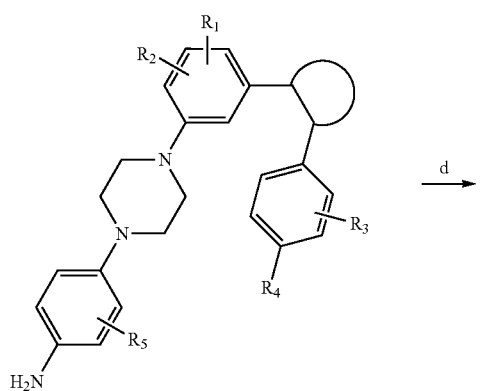

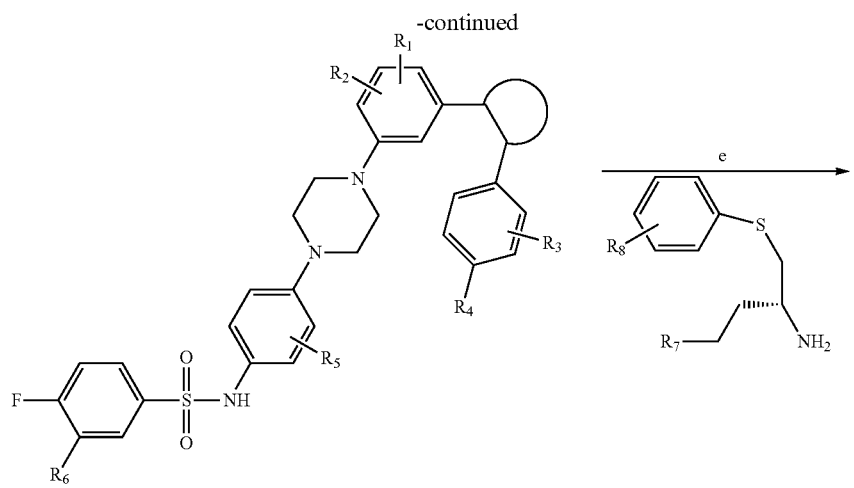
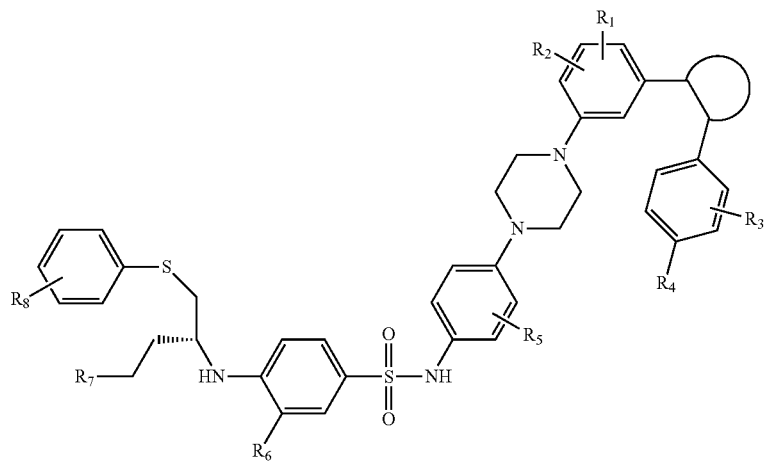
a) 1-(4-Nitrophenyl)piperazine, CuI, L-proline, K₂CO₃, DMSO, 100° C.; b) Fe, HCl, EtOH/H₂O, 65° C.; c) H₂, Pd/C; d) ArSO₂Cl, pyridine 0° C.; h) DIPEA, DMF, room temp;
General Scheme 2
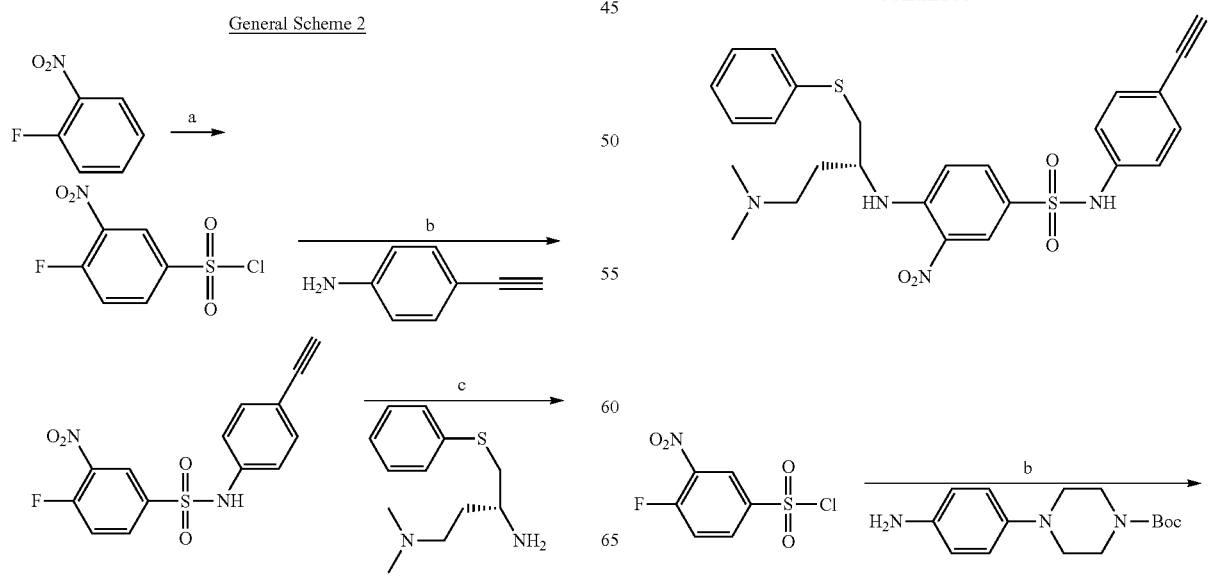

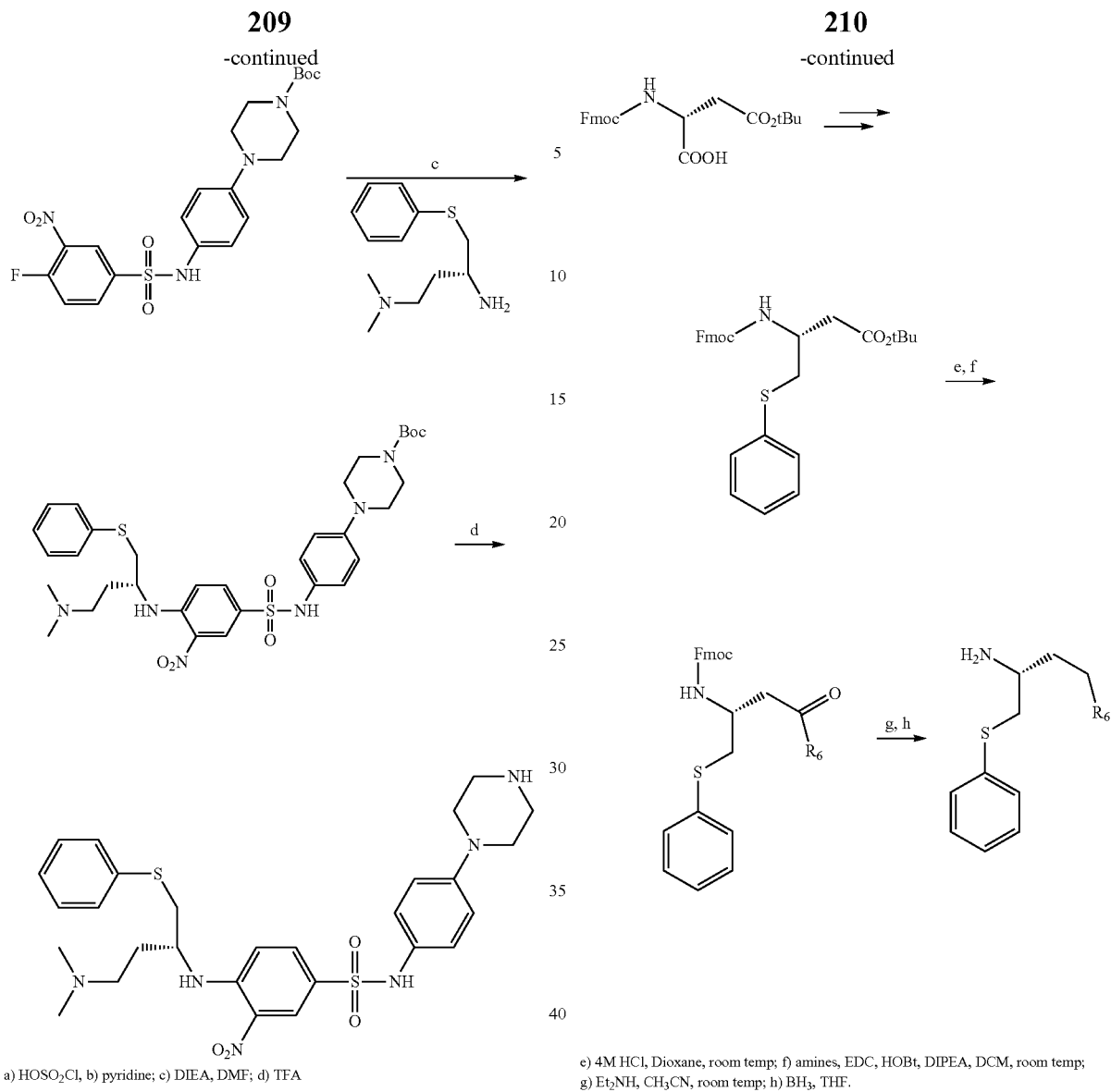
a) HOSO$_2$Cl, b) pyridine; c) DIEA, DMF; d) TFA
e) 4M HCl, Dioxane, room temp; f) amines, EDC, HOBt, DIPEA, DCM, room temp;
g) Et$_2$NH, CH$_3$CN, room temp; h) BH$_3$, THF.
General scheme 3, triple bond as linker
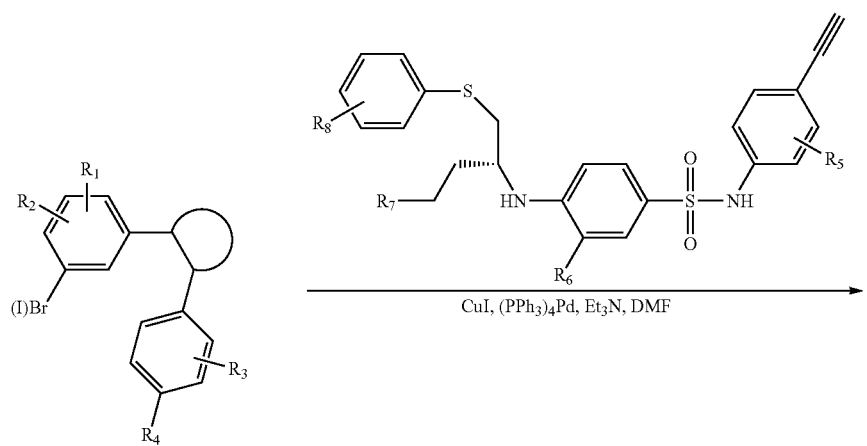

-continued
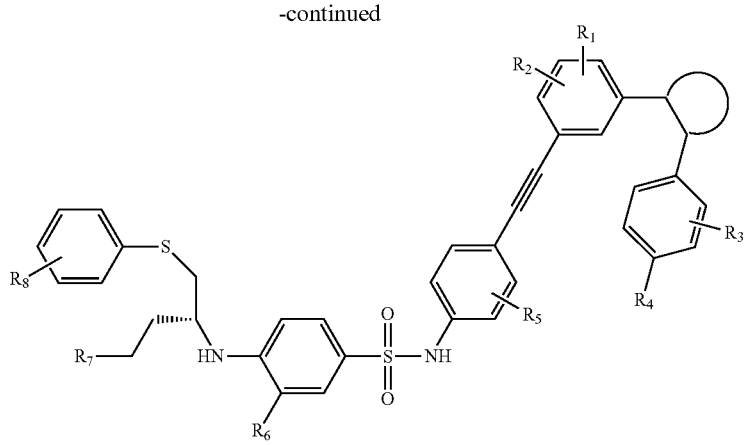
General scheme 4, trizole as linker
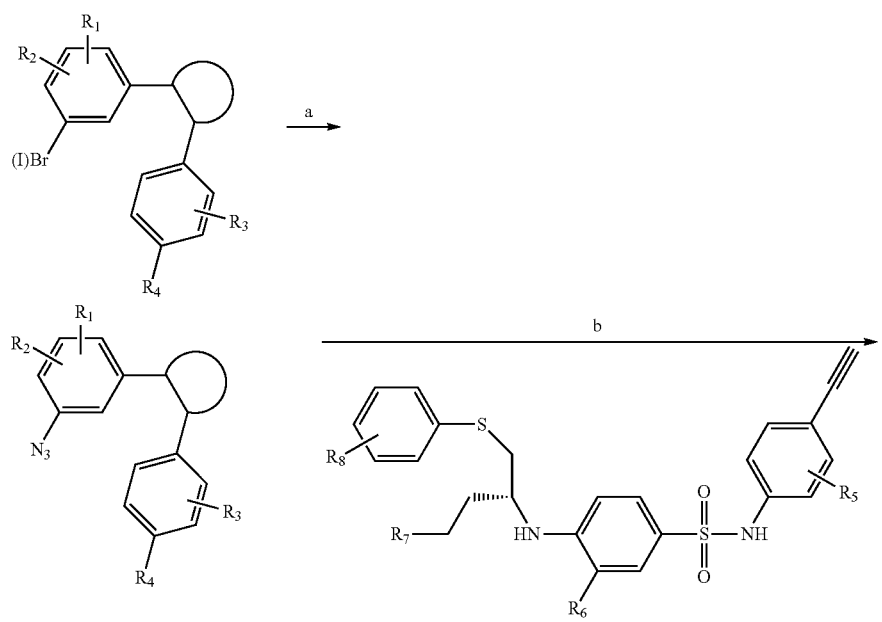
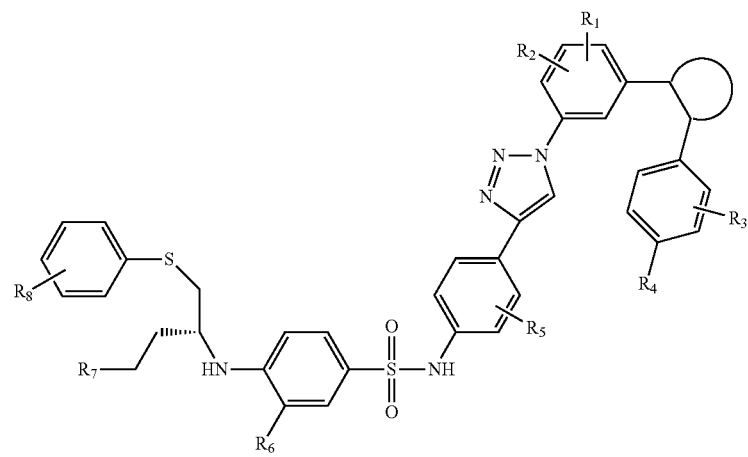
a) NaN3, CuI, L-Proline, DMSO; b) CuSO4, Sodium ascorbate, t-BuOH, H2O General scheme 4, piperazine as linker
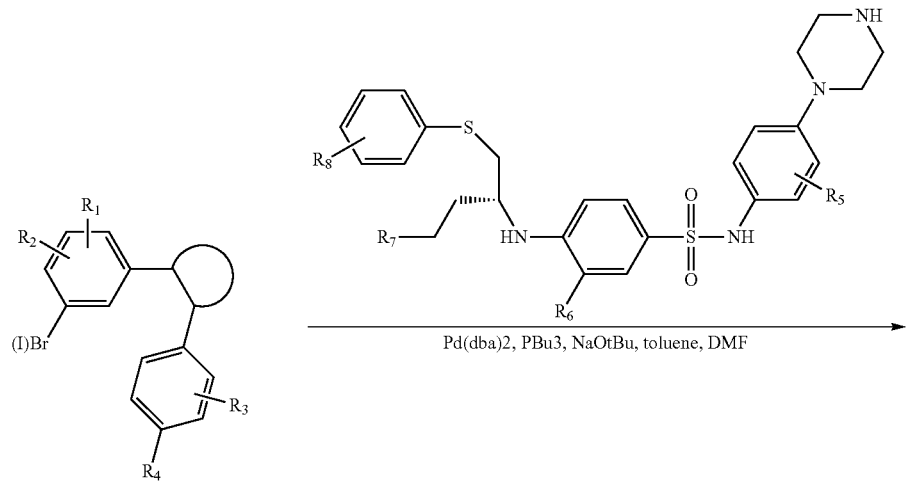
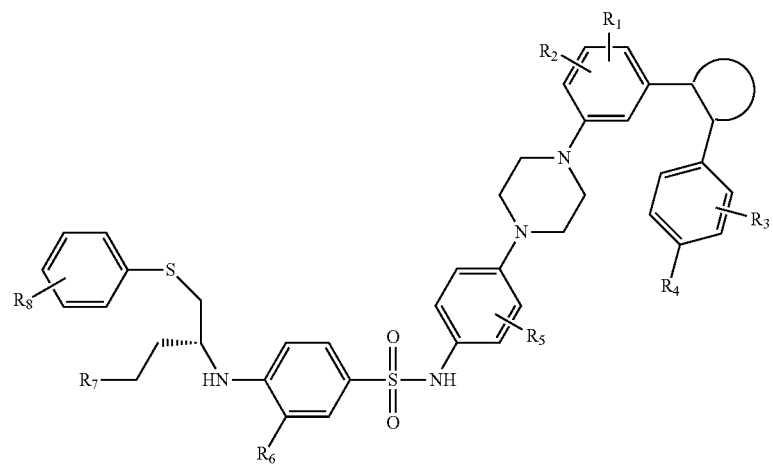
General scheme 5, alkylsulfonyl compounds
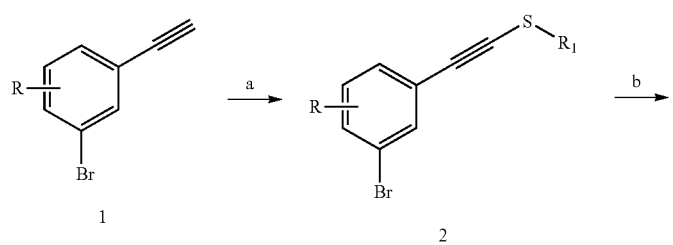

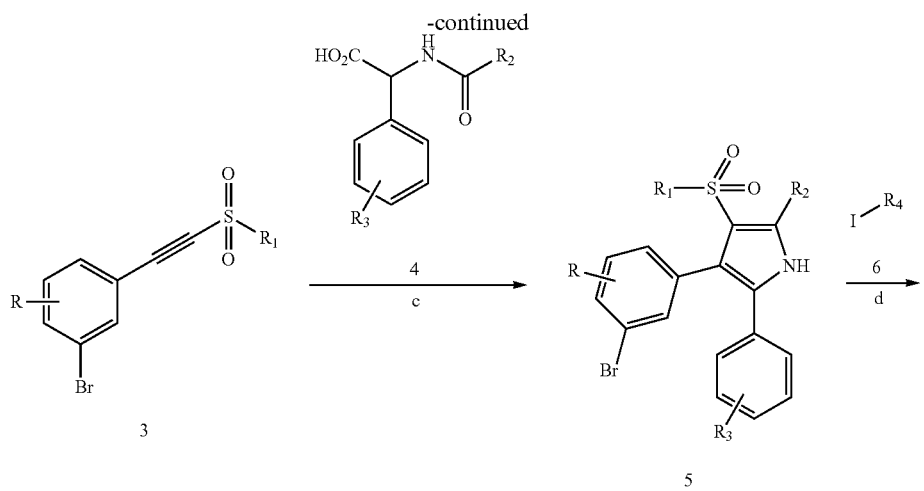
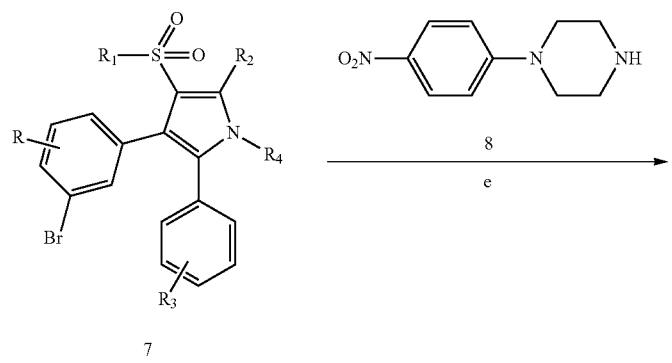
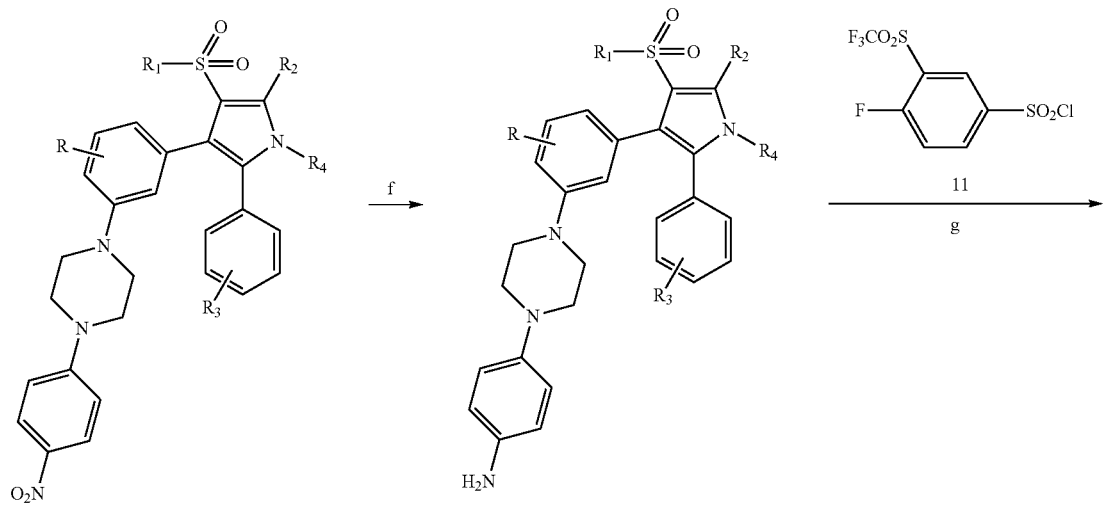

-continued
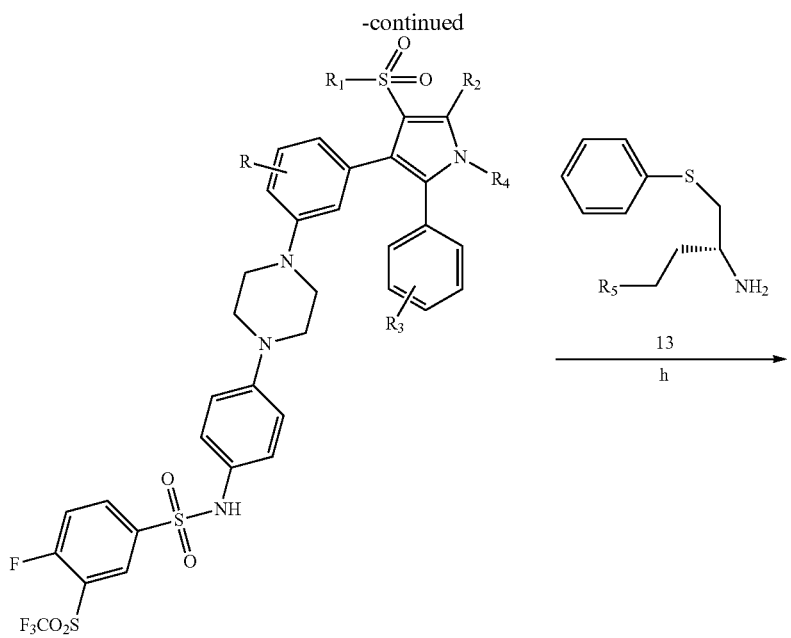
12
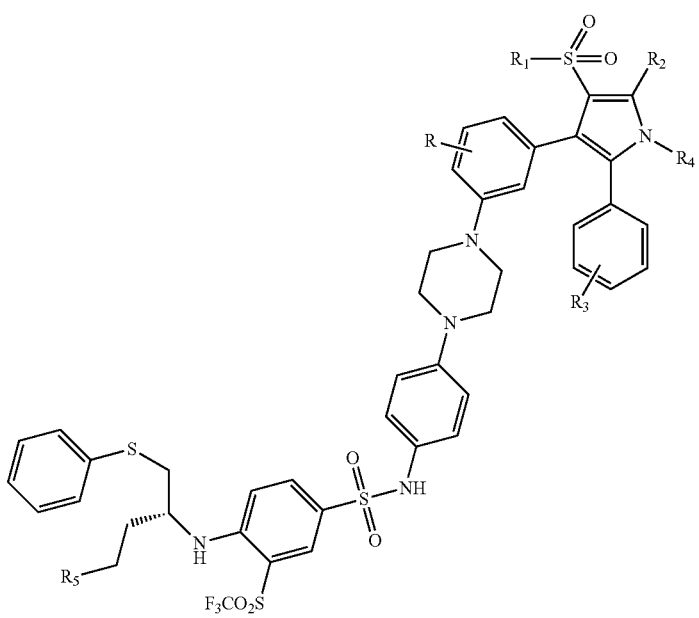
14
Reagents and Conditions: a) i) nBuLi, -78° C., THF: ii) R₁SSR₁, THF; iii) 1-(bromomethyl)-4-nitrobenzene, THF; b) mCPBA (2 eq.), CH₂Cl₂, 0-25° C.;
c) 4, Ac₂O, 120° C., 2 h; d) 6, NaH, DMF; e) 8, CuI, L-proline, K₂CO₃, 120° C., overnight; f) Pd/C, H₂, MeOH; g) 11, Pyridine; h) 13, DIPEA, DMF.

Compound 136

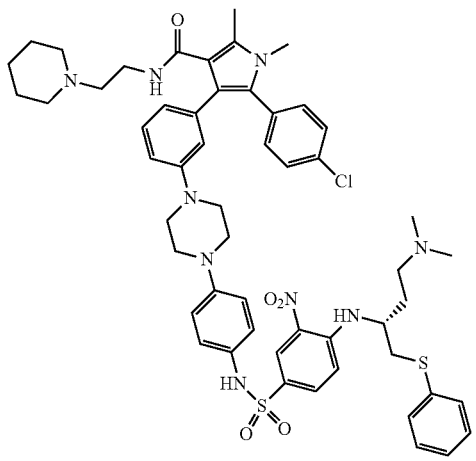

Chemical Formula: C54H64ClN9O5S2
Exact Mass: 1017.42
Molecular Weight: 1018.73

MS: 1019.50; ¹H-NMR (300 MHz, CD$_3$OD) δ ppm 8.30 (d, J=2.0, 1H), 7.61 (dd, J=2, 9 Hz, 1H), 7.31 (d, J=8.4 Hz, 3H), 7.24-7.11 (m, 5H), 7.08-7.01 (m, 4H), 6.99-6.83 (m, 4H), 6.70-6.63 (m, 2H), 4.18-4.06 (m, 1H), 3.53-3.43 (m, 11H), 3.24-3.08 (m, 12H), 2.87 (s, 6H), 2.49 (s, 3H), 2.36-2.14 (m, 2H) 1.96-1.60 (m, 6H)

Compound 133

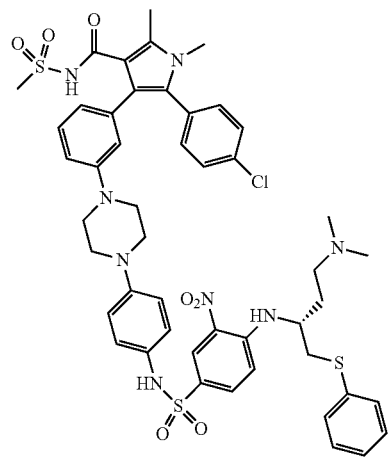

Chemical Formula: C48H53ClN8O7S3
Exact Mass: 984.29
Molecular Weight: 985.63

MS=986.58; ¹H-NMR (300 MHz, CD$_3$OD) δ ppm 8.36 (d, J=2.0 Hz, 1H), 7.58 (dd, J=2.0, 9.0 Hz, 1H), 7.33 (d, J=8.0 Hz, 2H), 7.21-7.15 (m, 5H), 7.10-7.03 (m, 5H), 7.00-6.93 (m, 3H), 6.91 (d, J=9.0 Hz, 1H), 6.88 (bs, 1H), 6.71 (d, J=8.0 Hz, 1H), 4.15-4.02 (m, 1H), 3.44 (s, 3H), 3.22 (s, 3H), 2.87 (s, 6H), 2.54 (s, 3H), 2.28-2.12 (m, 2H)

Compound 135

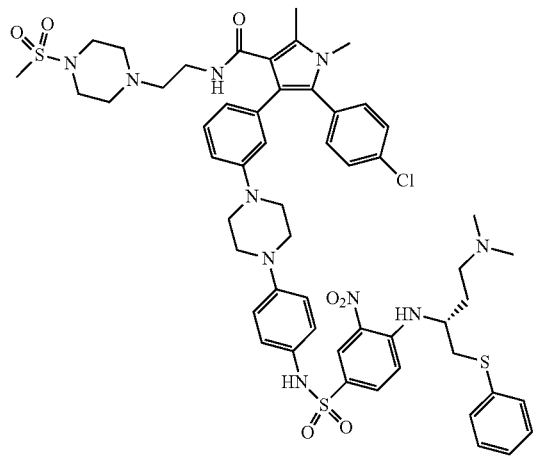

Chemical Formula: C54H65ClN10O7S3
Exact Mass: 1096.39
Molecular Weight: 1097.80

MS=1098.42; ¹H-NMR (300 MHz, 10:1 CDCl$_3$:CD$_3$OD) δ ppm 8.43 (d, J=2.0 Hz, 1H), 7.62 (dd, J=2.0, 9.0 Hz, 1H) 7.28-7.22 (m, 4H), 7.17-7.11 (m, 4H), 7.07-7.02 (m, 4H), 6.86 (d, J=8.9 Hz, 2H), 6.80-6.75 (m, 2H), 6.67-6.64 (m, 2H), 3.42-3.41 (m, 5H), 3.30-3.11 (m, 15H), 2.82 (s, 6H), 2.79 (s, 3H), 2.73-2.60 (m, 6H), 2.54 (s, 3H), 2.42-2.07 (m, 2H)

Compound 132

Chemical Formula: C47H51ClN8O5S2
Exact Mass: 906.31
Molecular Weight: 907.54

MS=907.67; ¹H-NMR (300 MHz, 10:1 CDCl$_3$:CD$_3$OD) δ ppm 8.45 (d, J=2.2 Hz, 1H), 7.63 (dd, J=2.3, 9.1 Hz, 1H), 7.28-7.22 (m, 4H), 7.19-7.13 (m, 4H), 7.10-7.03 (m, 4H), 6.95-6.86 (m, 3H), 6.78-6.76 (m, 3H), 4.13-4.05 (m, 1H), 3.43 (s, 3H), 3.28-3.22 (m, 9H), 3.17-3.11 (m, 3H), 2.82 (s, 6H), 2.62 (s, 3H), 2.40-2.08 (m, 2H)

Compound 131

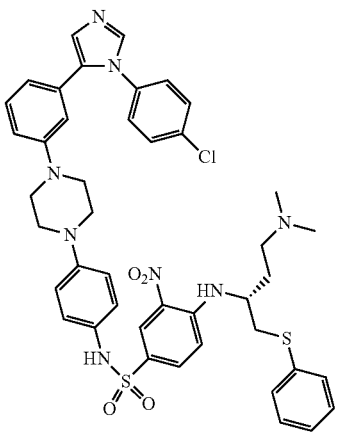

Chemical Formula: C₄₃H₄₅ClN₈O₄S₂
Exact Mass: 836.27
Molecular Weight: 837.45

MS=837.50; ¹H-NMR (300 MHz, 10:1 CDCl₃:CD₃OD) δ ppm 9.32 (s, 1H), 8.33 (d, J=2.0 Hz, 1H), 7.83 (s, 1H), 7.60 (dd, J=2.0, 9.0 Hz, 1H), 7.55 (d, J=8.8 Hz, 2H), 7.43 (d, J=8.8 Hz, 2H), 7.30-7.16 (m, 3H), 7.12-7.00 (m, 6H), 7.00-6.90 (m, 3H), 6.80-6.71 (m, 2H), 4.19-4.04 (m, 1H), 3.28-3.12 (m, 12H), 2.87 (s, 6H), 2.35-2.09 (m, 2H)

Compound 129

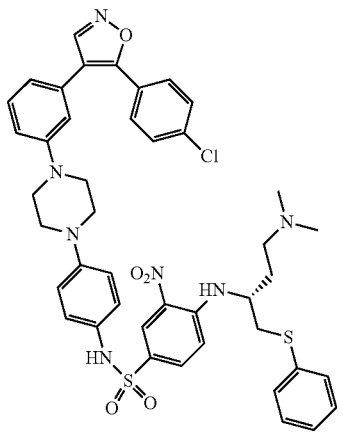

Chemical Formula: C₄₃H₄₄ClN₇O₅S₂
Exact Mass: 837.25
Molecular Weight: 838.44

MS=839.33; ¹H-NMR (300 MHz, 10:1 CDCl₃:CD₃OD) δ ppm 8.45 (d, J=2.2 Hz, 1H), 8.38 (s, 1H), 7.64 (dd, J=2.3, 9.1 Hz, 1H), 7.61-7.58 (m, 2H), 7.39-7.32 (m, 3H), 7.28-7.24 (m, 2H), 7.17-7.10 (m, 5H), 7.50-7.01 (m, 3H), 6.98-6.91 (m, 2H), 6.78 (d, J=9.4 Hz, 1H), 4.14-4.07 (m, 1H), 3.41-3.37 (m, 9H), 3.28-3.11 (m, 4H), 2.82 (s, 6H), 2.37-2.09 (m, 2H)

Compound 130

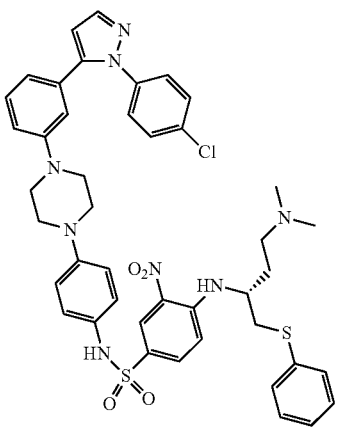

Chemical Formula: C₄₃H₄₅ClN₈O₄S₂
Exact Mass: 836.27
Molecular Weight: 837.45

MS=837.50; ¹H-NMR (300 MHz, 10:1 CDCl₃:CD₃OD) δ ppm 8.35 (d, J=2.0 Hz, 1H), 7.73 (d, J=1.8 Hz, 1H), 7.59 (dd, J=2.0, 9.0 Hz, 1H), 7.40 (d, J=8.8 Hz, 2H), 7.28-7.24 (m, 3H), 7.21-7.18 (m, 2H), 7.09-7.05 (m, 4H), 7.02-6.98 (m, 3H), 6.95-6.90 (m, 2H), 6.78-6.76 (m, 2H), 6.60 (d, J=1.9 Hz, 1H), 4.15-4.03 (m, 1H), 3.28-3.12 (m, 10H), 2.87 (s, 6H), 2.31-2.09 (m, 2H)

Compound 128

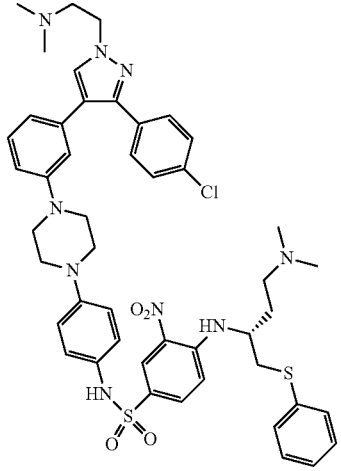

Chemical Formula: C₄₇H₅₄ClN₉O₄S₂
Exact Mass: 907.34
Molecular Weight: 908.57

MS=908.25

Compound 127

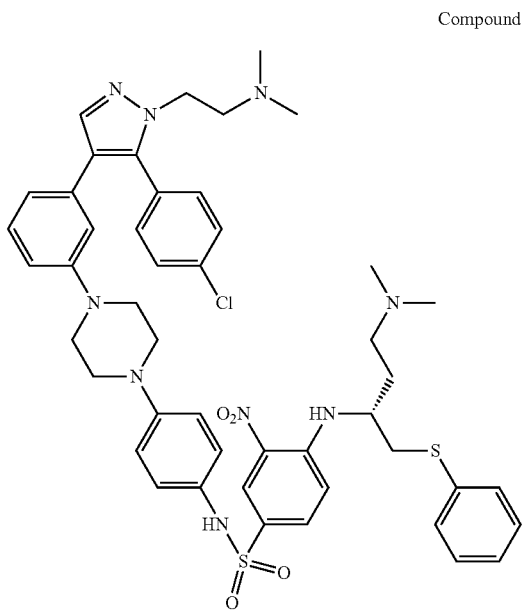

Chemical Formula: C₄₇H₅₄ClN₉O₄S₂
Exact Mass: 907.34
Molecular Weight: 908.57

MS=908.25; ¹H-NMR (300 MHz, 10:1 CDCl₃:CD₃OD) δ ppm 8.30 (d, J=2.0 Hz, 1H), 7.61 (s, 1H), 7.47 (dd, J=2.0, 9.0 Hz, 1H), 7.29-7.26 (m, 2H), 7.17-7.05 (m, 5H), 7.02-6.95 (m, 3H), 6.91 (d, J=9.0 Hz, 2H), 6.76-6.71 (m, 3H), 6.67-6.60 (m, 3H), 4.48 (t, J=6.3 Hz, 2H), 3.50 (t, J=6.0 Hz, 2H), 3.15-2.95 (m, 11H), 2.69 (s, 6H), 2.66 (s, 6H), 2.21-1.96 (m, 4H)

Compound 125

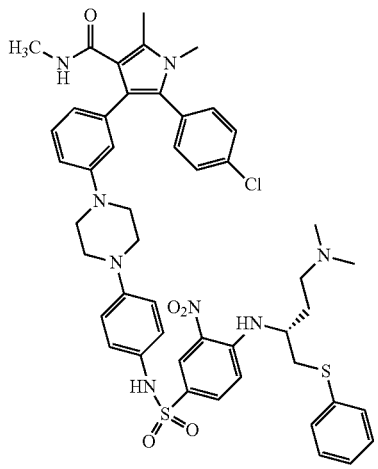

Chemical Formula: C₄₈H₅₃ClN₈O₅S₂
Exact Mass: 920.33
Molecular Weight: 921.57

MS=922.50; ¹H-NMR (300 MHz, 10:1 CDCl₃:CD₃OD) δ ppm 8.45 (d, J=2.3 Hz, 1H), 7.63 (dd, J=2.3, 9.1 Hz, 1H), 7.27-7.24 (m, 4H), 7.19-7.11 (m, 4H), 7.10-7.00 (m, 5H), 6.90-6.79 (m, 3H), 6.76 (d, J=9.3 Hz, 1H), 6.67-6.65 (m, 2H), 4.14-4.05 (m, 1H), 3.42 (s, 3H), 3.24-3.06 (m, 13H), 2.82 (s, 6H), 2.66 (s, 3H), 2.58 (s, 3H), 2.32-2.09 (m, 2H)

Compound 126

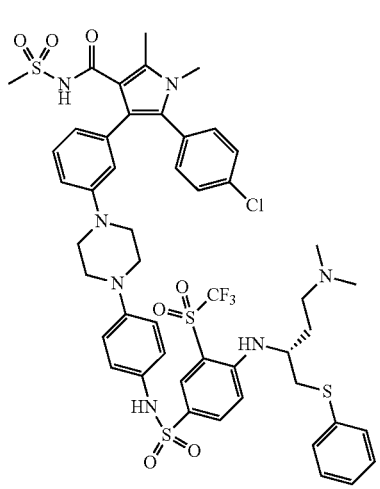

Chemical Formula: C₄₉H₅₃ClF₃N₇O₇S₄
Exact Mass: 1071.25
Molecular Weight: 1072.70

MS=1073.42; ¹H-NMR (300 MHz, 10:1 CDCl₃:CD₃OD) δ ppm 8.02 (d, J=2.0 Hz, 1H), 7.70 (dd, J=2.2, 9.2 Hz, 1H), 7.36-7.33 (m, 2H), 7.31-7.22 (m, 6H), 7.11-7.07 (m, 2H), 7.02 (d, J=9.0 Hz, 2H), 6.92-6.85 (m, 3H), 6.74-6.63 (m, 3H), 4.00-3.87 (m, 1H), 3.46 (s, 3H), 3.28-3.18 (m, 9H), 3.15-3.00 (m, 5H), 2.80 (s, 6H), 2.65 (s, 3H), 2.34-2.17 (m, 1H), 2.11-1.93 (m, 1H)

Compound 124

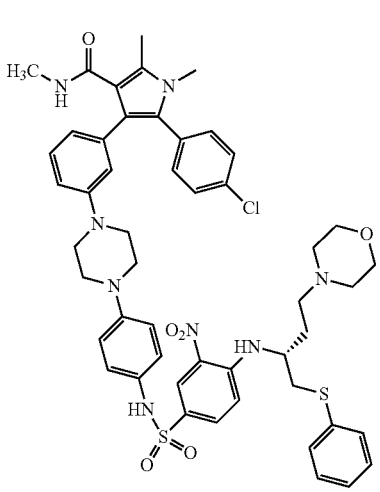

Chemical Formula: C₅₀H₅₅ClN₈O₆S₂
Exact Mass: 962.34
Molecular Weight: 963.60

MS=964.50; ¹H-NMR (300 MHz, 10:1 CDCl₃:CD₃OD) δ ppm 8.45 (d, J=2.2 Hz, 1H), 7.62 (dd, J=2.2, 9.1 Hz, 1H), 7.27-7.24 (m, 4H), 7.20-7.11 (m, 4H), 7.10-7.04 (m, 4H), 6.90-6.81 (m, 3H), 6.74-6.66 (m, 3H), 4.09-4.00 (m, 1H), 3.94 (bs, 4H), 3.42 (s, 3H), 3.27-3.10 (m, 14H), 2.66 (s, 3H), 2.58 (s, 3H), 2.38-2.11 (m, 2H)

Compound 123

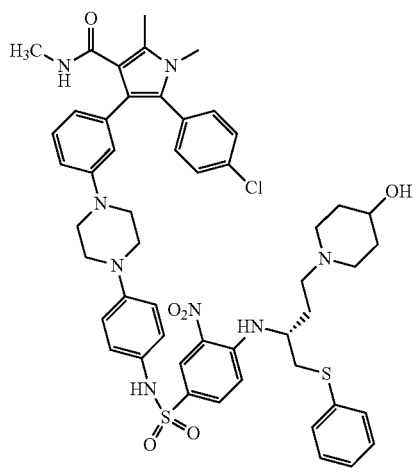

Chemical Formula: C$_{51}$H$_{57}$ClN$_8$O$_6$S$_2$
Exact Mass: 976.35
Molecular Weight: 977.63

MS=978.75; $^1$H-NMR (300 MHz, 10:1 CDCl$_3$:CD$_3$OD) δ ppm 8.44 (d, J=2.2 Hz, 1H), 7.63 (dd, J=2.2, 9.1 Hz, 1H), 7.28-7.23 (m, 4H), 7.20-7.12 (m, 4H), 7.10-7.04 (m, 4H), 6.93-6.82 (m, 3H), 6.76 (d, J=9.3 Hz, 1H), 6.70-6.67 (m, 2H), 4.10-4.03 (m, 2H), 3.42 (s, 3H), 3.29-3.02 (m, 15H), 2.67 (s, 3H), 2.57 (s, 3H), 2.89-1.82 (m, 6H)

Compound 122

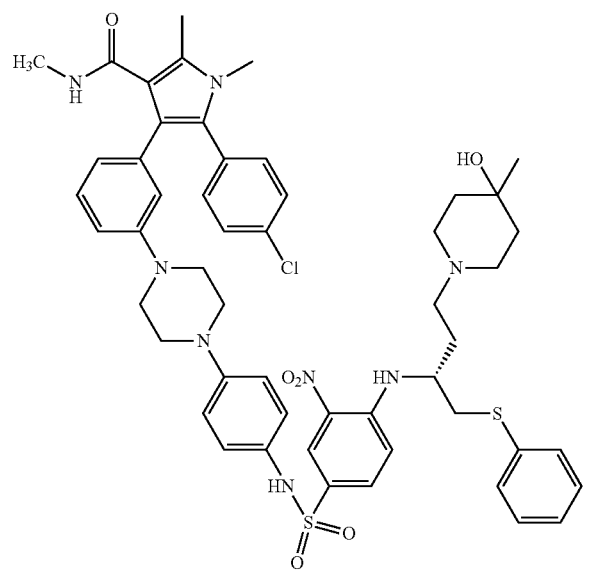

Chemical Formula: C$_{52}$H$_{59}$ClN$_8$O$_6$S$_2$
Exact Mass: 990.37
Molecular Weight: 991.66

MS=992.75; $^1$H-NMR (300 MHz, 10:1 CDCl$_3$:CD$_3$OD) δ ppm 8.44 (d, J=2.1 Hz, 1H), 7.62 (dd, J=2.1, 9.1 Hz, 1H), 7.27-7.23 (m, 4H), 7.19-7.12 (m, 4H), 7.07-7.03 (m, 4H), 6.88-6.74 (m, 4H), 6.66-6.63 (m, 2H), 4.11-4.01 (m, 1H), 3.42 (s, 3H), 3.29-3.06 (m, 14H), 2.66 (s, 3H), 2.58 (s, 3H), 2.37-2.09 (m, 3H), 2.03-1.65 (m, 5H), 1.30 (s, 3H)

Compound 121

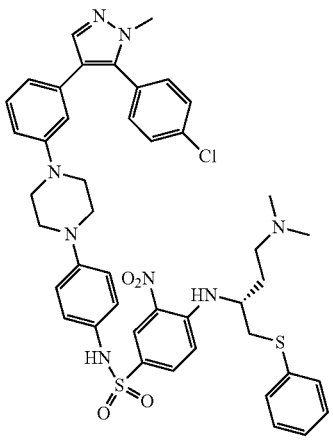

Chemical Formula: C$_{44}$H$_{47}$ClN$_8$O$_4$S$_2$
Exact Mass: 850.29
Molecular Weight: 851.48

MS=851.58; $^1$H-NMR (300 MHz, 10:1 CDCl$_3$:CD$_3$OD) ppm 8.45 (d, J=2.2 Hz, 1H), 7.62 (dd, J=2.2, 9.1 Hz, 1H), 7.52 (s, 1H), 7.42 (d, J=8.5 Hz, 2H), 7.29-7.21 (m, 5H), 7.16-7.11 (m, 3H), 7.07 (d, J=8.9 Hz, 2H), 6.92-6.74 (m, 6H), 4.11-4.04 (m, 1H), 3.97 (s, 3H), 3.28-3.10 (m, 12H), 2.82 (s, 6H), 2.36-2.08 (m, 2H)

Compound 120

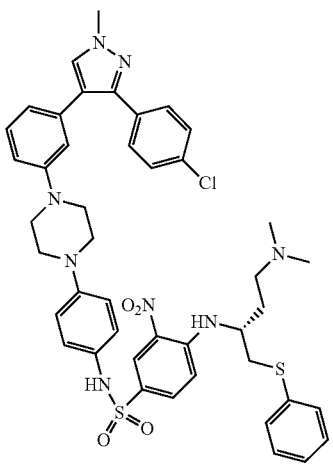

Chemical Formula: C$_{44}$H$_{47}$ClN$_8$O$_4$S$_2$
Exact Mass: 850.29
Molecular Weight: 851.48

MS=851.33; $^1$H-NMR (300 MHz, 10:1 CDCl$_3$:CD$_3$OD) δ ppm 8.45 (bs, 1H), 7.72-7.64 (m, 2H), 7.44 (d, J=8.2 Hz, 2H), 7.29-6.99 (m, 10H), 6.87-6.68 (m, 6H), 4.15-4.04 (m, 1H), 3.77 (s, 3H), 3.34-3.00 (m, 12H), 2.81 (s, 6H), 2.37-2.04 (m, 2H)

Compound 119

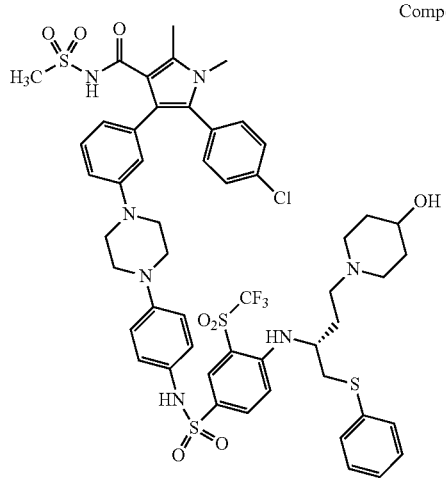

Chemical Formula: C₅₂H₅₇ClF₃N₇O₈S₄
Exact Mass: 1127.28
Molecular Weight: 1128.76

MS=1129.58; ¹H-NMR (300 MHz, 10:1 CDCl₃:CD₃OD) δ ppm 8.01 (d, J=2.1 Hz, 1H), 7.71 (dd, J=2.1, 9.1 Hz, 1H), 7.36-7.32 (m, 2H), 7.30-7.22 (m, 6H), 7.10-7.05 (m, 2H), 7.04-7.00 (m, 2H), 6.93-6.85 (m, 3H), 6.77-6.68 (m, 2H), 6.62 (d, J=9.3 Hz, 1H), 4.10 (bs, 1H), 3.46 (s, 3H), 3.29-3.18 (m, 12H), 3.17-2.96 (m, 6H), 2.65 (s, 3H), 2.36-1.81 (m, 6H)

Compound 118

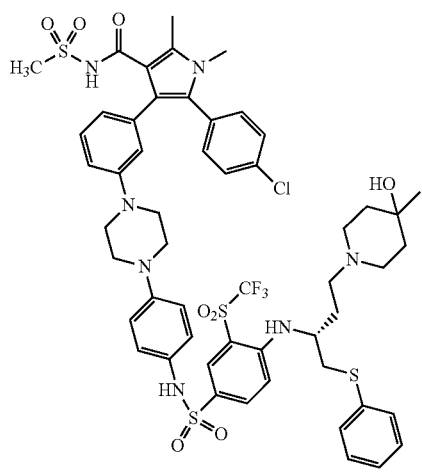

Chemical Formula: C₅₃H₅₉ClF₃N₇O₈S₄
Exact Mass: 1141.29
Molecular Weight: 1142.79

MS=1143.75; ¹H-NMR (300 MHz, 10:1 CDCl₃:CD₃OD) δ ppm 8.00 (d, J=2.1 Hz, 1H), 7.71 (dd, J=2.2, 9.1 Hz, 1H), 7.35-7.32 (m, 2H), 7.29-7.22 (m, 6H), 7.10-7.06 (m, 2H), 7.04-7.00 (m, 2H), 6.94-6.85 (m, 3H), 6.77-6.68 (m, 2H), 6.63 (d, J=9.3 Hz, 1H), 3.96-3.87 (m, 1H), 3.45 (s, 3H), 3.34-3.18 (m, 13H), 3.16-2.98 (m, 6H), 2.65 (s, 3H), 2.35-1.70 (m, 6H), 1.29 (s, 3H)

Compound 209

Chemical Formula: C₅₂H₆₀ClN₁₁O₅S₂
Exact Mass: 1017.39
Molecular Weight: 1018.69

MS=1018.25; ¹H-NMR (300 MHz, 10:1 CDCl₃:CD₃OD) δ ppm 9.32 (s, 1H), 8.45 (d, J=2.2 Hz, 1H), 7.63 (dd, J=2.3, 9.1, Hz, 1H), 7.48-7.42 (m, 3H), 7.33-7.30 (m, 2H), 7.28-7.20 (m, 3H), 7.19-7.10 (m, 3H), 7.07-6.97 (m, 3H), 6.94-6.83 (m, 3H), 6.80-6.76 (m, 1H), 4.17-4.02 (m, 2H), 3.29-3.05 (m, 11H), 2.86-2.69 (m, 11H), 2.39-2.00 (m, 6H)

Compound 134

Chemical Formula: C₅₂H₆₀ClN₁₁O₅S₂
Exact Mass: 1017.39
Molecular Weight: 1018.69

MS=1019.17; ¹H-NMR (300 MHz, 10:1 CDCl₃:CD₃OD) δ ppm 9.32 (s, 1H), 8.43 (d, J=2.3 Hz, 1H), 7.68-7.62 (m, 1H), 7.46-7.40 (m, 2H), 7.30-7.24 (m, 4H), 7.21-6.95 (m, 8H), 6.91-6.73 (m, 4H), 4.17-4.07 (m, 2H), 3.67-3.63 (m, 2H), 3.24-3.04 (m, 12H), 2.86-2.70 (m, 11H), 2.37-2.10 (m, 6H)

Compound 117

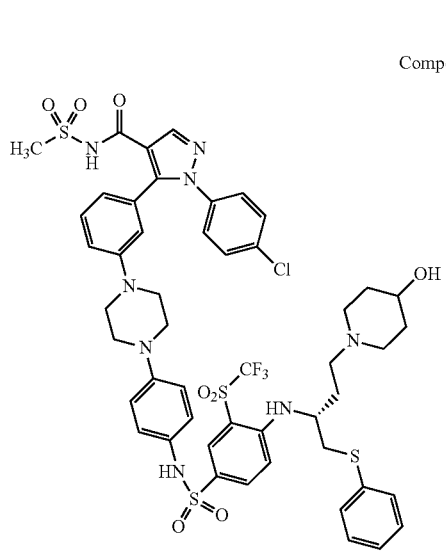

Chemical Formula: C₄₉H₅₂ClF₃N₈O₈S₄
Exact Mass: 1100.24
Molecular Weight: 1101.69

MS=1102.75; ¹H-NMR (300 MHz, 10:1 CDCl₃:CD₃OD) δ ppm 8.24 (s, 1H), 8.00 (d, J=1.8 Hz, 1H), 7.72 (dd, J=2.1, 9.2 Hz, 1H), 7.35-7.23 (m, 8H), 7.17 (d, 0.1=8.8 Hz, 2H), 7.07-6.93 (m, 6H), 6.75 (d, J=7.5 Hz, 1H), 6.65 (d, J=9.3 Hz, 1H), 4.10 (bs, 1H), 4.00-3.85 (m, 2H), 3.36-2.94 (m, 17H), 2.37-1.79 (m, 6H)

Compound 116

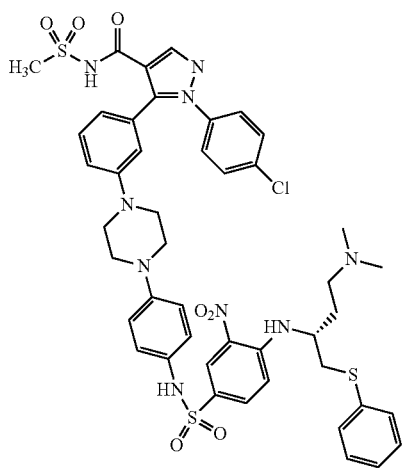

Chemical Formula: C₄₅H₄₈ClN₉O₇S₃
Exact Mass: 957.25
Molecular Weight: 958.57

MS=959.83; ¹H-NMR (300 MHz, 10:1 CDCl₃:CD₃OD) δ ppm 8.45 (d, J=2.1 Hz, 1H), 8.24 (s, 1H), 7.63 (dd, J=2.0, 9.1 Hz, 1H), 7.32-7.24 (m, 5H), 7.18-7.01 (m, 8H), 6.97-6.91 (m, 3H), 6.79-6.72 (m, 2H), 4.15-4.05 (m, 1H), 3.35-3.04 (m, 15H), 2.81 (s, 6H), 2.37-2.08 (m, 2H)

Compound 115

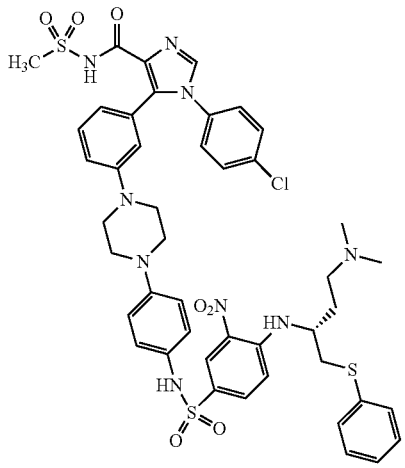

Chemical Formula: C₄₅H₄₈ClN₉O₇S₃
Exact Mass: 957.25
Molecular Weight: 958.57

MS=959.42; ¹H-NMR (300 MHz, 10:1 CDCl₃:CD₃OD) δ ppm 8.45 (d, J=2.2 Hz, 1H), 7.71 (s, 1H), 7.63 (dd, J=2.1, 9.1 Hz, 1H), 7.36 (d, J=9.0, 2H), 7.28-7.06 (m, 10H), 7.00-6.91 (m, 4H), 6.77 (d, J=9.3 Hz, 1H), 6.71 (d, J=7.6 Hz, 1H), 4.14-4.05 (m, 1H), 3.32 (s, 3H), 3.30-3.05 (m, 12H), 2.81 (s, 6H), 2.36-2.08 (m, 2H)

Compound 114

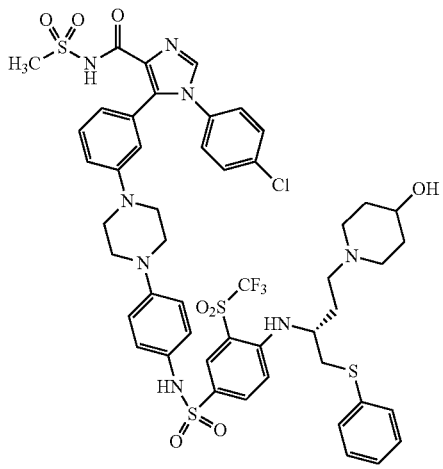

Chemical Formula: C₄₉H₅₂ClF₃N₈O₈S₄
Exact Mass: 1100.24
Molecular Weight: 1101.69

MS=1101.67; ¹H-NMR (300 MHz, 10:1 CDCl₃:CD₃OD) δ ppm 8.00 (d, J=2.2 Hz, 1H), 7.73-7.69 (m, 2H), 7.38-7.32 (m, 4H), 7.29-7.18 (m, 4H), 7.10-6.93 (m, 5H), 6.89-6.83 (m, 3H), 6.73 (d, J=8.0 Hz, 1H), 6.62 (d, J=9.3 Hz, 1H), 4.17 (bs, 1H), 3.93-3.87 (m, 2H), 3.34 (s, 3H), 3.21 (s, 7H), 3.13-2.99 (m, 5H), 2.38-1.81 (m, 7H)

Compound 113

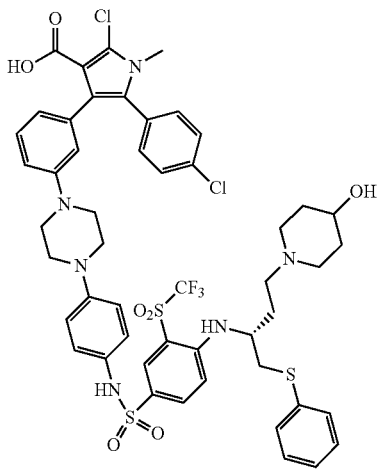

Chemical Formula: C₅₀H₅₁Cl₂F₃N₆O₇S₃
Exact Mass: 1070.23
Molecular Weight: 1072.07

MS=1072.83; ¹H-NMR (300 MHz, 10:1 CDCl₃:CD₃OD) δ ppm 8.00 (d, J=2.1 Hz, 1H), 7.72 (dd, J=2.2, 9.1 Hz, 1H), 7.35-7.32 (m, 2H), 7.30-7.22 (m, 5H), 7.16-7.02 (m, 5H), 6.91-6.75 (m, 5H), 6.64 (d, J=9.3 Hz, 1H), 4.10 (bs, 1H), 4.00-3.87 (m, 2H), 3.52 (s, 3H), 3.32-3.19 (m, 9H), 3.13-2.98 (m, 5H), 2.85-2.62 (m, 1H), 2.36-1.81 (m, 6H)

Compound 112

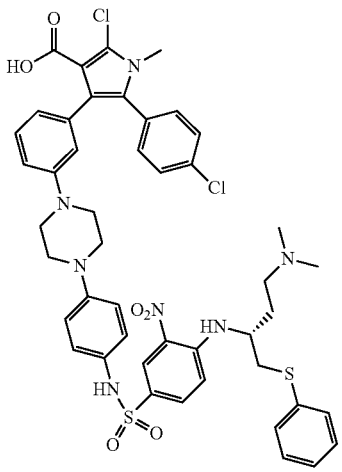

Chemical Formula: C₄₆H₄₇Cl₂N₇O₆S₂
Exact Mass: 927.24
Molecular Weight: 928.94

MS=929.83; ¹H-NMR (300 MHz, 10:1 CDCl₃:CD₃OD) δ ppm 8.45 (d, J=2.3 Hz, 1H), 7.62 (dd, J=2.3, 9.1 Hz, 1H), 7.30-7.24 (m, 4H), 7.17-7.12 (m, 4H), 7.10-7.05 (m, 4H), 6.92-6.87 (m, 3H), 6.82-6.80 (m, 1H), 6.76 (d, J=9.2 Hz, 2H), 4.13-4.04 (m, 1H), 3.51 (s, 3H), 3.28-3.08 (m, 12H), 2.81 (s, 6H), 2.35-2.08 (m, 2H)

Compound 111

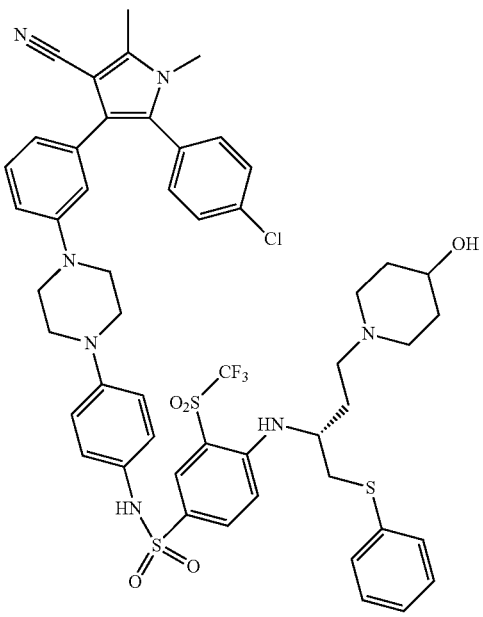

Chemical Formula: C₅₁H₅₃ClF₃N₇O₅S₃
Exact Mass: 1031.29
Molecular Weight: 1032.65

MS=1033.50; ¹H-NMR (300 MHz, 10:1 CDCl₃:CD₃OD) δ ppm 8.02 (d, J=2.1 Hz, 1H), 7.71 (dd, J=2.2, 9.1 Hz, 1H), 7.38-7.33 (m, 3H), 7.27-7.24 (m, 3H), 7.20-7.12 (m, 3H), 7.02 (d, J=8.9 Hz, 2H), 6.89-6.81 (m, 5H), 6.72 (d, J=7.6 Hz, 1H), 6.61 (d, J=9.2 Hz, 1H), 4.10 (bs, 1H), 3.98-3.85 (m, 1H), 3.43 (s, 3H), 3.28-3.15 (m, 9H), 3.14-2.91 (m, 6H), 2.82-2.62 (m, 1H), 2.49 (s, 3H), 2.39-1.27 (m, 6H)

Compound 110

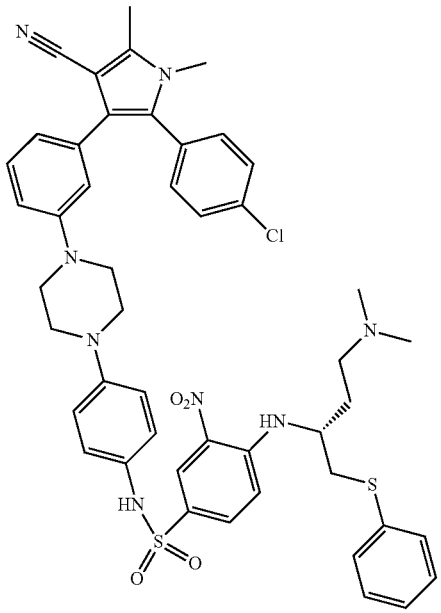

Chemical Formula: C₄₇H₄₉ClN₈O₄S₂
Exact Mass: 888.30
Molecular Weight: 889.53

MS=890.58; ¹H-NMR (300 MHz, 10:1 CDCl₃:CD₃OD) δ ppm 8.46 (d, J=2.2 Hz, 1H), 7.61 (dd, J=2.2, 9.1 Hz, 1H), 7.36 (d, J=9.0 Hz, 2H), 7.27-7.24 (m, 2H), 7.19-7.11 (m, 6H), 7.05 (d, H=8.9 Hz, 2H), 6.87 (d, J=9.0 Hz, 2H), 6.81-6.70 (m, 4H), 4.12-4.02 (m, 1H), 3.43 (s, 3H), 3.25-3.11 (m, 12H), 2.82 (s, 6H), 2.49 (s, 3H), 2.39-2.09 (m, 2H)

Compound 108

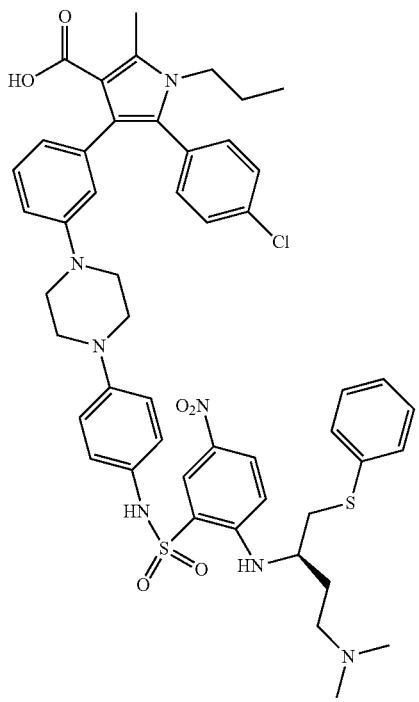

Chemical Formula: C₄₉H₅₄ClN₇O₆S₂
Exact Mass: 935.33
Molecular Weight: 936.58

MS=936.42; ¹H-NMR (300 MHz, 10:1 CDCl₃:CD₃OD) δ ppm 8.52 (d, J=2.7 Hz, 1H), 7.97 (dd, J=2.7, 9.3 Hz, 1H), 7.46-7.37 (m, 3H), 7.26-7.22 (m, 3H), 7.11-7.00 (m, 5H), 6.84-6.65 (m, 5H), 6.24 (d, J=9.5 Hz, 1H), 3.71-3.60 (m, 2H), 3.30-2.92 (m, 13H), 2.83 (s, 6H), 2.62 (s, 3H), 2.52-2.42 (m, 1H), 2.21-2.12 (m, 1H), 1.62-1.48 (m, 2H), 0.77 (t, J=7.3 Hz, 3H)

Compound 109

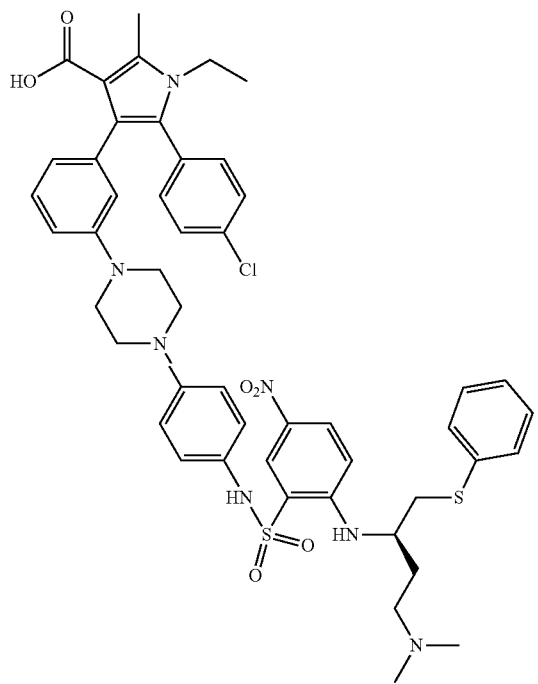

Chemical Formula: C₄₈H₅₂ClN₇O₆S₂
Exact Mass: 921.31
Molecular Weight: 922.55

MS=922.42; ¹H-NMR (300 MHz, 10:1 CDCl₃:CD₃OD) δ ppm 8.52 (d, J=2.7 Hz, 1H), 7.97 (dd, J=2.7, 9.3 Hz, 1H), 7.46-7.37 (m, 5H), 7.26 (d, J=8.4 Hz, 2H), 7.12-7.07 (m, 3H), 7.02 (d, J=8.9 Hz, 2H), 6.85-6.75 (m, 5H), 6.24 (d, J=9.5 Hz, 1H), 3.88-3.81 (m, 2H), 3.72-3.61 (m, 1H), 3.33-2.88 (m, 13H), 2.83 (s, 6H), 2.64 (s, 3H), 2.53-2.10 (m, 2H), 1.17 (t, J=7.1 Hz, 3H)

Compound 107

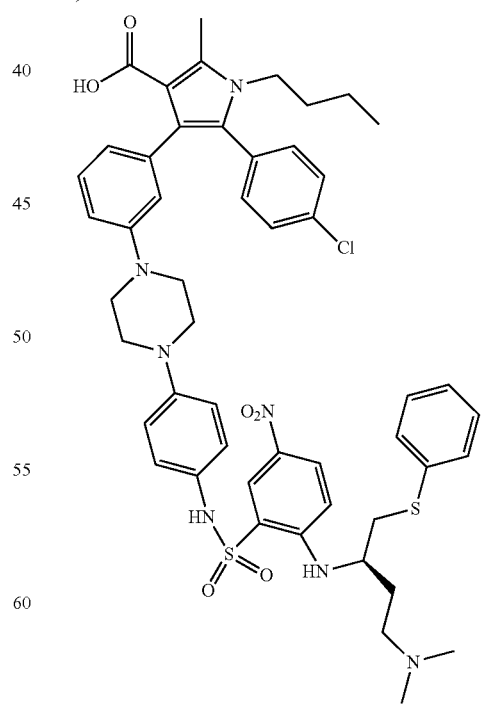

Chemical Formula: C₅₀H₅₆ClN₇O₆S₂
Exact Mass: 949.34
Molecular Weight: 950.61

MS=950.42; ¹H-NMR (300 MHz, 10:1 CDCl₃:CD₃OD) δ ppm 8.53 (d, J=2.7 Hz, 1H), 7.96 (dd, J=2.7, 9.3 Hz, 1H), 7.46-7.35 (m, 4H), 7.27-7.22 (m, 2H), 7.15-7.00 (m, 5H), 6.85-6.67 (m, 5H), 6.20 (d, J=9.5 Hz, 1H), 3.80-3.75 (m, 2H), 3.69-3.59 (m, 1H), 3.25-3.09 (m, 9H), 3.03-2.87 (m, 3H), 2.83 (s, 6H), 2.62 (s, 3H), 2.55-2.42 (m, 1H), 2.22-2.10 (m, 1H), 1.54-1.42 (m, 2H), 1.23-1.10 (m, 2H), 0.79 (t, J=7.3 Hz, 3H)

MS=1043.17; ¹H-NMR (300 MHz, 10:1 CDCl₃:CD₃OD) δ ppm 8.02 (d, J=1.9 Hz, 1H), 7.73-7.68 (m, 1H), 7.33-7.23 (m, 6H), 7.17-7.11 (m, 3H), 7.01 (d, J=8.9 Hz, 2H), 6.87-6.74 (m, 5H), 6.63 (d, J=9.1 Hz, 1H), 4.15-4.06 (m, 1H), 4.00-3.89 (m, 1H), 3.43 (s, 3H), 3.26-2.97 (m, 13H), 2.34 (s, 3H), 2.31-1.80 (m, 6H)

Compound 106

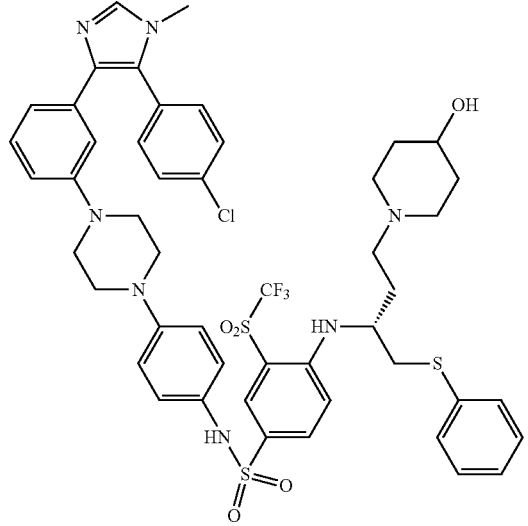

Chemical Formula: C₄₈H₅₁ClF₃N₇O₅S₃
Exact Mass: 993.28
Molecular Weight: 994.61

MS=994.25; ¹H-NMR (300 MHz, 10:1 CDCl₃:CD₃OD) δ ppm 8.96 (s, 1H), 8.48 (dd, J=2.2, 6.3 Hz, 1H), 8.37-8.32 (m, 1H), 7.99 (d, J=1.9 Hz, 1H), 7.74-7.69 (m, 1H), 7.57-7.53 (m, 2H), 7.43-7.36 (m, 4H), 7.27-7.16 (m, 3H), 7.03-6.90 (m, 3H), 6.86 (d, J=9.0 Hz, 2H), 6.68 (t, 7.4 Hz, 2H), 4.15-4.07 (m, 1H), 4.00-3.95 (m, 2H), 3.73 (s, 3H), 3.31-2.98 (m, 14H), 2.40-1.81 (m, 6H)

Compound 105

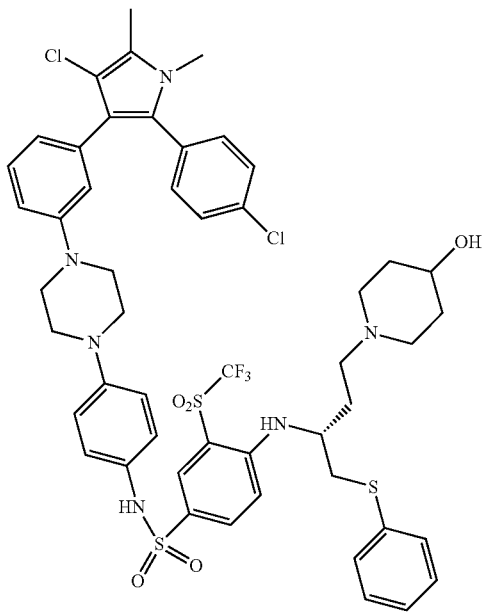

Chemical Formula: C₅₀H₅₃Cl₂F₃N₆O₅S₃
Exact Mass: 1040.26
Molecular Weight: 1042.09

Compound 104

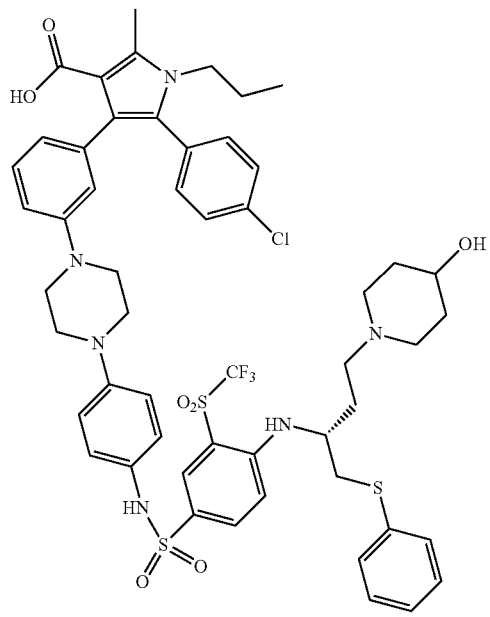

Chemical Formula: C₅₃H₅₈ClF₃N₆O₇S₃
Exact Mass: 1078.32
Molecular Weight: 1079.71

MS=1080.33; ¹H-NMR (300 MHz, 10:1 CDCl₃:CD₃OD) δ ppm 8.01 (d, J=1.9 Hz, 1H), 7.70 (dd, J=2.3, 8.5 Hz, 1H), 7.29-7.23 (m, 6H), 7.12-7.00 (m, 6H), 6.87-6.80 (m, 3H), 6.77-6.71 (m, 2H), 6.61 (d, J=9.2 Hz, 1H), 4.15-4.04 (m, 1H), 3.95-3.85 (m, 1H), 3.78-3.72 (m, 2H), 3.23-2.93 (m, 14H), 2.62 (s, 3H), 2.36-1.80 (m, 6H), 1.61-1.46 (m, 2H), 0.77 (t, J=7.3 Hz, 3H)

Compound 103

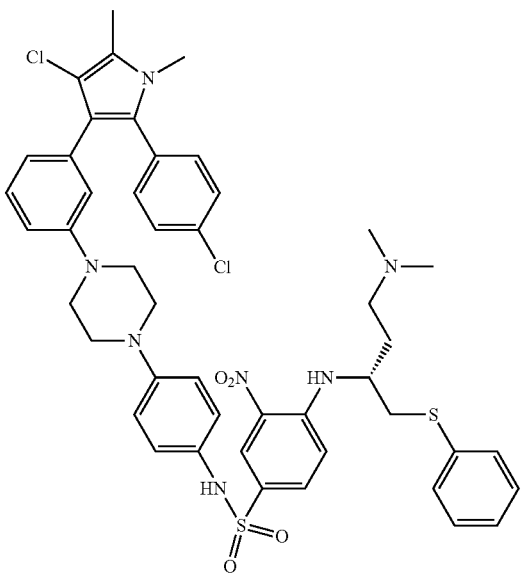

Chemical Formula: C₄₆H₄₉Cl₂N₇O₄S₂
Exact Mass: 897.27
Molecular Weight: 898.96

MS=900.17; ¹H-NMR (300 MHz, 10:1 CDCl₃:CD₃OD) δ ppm 8.45 (d, J=2.2 Hz, 1H), 7.62 (dd, J=2.3, 9.1 Hz, 1H), 7.30-7.24 (m, 4H), 7.18-7.02 (m, 8H), 6.90-6.75 (m, 6H), 4.17-4.07 (m, 1H), 3.43 (s, 3H), 3.29-3.06 (m, 13H), 2.81 (s, 6H), 2.33 (s, 3H), 2.40-2.10 (m, 2H)

Compound 102

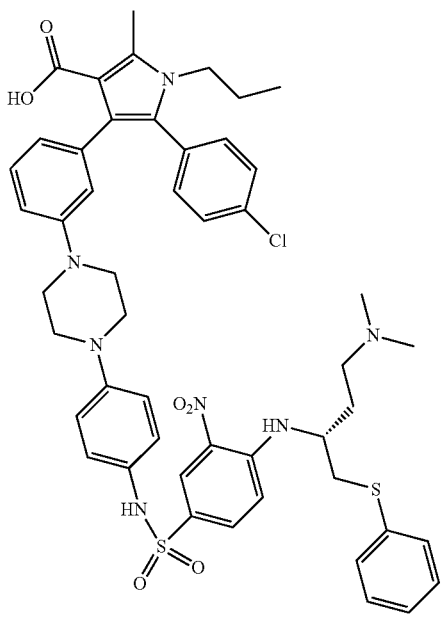

Chemical Formula: C₄₉H₅₄ClN₇O₆S₂
Exact Mass: 935.33
Molecular Weight: 936.58

MS=937.17; ¹H-NMR (300 MHz, 10:1 CDCl₃:CD₃OD) δ ppm 8.46 (d, J=2.2 Hz, 1H), 7.61 (dd, J=2.2, 9.1 Hz, 1H), 7.27-7.23 (m, 4H), 7.20-7.13 (m, 4H), 7.10-7.03 (m, 4H), 6.85 (d, J=9.0 Hz, 2H), 6.78-6.69 (m, 4H), 4.12-4.04 (m, 1H), 3.74 (t, J=7.8 Hz, 2H), 3.22-3.03 (m, 13H), 2.81 (s, 6H), 2.37-2.09 (m, 2H), 0.77 (t, J=7.4 Hz, 3H)

Compound 101

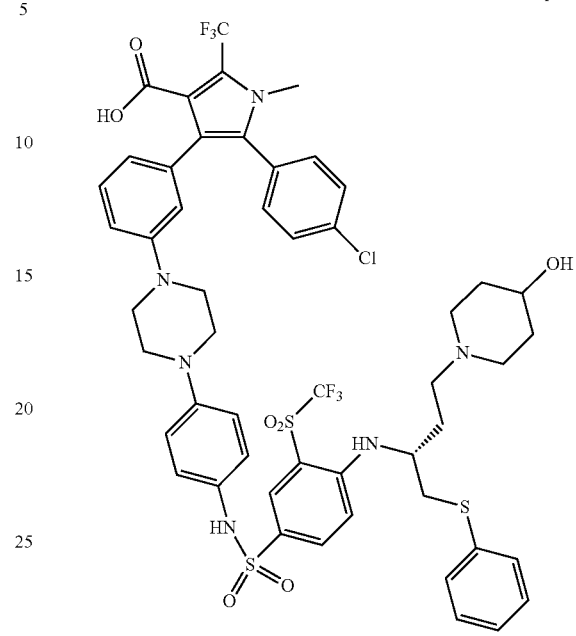

Chemical Formula: C₅₁H₅₁ClF₆N₆O₇S₃
Exact Mass: 1104.26
Molecular Weight: 1105.63

MS=1106.08; ¹H-NMR (300 MHz, 10:1 CDCl₃:CD₃OD) δ ppm 8.01 (d, J=2.0 Hz, 1H), 7.73-7.69 (m, 1H), 7.29-7.21 (m, 4H), 7.16-7.06 (m, 4H), 7.01 (d, J=8.9 Hz, 2H), 6.85 (d, J=8.9 Hz, 2H), 6.81-6.60 (m, 4H), 4.15-4.05 (m, 1H), 4.00-3.91 (m, 2H), 3.59 (s, 3H), 3.20-2.89 (m, 15H), 2.37-1.80 (m, 6H)

Compound 100

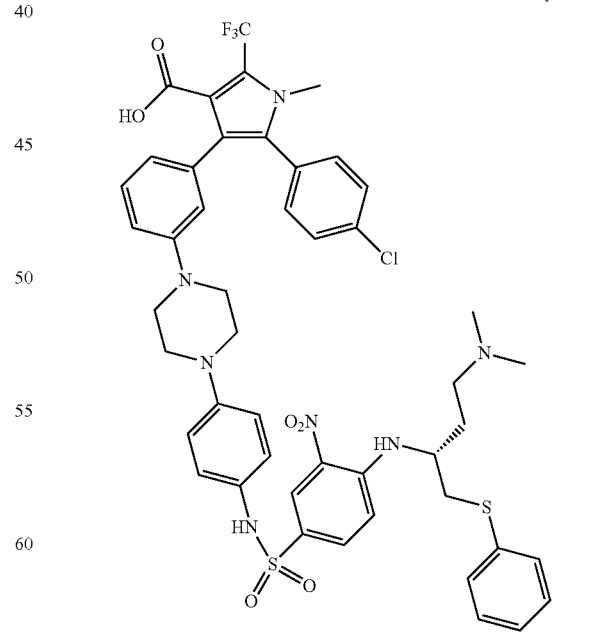

Chemical Formula: C₄₇H₄₇ClF₃N₇O₆S₂
Exact Mass: 961.27
Molecular Weight: 962.50

239

MS=963.25; $^1$H-NMR (300 MHz, 10:1 CDCl$_3$:CD$_3$OD) δ ppm 8.45 (d, J=1.7 Hz, 1H), 7.61 (d, J=9.1 Hz, 1H), 7.27-7.03 (m, 10H), 6.87-6.60 (m, 6H), 4.12-4.04 (m, 1H), 3.58 (s, 3H), 3.27-3.05 (m, 12H), 2.81 (s, 6H), 2.36-2.07 (m, 2H)

Compound 99

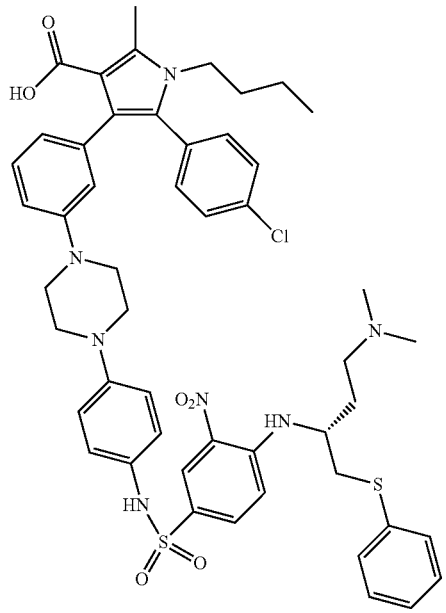

Chemical Formula: C$_{50}$H$_{56}$ClN$_7$O$_6$S$_2$
Exact Mass: 949.34
Molecular Weight: 950.61

MS=951.17; $^1$H-NMR (300 MHz, 10:1 CDCl$_3$:CD$_3$OD) δ ppm 8.46 (bs, 1H), 7.65-7.59 (m, 1H), 7.30-6.97 (m, 12H), 6.86-6.61 (m, 6H), 4.12-4.04 (m, 1H), 3.84-3.67 (m, 2H), 3.18-3.02 (m, 8H), 2.81 (s, 6H), 2.65-2.62 (m, 2H), 2.38-2.03 (m, 7H), 1.74-1.63 (m, 2H), 1.22-1.10 (m, 2H), 0.79 (t, 7.1 Hz, 3H)

Compound 98

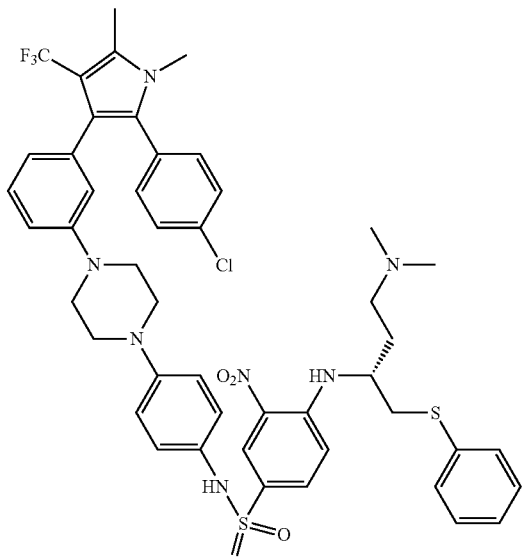

Chemical Formula: C$_{47}$H$_{49}$ClF$_3$N$_7$O$_4$S$_2$
Exact Mass: 931.29
Molecular Weight: 932.51

240

MS=932.42; $^1$H-NMR (300 MHz, 10:1 CDCl$_3$:CD$_3$OD) δ ppm 8.46 (d, J=2.2 Hz, 1H), 7.61 (dd, J=2.2, 9.1 Hz, 1H), 7.27-7.24 (m, 4H), 7.17-7.12 (m, 4H), 7.09-7.02 (m, 4H), 6.089-6.69 (m, 6H), 4.12-4.04 (m, 1H), 3.44 (s, 3H), 3.28-3.06 (m, 12H), 2.82 (s, 6H), 2.45 (d, J=1.4 Hz, 3H), 2.37-2.08 (m, 2H)

Compound 97

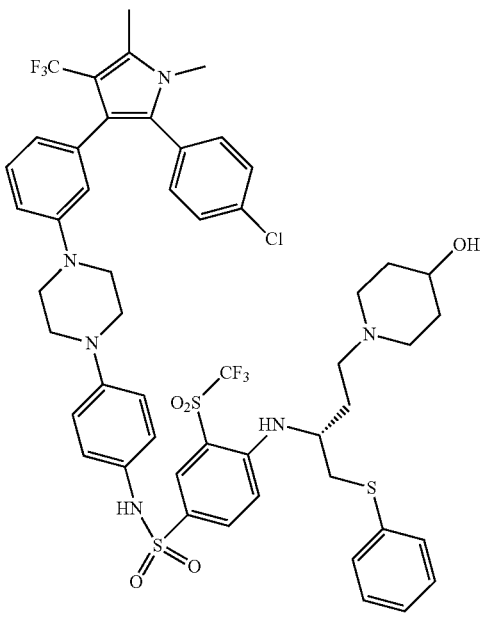

Chemical Formula: C$_{51}$H$_{53}$ClF$_6$N$_6$O$_5$S$_3$
Exact Mass: 1074.28
Molecular Weight: 1075.64

MS=1076.08; $^1$H-NMR (300 MHz, 10:1 CDCl$_3$:CD$_3$OD) δ ppm 8.01 (d, J=2.1 Hz, 1H), 7.71 (dd, J=2.1, 9.1 Hz, 1H), 7.28-7.20 (m, 5H), 7.16-7.00 (m, 5H), 6.89-6.83 (m, 3H), 6.77-6.71 (m, 2H), 6.62 (d, J=9.1 Hz, 1H), 4.10 (bs, 1H), 3.96-3.87 (m, 1H), 3.43 (s, 3H), 3.32-2.93 (m, 15H), 2.77-2.63 (m, 1H), 2.45 (d, J=1.4 Hz, 3H), 2.36-1.79 (m, 6H)

Compound 96

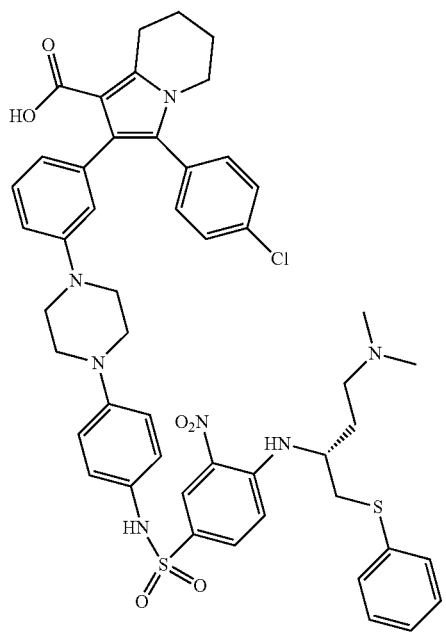

Chemical Formula: C₄₉H₅₂ClN₇O₆S₂
Exact Mass: 933.31
Molecular Weight: 934.56

MS=935.50; ¹H-NMR (300 MHz, 10:1 CDCl₃:CD₃OD) δ ppm 8.45 (d, J=2.1 Hz, 1H), 7.62 (dd, J=2.1, 9.1 Hz, 1H), 7.28-7.22 (m, 4H), 7.18-7.01 (m, 8H), 6.95-6.82 (m, 4H), 6.76 (d, J=9.3 Hz, 2H), 4.12-4.04 (m, 1H), 3.78-3.72 (m, 2H), 3.29-3.05 (m, 14H), 2.81 (s, 6H), 2.35-2.08 (m, 2H), 2.00-1.87 (m, 4H)

Compound 95

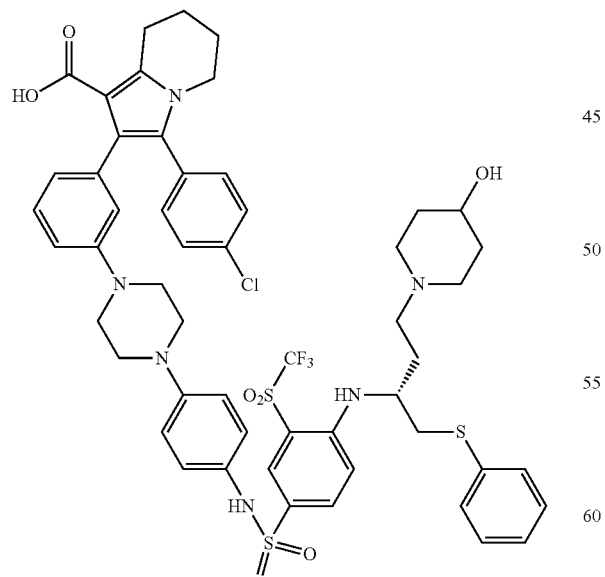

Chemical Formula: C₅₃H₅₆ClF₃N₆O₇S₃
Exact Mass: 1076.30
Molecular Weight: 1077.69

MS=1078.33; ¹H-NMR (300 MHz, 10:1 CDCl₃:CD₃OD) δ ppm 8.00 (d, J=2.1 Hz, 1H), 7.71 (dd, J=2.0, 9.1 Hz, 1H), 7.29-7.12 (m, 6H), 7.08-6.81 (m, 8H), 6.63 (d, J=9.3 Hz, 1H), 4.10 (bs, 1H), 4.00-3.84 (m, 1H), 3.80-3.72 (m, 2H), 3.45-2.86 (m, 16H), 2.76-2.47 (m, 1H), 2.37-1.81 (m, 10H)

Compound 94

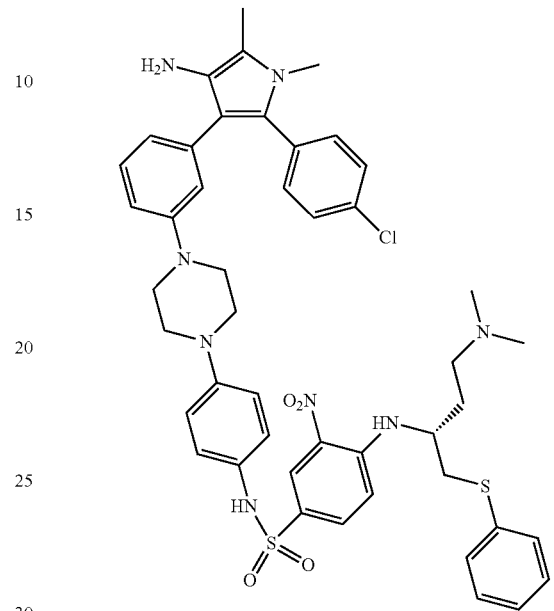

Chemical Formula: C₄₆H₅₁ClN₈O₄S₂
Exact Mass: 878.32
Molecular Weight: 879.53

MS=879.42;

Compound 93

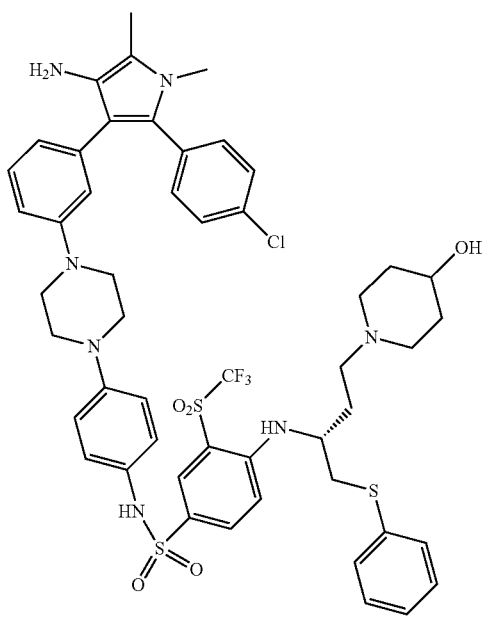

Chemical Formula: C₅₀H₅₅ClF₃N₇O₅S₃
Exact Mass: 1021.31
Molecular Weight: 1022.66

MS=1022.33;

Compound 92

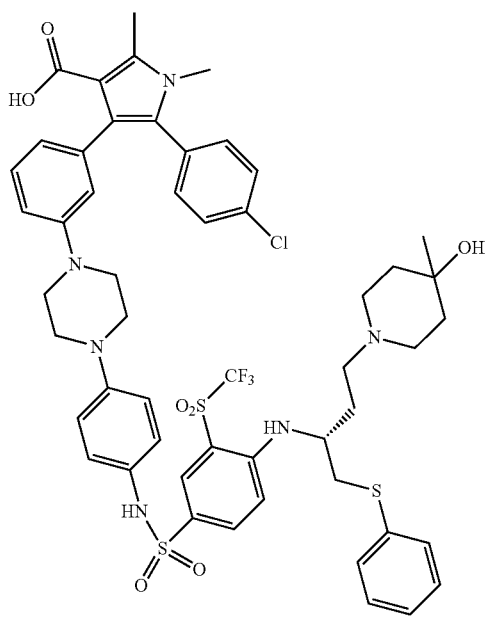

Chemical Formula: C₅₂H₅₆ClF₃N₆O₇S₃
Exact Mass: 1064.30
Molecular Weight: 1065.68

MS=1066.42; ¹H-NMR (300 MHz, 10:1 CDCl₃:CD₃OD) δ ppm 8.01 (bs, 1H), 7.73-7.70 (m, 1H), 7.35-7.22 (m, 7H), 7.15-7.01 (m, 5H), 6.92-6.75 (m, 5H), 6.63 (d, J=9.2 Hz, 1H), 4.00-3.90 (m, 1H), 3.43 (s, 3H), 3.32-2.97 (m, 15H), 2.63 (s, 3H), 2.35-1.67 (m, 6H), 1.47-1.37 (m, 1H), 1.29 (s, 3H)

3.41 (s, 3H), 3.32-2.85 (m, 18H), 2.70-2.57 (m, 1H), 2.37-1.67 (m, 11H), 1.29 (s, 3H), 1.11 (bs, 1H)

Compound 90

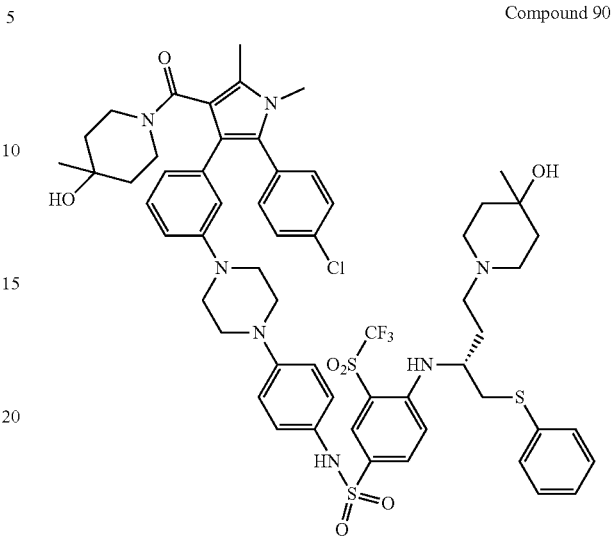

Chemical Formula: C₅₈H₆₇ClF₃N₇O₇S₃
Exact Mass: 1161.39
Molecular Weight: 1162.84

MS=1163.58; ¹H-NMR (300 MHz, 10:1 CDCl₃:CD₃OD) δ ppm 8.00 (d, J=1.7 Hz, 1H), 7.72 (dd, J=2.2, 8.9 Hz, 1H), 7.35-7.23 (m, 7H), 7.20-7.01 (m, 5H), 6.92-6.75 (m, 3H), 6.68-6.59 (m, 3H), 4.29-4.20 (m, 1H), 3.41 (s, 3H), 3.32-2.98 (m, 18H), 2.84-2.75 (m, 1H), 2.33-2.21 (m, 4H), 2.11-1.67 (m, 6H), 1.57-1.38 (m, 2H), 1.29 (s, 3H), 0.91 (s, 3H)

Compound 91

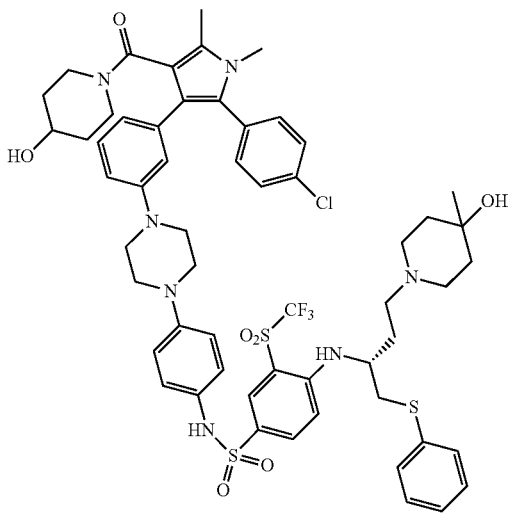

Chemical Formula: C₅₇H₆₅ClF₃N₇O₇S₃
Exact Mass: 1147.37
Molecular Weight: 1148.81

MS=1149.50; ¹H-NMR (300 MHz, 10:1 CDCl₃:CD₃OD) δ ppm 8.00 (d, J=2.0 Hz, 1H), 7.75-7.70 (m, 1H), 7.35-7.23 (m, 6H), 7.20-7.02 (m, 5H), 6.91-6.73 (m, 3H), 6.70-6.56 (m, 3H), 4.26-4.17 (m, 1H), 4.09-3.92 (m 2H), 3.72-3.51 (m, 2H), Compound 89

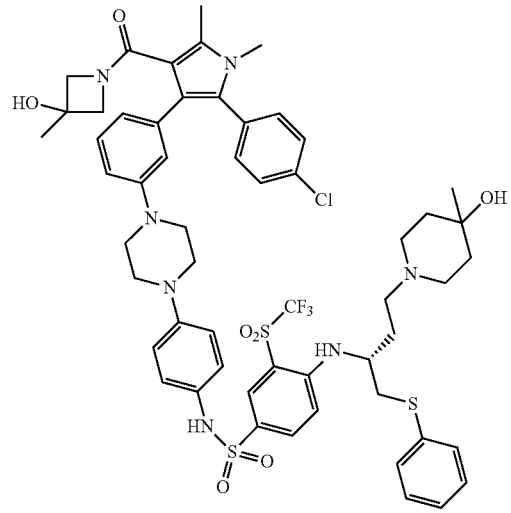

Chemical Formula: C₅₆H₆₃ClF₃N₇O₇S₃
Exact Mass: 1133.36
Molecular Weight: 1134.79

MS=1134.83; ¹H-NMR (300 MHz, 10:1 CDCl₃:CD₃OD) δ ppm 8.00 (d, J=2.1 Hz, 1H), 7.72 (dd, J=2.2, 9.1 Hz, 1H), 7.36-7.29 (m, 4H), 7.27-7.20 (m, 3H), 7.15-7.10 (m, 3H), 7.04 (d, J=8.9 Hz, 2H), 6.90 (d, J=9.0 Hz, 2H), 6.85-6.81 (m, 1H), 6.72 (bs, 1H), 6.66-6.62 (m, 2H), 3.86-3.79 (m, 1H), 3.40 (s, 3H), 3.33-2.97 (m, 16H), 2.39 (s, 3H), 2.34-1.68 (m, 7H), 1.45-1.35 (m, 1H), 1.29 (s, 3H), 1.13 (s, 3H)

4H), 6.93-6.82 (m, 2H), 6.69-6.63 (m, 2H), 6.41 (s, 1H), 4.00-3.84 (m, 1H), 3.40 (s, 3H), 3.33-3.00 (m, 12H), 2.39 (s, 3H), 2.34-1.67 (m, 7H), 1.41 (p, 7.0 Hz, 1H), 1.29 (s, 3H)

Compound 88

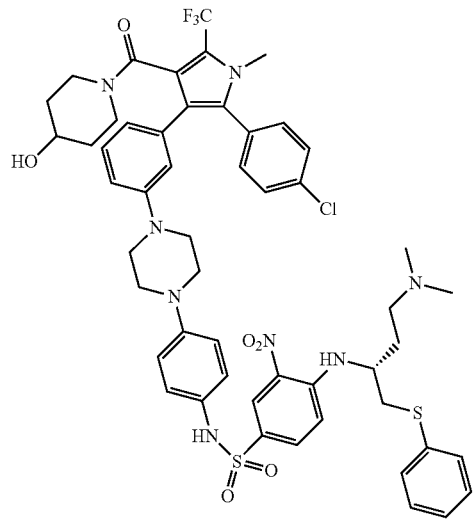

Chemical Formula: C$_{52}$H$_{56}$ClF$_3$N$_8$O$_6$S$_2$
Exact Mass: 1044.34
Molecular Weight: 1045.63

MS=1046.00; $^1$H-NMR (300 MHz, 10:1 CDCl$_3$:CD$_3$OD) δ ppm 8.45 (m, 1H), 7.65-7.60 (m, 1H), 7.28-7.02 (m, 10H), 6.86 (d, J=8.9 Hz, 2H), 6.78-6.67 (m, 3H), 6.53 (t, 6.8 Hz, 1H) 4.15-4.03 (m, 2H), 3.60 (s, 3H), 3.30-3.00 (m, 13H), 2.82 (s, 6H), 2.38-2.11 (m, 5H)

Compound 86

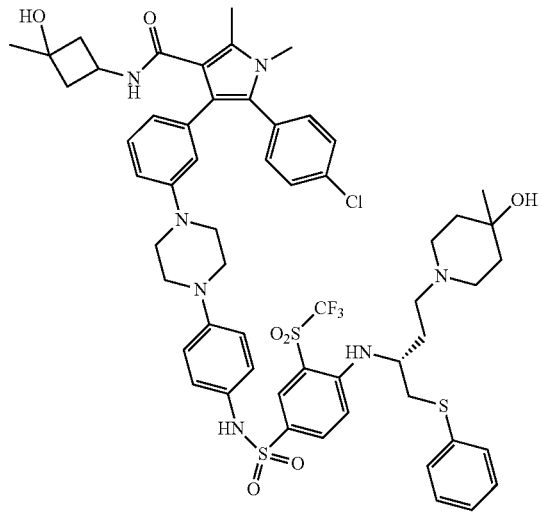

Chemical Formula: C$_{57}$H$_{65}$ClF$_3$N$_7$O$_7$S$_3$
Exact Mass: 1147.37
Molecular Weight: 1148.81

MS=1149.42; $^1$H-NMR (300 MHz, 10:1 CDCl$_3$:CD$_3$OD) δ ppm 8.00 (d, J=2.0 Hz, 1H), 7.72 (dd, J=2.2, 9.0 Hz, 1H), 7.35-7.32 (m, 2H), 7.28-7.17 (m, 6H), 7.10-7.02 (m, 4H), 6.91-6.85 (m, 3H), 6.74-6.62 (m, 3H), 4.00-3.88 (m, 2H), 3.42 (s, 3H), 3.32-2.98 (m, 16H) 2.57 (s, 3H), 2.34-2.24 (m, 3H), 2.12-1.48 (m, 8H), 1.29 (s, 3H), 1.27 (s, 3H)

Compound 87

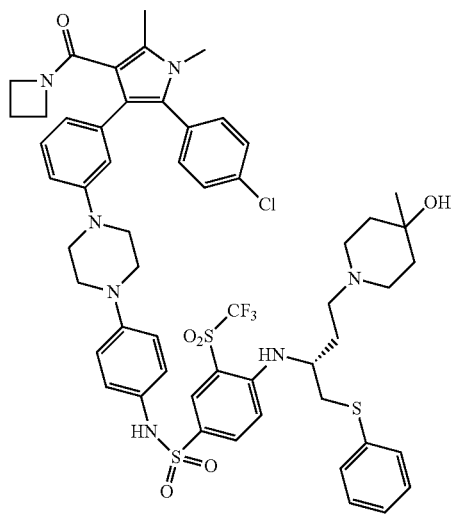

Chemical Formula: C$_{55}$H$_{61}$ClF$_3$N$_7$O$_6$S$_3$
Exact Mass: 1103.35
Molecular Weight: 1104.76

MS=1105.67; $^1$H-NMR (300 MHz, 10:1 CDCl$_3$:CD$_3$OD) δ ppm 8.07 (d, J=8.4 Hz, 1H), 8.00 (d, J=2.0 Hz, 1H), 7.93 (d, J=8.3 Hz, 1H), 7.73 (dd, J=2.2, 9.1 Hz, 1H), 7.66-7.60 (m, 1H), 7.54-7.48 (m, 1H), 7.36-7.20 (m, 5H), 7.17-7.03 (m, Compound 85

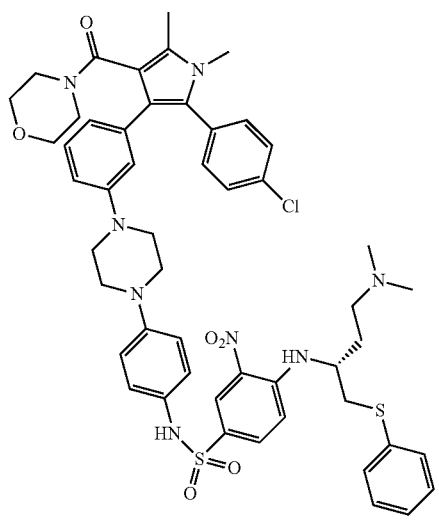

Chemical Formula: C$_{51}$H$_{57}$ClN$_8$O$_6$S$_2$
Exact Mass: 976.35
Molecular Weight: 977.63

MS=977.42; $^1$H-NMR (300 MHz, 10:1 CDCl$_3$:CD$_3$OD) δ ppm 8.37 (d, J=2.1 Hz, 1H), 7.56 (dd, J=2.0, 9.0 Hz, 1H), 7.25-7.17 (m, 4H), 7.09-6.98 (m, 8H), 6.84 (d, J=8.9 Hz, 2H), 6.72-6.68 (m, 2H), 6.54-6.49 (m, 2H), 4.08-3.99 (m, 1H), 3.75-3.51 (m, 2H), 3.33 (s, 3H), 3.21-2.94 (m, 16H), 2.74 (s, 6H), 2.41-2.02 (m, 2H), 2.26 (s, 3H)

Compound 84

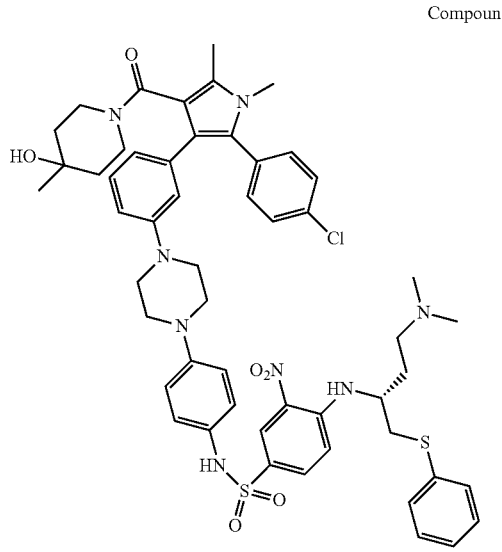

Chemical Formula: C$_{53}$H$_{61}$ClN$_8$O$_6$S$_2$
Exact Mass: 1004.38
Molecular Weight: 1005.68

MS=1005.58; $^1$H-NMR (300 MHz, 10:1 CDCl$_3$:CD$_3$OD) δ ppm 8.36 (s, 1H), 7.53 (dd, J=2.1, 9.1 Hz, 1H), 7.23-7.15 (m, 4H), 7.08-6.95 (m, 814), 6.84-6.65 (m, 4H), 6.59-6.49 (m, 2H), 4.20-4.09 (m, 1H), 4.03-3.93 (m, 1H), 3.31 (s, 3H), 3.21-2.97 (m, 15H), 2.72 (s, 6H), 2.23-1.99 (m, 2H), 2.20 (s, 3H), 1.50-1.28 (m, 2H), 0.81 (s, 3H)

Compound 83

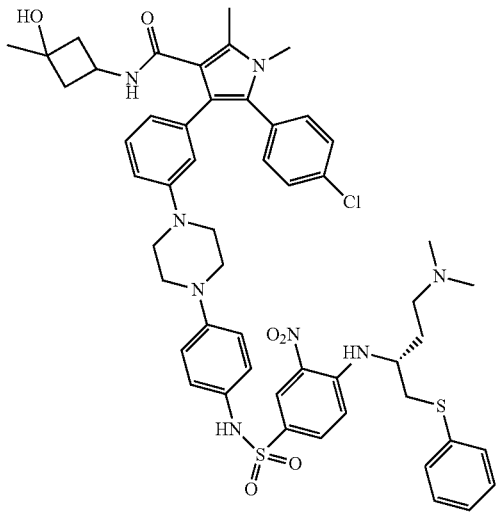

Chemical Formula: C$_{52}$H$_{59}$ClN$_8$O$_6$S$_2$
Exact Mass: 990.37
Molecular Weight: 991.66

MS=991.42; $^1$H-NMR (300 MHz, 10:1 CDCl$_3$:CD$_3$OD) δ ppm 8.37 (d, J=2.1 Hz, 1H), 7.55 (dd, J=2.1, 9.1 Hz, 1H), 7.21-7.15 (m, 4H), 7.14-7.05 (m, 4H), 7.03-6.95 (m, 4H), 6.85-6.79 (m, 3H), 6.70-6.60 (m, 3H), 4.06-3.96 (m, 1H), 3.80 (p, 7.9 Hz, 1H), 3.34 (s, 3H), 3.20-3.03 (m, 12H), 2.73 (s, 6H), 2.49 (s, 3H), 2.28-2.00 (m, 4H), 1.46-1.39 (m, 2H), 1.18 (s, 3H)

Compound 82

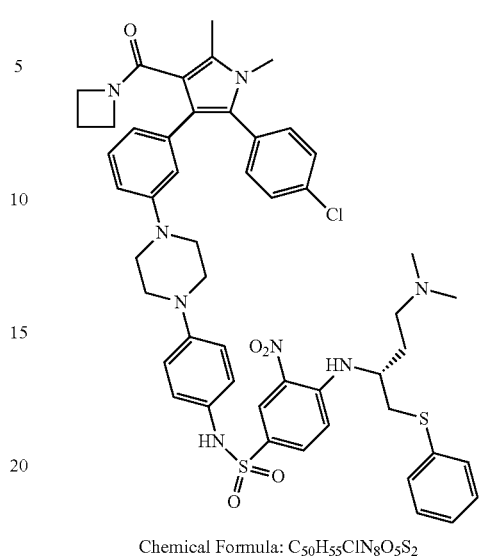

Chemical Formula: C$_{50}$H$_{55}$ClN$_8$O$_5$S$_2$
Exact Mass: 946.34
Molecular Weight: 947.61

MS=948.50; $^1$H-NMR (300 MHz, 10:1 CDCl$_3$:CD$_3$OD) δ ppm 8.45 (d, J=2.2 Hz, 1H), 7.63 (dd, J=2.2, 9.1 Hz, 1H), 7.32-7.24 (m, 4H), 7.18-7.01 (m, 8H), 6.90 (d, J=9.0 Hz, 2H), 6.82-6.75 (m, 2H), 6.66-6.63 (m, 2H), 4.13-4.06 (m, 1H), 4.00 (t, J=7.4 Hz, 2H), 3.39 (s, 3H), 3.29-3.10 (m, 12H), 2.82 (s, 6H), 2.39 (s, 3H), 2.36-2.10 (m, 2H), 1.96 (p, J=7.5 Hz, 2H)

Compound 81

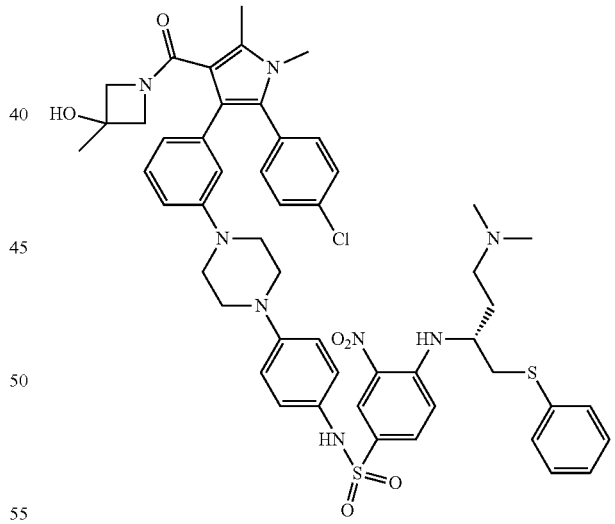

Chemical Formula: C$_{51}$H$_{57}$ClN$_8$O$_6$S$_2$
Exact Mass: 976.35
Molecular Weight: 977.63

MS=977.17; $^1$H-NMR (300 MHz, 10:1 CDCl$_3$:CD$_3$OD) δ ppm 8.45 (d, J=2.2 Hz, 1H), 7.63 (dd, J=2.2, 9.1 Hz, 1H)7.33-7.24 (m, 4H), 7.19-7.03 (m, 8H), 6.89 (d, J=9.0 Hz, 2H), 6.81-6.75 (m, 2H), 6.67 (bs, 1H), 6.61 (d, J=7.6 Hz, 1H), 4.13-4.05 (m, 1H), 3.83 (q, 10 Hz, 2H), 3.40 (s, 3H), 3.30-3.11 (m, 13H), 2.82 (s, 6H), 2.39 (s, 3H), 2.36-2.10 (m, 2H), 1.11 (s, 3H),

Compound 137

4-(4-chlorophenyl)-1-((S)-3,4-dihydroxybutyl)-3-(3-((4-(4-(((R)-4-(dimethylamino)-1-(phenylthio)butan-2-yl)amino)-3-nitrophenylsulfonamido)phenyl)ethynyl)phenyl)-N-(3-(4-methylpiperazin-1-yl)propyl)-1H-pyrrole-2-carboxamide

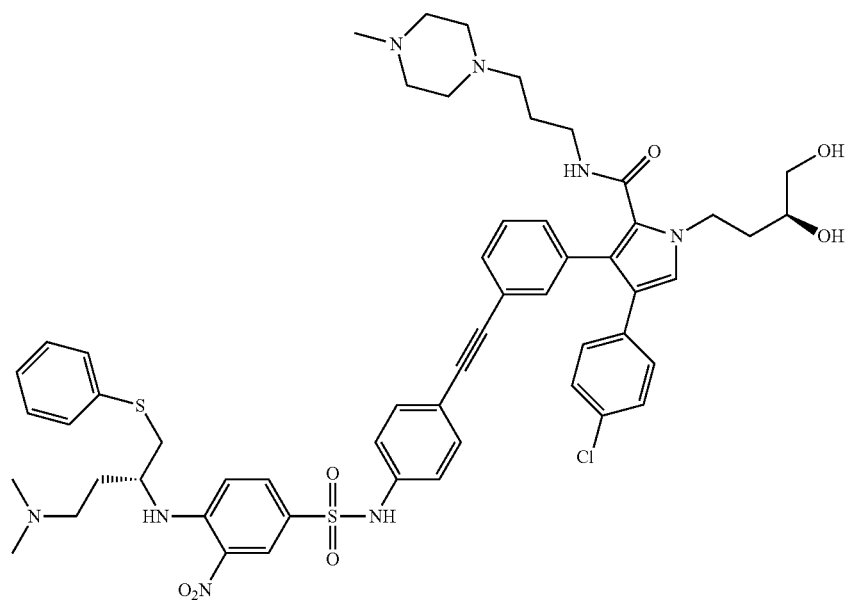

$^1$HNMR (300 MHz, CD$_3$OD), δ 8.39 (d, J=2.2, 1H), 7.63 (dd, J=2.2, 9.0, 1H), 7.60~7.40 (m, 3H), 7.32~7.27 (m, 2H), 7.15~7.10 (m, 8H), 7.01~6.89 (m, 6H), 4.30~4.28 (m, 2H), 4.11~4.08 (m, 1H), 3.55~3.49 (m, 1H), 3.45~3.43 (m, 2H), 3.35~3.31 (m, 5H), 3.19~3.14 (m, 9H), 2.82 (s, 9H), 2.70~2.68 (m, 2H), 2.20~2.00 (m, 3H), 1.68~1.64 (m, 3H); $^{13}$C NMR (75 MHz, CD$_3$OD), δ 165.4, 148.1, 139.4, 136.6, 136.2, 134.8, 134.4, 134.3, 133.7, 132.7, 132.2, 132.0, 131.5, 131.2, 130.5, 130.1, 129.8, 129.3, 128.0, 127.9, 126.7, 125.2, 124.7, 124.6, 123.5, 121.1, 120.1, 116.3 90.2, 90.0, 70.2, 67.3, 55.9, 55.4, 52.7, 52.3, 50.5, 46.1, 43.6, 43.5, 39.4, 37.6, 36.4, 30.1, 25.7;

Compound 138

(R)-5-(4-chlorophenyl)-4-(3-((4-(4-((4-(dimethylamino)-1-(phenylthio)butan-2-yl)amino)-3-nitrophenylsulfonamido)phenyl)ethynyl)phenyl)-1,2-dimethyl-N-(3-(4-methylpiperazin-1-yl)propyl)-1H-pyrrole-3-carboxamide

BM-749

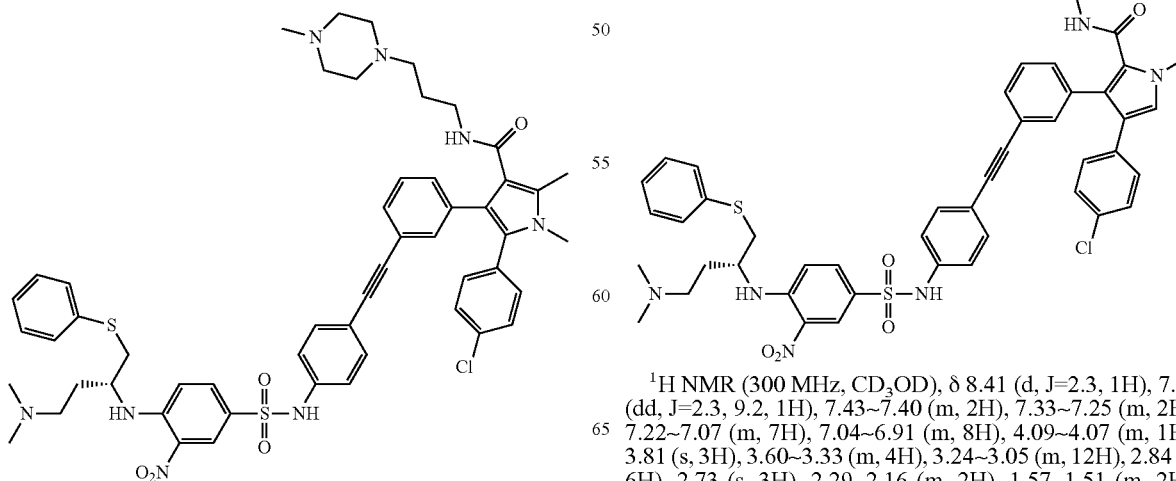

$^1$H NMR (300 MHz, CD$_3$OD), δ 8.38 (d, J=2.0, 1H), 7.62 (dd, J=1.9, 9.1, 1H), 7.37~6.90 (m, 18H), 4.09~4.07 (m, 1H), 3.38~3.33 (m, 3H), 3.24~3.14 (m, 14H), 2.82~2.80 (m, 11H), 2.41 (s, 3H), 2.20~2.15 (m, 2H), 1.77~1.72 (m, 2H); $^{13}$C NMR (75 MHz, CD$_3$OD), δ 170.3, 148.1, 139.4, 137.1, 136.2, 134.9, 134.4, 134.3, 133.8, 133.7, 133.3, 133.2, 131.74, 131.68, 131.5, 131.4, 130.4, 130.1, 129.6, 129.4, 128.0, 127.9, 127.4, 124.1, 121.7, 121.1, 120.2, 116.4, 116.3, 90.2, 89.9, 55.9, 55.2, 52.4, 50.3, 43.5, 39.3, 37.3, 32.0, 30.1, 25.8, 11.4;

Compound 139

(R)-4-(4-chlorophenyl)-3-(3-((4-(4-((4-(dimethylamino)-1-(phenylthio)butan-2-yl)amino)-3-nitrophenylsulfonamido)phenyl)ethynyl)phenyl)-1-methyl-N-(3-(4-methylpiperazin-1-yl)propyl)-1H-pyrrole-2-carboxamide

BM-752

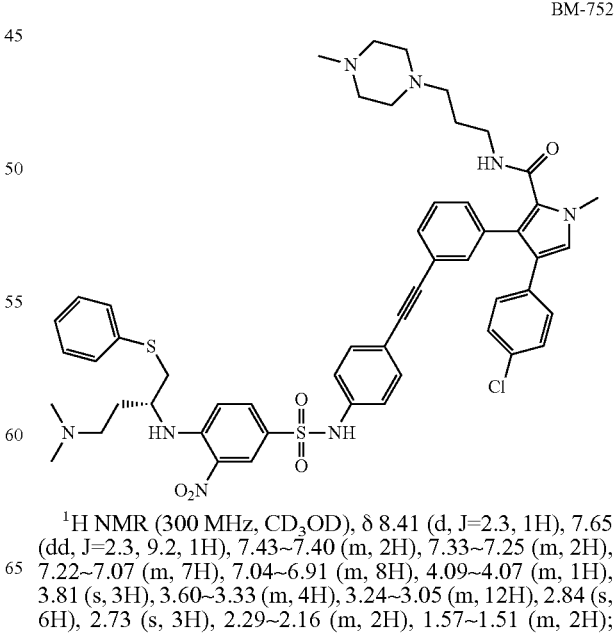

$^1$H NMR (300 MHz, CD$_3$OD), δ 8.41 (d, J=2.3, 1H), 7.65 (dd, J=2.3, 9.2, 1H), 7.43~7.40 (m, 2H), 7.33~7.25 (m, 2H), 7.22~7.07 (m, 7H), 7.04~6.91 (m, 8H), 4.09~4.07 (m, 1H), 3.81 (s, 3H), 3.60~3.33 (m, 4H), 3.24~3.05 (m, 12H), 2.84 (s, 6H), 2.73 (s, 3H), 2.29~2.16 (m, 2H), 1.57~1.51 (m, 2H);

Compound 140

(R)-5-(4-chlorophenyl)-1,2-dimethyl-N-(3-(4-methylpiperazin-1-yl)propyl)-4-(3-((4-(4-((4-morpholino-1-(phenylthio)butan-2-yl)amino)-3-((trifluoromethyl)sulfonyl)phenylsulfonamido)phenyl)ethynyl)phenyl)-1H-pyrrole-3-carboxamide

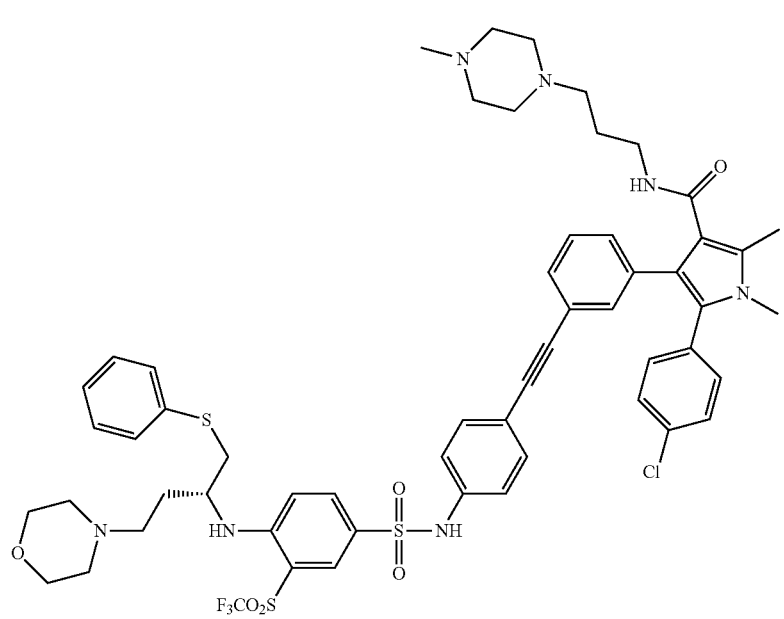

$^1$H NMR (300 MHz, CD$_3$OD), δ 7.98 (d, J=1.9, 1H), 7.72 (dd, J=1.9, 9.1, 1H), 7.73~6.98 (d, J=8.9, 1H), 6.80 (d, J=9.4, 1H), 4.01~3.90 (m, 3H), 3.79~3.69 (m, 3H), 3.52~3.30 (m, 12H), 3.25~3.03 (m, 9H), 2.86~2.41 (m,7H), 2.21~2.17 (m, 1H), 2.09~2.06 (m, 1H), 1.79~1.74 (m, 2H);

Compound 141

(R)-5-(4-chlorophenyl)-4-(3-((4-(4-((4-(dimethylamino)-1-(phenylthio)butan-2-yl)amino)-3-((trifluoromethyl)sulfonyl)phenylsulfonamido)phenyl)ethynyl)phenyl)-1,2-dimethyl-N-(3-(4-methylpiperazin-1-yl)propyl)-1H-pyrrole-3-carboxamide

BM-761

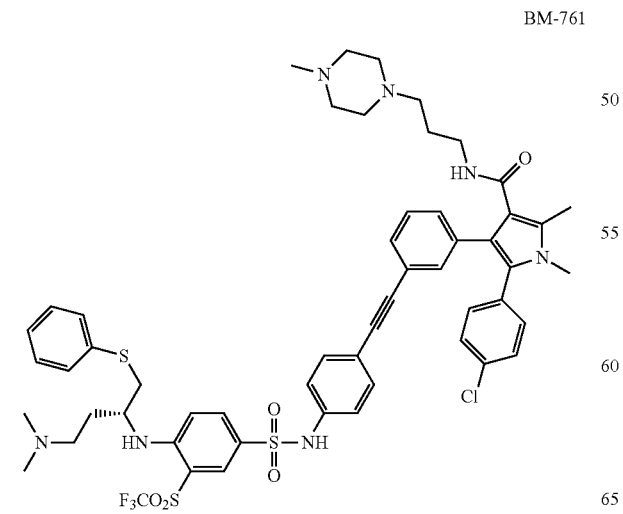

BM-761: $^1$H NMR (300 MHz, CD$_3$OD), δ 8.01 (d, J=2.0, 1H), 7.71~7.75 (m, 2H), 7.43~6.81 (m, 18H), 3.99~3.94 (m, 1H), 3.83~3.36 (m, 5H), 3.18~3.06 (m, 11H), 2.89~2.44 (m, 15H), 2.20~2.07 (m, 2H), 1.70~4.68 (m, 2H);

BM-760

Compound 142

(R)-4-(3-((4-(4-((4-(dimethylamino)-1-(phenylthio)butan-2-yl)amino)-3-nitrophenylsulfonamido)phenyl)ethynyl)phenyl)-5-(4-fluorophenyl)-1,2-dimethyl-N-(3-(4-methylpiperazin-1-yl)propyl)-1H-pyrrole-3-carboxamide

BM-762

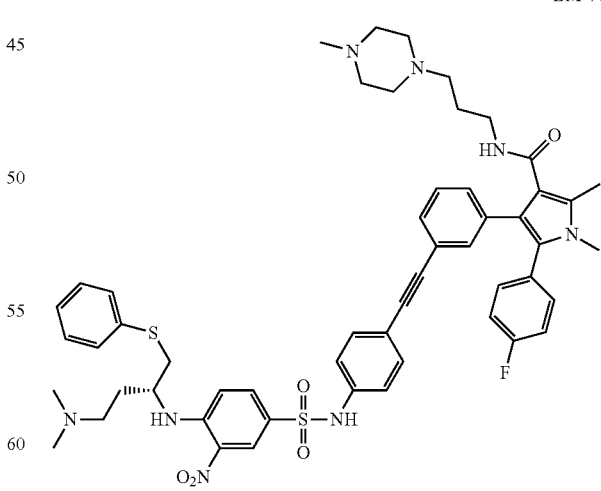

$^1$H NMR (300 MHz, CD$_3$OD), δ 8.42 (d, J=2.3, 1H), 7.66 (dd, J=2.2, 9.2, 1H), 7.41~7.38 (m, 3H), 7.28~7.09 (m, 9H), 7.07~6.93 (m, 6H), 4.11~4.09 (m, 1H), 3.82~3.35 (m, 6H), 3.25~3.06 (m, 9H), 2.93~2.43 (m, 16H), 2.23~2.17 (m, 2H), 1.70~1.65 (m, 2H);

Compound 143

(R)-4-(3-((4-(4-((4-(dimethylamino)-1-(phenylthio)butan-2-yl)amino)-3-((trifluoromethyl)sulfonyl)phenylsulfonamido)phenyl)ethynyl)phenyl)-5-(4-fluorophenyl)-1,2-dimethyl-N-(3-(4-methylpiperazin-1-yl)propyl)-1H-pyrrole-3-carboxamide

BM-763

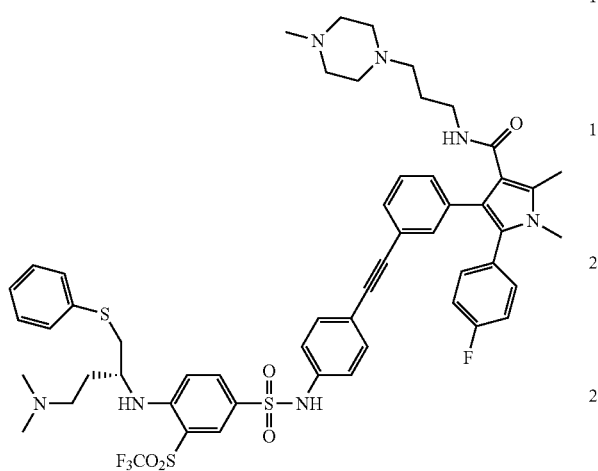

$^1$H NMR (300 MHz, CD$_3$OD), δ 8.00 (d, J=2.0, 1H), 7.75 (d, J=9.2, 1H), 7.39~7.23 (m, 7H), 7.20~7.00 (m, 9H), 6.90 (d, J=9.0, 1H), 6.83 (d, J=9.3, 1H), 3.99~3.97 (m, 1H), 3.82~3.36 (m, 5H), 3.28~3.04 (m, 12H), 2.91~2.44 (m, 14H), 2.20~2.04 (m, 2H), 1.75~1.71 (m, 2H);

Compound 144

(R)-5-(4-fluorophenyl)-1,2-dimethyl-N-(3-(4-methylpiperazin-1-yl)propyl)-4-(3-((4-(4-((4-morpholino-1-(phenylthio)butan-2-yl)amino)-3-((trifluoromethyl)sulfonyl)phenylsulfonamido)phenyl)ethynyl)phenyl)-1H-pyrrole-3-carboxamide

BM-764

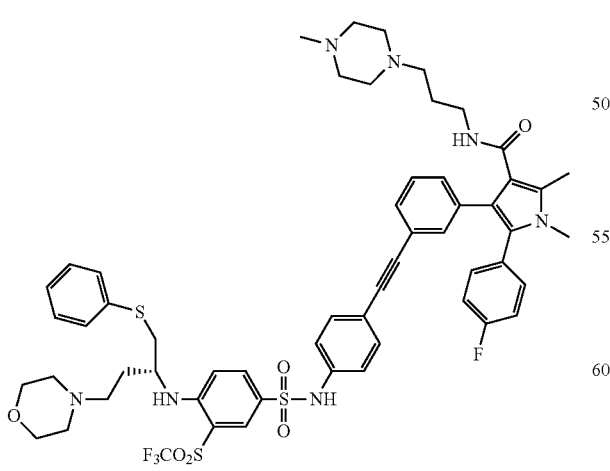

$^1$H NMR (300 MHz, CD$_3$OD), δ 7.98 (d, J=2.0, 1H), 7.73 (dd, J=2.0, 9.2, 1H), 7.36~6.88 (m, 17H), 6.81 (d, J=9.4, 1H), 3.99~3.95 (m, 3H), 3.80~3.48 (m, 13H), 3.26~2.93 (m, 11H), 2.84~2.42 (m, 7H), 2.22~2.19 (m, 1H), 2.09~2.05 (m, 1H), 1.76~1.76 (m, 2H);

Compound 145

(R)-5-(4-chlorophenyl)-1,2-dimethyl-N-(3-(4-methylpiperazin-1-yl)propyl)-4-(3-((4-(4-((4-morpholino-1-(phenylthio)butan-2-yl)amino)-3-nitrophenylsulfonamido)phenyl)ethynyl)phenyl)-1H-pyrrole-3-carboxamide

BM-765

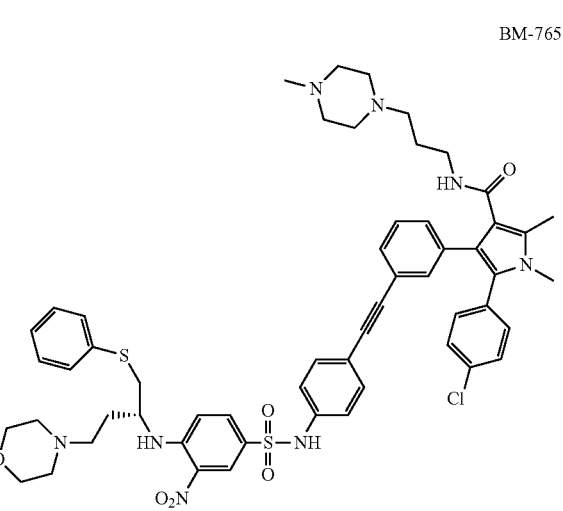

$^1$H NMR (300 MHz, CD$_3$OD), δ 8.39 (d, J=2.3, 1H), 7.64 (dd, J=2.2, 9.2, 1H), 7.39~7.07 (m, 13H), 7.00~6.91 (m, 5H), 4.10~3.71 (m, 6H), 3.53~3.33 (m, 8H), 3.21~3.12 (m, 13H), 2.83~2.41 (m, 7H), 2.28~2.19 (m, 2H), 1.74~4.70 (m, 2H);

Compound 146

(R)-1-cyclopropyl-4-(3-((4-(4-((4-(dimethylamino)-1-(phenylthio)butan-2-yl)amino)-3-nitrophenylsulfonamido)phenyl)ethynyl)phenyl)-5-(4-fluorophenyl)-2-methyl-N-(3-(4-methylpiperazin-1-yl)propyl)-1H-pyrrole-3-carboxamide

BM-767

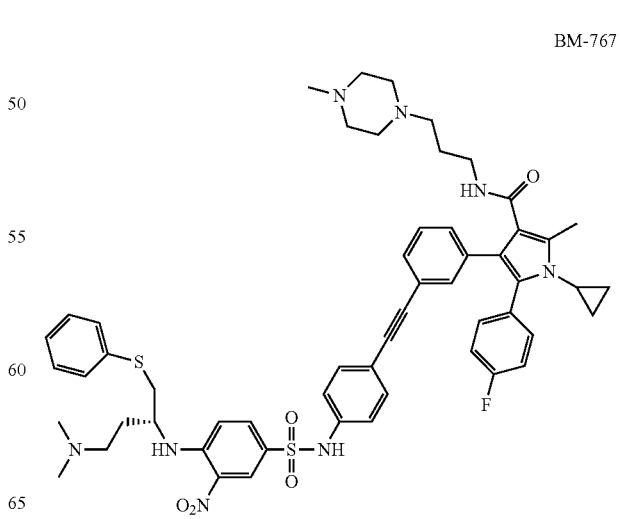

255

¹H NMR (300 MHz, CD$_3$OD), δ 8.41 (d, J=2.3, 1H), 7.66~7.63 (m, 1H), 7.40~7.24 (m, 4H), 7.20~7.09 (m, 7H), 7.04~6.92 (m, 7H), 4.11~4.09 (m, 1H), 3.41~3.34 (m, 4H), 3.23~2.89 (m, 12H), 2.84~2.51 (m, 13H), 2.26~2.14 (m, 2H), 1.80~1.64 (m, 2H), 0.96~0.83 (m, 2H), 0.60~0.47 (m, 2H);

Compound 147

(R)-5-(4-chlorophenyl)-4-(3-((4-(4-((4-(dimethylamino)-1-(phenylthio)butan-2-yl)amino)-3-nitrophenylsulfonamido)phenyl)ethynyl)phenyl)-1,2-dimethyl-N-(2-(pyrrolidin-1-yl)ethyl)-1H-pyrrole-3-carboxamide

BM-768

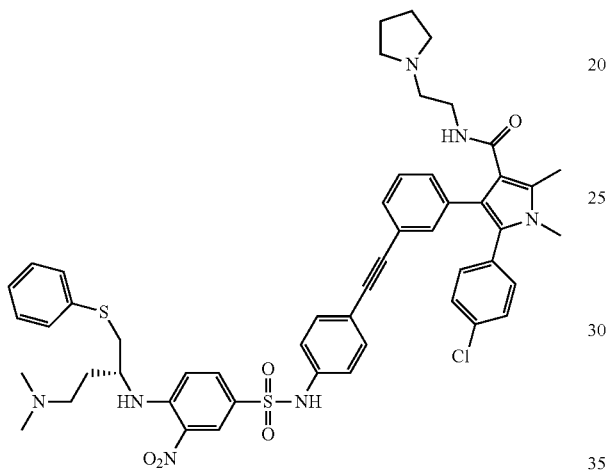

256

¹H NMR (300 MHz, CD$_3$OD), δ 8.41 (d, J=2.3, 1H), 7.66 (dd, J=2.3, 9.2, 1H), 7.41~7.10 (m, 13H), 7.02~6.93 (m, 5H), 4.12~4.09 (m, 1H), 3.84~3.34 (m, 9H), 3.23~3.15 (m, 7H), 3.93~3.89 (m, 2H), 2.84 (s, 6H), 2.45 (s, 3H), 2.26~1.99 (m, 6H);

Compound 148

(R)-4-(3-((4-(4-((4-(dimethylamino)-1-(phenylthio)butan-2-yl)amino)-3-nitrophenylsulfonamido)phenyl)ethynyl)phenyl)-5-(4-fluorophenyl)-1-(2-hydroxyethyl)-2-methyl-N-(3-(4-methylpiperazin-1-yl)propyl)-1H-pyrrole-3-carboxamide

BM-769

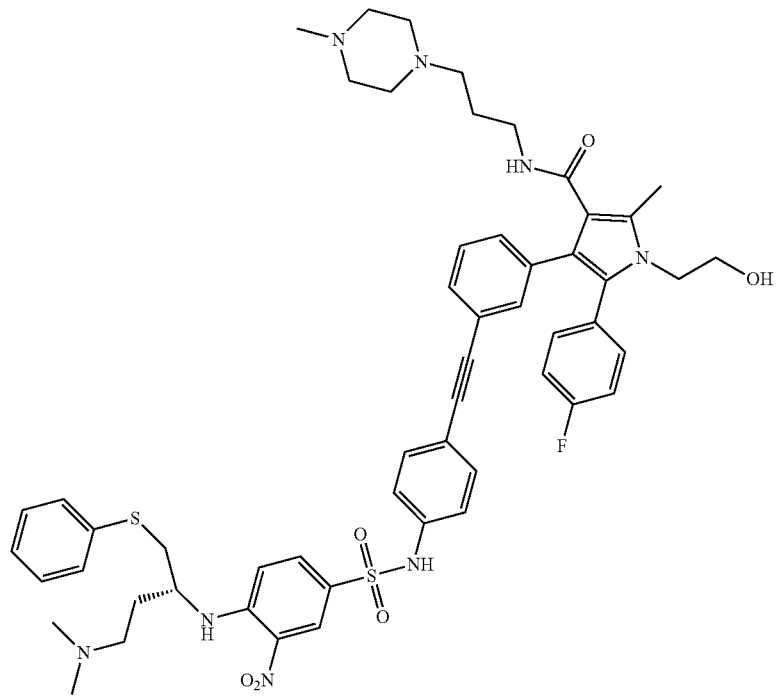

¹H NMR (300 MHz, CD₃OD), δ 8.41 (d, J=2.3, 1H), 7.67~7.64 (m, 1H), 7.40~6.93 (m, 18H), 4.09~3.34 (m, 9H), 3.23~3.06 (m, 9H), 2.85~2.47 (m, 15H), 2.20~2.14 (m, 2H), 1.71~1.60 (m, 2H);

Compound 149

(R)—N-(4-(4-((4'-chloro-[1,1'-biphenyl]-2-yl)methyl)piperazin-1-yl)phenyl)-4-((4-(dimethylamino)-1-(phenylthio)butan-2-yl)amino)-3-nitrobenzenesulfonamide

BM-770

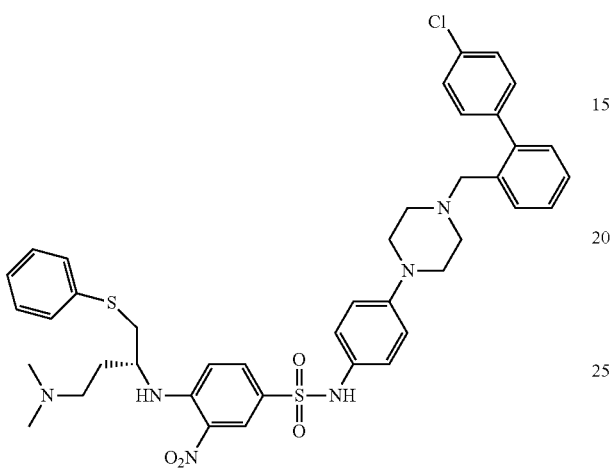

¹H NMR (300 MHz, CD₃OD), δ 8.24 (s, 1H), 7.70~7.68 (m, 1H), 7.58~7.47 (m, 5H), 7.39~7.31 (m, 3H), 7.12 (d, J=7.0, 2H), 7.02~6.89 (m, 6H), 8.18 (d, J=8.7, 2H), 4.40 (s, 2H), 4.08 (br. 1H), 3.38~3.31 (m, 3H), 3.21~3.08 (m, 9H), 2.84 (s, 6H), 2.25~2.15 (m, 2H); ¹³C NMR (75 MHz, CD₃OD), δ 148.6, 147.9, 144.4, 139.7, 136.2, 135.3, 134.4, 132.6, 132.3, 132.2, 132.1, 131.6, 131.4, 130.2, 130.1, 130.0, 128.0, 127.8, 127.6, 127.5, 124.3, 118.6, 116.2, 58.0, 55.9, 52.8, 52.4, 47.5, 43.5, 39.6, 30.1;

Compound 150

(R)-5-(4-chlorophenyl)-4-(3-((4-(4-((4-(dimethylamino)-1-(phenylthio)butan-2-yl)amino)-3-((trifluoromethyl)sulfonyl)phenylsulfonamido)phenyl)ethynyl)phenyl)-N-(2-(dimethylamino)ethyl)-1,2-dimethyl-1H-pyrrole-3-carboxamide

BM-771

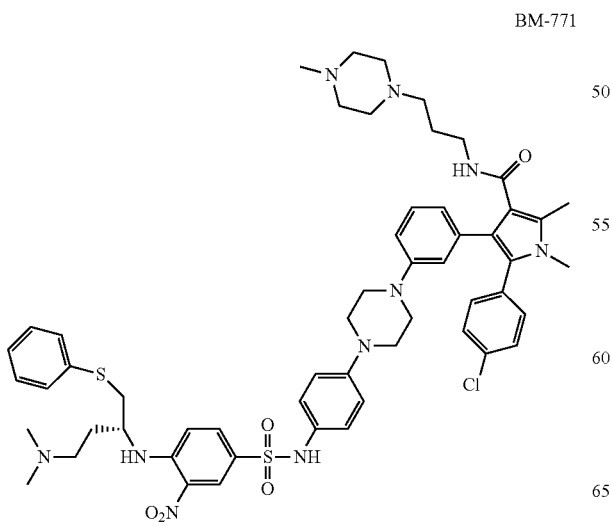

¹H NMR (300 MHz, CD₃OD), δ 8.29 (d, J=2.1, 1H), 7.58 (dd, J=2.1, 9.0, 1H), 7.26 (d, J=8.3, 2H), 7.17~6.89 (m, 14H), 6.73~6.70 (m, 2H), 4.10~4.05 (m, 1H), 3.38~3.31 (m, 10H), 3.24~3.18 (m, 15H), 2.82~2.87 (m, 11H), 2.42 (s, 3H), 2.20~2.16 (m, 2H), 1.78~1.71 (m, 2H); ¹³C NMR (75 MHz, CD₃OD), δ 170.3, 150.3, 148.5, 148.0, 137.7, 136.2, 134.8, 134.4, 133.8, 133.3, 132.5, 132.2, 132.1, 131.6, 131.2, 130.2, 130.1, 129.6, 128.0, 127.9, 127.6, 125.1, 124.2, 122.6, 120.6, 118.9, 116.3, 116.2, 55.9, 55.3, 52.6, 52.4, 51.1, 50.9, 50.4, 43.6, 43.5, 39.5, 37.4, 32.0, 30.1, 25.9, 11.4;

Compound 151

(R)-5-(4-chlorophenyl)-4-(3-((4-(4-((4-(dimethylamino)-1-(phenylthio)butan-2-yl)amino)-3-((trifluoromethyl)sulfonyl)phenylsulfonamido)phenyl)ethynyl)phenyl)-N-(2-(dimethylamino)ethyl)-1,2-dimethyl-1H-pyrrole-3-carboxamide

BM-722

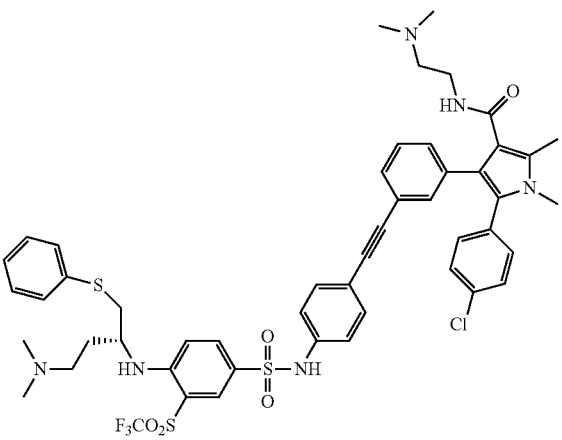

ESI MS: m/z 1005.5 (M+H)⁺;

Compound 152

(R)-5-(4-chlorophenyl)-4-(3-(4-(4-(4-((4-(dimethylamino)-1-(phenylthio)butan-2-yl)amino)-3-((trifluoromethyl)sulfonyl)phenylsulfonamido)phenyl)piperazin-1-yl)phenyl)-1,2-dimethyl-N-(3-(4-methylpiperazin-1-yl)propyl)-1H-pyrrole-3-carboxamide

BM-773

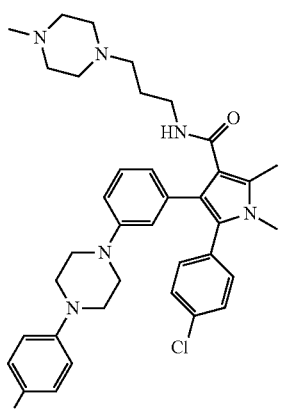

¹H NMR (300 MHz, CD₃OD), δ 7.86 (d, J=1.8, 1H), 7.69 (dd, J=2.0, 9.2, 1H), 7.29~2.26 (m, 4H), 7.20~7.08 (m, 6H), 7.04~6.74 (m, 8H), 3.97~3.94 (m, 1H), 3.52~3.30 (m, 7H), 3.25~3.01 (m, 18H), 2.84~2.80 (m, 11H), 2.42 (s, 3H), 2.18~2.14 (m, 1H), 2.05~2.01 (m, 1H), 1.79~1.75 (m, 2H);

Compound 153

(R)-5-(4-chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1,2-dimethyl-N-(2-(pyrrolidin-1-yl)ethyl)-1H-pyrrole-3-carboxamide

BM-774

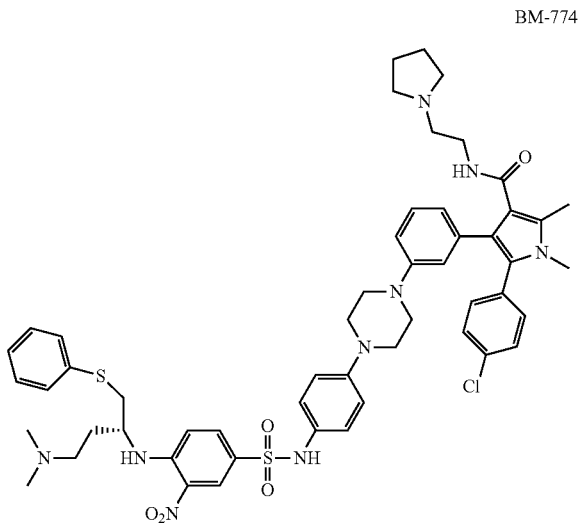 [SMILES: Cc1c(C(=O)NCCN2CCCC2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C]

¹H NMR (300 MHz, CD₃OD), δ 8.30 (d, J=2.3, 1H), 7.58 (dd, J=2.3, 9.2, 1H), 7.29~7.26 (m, 2H), 7.17~6.84 (m, 14H), 6.69~6.66 (m, 2H), 4.09~4.06 (m, 1H), 3.58~3.31 (m, 8H), 3.19~3.12 (m, 13H), 2.95~2.94 (m, 2H), 2.83 (s, 6H), 2.45 (s, 3H), 2.24~1.92 (m, 6H); ESI MS: m/z 1004.7 (M+H)⁺;

Compound 154

(R)-4-(3-(4-(4-(4-((4-(dimethylamino)-1-(phenylthio)butan-2-yl)amino)-3-nitrophenylsulfonamido)phenyl)piperazin-1-yl)phenyl)-5-(4-fluorophenyl)-1,2-dimethyl-N-(3-(4-methylpiperazin-1-yl)propyl)-1H-pyrrole-3-carboxamide

BM-775

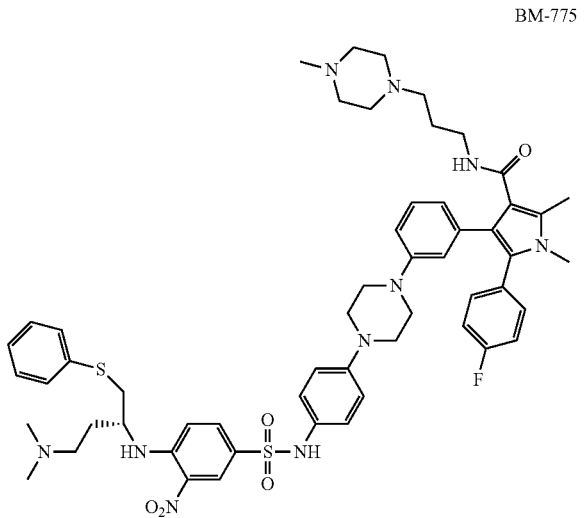 [SMILES: Cc1c(C(=O)NCCCN2CCN(C)CC2)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(F)cc2)n1C]

¹H NMR (300 MHz, CD₃OD), δ 8.27 (d, J=2.2, 1H), 7.58 (dd, J=2.2, 9.2, 1H), 7.19~6.88 (m, 16H), 6.80-6.77 (m, 2H), 4.08~4.07 (m, 1H), 3.46~3.44 (m, 4H), 3.34~3.29 (m, 17H), 3.19~3.13 (m, 4H), 2.91~2.86 (m, 5H), 2.81 (s, 6H), 2.40 (s, 3H), 2.18~2.13 (m, 2H), 1.81~1.77 (m, 2H);

Compound 155

(R)-5-(4-chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-N-(2-(dimethylamino)ethyl)-1,2-dimethyl-1H-pyrrole-3-carboxamide

BM-777

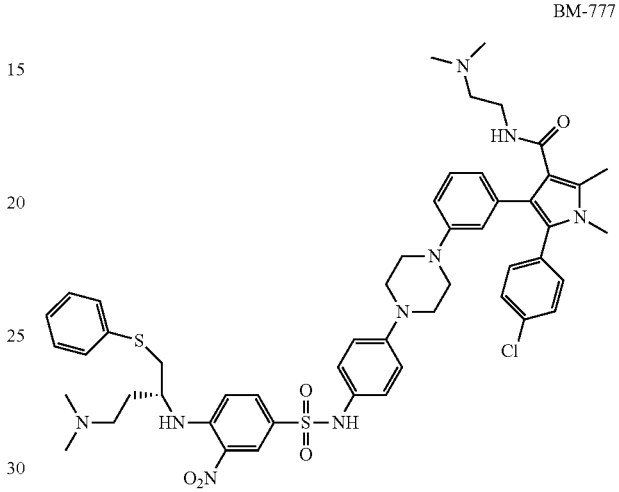

¹H NMR (300 MHz, CD₃OD), δ 8.30 (d, J=2.2, 1H), 7.57 (dd, J=2.1, 9.1, 1H), 7.30~7.27 (m, 2H), 7.16~6.80 (m, 14H), 6.64~6.62 (m, 2H), 4.08~4.06 (m, 1H), 3.51~3.31 (m, 6H), 3.21~3.04 (m, 13H), 2.84 (s, 6H), 2.83 (s, 6H), 2.46 (s, 3H), 2.24~2.14 (m, 2H);

Compound 156

(R)-4-(3-(4-(4-(4-((4-(dimethylamino)-1-(phenylthio)butan-2-yl)amino)-3-((trifluoromethyl)sulfonyl)phenylsulfonamido)phenyl)piperazin-1-yl)phenyl)-5-(4-fluorophenyl)-1,2-dimethyl-N-(3-(4-methylpiperazin-1-yl)propyl)-1H-pyrrole-3-carboxamide

BM-779

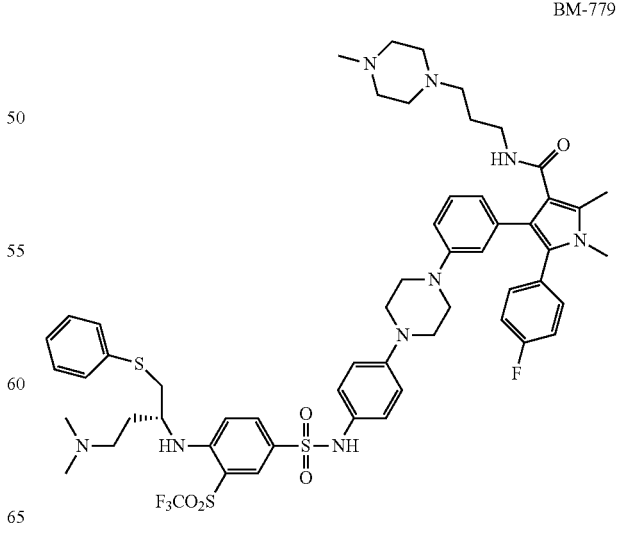

ESI MS: m/z 1118.3 (M+H)⁺;

Compound 157

(R)-5-(4-chlorophenyl)-1,2-dimethyl-N-(3-(4-methylpiperazin-1-yl)propyl)-4-(3-(4-(4-(4-((4-morpholino-1-(phenylthio)butan-2-yl)amino)-3-nitrophenylsulfonamido)phenyl)piperazin-1-yl)phenyl)-1H-pyrrole-3-carboxamide

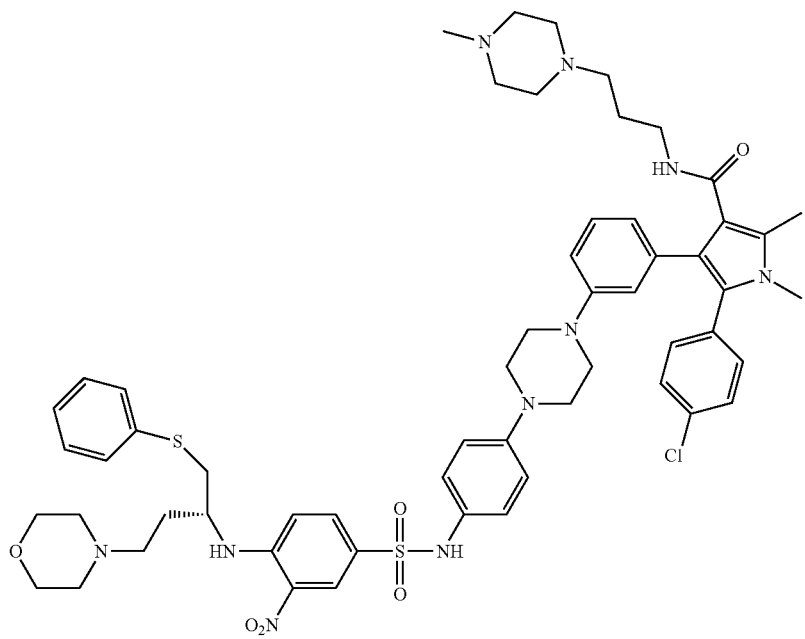

BM-780

$^1$H NMR (300 MHz, CD$_3$OD), δ 8.29 (d, J=2.2, 1H), 7.60 (dd, J=2.2, 9.2, 1H), 7.29~6.90 (m, 16H), 6.75~6.74 (m, 2H), 4.09~3.98 (m, 3H), 3.72~3.69 (m, 2H), 3.39~3.32 (m, 12H), 3.26~3.06 (m, 17H), 2.84~2.78 (m, 5H), 2.99 (s, 3H), 2.28~2.18 (m, 2H), 1.79~1.74 (m, 2H);

Compound 158

(R)-5-(4-chlorophenyl)-1,2-dimethyl-N-(3-(4-methylpiperazin-1-yl)propyl)-4-(3-(4-(4-(4-((4-morpholino-1-(phenylthio)butan-2-yl)amino)-3-((trifluoromethyl)sulfonyl)phenylsulfonamido)phenyl)piperazin-1-yl)phenyl)-1H-pyrrole-3-carboxamide

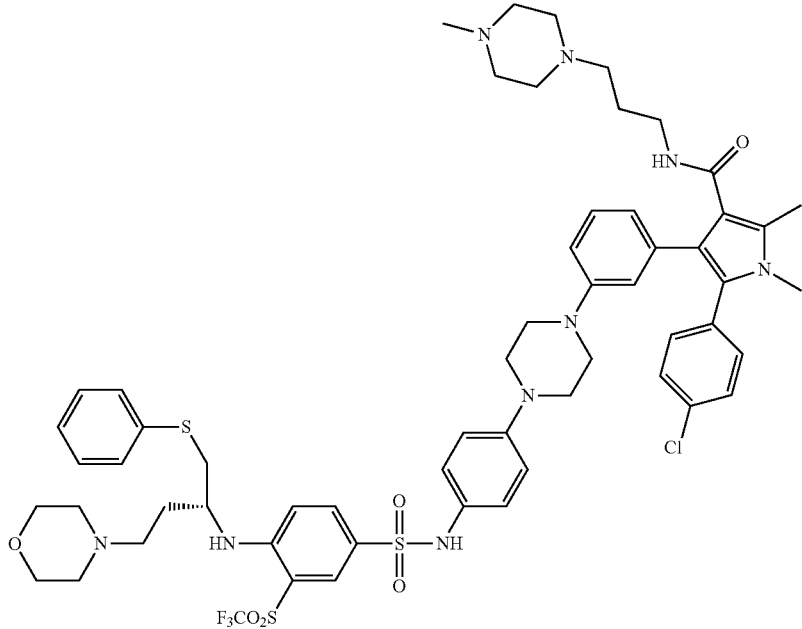

BM-781

¹H NMR (300 MHz, CD₃OD), δ 7.88 (d, J=2.1, 1H), 7.70 (dd, J=2.2, 9.2, 1H), 7.30~7.26 (m, 4H), 7.19~7.09 (m, 6H), 7.04~6.88 (m, 5H), 6.85~6.71 (m, 3H), 3.99~3.97 (m, 3H), 3.72~3.70 (m, 2H), 3.40~3.32 (m, 9H), 3.26~3.11 (m, 20H), 2.81 (s, 3H), 2.72 (t, J=7.1, 2H), 2.44 (s, 3H), 2.24~2.20 (m, 1H), 2.10~2.08 (m, 1H), 1.76~4.71 (m, 2H);

Compound 159
(R)-5-(4-fluorophenyl)-1,2-dimethyl-N-(3-(4-methylpiperazin-1-yl)propyl)-4-(3-(4-(4-(4-((4-morpholino-1-(phenylthio)butan-2-yl)amino)-3-((trifluoromethyl)sulfonyl)phenylsulfonamido)phenyl)piperazin-1-yl)phenyl)-1H-pyrrole-3-carboxamide

FM-782

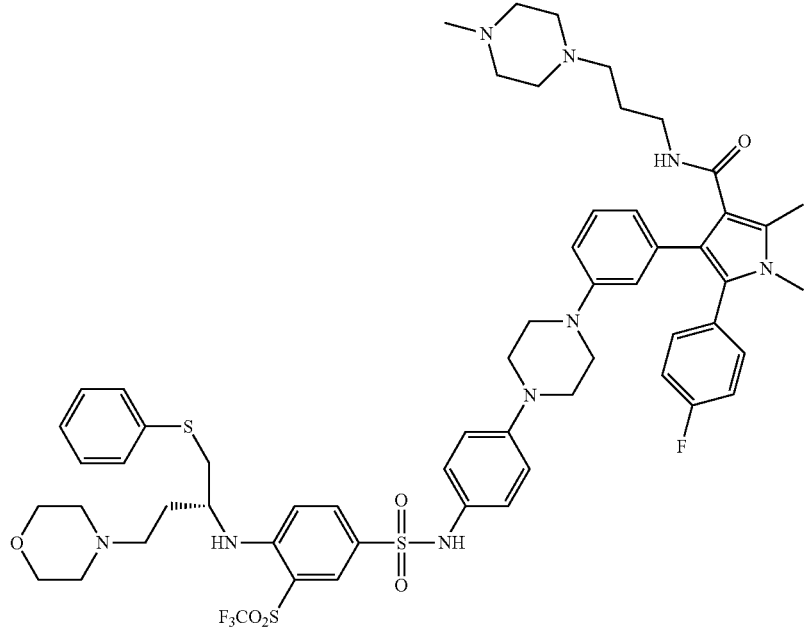

¹H NMR (300 MHz, CD₃OD), δ 7.85 (d, J=2.0, 1H), 7.69 (dd, J=2.2, 9.2, 1H), 7.26~7.23 (m, 2H), 7.20~7.10 (m, 6H), 7.05~6.93 (m, 7H), 6.80~6.77 (m, 3H), 3.97~3.94 (m, 3H), 3.69~3.67 (m, 2H), 3.45~3.29 (m, 18H), 3.25~3.04 (m, 11H), 2.90~2.86 (m, 5H), 2.40 (s, 3H), 2.21~2.17 (m, 1H), 2.07~2.03 (m, 1H), 1.81~4.77 (m, 2H);

Compound 160
(R)-5-(4-fluorophenyl)-1,2-dimethyl-N-(3-(4-methylpiperazin-1-yl)propyl)-4-(3-(4-(4-(4-((4-morpholino-1-(phenylthio)butan-2-yl)amino)-3-nitrophenylsulfonamido)phenyl)piperazin-1-yl)phenyl)-1H-pyrrole-3-carboxamide

BM-783

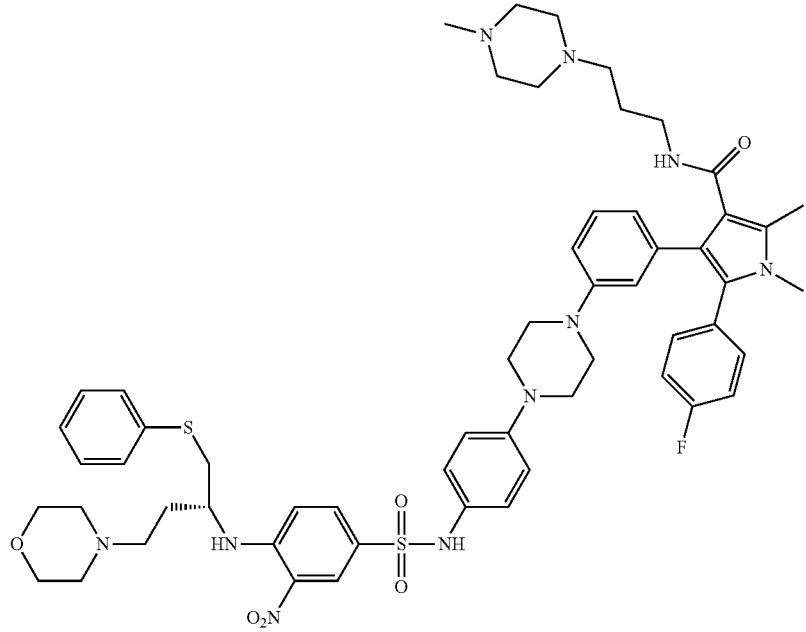

¹H NMR (300 MHz, CD₃OD), δ 8.28 (d, J=2.3, 1H), 7.59 (dd, J=2.3, 9.2, 1H), 7.20~6.89 (m, 16H), 6.79~6.77 (m, 2H), 4.11~4.08 (m, 1H), 3.97~3.94 (m, 2H), 3.73~3.69 (m, 2H), 3.49~3.29 (m, 18H), 3.24~3.04 (m, 11H), 2.90~2.86 (m, 5H), 2.40 (s, 3H), 2.27~2.17 (m, 2H), 1.81~1.77 (m, 2H);

Compound 161

(R)-4-(3-(4-(4-(4-((4-(dimethylamino)-1-(phenylthio)butan-2-yl)amino)-3-nitrophenylsulfonamido)phenyl)piperazin-1-yl)phenyl)-5-(4-fluorophenyl)-N,1,2-trimethyl-1H-pyrrole-3-carboxamide

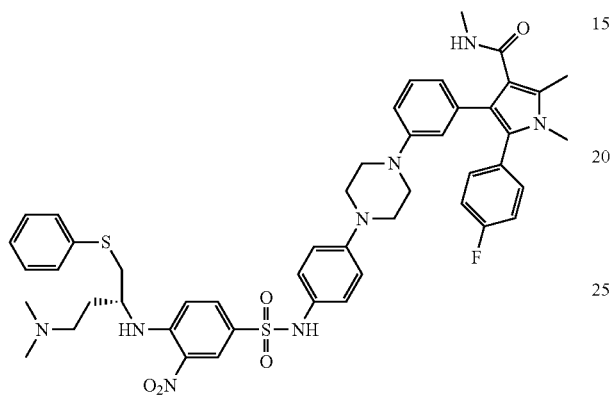

BM-784

¹H NMR (300 MHz, CD₃OD), δ 8.29 (d, J=2.3, 1H), 7.59 (dd, J=2.3, 9.2, 1H), 7.19~6.89 (m, 17H), 6.81 (d, J=7.7, 1H), 4.09~4.06 (m, 1H), 3.34~3.31 (m, 12H), 3.20~3.13 (m, 3H), 2.82 (s, 6H), 2.67 (s, 3H), 2.38 (s, 3H), 2.23~2.14 (m, 2H);

Compound 162

(R)-5-(4-fluorophenyl)-N,1,2-trimethyl-4-(3-(4-(4-(4-((4-morpholino-1-(phenylthio)butan-2H)amino)-3-nitrophenylsulfonamido)phenyl)piperazin-1-yl)phenyl)-1H-pyrrole-3-carboxamide

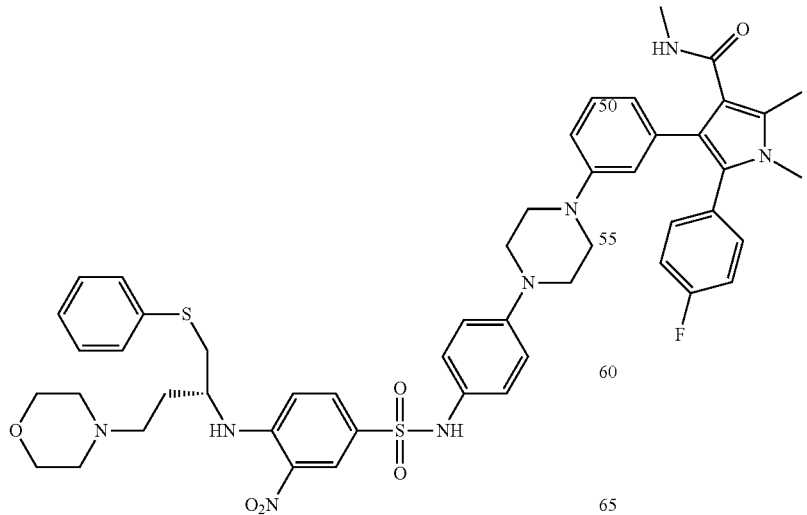

BM-785

¹H NMR (300 MHz, CD₃OD), δ 8.30 (d, J=2.2, 1H), 7.59 (dd, J=2.2, 9.2, 1H), 7.18~6.88 (m, 17H), 6.79 (d, J=7.7, 1H), 4.10~4.07 (m, 1H), 3.99~3.95 (m, 2H), 3.72~3.68 (m, 2H), 3.41~3.31 (m, 13H), 3.36~3.06 (m, 6H), 2.67 (s, 3H), 2.39 (s, 3H), 2.28~2.18 (m, 2H);

Compound 163

(R)-5-(4-fluorophenyl)-4-(3-(4-(4-(4-((4-(4-hydroxypiperidin-1-yl)-1-(phenylthio)butan-2-yl)-amino)-3-nitrophenylsulfonamido)phenyl)piperazin-1-yl)phenyl)-N,1,2-trimethyl-1H-pyrrole-3-carboxamide

BM-786

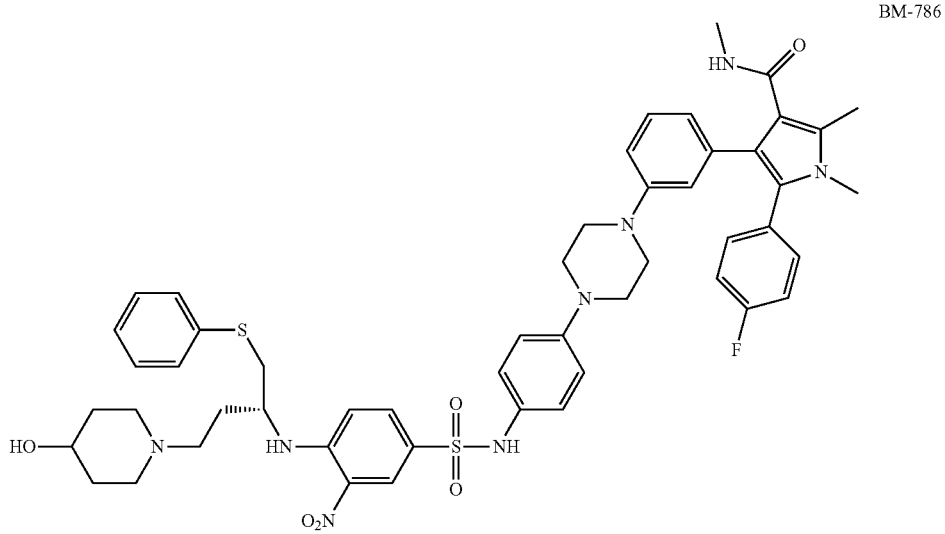 [SMILES: CNC(=O)c1c(-c2cccc(N3CCN(c4ccc(NS(=O)(=O)c5ccc(N[C@H](CCN6CCC(O)CC6)CSc6ccccc6)c([N+](=O)[O-])c5)cc4)CC3)c2)c(-c2ccc(F)cc2)n(C)c1C]

¹H NMR (300 MHz, CD₃OD), δ 8.30 (d, J=2.2, 1H), 7.58 (dd, J=2.3, 9.2, 1H), 7.16~6.89 (m, 16H), 6.83 (s, 1H), 6.74 (d, J=7.7, 1H), 4.04~3.70 (m, 2H), 3.52~3.50 (m, 1H), 3.36~3.29 (m, 7H), 3.26~3.14 (m, 10H), 2.99~2.91 (m, 1H), 2.67 (s, 3H), 2.40 (s, 3H), 2.28~2.06 (m, 3H), 1.90~4.87 (m, 2H), 1.66~1.62 (m, 1H);

Compound 164

(R)-4-(3-(4-(4-(4-((4-(dimethylamino)-1-(phenylthio)butan-2-yl)amino)-3-((trifluoromethyl)sulfonyl)phenylsulfonamido)phenyl)piperazin-1-yl)phenyl)-5-(4-fluorophenyl)-N,1,2-trimethyl-1H-pyrrole-3-carboxamide

BM-787

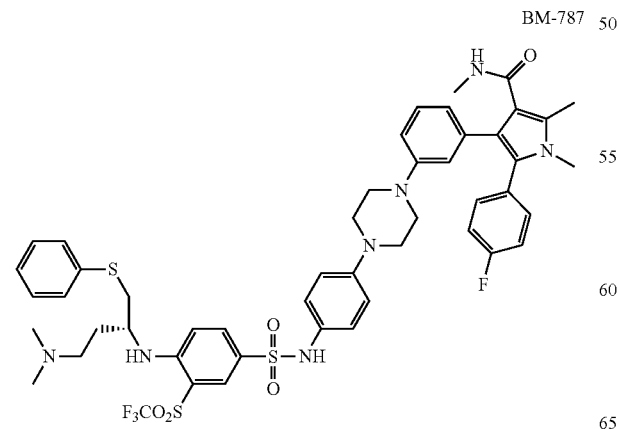

269

$^1$H NMR (300 MHz, CD$_3$OD), δ 7.87 (d, J=2.0, 1H), 7.70 (m, J=2.2, 9.2, 1H), 7.28~7.25 (m, 2H), 7.20~7.12 (m, 6H), 7.06~6.99 (m, 7H), 6.90 (s, 1H), 6.81~6.78 (m, 2H), 3.99~3.94 (m, 1H), 3.35~3.28 (m, 11H), 3.20~3.03 (m, 4H), 2.81 (s, 6H), 2.68 (s, 3H), 2.39 (s, 3H), 2.18~2.01 (m, 2H);

270

Compound 165

(R)-5-(4-fluorophenyl)-N,1,2-trimethyl-4-(3-(4-(4-(4-((4-morpholino-1-(phenylthio)butan-2-yl)amino)-3-((trifluoromethyl)sulfonyl)phenylsulfonamido)phenyl)piperazin-1-yl)phenyl)-1H-pyrrole-3-carboxamide

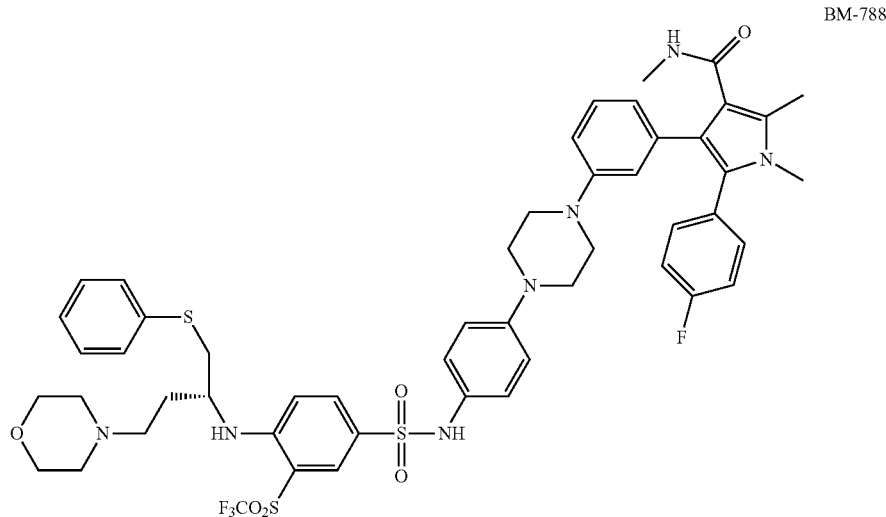

BM-788

$^1$H NMR (300 MHz, CD$_3$OD), δ 7.87 (d, J=1.9, 1H), 7.70 (dd, J=2.2, 9.2, 1H), 7.28~7.25 (m, 2H), 7.20~7.12 (m, 6H), 7.06~6.99 (m, 7H), 6.90 (s, 1H), 6.81~6.78 (m, 2H), 3.98~3.95 (m, 3H), 3.70~3.68 (m, 2H), 3.45~3.33 (m, 13H), 3.23~3.05 (m, 6H), 2.68 (s, 3H), 2.39 (s, 3H), 2.22~2.18 (m, 1H), 2.08~2.04 (m, 1H);

Compound 166

(R)-5-(4-fluorophenyl)-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-N,1,2-trimethyl-1H-pyrrole-3-carboxamide

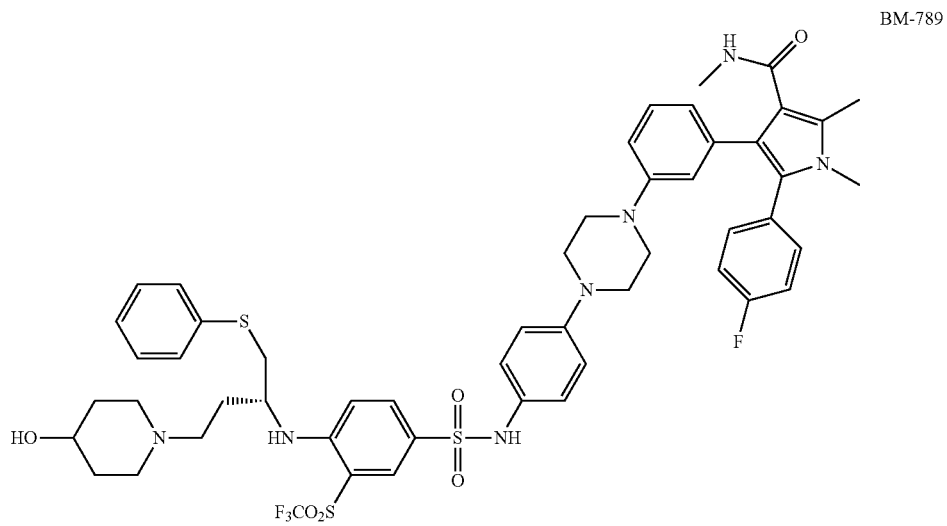

BM-789

¹H NMR (300 MHz, CD₃OD), δ 7.88 (d, J=2.0, 1H), 7.69 (dd, J=2.0, 9.2, 1H), 7.27~7.26 (m, 2H), 7.18~7.12 (m, 6H), 7.05~6.95 (m, 7H), 6.87 (s, 1H), 6.81~6.76 (m, 2H), 4.03~3.75 (m, 2H), 3.50~3.30 (m, 13H), 3.21~2.89 (m, 6H), 2.68 (s, 3H), 2.40 (s, 3H), 2.20~2.18 (m, 1H), 2.06~2.04 (m, 2H), 1.89~1.86 (m, 2H), 1.65~1.62 (m, 1H)

Compound 167

(R)—N-(4-(4-(3-(2-(4-chlorophenyl)-1,5-dimethyl-1H-pyrrol-3-yl)phenyl)piperazin-1-yl)phenyl)-4-((4-(dimethylamino)-1-(phenylthio)butan-2-yl)amino)-3-((trifluoromethyl)sulfonyl)benzenesulfonamide ESI MS: m/z 951.3 (M+H)⁺;

Compound 168

(R)—N-(4-(4-(3-(2-(4-chlorophenyl)-1,5-dimethyl-1H-pyrrol-3-yl)phenyl)piperazin-1-yl)phenyl)-4-((4-(dimethylamino)-1-(phenylthio)butan-2-yl)amino)-3-nitrobenzenesulfonamide

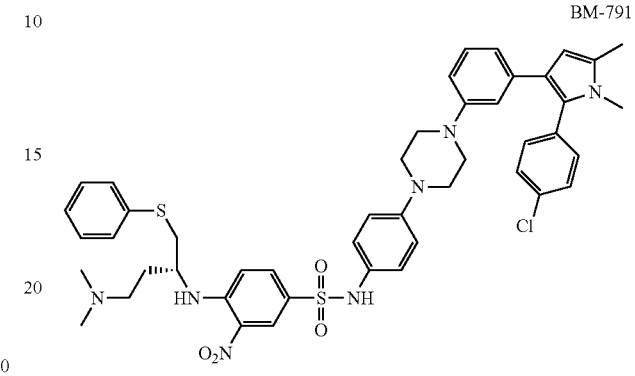

¹H NMR (300 MHz, CD₃OD), δ 8.28 (d, J=2.2, 1H), 7.59 (dd, J=2.2, 9.1, 1H), 7.34 (d, J=8.4, 2H), 7.18~6.89 (m, 17H), 4.09~4.05 (m, 1H), 3.36~3.27 (m, 1H), 3.20~3.14 (m, 4H), 2.82 (s, 6H), 2.24 (s, 3H), 2.16~2.14 (m, 2H); ¹³C NMR (75 MHz, CD₃OD), δ 148.02, 148.95, 147.2, 140.1, 136.2, 134.7, 134.4, 134.0, 133.7, 132.7, 132.2, 131.6, 131.2, 130.6, 130.1, 130.0, 128.0, 127.9, 127.5, 125.5, 124.1, 122.0, 119.0, 118.9, 116.2, 55.9, 53.2, 52.4, 50.2, 43.5, 39.5, 31.6, 30.1, 12.4;

Compound 169

(R)-5-(4-chlorophenyl)-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-1,2-dimethyl-1H-pyrrole-3-carboxylic acid ¹H NMR (300 MHz, CD₃OD), δ 7.86 (1H, s), 7.71 (d, J=9.2, 1H), 7.27~7.25 (m, 4H), 7.20~6.79 (m, 14H), 4.03~3.75 (m, 2H), 3.49~3.31 (m, 13H), 3.14~2.89 (m, 6H), 2.58 (s, 3H), 2.26~1.88 (m, 5H), 1.67~1.63 (m, 1H);

Compound 170

(R)—N-(4-(4-(3-(2-(4-chlorophenyl)-4-(4-hydrox-
ypiperidine-1-carbonyl)-1,5-dimethyl-1H-pyrrol-3-
yl)phenyl)piperazin-1-yl)phenyl)-4-(4-(4-hydroxypi-
peridin-1-yl)-1-(phenylthio)butan-2-yl)amino)-3-
((trifluoromethyl)sulfonyl)benzenesulfonamide

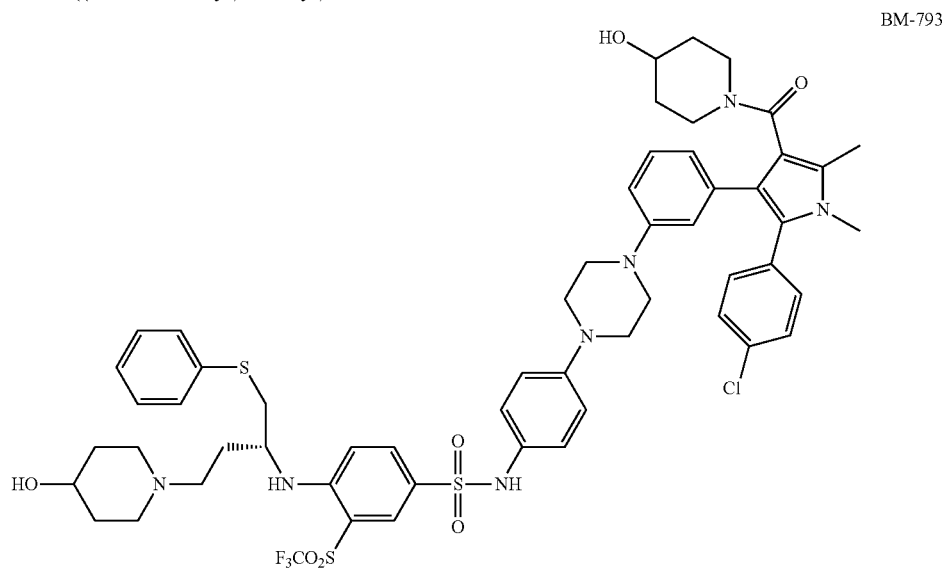

BM-793

$^1$H NMR (300 MHz, CD$_3$OD), δ 7.88 (d, J=2.0, 1H), 7.70 (d, J=9.3, 1H), 7.34~7.25 (m, 4H), 7.16~6.71 (m, 14H), 4.12~3.28 (m, 16H), 3.16~2.89 (m, 10H), 2.27~2.24 (m, 4H), 2.06~2.02 (m, 2H), 1.88~1.86 (m, 2H), 1.73~4.06 (m, 5H);

Compound 171

5-(4-chlorophenyl)-N-((1r,4r)-4-hydroxycyclo-
hexyl)-4-(3-(4-(4-(4-(((R)-4-(4-hydroxypiperidin-1-
yl)-1-(phenylthio)butan-2-yl)amino)-3-((trifluorom-
ethyl)sulfonyl)phenylsulfonamido)phenyl)piperazin-
1-yl)phenyl)-1,2-dimethyl-1H-pyrrole-3-
carboxamide

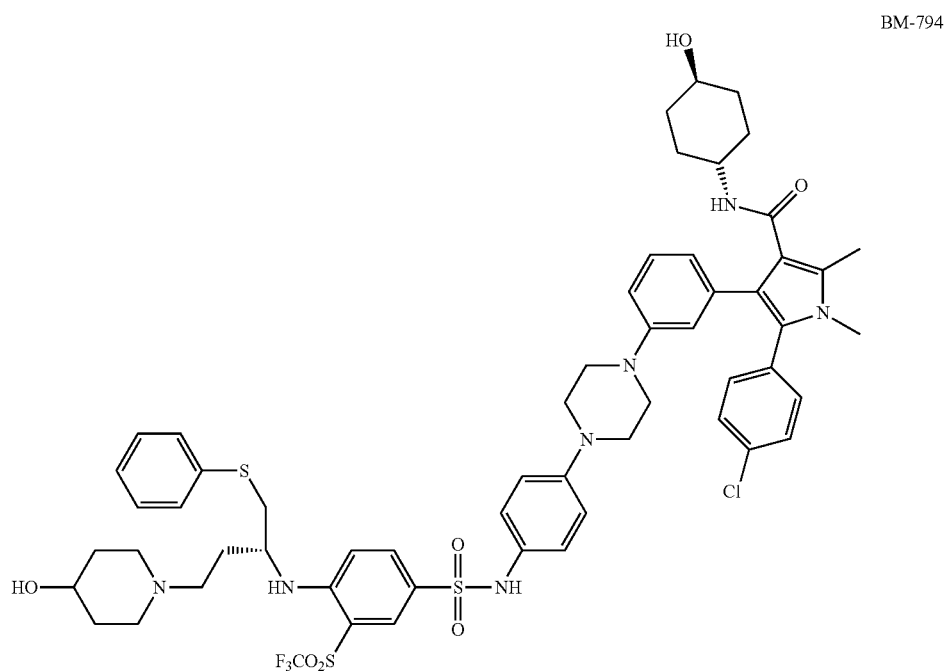

BM-794

275

$^1$H NMR (300 MHz, CD$_3$OD), δ 7.86 (d, J=2.1, 1H), 7.67 (dd, J=2.2, 9.2, 1H), 7.27~7.24 (m, 4H), 7.18~7.04 (m, 6H), 7.01~6.94 (m, 5H), 6.80~6.75 (m, 3H), 4.01~3.28 (m, 15H), 3.19~2.87 (m, 8H), 2.40 (s, 3H), 2.18~4.60 (m, 10H), 1.30~4.18 (m, 2H), 1.03~0.92 (m, 2H);

276

Compound 172

(R)—N-(4-(4-(3-(2-(4-chlorophenyl)-4-(4-hydroxy-4-methylpiperidine-1-carbonyl)-1,5-dimethyl-1H-pyrrol-3-yl)phenyl)piperazin-1-yl)phenyl)-4-((4-(4-hydroxypiperidin-1-yl)-1-(phenylthio)butan-2-yl)amino)-3-((trifluoromethyl)sulfonyl)benzenesulfonamide

BM-795

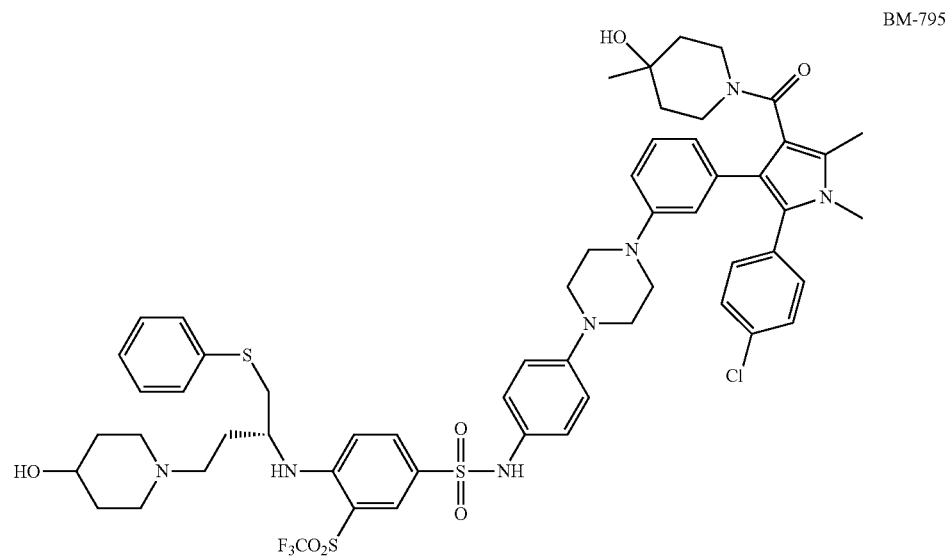

$^1$H NMR (300 MHz, CD$_3$OD), δ 7.89 (s, 1H), 7.69~7.67 (m, 1H), 7.35~7.27 (m, 4H), 7.18~7.12 (m, 5H), 7.09~6.94 (m, 5H), 6.87~6.58 (m, 4H), 4.27~4.22 (m, 1H), 4.08~3.95 (m, 2H), 3.75~3.50 (m, 2H), 3.40 (s, 3H), 3.31~3.29 (m, 6H), 3.22~2.90 (m, 11H), 2.28~2.25 (m, 4H), 2.10~2.07 (m, 2H), 1.98~4.88 (m, 2H), 1.66~4.42 (m, 3H), 1.25~0.86 (m, 5H);

Compound 173

(R)—N-(4-(4-(3-(2-(4-chlorophenyl)-1,5-dimethyl-4-(4-(methylsulfonyl)piperazine-1-carbonyl)-1H-pyrrol-3-yl)phenyl)piperazin-1-yl)phenyl)-4-((4-(4-hydroxypiperidin-1-yl)-1-(phenylthio)butan-2-yl)amino)-3-((trifluoromethyl)sulfonyl)benzenesulfonamide

BM-796

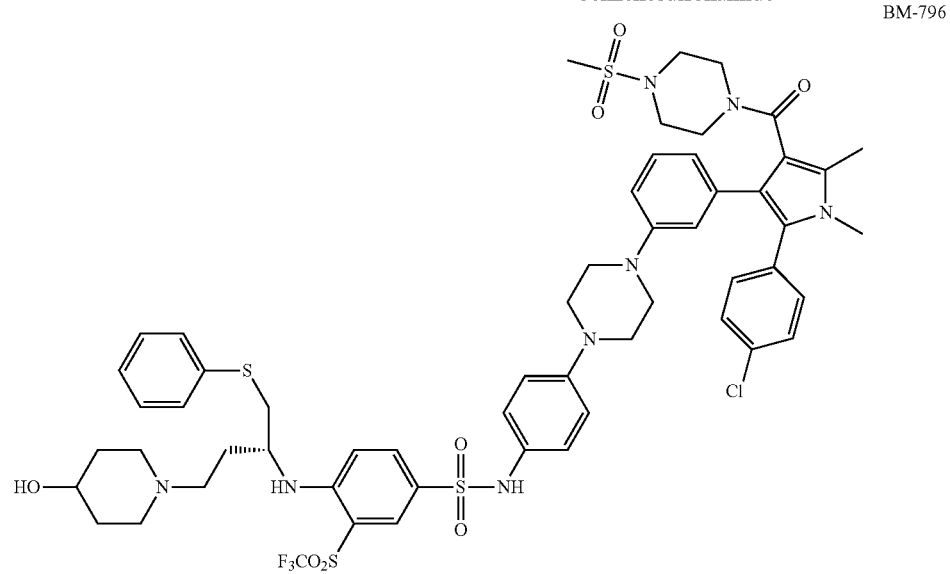

277

¹H NMR (300 MHz, CD₃OD), δ 7.90 (d, J=1.9, 1H), 7.67 (dd, J=1.9, 9.1, 1H), 7.34 (d, J=8.5, 2H), 7.28~7.25 (m, 2H), 7.19~6.83 (m, 11H), 6.77 (dd, J=3.4, 9.3, 1H), 6.68 (s, 1H), 6.57 (d, J=7.6, 1H), 4.09~3.76 (m, 3H), 3.56~3.29 (m, 9H), 3.24~2.83 (m, 16H), 2.59~2.57 (m, 1H), 2.56 (s, 3H), 2.29 (s, 3H), 2.23~2.07 (m, 3H), 1.88 (br. 2H), 1.66~1.61 (m, 1H);

278

Compound 174

(R)—N-(4-(4-(3-(2-(4-chlorophenyl)-1,5-dimethyl-4-(4-methylpiperazine-1-carbonyl)-1H-pyrrol-3-yl)phenyl)piperazin-1-yl)phenyl)-4-((4-(4-hydroxypiperidin-1-yl)-1-(phenylthio)butan-2H)amino)-3-((trifluoromethyl)sulfonyl)benzenesulfonamide

BM-797

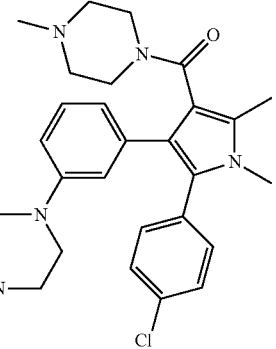
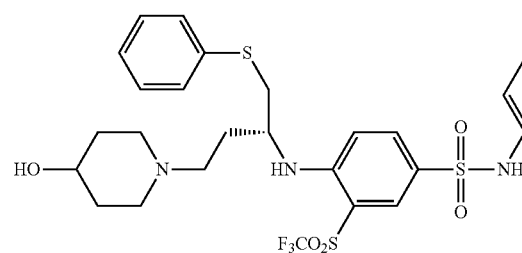

¹H NMR (300 MHz, CD₃OD), δ 7.87 (d, J=1.8, 1H), 7.69 (dd, J=1.9, 9.2, 1H), 7.34 (d, J=8.4, 2H), 7.29~7.26 (m, 2H), 7.18~7.15 (m, 6H), 7.04~6.96 (m, 4H), 6.89 (d, J=7.4, 1H), 6.80 (d, J=9.2, 1H), 6.64 (s, 1H), 6.59 (d, J=7.5, 1H), 4.64 (br., 1H), 4.04~3.96 (m, 2H), 3.75~3.31 (m, 8H), 3.21~2.54 (m, 21H), 2.30 (s, 3H), 2.22~1.88 (m, 5H), 1.67~1.63 (m, 1H);

Compound 175

(R)—N-(4-(4-(3-(2-(4-chlorophenyl)-1,5-dimethyl-4-(morpholine-4-carbonyl)-1H-pyrrol-3-yl)phenyl)piperazin-1-yl)phenyl)-4-((4-(4-hydroxypiperidin-1-yl)-1-(phenylthio)butan-2-yl)amino)-3-((trifluoromethyl)sulfonyl)benzenesulfonamide

BM-798

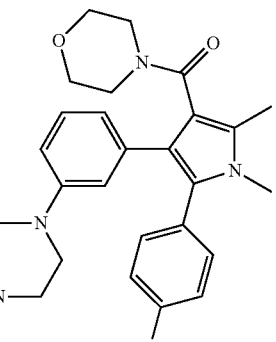
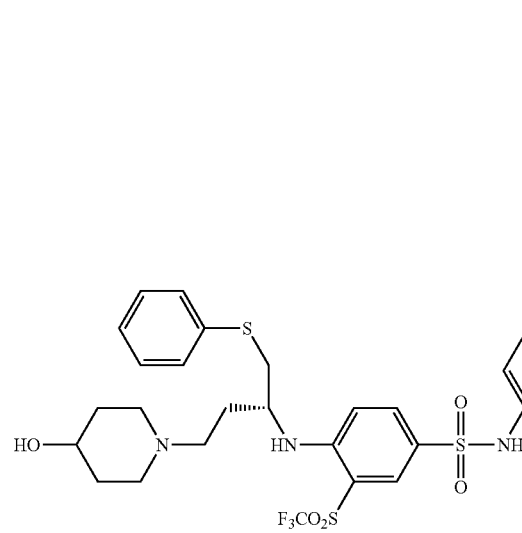

¹H NMR (300 MHz, CD₃OD), δ 7.90 (d, J=2.0, 1H), 7.69 (dd, J=2.0, 9.2, 1H), 7.66 (d, J=8.6, 2H), 7.28~7.27 (m, 2H), 7.19~7.11 (m, 6H), 7.06~6.99 (m, 4H), 6.92~6.89 (m, 1H), 6.81~6.78 (m, 1H), 6.71 (s, 1H), 6.62 (d, J=7.7, 1H), 4.04~3.72 (m, 3H), 3.55~3.29 (m, 10H), 3.22~2.90 (m, 15H), 2.39 (br. 1H), 2.28 (s, 3H), 2.23~2.21 (m, 1H), 2.10~2.07 (m, 2H), 1.88 (br. 2H), 1.66~1.62 (m, 1H);

Compound 176

(R)—N-(4-(4-(3-(2-(4-chlorophenyl)-4-(2-hydroxyethyl)piperazine-1-carbonyl)-1,5-dimethyl-1H-pyrrol-3-yl)phenyl)piperazin-1-yl)phenyl)-4-((4-(4-hydroxypiperidin-1-yl)-1-(phenylthio)butan-2-yl)amino)-3-((trifluoromethyl)sulfonyl)benzenesulfonamide

BM-799

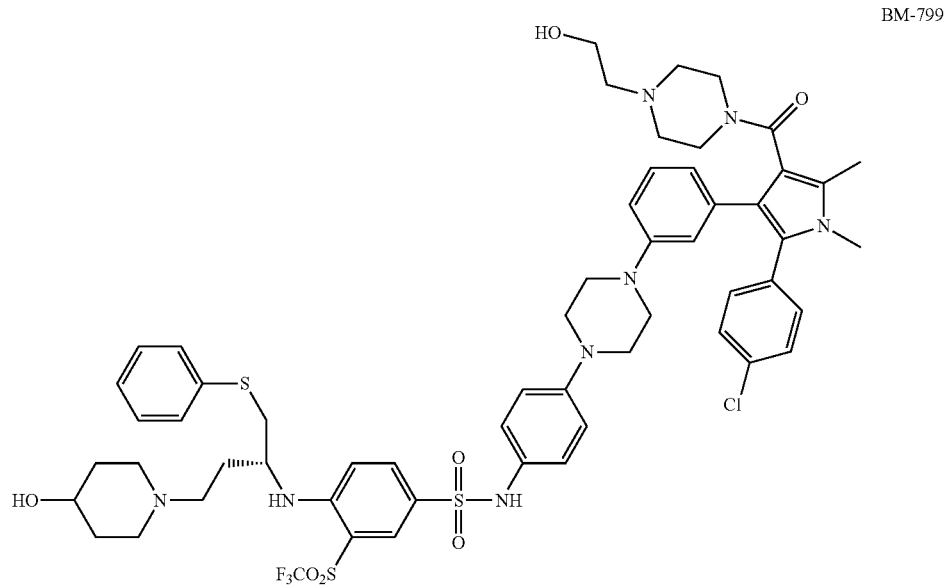

¹H NMR (300 MHz, CD₃OD), δ 7.88 (d, J=2.0, 1H), 7.69 (dd, J=2.1, 9.2, 1H), 7.35 (d, J=8.6, 2H), 7.29~7.27 (m, 2H), 7.19~7.16 (m, 6H), 7.02 (d, J=9.1, 2H), 6.94 (d, J=9.1, 2H), 6.88~6.85 (m, 1H), 6.80 (d, J=9.2, 1H), 6.62 (s, 1H), 6.57 (d, J=7.7, 1H), 4.06~3.95 (m, 2H), 3.71~3.32 (m, 10H), 3.18~2.91 (m, 21H), 2.31 (s, 3H), 2.24~4.99 (m, 3H), 1.89 (br. 2H), 1.67~1.63 (m, 1H);

Compound 177

(R)-4-(4-(dimethylamino)-1-(phenylthio)butan-2-yl)amino)-3-nitro-N-phenylbenzenesulfonamide

BM-902

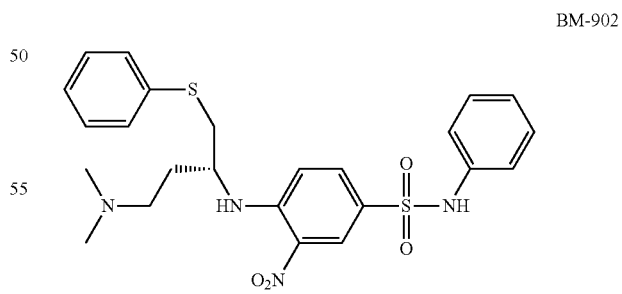

¹H NMR (300 MHz, CD₃OD), δ 8.38 (d, J=2.2 Hz, 1H), 8.15 (d, J=9.3, 1H), 7.62 (dd, J=2.1, 9.1, 1H), 7.28~7.23 (m, 2H), 7.18~6.97 (m, 8H), 6.90, (d, J=9.3, 1H), 4.11~4.07 (m, 1H), 3.40~3.33 (m, 1H), 3.23~3.09 (m, 3H), 2.85 (s, 6H), 2.31~2.11 (m, 2H); ¹³C NMR (75 MHz, CD₃OD), δ 147.9, 139.0, 136.1, 134.4, 132.3, 131.5, 130.3, 128.0, 127.9, 127.7, 125.8, 121.8, 116.1, 55.9, 52.3, 43.5, 39.4, 30.1;

Compound 178

(R)-5-(4-chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1,2-dimethyl-1H-pyrrole-3-carboxylic acid

BM-903

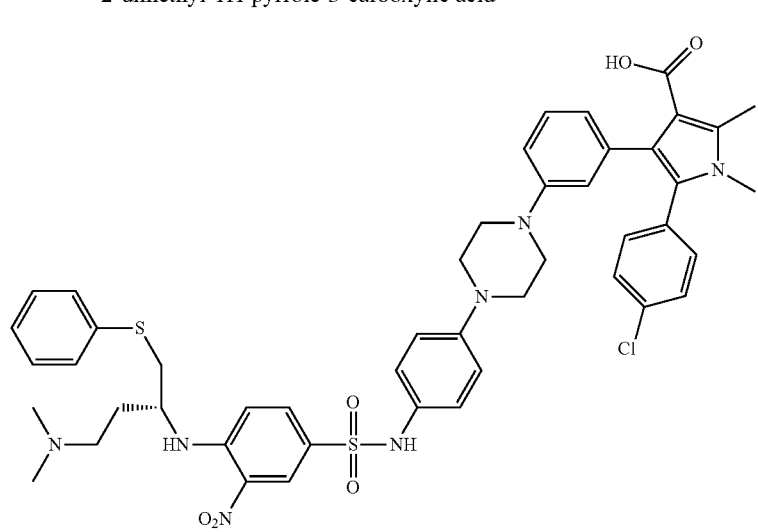

$^1$H NMR (300 MHz, CD$_3$OD), δ 8.30 (d, J=2.2 Hz, 1H), 7.59 (dd, J=2.2, 9.2, 1H), 7.26~7.23 (m, 2H), 7.18~7.13 (m, 3H), 7.09~6.88 (m, 13H), 4.10~4.07 (m, 1H), 3.40 (s, 3H), 3.36~3.29 (m, 9H), 3.21~3.15 (m, 3H), 2.83 (s, 6H), 2.58 (s, 3H), 2.26~2.10 (m, 2H); $^{13}$C NMR (75 MHz, CD$_3$OD), δ 169.1, 148.5, 148.0, 146.9, 139.0, 138.4, 136.2, 134.8, 134.4, 134.0, 132.3, 132.2, 132.1, 131.9, 131.6, 130.1, 129.6, 129.5, 129.0, 128.0, 127.9, 127.6, 124.8, 124.3, 122.9, 118.9, 117.2, 116.2, 111.5, 55.9, 53.2, 52.4, 50.1, 43.5, 39.5, 32.2, 30.1, 12.1;

Compound 179

5-(4-chlorophenyl)-N-((1s,3s)-3-hydroxy-3-methylcyclobutyl)-4-(3-(4-(4-(4-(((R)-4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-1,2-dimethyl-1H-pyrrole-3-carboxamide

BM-904

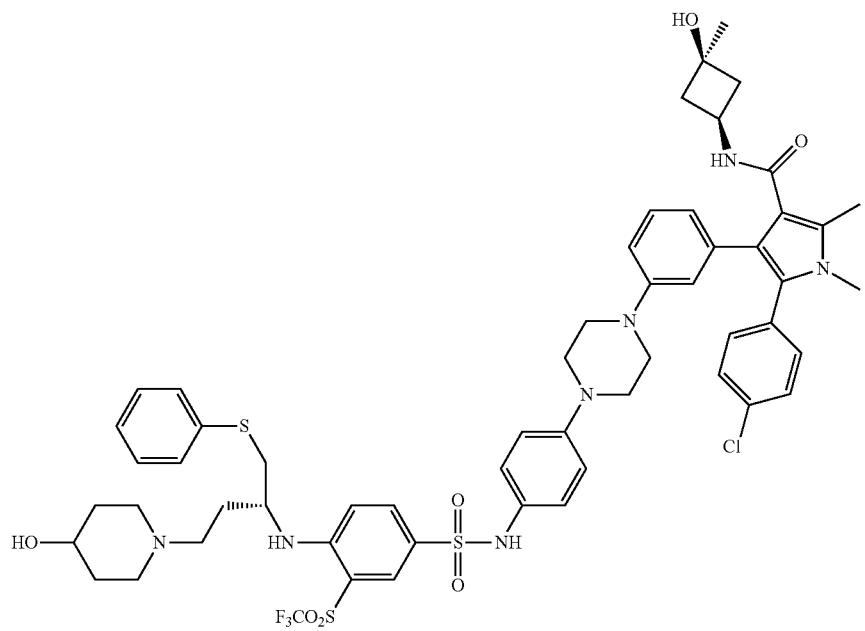

$^1$H NMR (300 MHz, CD$_3$OD), δ 7.90 (d, J=2.1, 1H), 7.38 (dd, J=2.0, 9.1, 1H), 7.31~7.28 (m, 4H), 7.21~7.11 (m, 6H), 7.07~6.97 (m, 5H), 6.84~6.75 (m, 3H), 4.04~3.86 (m, 3H), 3.50~3.30 (m, 10H), 3.27~2.91 (m, 8H), 2.43 (s, 3H), 2.31~2.19 (m, 3H), 2.10~2.07 (m, 2H), 1.88 (br., 2H), 1.73~1.62 (m, 3H), 1.26 (s, 3H);

Compound 180

(R)-5-(4-chlorophenyl)-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-1,2-dimethyl-N-(1-methylazetidin-3-yl)-1H-pyrrole-3-carboxamide

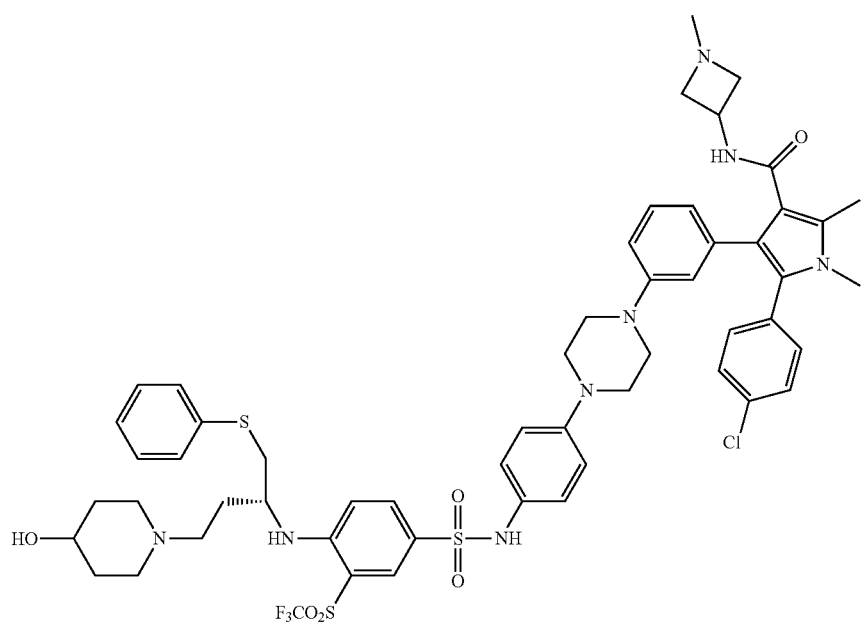

BM-905

$^1$H NMR (300 MHz, CD$_3$OD), δ 7.87 (s, 1H), 7.68 (d, J=9.1, 1H), 7.30~7.24 (m, 4H), 7.18~7.09 (m, 5H), 7.00~6.87 (m, 5H), 6.79~6.66 (m, 4H), 4.19~3.40 (m, 12H), 3.20~2.43 (m, 19H), 2.24~2.21 (m, 1H), 2.09~2.05 (m, 2H), 1.87 (br., 2H), 1.64~1.60 (m, 1H);

Compound 181

(R)-4-(4-chlorophenyl)-3-(3-(4-(4-(4-((4-(dimethylamino)-1-(phenylthio)butan-2-yl)amino)-3-nitrophenylsulfonamido)phenyl)piperazin-1-yl)phenyl)-1-methyl-N-(3-(4-methylpiperazin-1-yl)propyl)-1H-pyrrole-2-carboxamide

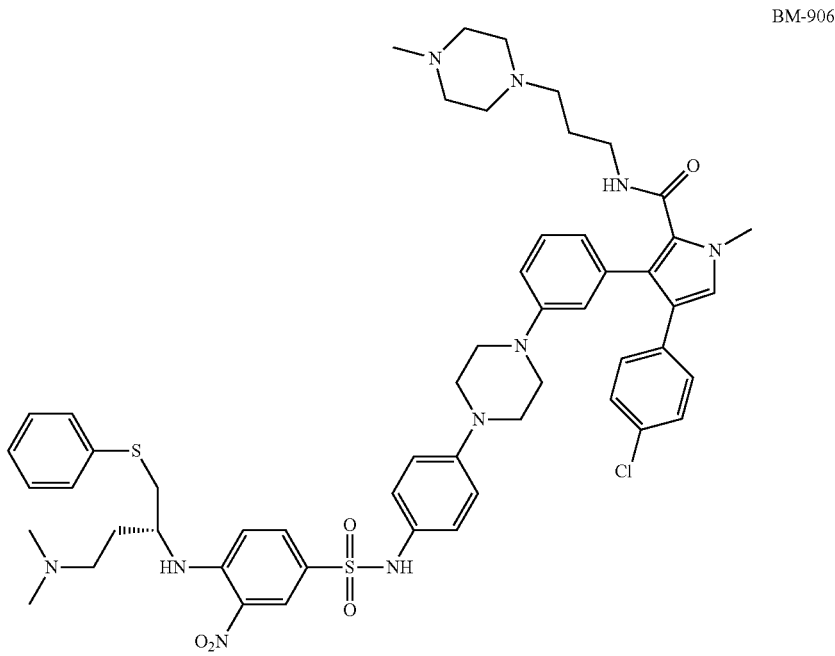 [SMILES: CN(C)CC[C@H](CSc1ccccc1)Nc1ccc(S(=O)(=O)Nc2ccc(N3CCN(c4cccc(-c5c(-c6ccc(Cl)cc6)cn(C)c5C(=O)NCCCN5CCN(C)CC5)c4)CC3)cc2)cc1[N+](=O)[O-]]

BM-906

$^1$H NMR (300 MHz, CD$_3$OD), δ 8.30 (d, J=2.2, 1H), 7.59 (dd, J=2.2, 9.1, 1H), 7.28 (t, J=7.9, 1H), 7.16~6.89 (m, 16H), 6.82~6.77 (m, 2H), 4.09~4.06 (m, 1H), 3.82 (s, 1H), 3.33~3.28 (m, 6H), 3.25~3.09 (m, 16H), 2.83 (s, 9H), 2.62~2.57 (m, 2H), 2.24~2.14 (m, 2H), 1.65~1.61 (m, 2H););
$^{13}$C NMR (75 MHz, CD$_3$OD), δ 165.1, 151.6, 147.9, 137.4, 136.2, 135.0, 134.4, 132.5, 132.2, 131.6, 130.7, 130.4, 130.1, 129.2, 128.0, 127.9, 127.6, 126.7, 126.4, 125.8, 124.2, 123.3, 120.1, 118.9, 116.9, 116.2, 55.9, 55.4, 52.9, 52.4, 51.1, 50.6, 50.5, 43.6, 43.5, 39.5, 37.5, 36.3, 30.1, 25.9;

Compound 182

4-(4-chlorophenyl)-1-((S)-3,4-dihydroxybutyl)-3-(3-(4-(4-(((R)-4-(dimethylamino)-1-(phenylthio) butan-2-yl)amino)-3-nitrophenylsulfonamido)phenyl)piperazin-1-yl)phenyl)-N-(3-(4-methylpiperazin-1-yl)propyl)-1H-pyrrole-2-carboxamide

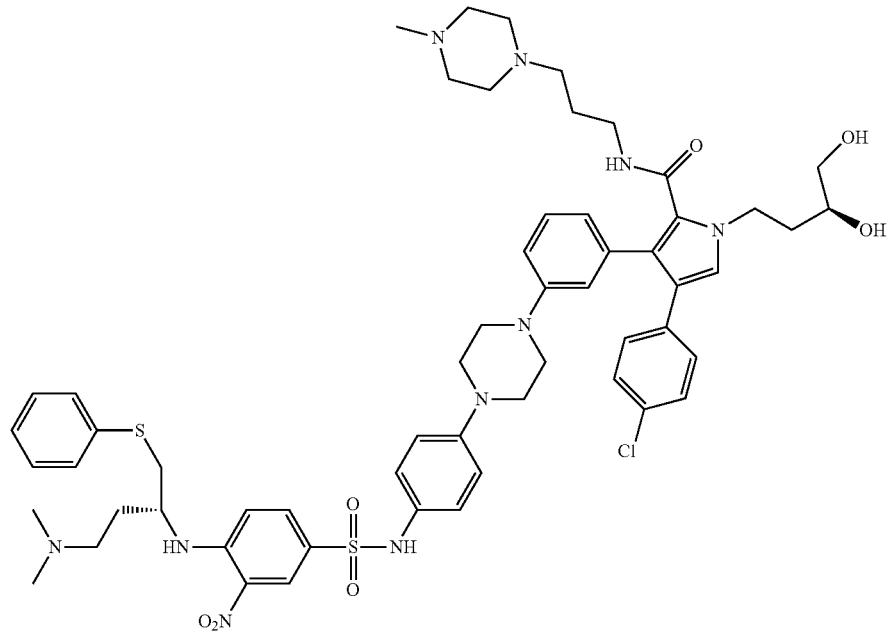

BM-907

$^1$H NMR (300 MHz, CD$_3$OD), δ 8.30 (d, J=2.2, 1H), 7.59 (dd, J=2.2, 1H), 7.59 (dd, J=2.3, 9.2, 1H), 7.28 (t, J=7.9, 1H), 7.18~6.98 (m, 14H), 6.91 (d, J=9.4, 1H), 6.83 (s, 1H), 6.78 (d, J=7.5, 1H), 4.38~4.28 (m, 2H), 4.09~4.08 (m, 2H), 3.55~3.32 (m, 11H), 3.21~3.15 (m, 14H), 2.84 (s, 3H), 2.83 (s, 6H), 2.70~2.65 (m, 2H), 2.25~1.99 (m, 3H), 1.78~1.64 (m, 3H);

Compound 183
4-(4-chlorophenyl)-1-(S)-3,4-dihydroxybutyl)-3-(3-(4-(4-(4-(((R)-4-(dimethylamino)-1-(phenylthio)butan-2-yl)amino)-3-nitrophenylsulfonamido)phenyl)-1H-1,2,3-triazol-1-yl)phenyl)-N-(3-(4-methylpiperazin-1-yl)propyl)-1H-pyrrole-2-carboxamide
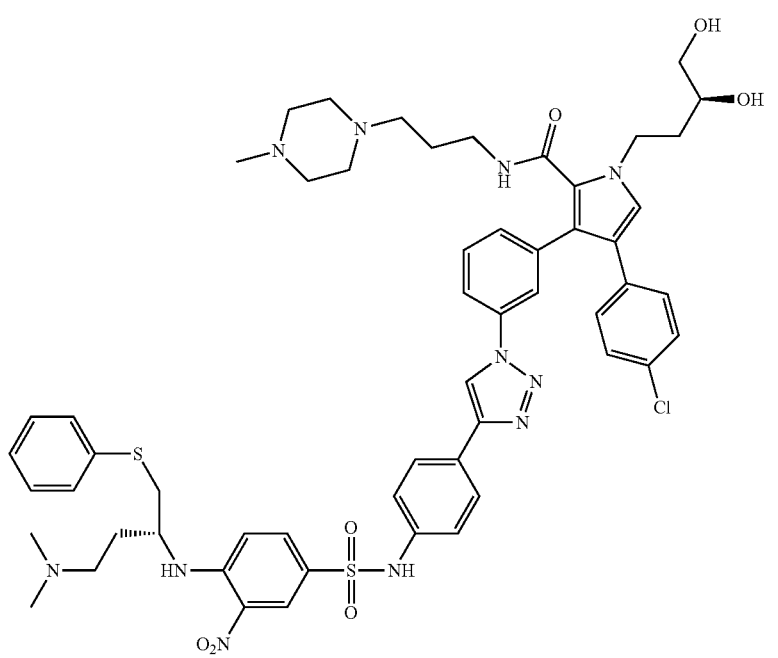
BM-908
$^{1}$H NMR (300 MHz, CD$_{3}$OD), δ 8.67 (s, 1H), 8.38 (d, J=2.2, 1H), 7.78~7.70 (m, 4H), 7.62 (dd, J=2.2, 9.2, 1H), 7.47 (t, J=7.0, 1H), 7.24~7.21 (m, 3H), 7.12~7.01 (m, 7H), 6.94~6.88 (m, 4H), 4.35~4.28 (m, 2H), 4.07~4.06 (m, 1H), 3.54~3.34 (m, 9H), 3.20~3.11 (m, 8H), 2.84~2.80 (m, 11H), 2.19~2.15 (m, 3H), 1.71~1.66 (m, 3H); $^{13}$C NMR (75 MHz, CD$_{3}$OD), δ 165.4, 148.9, 148.1, 139.3, 138.3, 138.0, 136.1, 134.7, 134.3, 132.9, 132.4, 132.2, 131.5, 131.0, 130.8, 130.0, 129.4, 128.1, 127.8, 127.7, 127.4, 127.1, 124.8, 124.5, 123.6, 123.4, 121.9, 120.1, 119.9, 116.4, 70.2, 67.3, 55.9, 55.5, 52.4, 50.3, 46.1, 43.5, 39.4, 37.7, 36.4, 30.1, 25.7;

Compound 184

4-(4-chlorophenyl)-1-((S)-3,4-dihydroxybutyl)-3-(4-((4-(4-(((R)-4-(dimethylamino)-1-(phenylthio)butan-2-yl)amino)-3-nitrophenylsulfonamido)phenyl)ethynyl)phenyl)-N-(3-(4-methylpiperazin-1-yl)propyl)-1H-pyrrole-2-carboxamide

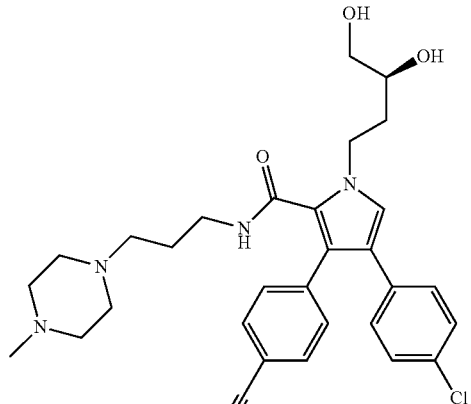

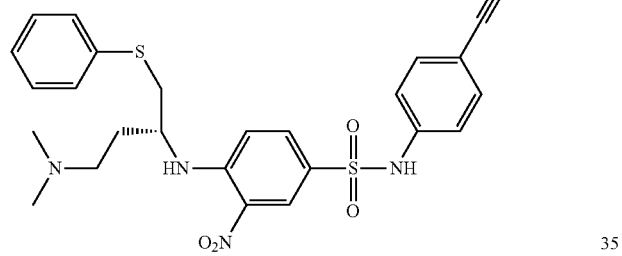

BM-909

$^1$H NMR (300 MHz, CD$_3$OD), δ 8.32 (d, J=1.8, 1H), 7.56 (d, J=9.1, 1H), 7.57~7.54 (m, 4H), 7.08~6.83 (m, 15H), 4.26~4.17 (m, 2H), 4.01~3.09 (m, 1H), 3.43~3.25 (m, 7H), 3.12~3.00 (m, 10H), 2.74 (s, 6H), 2.67 (s, 3H), 2.39~2.37 (m, 2H), 2.16~2.07 (m, 3H), 1.69~1.54 (m, 3H); $^{13}$C NMR (75 MHz, CD$_3$OD), δ 164.0, 146.7, 138.0, 135.0, 134.8, 133.4, 132.9, 132.3, 131.3, 131.1, 130.8, 130.5, 130.1, 129.2, 128.7, 127.9, 126.6, 126.5, 126.1, 125.4, 123.9, 123.3, 122.0, 121.6, 119.7, 118.9, 114.9, 89.0, 88.8, 68.8, 65.8, 54.5, 54.1, 51.7, 50.9, 49.4, 44.7, 42.2, 42.1, 38.0, 36.4, 35.0, 28.7, 24.5;

Compound 185

(R)-5-(4-chlorophenyl)-4-(3-(4-(4-(4-((4-(dimethylamino)-1-(phenylthio)butan-2-yl)amino)-3-((trifluoromethyl)sulfonyl)phenylsulfonamido)phenyl)piperazin-1-yl)phenyl)-1,2-dimethyl-1H-pyrrole-3-carboxylic acid

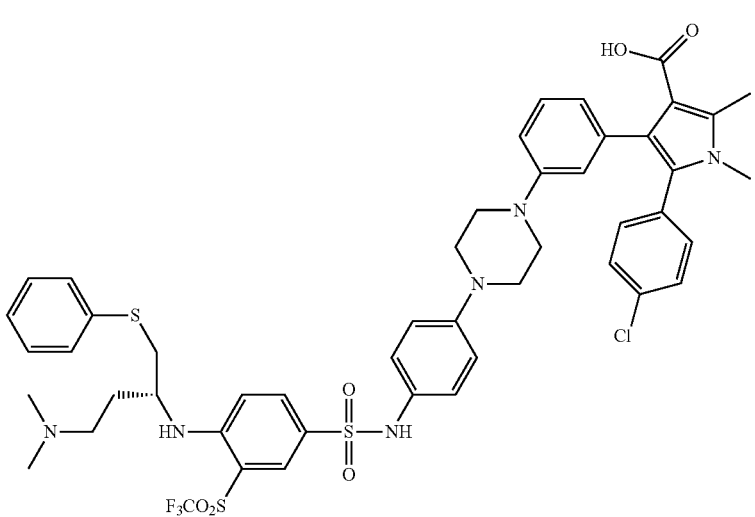

BM-910

¹H NMR (300 MHz, CD₃OD), δ 7.85 (d, J=2.0, 1H), 7.70 (dd, J=2.2, 9.2, 1H), 7.26~6.96 (m, 16H), 6.86~6.78 (m, 2H), 3.98~3.91 (m, 1H), 3.42~3.31 (m, 11H), 3.20~3.02 (m, 4H), 2.80 (s, 6H), 2.57 (s, 3H), 2.25~1.98 (m, 2H);

Compound 186

(R)-5-(4-chlorophenyl)-1,2-dimethyl-4-(3-(4-(4-(4-((4-morpholino-1-(phenylthio)butan-2-yl)amino)-3-((trifluoromethyl)sulfonyl)phenylsulfonamido)phenyl)piperazin-1-yl)phenyl)-1H-pyrrole-3-carboxylic acid

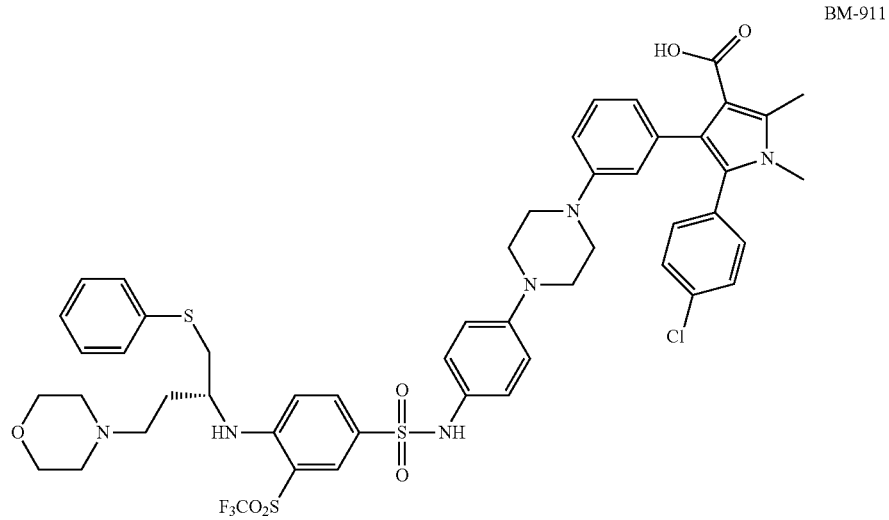

BM-911

¹H NMR (300 MHz, CD₃OD), δ 7.93 (d, J=2.1, 1H), 7.74 (dd, J=2.2, 9.2, 1H), 7.44~6.89 (m, 17H), 6.83 (d, J=9.4, 1H), 4.03~3.98 (m, 3H), 3.78~3.71 (m, 2H), 3.56~3.36 (m, 11H), 3.25~3.09 (m, 8H), 2.64 (s, 3H), 2.32~2.24 (m, 1H), 2.13~2.09 (m, 1H);

Compound 187

(R)-5-(4-chlorophenyl)-1,2-dimethyl-4-(3-(4-(4-(4-((4-morpholino-1-(phenylthio)butan-2-yl)amino)-3-nitrophenylsulfonamido)phenyl)piperazin-1-yl)phenyl)-1H-pyrrole-3-carboxylic acid

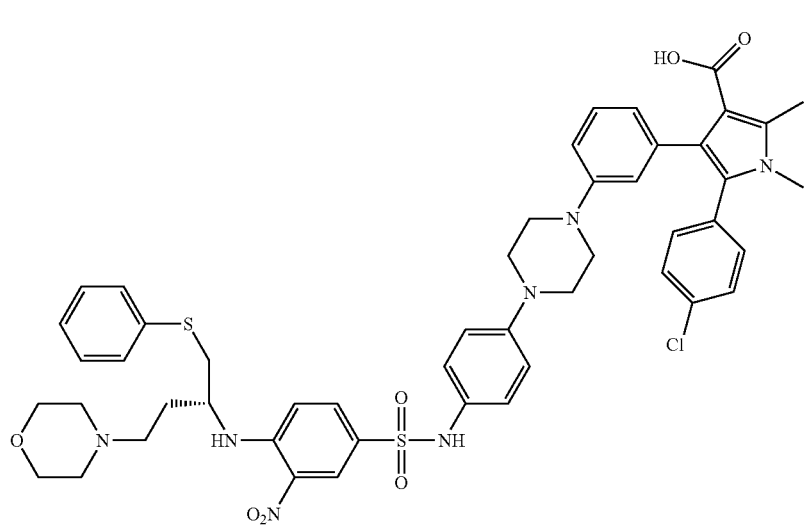

BM-912

¹H NMR (300 MHz, CD₃OD), δ 8.30 (d, J=2.3, 1H), 7.61 (dd, J=2.3, 9.2, 1H), 7.38~6.91 (m, 18H), 4.11~3.99 (m, 3H), 3.71~3.70 (m, 2H), 3.41~3.32 (m, 13H), 3.25~3.08 (m, 6H), 2.58 (s, 3H), 2.29~2.18 (m, 2H);

Compound 188

(R)-5-(4-chlorophenyl)-4-(3-(4-(4-(4-((4-(4-hydroxypiperidin-1-yl)-1-(phenylthio)butan-2-yl)amino)-3-nitrophenylsulfonamido)phenyl)Piperazin-1-yl)phenyl)-1,2-dimethyl-1H-pyrrole-3-carboxylic acid

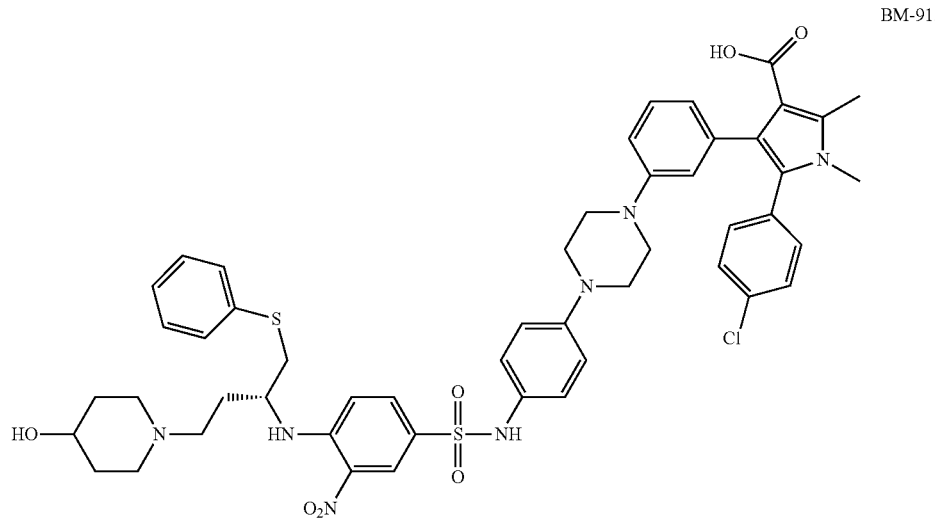

BM-913

$^1$H NMR (300 MHz, CD$_3$OD), δ 8.29 (d, J=2.2, 1H), 7.59 (dd, J=2.2, 9.1, 1H), 7.37~6.87 (m, 18H), 4.07~3.75 (m, 2H), 3.53~3.50 (m, 1H), 3.40~3.32 (m, 11H), 3.20~3.04 (m, 6H), 2.99~2.90 (m, 1H), 2.58 (s, 3H), 2.26~2.06 (m, 3H), 1.89~1.83 (m, 2H), 1.67~1.63 (m, 1H);

Compound 189

(R)-4-(4-chlorophenyl)-3-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-1-methyl-1H-pyrrole-2-carboxylic acid

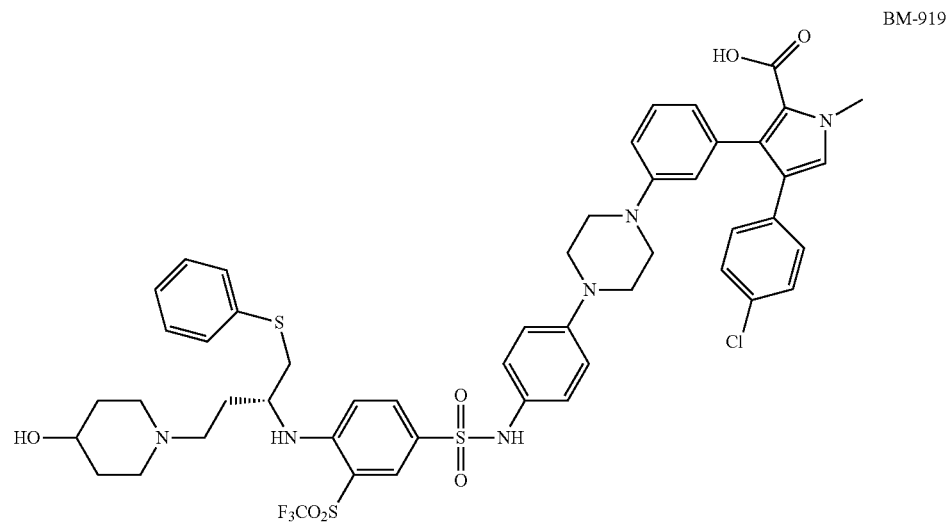

BM-919

$^1$H NMR (300 MHz, CD$_3$OD), δ 7.88 (d, J=2.0, 1H), 7.72~7.69 (m, 1H), 7.30~7.23 (m, 3H), 7.20~6.95 (m, 14H), 6.84~6.78 (m, 2H), 4.05~4.03 (m, 1H), 3.95 (s, 3H), 3.85~3.68 (m, 1H), 3.49~3.36 (m, 10H), 3.21~2.89 (m, 6H), 2.22~1.88 (m, 5H), 1.66~1.62 (m, 1H);

Compound 120

(R)-4-(4-chlorophenyl)-3-(3-(4-(4-(4-((4-(dimethylamino)-1-(phenylthio)butan-2-yl)amino)-3-nitrophenylsulfonamido)phenyl)piperazin-1-yl)phenyl)-1-methyl-1H-pyrrole-2-carboxylic acid

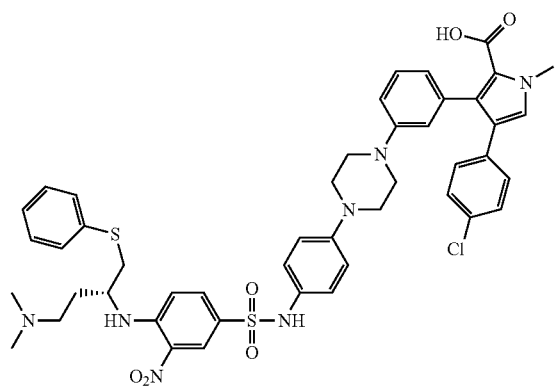

$^1$H NMR (300 MHz, CD$_3$OD), δ 8.29 (d, J=2.2, 1H), 7.58 (dd, J=2.3, 9.2, 1H), 7.27 (t, J=7.8, 1H), 7.15~6.89 (m, 18H), 4.08~4.05 (m, 1H), 3.93 (s, 3H), 3.67~3.30 (m, 9H), 3.20~3.14 (m, 3H), 2.82 (s, 6H), 2.23~2.14 (m, 2H); $^{13}$C NMR (75 MHz, CD$_3$OD), δ 164.3, 147.9, 138.9, 136.2, 134.8, 134.4, 132.8, 132.6, 132.2, 131.7, 131.6, 130.6, 130.1, 130.0, 129.2, 128.7, 128.3, 128.0, 127.9, 127.6, 124.1, 124.0, 122.4, 122.0, 119.1, 117.8, 116.2, 55.9, 52.8, 52.4, 50.6, 43.5, 39.5, 38.1, 30.1;

Compound 121

(R)-4-(4-chlorophenyl)-3-(3-(4-(4-(4-((4-(4-hydroxypiperidin-1-yl)-1-(phenylthio)butan-2-yl)amino)-3-nitrophenylsulfonamido)phenyl)piperazin-1-yl)phenyl)-1-methyl-1H-pyrrole-2-carboxylic acid

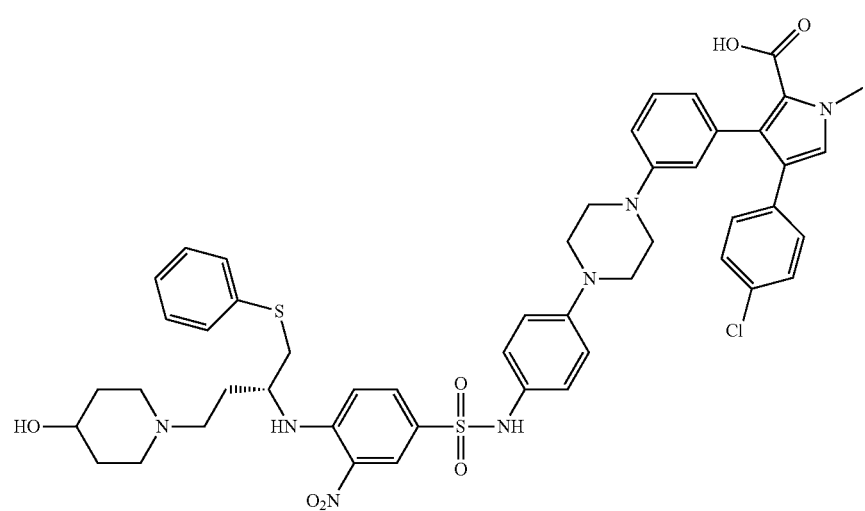

ESI MS: m/z 950.3 (M+H)$^+$;

Compound 192

(R)-5-chloro-4-(4-chlorophenyl)-3-(3-(4-(4-(4-((4-(dimethylamino)-1-(phenylthio)butan-2-yl)amino)-3-nitrophenylsulfonamido)phenyl)piperazin-1-yl)phenyl)-1-methyl-1H-pyrrole-2-carboxylic acid

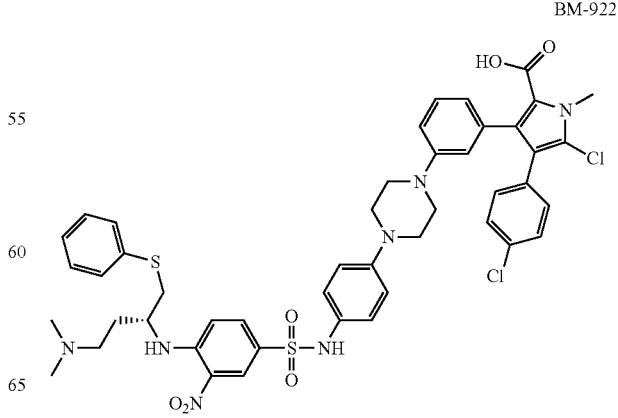

¹H NMR (300 MHz, CD₃OD), δ 8.34 (d, J=2.2, 1H), 7.55 (dd, J=2.3, 9.2, 1H), 7.28~6.60 (m, 18H), 4.08~4.06 (m, 1H), 3.97 (s, 3H), 3.56~3.51 (m, 2H), 3.22~3.05 (m, 10H), 2.85 (s, 6H), 2.18~2.15 (m, 2H);

Compound 193

(R)-5-chloro-4-(4-chlorophenyl)-3-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-1-methyl-1H-pyrrole-2-carboxylic acid

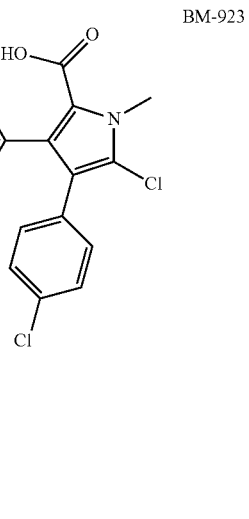

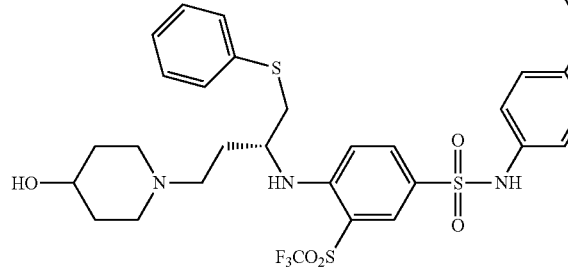

¹H NMR (300 MHz, CD₃OD), δ 7.91 (s, 1H), 7.62 (d, J=9.5, 1H), 7.28~6.59 (m, 18H), 3.93~3.52 (m, 5H), 3.23~3.05 (m, 16H), 2.20~2.14 (m, 1H), 2.02~1.97 (m, 2H), 1.75~1.58 (m, 3H);

Compound 194

(R)-5-(4-chlorophenyl)-N-cyclopropyl-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-1,2-dimethyl-1H-pyrrole-3-carboxamide

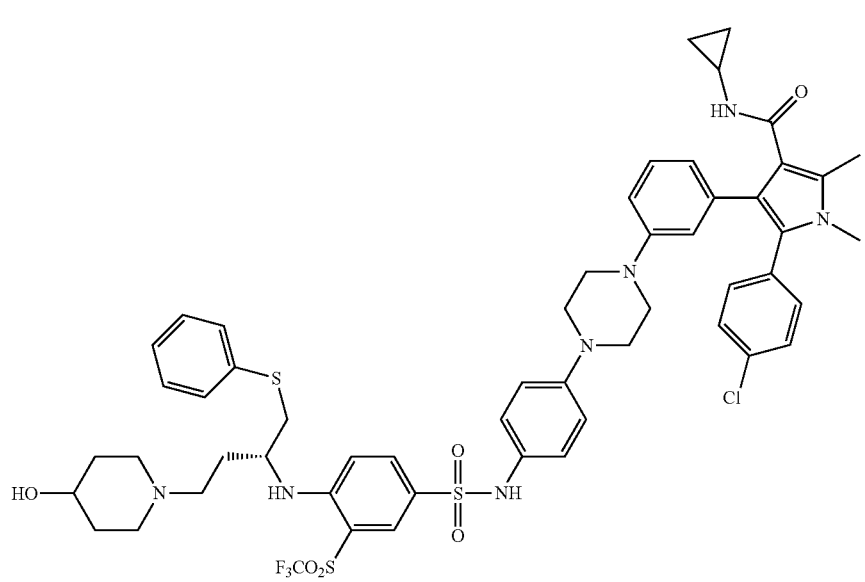

¹H NMR (300 MHz, CD₃OD), δ 7.89 (d, J=2.0, 1H), 7.70 (dd, J=2.0, 9.1, 1H), 7.30~7.26 (m, 4H), 7.20~7.09 (m, 6H), 7.07~6.97 (m, 5H), 6.85~6.73 (m, 3H), 4.04~3.70 (m, 2H), 3.53~3.38 (m, 13H), 3.22~2.94 (m, 6H), 2.63~2.57 (m, 6H), 2.63~2.57 (m, 1H), 2.42 (s, 3H), 2.20~2.06 (m, 3H), 1.89~1.86 (m, 2H), 1.66~1.62 (m, 1H), 0.64~0.57 (m, 2H), 0.23~0.18 (m, 2H);

Compound 195

(R)—N-(4-(4-(3-(4-(azetidine-1-carbonyl)-2-(4-chlorophenyl)-1,5-dimethyl-1H-pyrrol-3-yl)phenyl)piperazin-1-yl)phenyl)-4-(4-(4-hydroxypiperidin-1-yl)-1-(phenylthio)butan-2-yl)amino)-3-((trifluoromethyl)sulfonyl)benzenesulfonamide

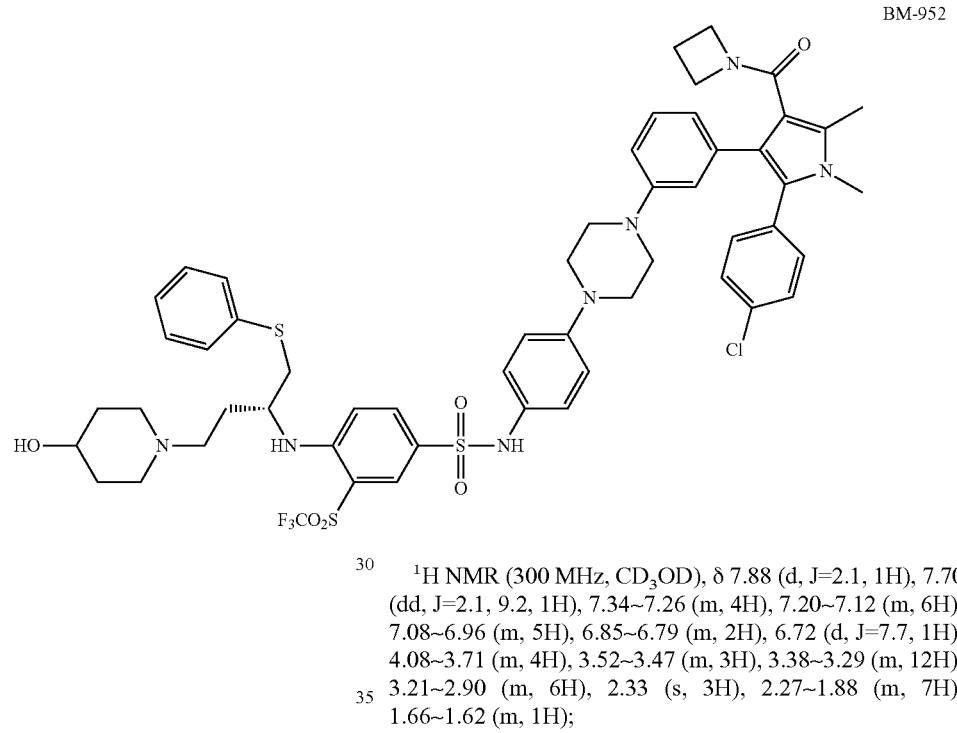

BM-952

¹H NMR (300 MHz, CD₃OD), δ 7.88 (d, J=2.1, 1H), 7.70 (dd, J=2.1, 9.2, 1H), 7.34~7.26 (m, 4H), 7.20~7.12 (m, 6H), 7.08~6.96 (m, 5H), 6.85~6.79 (m, 2H), 6.72 (d, J=7.7, 1H), 4.08~3.71 (m, 4H), 3.52~3.47 (m, 3H), 3.38~3.29 (m, 12H), 3.21~2.90 (m, 6H), 2.33 (s, 3H), 2.27~1.88 (m, 7H), 1.66~1.62 (m, 1H);

Compound 196

(R)—N-(4-(4-(3-(2-(4-chlorophenyl)-4-(4-hydroxypiperidine-1-carbonyl)-1,5-dimethyl-1H-pyrrol-3-yl)phenyl)piperazin-1-yl)phenyl)-4-((4-(dimethylamino)-1-(phenylthio)butan-2-yl)amino)-3-nitrobenzenesulfonamide

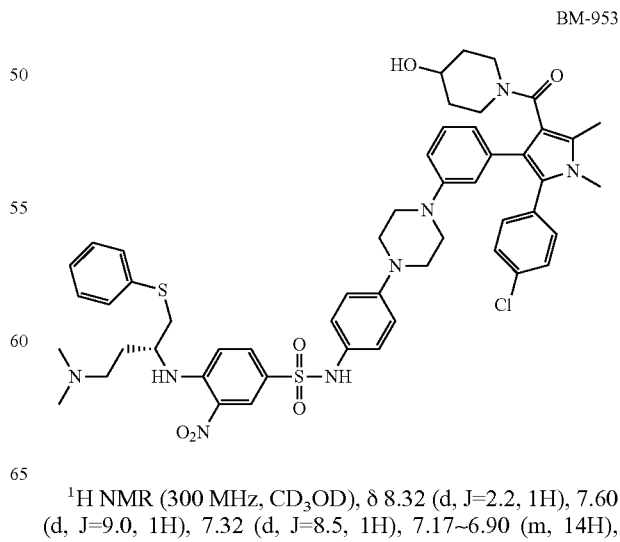

BM-953

¹H NMR (300 MHz, CD₃OD), δ 8.32 (d, J=2.2, 1H), 7.60 (d, J=9.0, 1H), 7.32 (d, J=8.5, 1H), 7.17~6.90 (m, 14H), 6.78~6.63 (m, 2H), 4.10~3.85 (m, 2H), 3.62~3.51 (m, 1H), 3.40~3.32 (m, 9H), 3.21~2.90 (m, 9H), 2.83 (s, 6H), 2.28~1.98 (m, 5H), 1.73~1.06 (m, 4H);

Compound 197

5-(4-chlorophenyl)-4-(3-(4-(4-(4-WR)-4-(dimethy-lamino)-1-(phenylthio)butan-2H)amino)-3-nitrophe-nylsulfonamido)phenyl)piperazin-1-yl)phenyl)-N-((1r,4r)-4-hydroxycyclohexyl)-1,2-dimethyl-1H-pyrrole-3-carboxamide

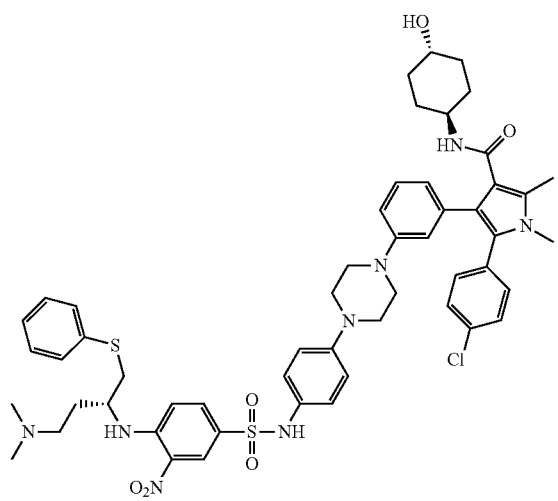

BM-954

$^1$H NMR (300 MHz, CD$_3$OD), δ 8.32 (d, J=2.0, 1H), 7.60 (dd, J=2.0, 9.1, 1H), 7.27 (d, J=8.4, 2H), 7.20~6.90 (m, 14H), 6.82~6.77 (m, 2H), 4.09~4.06 (m, 1H), 3.65~3.57 (m, 1H), 3.38~3.30 (m, 9H), 3.22~3.09 (m, 7H), 2.84 (s, 6H), 2.43 (s, 3H), 2.25~2.16 (m, 2H), 1.78~1.75 (m, 4H), 1.27~1.19 (m, 2H), 1.05~0.94 (m, 2H);

Compound 198

(R)-5-(4-chlorophenyl)-4-(3-(4-(4-(4-((4-(dimethy-lamino)-1-(phenylthio)butan-2-yl)amino)-3-nitro-phenylsulfonamido)phenyl)piperazin-1-yl)phenyl)-1-ethyl-2-methyl-1H-pyrrole-3-carboxylic acid

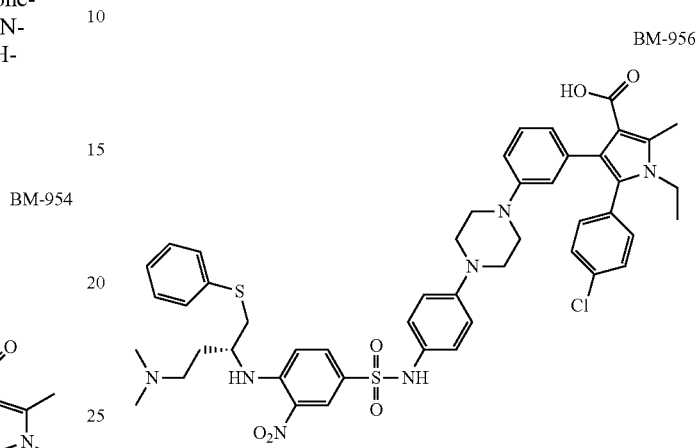

BM-956

$^1$H NMR (300 MHz, CD$_3$OD), δ 8.31 (d, J=2.2, 1H), 7.59 (dd, J=2.2, 9.1, 1H), 7.28~6.86 (m, 18H), 4.10~4.06 (m, 1H), 3.87 (q, J=7.1, 2H), 3.39~3.29 (m, 9H), 3.22~3.15 (m, 3H), 2.84 (s, 6H), 2.60 (s, 3H), 2.20~2.18 (m, 2H), 1.10 (t, J=7.1, 3H);

Compound 199

(R)-5-(4-chlorophenyl)-1-ethyl-4-(3-(4-(4-(4-((4-(4-hydroxypiperidin-1-yl)-1-(phenylthio)butan-2-yl)amino)-3-((trifluoromethyl)sulfonyl)phenylsulfona-mido)phenyl)piperazin-1-yl)phenyl)-2-methyl-1H-pyrrole-3-carboxylic acid

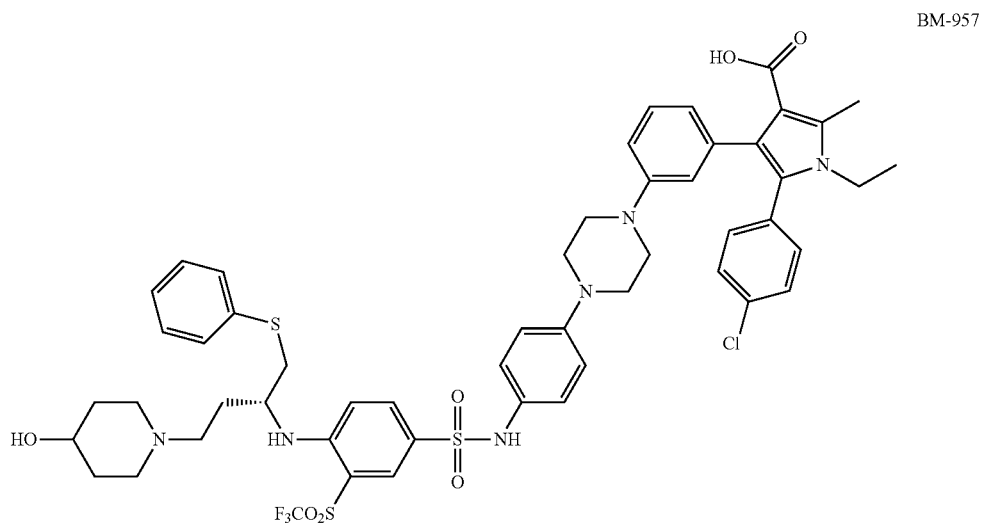

BM-957

303

¹H NMR (300 MHz, CD₃OD), δ 7.87 (s, 1H), 7.69 (d, J=9.1, 1H), 7.29~7.26 (m, 4H), 7.15~6.78 (m, 14H), 4.04~3.77 (m, 4H), 3.49~3.28 (m, 8H), 3.17~2.94 (m, 8H), 2.60 (s, 3H), 2.05~1.69 (m, 6H), 1.10 (t, J=6.9, 3H);

Compound 200

(R)—N-(4-(4-(3-(4-(4-chlorophenyl)-1-methyl-1H-pyrrol-3-yl)phenyl)piperazin-1-yl)phenyl)-4-((4-(dimethylamino)-1-(phenylthio)butan-2-yl)amino)-3-nitrobenzenesulfonamide

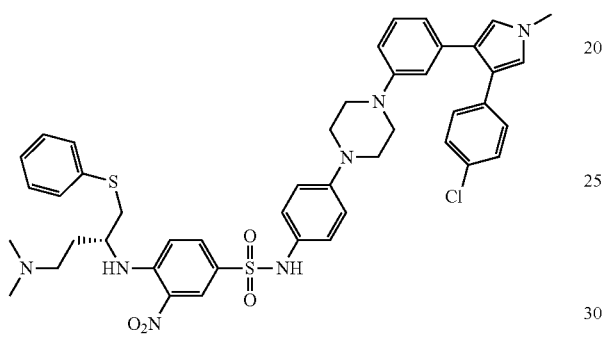
BM-958

304

¹H NMR (300 MHz, CD₃OD), δ 8.30 (d, J=2.2, 1H), 7.59 (dd, J=2.2, 9.2, 1H), 7.25 (m, 1H), 7.18~6.89 (m, 17H), 6.80 (dd, J=2.3, 9.7, 2H), 4.10~4.06 (m, 1H), 3.67 (s, 3H), 3.35~3.30 (m, 9H), 3.20~3.14 (m, 3H), 2.82 (s, 6H), 2.23~2.14 (m, 2H); ¹³C NMR (75 MHz, CD₃OD), δ 148.0, 147.9, 139.3, 136.3, 136.2, 134.4, 133.0, 132.34, 132.25, 131.6, 131.0, 130.8, 130.1, 129.3, 128.0, 127.9, 127.6, 126.0, 124.1, 123.6, 123.4, 123.2, 123.1, 123.0, 119.7, 119.2, 116.8, 116.2, 55.9, 53.0, 52.4, 50.5, 43.5, 39.5, 36.4, 30.1;

Compound 201

N-(4-(4-(3-(4-(4-chlorophenyl)-1-((S)-3,4-dihydroxybutyl)-1H-pyrrol-3-yl)phenyl)-1,4-diazepan-1-yl)phenyl)-4-(((R)-4-(dimethylamino)-1-(phenylthio)butan-2-yl)amino)-3-nitrobenzenesulfonamide

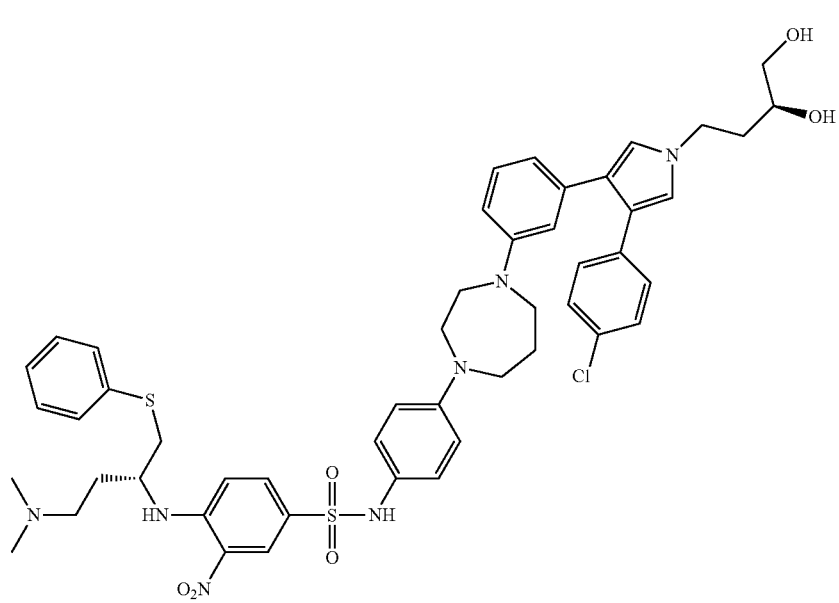
BM-959

¹H NMR (300 MHz, CD₃OD), δ 8.28 (d, J=2.2, 1H), 7.52 (dd, J=2.2, 9.1, 1H), 7.19~7.03 (m, 10H), 6.93 (d, J=8.9, 2H), 6.86~6.82 (m, 3H), 6.65~6.59 (m, 4H), 6.41 (s, 1H), 4.06~4.04 (m, 3H), 3.60~3.33 (m, 8H), 3.27~3.13 (m, 7H), 2.84 (s, 6H), 2.25~2.00 (m, 3H), 1.82~1.73 (m, 3H);

Compound 202

(R)-5-(4-chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1-isopropyl-2-methyl-1H-pyrrole-3-carboxylic acid

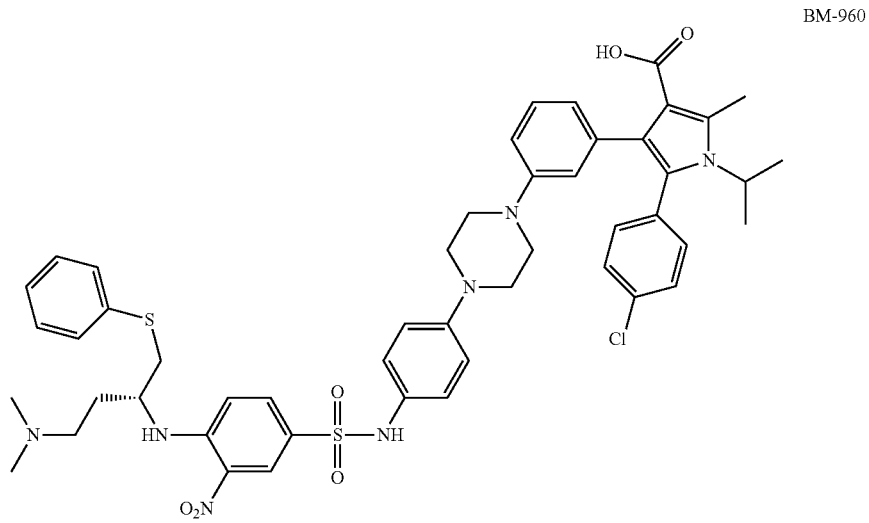 [SMILES: Cc1c(C(=O)O)c(-c2cccc(N3CCN(c4ccc(NS(=O)(=O)c5ccc(N[C@H](CCN(C)C)CSc6ccccc6)c([N+](=O)[O-])c5)cc4)CC3)c2)c(-c2ccc(Cl)cc2)n1C(C)C]

BM-960

$^1$H NMR (300 MHz, CD$_3$OD), δ 8.29 (d, J=2.2, 1H), 7.60 (dd, J=2.2, 9.2, 1H), 7.26~6.90 (m, 18H), 4.41~4.36 (m, 1H), 4.10~4.08 (m, 1H), 3.38~3.31 (m, 9H), 3.21~3.15 (m, 3H), 2.83 (s, 6H), 2.68 (s, 3H), 2.24~2.14 (m, 2H), 1.39 (d, J=7.1, 6H);

Compound 203

(R)-5-(4-chlorophenyl)-1-cyclopropyl-4-(3-(4-(4-(4-((4-(dimethylamino)-1-(phenylthio)butan-2-yl)amino)-3-nitrophenylsulfonamido)phenyl)piperazin-1-yl)phenyl)-2-methyl-1H-pyrrole-3-carboxylic acid

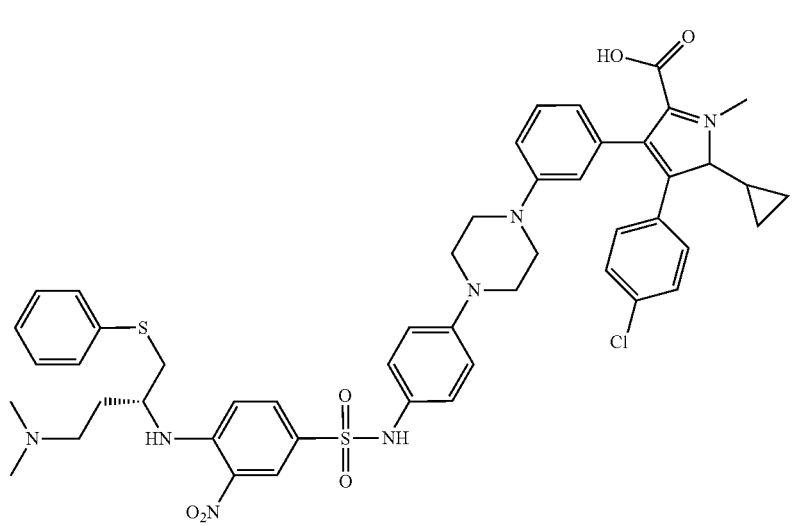

BM-961

$^1$H NMR (300 MHz, CD$_3$OD), δ 8.29 (d, J=2.3, 1H), 7.60 (dd, J=2.3, 9.2, 1H), 7.24~6.91 (m, 18H), 4.12~4.07 (m, 1H), 3.39~3.31 (m, 9H), 3.24~3.14 (m, 4H), 2.83 (s, 6H), 2.67 (s, 3H), 2.24~2.15 (m, 2H), 0.89~0.82 (m, 2H), 0.50~0.44 (m, 2H);

Compound 204

(R)-5-(4-chlorophenyl)-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-1-isopropyl-2-methyl-1H-pyrrole-3-carboxylic acid

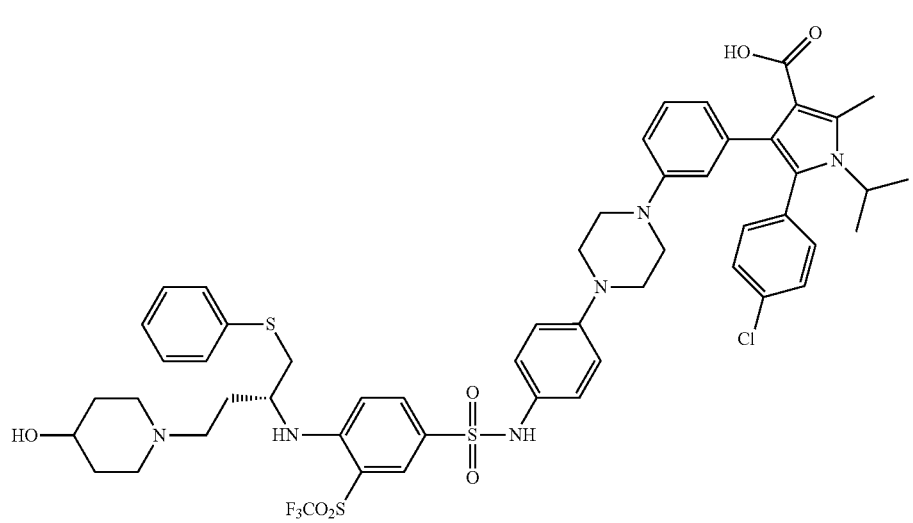

BM-962

$^1$H NMR (300 MHz, CD$_3$OD), δ 7.84 (d, J=2.0, 1H), 7.70 (dd, J=2.1, 9.2, 1H), 7.26~7.22 (m, 4H), 7.20~7.07 (m, 7H), 7.04~6.95 (m, 6H), 6.80 (d, J=9.2, 1H), 4.42~4.33 (m, 1H), 4.02~3.73 (m, 2H), 3.48~3.31 (m, 10H), 3.25~2.88 (m, 6H), 2.67 (s, 3H), 2.37~4.87 (m, 5H), 1.66~1.62 (m, 1H), 1.38 (d, J=7.1, 6H);

Compound 205

(R)-5-(4-chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1-methyl-1H-pyrazole-3-carboxylic acid

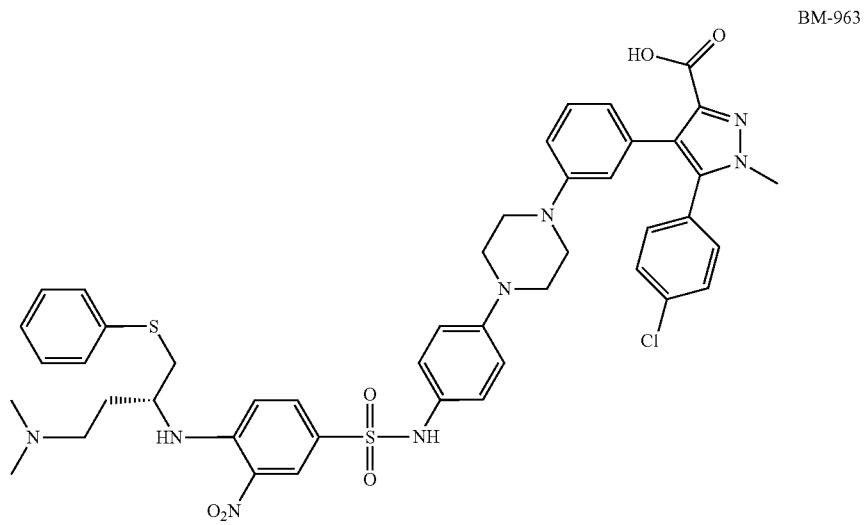

BM-963

$^1$H NMR (300 MHz, CD$_3$OD), δ 8.31 (d, J=2.2, 1H), 7.60 (dd, J=2.3, 9.2, 1H), 7.38~7.35 (m, 2H), 7.26~6.90 (m, 15H), 6.85 (d, J=7.6, 1H), 4.11~4.07 (m, 1H), 3.82 (s, 3H), 3.45~3.33 (m, 9H), 3.21~3.14 (m, 3H), 2.84 (s, 6H), 2.25~2.15 (m, 2H);

Compound 206

(R)-3-(4-chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-1-methyl-1H-pyrazole-5-carboxylic acid

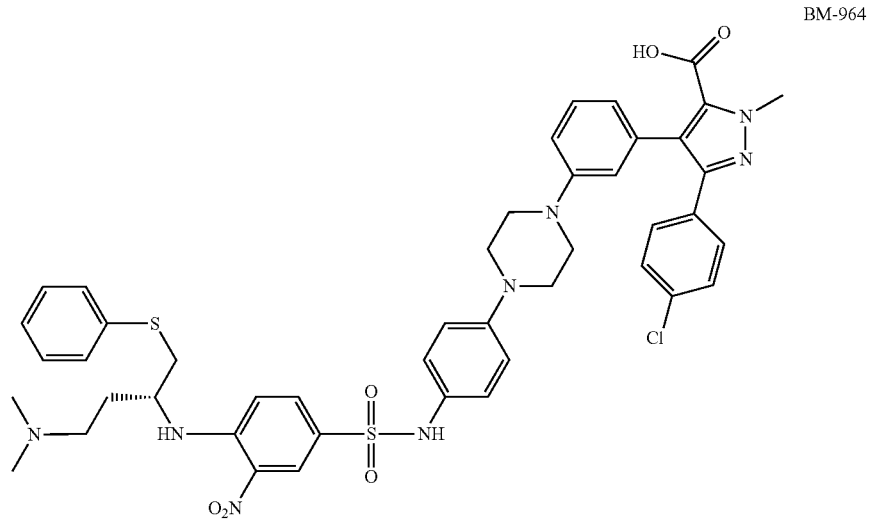

BM-964

$^1$H NMR (300 MHz, CD$_3$OD), δ 8.32 (d, J=2.3, 1H), 7.58 (dd, J=2.3, 9.2, 1H), 7.30~7.25 (m, 3H), 7.20~7.14 (m, 4H), 7.09~6.96 (m, 9H), 6.90 (d, J=10.2, 1H), 6.85 (d, J=7.6, 1H), 4.18 (s, 3H), 4.10~4.06 (m, 1H), 3.37~3.31 (m, 9H), 3.21~3.15 (m, 3H), 2.84 (s, 6H), 2.24~2.13 (m, 2H);

Compound 207

(R)—N-(4-(4-(3-(2-(4-chlorophenyl)-4-(3-hydroxy-3-methylazetidine-1-carbonyl)-1,5-dimethyl-1H-pyrrol-3-yl)phenyl)piperazin-1-yl)phenyl)-4-((4-(4-hydroxypiperidin-1-yl)-1-(phenylthio)butan-2-yl)amino)-3-((trifluoromethyl)sulfonyl)benzenesulfonamide

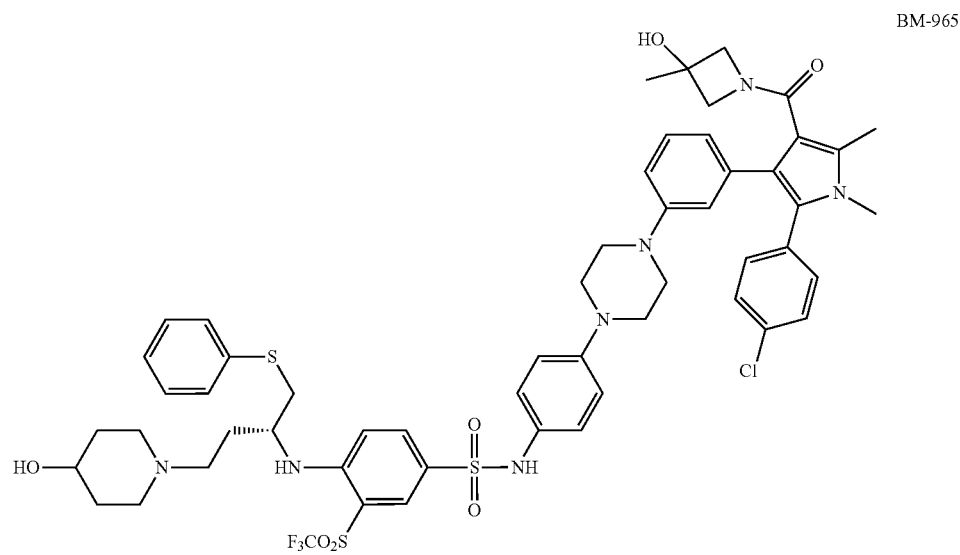

BM-965

$^1$H NMR (300 MHz, CD$_3$OD), δ 7.89 (d, J=2.1, 1H), 7.69 (dd, J=2.1, 9.1, 1H), 7.34~7.26 (m, 4H), 7.18~6.78 (m, 13H), 6.67 (d, J=7.7, 1H), 4.04~3.73 (m, 4H), 3.49~3.31 (m, 14H), 3.22~3.31 (m, 14H), 3.22~2.94 (m, 7H), 2.76 (s, 3H), 2.22~2.06 (m, 3H), 1.90~1.85 (m, 2H), 1.69~1.63 (m, 1H), 1.07 (s, 3H);

Compound 208
(R)-5-(4-chlorophenyl)-4-(3-(4-(4-(4-((4-(dimethylamino)-1-(phenylthio)butan-2-yl)amino)-3-nitrophenylsulfonamido)phenyl)piperazin-1-yl)phenyl)-2-methylfuran-3-carboxylic acid
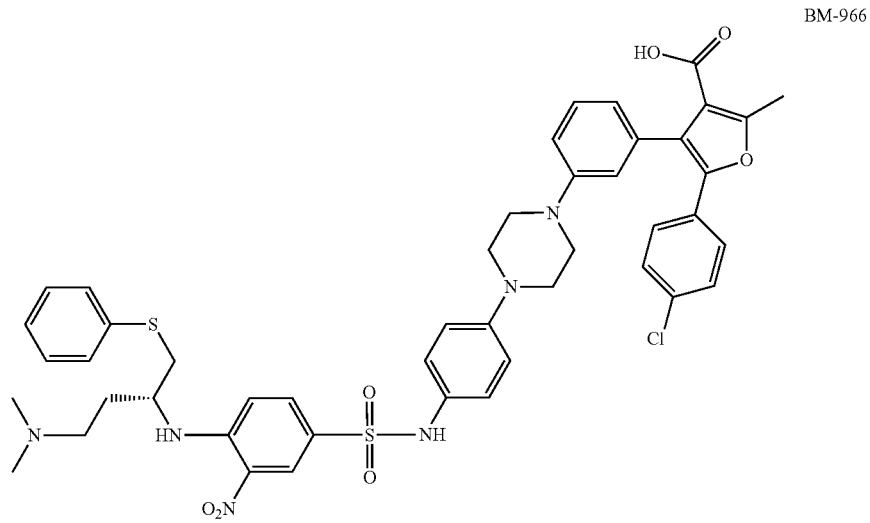
BM-966
¹H NMR (300 MHz, CD₃OD), δ 8.32 (d, J=2.2, 1H), 7.58 (dd, J=2.3, 9.2, 1H), 7.35~6.97 (m, 16H), 6.91~6.88 (m, 2H), 4.09~4.07 (m, 1H), 3.34~3.31 (m, 9H), 3.21~3.15 (m, 3H), 2.84 (s, 6H), 2.65 (s, 3H), 2.25~2.15 (m, 2H);
Compound 210
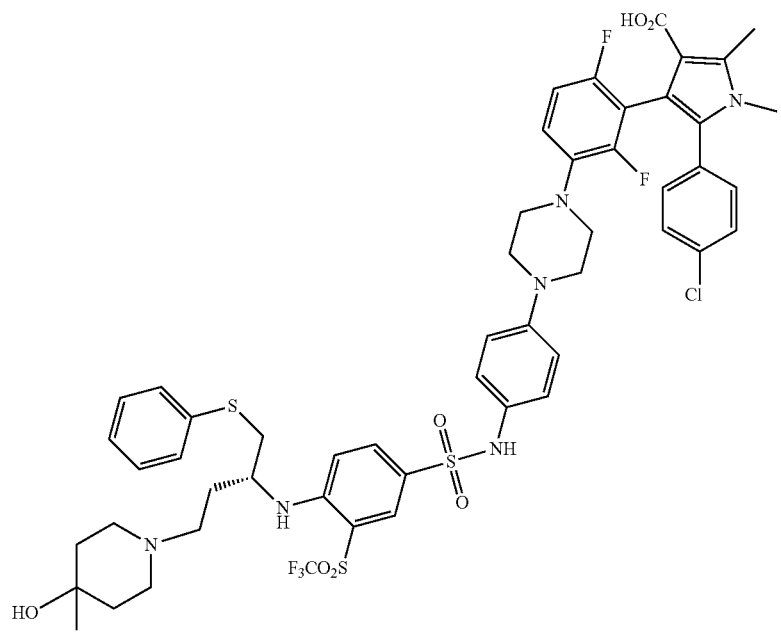
Chemical Formula: C₅₂H₅₄ClF₅N₆O₇S₃
Exact Mass: 1100.28
Molecular Weight: 1101.66
BM-1160
BM-1160: ¹H NMR (300 M Hz, CD₃OD): δ 7.94 (s, 1H), 7.66 (d, J=8.7 Hz, 1H), 7.40-7.13 (m, 9H), 7.00-6.69 (m, 7H), 3.97 (br, 1H), 3.48 (s, 3H), 3.19-2.88 (m, 16H), 2.62 (s, 3H), 2.31-2.10 (m, 2H), 1.79 (br, 4H), 1.27 (s, 3H).

Compound 211
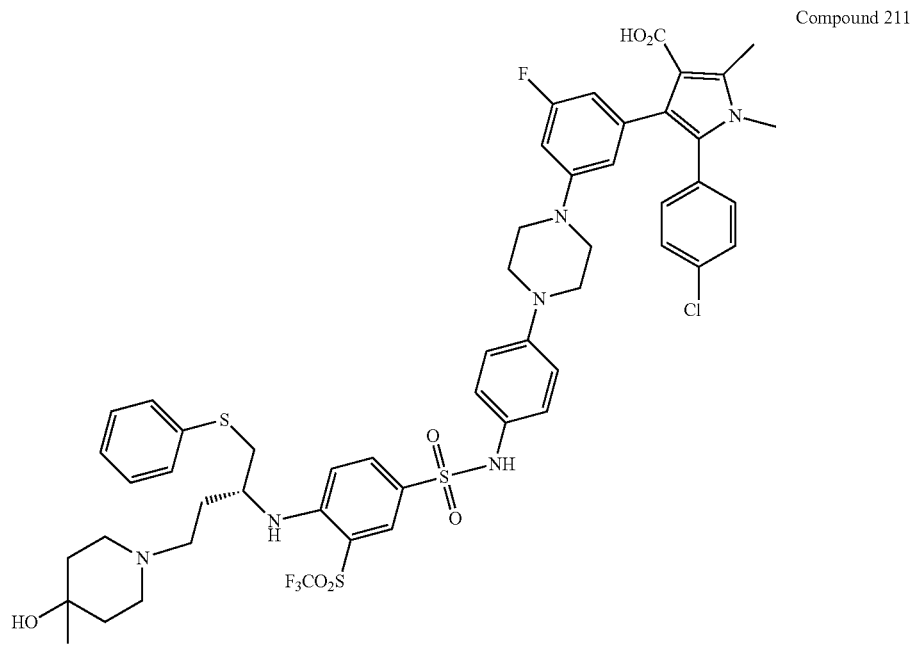
Chemical Formula: $C_{52}H_{55}ClF_4N_6O_7S_3$
Exact Mass: 1082.29
Molecular Weight: 1083.67
BM-1161
BM-1161: $^1$H NMR (300 M Hz, CD$_3$OD): δ 7.94 (s, 1H), 7.65 (d, J=7.8 Hz, 1H), 7.45-6.77 (m, 14H), 3.95 (br, 1H), 3.48 (s, 3H), 3.40-2.93 (m, 16H), 2.60 (s, 3H), 2.35-2.10 (m, 2H), 1.81 (br, 4H), 1.33 (s, 3H).
Compound 212
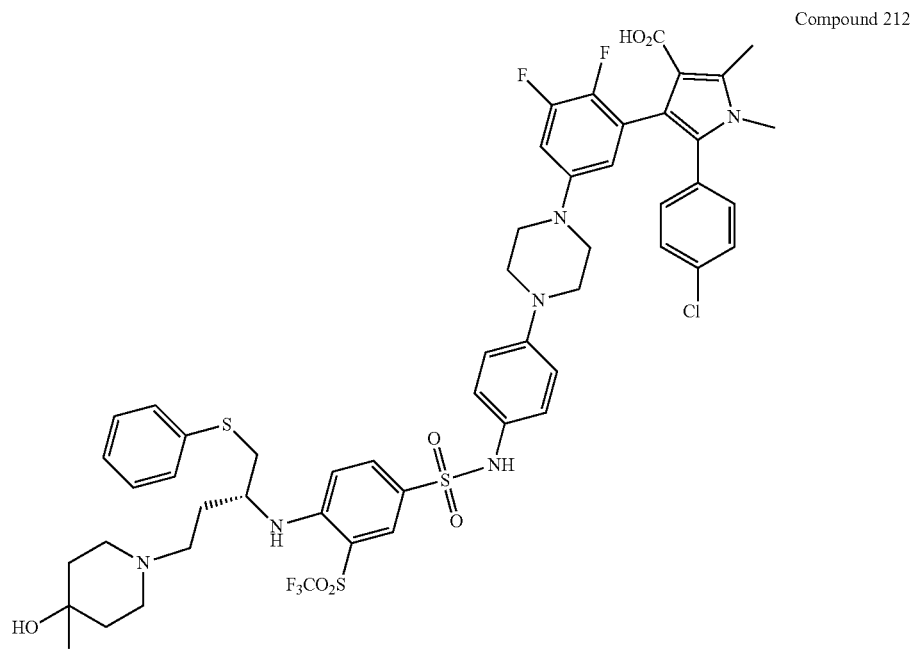
Chemical Formula: $C_{52}H_{54}ClF_5N_6O_7S_3$
Exact Mass: 1100.28
Molecular Weight: 1101.66
BM-1162

BM-1162: ¹H NMR (300 M Hz, CD₃OD): δ 7.94 (s, 1H), 7.67 (d, J=9.0 Hz, 1H), 7.33-6.67 (m, 15H), 6.31 (br, 1H), 3.97 (br, 1H), 3.45 (s, 3H), 3.15-2.88 (m, 16H), 2.63 (s, 3H), 2.62-2.06 (m, 2H), 1.79 (br, 4H), 1.28 (s, 3H).
Compound 213
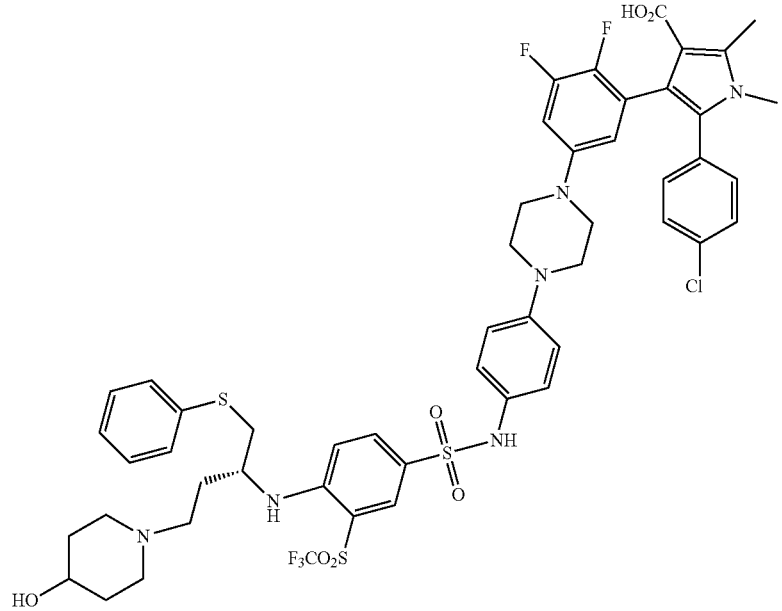
Chemical Formula: C₅₁H₅₂ClF₅N₆O₇S₃
Exact Mass: 1086.27
Molecular Weight: 1086.63
BM-1163
BM-1163: ¹H NMR (300 M Hz, CD₃OD): δ 7.94 (s, 1H), 7.68 (d, J=9.0 Hz, 1H), 7.33-6.67 (m, 15H), 6.30 (br, 1H), 4.08-3.79 (m, 2H), 3.53-3.42 (m, 1H), 3.46 (s, 3H), 3.20-2.88 (m, 16H), 2.63 (s, 3H), 2.31-2.10 (m, 3H), 1.81 (br, 2H), 1.69-1.65 (m, 1H).
Compound 214
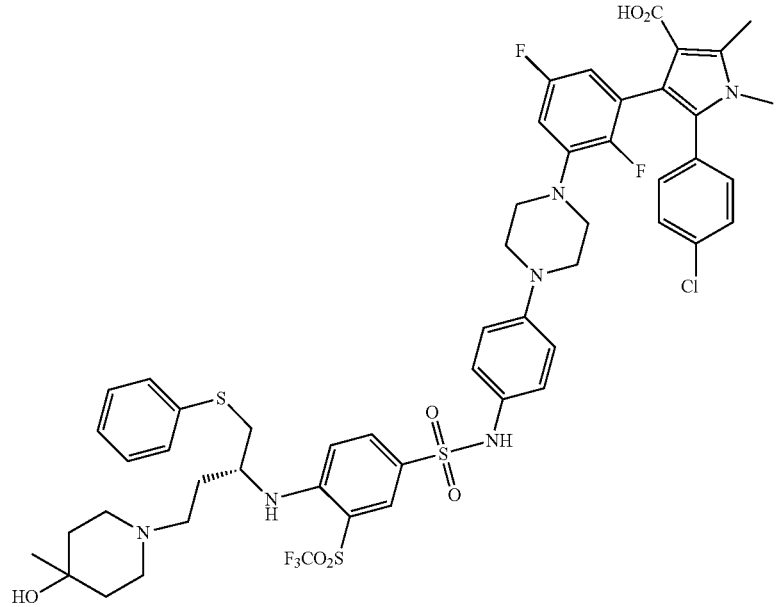
Chemical Formula: C₅₂H₅₄ClF₅N₆O₇S₃
Exact Mass: 1100.28
Molecular Weight: 1101.66
BM-1164

BM-1164: $^1$H NMR (300 MHz, CD$_3$OD): δ 7.95 (s, 1H), 7.68 (d, J=8.4 Hz, 1H), 7.34-6.60 (m, 15H), 6.34 (br, 1H), 3.98 (br, 1H), 3.46 (s, 3H), 3.23-3.09 (m, 16H), 2.63 (s, 3H), 2.30-2.10 (m, 2H), 1.80 (br, 4H), 1.28 (s, 3H).
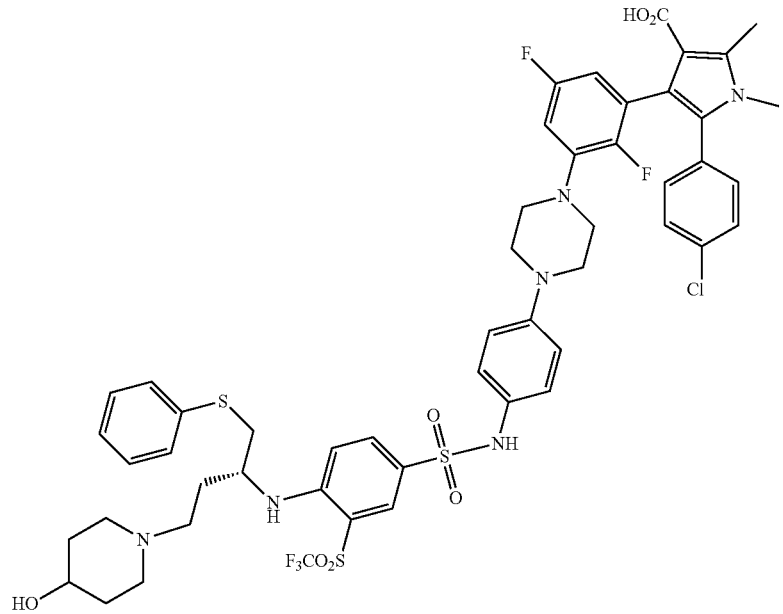
Compound 215
Chemical Formula: C$_{51}$H$_{52}$ClF$_5$N$_6$O$_7$S$_3$
Exact Mass: 1086.27
Molecular Weight: 1087.63
BM-1165
BM-1165: $^1$H NMR (300 MHz, CD$_3$OD): δ 7.94 (s, 1H), 7.67 (d, J=9.0 Hz, 1H), 7.34-6.63 (m, 15H), 6.35-6.32 (m, 1H), 4.08-3.80 (m, 2H), 3.53 (br, 1H), 3.46 (s, 3H), 3.23-2.88 (m, 16H), 2.63 (s, 3H), 2.30-2.10 (m, 3H), 1.91 (br, 2H), 1.69-1.65 (m, 1H).
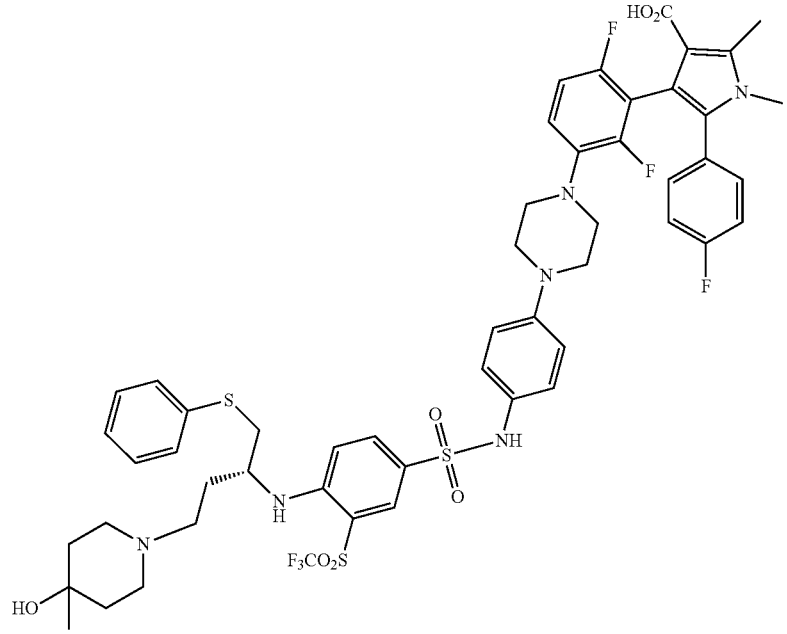
Compound 216
Chemical Formula: C$_{52}$H$_{54}$F$_6$N$_6$O$_7$S$_3$
Exact Mass: 1084.31
Molecular Weight: 1085.21
BM-1166

BM-1166: $^1$H NMR (300 M Hz, CD$_3$OD): δ 7.95 (s, 1H), 7.66 (d, J=9.6 Hz, 1H), 7.32-6.69 (m, 16H), 3.98 (br, 1H), 3.47 (s, 3H), 3.21-2.95 (m, 16H), 2.65 (s, 3H), 2.27-2.10 (m, 2H), 1.81 (br, 4H), 1.29 (s, 3H).
Compound 217
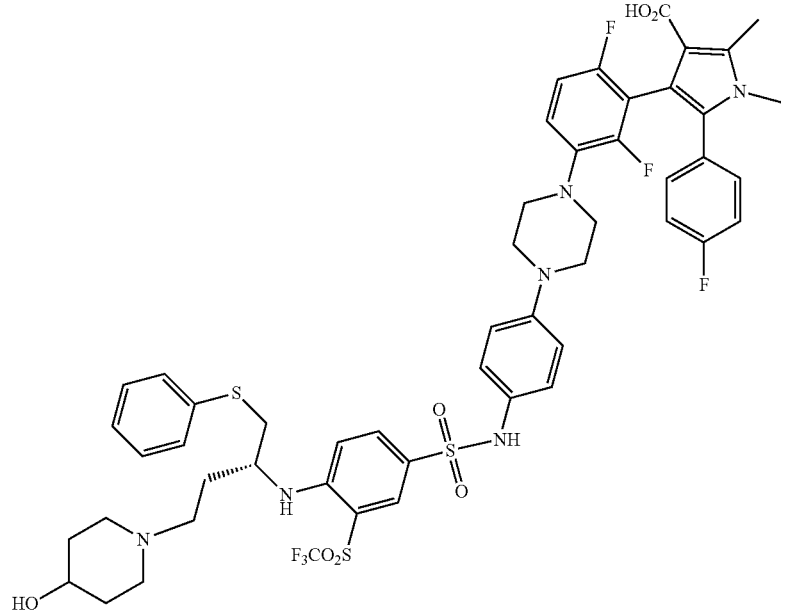
Chemical Formula: C$_{51}$H$_{52}$F$_6$N$_6$O$_7$S$_3$
Exact Mass: 1070.30
Molecular Weight: 1071.18
BM-1167
BM-1167: $^1$H NMR (300 M Hz, CD$_3$OD): δ 7.95 (s, 1H), 7.69 (d, J=9.0 Hz, 1H), 7.31-6.69 (m, 16H), 4.08-3.79 (m, 2H), 3.56 (br, 1H), 3.46 (s, 3H), 3.26-3.00 (m, 16H), 2.64 (s, 3H), 2.26-2.10 (m, 3H), 1.92 (br, 2H), 1.70-1.66 (m, 1H).
Compound 218
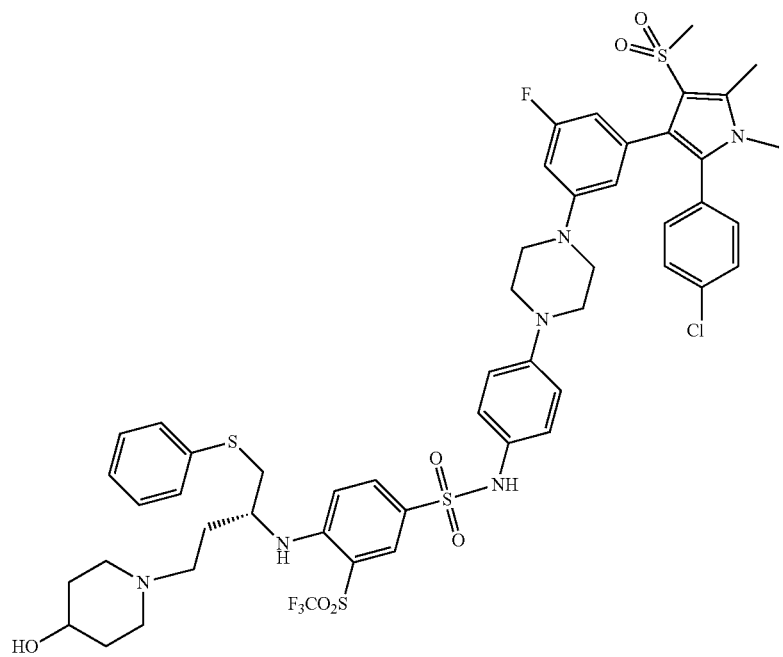
Chemical Formula: C$_{51}$H$_{55}$ClF$_4$N$_6$O$_7$S$_4$
Exact Mass: 1102.26
Molecular Weight: 1103.73
BM-1168

BM-1168: $^1$H NMR (300 M Hz, CD$_3$OD): δ 7.95 (d, J=2.1 Hz, 1H), 7.70 (dd, J=2.1, 9.0 Hz, 1H), 7.34-6.42 (m, 17H), 4.10-3.80 (m, 2H), 3.53 (bra, 1H), 3.46 (s, 3H), 3.34-2.88 (m, 16H), 2.82 (s, 3H), 2.63 (s, 3H), 2.25-2.04 (m, 3H), 1.91 (bra, 2H), 1.69-1.65 (m, 1H).

Compound 219

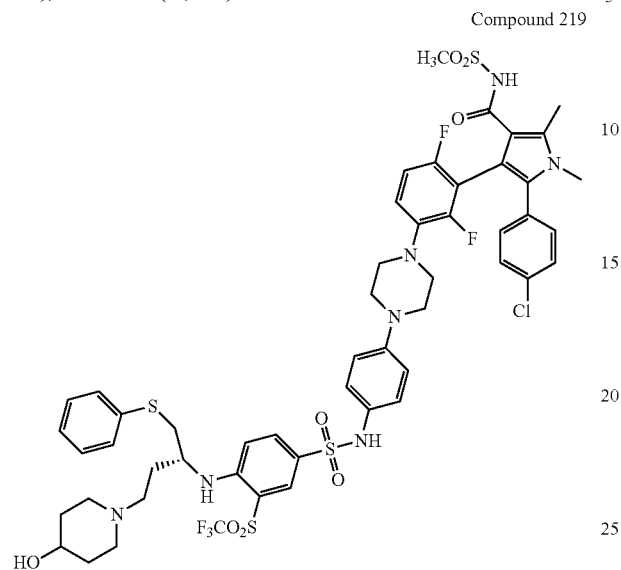

Chemical Formula: C$_{52}$H$_{55}$ClF$_5$N$_7$O$_8$S$_4$
Exact Mass: 1163.26
Molecular Weight: 1164.74
BM-1169

BM-1169: $^1$H NMR (300 M Hz, CD$_3$OD): δ 7.95 (s, 1H), 7.67 (d, J=9.0 Hz, 1H), 7.34-6.76 (m, 16H), 4.08-3.80 (m, 2H), 3.53-3.42 (m, 1H), 3.50 (s, 3H), 3.24-2.98 (m, 16H), 2.59 (s, 3H), 2.26-2.10 (m, 3H), 1.92 (br, 2H), 1.69-1.64 (m, 1H).

Compound 220

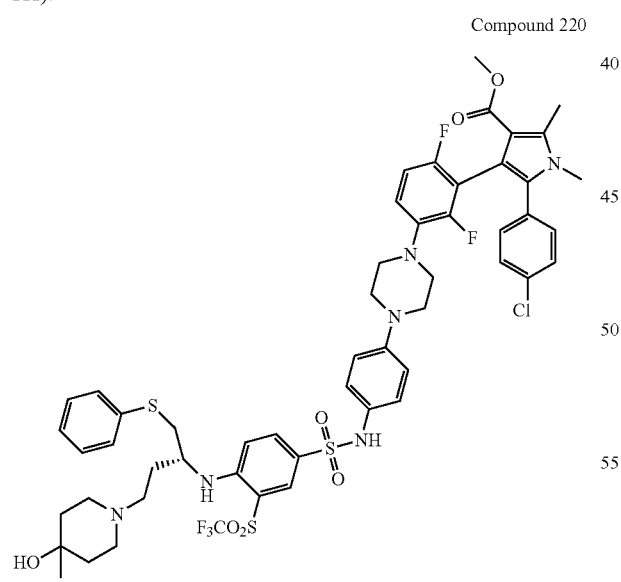

Chemical Formula: C$_{53}$H$_{56}$ClF$_5$N$_6$O$_7$S$_3$
Exact Mass: 1114.30
Molecular Weight: 1115.69
BM-1170

BM-1170: $^1$H NMR (300 M Hz, CD$_3$OD): δ 7.95 (s, 1H), 7.70 (d, J=7.8 Hz, 1H), 7.32-6.73 (m, 16H), 3.98 (br, 1H), 3.56 (s, 3H), 3.49 (s, 3H), 3.28-2.99 (m, 16H), 2.64 (s, 3H), 2.30-2.07 (m, 2H), 1.81 (br, 4H), 1.29 (s, 3H).

Compound 221

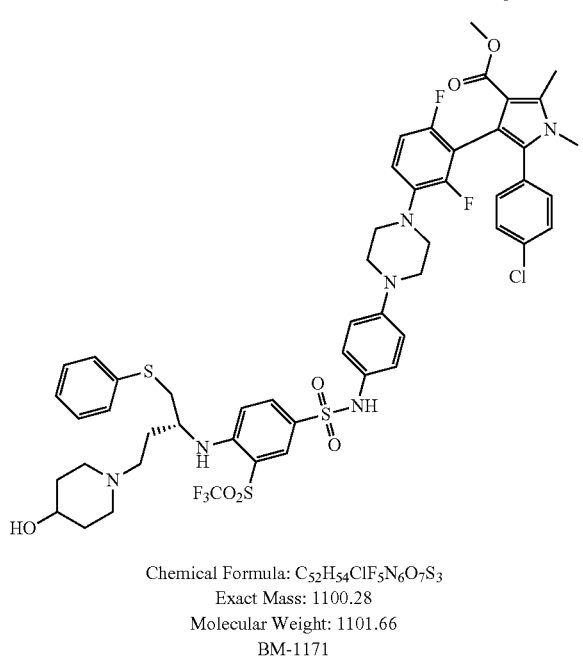

Chemical Formula: C$_{52}$H$_{54}$ClF$_5$N$_6$O$_7$S$_3$
Exact Mass: 1100.28
Molecular Weight: 1101.66
BM-1171

BM-1171: $^1$H NMR (300 M Hz, CD$_3$OD): δ 7.95 (s, 1H), 7.68 (d, J=9.0 Hz, 1H), 7.31-6.72 (m, 16H), 4.18-3.79 (m, 2H), 3.58-3.42 (m, 1H), 3.56 (s, 3H), 3.49 (s, 3H), 3.24-2.98 (m, 16H), 2.59 (s, 3H), 2.26-2.10 (m, 3H), 1.92 (br, 2H), 1.69-1.64 (m, 1H).

Compound 222

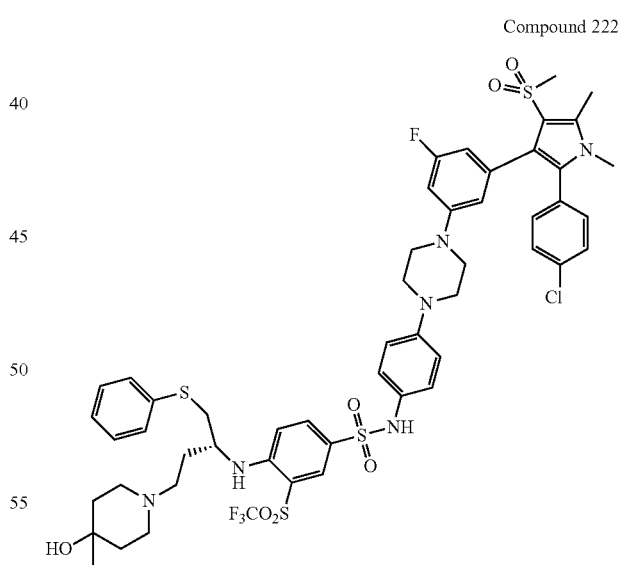

Chemical Formula: C$_{52}$H$_{57}$ClF$_4$N$_6$O$_7$S$_4$
Exact Mass: 1116.28
Molecular Weight: 1117.75
BM-1172

BM-1172: $^1$H NMR (300 M Hz, CD$_3$OD): δ 7.94 (s, 1H), 7.67 (d, J=8.1 Hz, 1H), 7.34-6.34 (m, 17H), 3.97 (br, 1H), 3.46 (s, 3H), 3.21-2.95 (m, 16H), 2.82 (s, 3H), 2.64 (s, 3H), 2.30-2.10 (m, 2H), 1.81 (br, 4H), 1.29 (s, 3H).

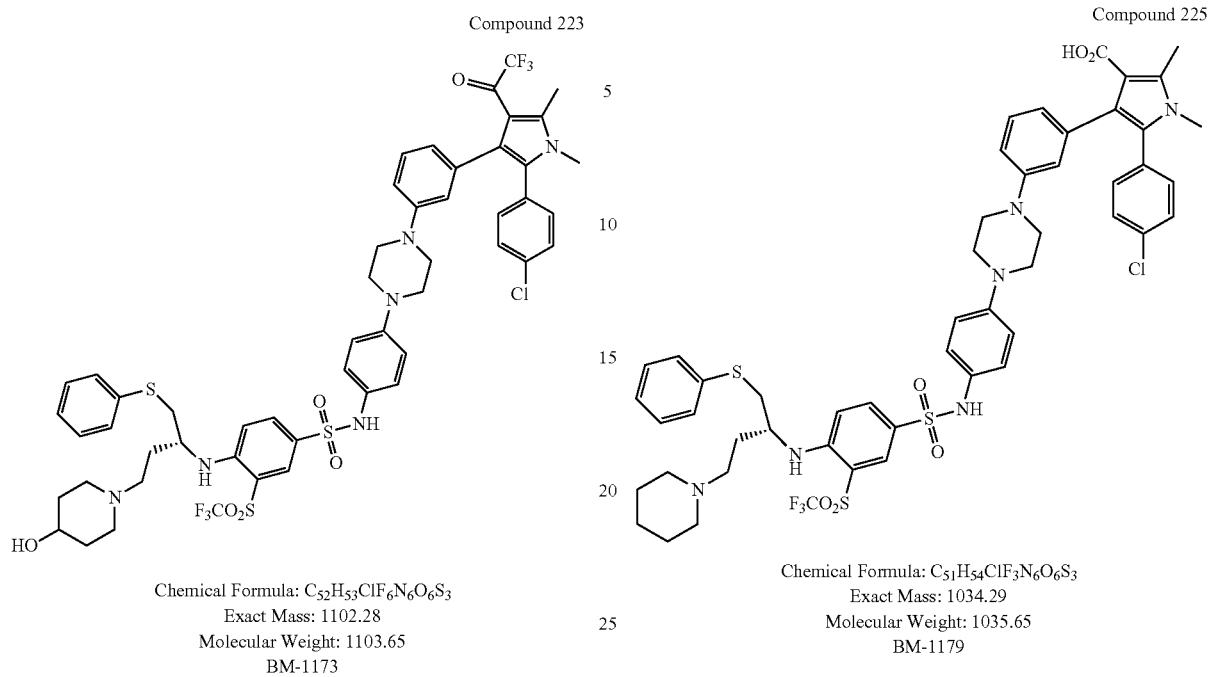
BM-1173: ¹H NMR (300 M Hz, CD$_3$OD): δ 7.94 (s, 1H), 7.70 (d, J=9.0 Hz, 1H), 7.33-6.69 (m, 18H), 4.07-3.79 (m, 2H), 3.53-3.42 (m, 1H), 3.47 (s, 3H), 3.26-2.94 (m, 16H), 2.54 (s, 3H), 2.26-2.10 (m, 3H), 1.92 (br, 2H), 1.73-1.65 (m, 1H).
BM-1179: ¹H NMR (300 M Hz, CD$_3$OD): δ 7.93 (s, 1H), 7.69 (d, J=9.0 Hz, 1H), 7.41-6.73 (m, 18H), 3.97 (bra, 1H), 3.57-2.88 (m, 16H), 3.44 (s, 3H), 2.61 (s, 3H), 2.29-1.46 (m, 8H).
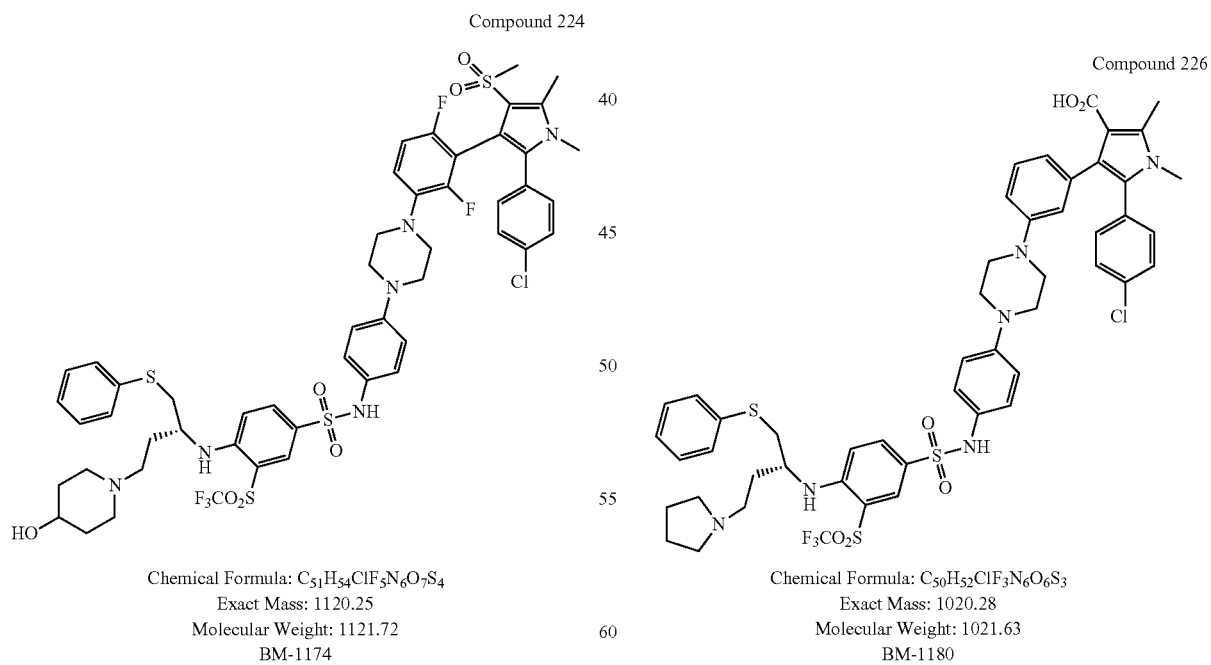
BM-1174: ¹H NMR (300 M Hz, CD$_3$OD): δ 7.94 (d, J=2.1 Hz, 1H), 7.72 (dd, J=2.1, 9.0 Hz, 1H), 7.32-6.77 (m, 16H), 4.06-3.78 (m, 2H), 3.58-3.42 (m, 1H), 3.49 (s, 3H), 3.37-3.02 (m, 16H), 2.97 (s, 3H), 2.62 (s, 3H), 2.25-1.60 (m, 6H).
BM-1180: ¹H NMR (300 M Hz, CD$_3$OD): δ 7.93 (s, 1H), 7.70 (d, J=9.6 Hz, 1H), 7.41-6.74 (m, 18H), 3.99 (bra, 1H), 3.60 (bra, 2H), 3.44 (s, 3H), 3.37-3.01 (m, 14H), 2.61 (s, 3H), 2.29-2.02 (m, 6H).

Compound 227

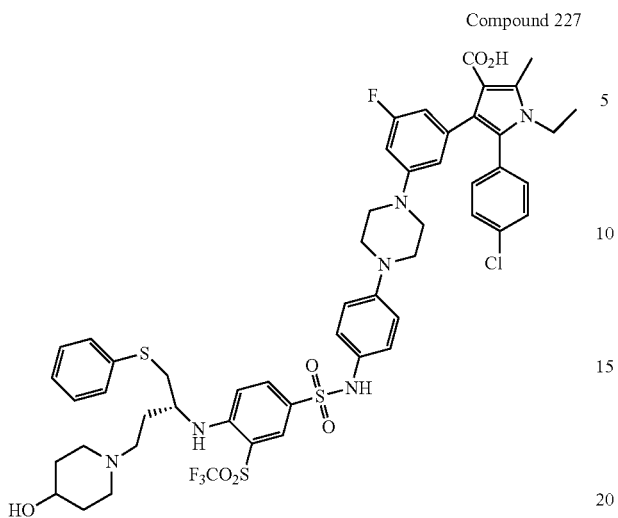

Chemical Formula: C₅₂H₅₅ClF₄N₆O₇S₃
Exact Mass: 1082.29
Molecular Weight: 1083.67
BM-1181

BM-1181: $^1$H NMR (300 M Hz, CD$_3$OD): δ 7.95 (s, 1H), 7.68 (d, J=9.0 Hz, 1H), 7.46-6.78 (m, 14H), 6.51-6.37 (m, 3H), 4.07-3.79 (m, 4H), 3.54 (bra, 1H), 3.17-2.94 (m, 16H), 2.62 (s, 3H), 2.31-1.64 (m, 6H), 1.15 (tri, J=6.9 Hz, 3H).

Compound 229

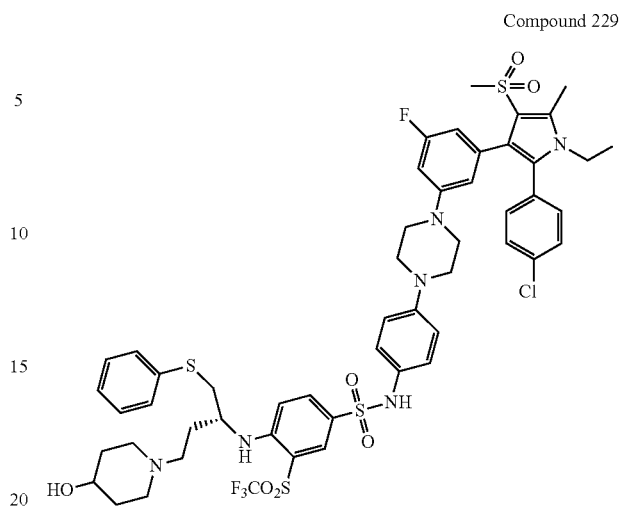

Chemical Formula : C₅₂H₅₇ClF₄N₆O₇S₄
Exact Mass: 1116.28
Molecular Weight: 1117.75
BM-1186

BM-1186: $^1$H NMR (300 M Hz, CD$_3$OD): δ 7.92 (d, J=1.8 Hz, 1H), 7.71 (dd, J=1.8, 9.0 Hz, 1H), 7.31-7.07 (m, 13H), 6.82-6.43 (m, 4H), 4.05-3.76 (m, 4H), 3.50 (bra, 1H), 3.28-2.91 (m, 16H), 2.81 (s, 3H), 2.63 (s, 3H), 2.22-1.63 (m, 6H), 1.14 (tri, J=6.9 Hz, 3H).

Compound 228

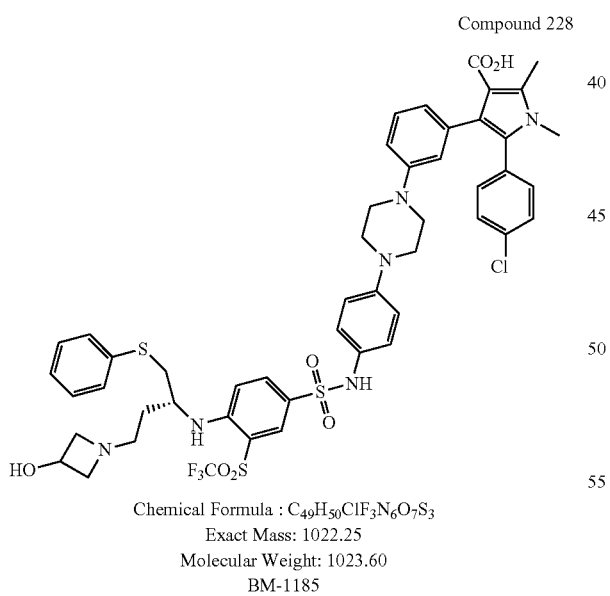

Chemical Formula : C₄₉H₅₀ClF₃N₆O₇S₃
Exact Mass: 1022.25
Molecular Weight: 1023.60
BM-1185

BM-1185: $^1$H NMR (300 M Hz, CD$_3$OD): δ 7.92 (s, 1H), 7.70 (d, J=9.0 Hz, 1H), 7.41-6.75 (m, 18H), 4.64-4.59 (m, 1H), 4.44 (bra, 1H), 4.14-3.79 (m, 4H), 3.44 (s, 3H), 3.36-3.10 (m, 12H), 2.62 (s, 3H), 2.03-1.92 (m, 2H).

Compound 230

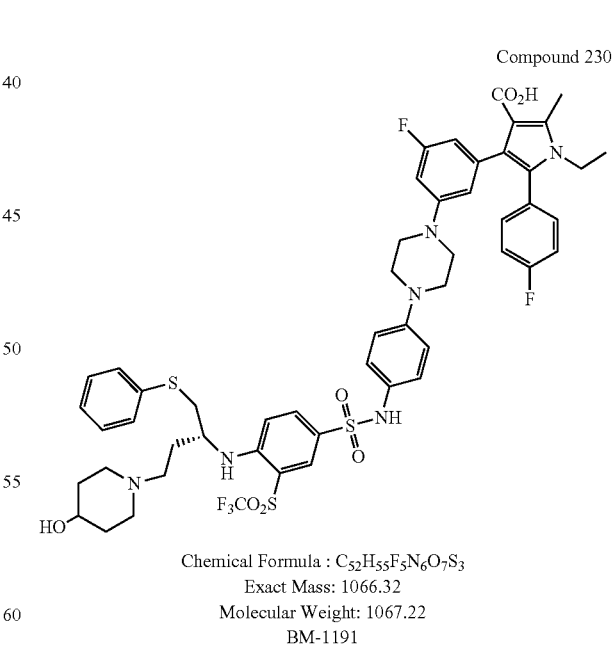

Chemical Formula : C₅₂H₅₅F₅N₆O₇S₃
Exact Mass: 1066.32
Molecular Weight: 1067.22
BM-1191

BM-1191: $^1$H NMR (300 M Hz, CD$_3$OD): δ 7.94 (s, 1H), 7.71 (d, J=9.0 Hz, 1H), 7.30-6.79 (m, 14H), 6.50-6.35 (m, 3H), 4.07-3.76 (m, 4H), 3.53 (bra, 1H), 3.35-2.93 (m, 16H), 2.62 (s, 3H), 2.25-1.66 (m, 6H), 1.12 (tri, J=6.9 Hz, 3H).

Compound 231

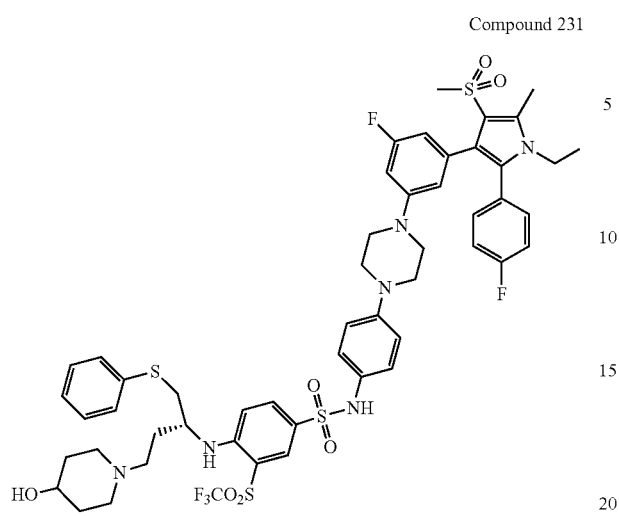

Chemical Formula : C₅₂H₅₇F₅N₆O₇S₄
Exact Mass: 1100.31
Molecular Weight: 1101.30
BM-1192

BM-1192: $^1$H NMR (300 M Hz, CD$_3$OD): δ 8.00 (s, 1H), 7.81 (d, J=9.0 Hz, 1H), 7.40-6.53 (m, 17H), 4.17-3.96 (m, 4H), 3.63 (bra, 1H), 3.42-3.03 (m, 16H), 2.93 (s, 3H), 2.74 (s, 3H), 2.36-1.78 (m, 6H), 1.23 (tri, J=6.9 Hz, 3H).

Compound 232

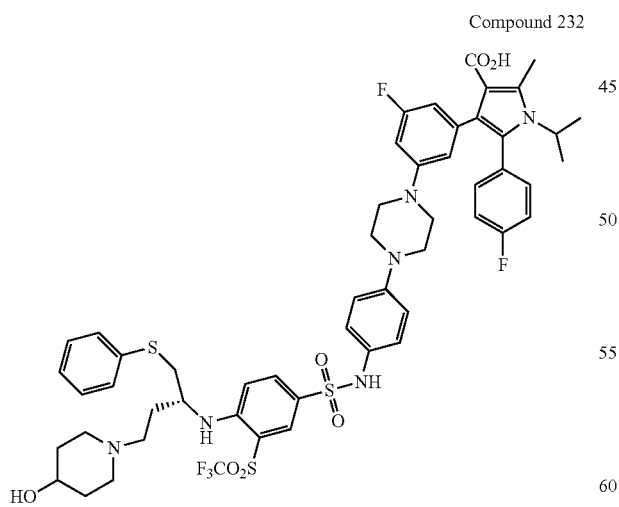

Chemical Formula : C₅₃H₅₇F₅N₆O₇S₃
Exact Mass: 1080.34
Molecular Weight: 1081.24
BM-1193

BM-1193: $^1$H NMR (300 M Hz, CD$_3$OD): δ 7.94 (s, 1H), 7.69 (d, J=9.0 Hz, 1H), 7.41-6.79 (m, 14H), 6.49-6.32 (m, 3H), 4.45-4.35 (m, 1H), 4.08-3.79 (m, 2H), 3.52 (bra, 1H), 3.35-2.93 (m, 16H), 2.70 (s, 3H), 2.25-1.66 (m, 6H), 1.43 (s, 3H), 1.41 (s, 3H).

Compound 233

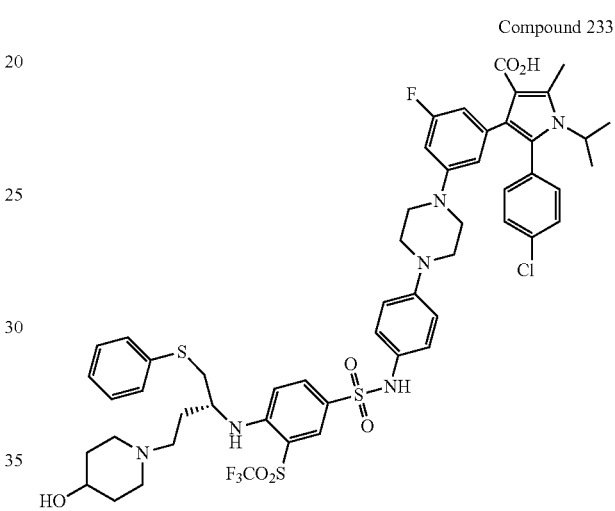

Chemical Formula : C₅₃H₅₇ClF₄N₆O₇S₃
Exact Mass: 1096.31
Molecular Weight: 1097.70
BM-1194

BM-1194: $^1$H NMR (300 M Hz, CD$_3$OD): δ 7.94 (s, 1H), 7.68 (d, J=9.0 Hz, 1H), 7.32-6.78 (m, 14H), 6.48-6.32 (m, 3H), 4.46-4.37 (m, 1H), 4.08-3.79 (m, 2H), 3.54 (bra, 1H), 3.35-2.94 (m, 16H), 2.70 (s, 3H), 2.26-1.65 (m, 6H), 1.44 (s, 3H), 1.42 (s, 3H).

Compound 234
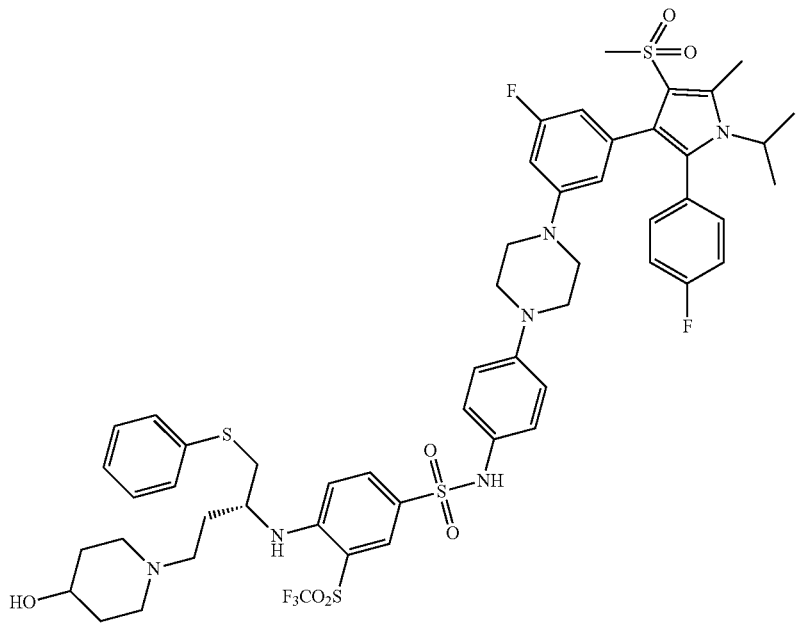
Chemical Formula: C$_{53}$H$_{59}$F$_5$N$_6$O$_7$S$_4$
Exact Mass: 1114.32
Molecular Weight: 1115.32
BM-1195
BM-1195: $^1$H NMR (300 M Hz, CD$_3$OD): δ 7.94 (s, 1H), 7.68 (d, J=9.0 Hz, 1H), 7.30-6.38 (m, 17H), 4.51-4.42 (m, 1H), 4.08-3.79 (m, 2H), 3.53 (bra, 1H), 3.35-2.94 (m, 16H), 2.83 (s, 3H), 2.74 (s, 3H), 2.26-1.65 (m, 6H), 1.44 (s, 3H), 1.42 (s, 3H).
Compound 235
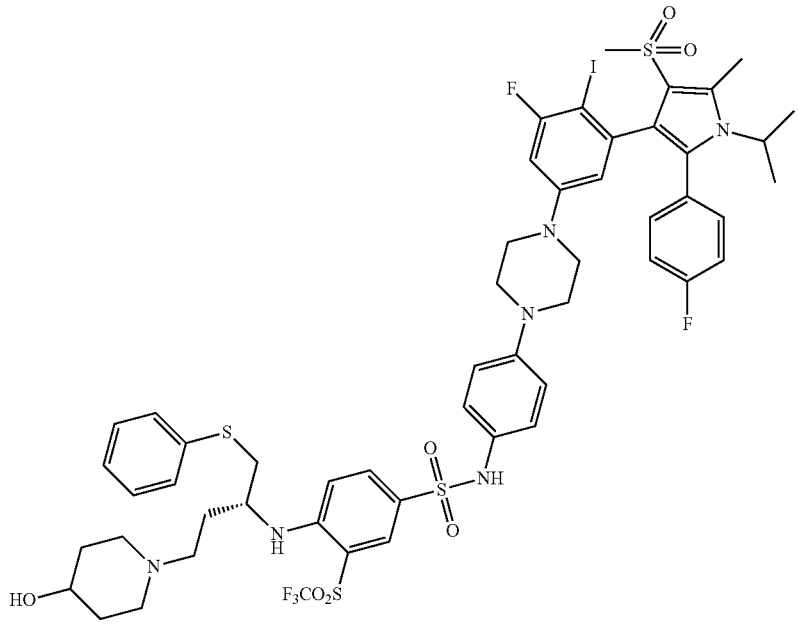
Chemical Formula: C$_{53}$H$_{58}$F$_5$IN$_6$O$_7$S$_4$
Exact Mass: 1240.22
Molecular Weight: 1241.22
BM-1196

BM-1196: ¹H NMR (300 M Hz, CD₃OD): δ 7.94 (s, 1H), 7.67 (d, J=9.0 Hz, 1H), 7.30-6.57 (m, 16H), 4.52-4.42 (m, 1H), 4.08-3.79 (m, 2H), 3.53 (bra, 1H), 3.35-2.94 (m, 16H), 2.94 (s, 3H), 2.73 (s, 3H), 2.26-1.65 (m, 6H), 1.44 (s, 3H), 1.42 (s, 3H).
Compound 236
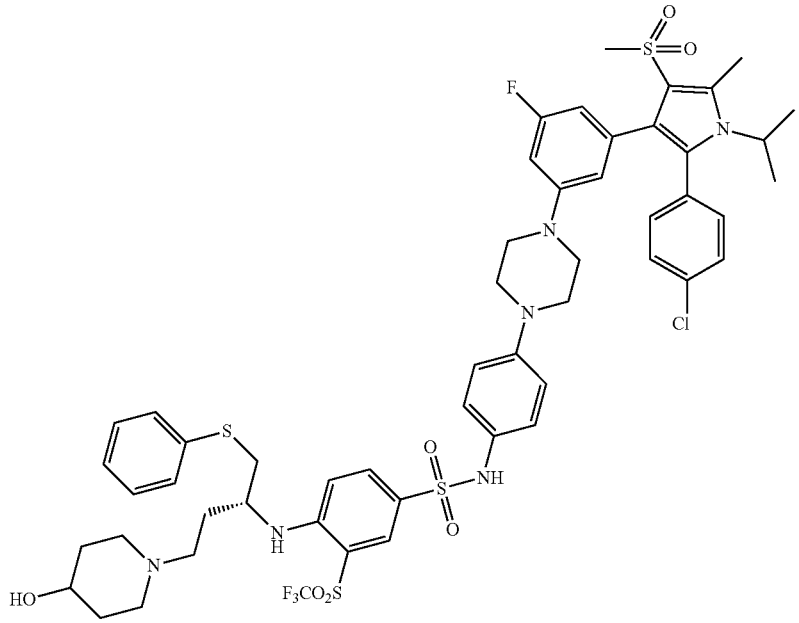
Chemical Formula: C₅₃H₅₉ClF₄N₆O₇S₄
Exact Mass: 1130.30
Molecular Weight: 1131.78
BM-1197
BM-1197: ¹H NMR (300 M Hz, CD₃OD): δ 7.94 (s, 1H), 7.68 (d, J=9.0 Hz, 1H), 7.33-6.39 (m, 17H), 4.51-4.42 (m, 1H), 4.08-3.79 (m, 2H), 3.53 (bra, 1H), 3.19-2.94 (m, 16H), 2.84 (s, 3H), 2.74 (s, 3H), 2.26-1.65 (m, 6H), 1.45 (s, 3H), 1.42 (s, 3H).
Compound 237
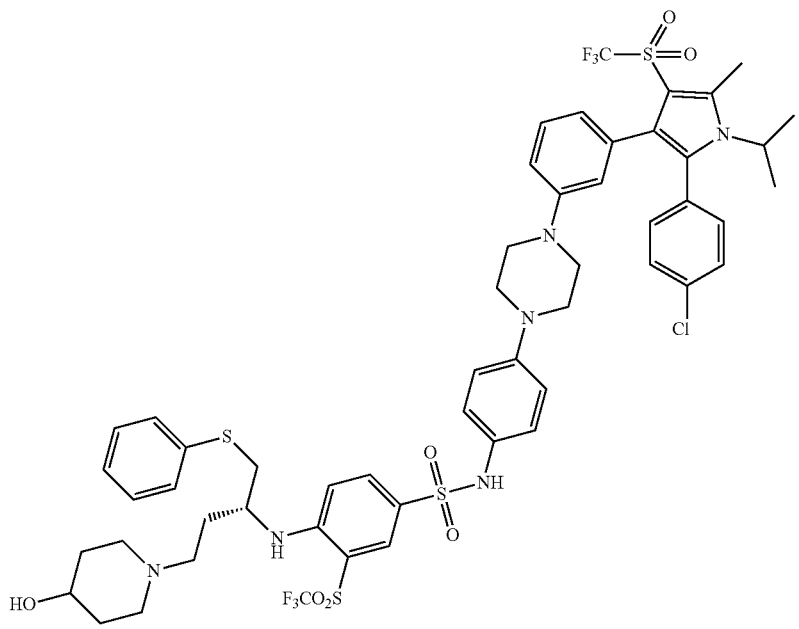
Chemical Formula: C₅₂H₅₅ClF₆N₆O₇S₄
Exact Mass: 1152.26
Molecular Weight: 1153.73
BM-1198

BM-1198: ¹H NMR (300 M Hz, CD₃OD): δ 7.95 (s, 1H), 7.71 (d, J=9.0 Hz, 1H), 7.34-6.79 (m, 18H), 4.08-3.96 (m, 4H), 3.54 (bra, 1H), 3.35-2.94 (m, 16H), 2.68 (s, 3H), 2.26-1.65 (m, 6H), 1.17 (tri, J=6.9 Hz, 3H).
Compound 238
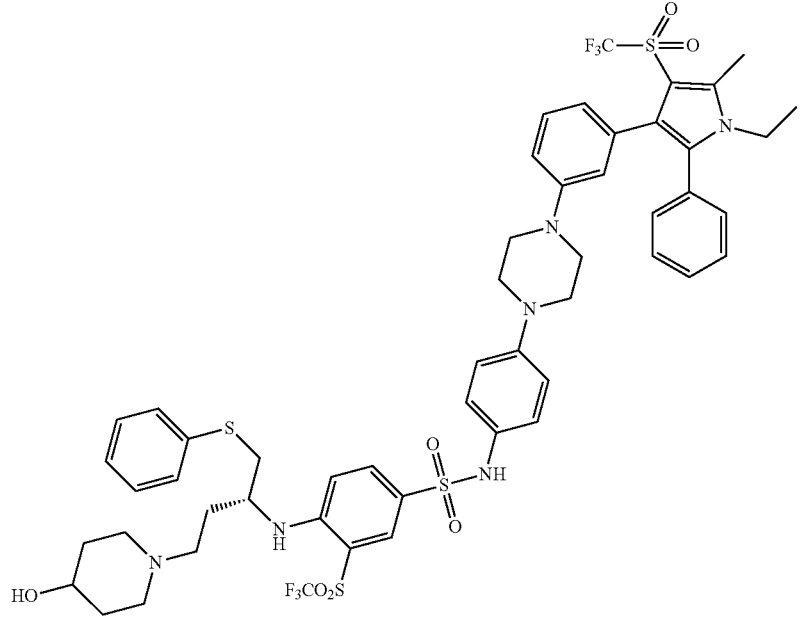
Chemical Formula: C₅₂H₅₆F₆N₆O₇S₄
Exact Mass: 1118.30
Molecular Weight: 1119.29
BM-1199
BM-1199: ¹H NMR (300 M Hz, CD₃OD): δ 7.94 (s, 1H), 7.70 (d, J=9.0 Hz, 1H), 7.31-6.79 (m, 19H), 4.08-3.96 (m, 4H), 3.54 (bra, 1H), 3.35-2.94 (m, 16H), 2.68 (s, 3H), 2.26-1.65 (m, 6H), 1.16 (tri, J=6.9 Hz, 3H).
Compound 239
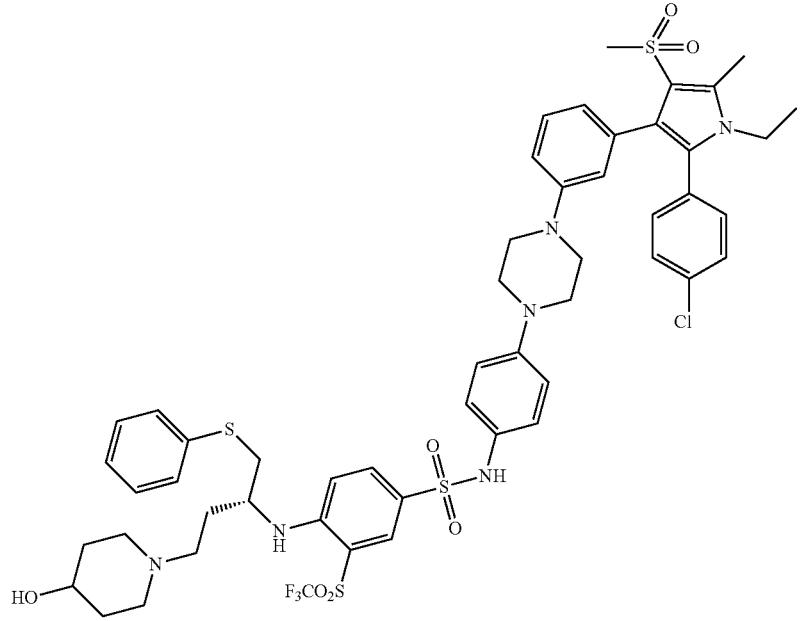
Chemical Formula: C₅₂H₅₈ClF₃N₆O₇S₄
Exact Mass: 1098.29
Molecular Weight: 1099.76
BM-1200

BM-1200: $^1$H NMR (300 M Hz, CD$_3$OD): δ 7.92 (s, 1H), 7.69 (d, J=9.0 Hz, 1H), 7.29-6.80 (m, 18H), 4.06-3.74 (m, 4H), 3.52 (bra, 1H), 3.30-2.92 (m, 16H), 2.78 (s, 3H), 2.64 (s, 3H), 2.25-1.66 (m, 6H), 1.13 (tri, J=6.9 Hz, 3H).
Compound 240
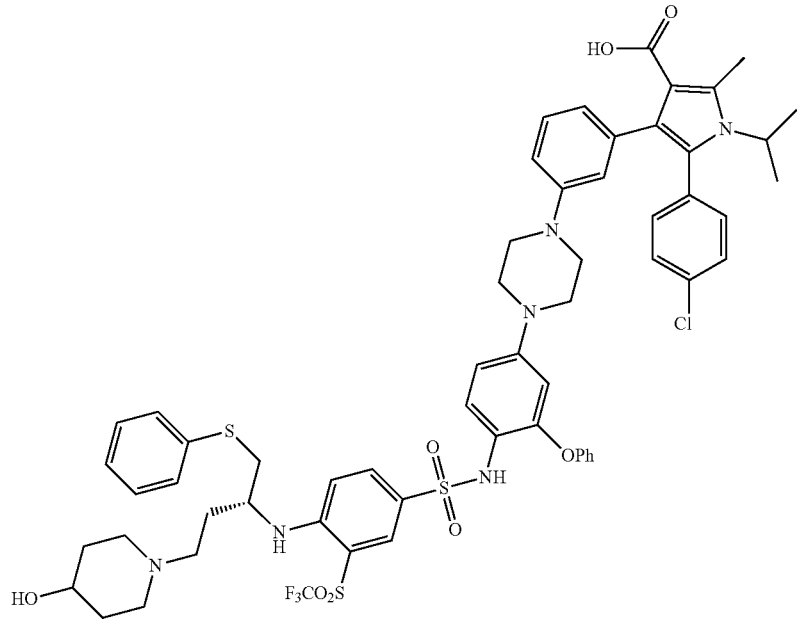
Chemical Formula: C$_{59}$H$_{62}$ClF$_3$N$_6$O$_8$S$_3$
Exact Mass: 1170.34
Molecular Weight: 1171.80
BM-1202
BM-1202: $^1$H NMR (300 M Hz, CD$_3$OD): δ 7.91 (s, 1H), 7.68 (d, J=9.0 Hz, 1H), 7.46-6.60 (m, 22H), 6.25 (s, 1H), 4.43-4.39 (m, 1H), 4.08-3.90 (m, 2H), 3.54 (bra, 1H), 3.35-2.88 (m, 16H), 2.70 (s, 3H), 2.30-1.65 (m, 6H), 1.44 (s, 3H), 1.42 (s, 3H).
Compound 241
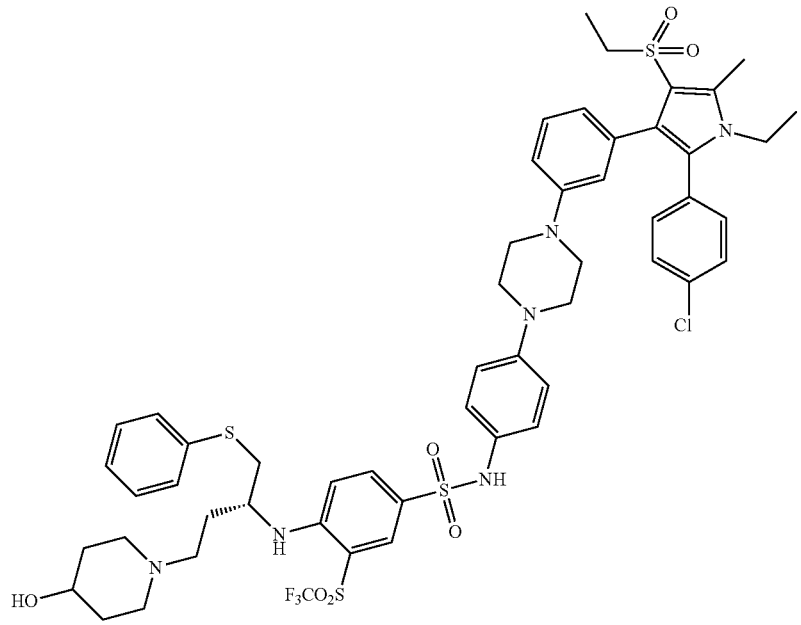
Chemical Formula: C$_{53}$H$_{60}$ClF$_3$N$_6$O$_7$S$_4$
Exact Mass: 1112.30
Molecular Weight: 1113.79
BM-1205

BM-1205: ¹H NMR (300 M Hz, CD₃OD): δ 8.02 (s, 1H), 7.88 (d, J=9.0 Hz, 1H), 7.42-6.96 (m, 18H), 4.17-3.90 (m, 4H), 3.63-2.89 (m, 18H), 2.74 (s, 3H), 2.36-1.80 (m, 6H), 1.26-1.90 (m, 6H).
Compound 242
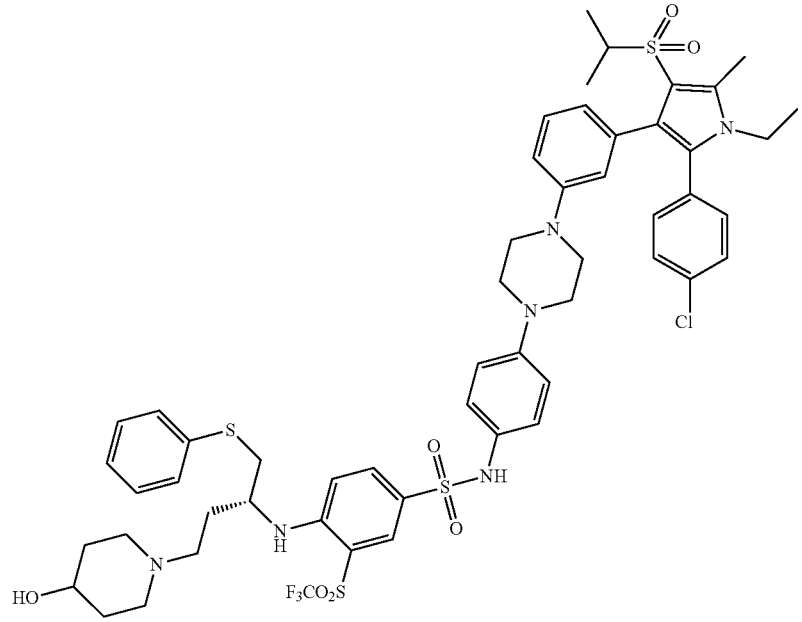
Chemical Formula: C₅₄H₆₂ClF₃N₆O₇S₄
Exact Mass: 1126.32
Molecular Weight: 1127.81
BM-1206
BM-1206: ¹H NMR (300 M Hz, CD₃OD): δ 7.94 (s, 1H), 7.68 (d, J=9.0 Hz, 1H), 7.31-6.74 (m, 18H), 4.08-3.79 (m, 4H), 3.54 (bra, 1H), 3.27-2.73 (m, 17H), 2.65 (s, 3H), 2.26-1.65 (m, 6H), 1.16-1.09 (m, 9H).
Compound 243
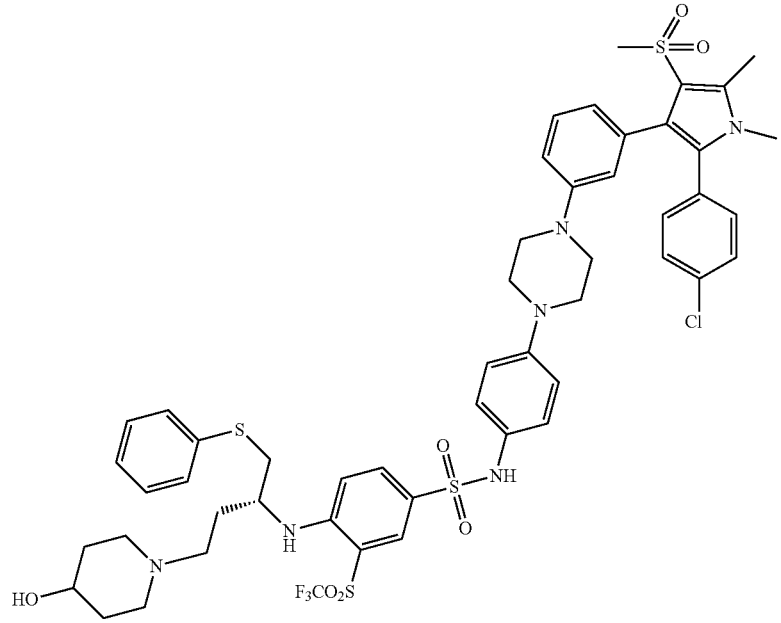
Chemical Formula: C₅₁H₅₆ClF₃N₆O₇S₄
Exact Mass: 1084.27
Molecular Weight: 1085.73
BM-1207

BM-1207: $^1$H NMR (300 M Hz, CD$_3$OD): δ 7.93 (s, 1H), 7.70 (d, J=9.0 Hz, 1H), 7.31-6.80 (m, 18H), 4.08-3.79 (m, 2H), 3.53 (bra, 1H), 3.47 (s, 3H), 3.20-2.94 (m, 16H), 2.78 (s, 3H), 2.64 (s, 3H), 2.25-1.65 (m, 6H).
Compound 244
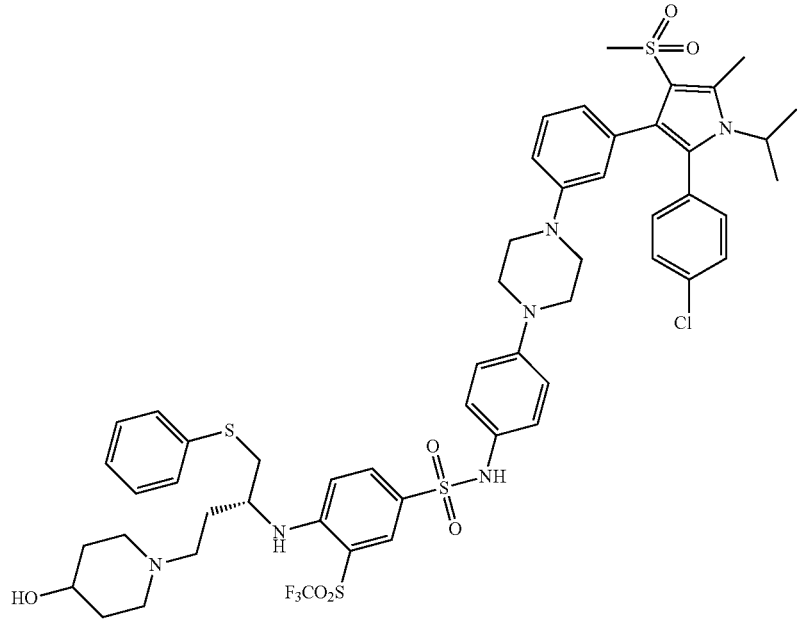
Chemical Formula: C$_{53}$H$_{60}$ClF$_3$N$_6$O$_7$S$_4$
Exact Mass: 1112.30
Molecular Weight: 1113.79
BM-1208
BM-1208: $^1$H NMR (300 M Hz, CD$_3$OD): δ 7.93 (s, 1H), 7.70 (d, J=9.0 Hz, 1H), 7.30-6.79 (m, 18H), 4.52-4.43 (m, 1H), 4.08-3.79 (m, 2H), 3.53 (bra, 1H), 3.20-2.94 (m, 16H), 2.80 (s, 3H), 2.75 (s, 3H), 2.26-1.65 (m, 6H), 1.45 (s, 3H), 1.43 (s, 3H).
Compound 245
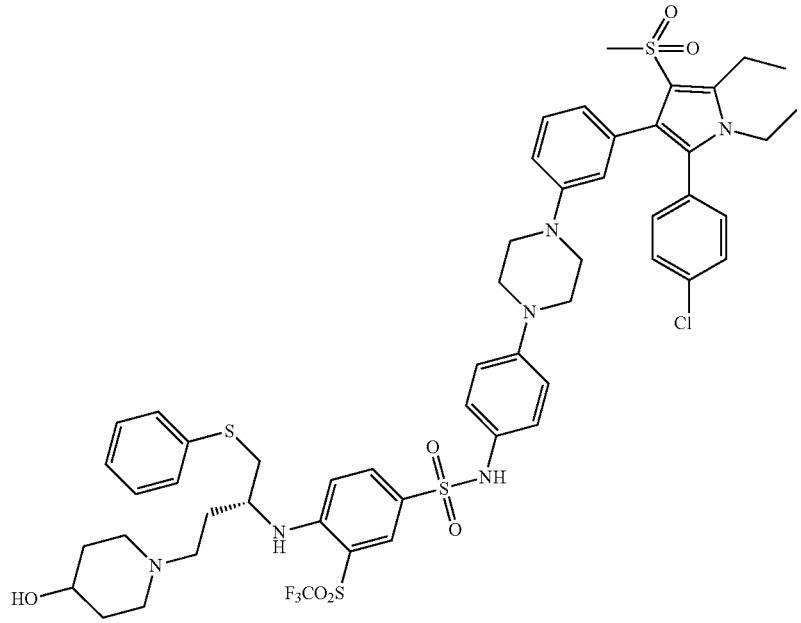
Chemical Formula: C$_{53}$H$_{60}$ClF$_3$N$_6$O$_7$S$_4$
Exact Mass: 1112.30
Molecular Weight: 1113.79
BM-1209

BM-1209: $^1$H NMR (300 M Hz, CD$_3$OD): δ 7.93 (s, 1H), 7.68 (bra, 1H), 7.28-6.80 (m, 18H), 4.06-3.79 (m, 4H), 3.52 (bra, 1H), 3.35-2.92 (m, 18H), 2.75 (s, 3H), 2.25-1.66 (m, 6H), 1.30 (bra, 3H), 1.09 (bra, 3H).
Compound 246
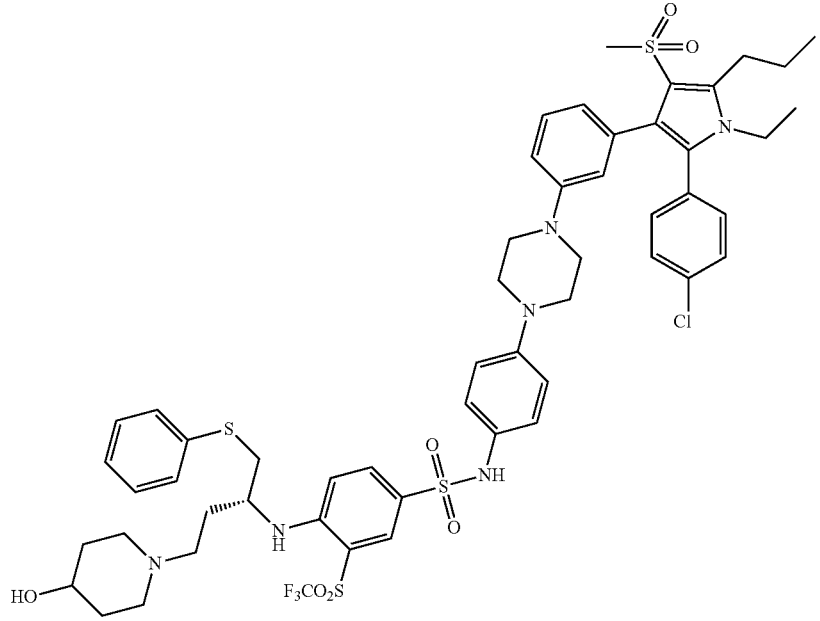
Chemical Formula: C$_{54}$H$_{62}$ClF$_3$N$_6$O$_7$S$_4$
Exact Mass: 1126.32
Molecular Weight: 1127.81
BM-1210
BM-1210: $^1$H NMR (300 M Hz, CD$_3$OD): δ 7.95 (s, 1H), 7.68 (d, J=9.0 Hz, 1H), 7.33-6.80 (m, 18H), 4.06-3.79 (m, 4H), 3.52 (bra, 1H), 3.25-2.94 (m, 18H), 2.66 (s, 3H), 2.25-1.66 (m, 8H), 1.14-1.06 (m, 6H).
Compound 247
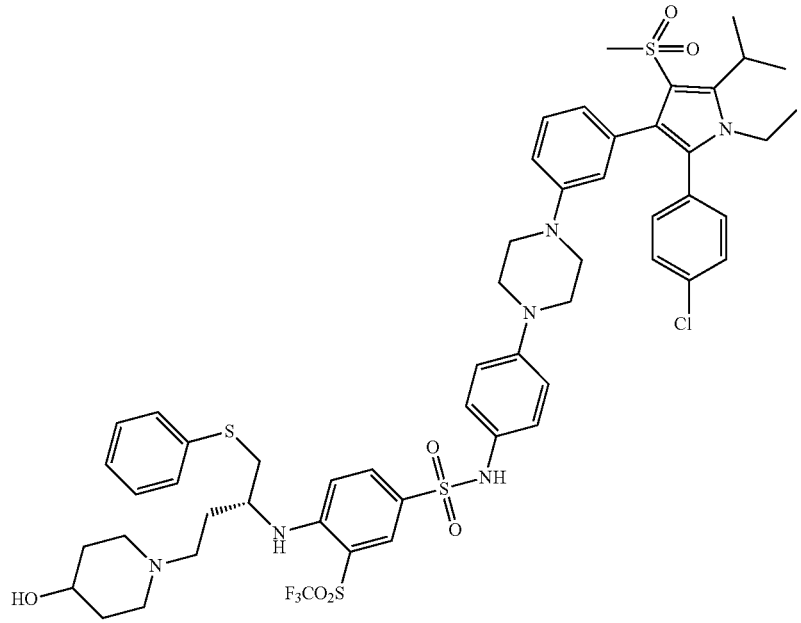
Chemical Formula: C$_{54}$H$_{62}$ClF$_3$N$_6$O$_7$S$_4$
Exact Mass: 1126.32
Molecular Weight: 1127.81
BM-1211

BM-1211: $^1$H NMR (300 MHz, CD$_3$OD): δ 7.94 (s, 1H), 7.69 (d, J=9.0 Hz, 1H), 7.31-6.78 (m, 18H), 4.08-3.79 (m, 5H), 3.54 (bra, 1H), 3.26-2.94 (m, 18H), 2.81 (s, 3H), 2.25-1.66 (m, 6H), 1.53 (s, 3H), 1.51 (s, 3H), 1.09 (tri, J=6.9 Hz, 6H).
Compound 248
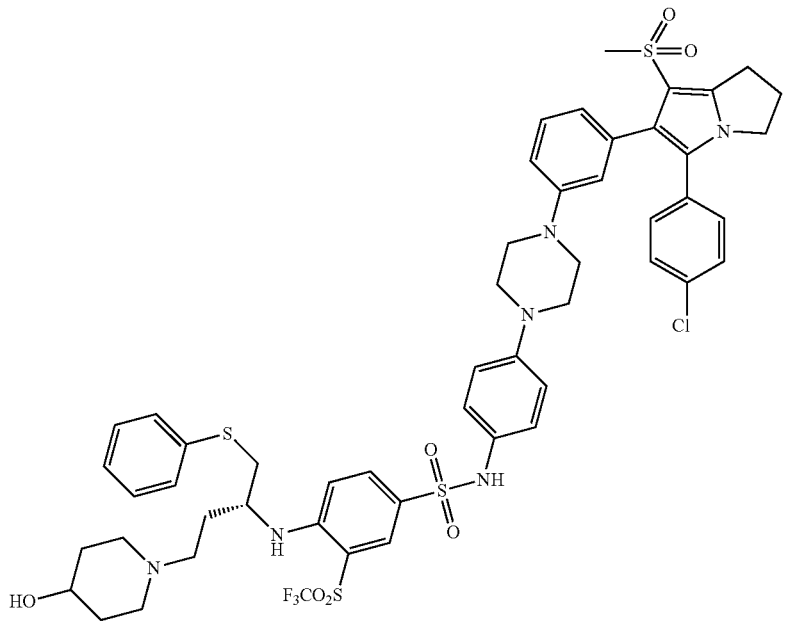
Chemical Formula: C$_{52}$H$_{56}$ClF$_3$N$_6$O$_7$S$_4$
Exact Mass: 1096.27
Molecular Weight: 1097.75
BM-1212
BM-1212: $^1$H NMR (300 MHz, CD$_3$OD): δ 8.04 (s, 1H), 7.86 (d, J=9.0 Hz, 1H), 7.40-7.23 (m, 15H), 7.06-6.94 (m, 3H), 4.20-3.89 (m, 5H), 3.57-3.04 (m, 16H), 2.85 (s, 3H), 2.74-2.62 (m, 2H), 2.36-1.74 (m, 6H).
Compound 249
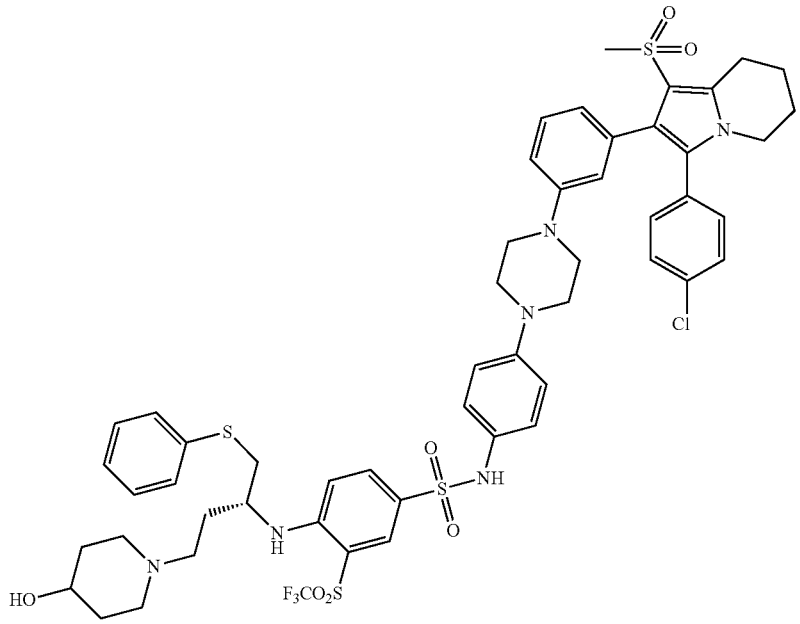
Chemical Formula: C$_{53}$H$_{58}$ClF$_3$N$_6$O$_7$S$_4$
Exact Mass: 1110.29
Molecular Weight: 1111.77
BM-1213

BM-1213: $^1$H NMR (300 M Hz, CD$_3$OD): δ 7.94 (s, 1H), 7.71 (d, J=9.0 Hz, 1H), 7.30-6.81 (m, 18H), 4.08-3.80 (m, 4H), 3.53 (bra, 1H), 3.19-2.94 (m, 18H), 2.76 (s, 3H), 2.26-1.65 (m, 10H).
Compound 250
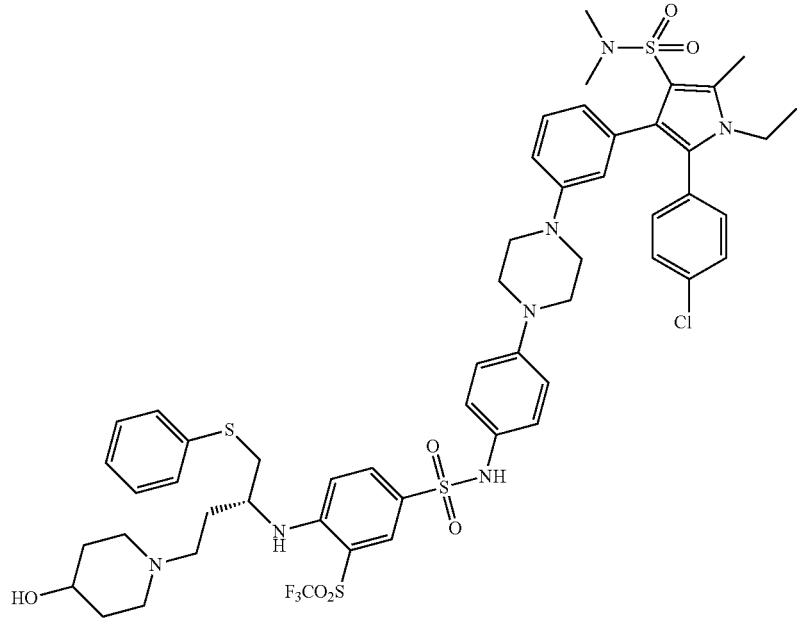
Chemical Formula: C$_{53}$H$_{61}$ClF$_3$N$_7$O$_7$S$_4$
Exact Mass: 1127.32
Molecular Weight: 1128.80
BM-1216
BM-1216: $^1$H NMR (300 M Hz, CD$_3$OD): δ 7.94 (s, 1H), 7.71 (d, J=9.0 Hz, 1H), 7.31-6.80 (m, 18H), 4.08-3.79 (m, 4H), 3.54 (bra, 1H), 3.22-2.94 (m, 15H), 2.64 (s, 3H), 2.39 (s, 6H), 2.25-1.68 (m, 6H), 1.14 (tri, J=6.9 Hz, 3H).
Compound 251
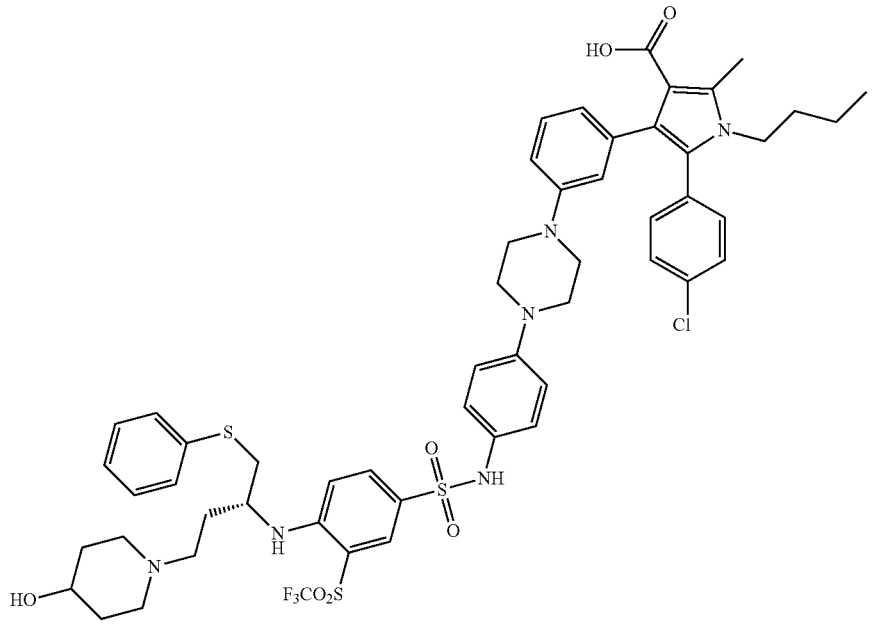
Chemical Formula: C$_{54}$H$_{60}$ClF$_3$N$_6$O$_7$S$_3$
Exact Mass: 1092.33
Molecular Weight: 1093.73
BM-1217

BM-1217: ¹H NMR (300 MHz, CD₃OD): δ 7.92 (s, 1H), 7.73 (d, J=9.0 Hz, 1H), 7.33-6.81 (m, 18H), 4.08-3.79 (m, 4H), 3.54 (bra, 1H), 3.36-2.94 (m, 15H), 2.63 (s, 3H), 2.32-1.11 (m, 10H), 0.78 (tri, J=6.9 Hz, 3H).
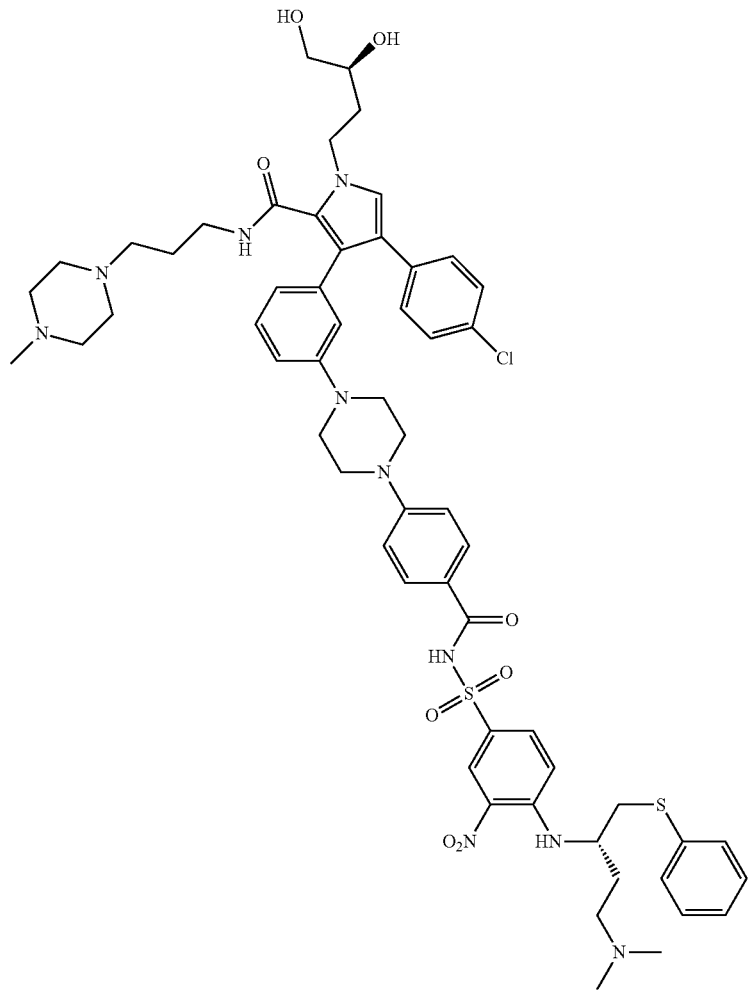
Compound 252
Chemical Formula: C₅₈H₇₁ClN₁₀O₈S₂
Exact Mass: 1134.46
Molecular Weight: 1135.83
BM-977
BM-977: ¹H NMR (300 MHz, CD₃OD), δ 8.66 (d, J=2.2, 1H), 7.93 (dd, J=2.2, 9.2, 1H), 7.75 (d, J=9.0, 2H), 7.29~6.95 (m, 15H), 6.81 (s, 1H), 6.74 (d, J=7.4, 1H), 4.38~4.27 (m, 2H), 4.16~4.13 (m, 1H), 3.54~3.32 (m, 11H), 3.24~3.08 (m, 14H), 2.84 (s, 6H), 2.82 (s, 3H), 2.61 (t, J=7.1, 2H), 2.27~2.14 (m, 2H), 2.03~2.00 (m, 1H), 1.78~4.75 (m, 1H), 1.66~4.61 (m, 2H); ¹³C NMR (75 MHz, CD₃OD), δ 167.2, 165.4, 155.8, 152.1, 148.5, 137.2, 136.2, 135.6, 135.0, 132.5, 132.2, 131.5, 130.6, 130.4, 130.1, 129.7, 127.8, 127.5, 126.8, 126.0, 124.9, 123.7, 123.5, 121.7, 119.7, 116.5, 115.7, 114.8, 70.2, 67.3, 55.9, 55.4, 53.0, 52.4, 50.7, 50.2, 48.0, 46.2, 43.6, 43.5, 39.3, 37.6, 36.4, 30.1, 25.9; ESI MS: m/z 1135.6 (M+H)⁺;

Compound 253
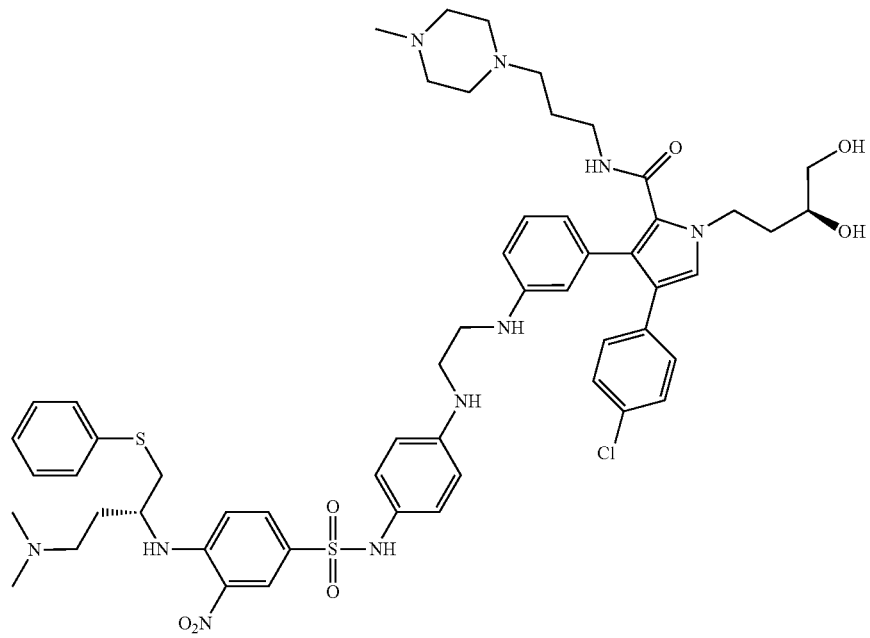
Chemical Formula: $C_{55}H_{69}ClN_{10}O_7S_2$
Exact Mass: 1080.45
Molecular Weight: 1081.78
BM-987
BM-987: $^1$H NMR (300 MHz, CD$_3$OD), δ 8.35 (d, J=1.9, 1H), 7.65 (d, J=7.4, 1H), 7.33~6.94 (m, 14H), 6.78~6.61 (m, 5H), 4.45~4.31 (m, 2H), 4.15~4.12 (m, 1H), 3.70~3.39 (m, 8H), 3.28~3.17 (m, 13H), 2.90~2.88 (m, 8H), 2.69~2.64 (m, 2H), 2.30~2.05 (m, 3H), 1.85~1.82 (m, 1H), 1.70~1.68 (m, 2H); $^{13}$C NMR (75 MHz, CD$_3$OD) 165.2, 147.9, 137.6, 136.2, 135.0, 134.5, 132.5, 132.3, 131.6, 130.9, 130.3, 130.1, 129.2, 128.02, 127.96, 127.7, 125.9, 125.1, 125.0, 123.4, 116.2, 70.2, 67.3, 55.9, 55.4, 53.0, 52.3, 50.7, 46.4, 43.7, 43.5, 39.6, 37.6, 36.4, 30.1, 25.8; ESI MS: m/z 1081.6 (M+H)$^+$;
Compound 254
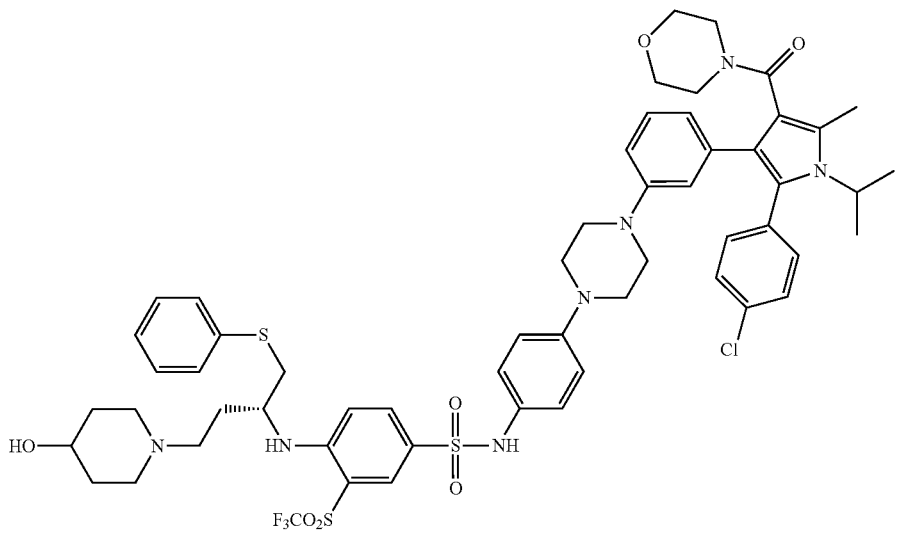
Chemical Formula: $C_{57}H_{65}ClF_3N_7O_7S_3$
Exact Mass: 1147.37
Molecular Weight: 1148.81
BM-988

BM-988: $^1$H NMR (300 MHz, CD$_3$OD), δ 7.92 (s, 1H), 7.75 (d, J=9.1, 1H), 7.35~7.29 (m, 4H), 7.21~7.12 (m, 9H), 6.99~6.83 (m, 3H), 6.76~6.72 (m, 2H), 4.43~4.34 (m, 1H), 4.06~3.73 (m, 3H), 3.58~3.30 (m, 9H), 3.20~2.92 (m, 13H), 2.62~2.41 (m, 4H), 2.24~1.90 (m, 5H), 1.69~1.66 (m, 1H), 1.48~1.28 (m, 6H);
Compound 255
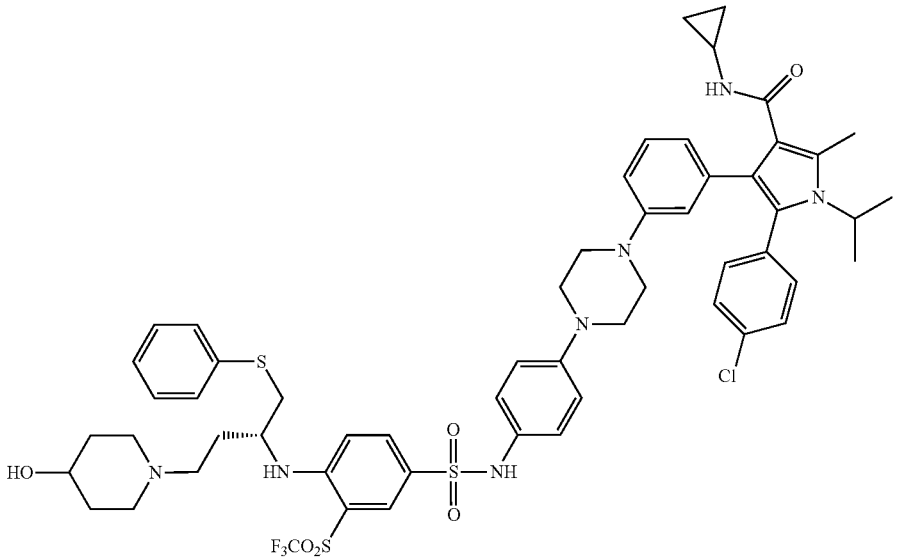
Chemical Formula: C$_{56}$H$_{63}$ClF$_3$N$_7$O$_6$S$_3$
Exact Mass: 1117.36
Molecular Weight: 1118.79
BM-989
BM-989: $^1$H NMR (300 MHz, CD$_3$OD), δ 7.90 (s, 1H), 7.75 (d, J=9.0, 1H), 7.32~7.30 (m, 4H), 7.22~7.02 (m, 11H), 6087~6.83 (m, 3H), 4.40~4.31 (m, 1H), 4.05~3.77 (m, 2H), 3.51~3.38 (m, 10H), 3.19~2.91 (m, 6H), 2.64 (br, 1H), 2.51 (s, 3H), 2.23~4.90 (m, 5H), 1.69~1.65 (m, 1H), 1.38 (d, J=6.9, 6H), 0.63~0.61 (m, 2H), 0.26~0.24 (m, 2H);
Compound 256
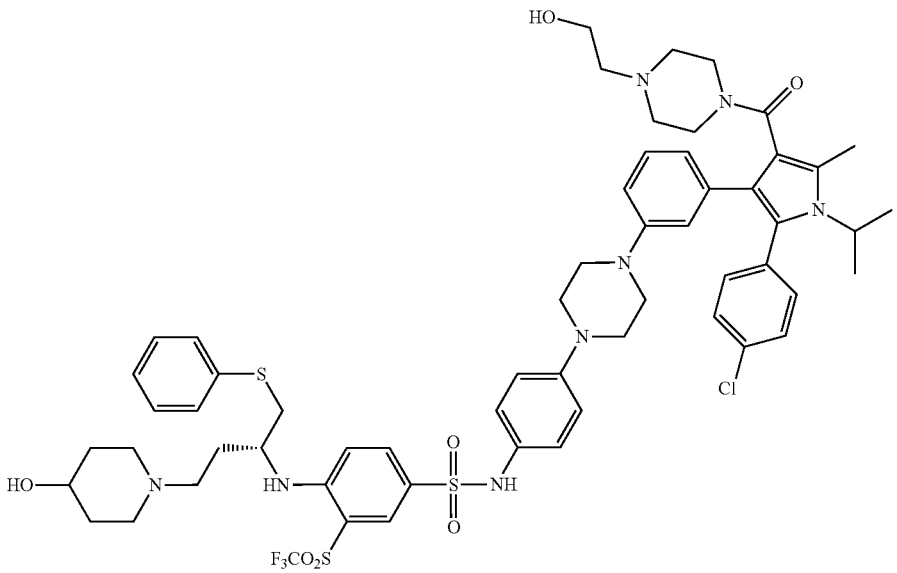
Chemical Formula: C$_{59}$H$_{70}$ClF$_3$N$_8$O$_7$S$_3$
Exact Mass: 1190.42
Molecular Weight: 1191.88
BM-990

BM-990: $^1$H NMR (300 MHz, CD$_3$OD), δ 7.90 (s, 1H), 7.74 (d, J=9.1, 1H), 7.34~7.09 (m, 14H), 6.94~6.91 (m, 1H), 6.85~6.81 (m, 1H), 6.67~6.65 (m, 2H), 4.43~4.34 (m, 1H), 4.04~3.98 (m, 2H), 3.50~3.33 (m, 13H), 3.25~2.69 (m, 15H), 2.42 (s, 3H), 2.23~1.89 (m, 5H), 1.69~1.65 (m, 1H), 1.40 (d, J=5.5, 6H);
Compound 257
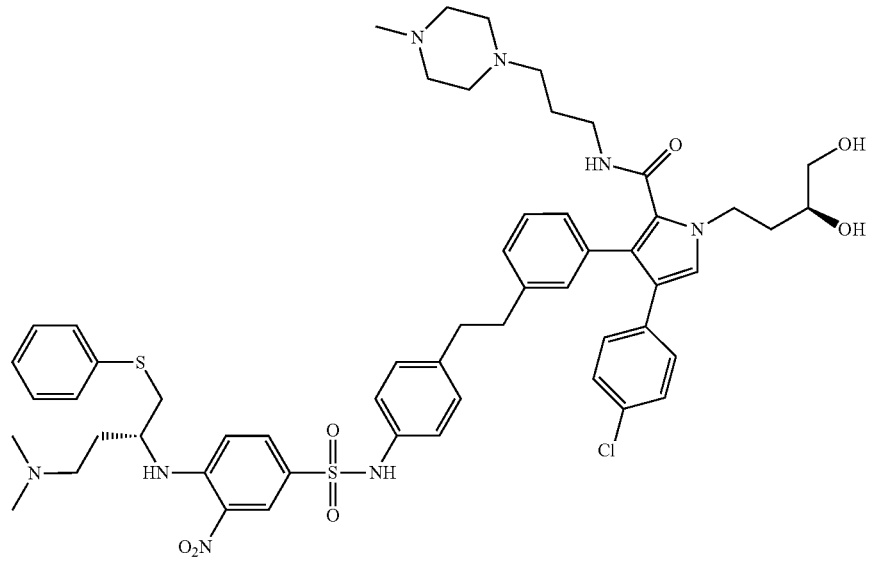
Chemical Formula: C$_{55}$H$_{67}$ClN$_8$O$_7$S$_2$
Exact Mass: 1050.43
Molecular Weight: 1051.75
BM-991
BM-991: $^1$H NMR (300 MHz, CD$_3$OD), δ 8.28 (d, J=1.9, 1H), 7.55 (dd, J=1.8, 9.1, 1H), 7.16 (t, J=7.6, 1H), 7.10~6.85 (m, 18H), 4.37~4.22 (m, 2H), 4.06~4.04 (m, 1H), 3.47~3.42 (m, 7H), 3.29~3.26 (m, 5H), 3.17~3.11 (m, 5H), 2.88 (s, 3H), 2.80~2.69 (m, 12H), 2.22~1.97 (m, 3H), 1.76~4.64 (m, 3H); $^{13}$C NMR (75 MHz, CD$_3$OD), δ; ESI MS: m/z 1051.4 (M+H)$^+$;
Compound 258
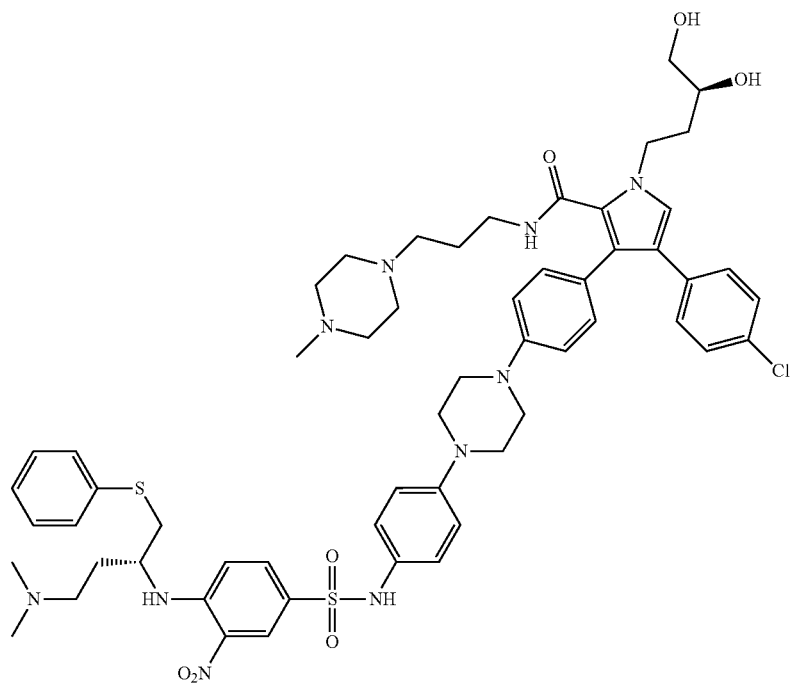
Chemical Formula: C$_{57}$H$_{71}$ClN$_{10}$O$_7$S$_2$
Exact Mass: 1106.46
Molecular Weight: 1107.82
BM-992

BM-992: ¹H NMR (300 MHz, CD₃OD), δ 8.36 (s, 1H), 7.66 (d, J=9.1, 1H), 7.22~7.04 (m, 18H), 6.97 (d, J=9.2, 1H), 4.43~4.31 (m, 2H), 4.15~4.13 (m, 1H), 3.59~3.37 (m, 17H), 3.26~3.21 (m, 8H), 2.90~2.82 (m, 11H), 2.30~2.05 (m, 3H), 1.83~1.74 (m, 3H); ¹³C NMR (75 MHz, CD₃OD), δ 165.6, 147.9, 136.2, 135.1, 134.4, 132.7, 132.5, 132.3, 131.6, 130.5, 130.1, 129.2, 128.0, 127.9, 127.7, 126.3, 125.9, 125.1, 124.2, 123.7, 119.2, 117.9, 116.2, 70.3, 67.3, 55.9, 55.5, 52.5, 52.4, 51.4, 50.6, 50.4, 46.3, 43.6, 43.5, 39.5, 37.5, 36.5, 30.1, 25.7; ESI MS: m/z 1107.7 (M+H)⁺;

Compound 259

Chemical Formula: C₄₈H₅₂ClN₇O₆S₂
Exact Mass: 921.31
Molecular Weight: 922.55
BM-993

BM-993: ¹H NMR (300 MHz, CD₃OD), δ 8.33 (d. J=1.9, 1H), 7.59 (d, J=9.1, 1H), 7.28 (t, J=7.9, 1H), 7.18~6.87 (m, 18H), 4.08~3.95 (m, 6H), 3.34~3.33 (m, 4H), 3.32~3.30 (m, 8H), 2.85 (s, 6H), 2.21~2.16 (m, 2H), 0.94 (t, J=7.1, 3H); ESI MS: m/z 922.8 (M+H)⁺;

Compound 260

Chemical Formula: C₄₇H₅₁ClN₈O₅S₂
Exact Mass: 906.31
Molecular Weight: 907.54
BM-994

BM-994: ¹H NMR (300 MHz, CD₃OD), δ 8.32 (d, J=1.2, 1H), 7.58 (d, J=9.1, 1H), 7.28 (t, J=7.9, 1H), 7.17~6.99 (m, 15H), 6.90 (d, J=9.3, 1H), 6.86 (s, 1H), 6.80 (d, J=7.5, 1H), 4.09~4.07 (m, 1H), 3.80 (s, 3H), 3.45~3.33 (m, 9H), 3.21~3.08 (m, 3H), 2.84 (s, 6H), 3.05 (s, 3H), 2.25~2.10 (m, 2H); ¹³C NMR (75 MHz, CD₃OD), δ; ESI MS: m/z 907.6 (M+H)⁺;

Compound 261

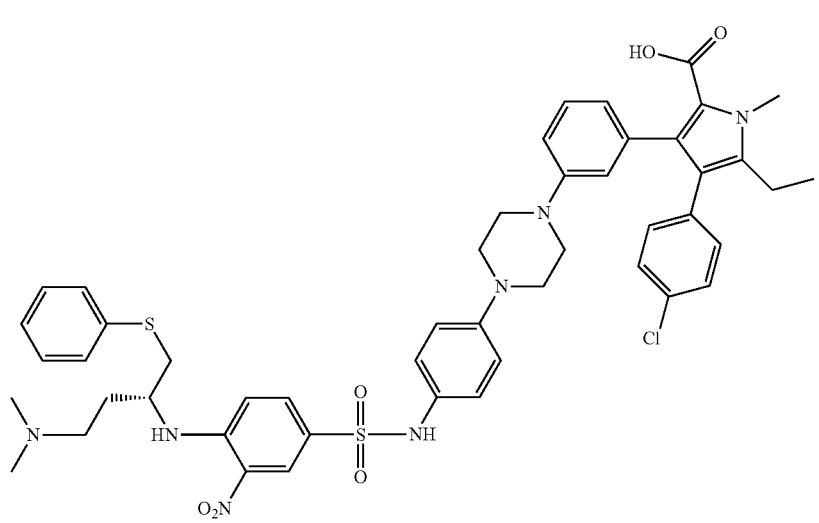

Chemical Formula: C₄₈H₅₂ClN₇O₆S₂
Exact Mass: 921.31
Molecular Weight: 922.55
BM-995

BM-995: ESI MS: m/z 922.5 (M+H)$^+$;

To demonstrate the ability of the present Bcl-2/Bcl-xL inhibitors to bind to Bcl-2/Bcl-xL, to induce apoptosis, and to inhibit tumor growth in vivo, compounds of the invention were assayed.

Compound 262

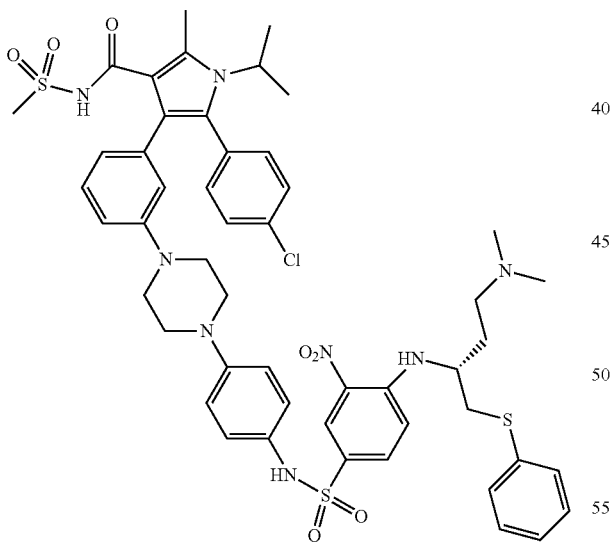

Chemical Formula: C₅₀H₅₇ClN₈O₇S₃
Exact Mass: 1012.32
Molecular Weight: 1013.68

BM-1074 $^1$H-NMR (300 MHz, CD₃OD) δ ppm 8.34 (d, J=2.2 Hz, 1H), 7.65 (dd, J=2.1, 9.1 Hz, 1H), 7.35 (d, J=8.4 Hz, 2H), 7.27-6.98 (m, 15H), 6.90 (d, J=7.3 Hz, 1H), 4.21-4.10 (m, 1H), 3.62-3.34 (m, 9H), 3.27-3.15 (m, 6H), 2.99 (s, 1H), 2.87 (s, 7H), 2.61 (s, 3H), 2.34-2.10 (m, 2H), 1.42 (d, J=7.0 Hz, 6H)

Compound 263

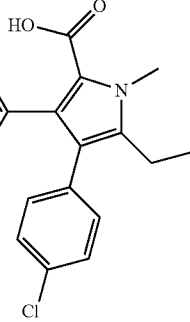

Chemical Formula: C₄₉H₅₅ClN₈O₇S₃
Exact Mass: 998.30
Molecular Weight: 999.66

BM-1075 $^1$H-NMR (300 MHz, CD₃OD) δ ppm 8.35 (d, J=2.2 Hz, 1H), 7.62 (dd, J=2.1, 9.1 Hz, 1H), 7.35 (d, J=8.5 Hz, 2H), 7.23-6.93 (m, 15H), 6.80 (d, J=7.6 Hz, 1H), 4.19-4.08 (m, 1H), 3.89 (q, J=7.0 Hz, 2H), 3.46-3.33 (m, 9H), 3.26-3.16 (m, 7H), 2.87 (s, 6H), 2.70 (s, 1H), 2.55 (s, 3H), 2.34-2.11 (m, 2H), 1.13 (t, J=7.1 Hz, 3H)

Fluorescence Polarization Based Binding Assays for Bcl-2/Bcl-xL/Mcl-1 Proteins

Sensitive and quantitative fluorescence polarization (FP)-based assays were developed and optimized to determine the binding affinities of Bcl-2 family protein inhibitors to the recombinant Bcl-2, Bcl-xL, and Mcl-1 proteins.

Determine $K_d$ Values of Fluorescent Probes to Proteins

Homemade fluorescein labeled BIM (81-106), Bak (72-87) and BID (79-99) peptides, named as Flu-BIM, Flu-BAK, and Flu-BID were used as the fluorescent probes in FP assays for Bcl-2, Bcl-xL, and Mcl-1 respectively. By monitoring the total fluorescence polarization of mixtures composed with fluorescent probes at fixed concentrations and proteins with increasing concentrations up to the full saturation, the $K_d$ values of Flu-BIM to Bcl-2, Flu-BAK to Bcl-xL, and Flu-BID to Mcl-1 were determined to be 0.55±0.15 nM, 4.4±0.8, and 6.8±1.5 nM, respectively. Fluorescence polarization values were measured using the Infinite M-1000 multi-mode plate reader (Tecan U.S., Research Triangle Park, N.C.) in Microfluor 2 96-well, black, round-bottom plates (Thermo Scientific). To each well, 1 nM of Flu-BIM or 2 nM of Flu-BAK or 2 nM of Flu-BID and increasing concentrations of Bcl-2 or Bcl-xL or Mcl-1 were added to a final volume of 125 μl in the assay buffer (100 mM potassium phosphate, pH 7.5, 100 μg/ml bovine γ-globulin, 0.02% sodium azide, Invitrogen, with 0.01% Triton X-100 and 4% DMSO). Plates were incubated at room temperature for 2 hours with gentle shaking to assure equilibrium. The polarization values in millipolarization units (mP) were measured at an excitation wavelength of 485 nm and an emission wavelength of 530 nm. Equilibrium dissociation constants ($K_d$) were then calculated by fitting the sigmoidal dose-dependent FP increases as a function of protein concentrations using Graphpad Prism 5.0 software (Graphpad Software, San Diego, Calif.).

Determine $K_i$ Values of Bcl-2 Family Protein Inhibitors $K_i$ values of Bcl-2 family protein inhibitors to Bcl-2/Bcl-xL/Mcl-1 proteins were determined through an inhibitor dose-dependent competitive binding experiment in which serial dilutions of inhibitors competed against the fluorescent probe with fixed concentration for binding to a fixed concentration of the protein. Mixtures of 5 μl of the tested inhibitor in DMSO and 120 μl of pre-incubated protein/probe complex in the assay buffer were added into assay plates and incubated at room temperature for 2 hours with gentle shaking. Final concentrations of the protein and probe are 1.5 nM and 1 nM for the Bcl-2 assay, 10 nM and 2 nM for the Bcl-xL assay, and 20 nM and 2 nM for the Mcl-1 assay, respectively. Negative controls containing protein/probe complex only (equivalent to 0% inhibition), and positive controls containing free probe only (equivalent to 100% inhibition), were included in each assay plate. FP values were measured as described above. $IC_{50}$ values were determined by nonlinear regression fitting of the competition curves. $K_i$ values of inhibitors were calculated using the home derived equation described before (Z. Nikolovska-Coleska et al., *Analytical Biochemistry*, 2004, 332, 261-273.), based upon the $IC_{50}$ values obtained, the $K_d$ values of the probes to the proteins, and the concentrations of the proteins and probes in the competitive assays. $K_i$ values were also calculated by using another very commonly used equation present in the literatures (X. Y. Huang, *Journal of Biomolecular Screening*, 2003, 8, 34-38.), results from which consisted with our results extremely well.

Cell Growth Assay

RS4;11 and H146 cells were seeded in 96-well cell culture plates at a density of 10,000 cells/well with serially diluted compounds and incubated at 37° C. in an atmosphere of 95% air and 5% $CO_2$ for 4 days. Cell viability was determined using the WST-8 (2-(2-methoxy-4-nitrophenyl)-3-(4-nitrophenyl)-5-(2,4-disulfophenyl)-2H-tetrazolium, monosodium salt) based Cell Counting-8 Kit (Dojindo Molecular Technologies, Inc., Rockville, Md.) according to the manufacture's instruction. Briefly, WST-8 was added to each well at a final concentration of 10% (v/v), and then the plates were incubated at 37° C. for 1~2 hours for color development. The absorbance was measured at 450 nm using a SPECTRAmax PLUS plate reader (Molecular Devices, Sunnyvale, Calif.). The half maximal inhibitory concentration ($IC_{50}$) was calculated using the GraphPad Prism 5 software (GraphPad Software, La Jolla, Calif.).

Cell Death Assay

Cell death assay was performed using a Trypan blue exclusion test of cell viability. One million cells were seeded in 6-well plates and incubated at 37° C. in an atmosphere of 95% air and 5% $CO_2$ with or without compounds for the indicated time points. At the end of treatment, cells were collected and centrifuged at 1000 rpm for 5 minutes. The cell pellets were re-suspended in PBS and mixed with 0.4% Trypan blue (Invitrogen) at 1:1 dilution to determine cell viability using Olympus CKX41 microscope (Olympus, Center Valley, Pa.).

Apoptosis Assay

Apoptosis assay was performed using the Annexin-V-FLUOS Staining kit (Roche Diagnostics, Indianapolis, Ind.) according to the manufacturer's instruction. Briefly, cells were treated with compounds for the indicated time points, harvested and washed with PBS. Cells were stained with Annexin V-FITC and Propidium iodide for 15 minutes at room temperature in the dark before analyzed with a BD Biosciences FACSCaliburs (Becton Dickinson).

Western Blot Analysis

Cells were lysed with lysis buffer (PBS containing 1% NP40, 0.5% Na-deoxycholate, and 0.1% SDS) supplemented with protease inhibitors (α-complete, Roche). The protein extracts were quantified using a calorimetric assay (Bradford Reagent) (BioRad, Hercules, Calif.). Proteins were electrophoresed onto 4-20% SDS-PAGE gels (Invitrogen) and transferred onto polyvinylidene difluoride membranes (Bio-Rad). Following blocking in 5% milk, membranes were incubated with a specific primary antibody, washed, and incubated with horseradish peroxidase-linked secondary antibody (Pierce). The signals were visualized with the chemiluminescent horseradish peroxidase antibody detection reagent (Denville Scientific).

Cytochrome c and Smac Release Assay

Four million of H146 or RS4;11 cells were treated with compounds at 37° C. in an atmosphere of 95% air and 5% $CO_2$ for the indicated time points, washed with PBS and re-suspended in 100 μl of digitonin buffer (75 mM NaCl, 8 mM $Na_2HPO4$, 1 mM $NaH2PO4$, 1 mM EDTA, 350 μg/ml digitonin, and 250 mM sucrose). Cytosolic fractions were separated from organelle membrane fraction by centrifugation at 13,000 rpm for 1 min. The cytosolic fractions were resolved on a 12% SDS-PAGE and probed using anti-cytochrome c antibody (BD Biosciences) and anti-Smac (Cell Signaling Technology, Danvers, Mass.) antibody.

In particular, a compound of the invention was assayed for affinity to Bcl-2, Bcl-xL, and Mcl-1. The assay results compared to assay results for ABT-737, a known, patent Bcl-2/Bcl-xL inhibitor, and to these peptides. The results are summarized in Table 1.

TABLE 2

Binding affinities to Bcl-2, Bcl-xL, and Mcl-1 proteins, as determined using established FP-based assays.

| | Binding Affinities | | | | |
|---|---|---|---|---|---|
| | Bcl-2 | | Bcl-xL | | Mcl-1 |
| Compound | $IC_{50} \pm SD$ | $K_i \pm SD$ | $IC_{50} \pm SD$ | $K_i \pm SD$ | $IC_{50} \pm SD$ |
| Compound 150 | 2 ± 0.6 (nM) | <1 (nM) | 9 ± 2 (nM) | 2.4 ± 0.5 | >10 (μM) |
| ABT-737 | 2 ± 0.2 (nM) | <1 (nM) | 6 ± 2 (nM) | 1.6 ± 0.5 (nM) | >1 (μM) |
| BIM | <1 (nM) | <1 (nM) | <1 (nM) | <1 (nM) | 5 ± 1 (nM) |
| BAD | 40 ± 8 (nM) | 10 ± 2 (nM) | 5 ± 0.3 (nM) | 1.5 ± 0.1 (nM) | 32 ± 2 (μM) |
| NOXA | 17 ± 1 (μM) | 3.6 (μM) | 11 ± 2 (μM) | 3.4 (μM) | 37 ± 3 (μM) |

3-5 independent experiments were performed for each compound for each protein. ABT-737, BIM, BAD, and NOXA peptides were tested as controls.

The data in Table 2 show that compound binds to Bcl-2 and Bcl-xL proteins with a high affinity, and has a very low affinity to Mcl-1.

A present Bcl-2/Bcl-xL inhibitor also was assayed in three cancer cell lines to determine its activity. ABT-737 and ABT-263 are highly potent and effective inhibitors of cell growth in certain cell lines with low levels of Mcl-1, including the RS4;11 acute lymphoblastic leukemia (ALL), H146 small-cell lung cancer, and the ML-2 acute myeloid leukemia (AML) cell lines.[26,33,34] Compound 150 binds to Bcl-2 and Bcl-xL with high affinities, has a very weak affinity for Mcl-1, and has the same binding profile as ABT-737. Compound 150 therefore was assayed in these three cancer cell lines. Cell lines from different tumor types were used to illustrate that antitumor activity of the present Bcl-2/Bcl-xL inhibitors is not limited to a simple tumor type, and also to directly compare a present Bcl-2/Bcl-xL inhibitor to ABT-737. The data are summarized in Table 3.

TABLE 3

Inhibition of cancer cell growth in three cancer cell lines.

| | Cell Growth Inhibition ($IC_{50} \pm SD$) | | |
|---|---|---|---|
| | RS4; 11 | H146 | ML-2 |
| Compound 150 | 38 ± 24 (nM) | 102 ± 44 (nM) | 185 ± 84 (nM) |
| ABT-737 | 12 ± 6 (nM) | 62 ± 39 (nM) | 16 ± 2 (nM) |

ABT-737 was used as a control

The data in Table 3 show that compound 150 inhibits all cell growth in all three cancer cell lines.

The functional antagonism of a present compound against Bcl-2, Bcl-xL, and Mcl-1 also was tested. Cell-free functional assays using purified mitochondria, recombinant Bcl-2/Bcl-xL/Mcl-1 proteins, and the high-affinity BIM BH3 peptide were used to provide direct evidence that compound 150 functions as a potent antagonist to Bcl-2 and Bcl-xL, but not Mcl-1. These cell-free functional assays were used to test the functional antagonism of compound 150, ABT-737, and BAD and Noxa BH3 peptides.

The Bim BH3 peptide at a concentration of 20 nM induces substantial release of cytochrome c and Smac proteins from mitochondria. Bcl-2 at 60 nM and Bcl-xL at 30 nM efficiently inhibit the release from mitochondria of cytochrome c and Smac proteins induced by 20 nM of the Bim BH3 peptide.

In the Bcl-2 functional assay, ABT-737 and compound 150 dose-dependently and effectively antagonize Bcl-2 and restore Bim-induced release of cytochrome c and Smac proteins from mitochondria. The BAD BH3 peptide also is capable of doing so in a dose-dependent manner, but the Noxa BH3 peptide fails to restore the release of cytochrome c and Smac.

In the Bcl-xL functional assay, compound 150 and ABT-737 are equally potent in restoring the release of cytochrome c and Smac induced by Bim BH3 peptide, but both are 3-times less potent than the Bad BH3 peptide. The Noxa BH3 peptide fails to antagonize Bcl-xL.

In the Mcl-1 functional assay, Mcl-1 at 60 nM effectively inhibits the release of cytochrome c and Smac induced by 20 nM of the BIM BH3 peptide. While the Noxa peptide can restore the release of cytochrome c and Smac induced by the BIM peptide in a dose-dependent manner, the BAD peptide, ABT-737, and compound 150 at concentrations as high as 10 μM all fail to do so.

These data provide clear evidence that compound 150, ABT-737, and the BAD peptide function as potent antagonists of Bcl-2 and Bcl-xL proteins, but not of Mcl-1. On the other hand, the Nova BH3 peptide antagonizes Mcl-1, but fails to antagonize both Bcl-2 and Bcl-xL proteins. These functional data are highly consistent with their binding profiles to these Bcl-2 proteins.

Apostosis/cell-death induction by compound 150 in the H146, RS4;11, and ML-2 cell lines was also tested. ABT-737 was included in the test as a control.

Both ABT-737 and compound 150 effectively induced cell death in the H146 small-cell lung cancer cell line as determined in a trypan blue assay. For example, compound 150 at 30 nM and 100 nM for 24-hr treatment induces 40% and >70% of H146 cells to undergo cell death, respectively.

Using Annexin-V/Propidium iodide (PI) double staining by flow cytometry, both ABT-737 and compound 150 effectively induced apoptosis in the ML-2 AML cell line in a dose- and time-dependent manner and about 50% of ML-2 cells underwent apoptosis when treated with both compounds at 300 nM for 24 hr.

Similarly, both compound 150 and ABT-737 are highly effective in induction of apoptosis in a time- and dose-dependent manner in the RS4;11 cell line by Annexin-V/PI double staining by flow cytometry. compound 150 at 100 and 300 nM induced 30% and 60% of the RS4;11 cells to undergo apoptosis within 4 hrs. compound 150 at 100 nM induced >50% of the RS4;11 tumor cells to undergo apoptosis at the 16 hr time-point.

Western blot analysis was performed to examine cleavage of PARP and caspase-3, two important biochemical markers of apoptosis, in these three cancer cell lines when treated with compound 150 or ABT-737. Both compound 150 and ABT-737 were highly effective in induction of cleavage of PARP and caspase-3 at concentrations as low as 100 nM with 8-hr treatment in the RS4;11, H146 and ML-2 cell lines.

Taken together, these data show that compound 150 and ABT-737 effectively induce apoptosis with similar potencies and kinetics in the RS4;11, H146 and ML-2 cancer cell lines.

Potent and bona fide Bcl-2/Bcl-xL inhibitors are predicted to induce apoptosis in cancer cells by binding to cellular Bcl-2 and Bcl-xL proteins, antagonizing their anti-apoptotic function and triggering rapid release of Smac and cytochrome c from mitochondria. Furthermore, the release of Smac and cytochrome c should take place before apoptosis. Accordingly, compound 150 was tested for its ability to induce cytochrome c and Smac release in the RS4;11 and H146 cell lines. It was found that compound 150 induced rapid, time- and dose-dependent release of cytochrome c and Smac from mitochondria in both cancer cell lines. At 300 nM, compound 150 induces strong release of cytochrome c and Smac within 2 hr in the H146 cell line. In the RS4;11 cell line, compound 150 at 100 nM induced robust release of cytochrome c and Smac within 30 minutes. These data show that release of cytochrome c and Smac from mitochondria by compound 150 are early biochemical events in apoptosis induction by compound 150 in these cell lines.

To determine the cellular molecular targets for compound 150, biotinylated analogue of compound 150 (Biotin-150) was designed and synthesized. In FP binding assays,[23] Biotin-150 binds to Bcl-2 and Bcl-xL proteins with high affinity, similar to that of compound 150, while showing no binding to Mcl-1 at 100 μM, indicating that the biotin label does not affect the interaction of compound 150 with these proteins.

Using Biotin-150, streptavidin-biotin pull-down experiments and competitive assays were performed to probe the cellular targets of compound 150 and ABT-737 in the ML-2 and H146 cell lysates. Biotin-150 dose-dependently pulled down the cellular Bcl-2 and Bcl-xL proteins, but not Mcl-1, in the streptavidin-biotin pull-down experiments. Furthermore, in the competitive experiment, compound 150 and ABT-737 both blocked the interaction of cellular Bcl-2/Bcl-xL and Biotin-150 in a dose-dependent manner. These pull-down experiments provide evidence that compound 150 and ABT-737 bind to cellular Bcl-2 and Bcl-xL proteins with similar high affinities.

Additional compounds of the present invention were tested for binding affinities to Bcl-2, Bcl-xL, and Mcl-1 and for cell growth inhibition. The results are summarized below in Table 4.

Compounds 150, 133, and 169 were tested for their toxicity in severe combined immunodeficiency (SCID) mice. SCID mice bearing xenograft tumors were treated with vehicle control, or a single dose of a compound, and tumors were removed at different time-points for western blot analysis of cleavage of PARP (CL-PARP) and caspase-3 (CL Cas-3).

The data show that female SCID mice treated intravenously (IV), daily, 5-times a week for 2 weeks with compound 150 or 130 at 25 mg/kg, or with compound 169 at 50 g/kg, suffered no or minimal weight loss or other signs of toxicity. Higher doses (50 mg/kg for compound 150 and compound 133 and 75 mg/kg for compound 169) caused weight loss of SCID mice. These experiments established the maximum tolerated doses (MTD).

The ability of compounds 150 and 169 to induce apoptosis at their MTD in RS4;11 or H146 xenograft tumors in SCID mice was tested. In these experiments, RS4;11 or H146 tumors were allowed to grow to 200-300 mm$^3$ in female SCID mice. A single dose of the compound was administered to the animals and tumor tissues were analyzed for cleavage of PARP and caspase-3.

Compound 169 had a strong effect in induction of cleavage of PARP and caspase-3 in tumor tissues in both RS4;11 and H146 models. For example, a single-dose of compound 169 at 50 mg/kg IV induced cleavage of PARP and caspase-3 at 3 hr and 6 hr-time points in both the H146 xenograft tumor tissues. These data suggest that compound 169 induces robust apoptosis in xenograft tumors in vivo.

The antitumor activity of compound 169 in the H146 xenograft tumor model also was tested. Compound 169 showed significant antitumor activity, while causing minimal (<3%) weight loss and no other signs of toxicity in mice during the entire experiment. At the end of the treatment (day 39), compound 169 inhibited the tumor growth by 100% ($p<0.0001$, t-test). The strong antitumor activity achieved by compound 169 also was persistent. At day 53, 2 weeks after the treatment was stopped, compound 169 still inhibited the tumor growth by 79% versus the vehicle-treated tumors ($p=0.0001$, t-test). This preliminary in vivo efficacy experiment provided evidence that compound 169 effectively inhibits tumor growth in the H146 xenograft model, while causing no toxicity in animals.

REFERENCES

1. D. Hanahan D, et al., *Cell* 2000; 100:57-70.
2. S. W. Lowe, et al., *Carcinogenesis* 2000, 21, 485-495.

TABLE 4

Binding affinities to Bcl-2, Bcl-xL, and Mcl-1 proteins in FP-based assays and inhibition of cell growth in three cancer cell lines.

| | Binding Affinities | | | | | Cell Growth Inhibition | | |
| | Bcl-2 | | Bcl-xL | | Mcl-1 | ($IC_{50}$ ± SD, nM) | | |
| Compounds | $IC_{50}$ ± SD (nM) | $K_i$ ± SD (nM) | $IC_{50}$ ± SD (nM) | $K_i$ ± SD (nM) | $IC_{50}$ ± SD (μM) | RS4;11 | H146 | ML-2 |
|---|---|---|---|---|---|---|---|---|
| Compound 125 | 5 ± 1 | 1.1 ± 0.2 | 6 ± 3 | 1.6 ± 0.8 | >10 | 74 ± 44 | 36 ± 26 | 215 ± 52 |
| Compound 178 | 1 ± 0.1 | <1* | 6 ± 4 | 1.6 ± 1.0 | >10 | 26 ± 4 | 87 ± 60 | 124 ± 62 |
| Compound 133 | 1 ± 0.2 | <1* | 5 ± 1 | 1.3 ± 0.3 | >10 | 87 ± 19 | 38 ± 22 | 160 ± 53 |
| Compound 168 | 99 ± 5 | 25 ± 2 | 11 ± 6 | 3 ± 1 | >10 | 3373 ± 1663 | 3944 ± 1681 | 3014 ± 703 |
| Compound 185 | 2.2 ± 1.6 | <1* | 5 ± 4 | 1.3 ± 1.0 | >10 | 81 ± 7 | 177 ± 73 | 550 ± 204 |
| Compound 186 | 14 ± 3 | 3.4 ± 0.6 | 6 ± 3 | 1.6 ± 0.8 | >10 | 493 ± 64 | 430 ± 207 | 1088 ± 562 |
| Compound 187 | 2 ± 1 | <1* | 5 ± 2 | 1.3 ± 0.6 | >10 | 99 ± 28 | 181 ± 61 | 225 ± 49 |
| Compound 168 | 2 ± 1 | <1* | 3 ± 0.4 | <1* | >5 | 115 ± 27 | 152 ± 63 | 330 ± 188 |
| Compound 124 | 14 ± 2 | 3 ± 0.6 | 5 ± 1 | 1 ± 0.2 | >10 | 89 ± 30 | 178 ± 65 | 382 ± 138 |

*Compound is more potent than the tracer based upon its $IC_{50}$ value and the $K_i$ is an estimate.

3. C. B. Thompson, *Science* 1995, 267, 1456-1462.
4. J C. Reed, *Nat Rev Drug Discov* 2002; 1:111-121.
5. D. W. Nicholson, *Nature* 2000, 407, 810-816.
6. D T Chao, et al., *Annu Rev Immunol* 1998; 16:395-419.
7. J C Reed, *Advances in Pharmacology* 1997; 41:501-553.
8. J C Reed, et al. *J Cell Biochem* 1996; 60:23-32.
9. A J Minn, et al., *Advances in Immunology* 1998; 70:245-279.
10. J M Adams, et al., *Science* 1998; 281:1322-1326.
11. A. Ziegler, et al., *J Natl Cancer Inst* 1997; 89:1027-1036.
12. U. Zangemeister-Wittke, et al., *Br. J. Cancer* 1998; 78:1035-1042.
13. B. Jansen, et al., *Nature Medicine* 1998; 4:232-234.
14. U. Zangemeister-Wittke, et al., *Br J Cancer* 1998; 78:1035-1042.
15. O. Gautschi, et al., *J Natl Cancer Inst* 2001; 93:463-471.
16. M. Strasberg Rieber M, et al., *Clin Cancer Res* 2001; 7; 1446-1451.
17. S. Hopkins-Donaldson, et al., *Int J Cancer* 2003; 106: 160-166.
18. G. Wang, et al., *Proc Natl Acad Sci USA* 2000; 97:7124-7129.
19. A. Degterev, et al., *Nat Cell Biol* 2001; 3:173-182.
20. S P Tzung, et al., *Nat Cell Biol* 2001; 3:183-191.
21. U Enyedy, et al., *J Med Chem* 2001; 44:4313-4324.
22. O. Kutzki, et al., *J Am Chem Soc* 2002; 124:11838-11839.
23. G. Wang, et al., *J Med. Chem.* 2006; 49:6139-6142.
24. G. Tang, et al., *J Med. Chem.* 2007 Apr. 19; 50(8):1723-6.
25. G. Tang, et al., *J Med. Chem.* 2007; 50(14): 3163-6.
26. T. Oltersdorf, et al., *Nature.* 2005, 435(7042):677-81.
27. M D Wendt, et al., *J Med. Chem.* 2006, 49(3):1165-81.
28. A M Petros, et al., *J Med. Chem.* 2006, 49(2):656-63.
29. C M Park, et al., *J Am Chem. Soc.* 2006 Dec. 20; 128(50): 16206-12.
30. A R Shoemaker, et al., *Cancer Res.* 2006, 66(17):8731-9.
31. M. Bruncko, et al., *J Med. Chem.* 2007, 50(4):641-62.
32. C M Park, et al., *J Med. Chem.* 2008, 51(21):6902-15.
33. A R Shoemaker, et al., *Clin Cancer Res.* 2008 Jun. 1; 14(11):3268-77.
34. C. Tse, et al., *Cancer Res.* 2008 May 1; 68(9):3421-8.
35. M. Vogler, et al., *Cell Death Differ.* 2009 March; 16(3): 360-7.
36. T N Chonghaile, et al., *Oncogene.* 2008; 27 Suppl 1:S149-57.
37. M H Kang, et al. *Clin Cancer Res.* 2009 Feb. 15; 15(4): 1126-32.
38. S W Muchmore, et al., *Nature* 1996; 381:335-341.
39. M. Aritomi, et al., *J Biol Chem* 1997; 272:27886-27892.
40. M. Sattler, et al., *Science* 1997; 275:983-986.
41. A M Petros, et al. *Protein Sci* 2000; 9:2528-2534.
42. A M Petros, et al. *Proc Natl Acad Sci USA* 2001; 98:3012-3017.
43. X Liu, et al. *Immunity.* 2003 September; 19(3):341-52.
44. E F Lee, et al., *Cell Death Differ.* 2007 September; 14(9): 1711-3. (PDB ID: 2YXJ).
45. http://www.clinicaltrials.gov/
46. S K Tahir S K, et al. *Cancer Res.* 2007; 67(3):1176-83.
47. V D G Moore, et al., *J Clin Invest.* 2007; 117:112-121.
48. M. Vogler, et al., *Cell Death Differ.* 2008; 15: 820-830.
49. M. Vogler, et al., *Blood.* 2009; 113:1710-1722.

What is claimed:
1. A compound having a structural formula:

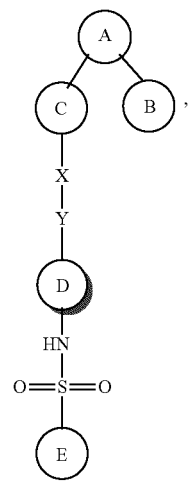

wherein A is an optionally substituted 2, 3-1H-pyrrolylene;
B and E individually are optionally substituted phenyl; C is optionally substituted 1,3-phenylene; D is optionally substituted 1,4-phenylene; and
X and Y taken together form

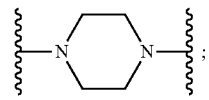

and
or a pharmaceutically acceptable salt thereof.
2. The compound of claim 1 wherein ring B is selected from the group consisting of

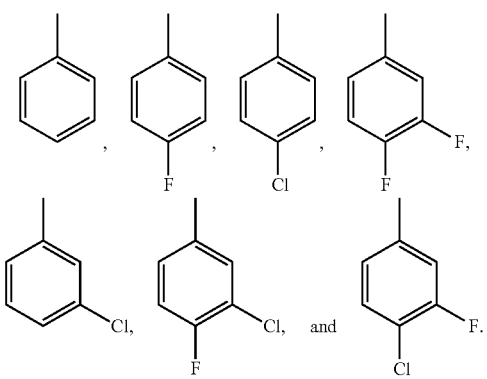

3. The compound of claim 1 wherein ring A is

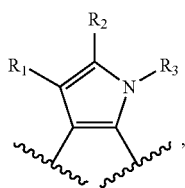

wherein $R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", COR', $CO_2R'$, OCOR', CONR'R", CONR'$SO_2$R", NR'COR", NR'CONR"R''', NR'C=SNR"R''', NR'$SO_2$R", $SO_2$R', and $SO_2$NR'R";

$R_3$ is selected from a group consisting of H, alkyl, cycloalkyl, alkenyl, cycloalkenyl, alkynyl, aryl, heteroaryl, heterocycloalkyl, OR', NR'R", $CO_2R'$, COR', CONR'R", CONR'$SO_2$R", $C_{1-3}$alkyleneCH(OH)$CH_2$OH, $SO_2$R', and $SO_2$NR'R";

R', R", and R''', independently, are H, alkyl, cycloalkyl, alkenyl, cycloalkenyl, alkynyl, $CF_3$, aryl, heteroaryl, $C_{1-3}$alkyleneheterocycloalkyl, or heterocycloalkyl;

R' and R", or R" and R''', can be taken together with the atom to which they are bound to form a 3 to 7 membered ring.

4. The compound of claim 1 wherein the nitrogen atom of ring A is substituted with $C_{1-6}$alkyl, cycloalkyl, —$(CH_2)_{1-3}$N$(C_{1-4}$-alkyl$)_2$ or —$(CH_2)_{1-3}$ CH(OH)$CH_2$OH or the nitrogen atom of the A ring and an adjacent carbon atom of the A ring are taken together to form a five or six membered ring.

5. The compound of claim 1 wherein one to three carbon atoms of ring A are substituted, independently, with $CH_3$, $C_2H_5$, $C_3H_7$, $CF_3$, $NH_2$, Cl, CN, $CO_2$H, C(=O)$CH_3$, C(=O)$C_2H_5$, C(=O)$CF_3$, $SO_2CH_3$, $SO_2C_2H_5$, $SO_2C_3H_7$, $SO_2CF_3$, $SO_2N(CH_3)_2$, C(=O)NH$SO_2CH_3$, C(=O)$NH_2$, C(=O)$NHCH_3$, C(=O)NH$(CH_2)_{1-3}$N$(CH_3)_2$, C(=O)NH$SO_2CH_3$,

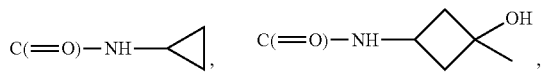

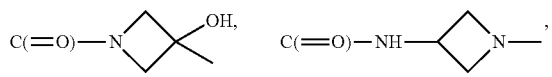

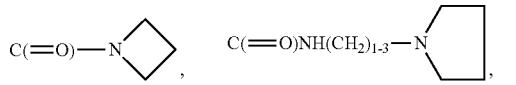

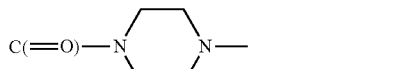

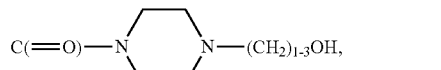

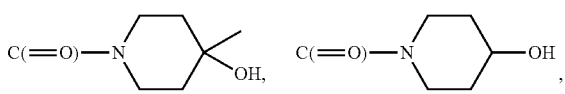

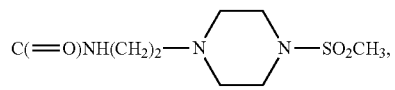

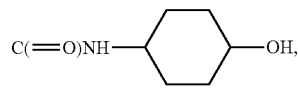

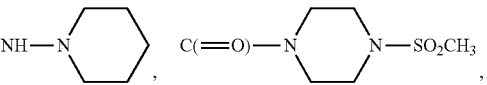

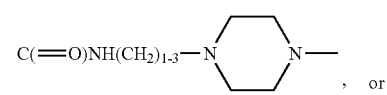

, or

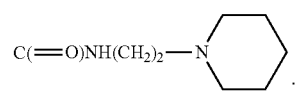

6. The compound of claim 1 having a structure:

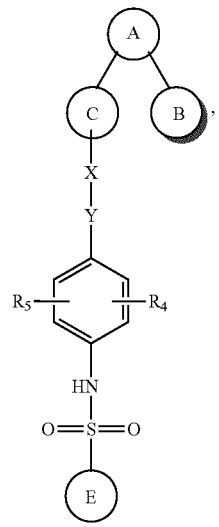

wherein $R_4$ and $R_5$, independently, are selected from a group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", CONR'$SO_2$R", NR'COR", NR'CONR"R''', NR'C=SNR"R''', NR'$SO_2$R", $SO_2$R', and $SO_2$NR'R".

7. The compound of claim 6 having a structure

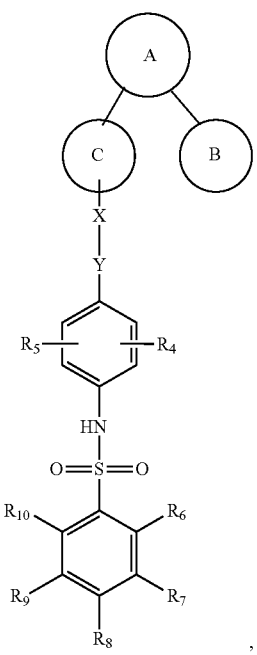

wherein $R_6$, $R_7$, $R_8$, $R_9$ and $R_{10}$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", $CONR'SO_2R"$, NR'COR", NR'CONR"R'", NR'C=SNR"R'", $NR'SO_2R"$, $SO_2R'$, and $SO_2NR'R"$.

8. The compound of claim 1 wherein ring E is substituted at a meta position to the —$SO_2NH$— group with $NO_2$ or $SO_2CF_3$.

9. The compound of claim 1 wherein ring E is substituted at a para position to the —$SO_2NH$— group with

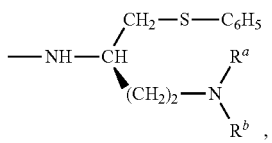

wherein $R^a$ and $R^b$, individually, are H, methyl, and

or $R^a$ and $R^b$ are taken together to form

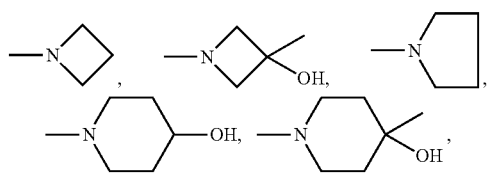

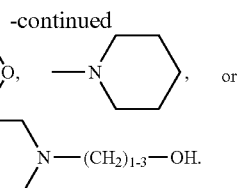

10. The compound of claim 7 having a structure

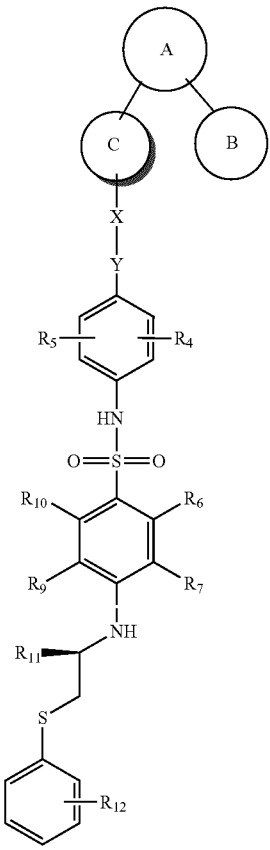

wherein the A ring is

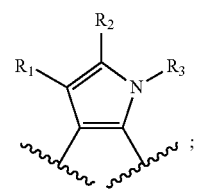

X, Y, $R_1$, $R_2$, $R_3$, $R_4$, $R_5$, $R_6$, $R_7$, $R_8$, $R_9$, $R_{10}$, R', R", R'" are defined as above; and $R_{11}$ and $R_{12}$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", $CONSO_2R'R"$, NR'COR", NR'CONR"R'", NR'C=SNR"R'", $NR'SO_2R"$, $SO_2R'$, and $SO_2NR'R"$;

or a pharmaceutically acceptable salt thereof.

11. A compound having a structure
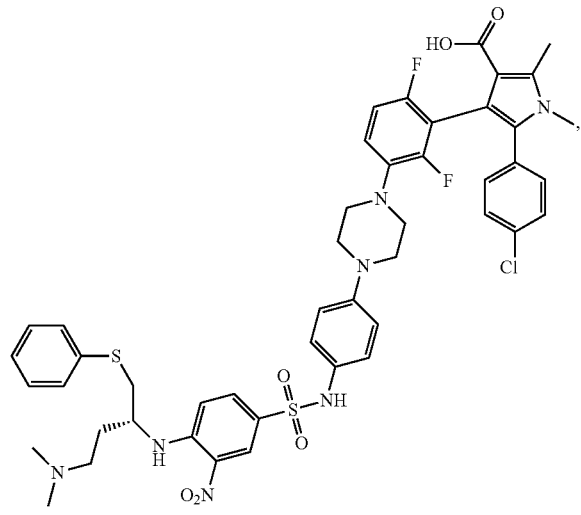
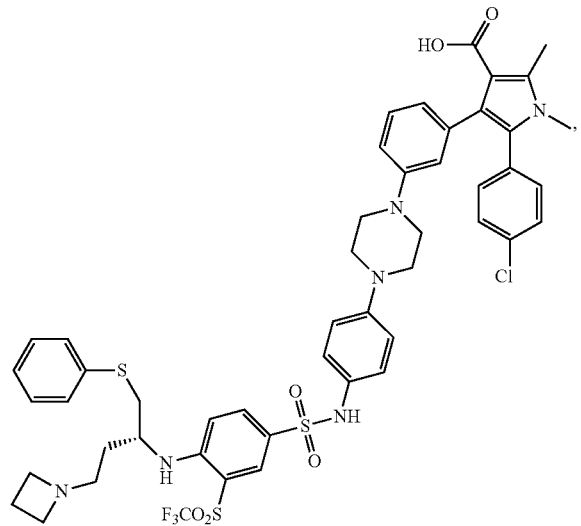
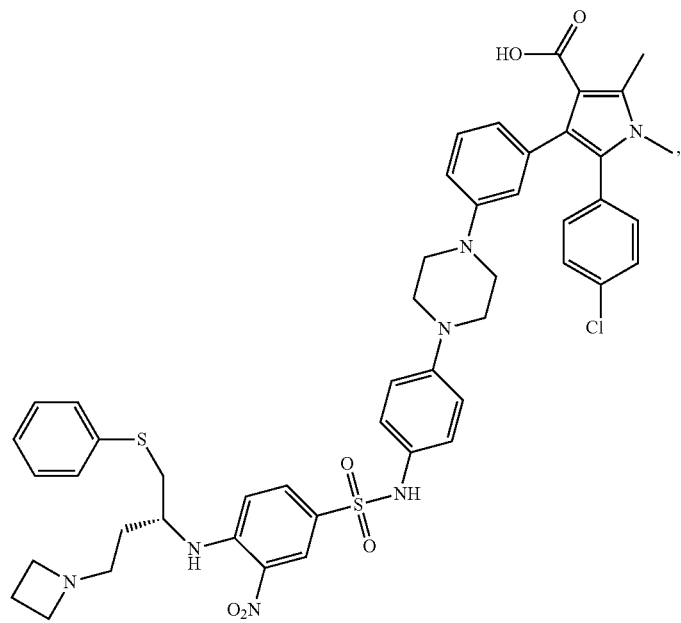

-continued
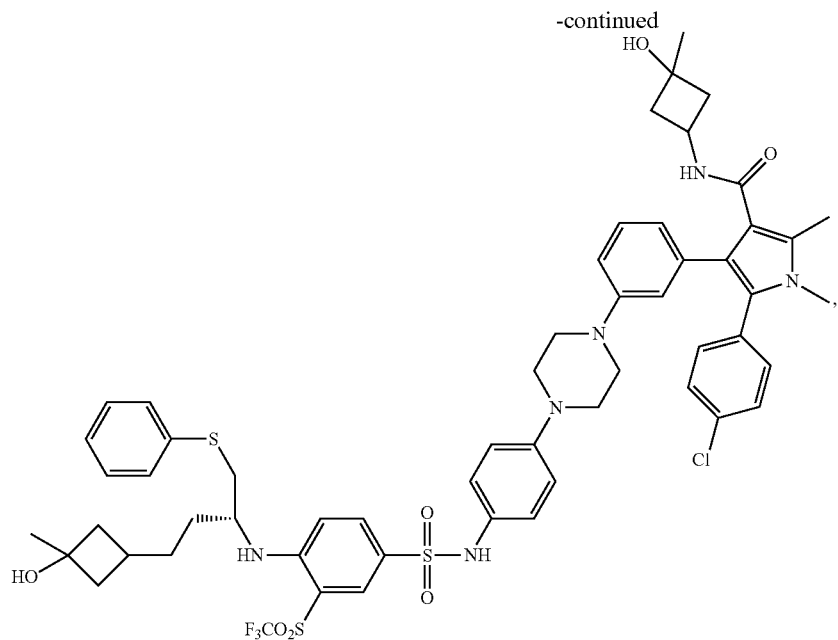
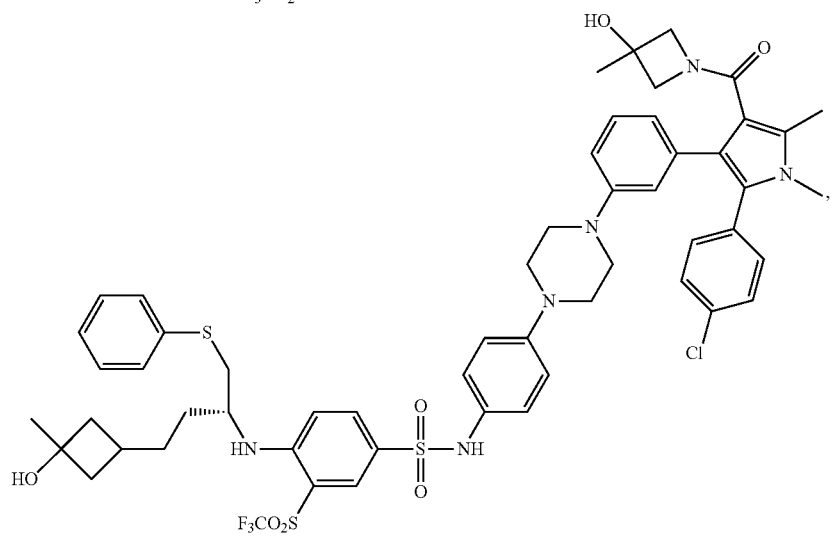
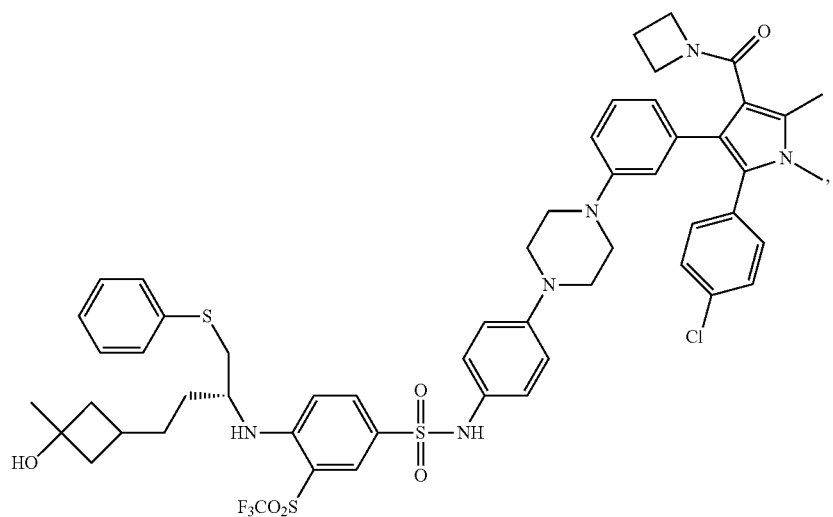

-continued
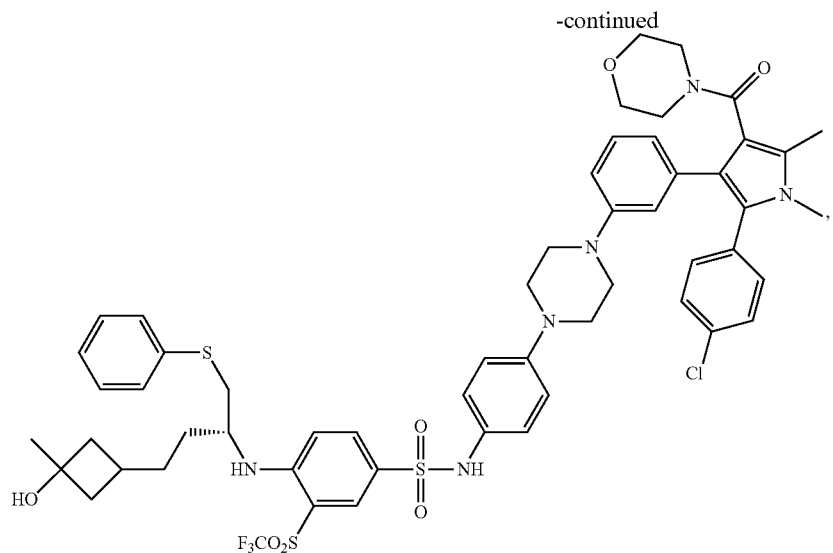
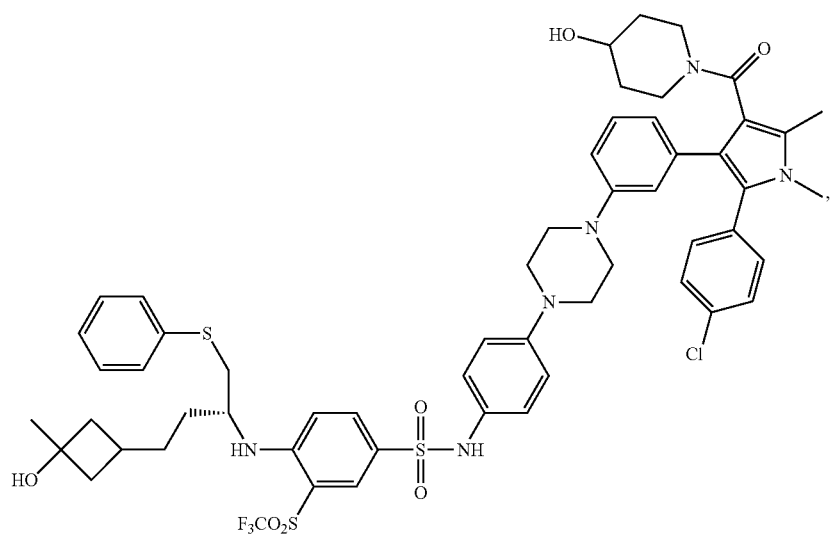
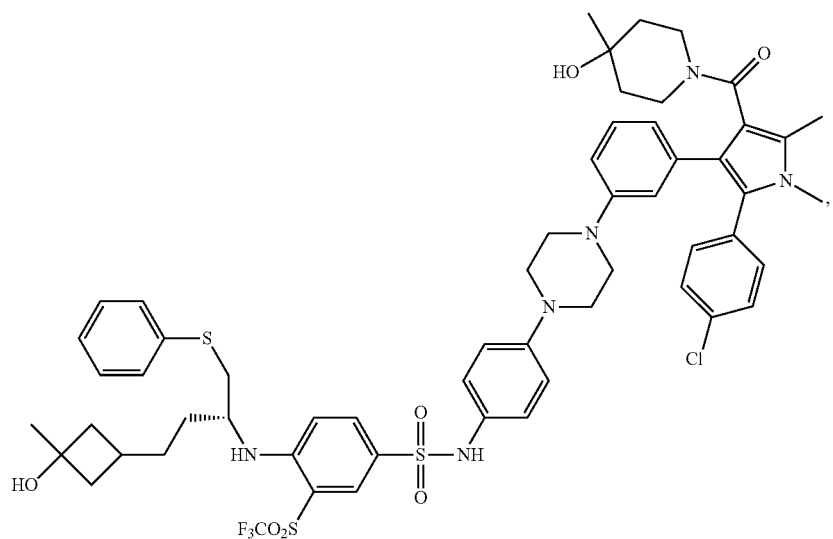

-continued
377
378
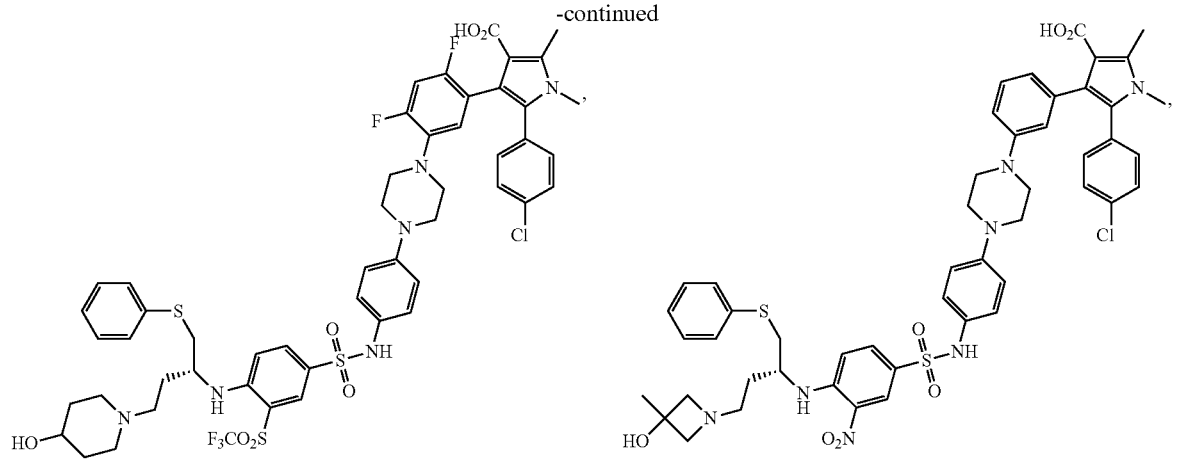
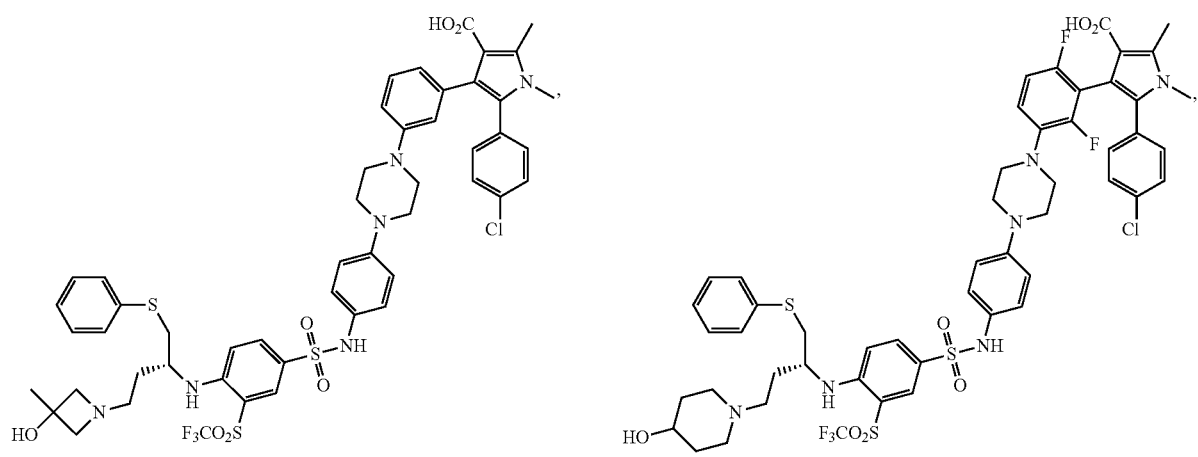
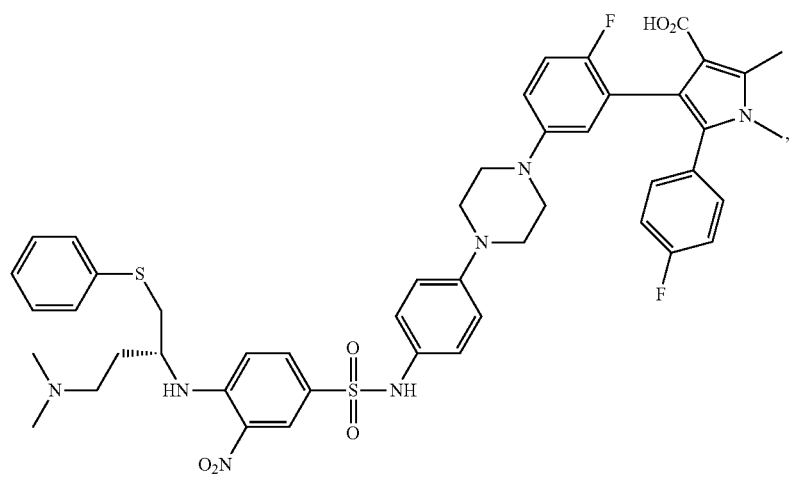

379
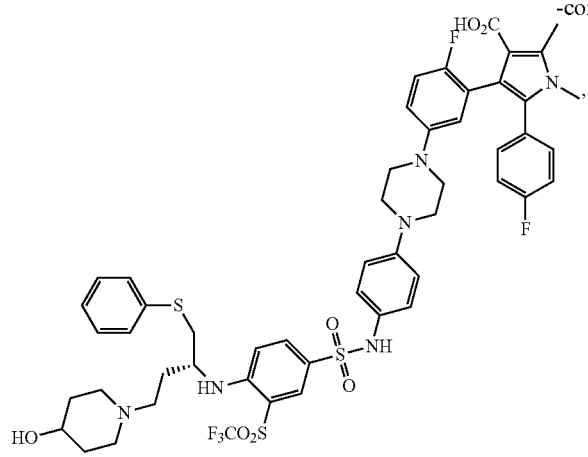
380
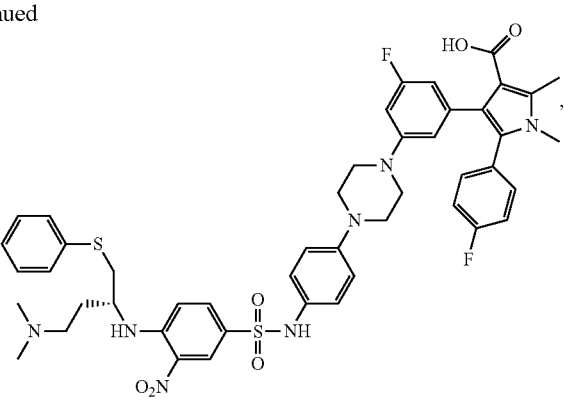
-continued
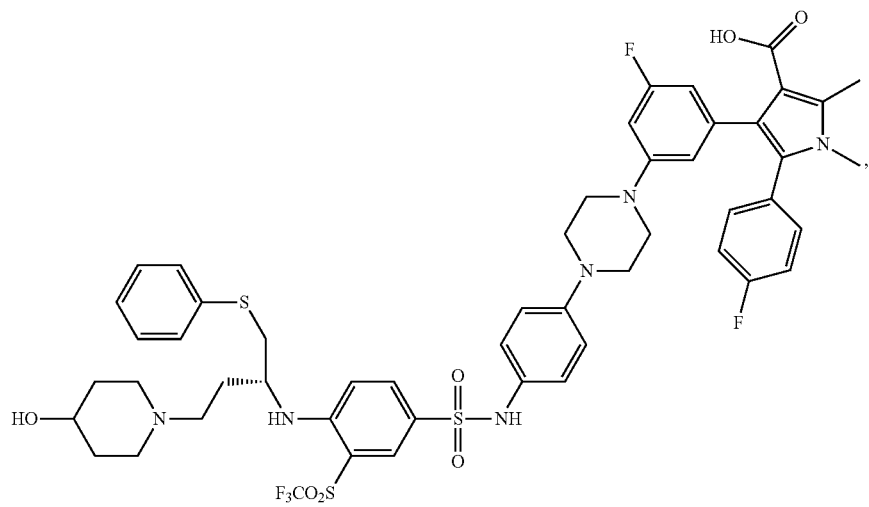
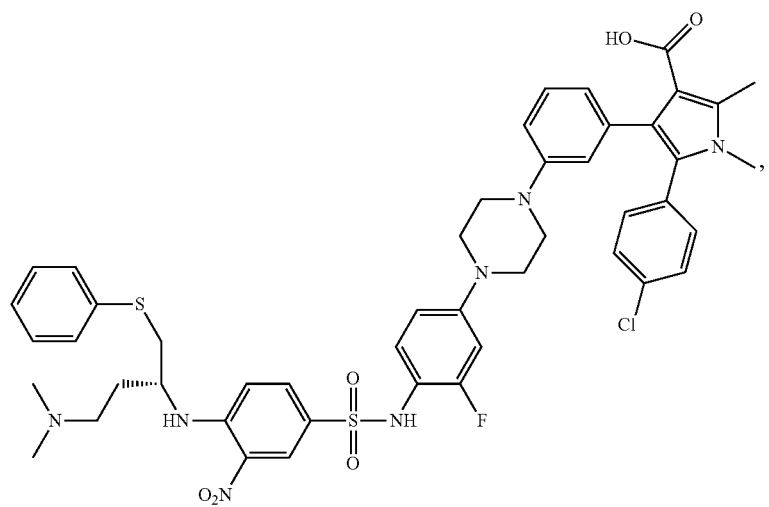

-continued
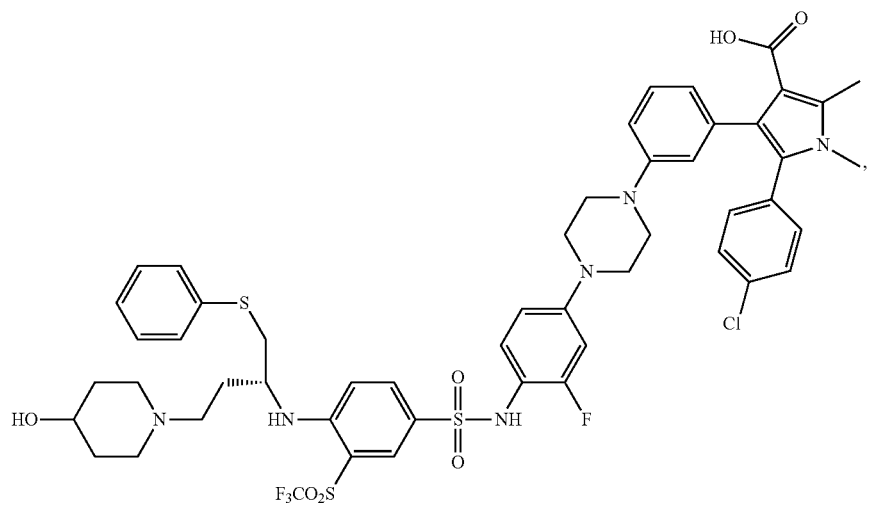
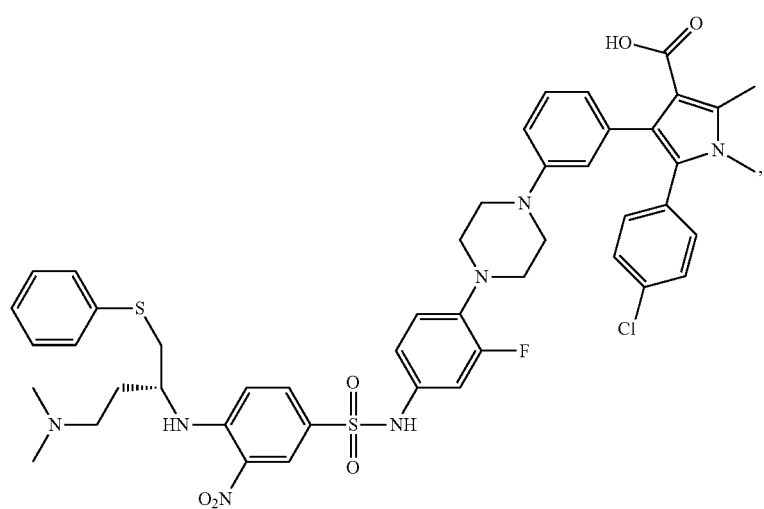
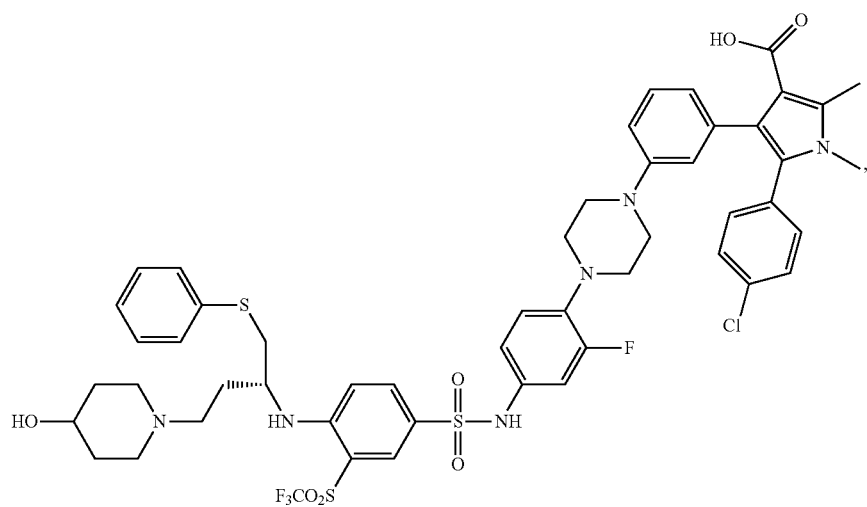

-continued
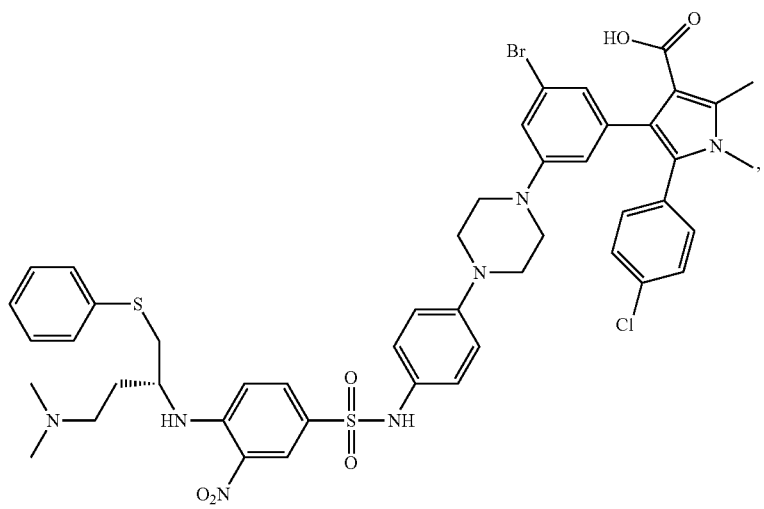
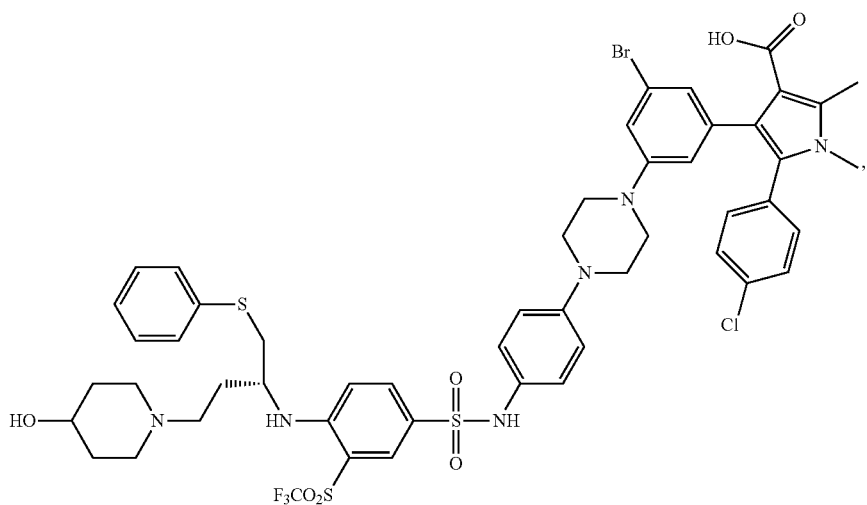
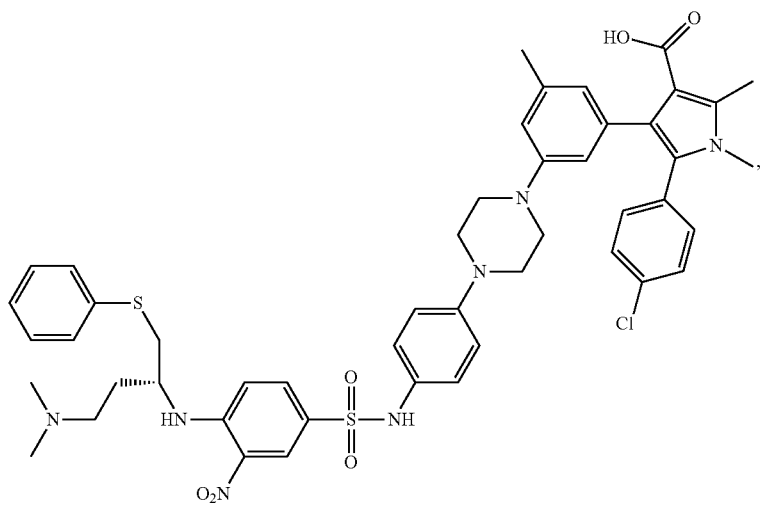

-continued
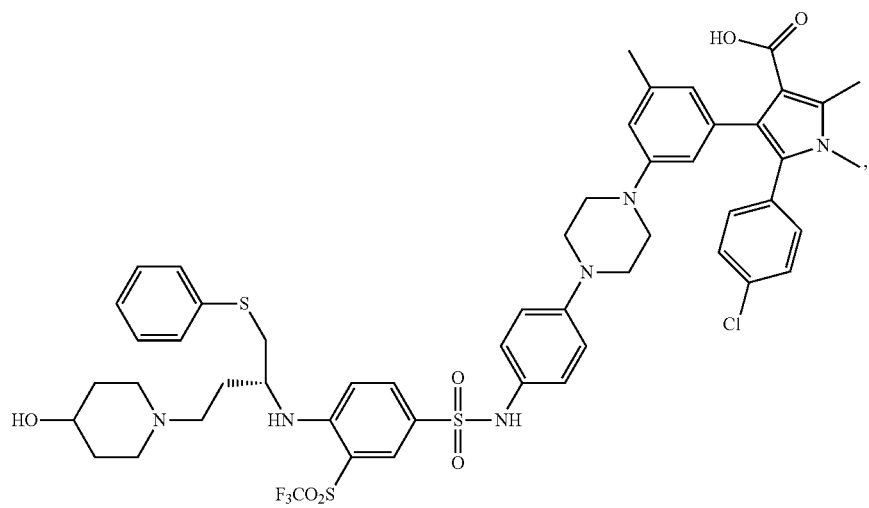
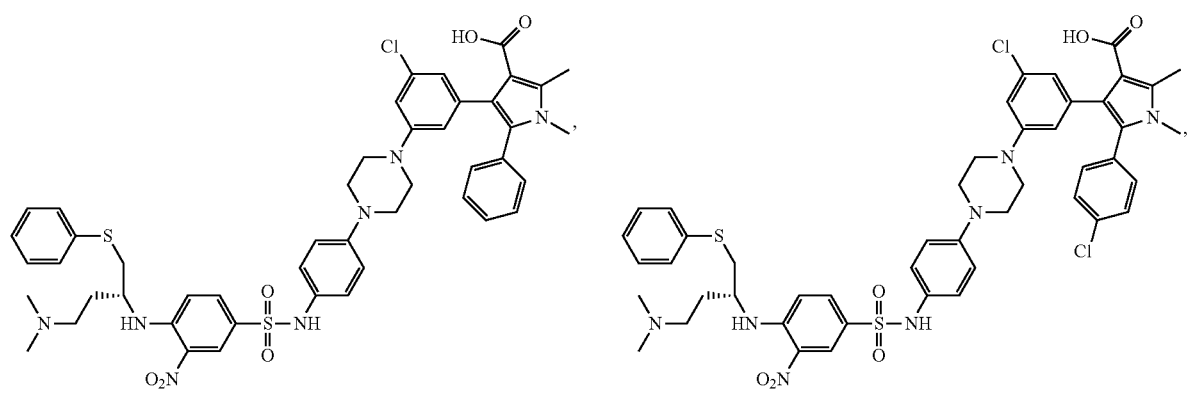
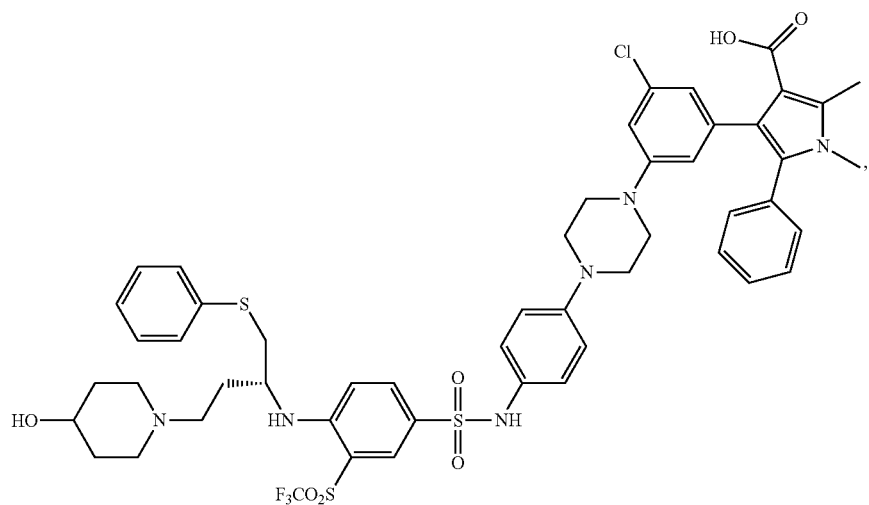

-continued
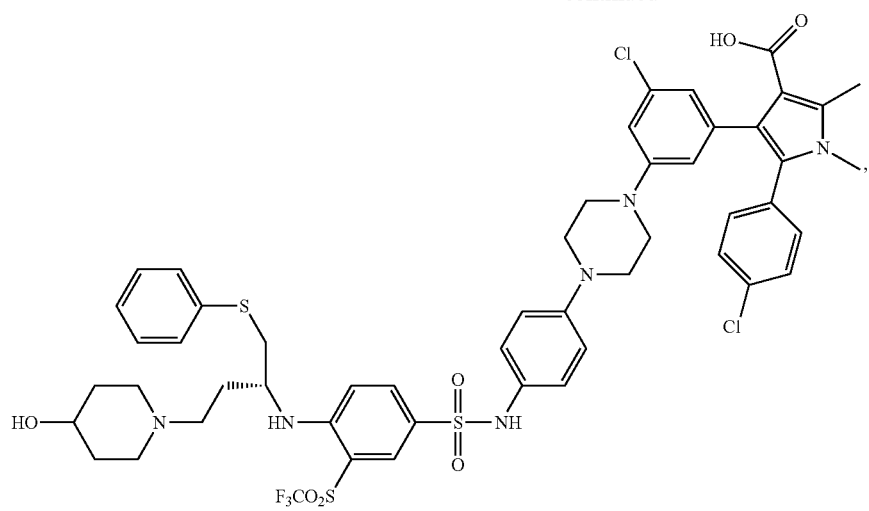
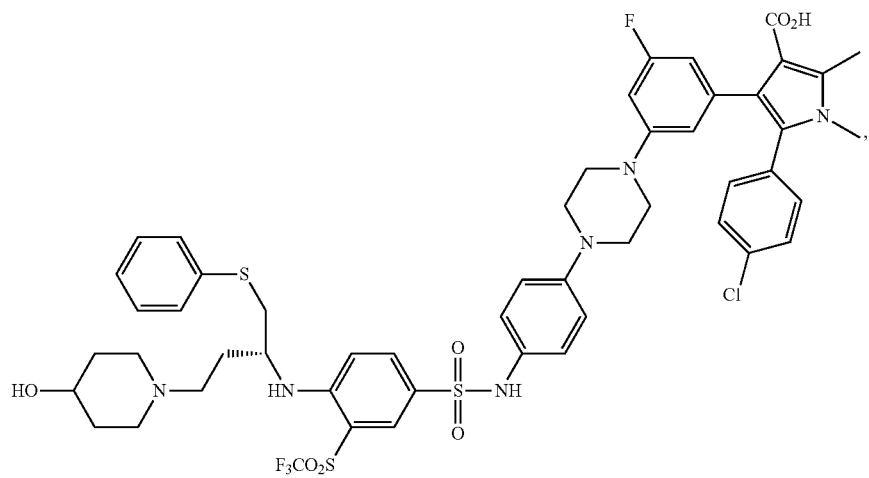
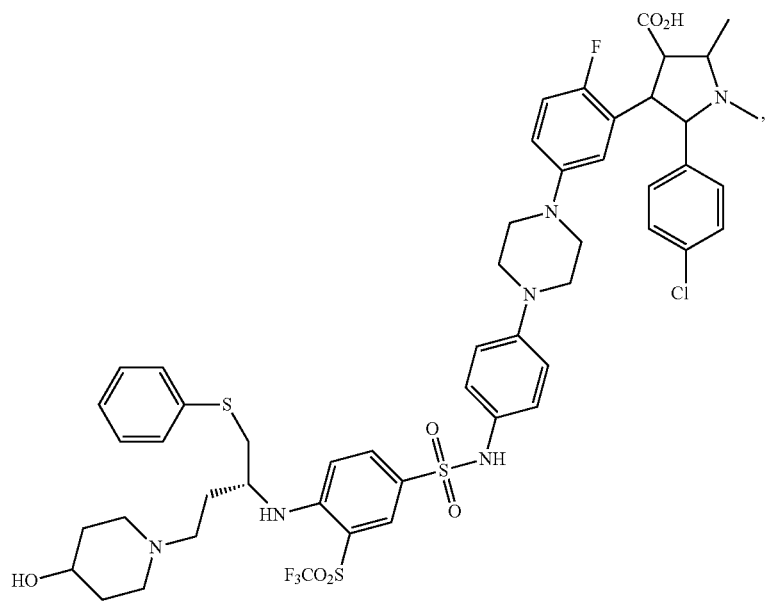

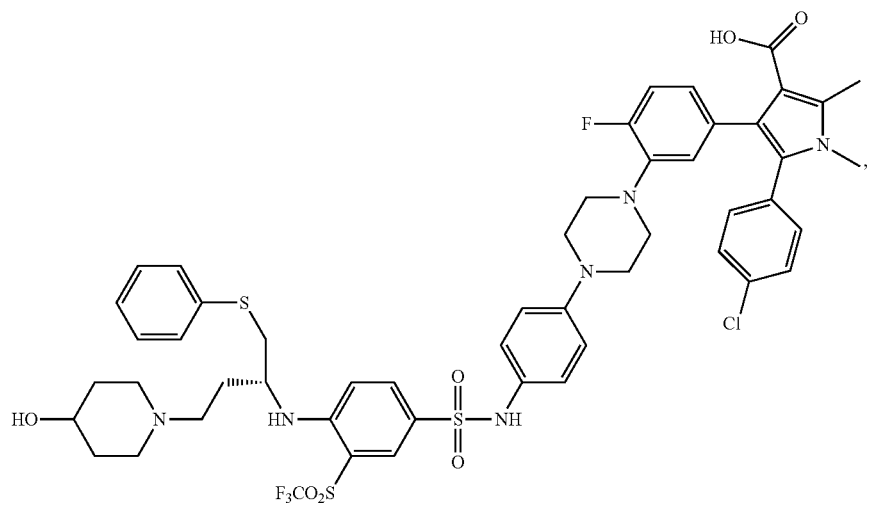
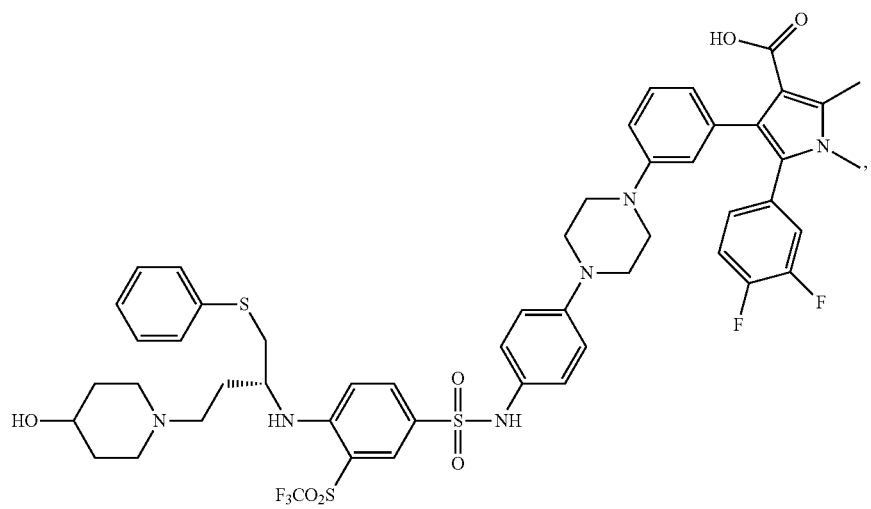
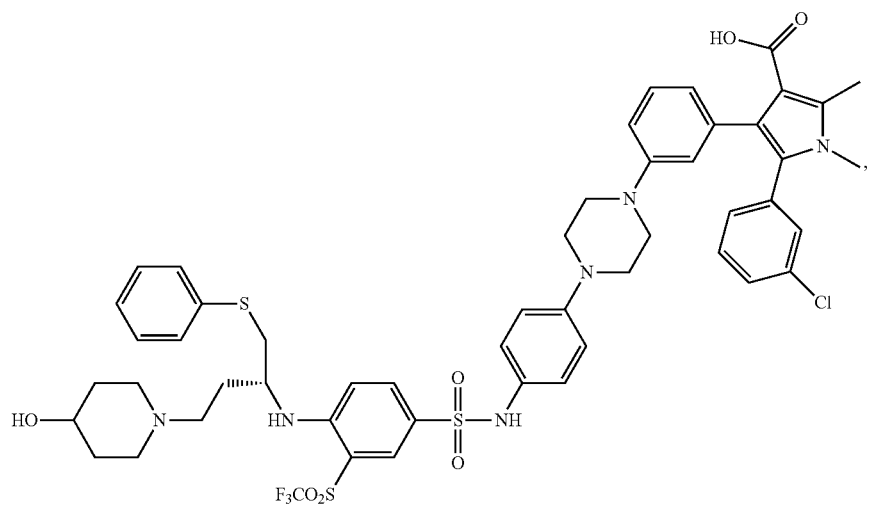

-continued
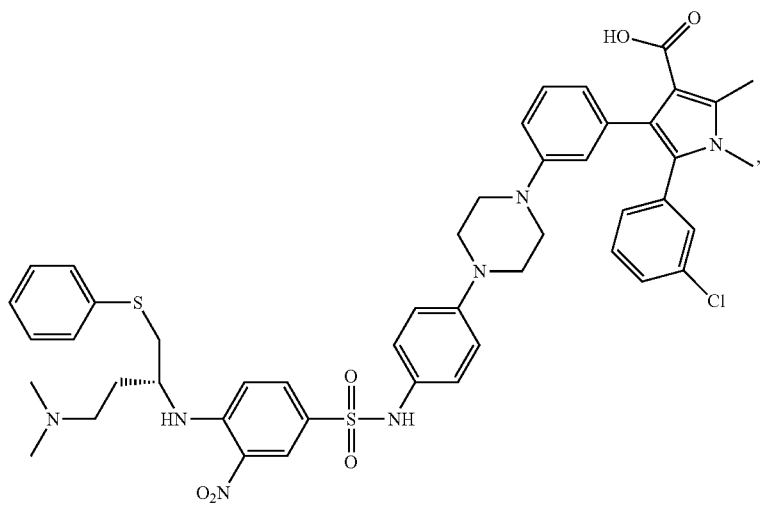
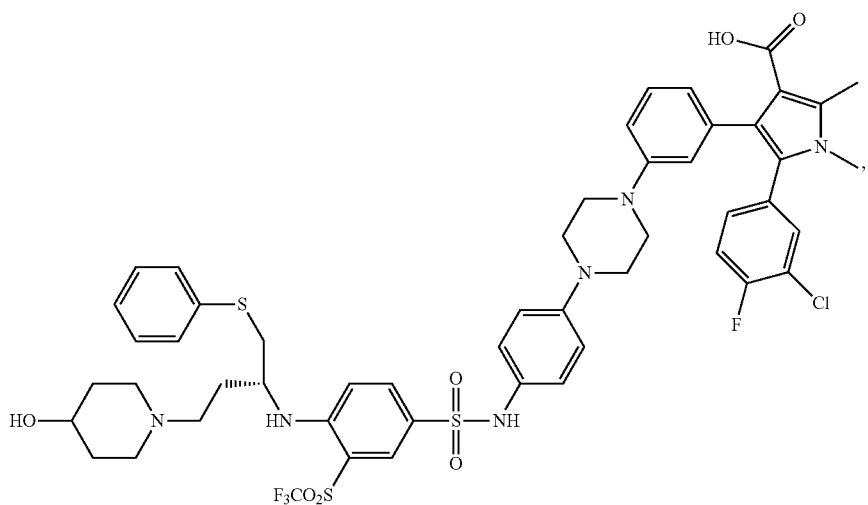
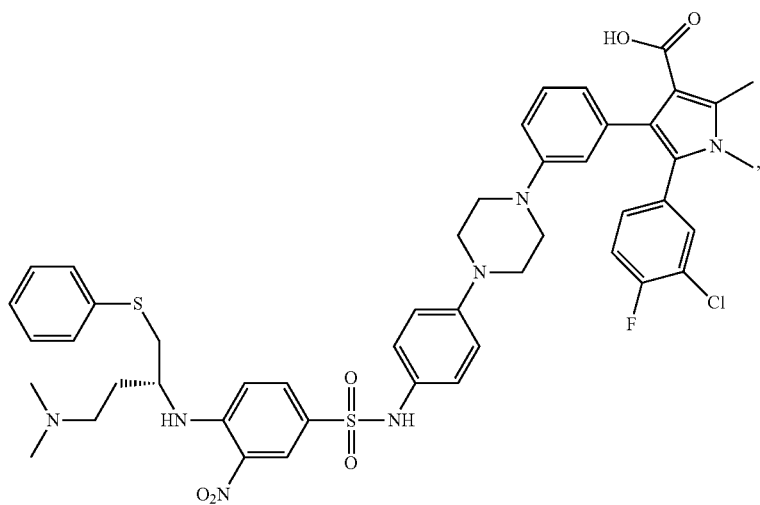

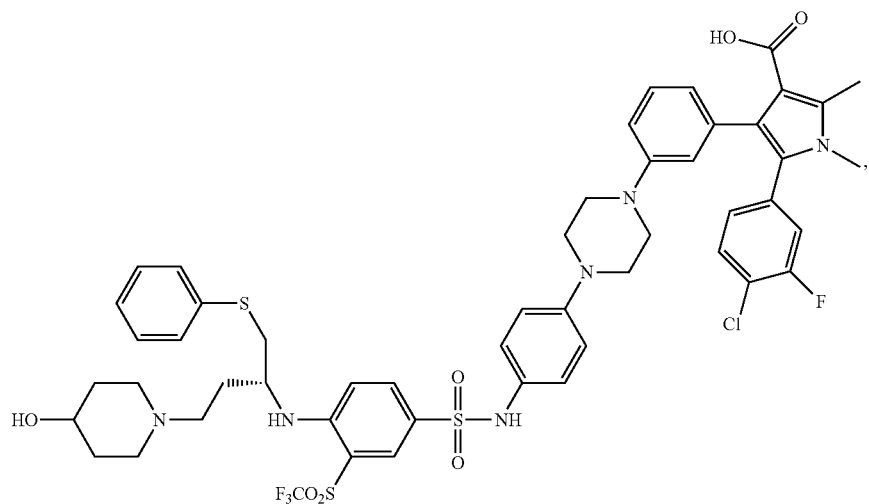
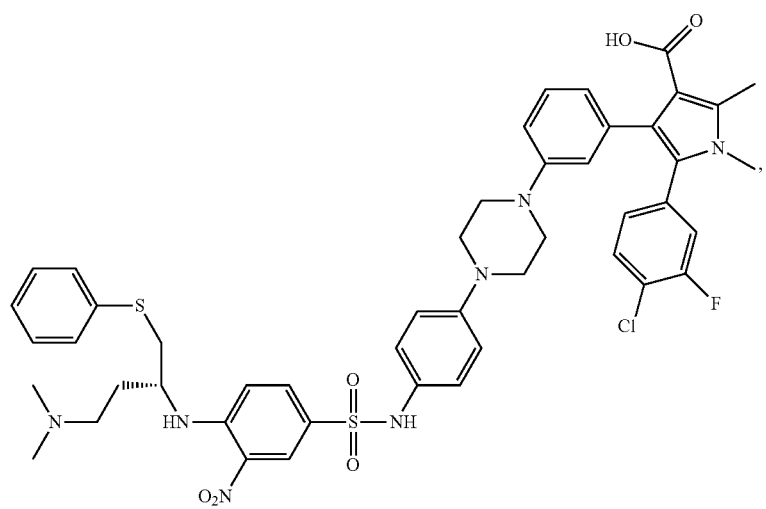
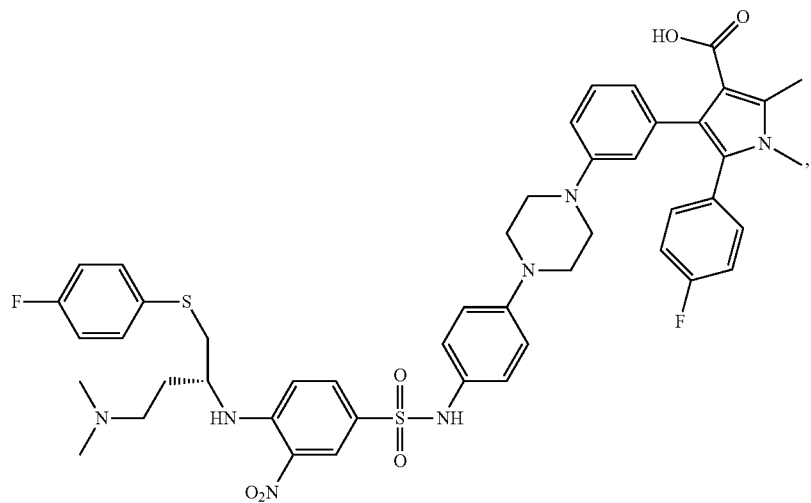

-continued
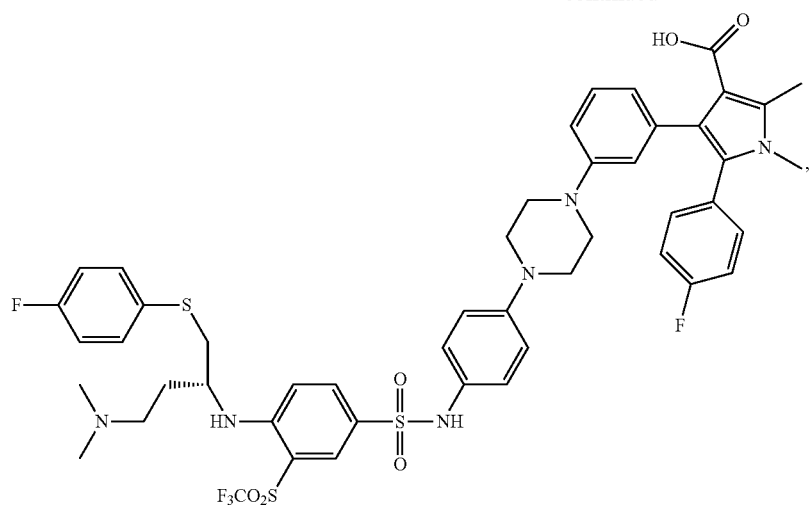
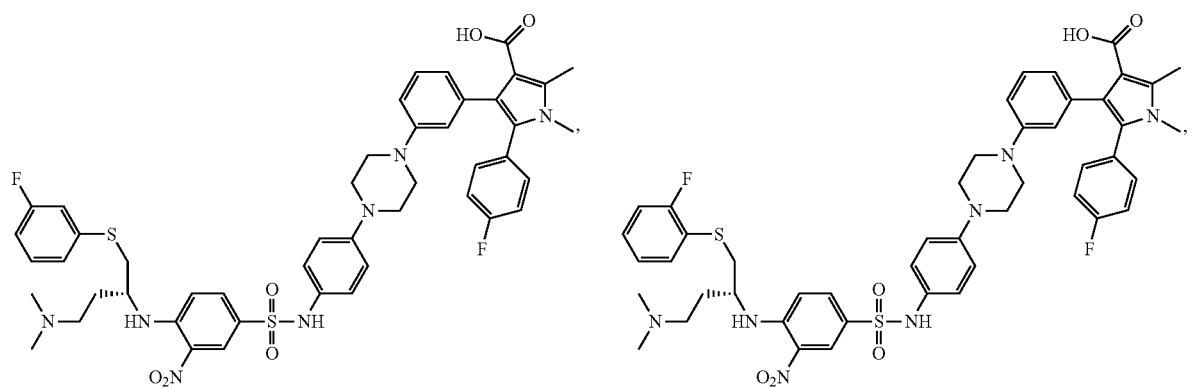
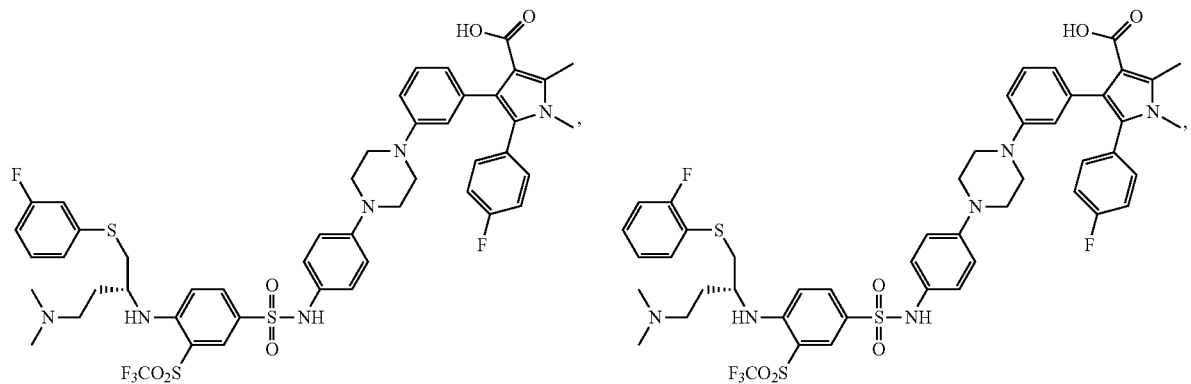

-continued
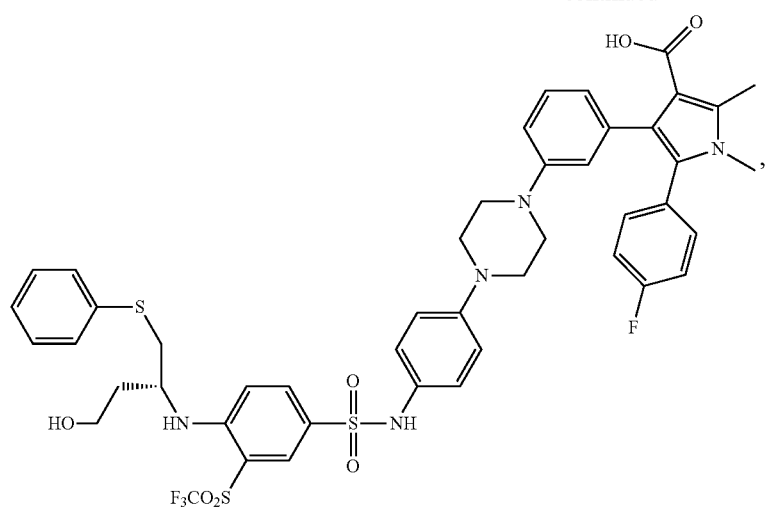
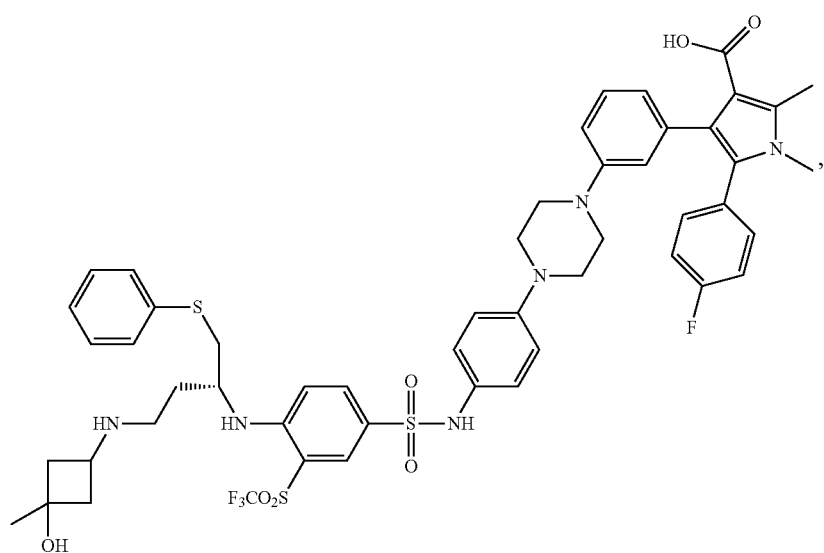
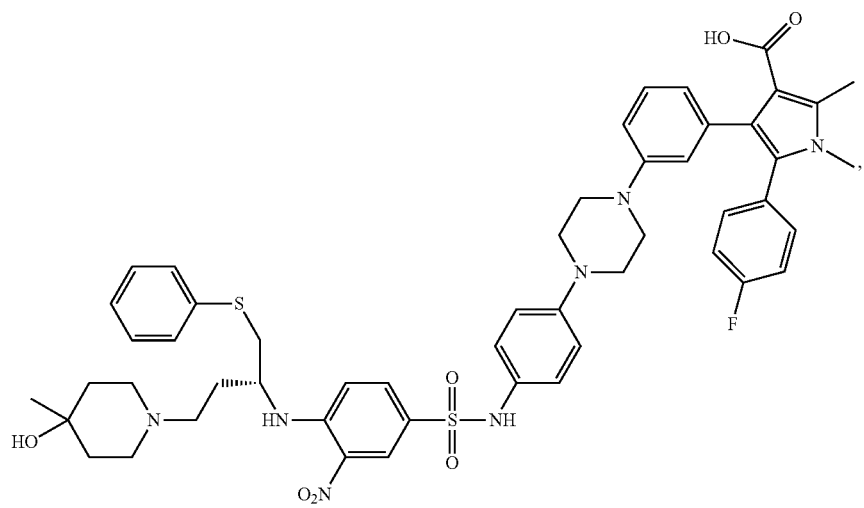

-continued
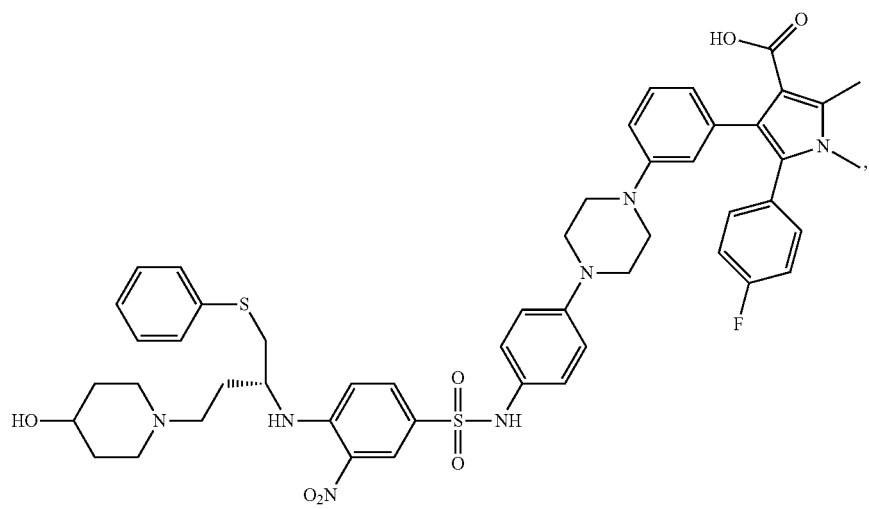
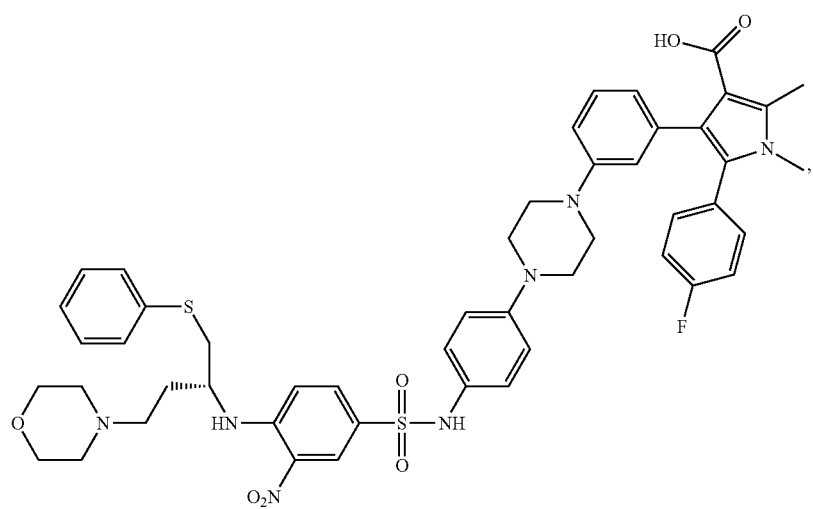
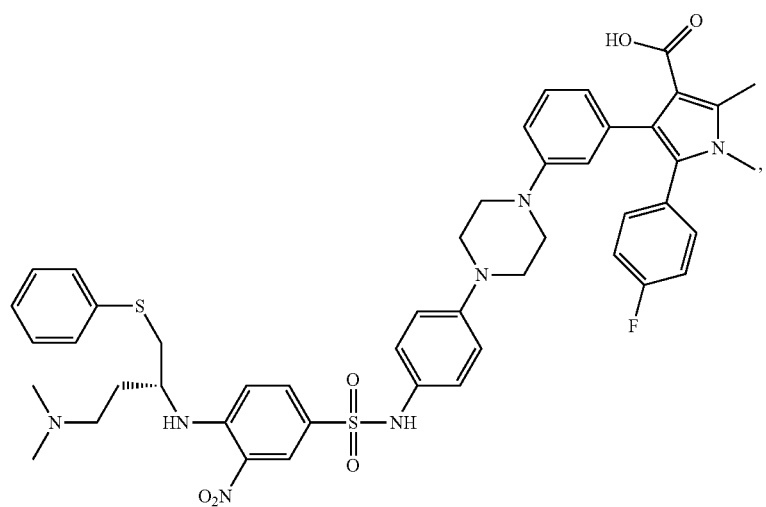

-continued
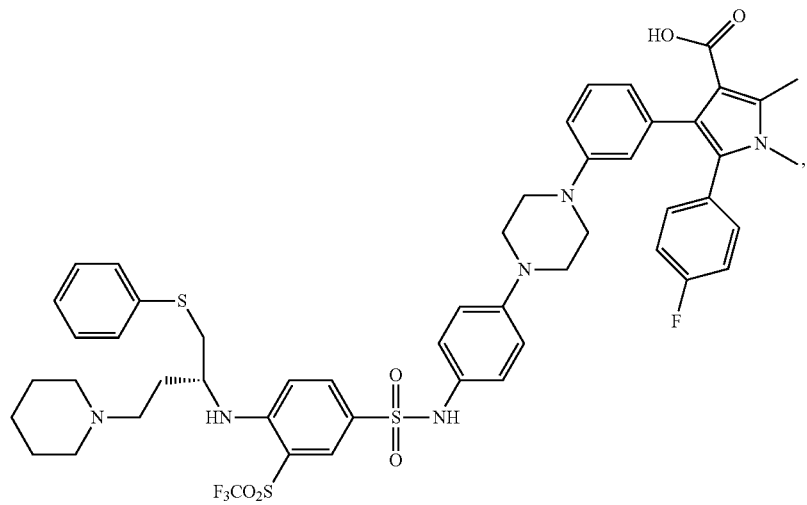
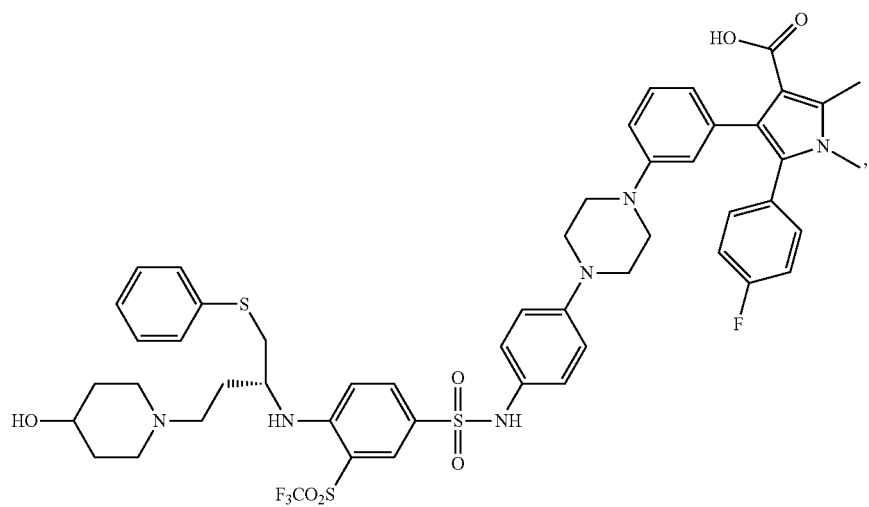
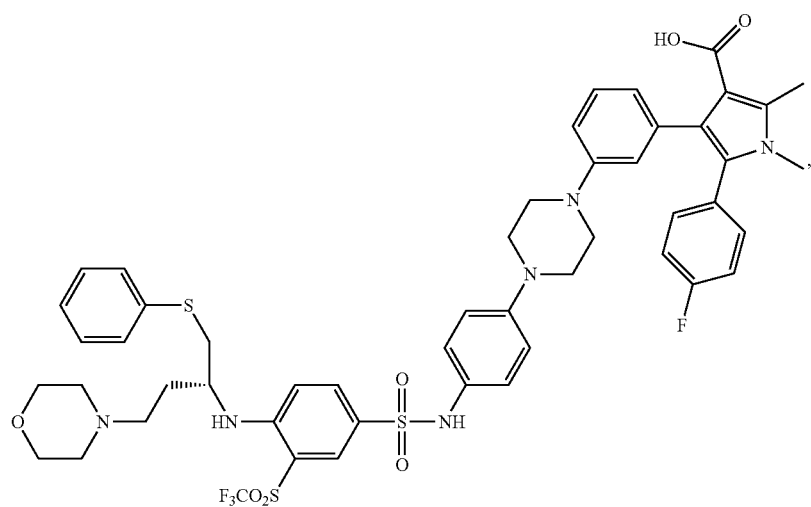

-continued
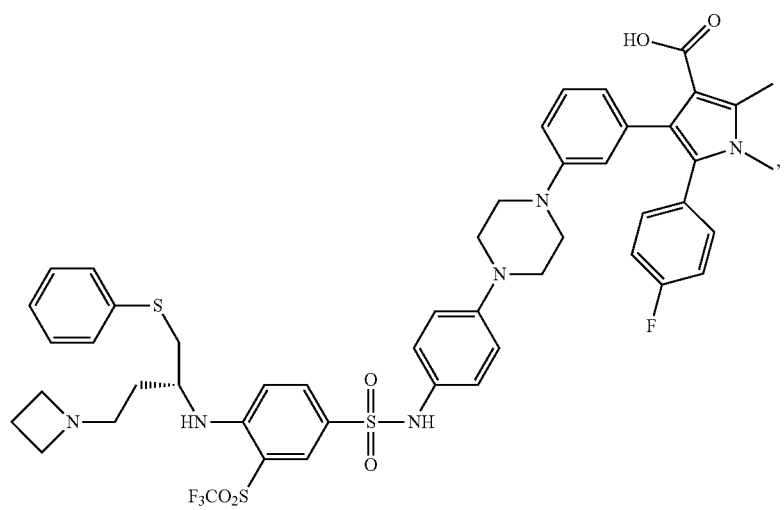
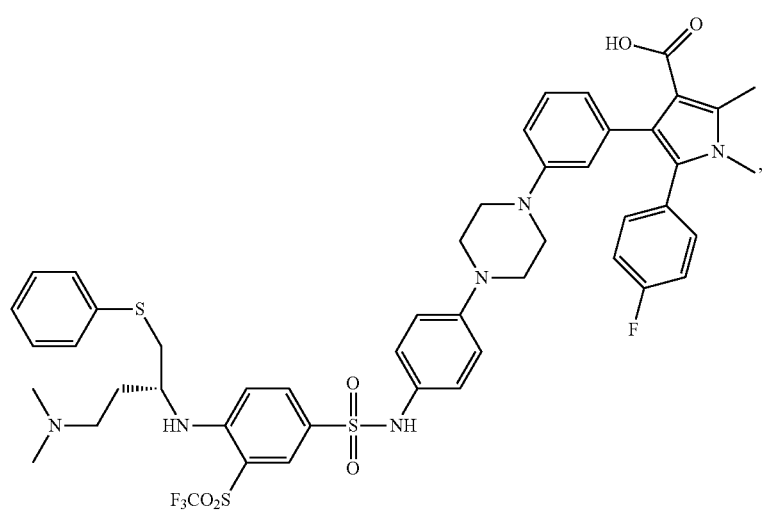
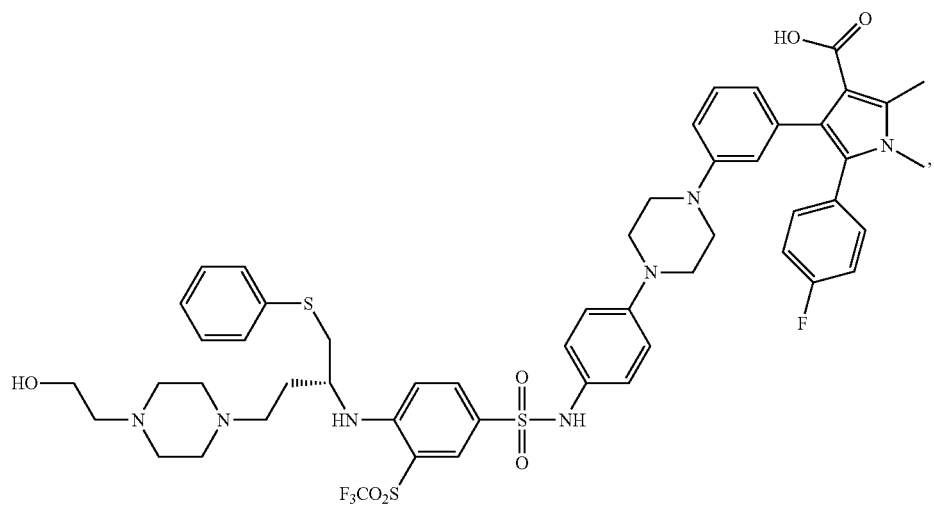

-continued
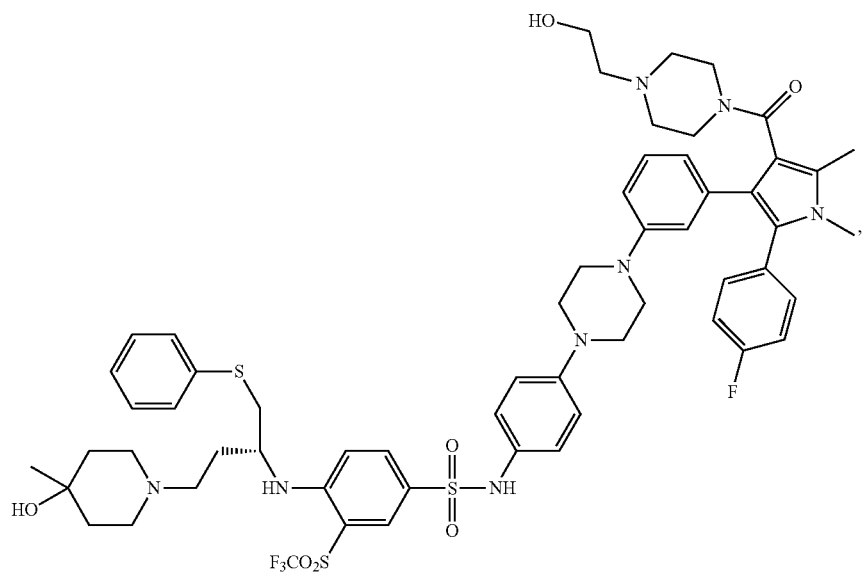
405
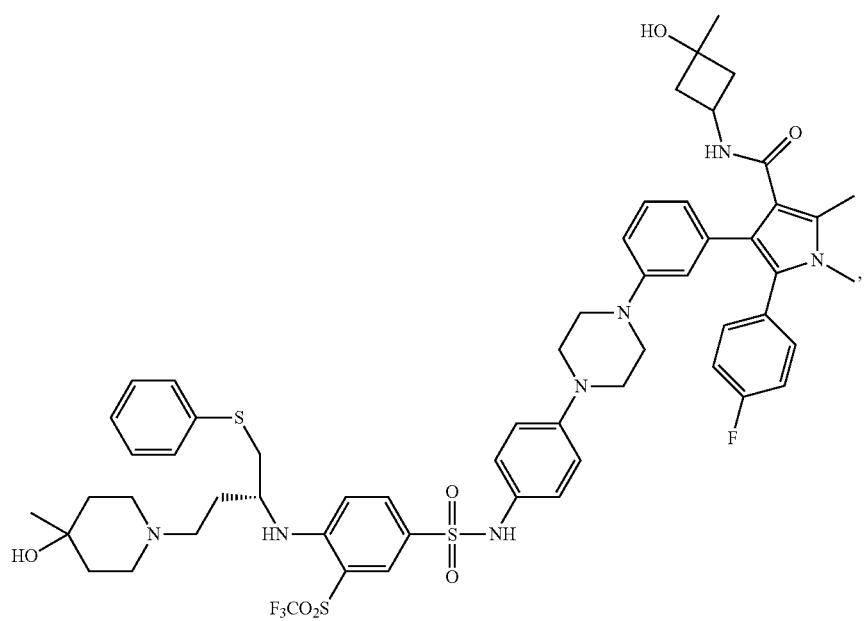
406

-continued
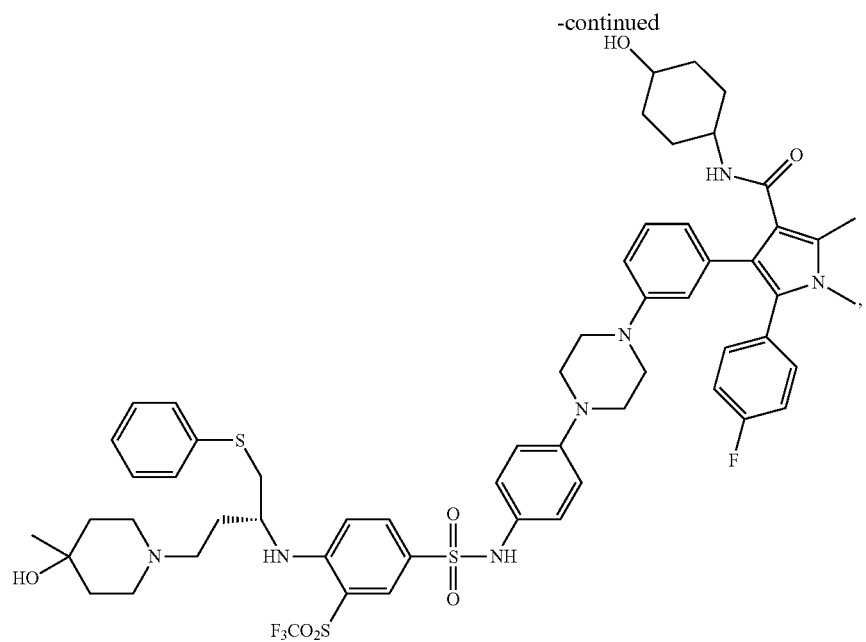
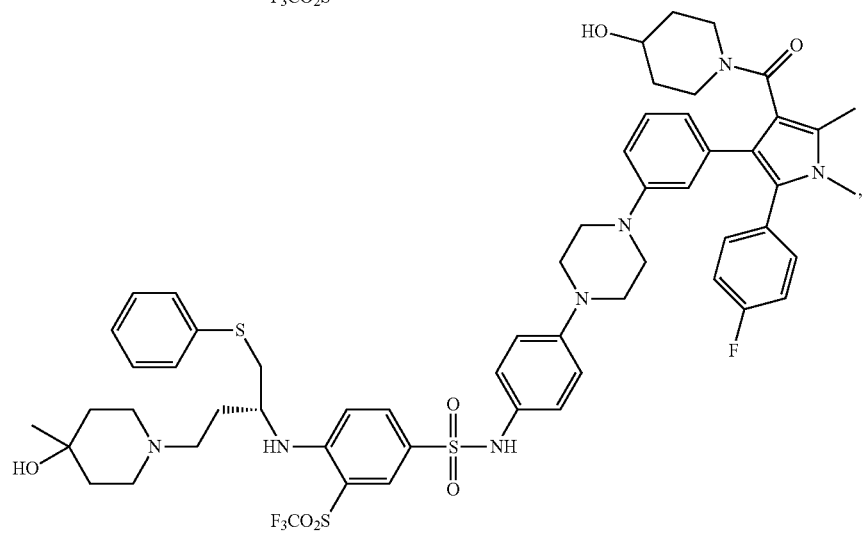
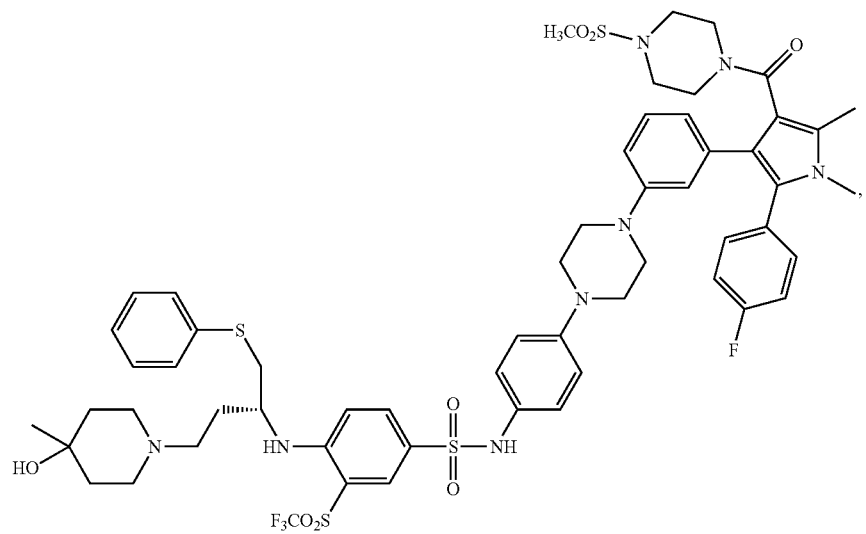

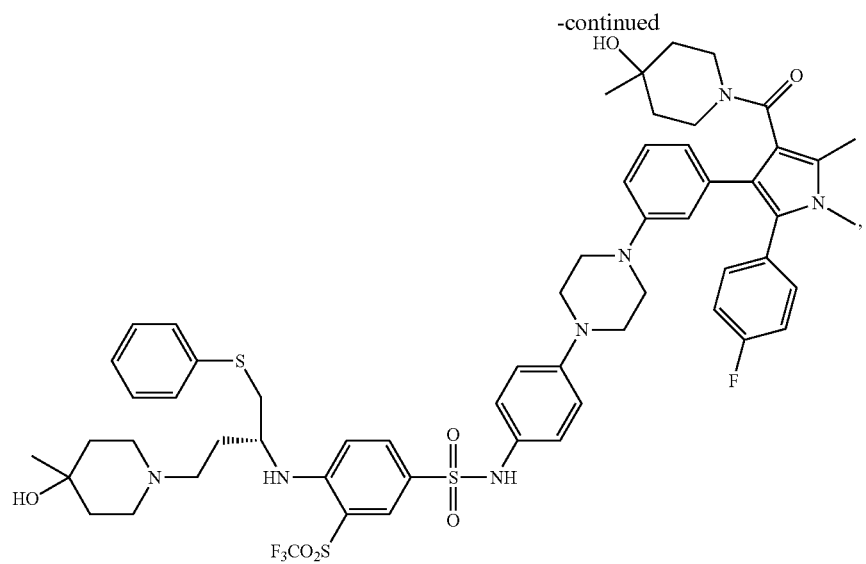
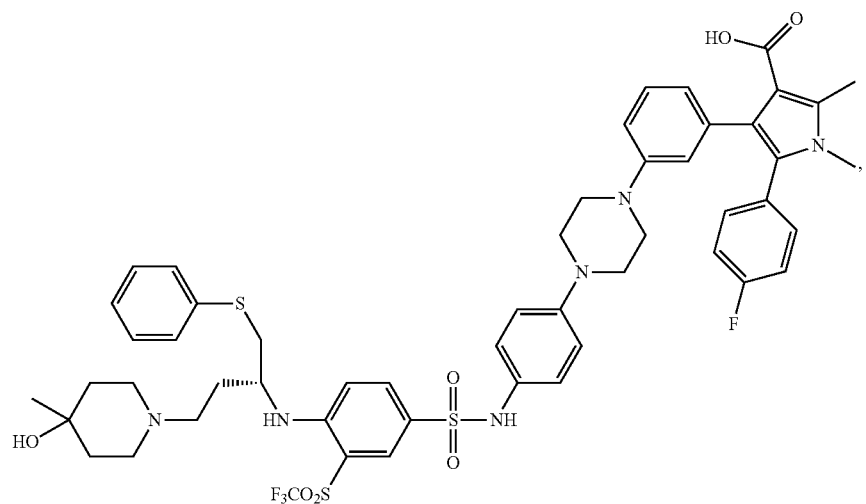
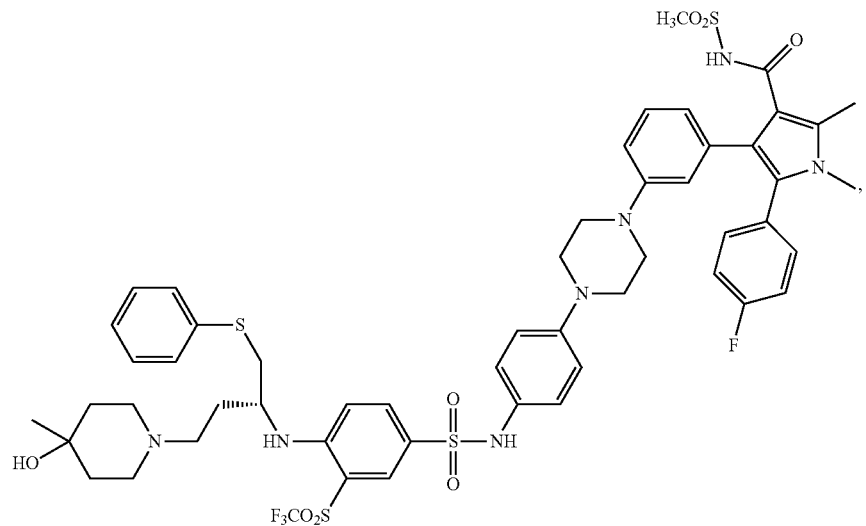

-continued
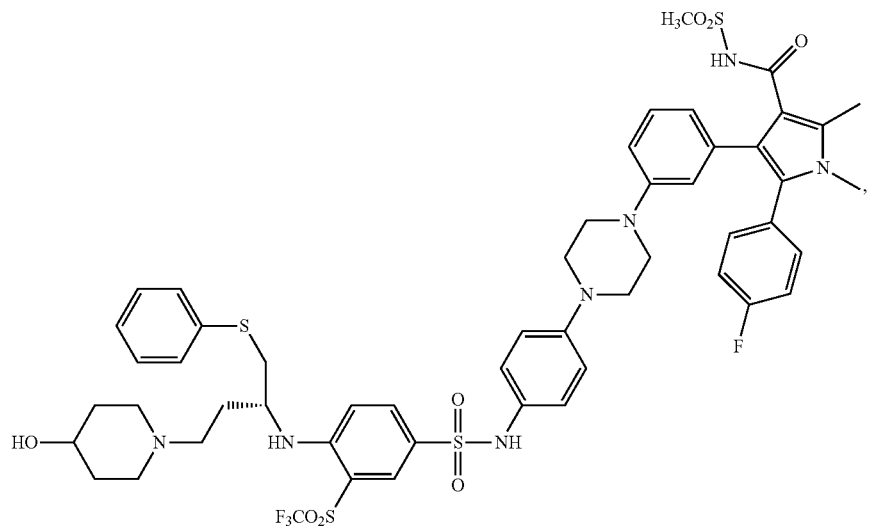
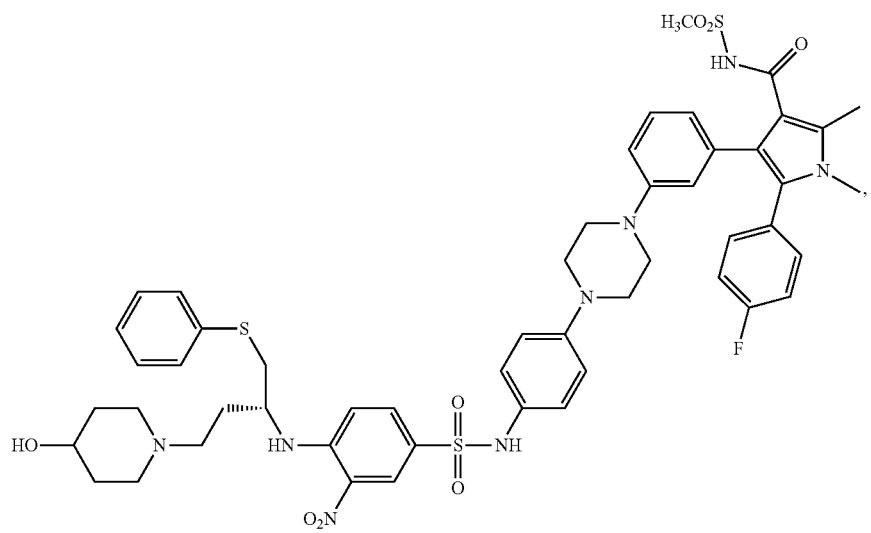
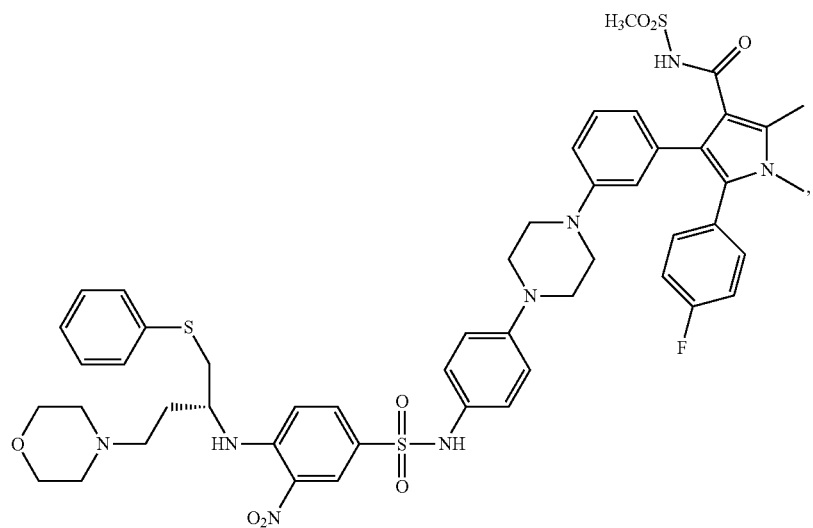

-continued
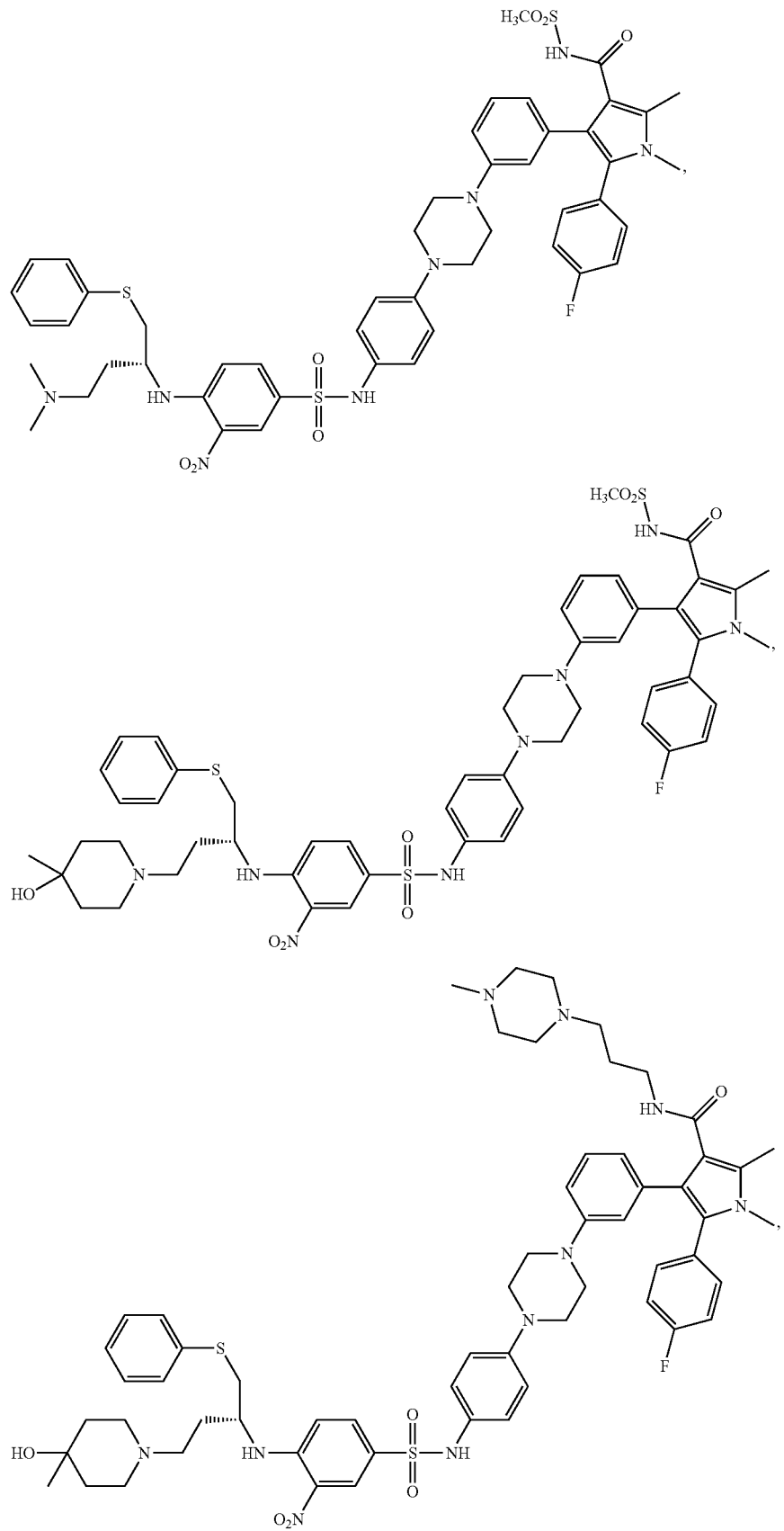

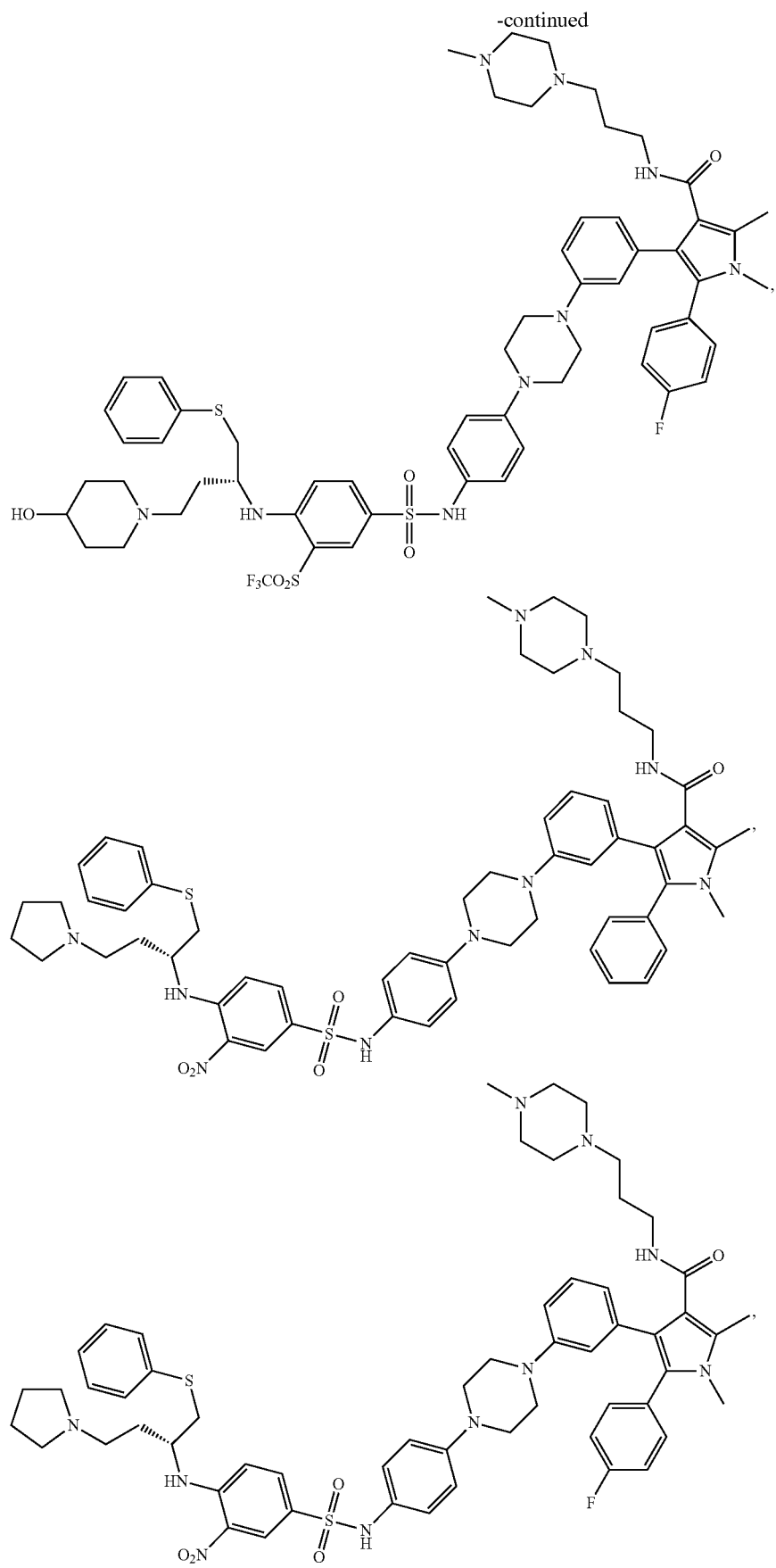

417 418
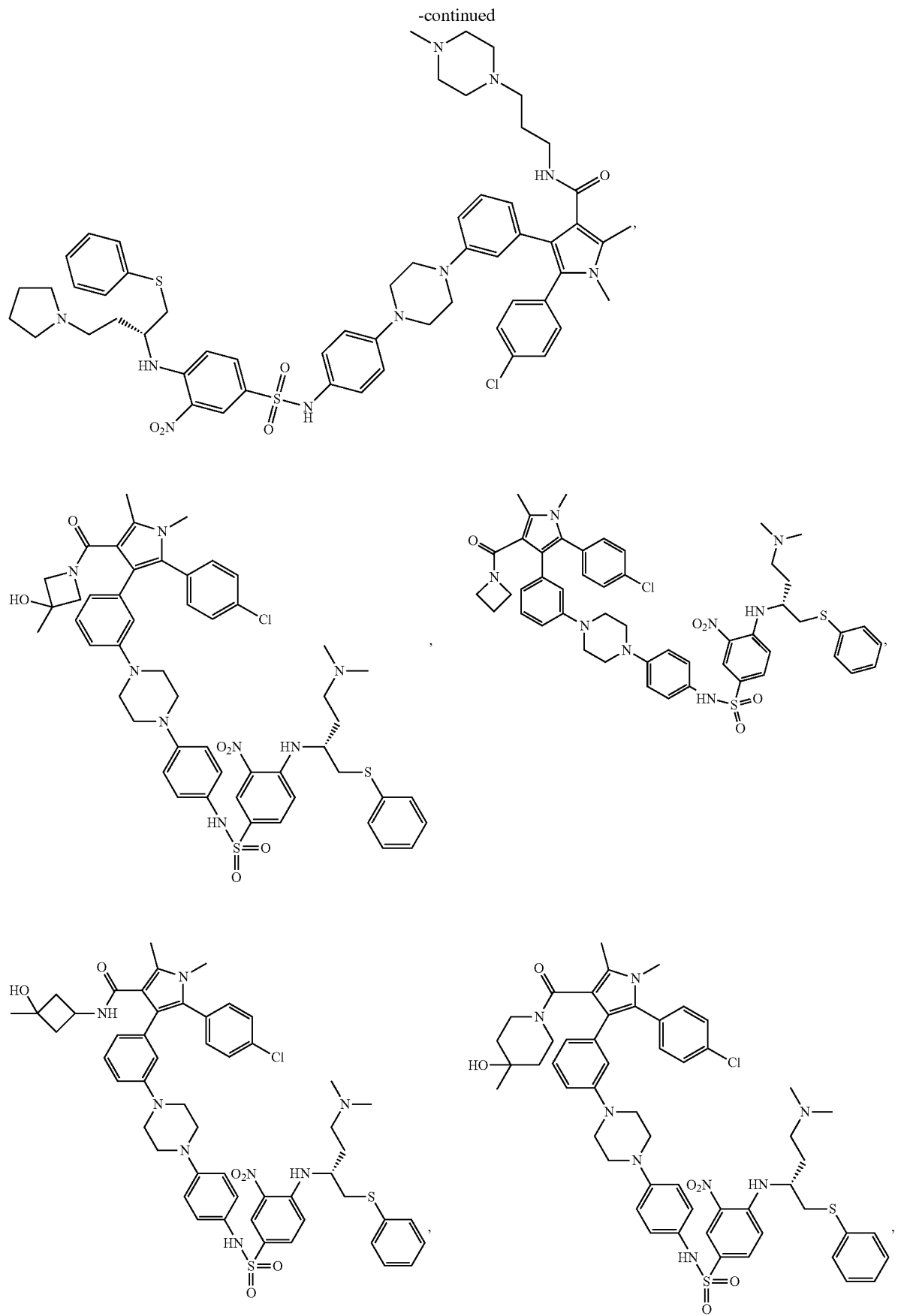

-continued
419
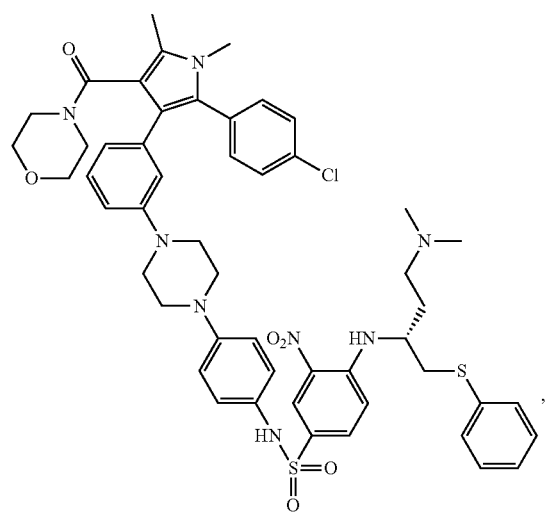
420
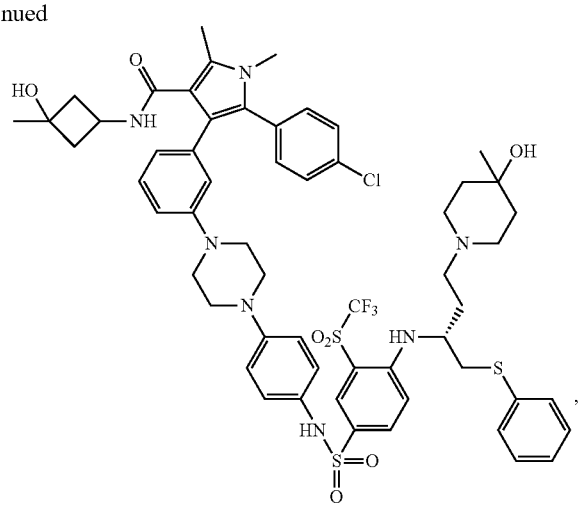
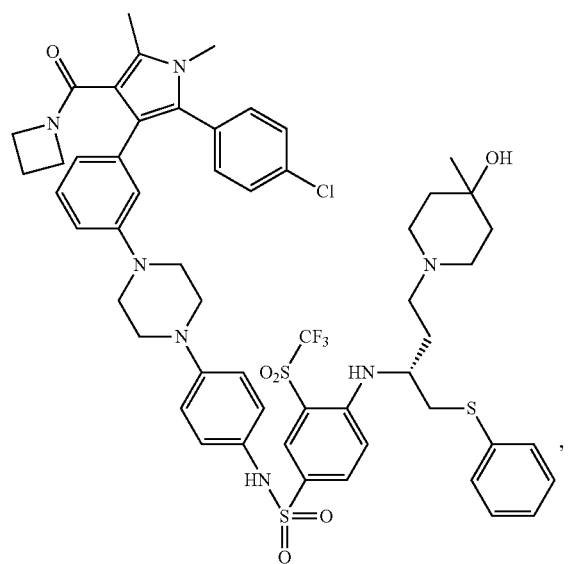
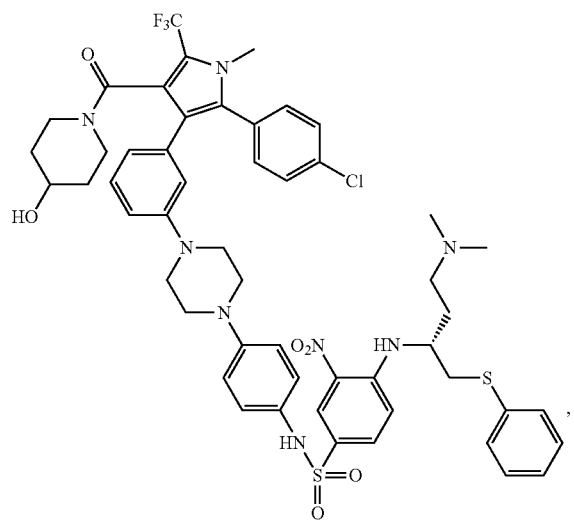
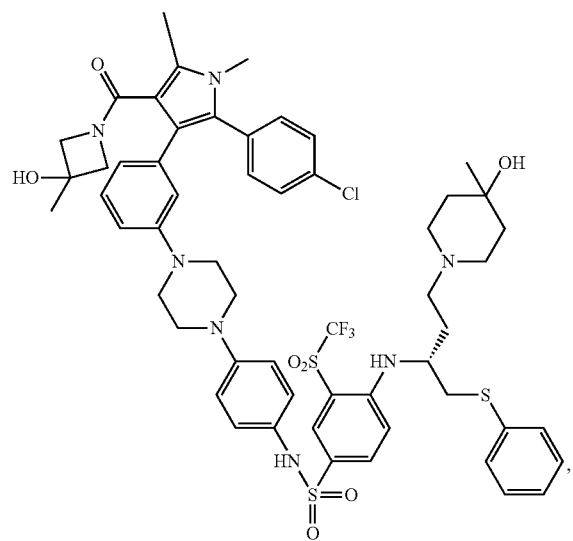
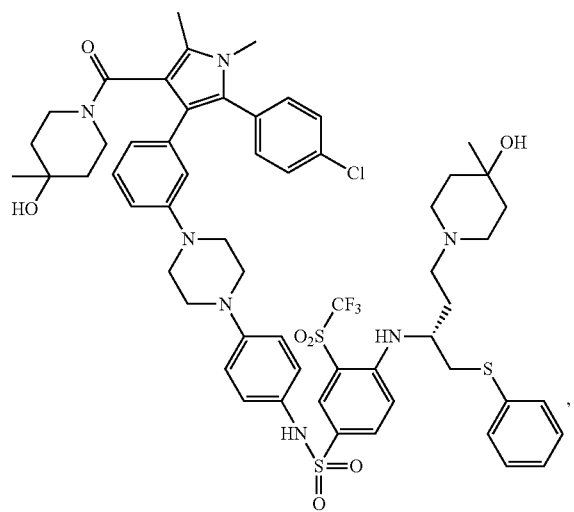

421
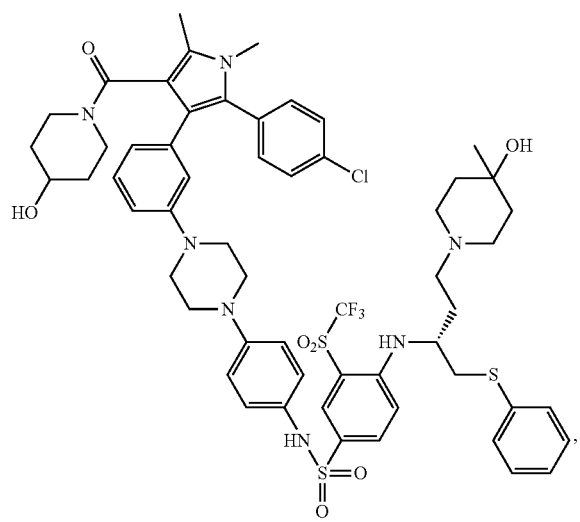
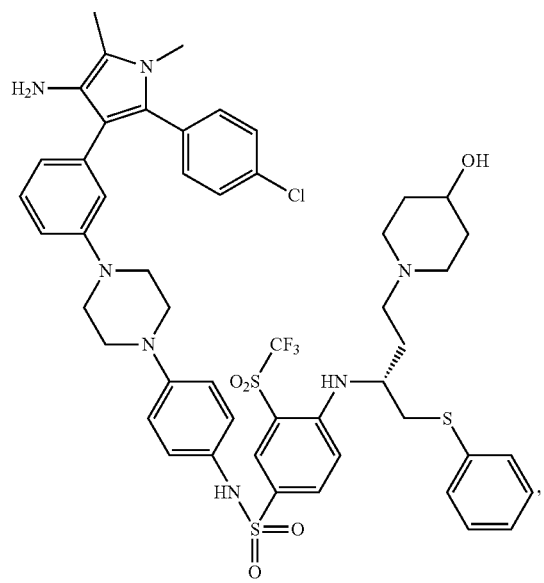
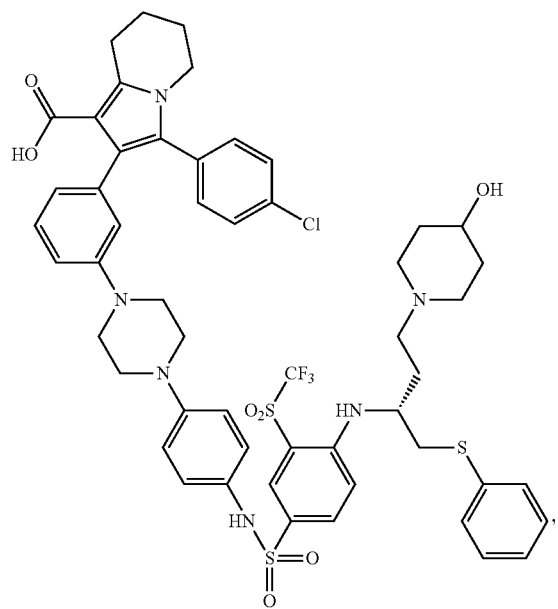
-continued
422
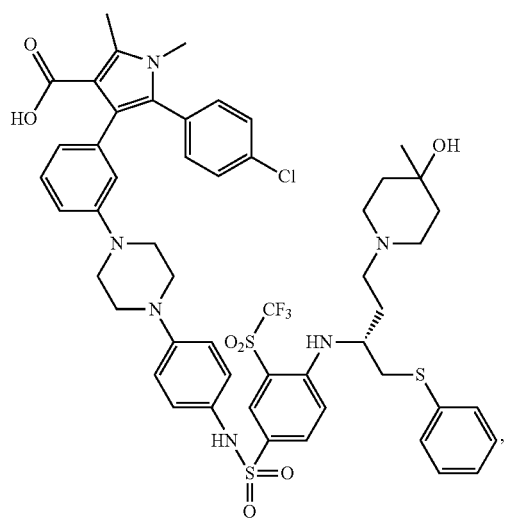
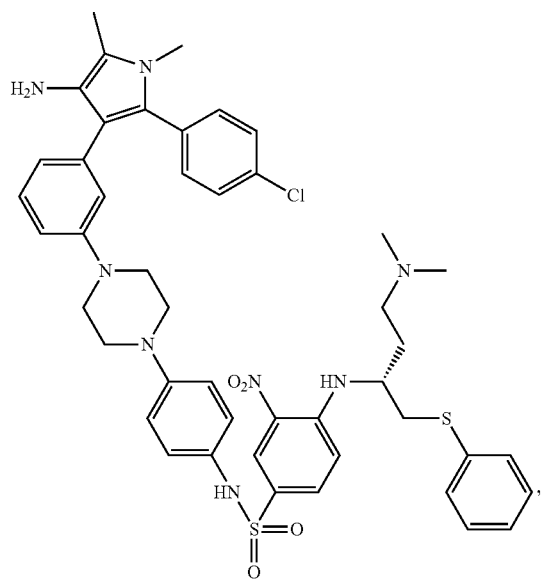
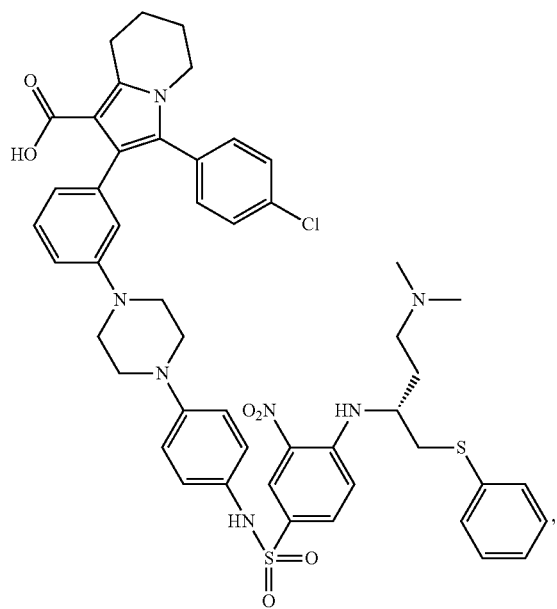

-continued
423
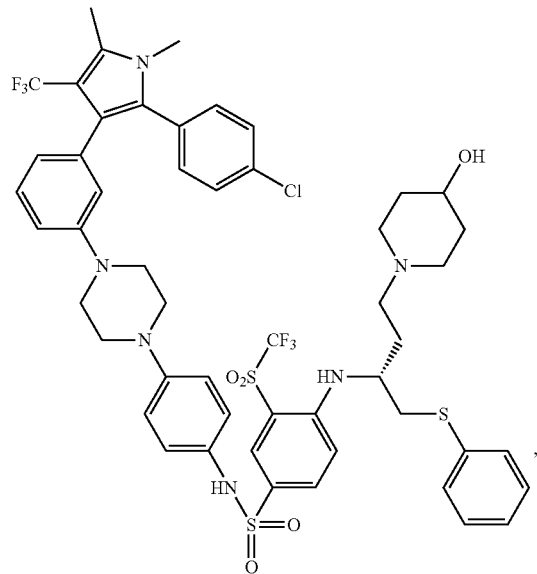
424
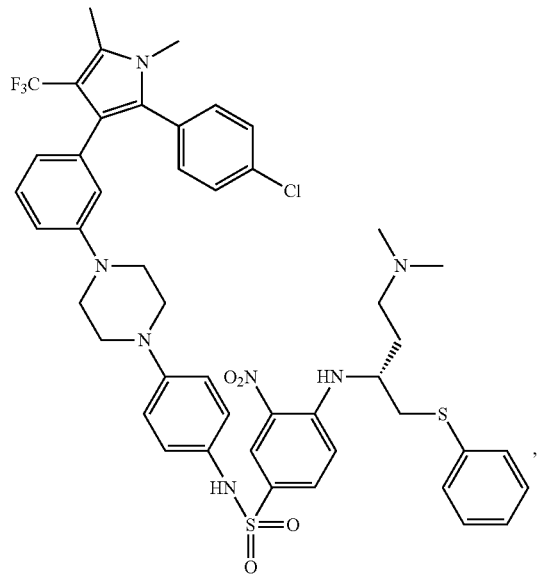
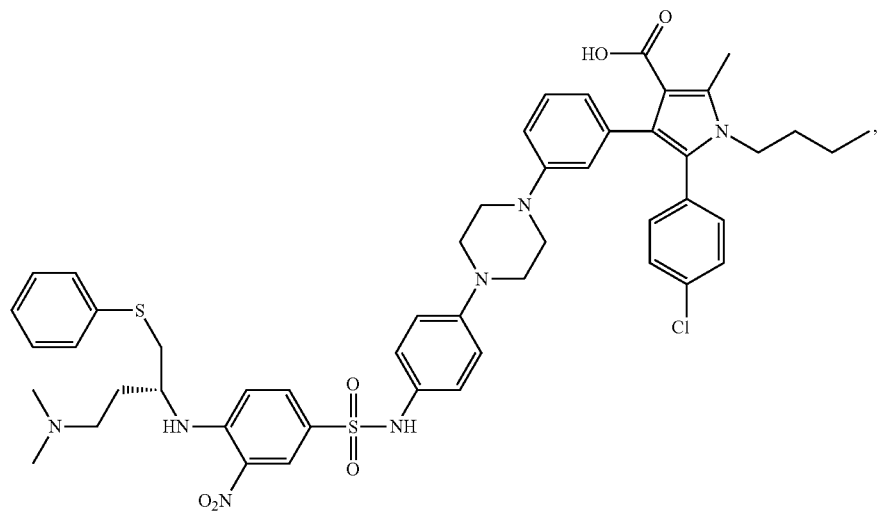
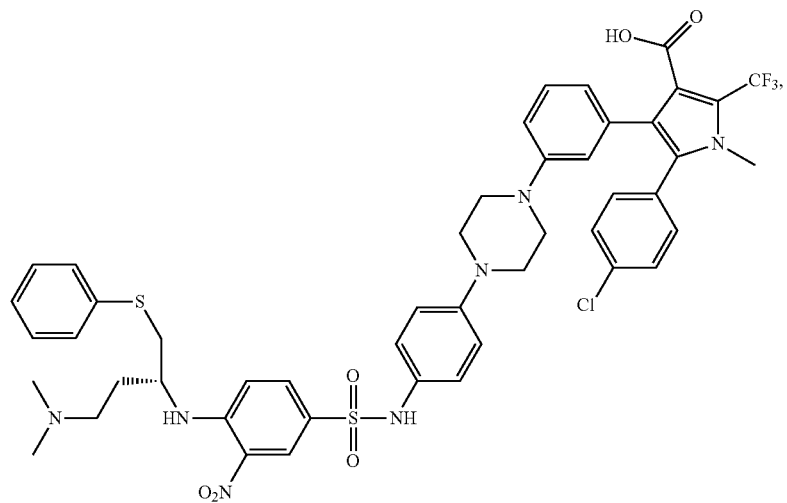

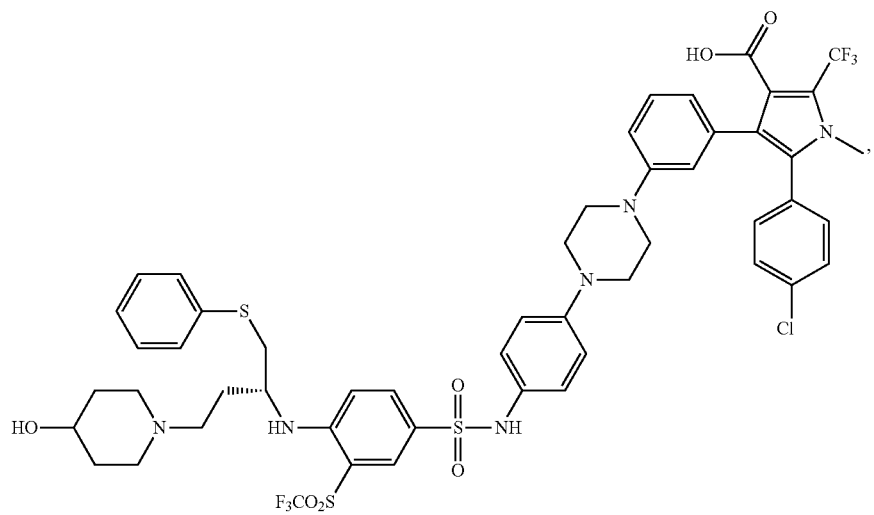
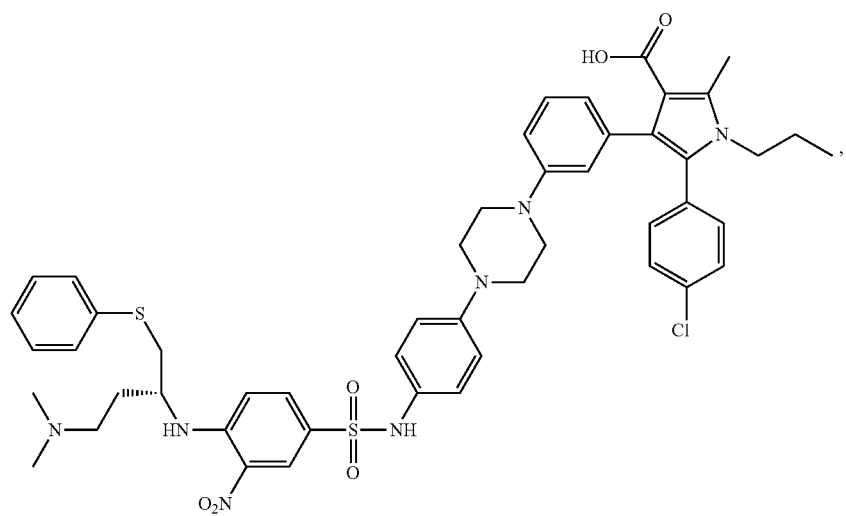
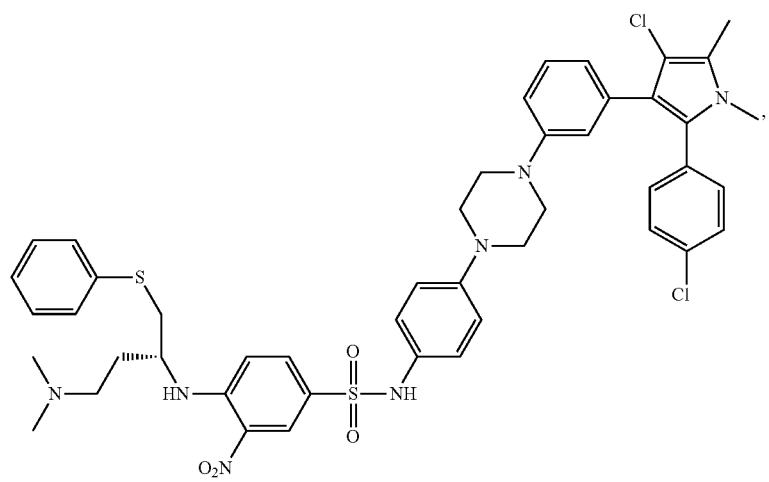

427 428
-continued
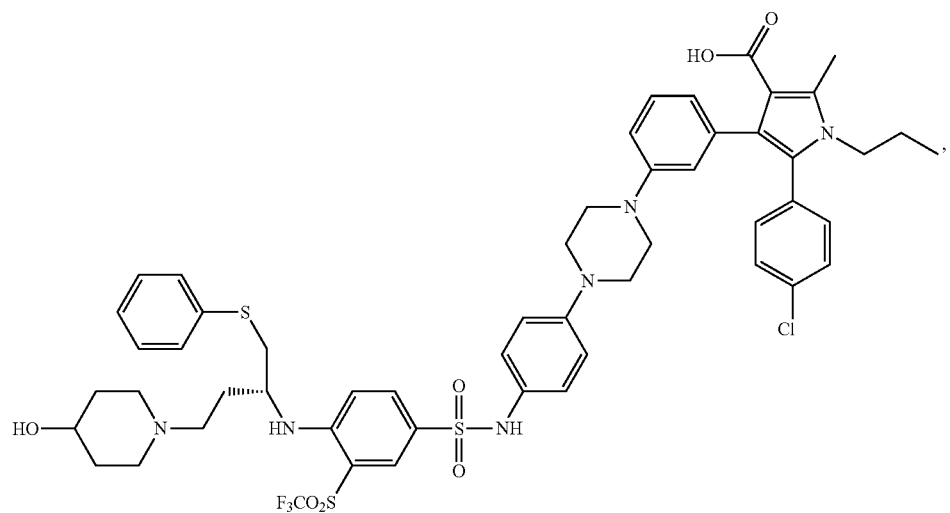
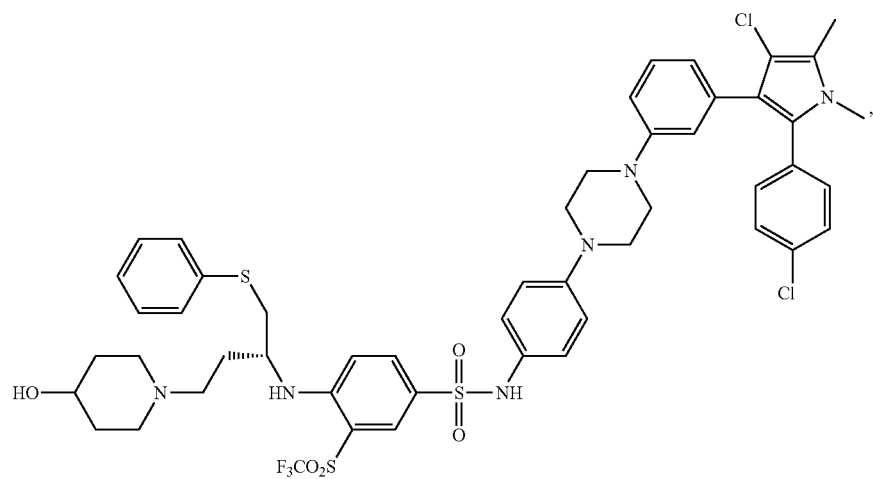
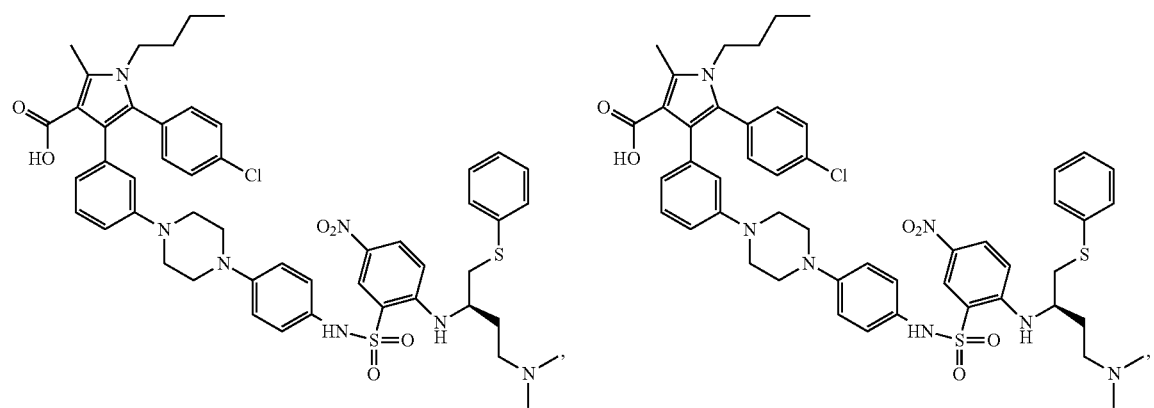

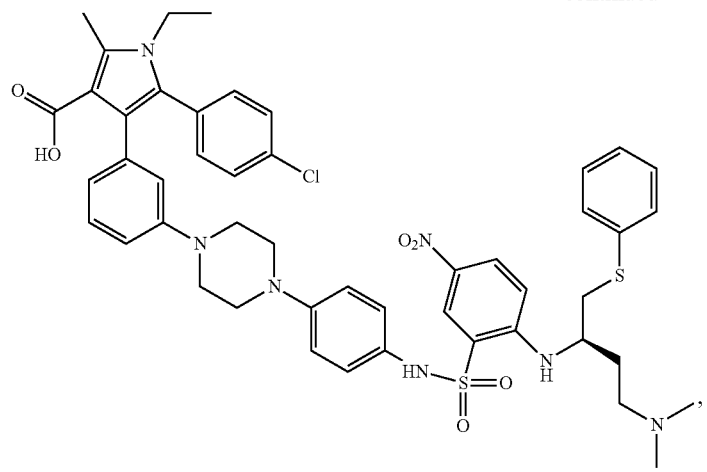
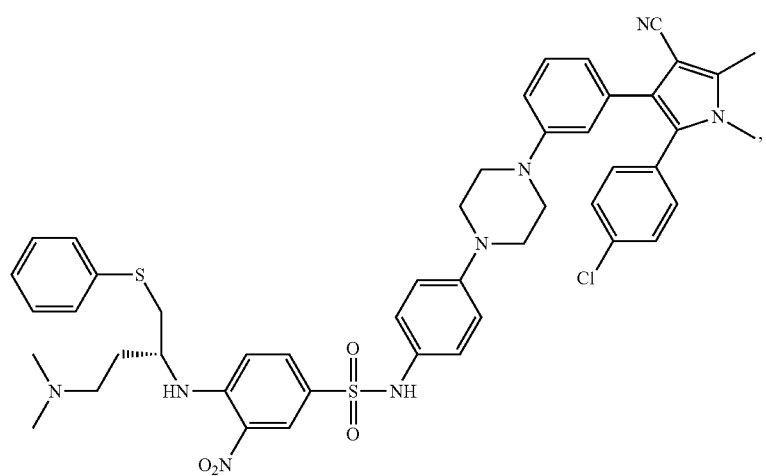
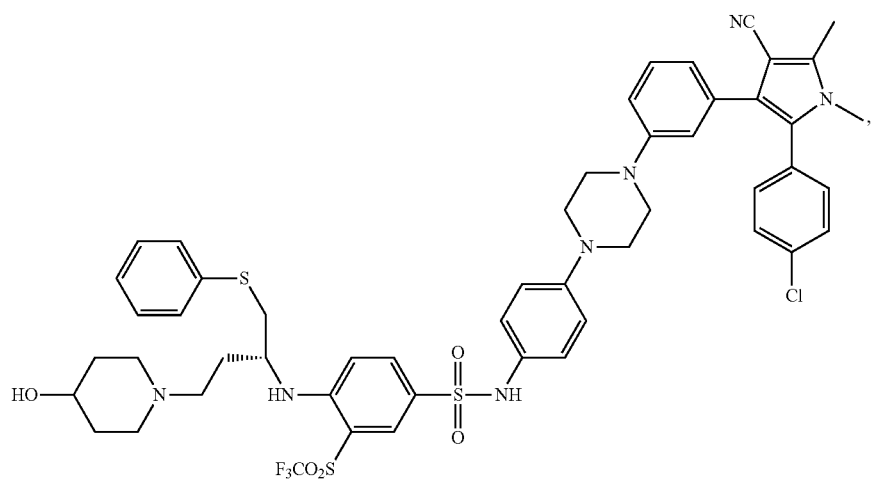

-continued
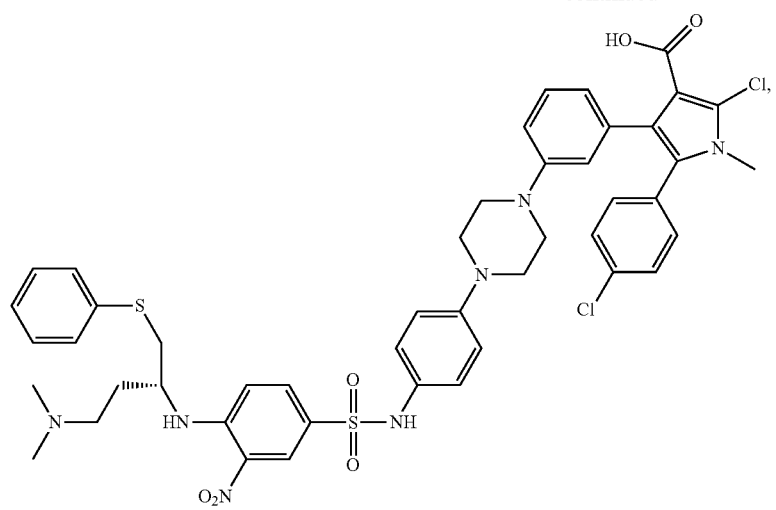
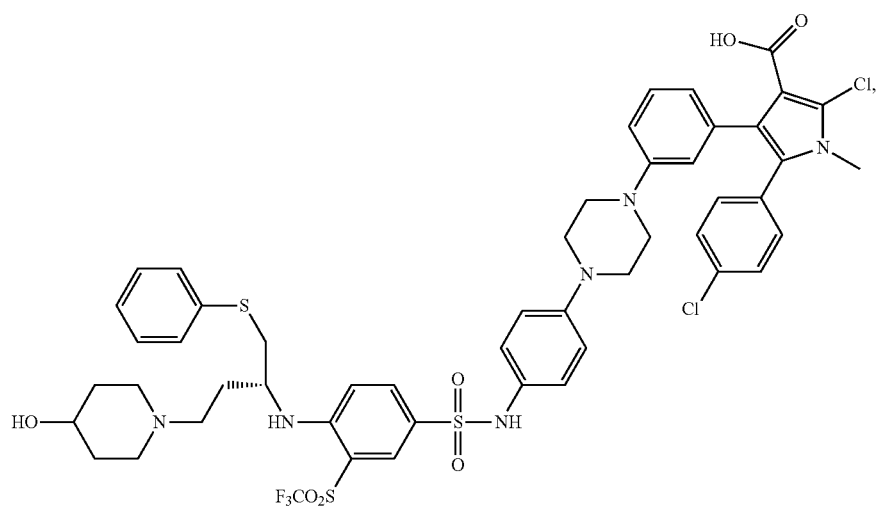
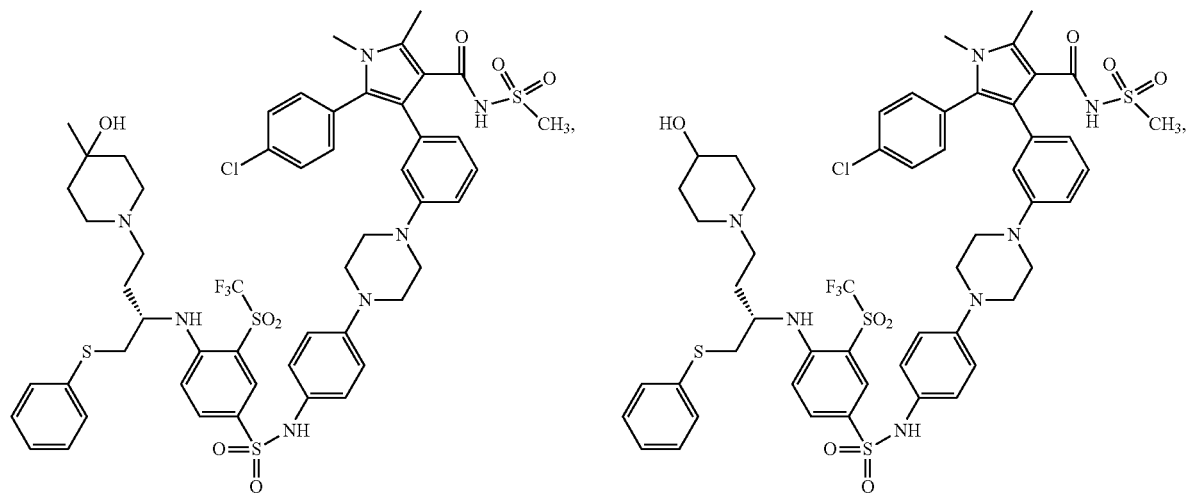

433     434
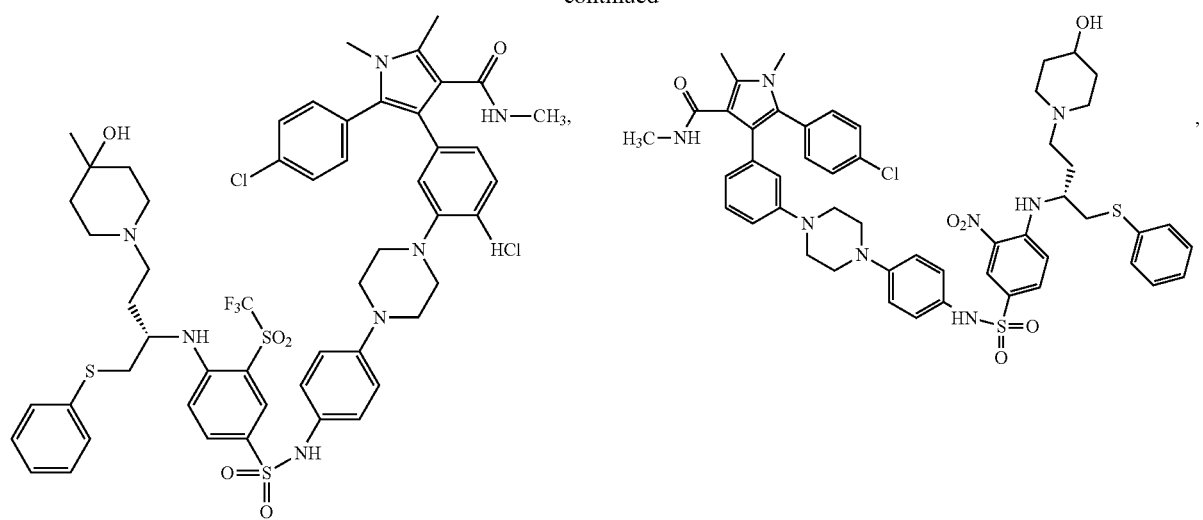
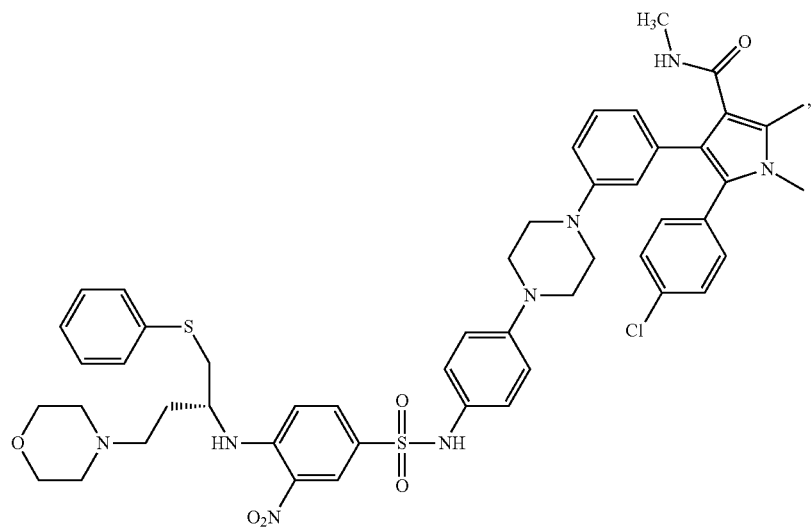
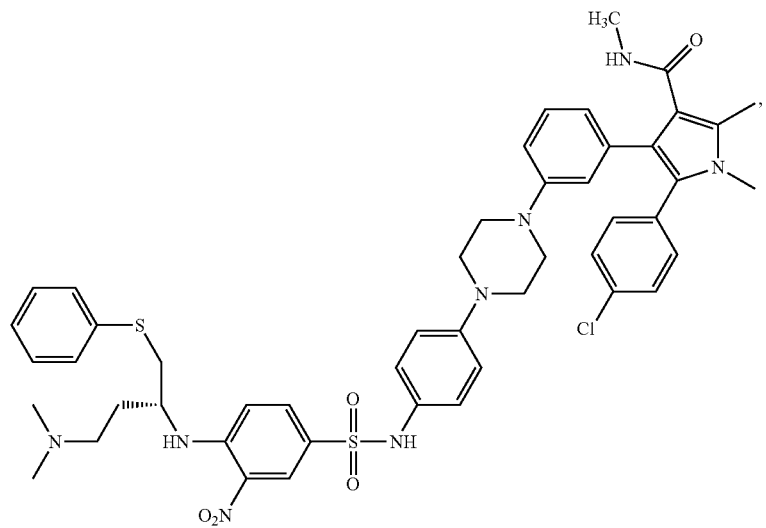

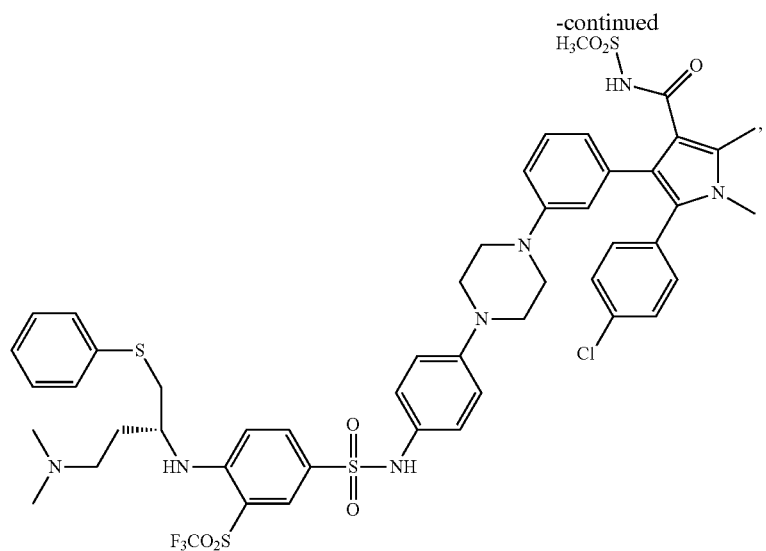
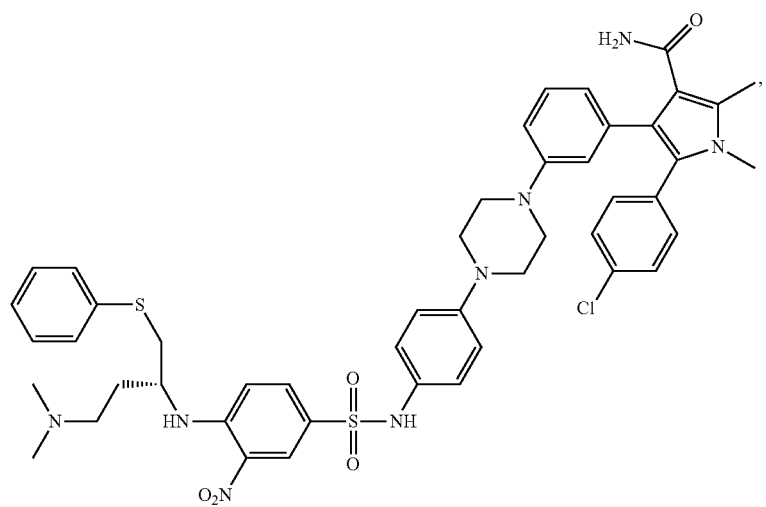
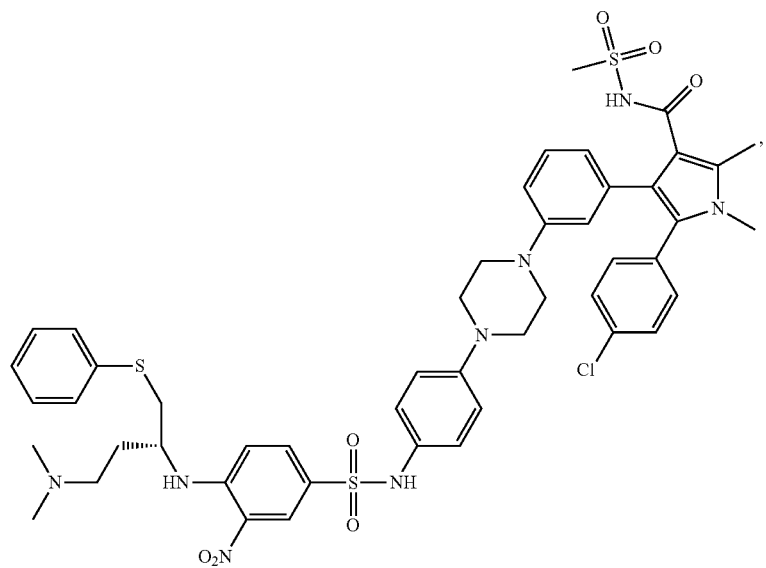

437
438
-continued
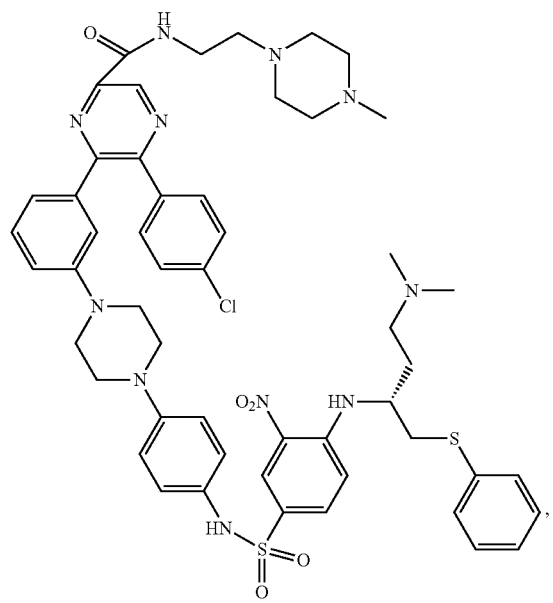
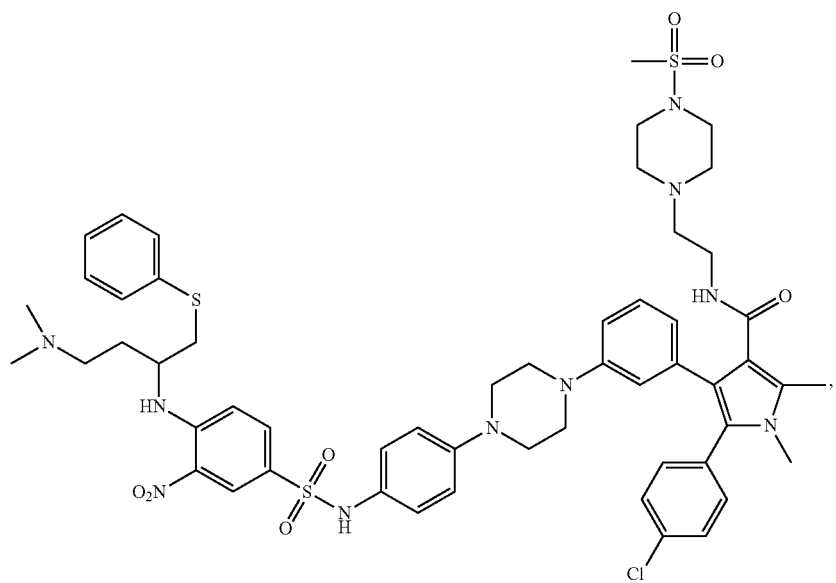
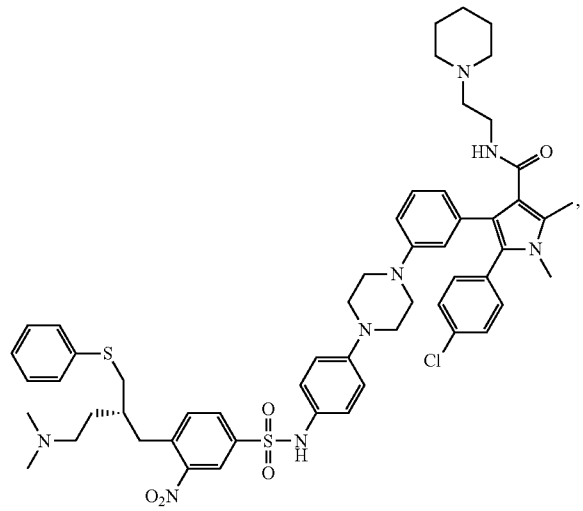
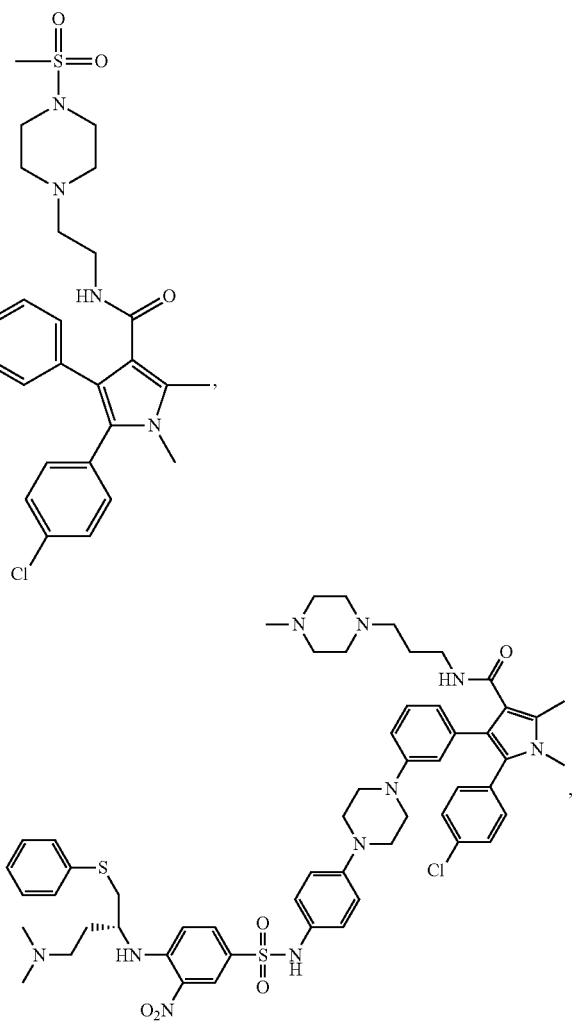

439
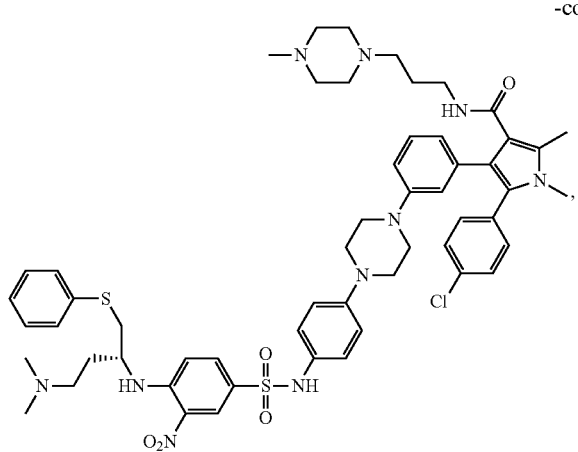
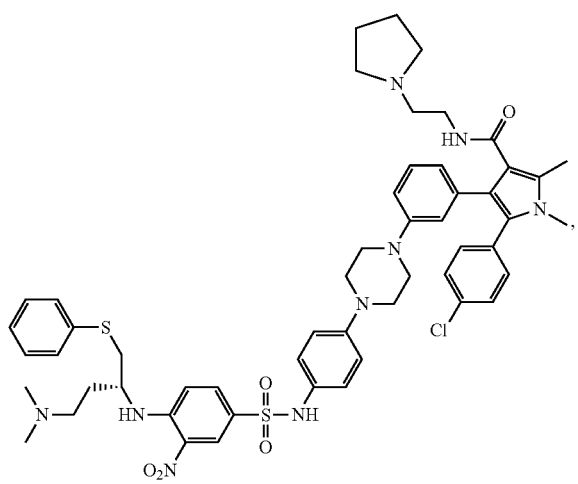
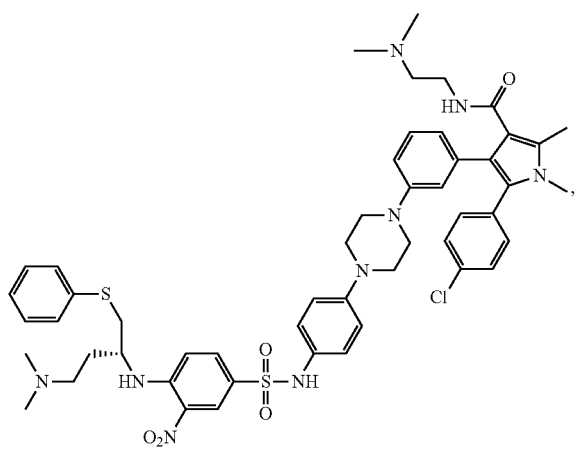
-continued
440
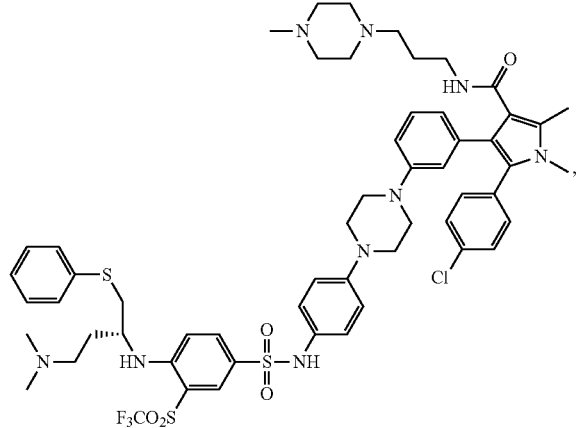
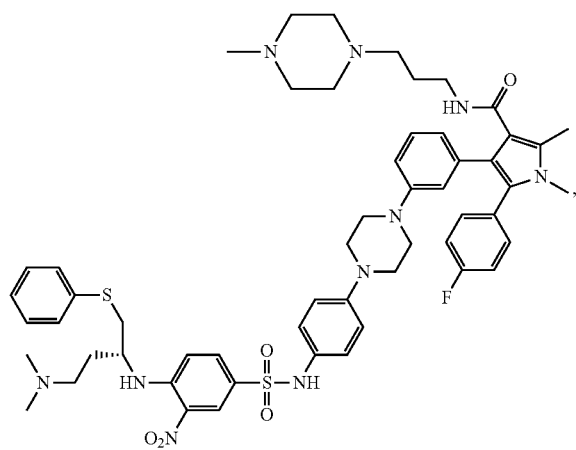
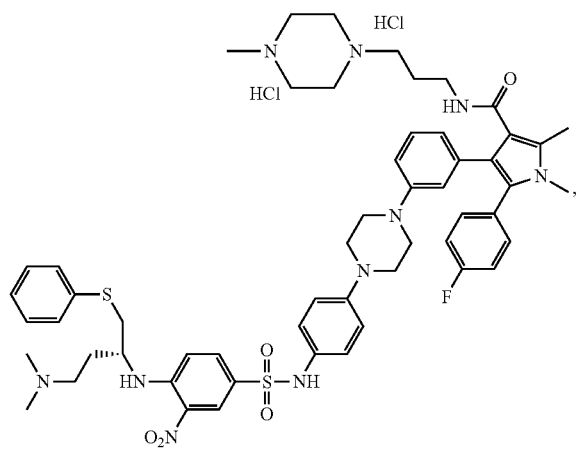

441
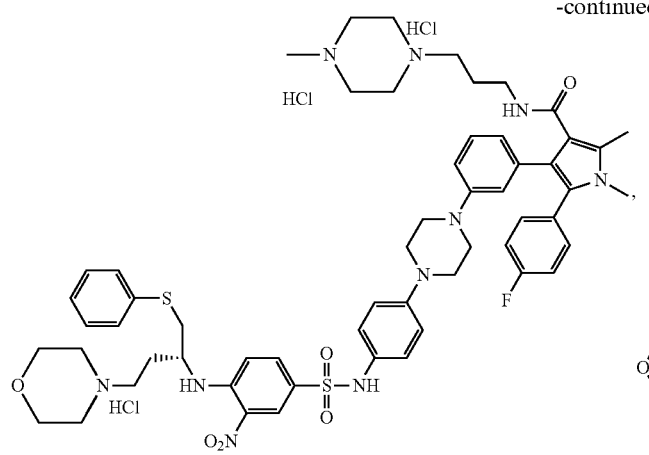
442
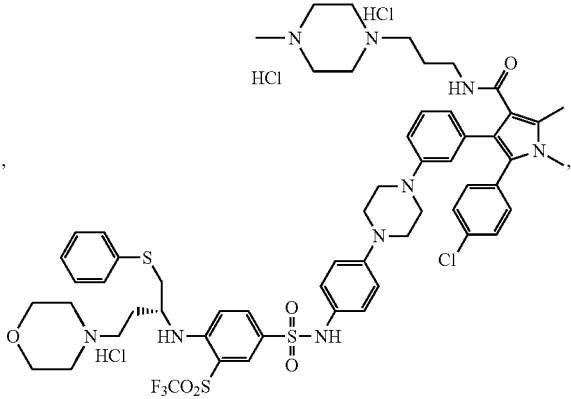
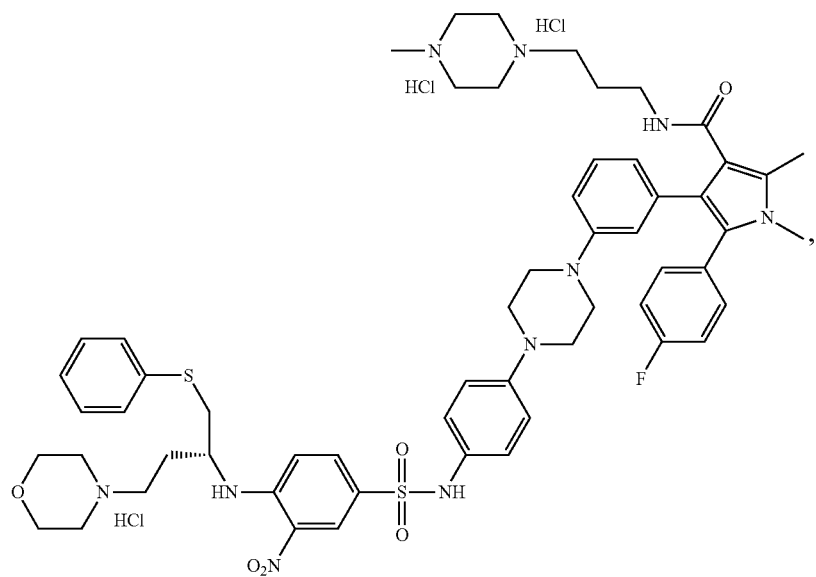
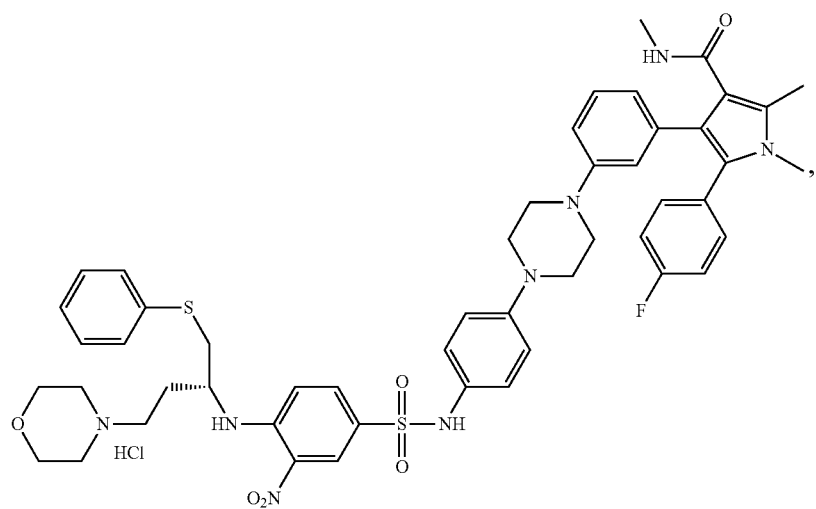

-continued
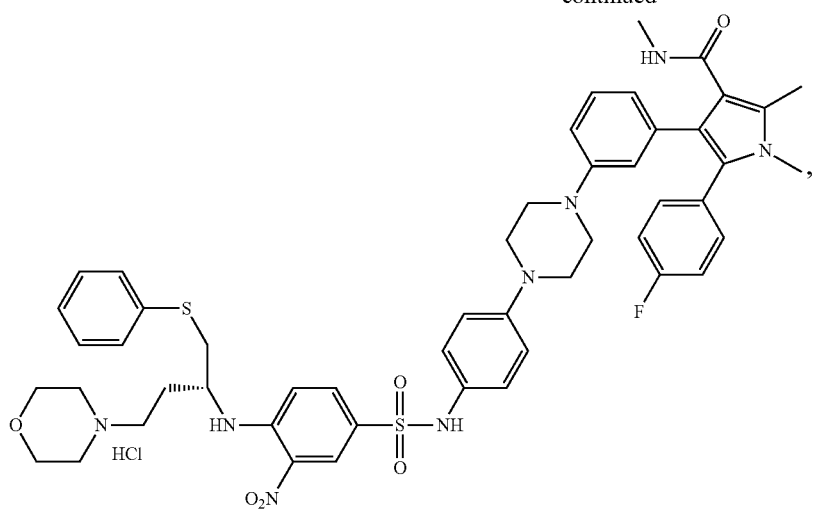
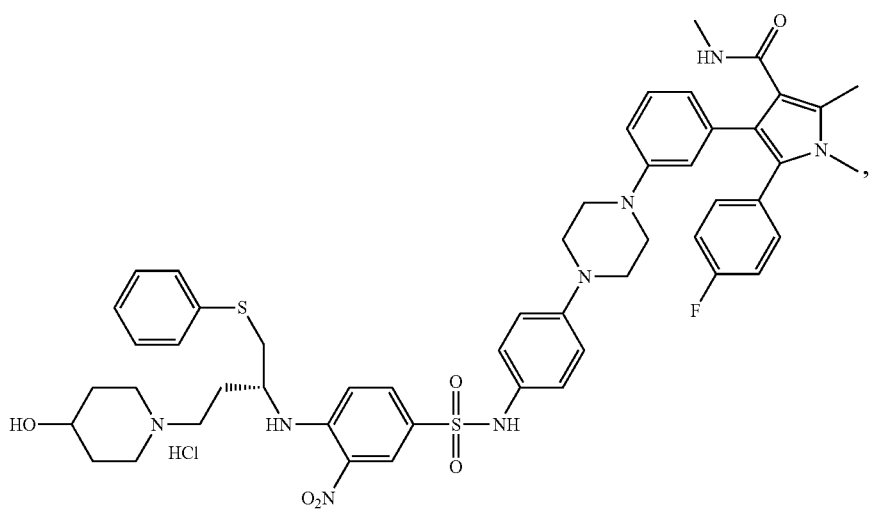
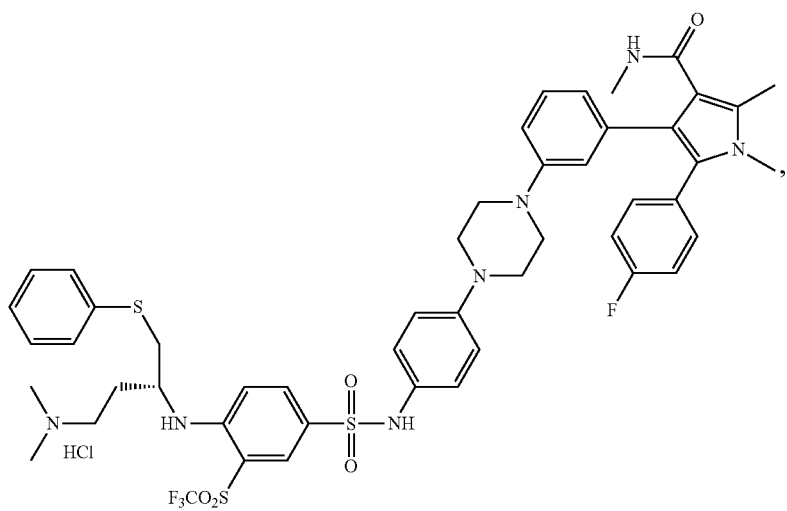

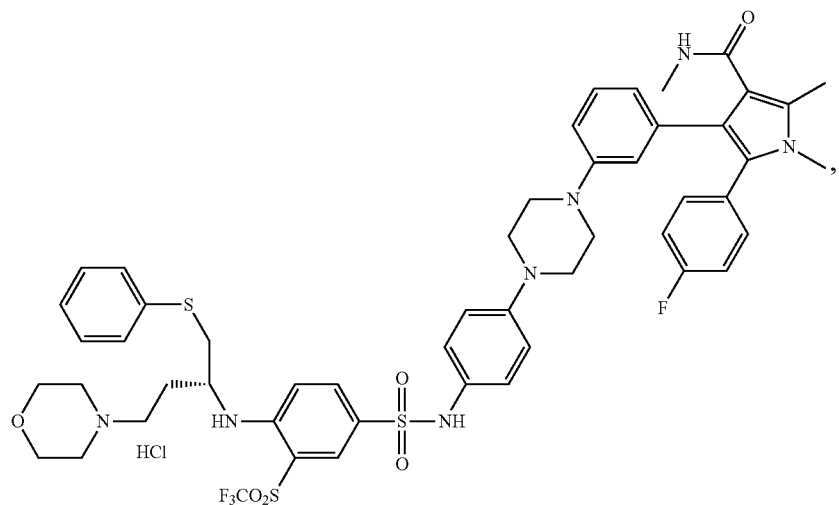
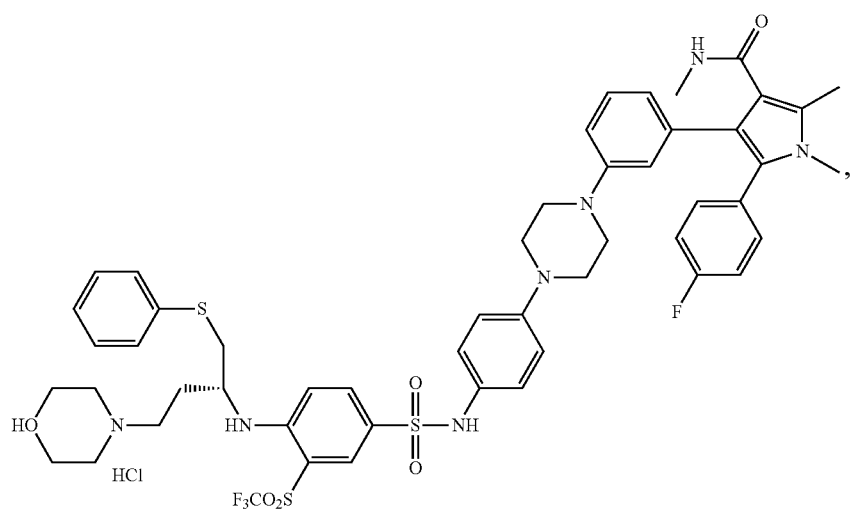
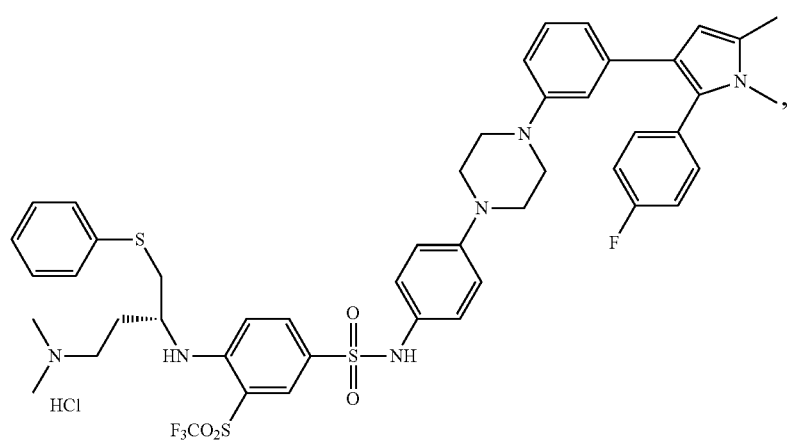

-continued
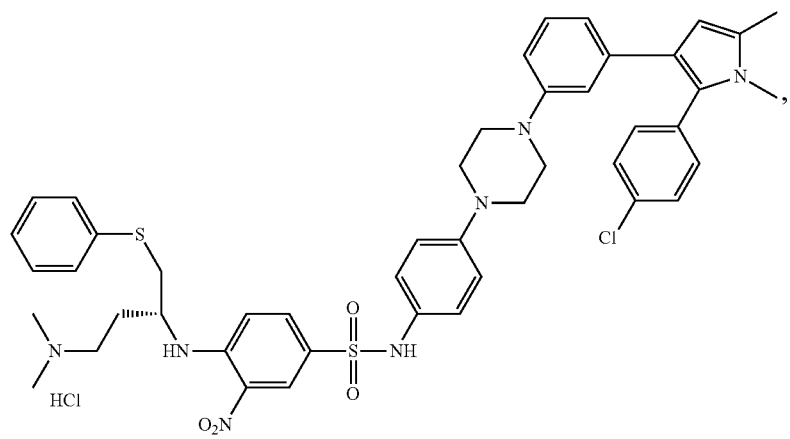
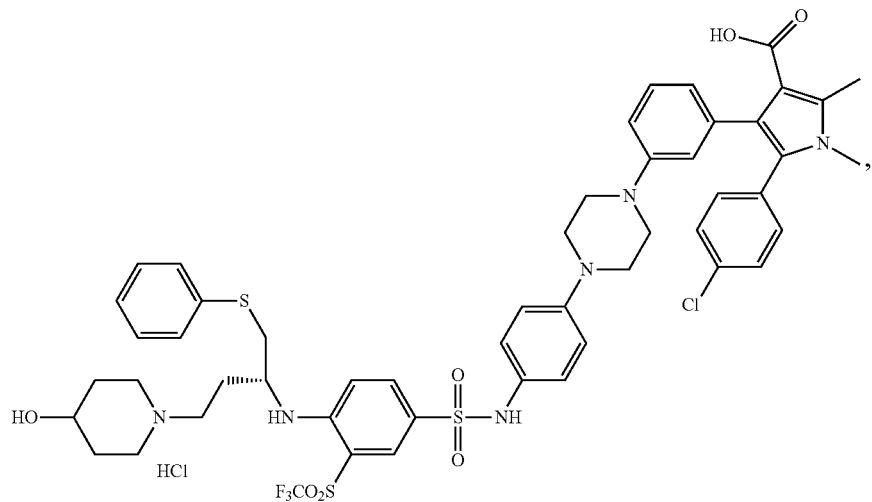
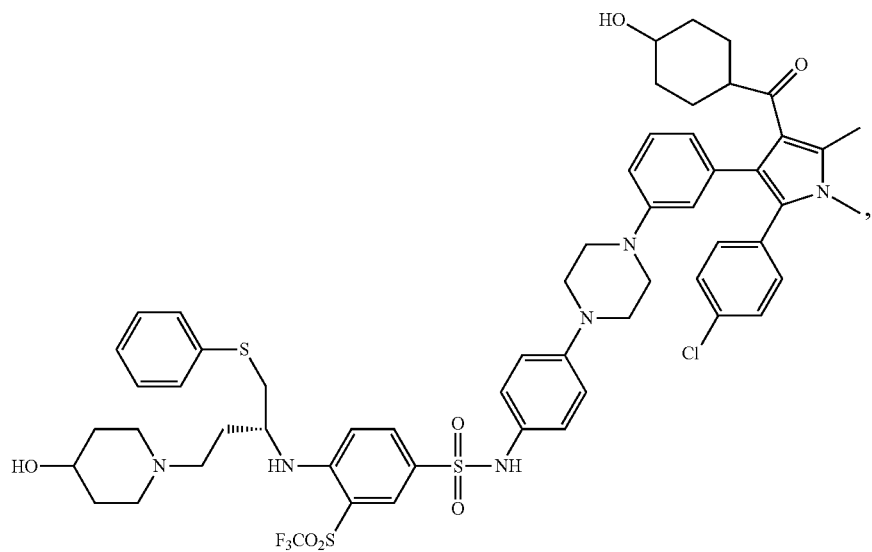

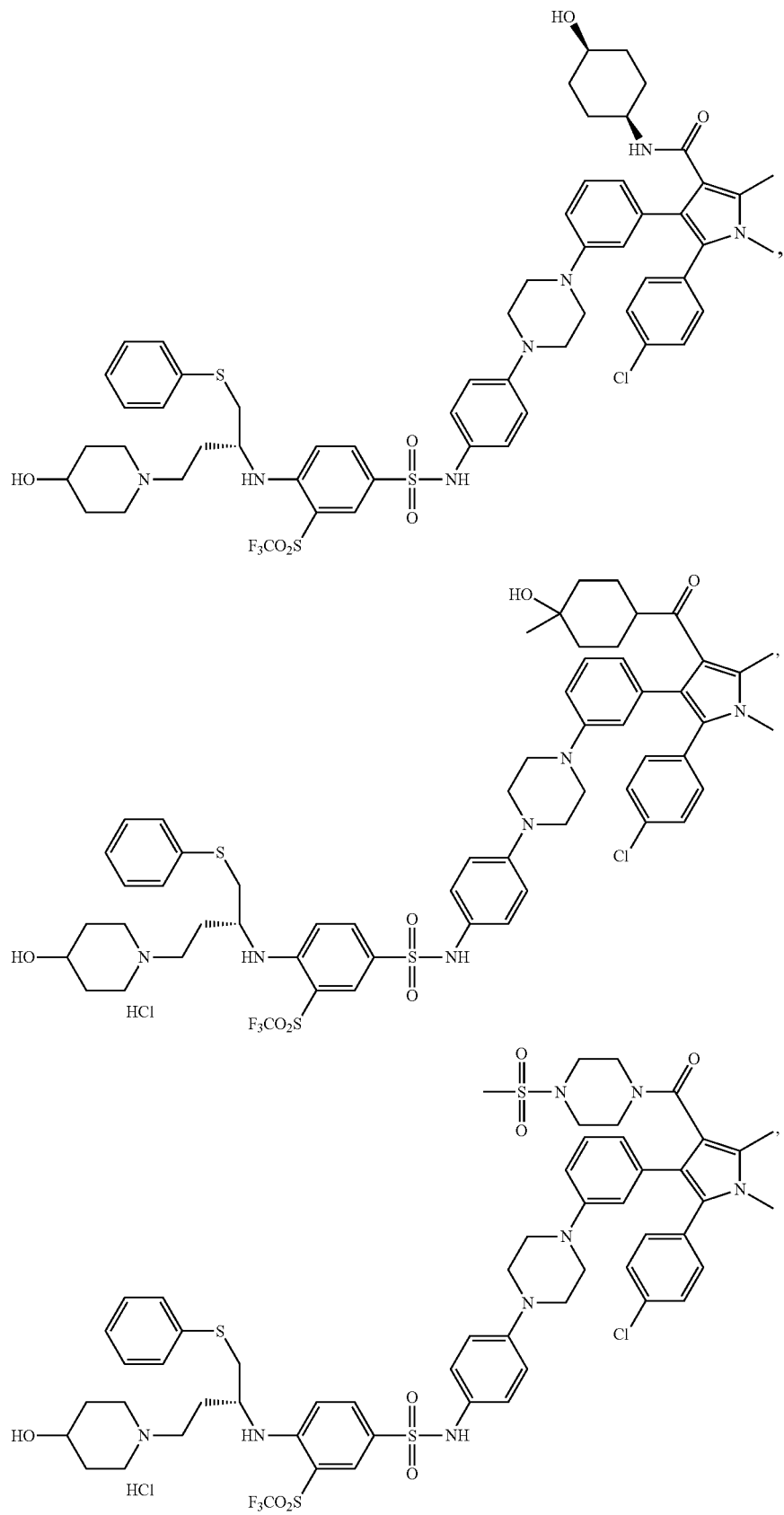

-continued
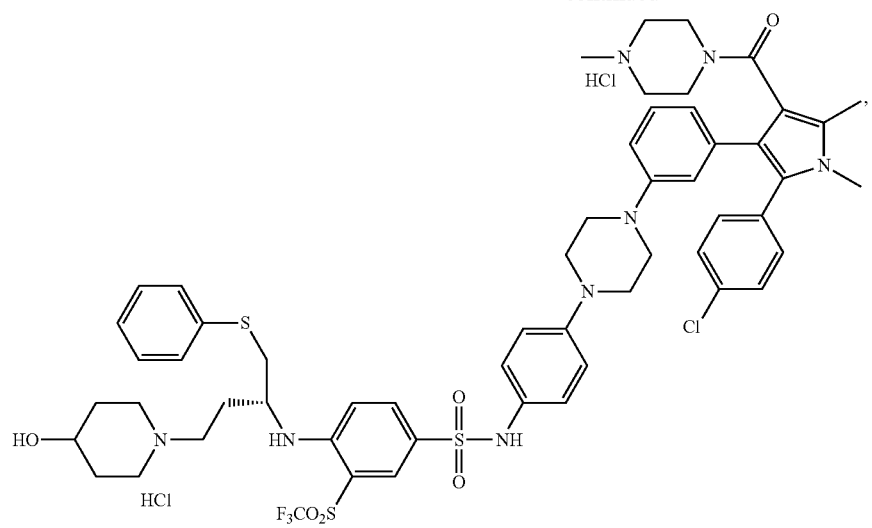
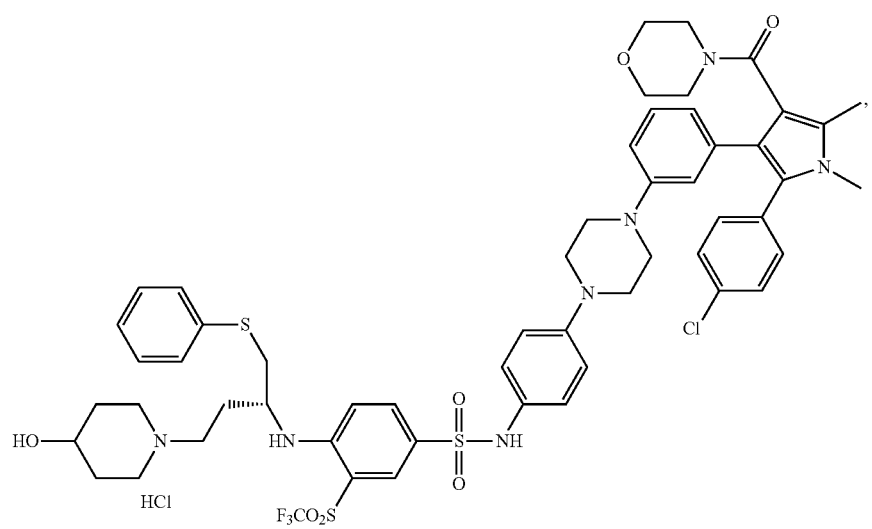
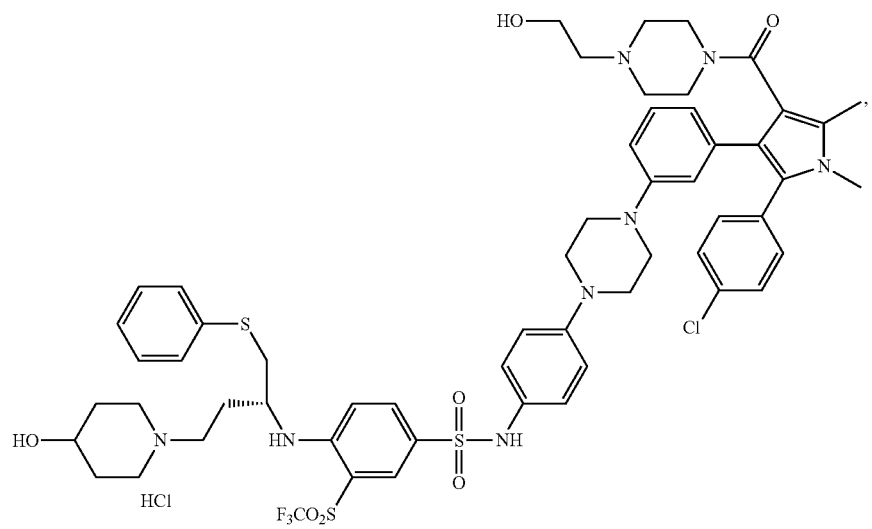

-continued
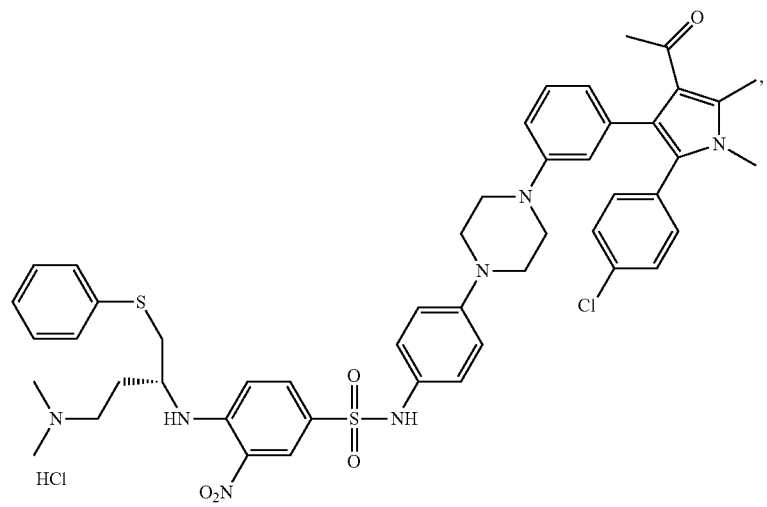
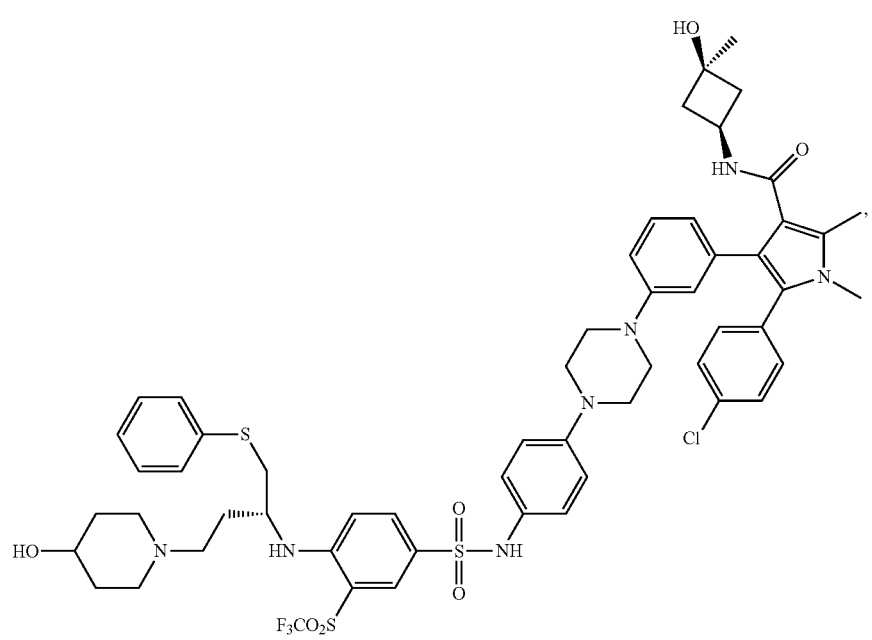

-continued
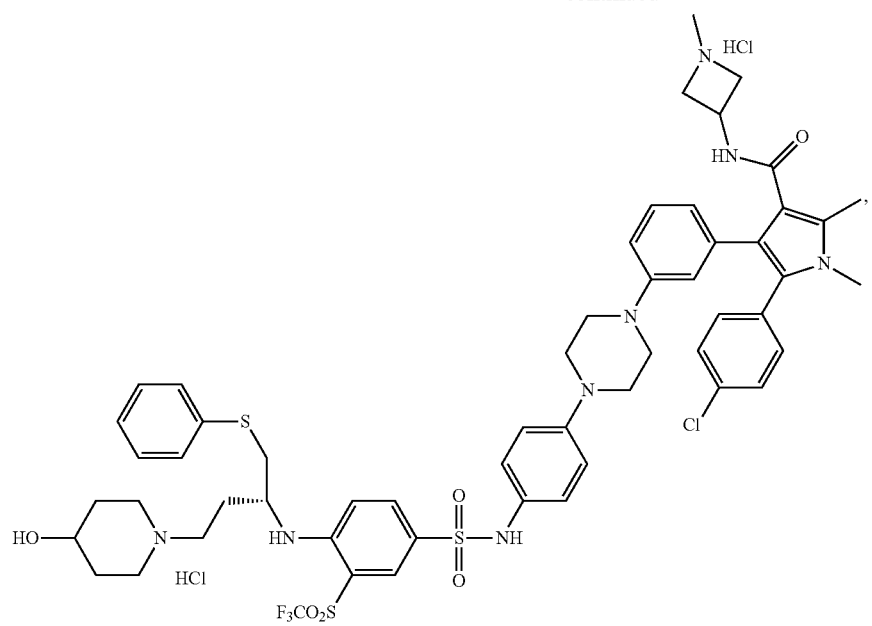
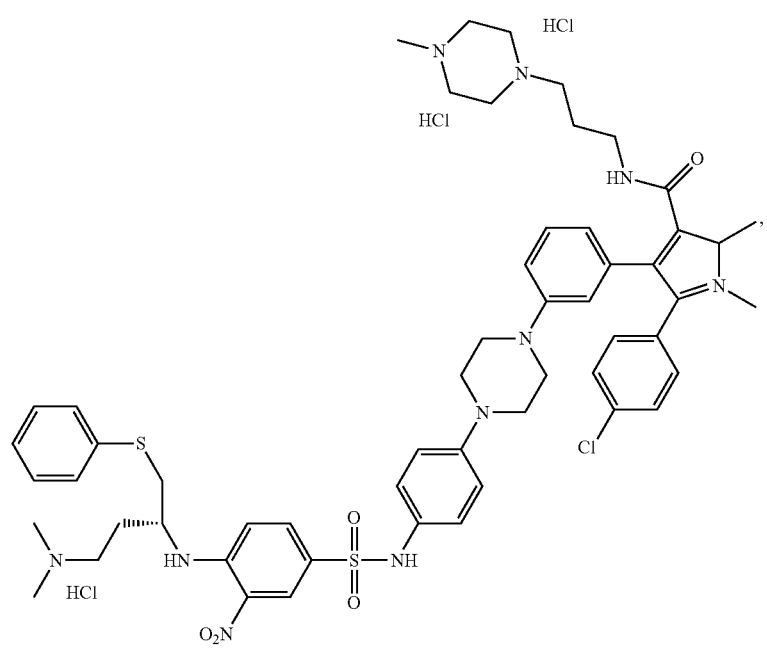

-continued
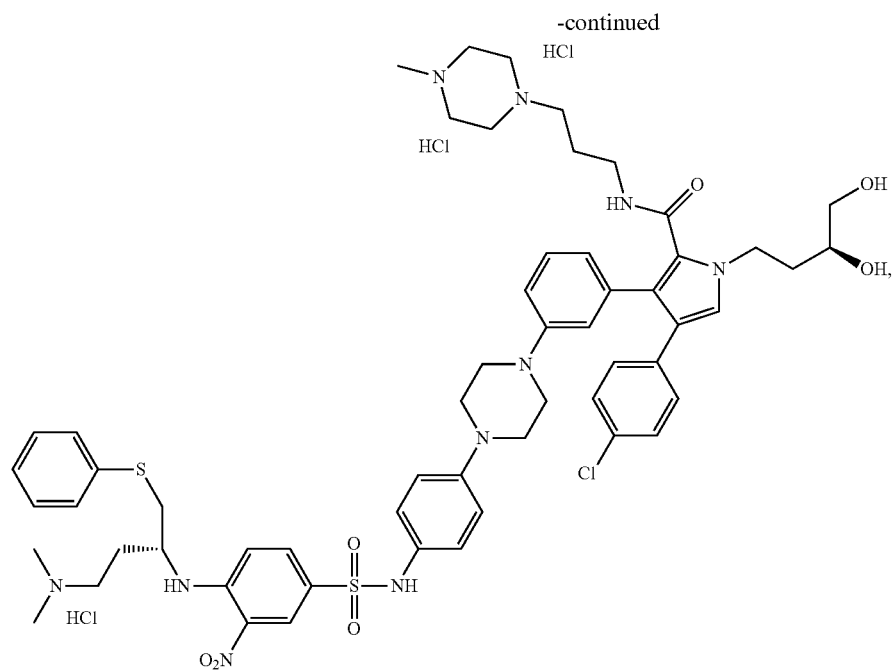
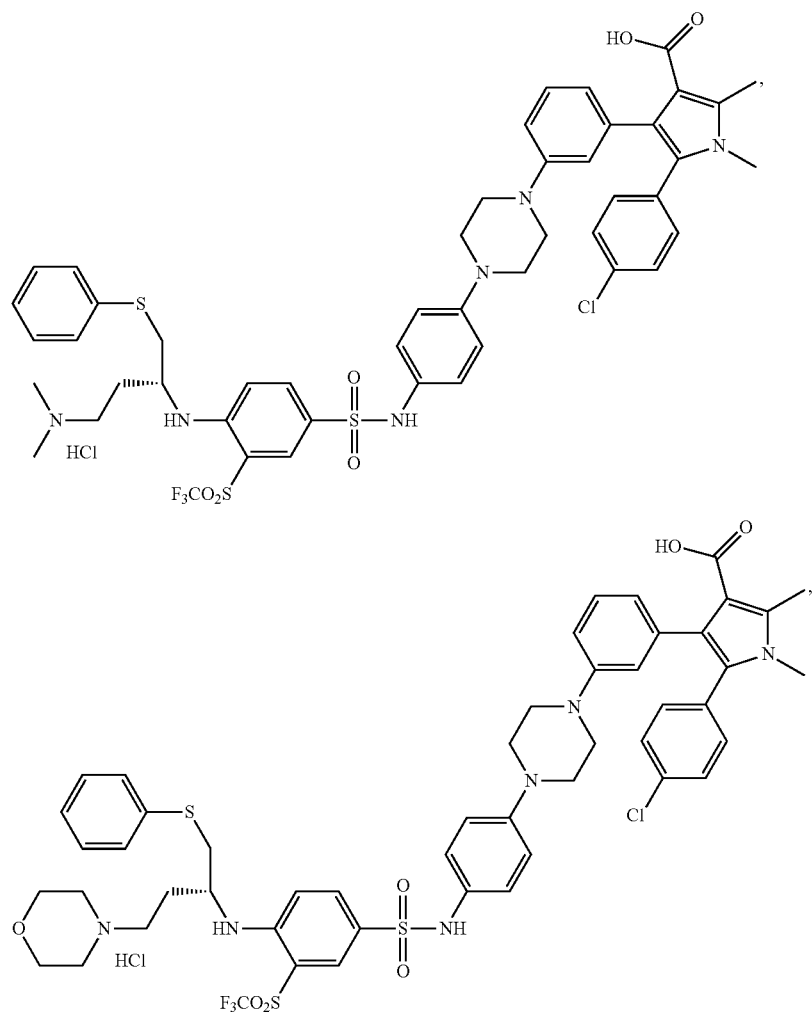

-continued
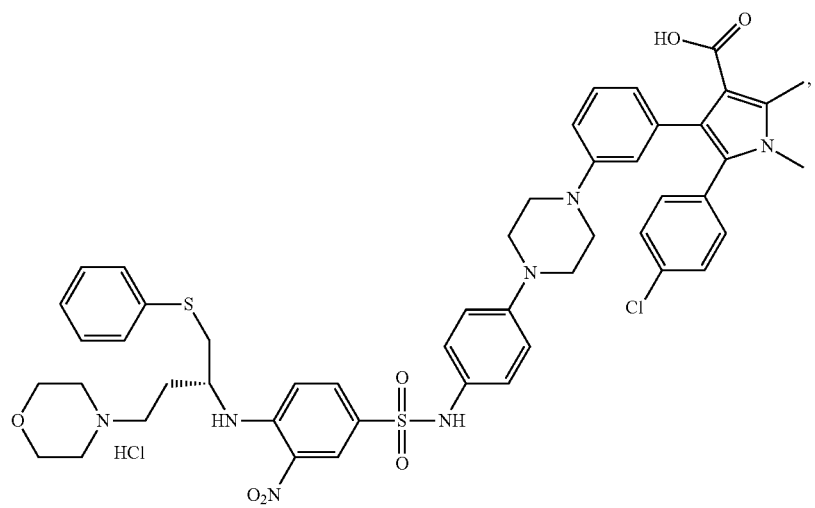
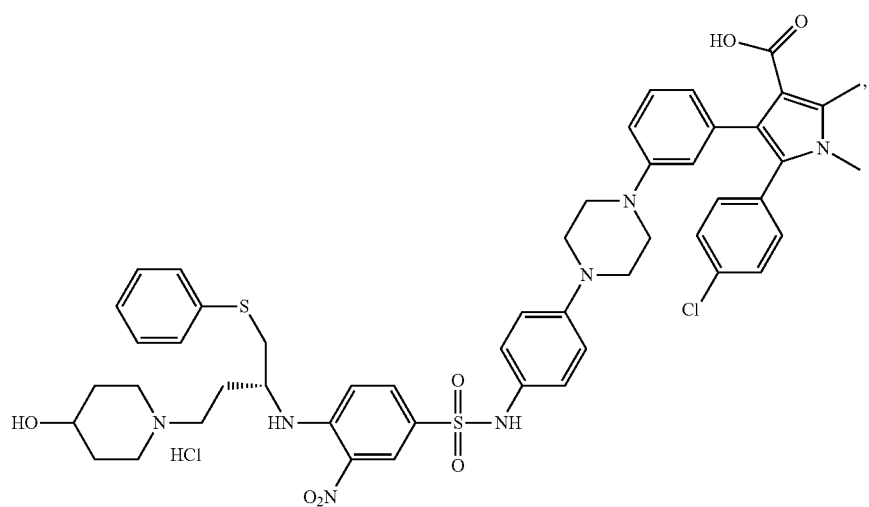
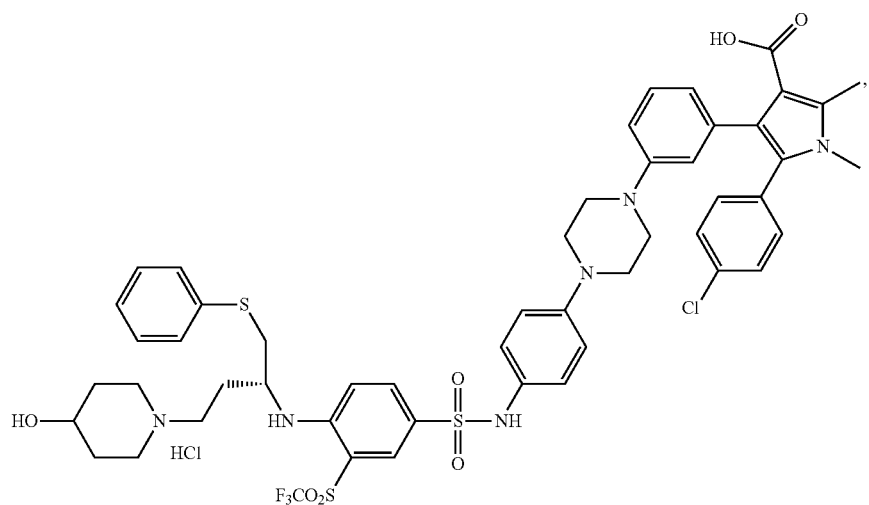

-continued
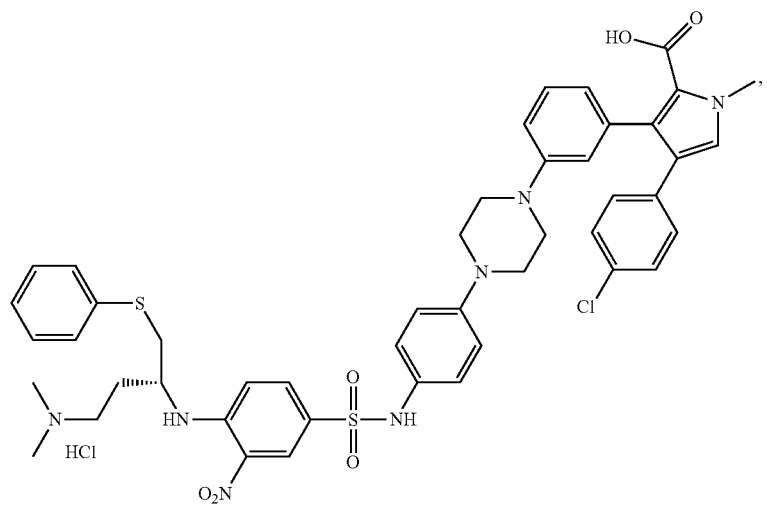
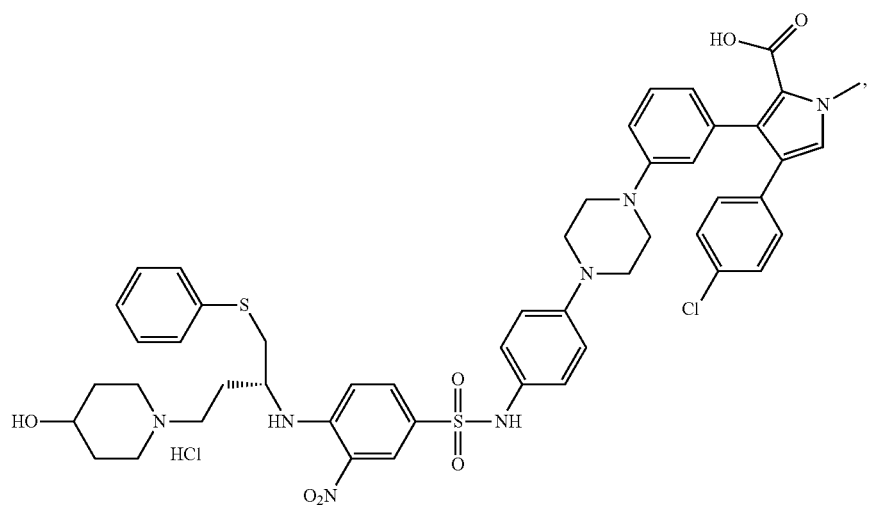
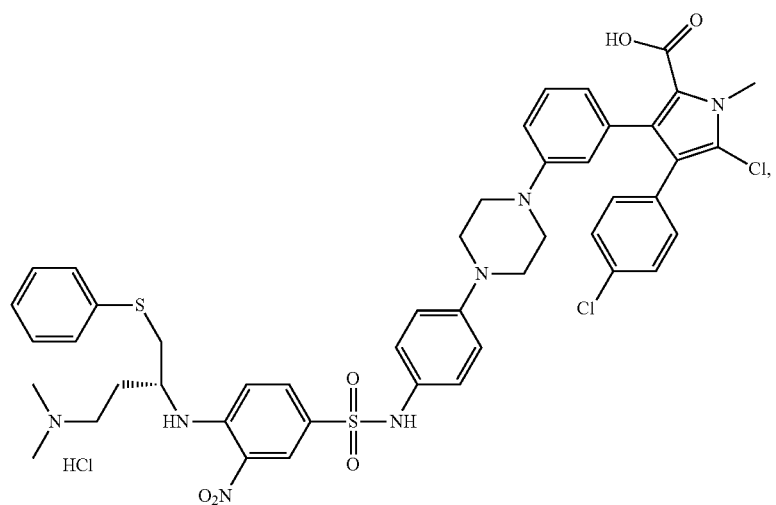

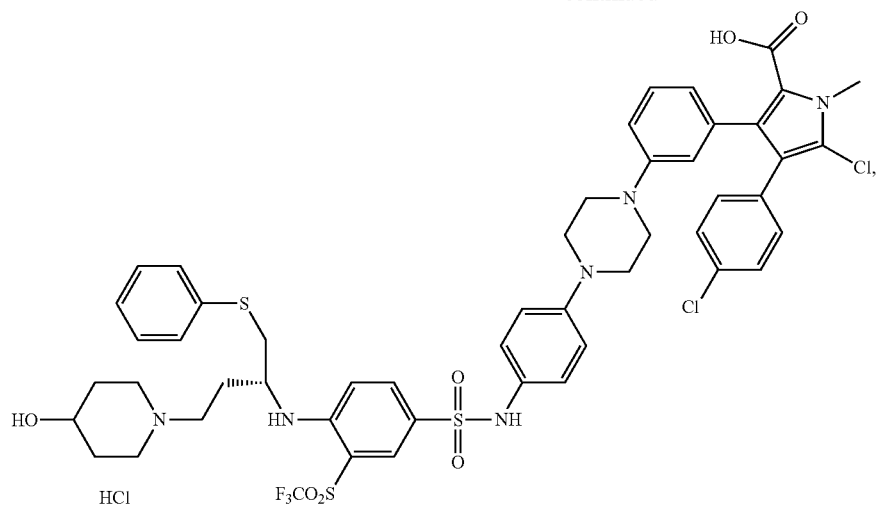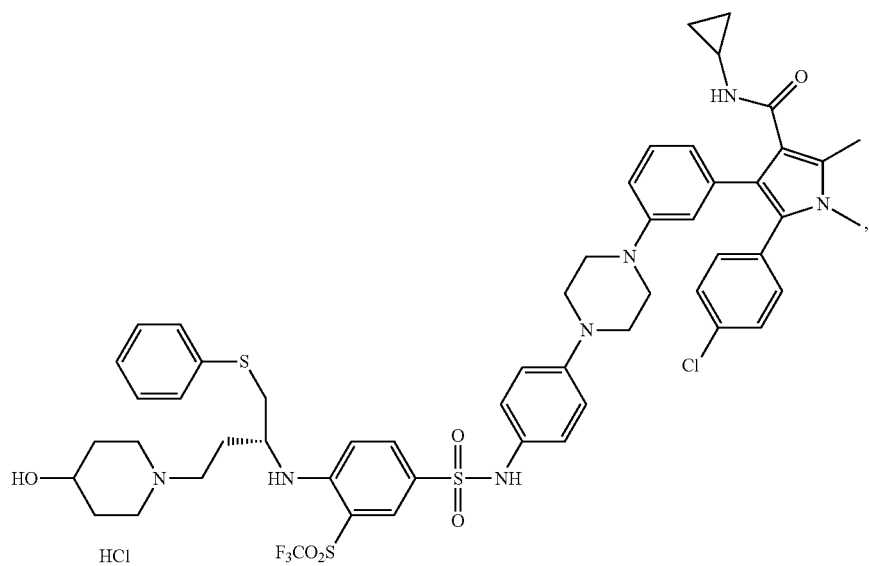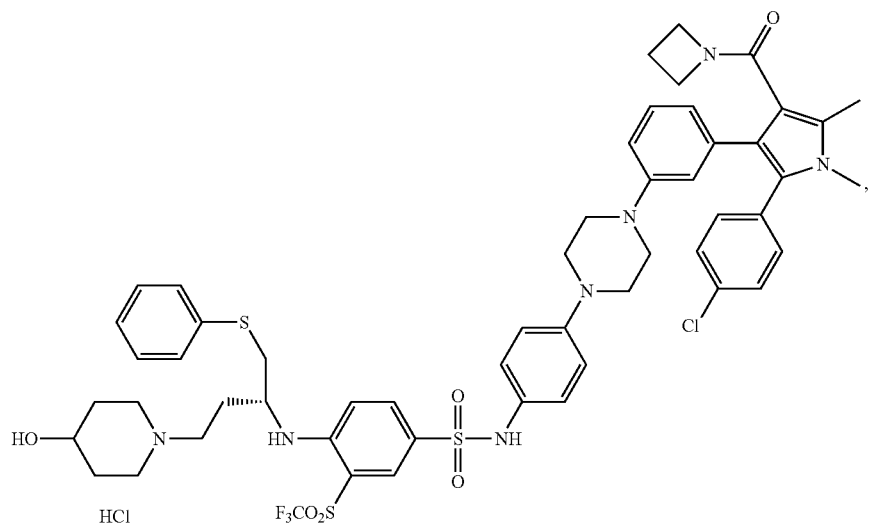

465
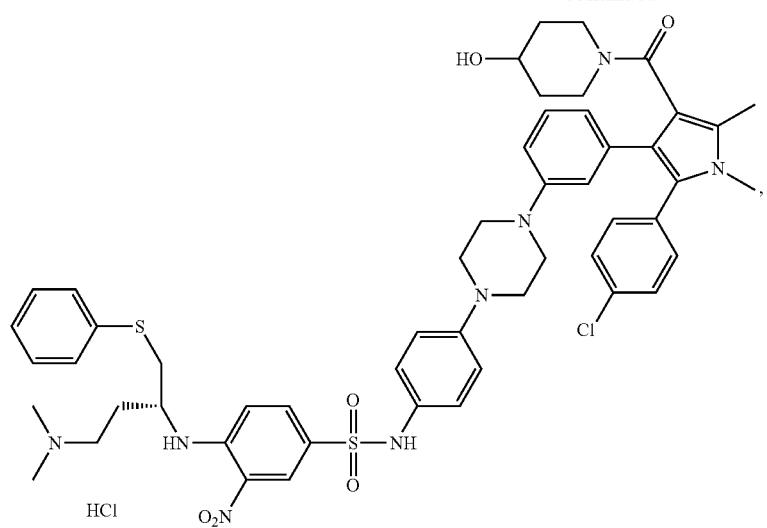
466
-continued
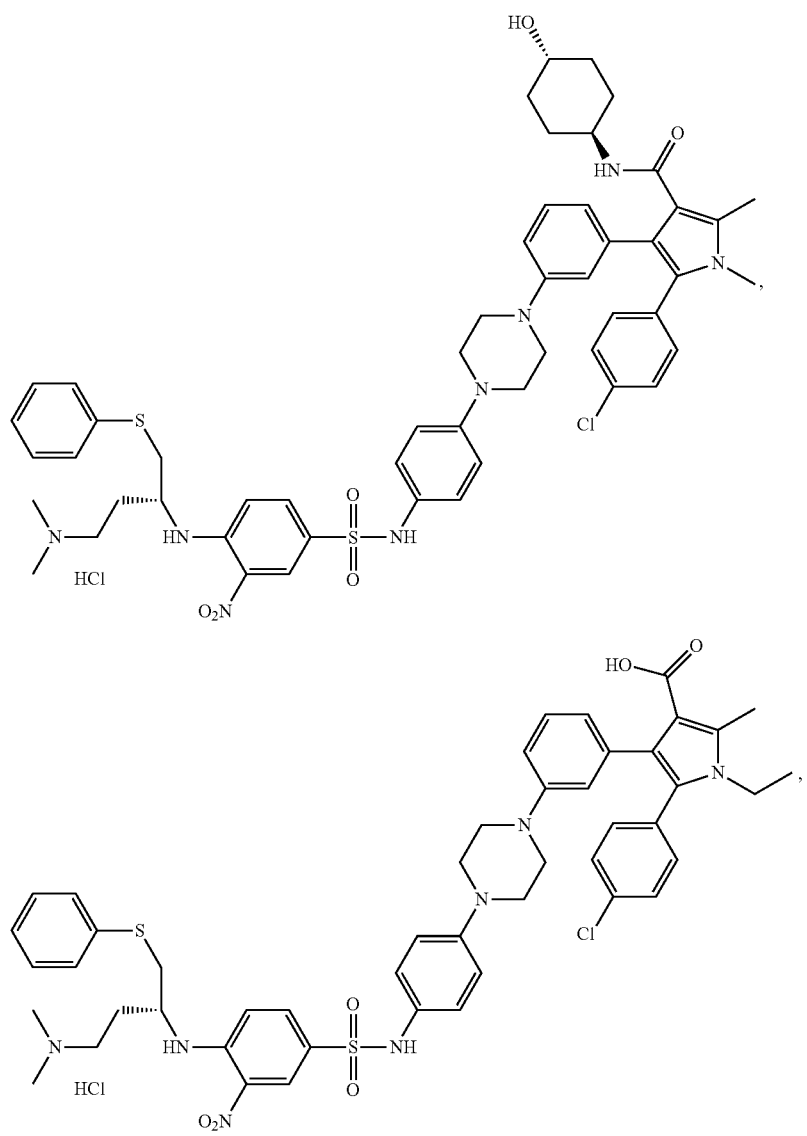

-continued
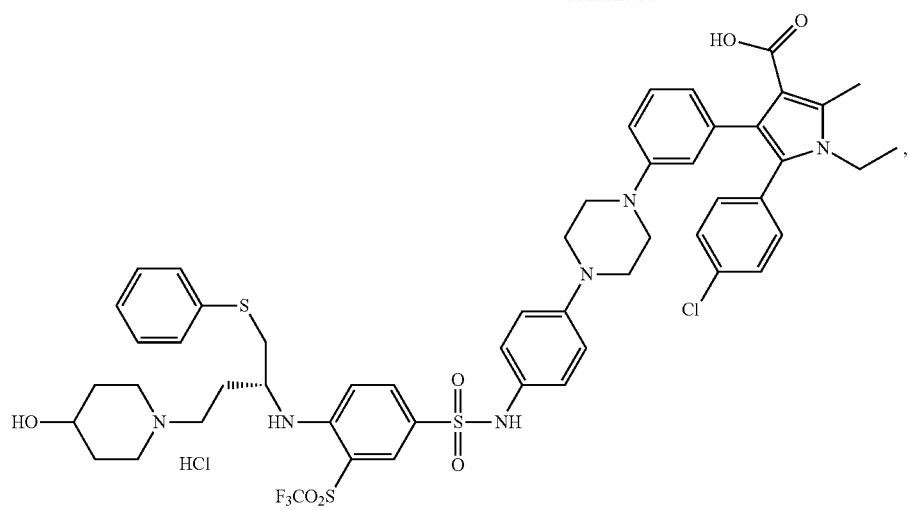
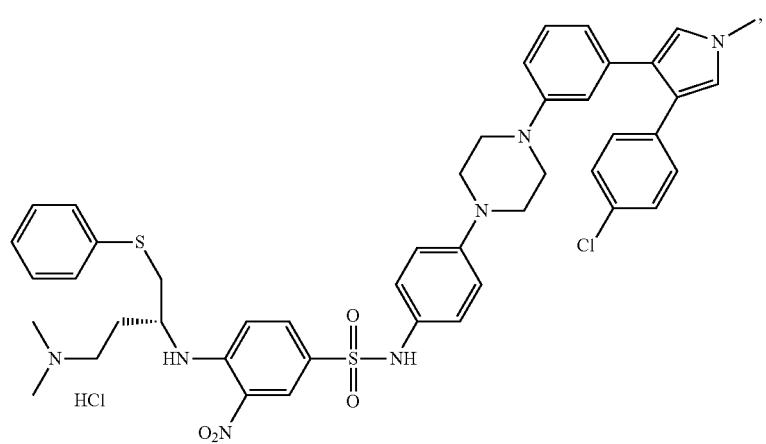
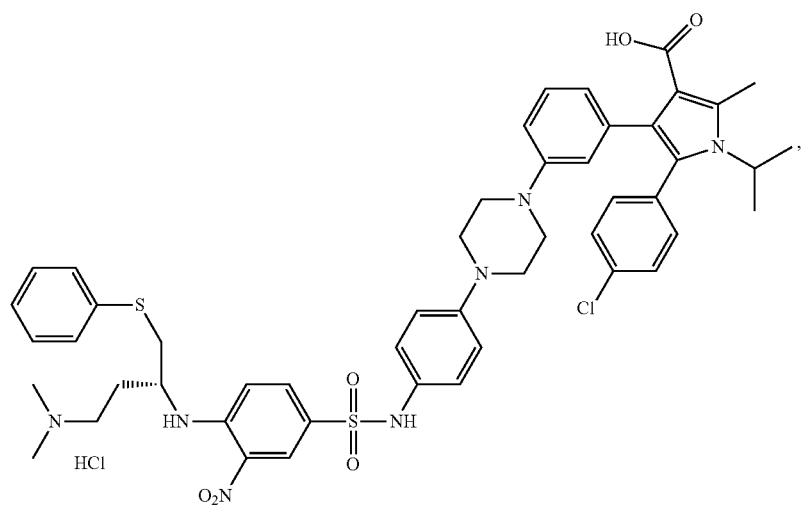

-continued
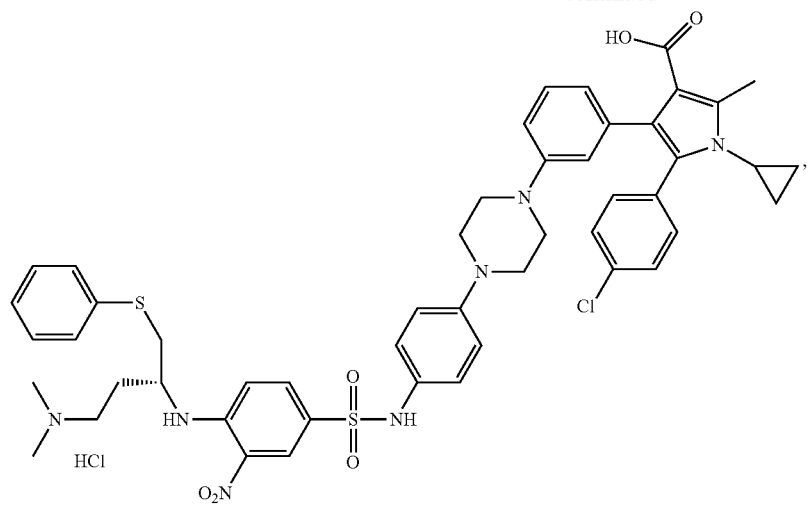
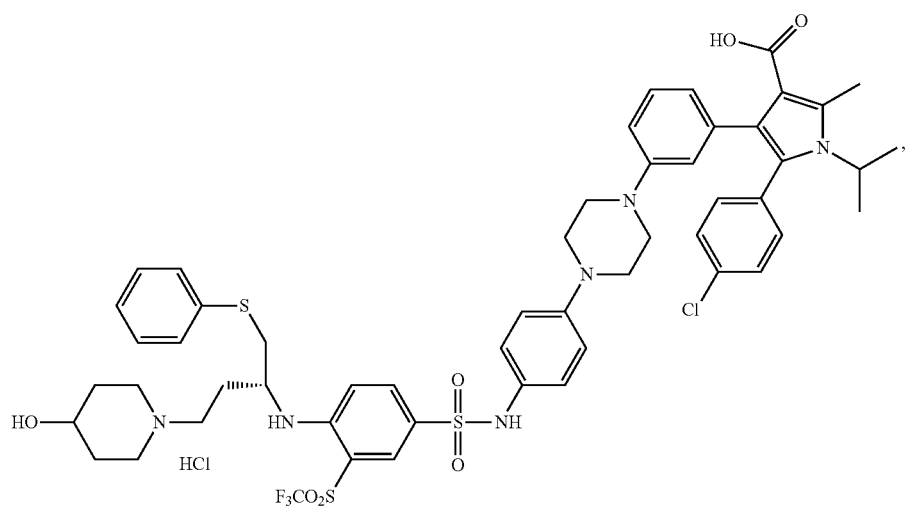
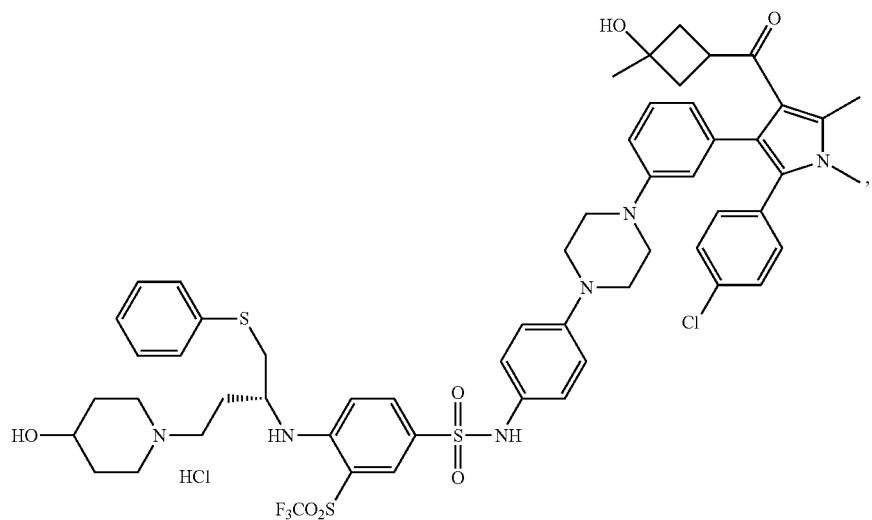

-continued
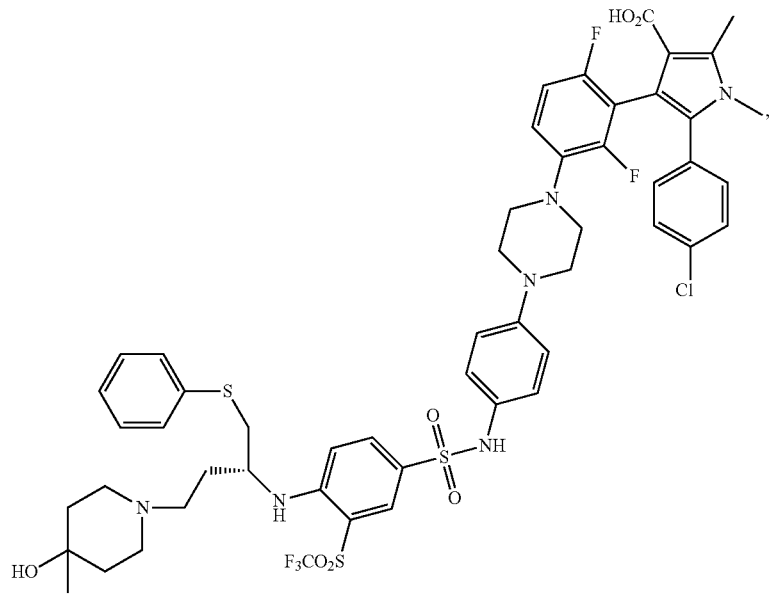
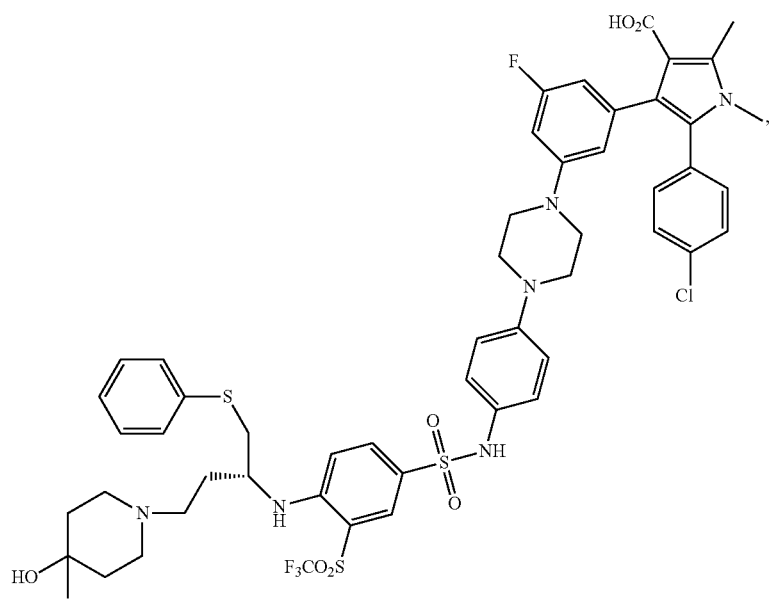

-continued
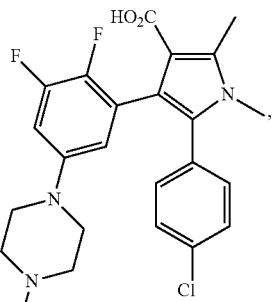
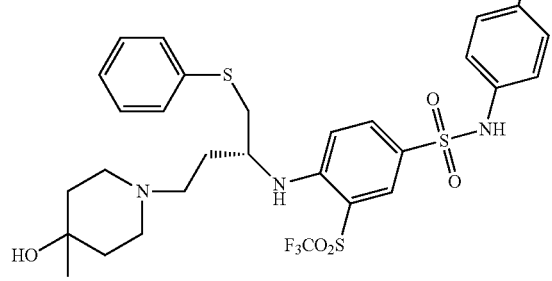
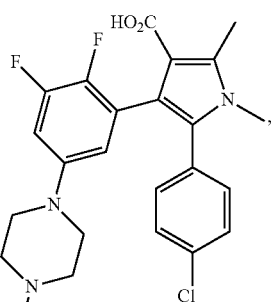
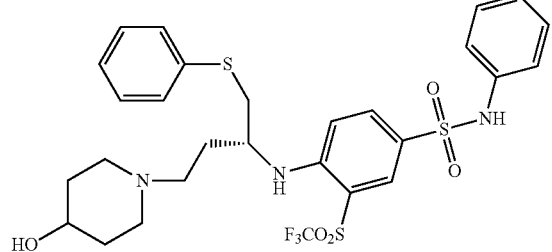

-continued
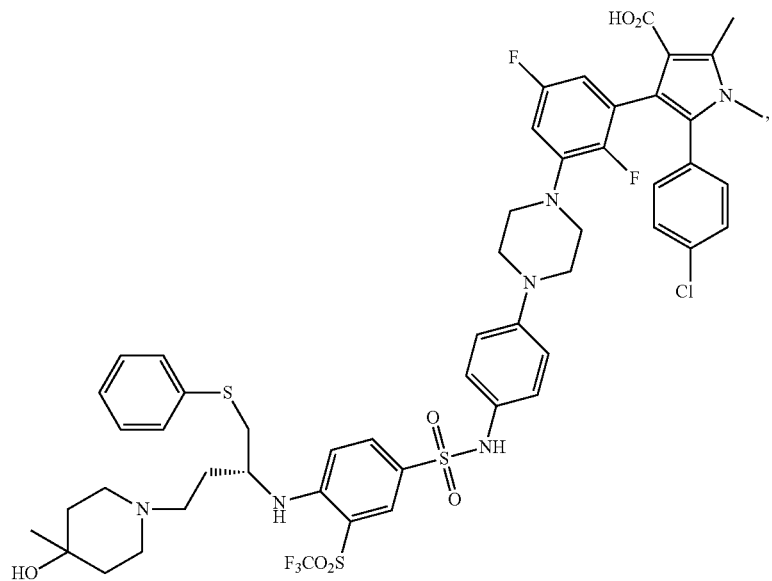
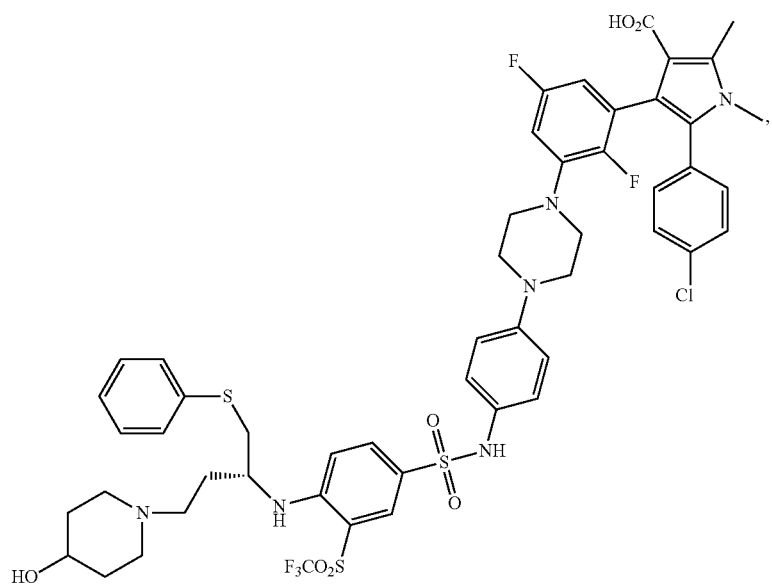

-continued
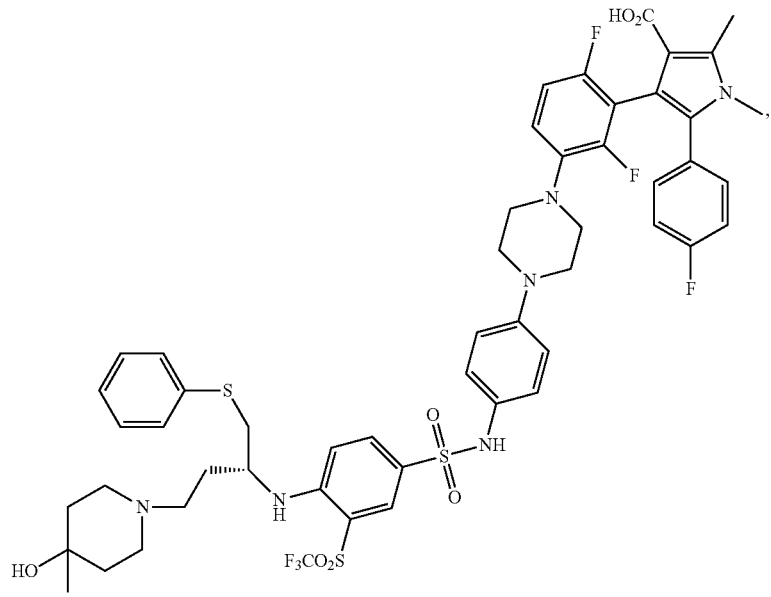
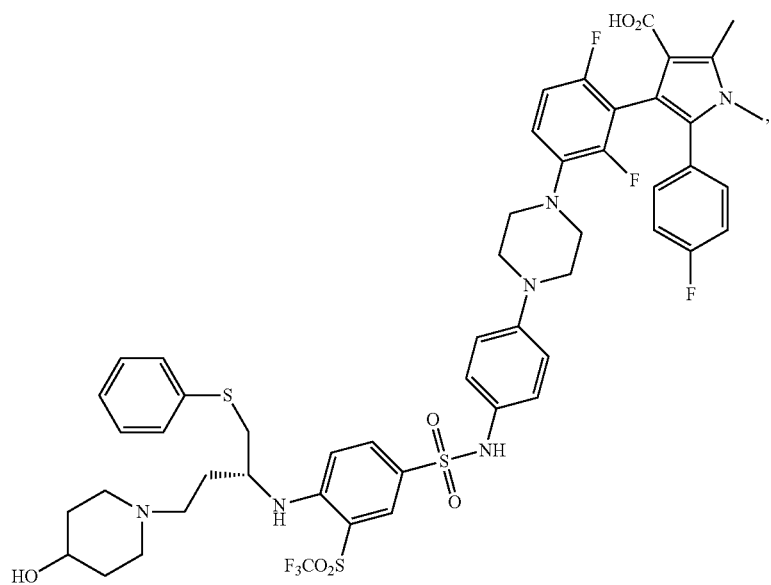

-continued
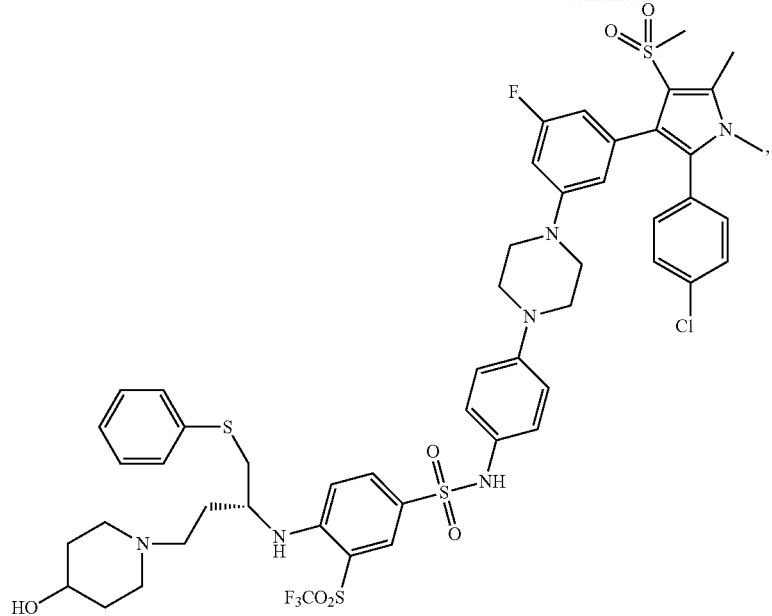
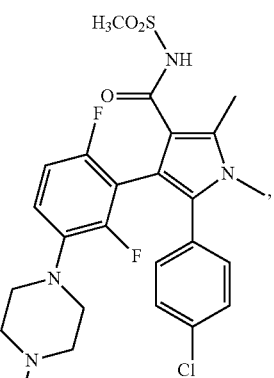
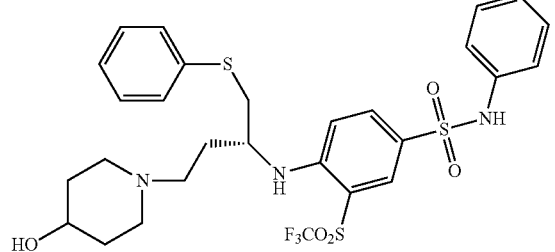

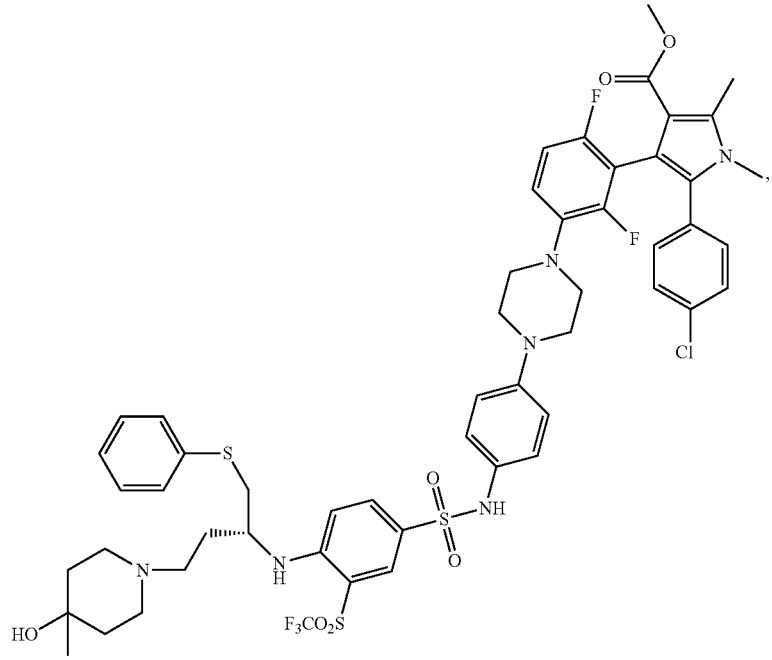
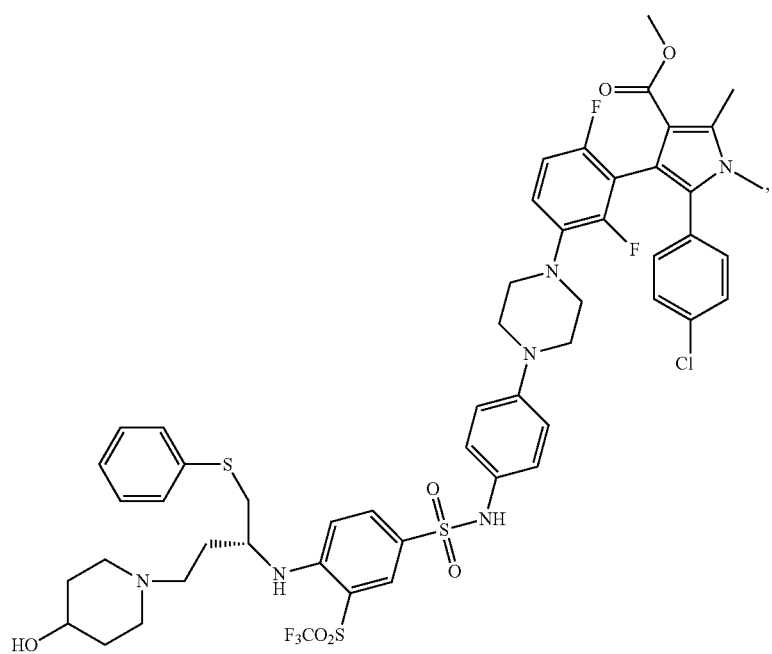

483
484
-continued
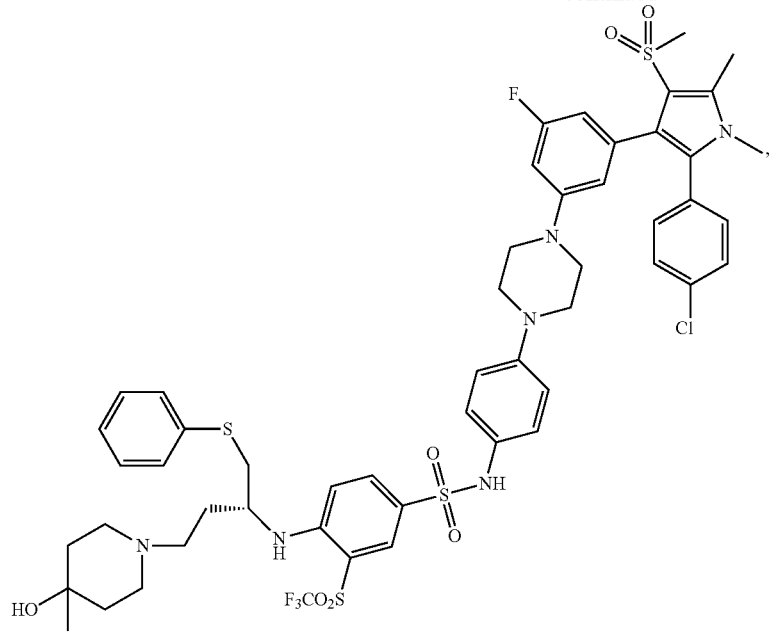
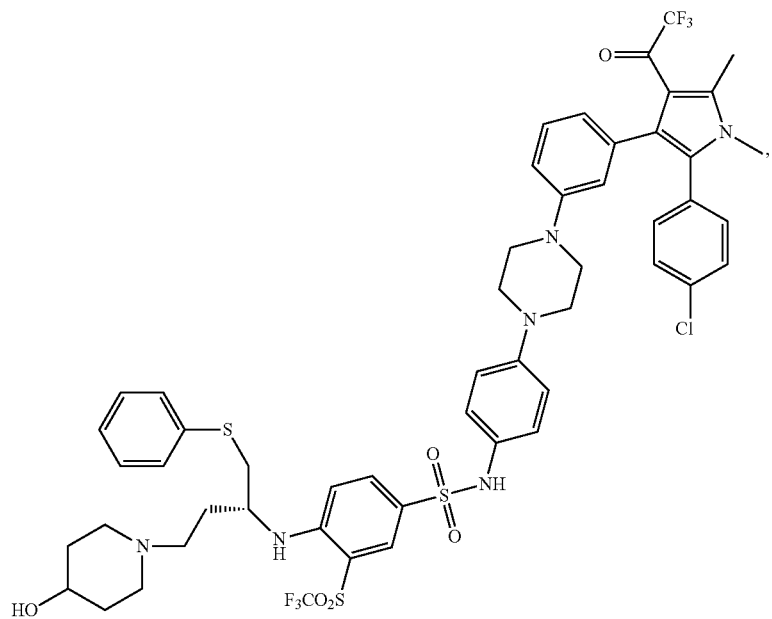

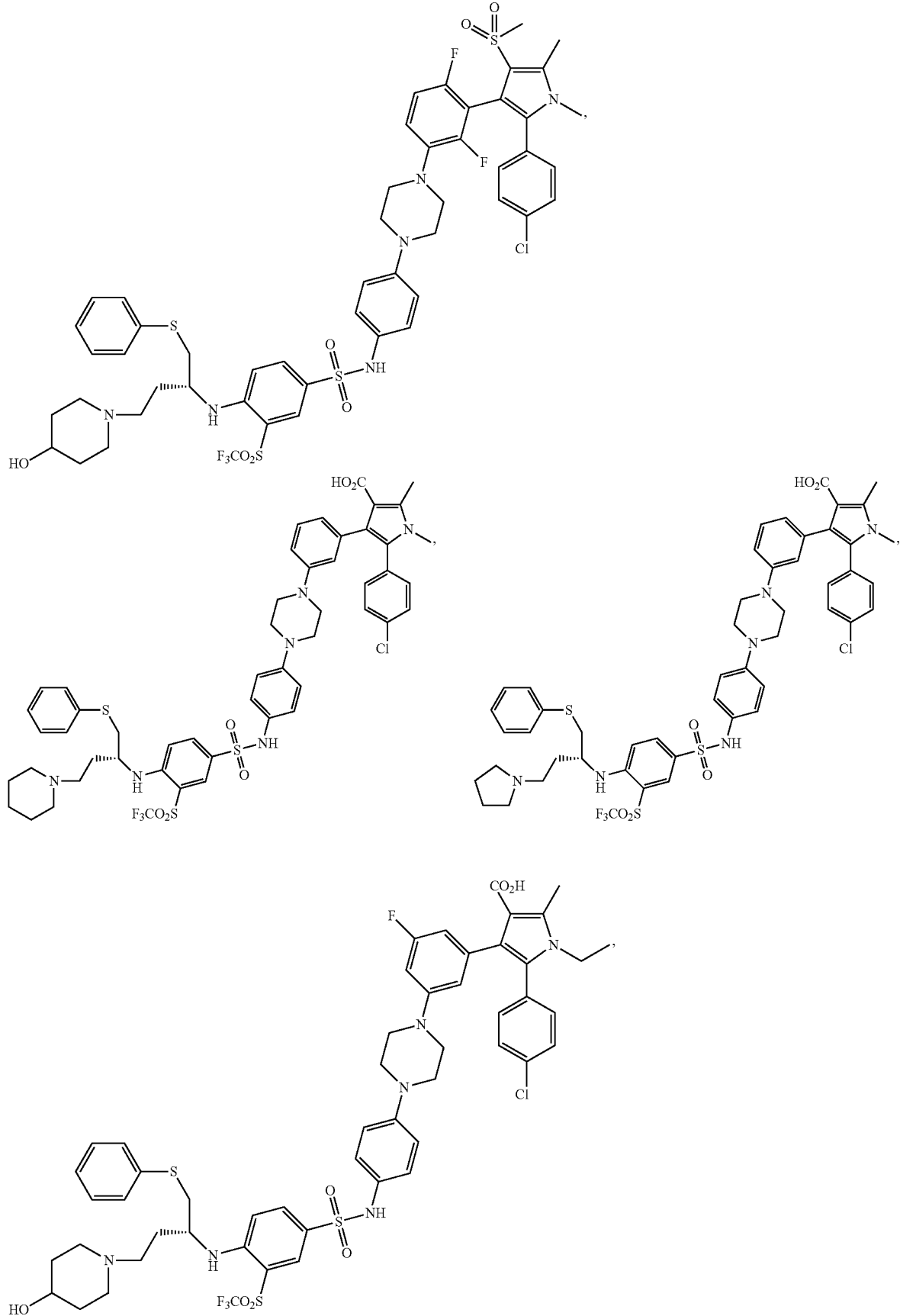

-continued
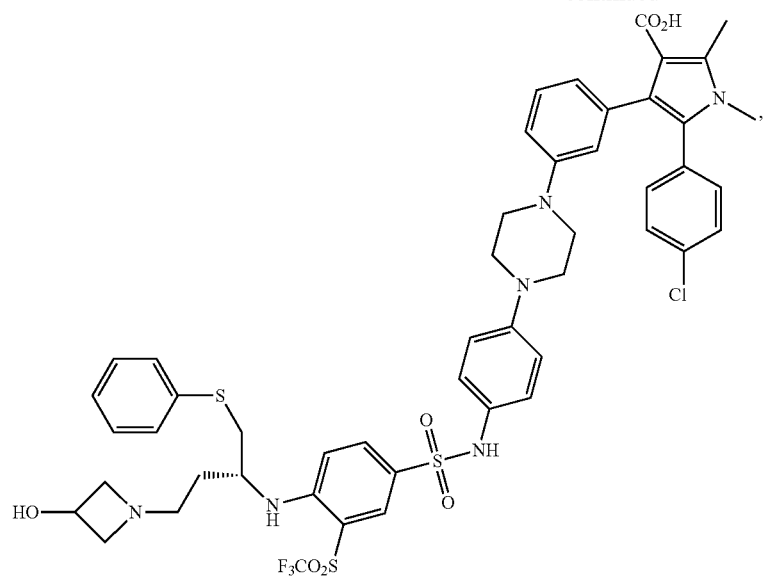
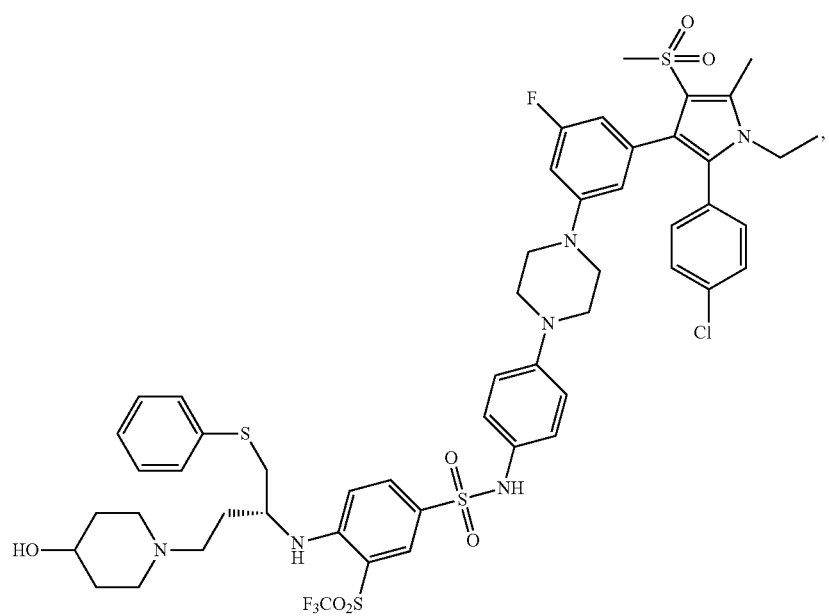

-continued
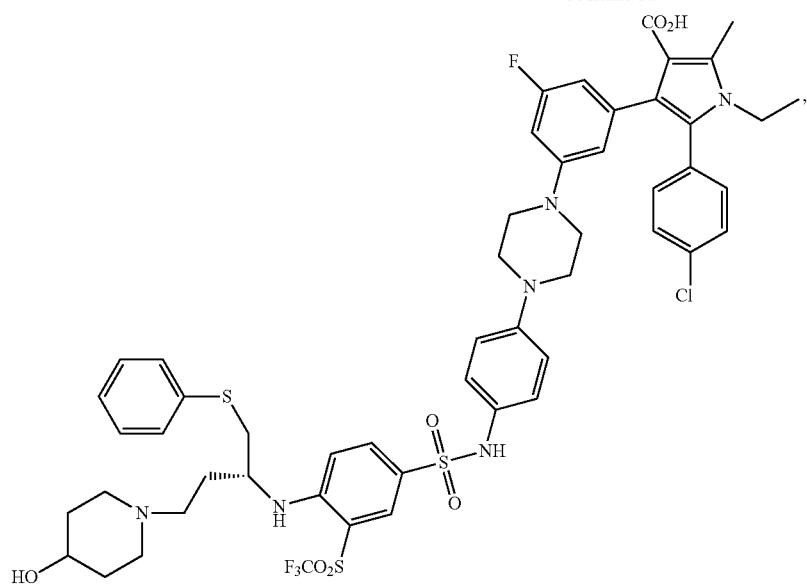
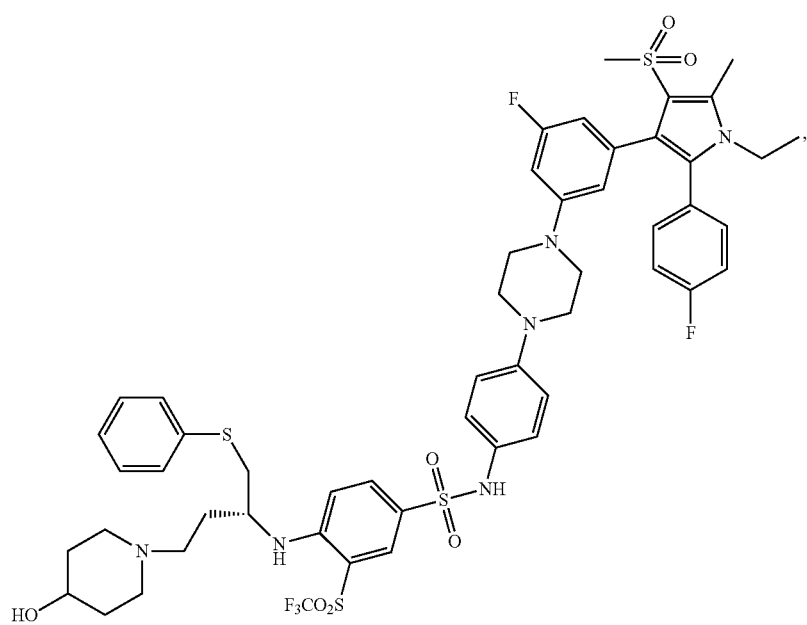

-continued
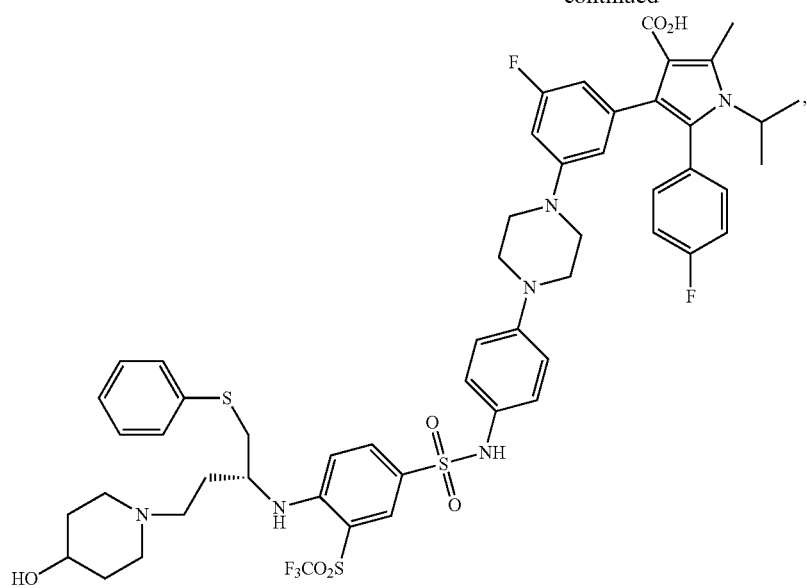
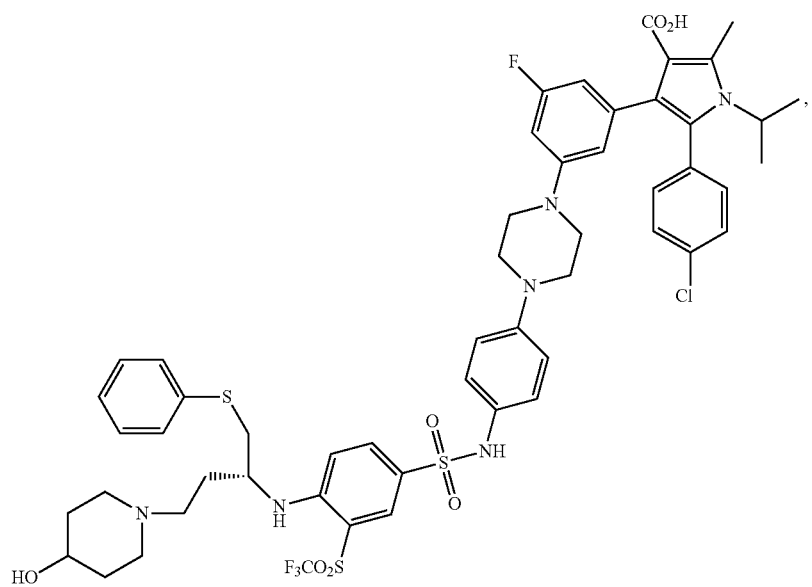

-continued
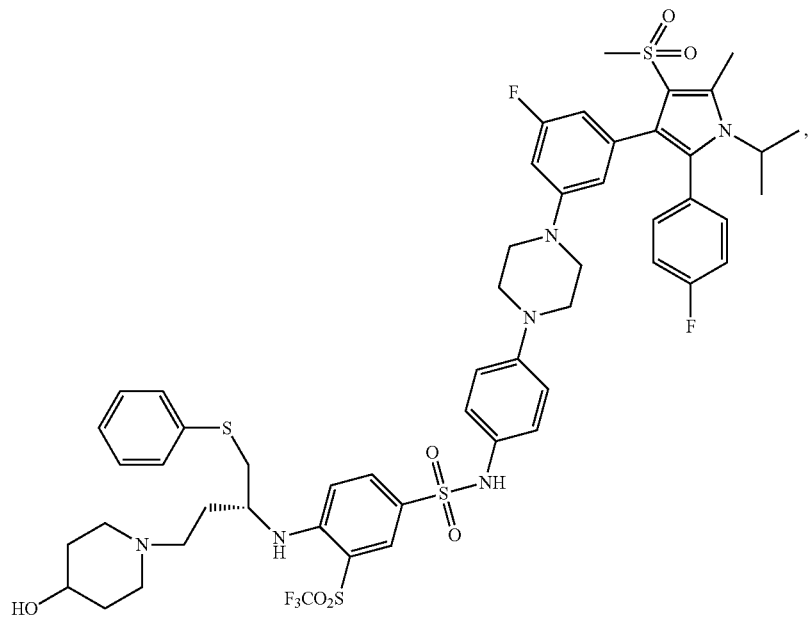
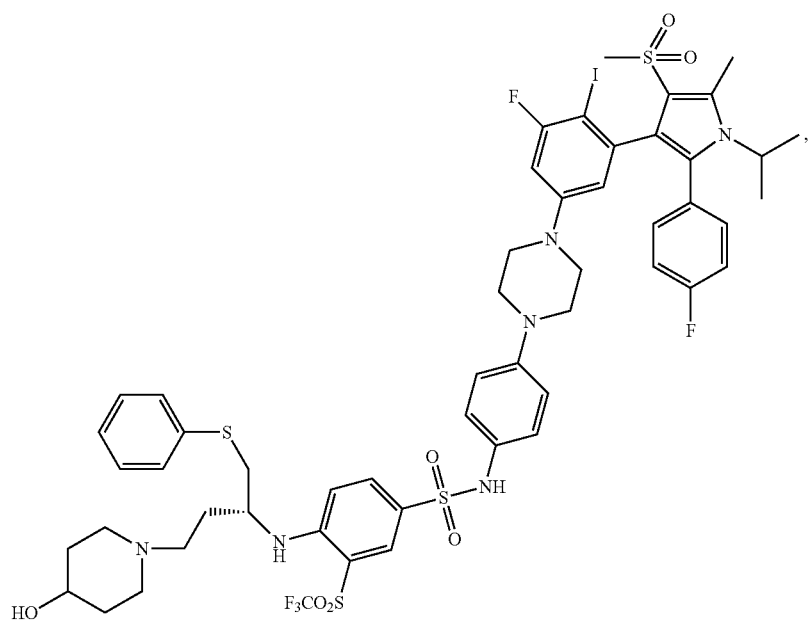

-continued
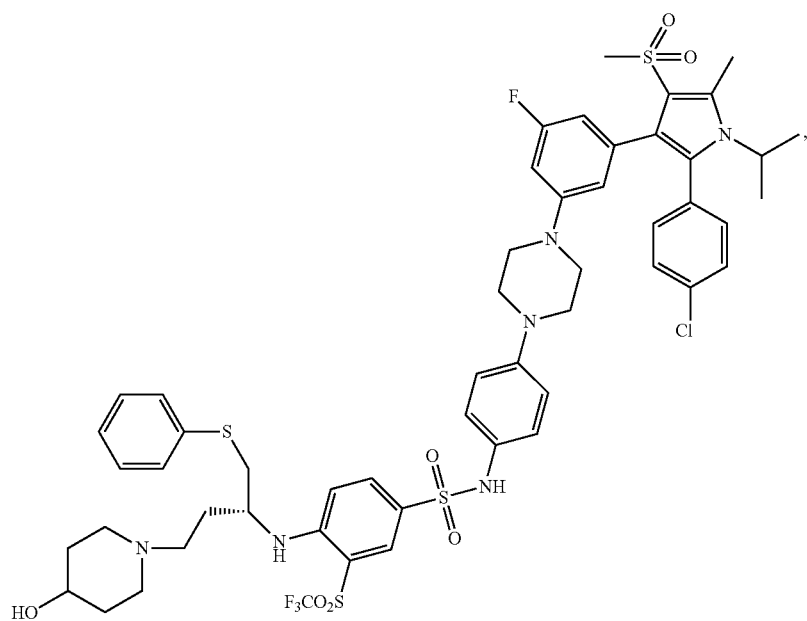
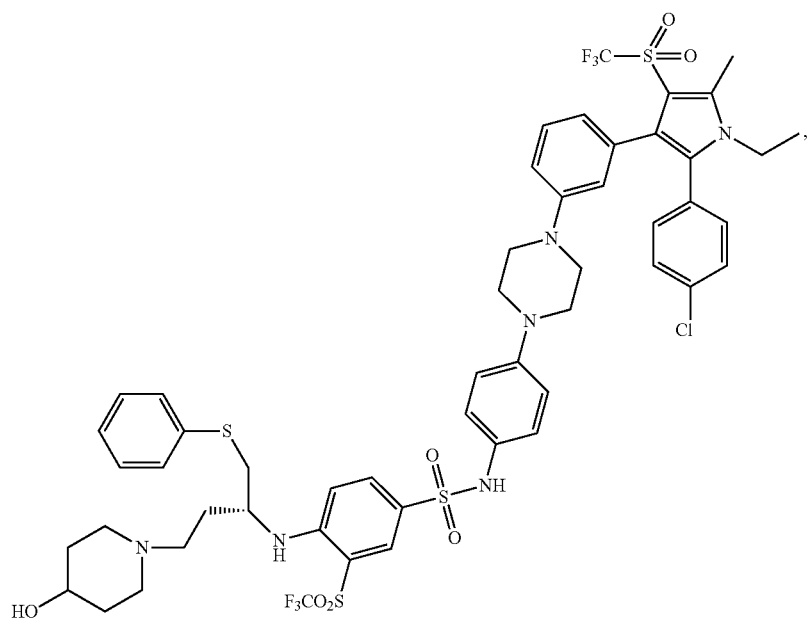

-continued
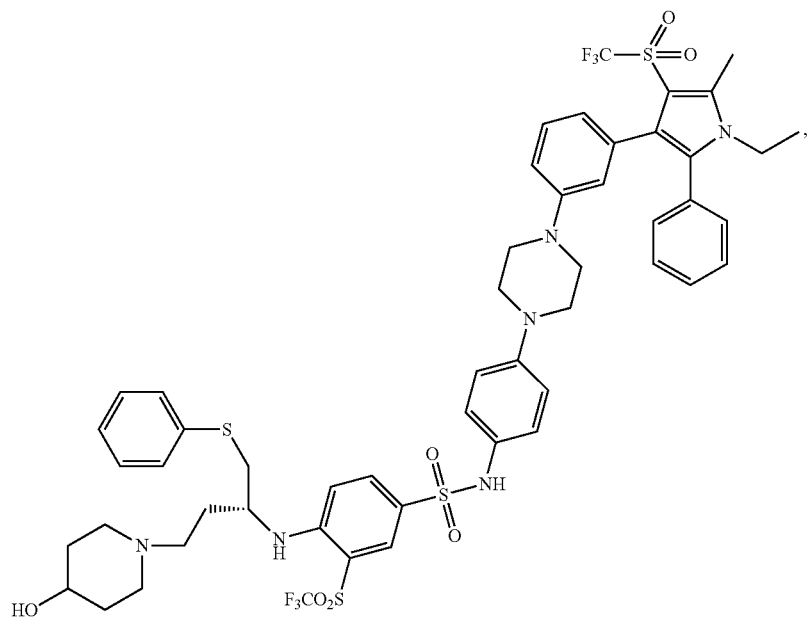
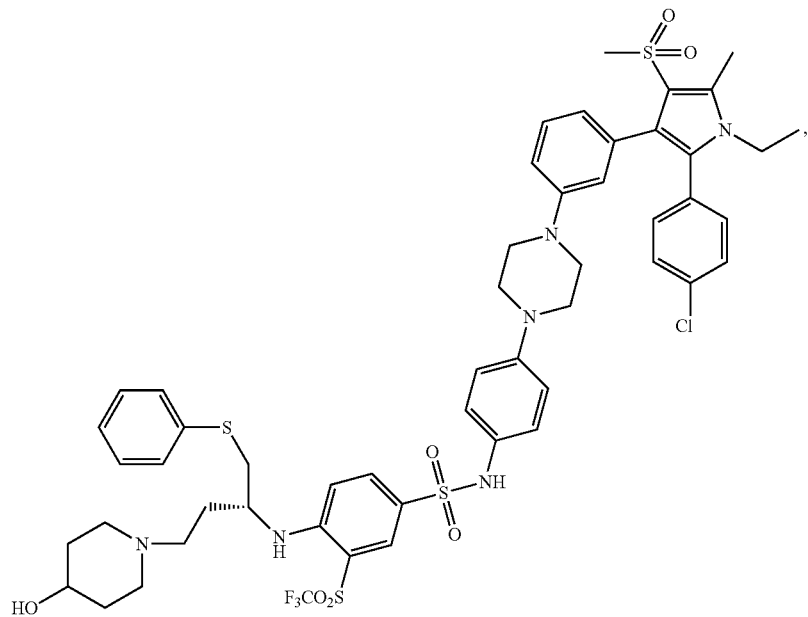

-continued
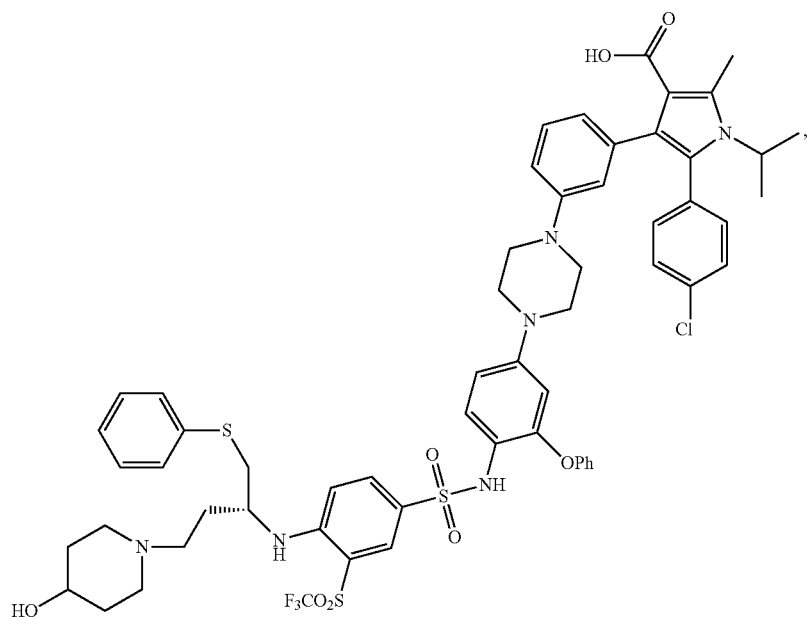
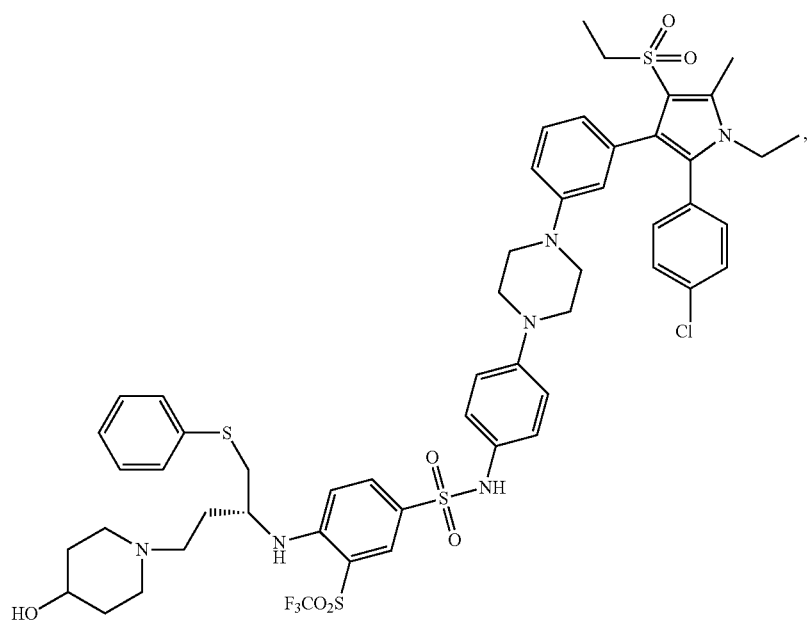

-continued
501
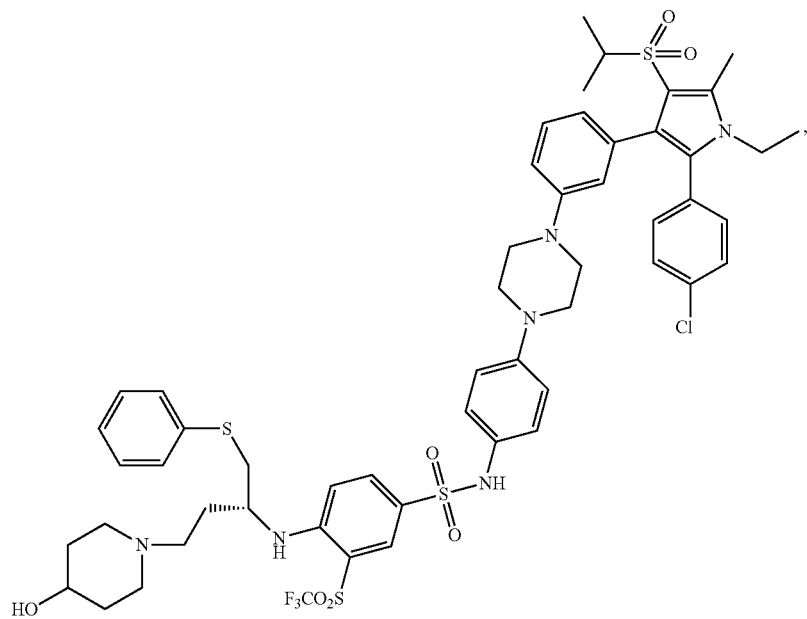
502
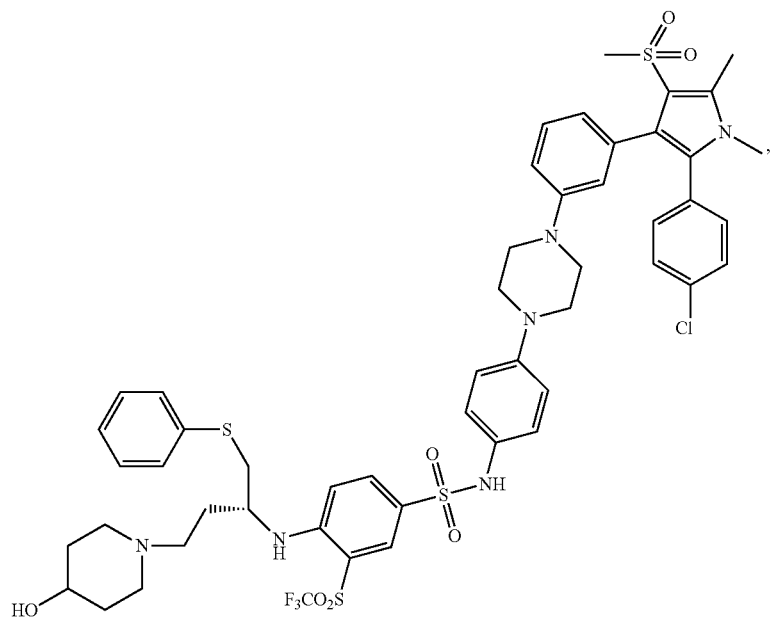

-continued
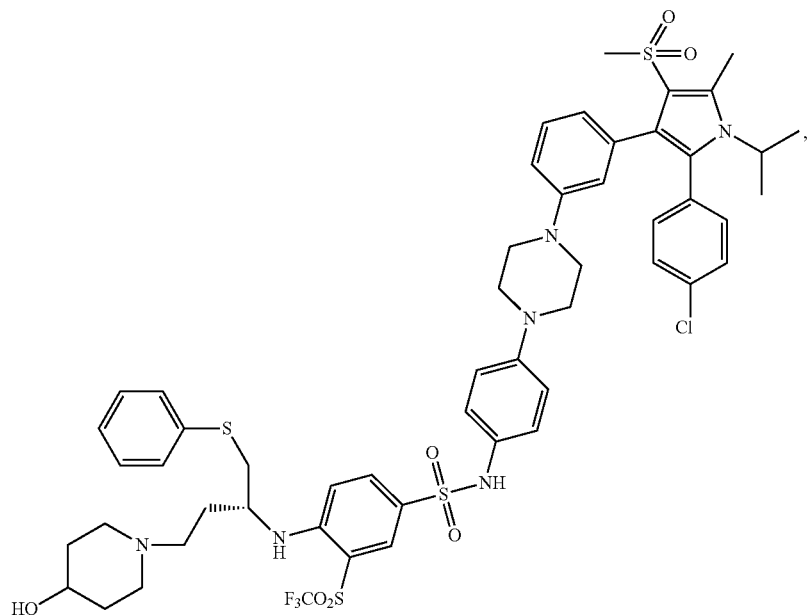
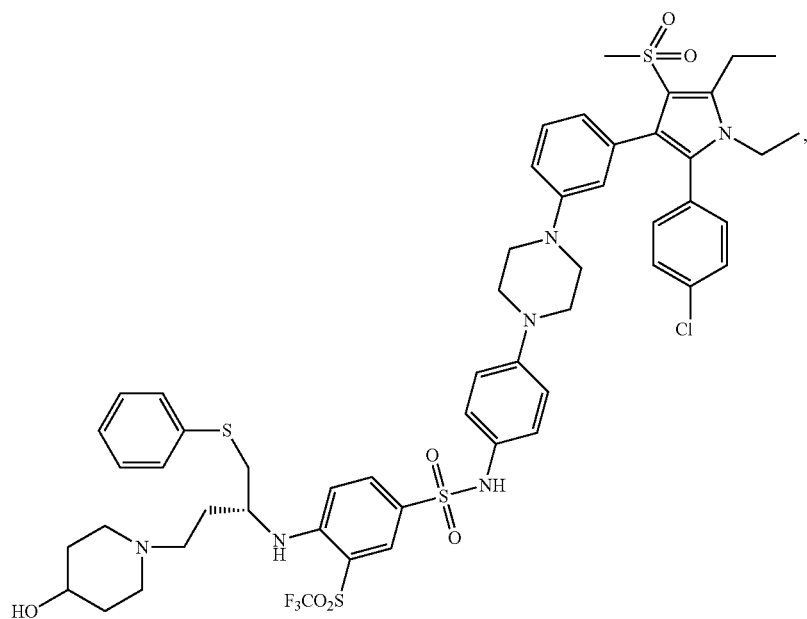

-continued
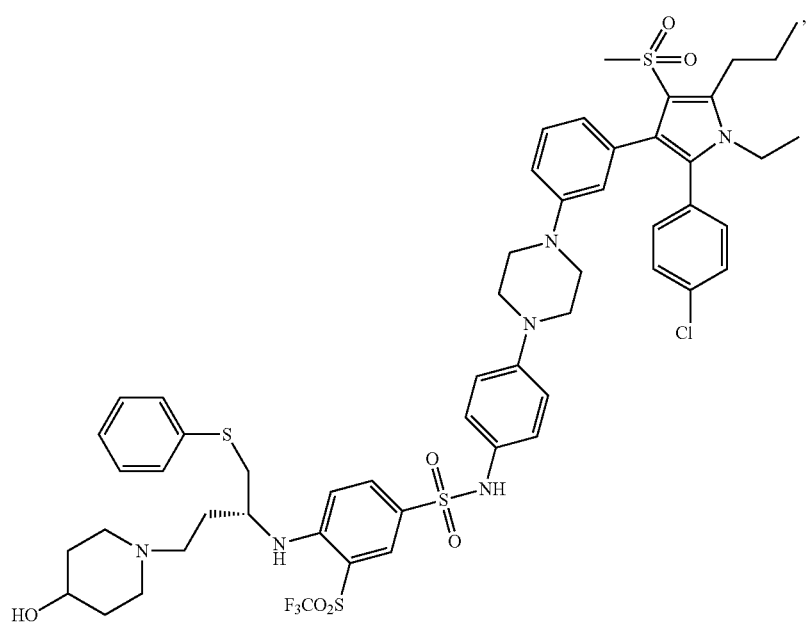
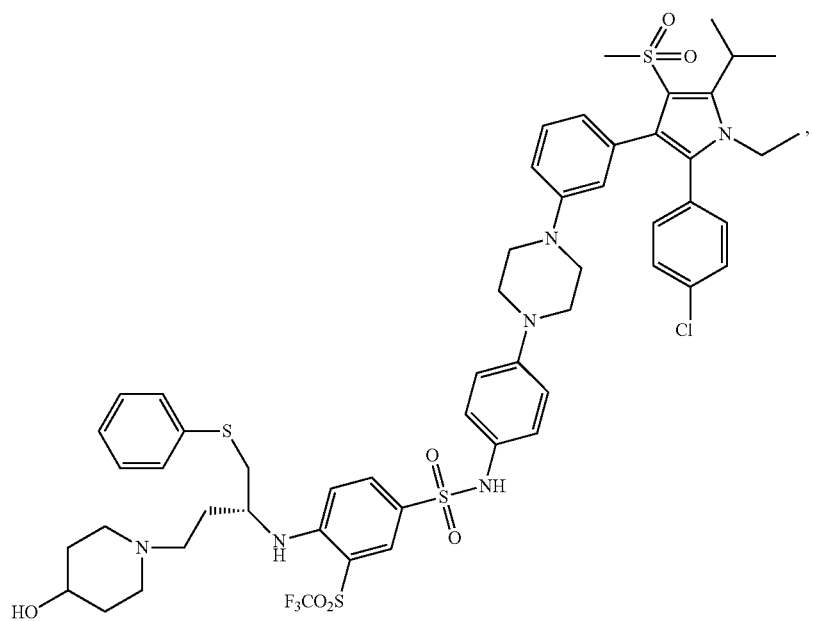

-continued
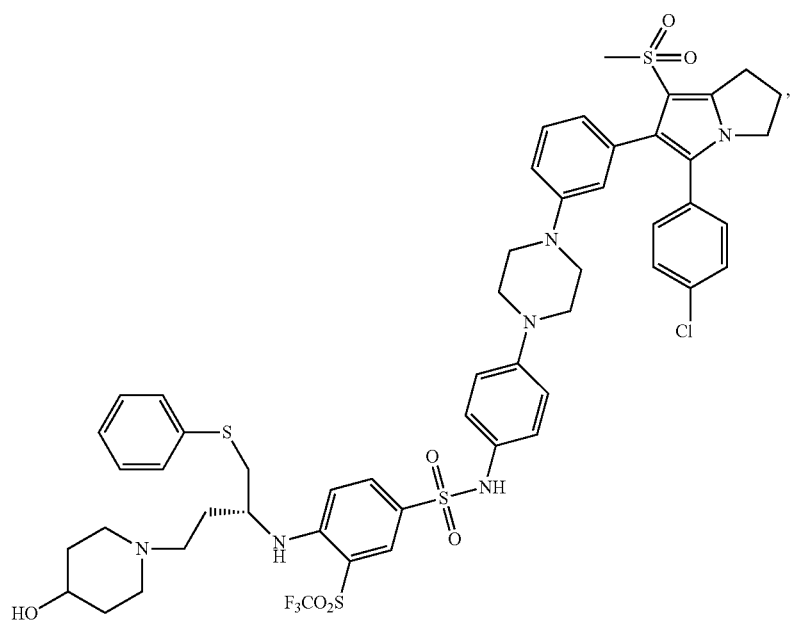
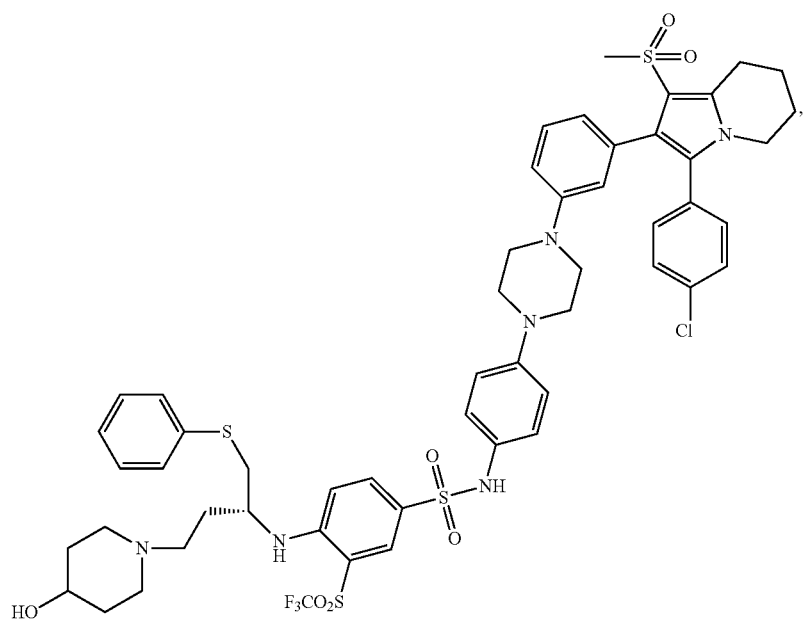

-continued
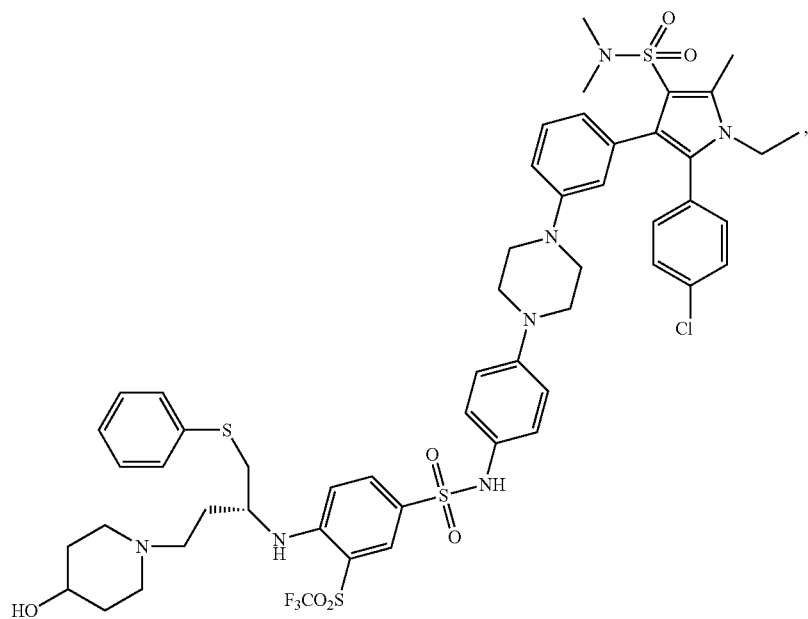
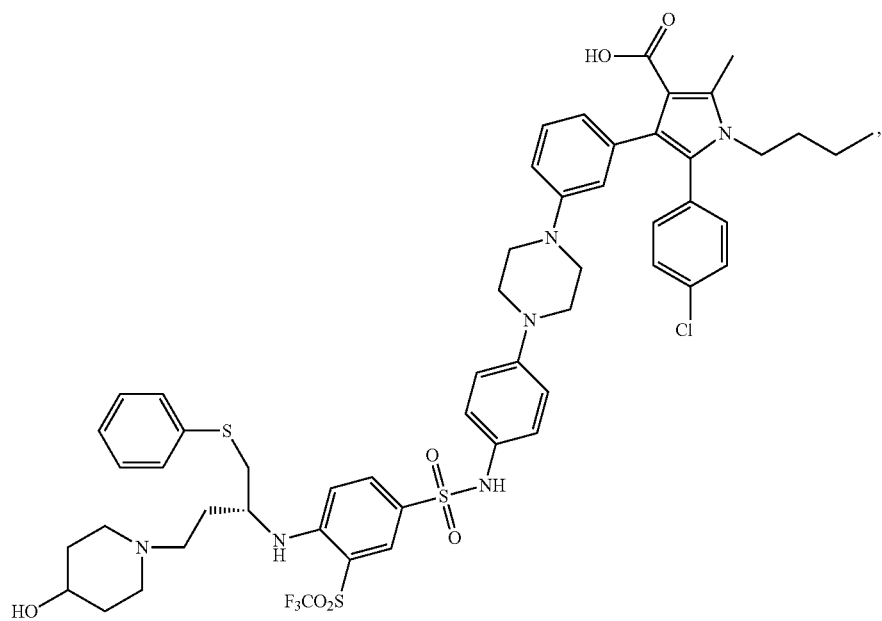

-continued
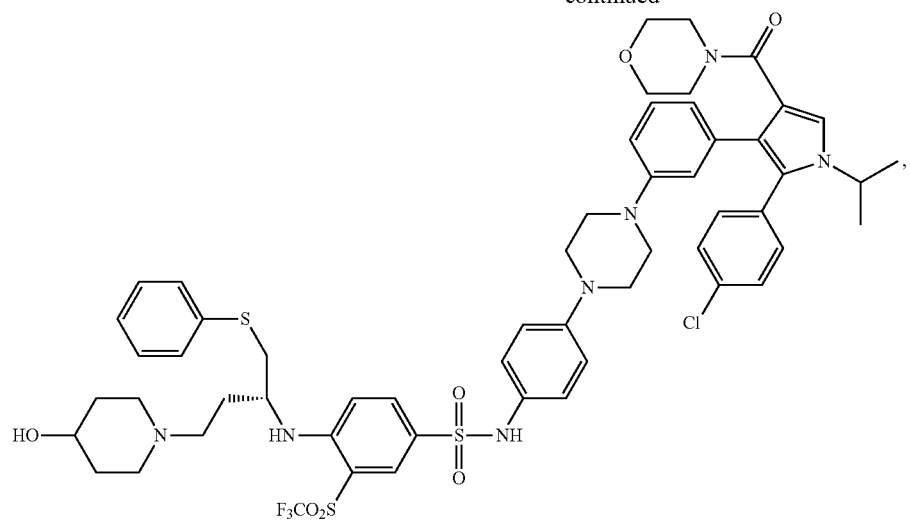
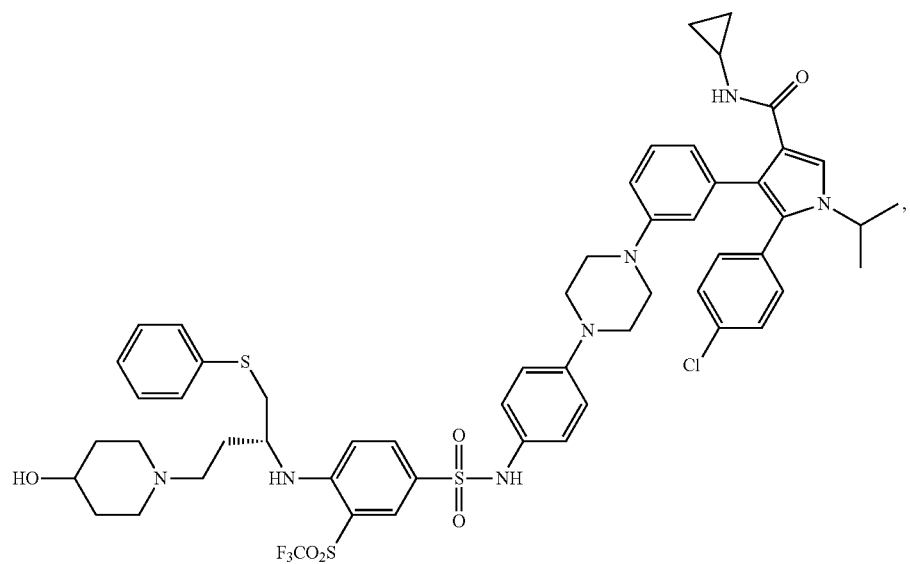
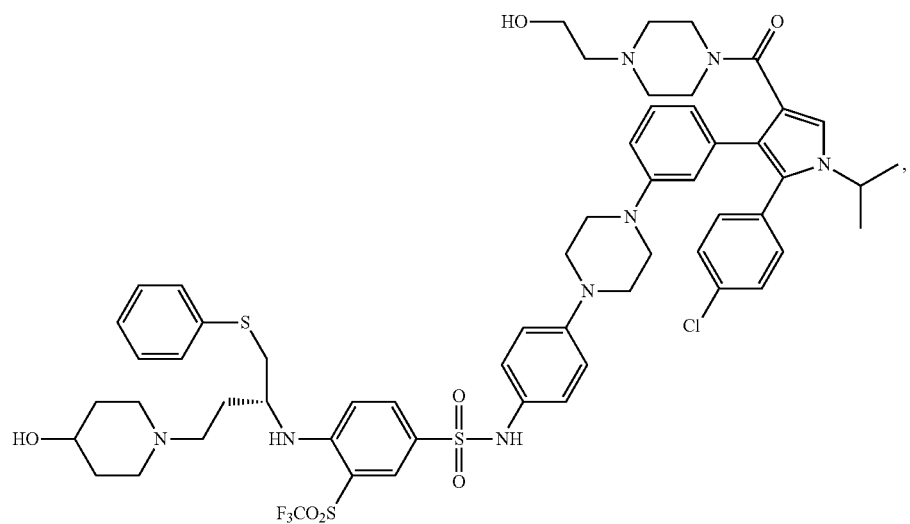

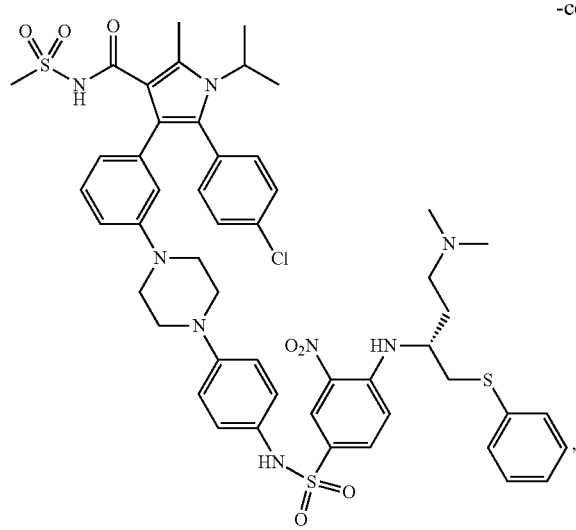

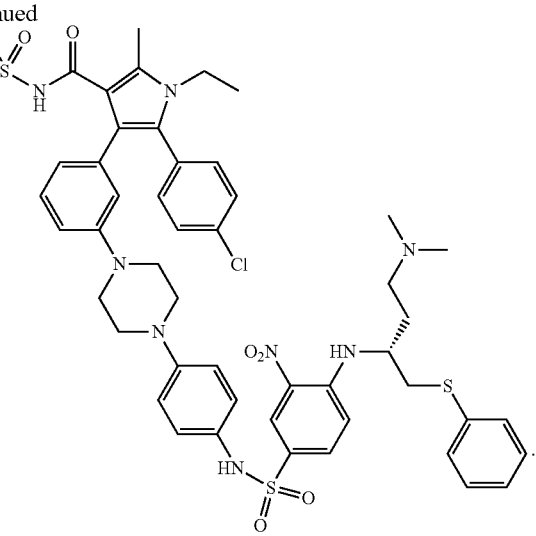

-continued

12. A composition comprising (a) compound of claim 1, (b) a second therapeutic agent useful in the treatment of a disease or condition wherein inhibition of Bcl-2 or Bcl-xL provides a benefit, and (c) an optional excipient and/or pharmaceutically acceptable carrier.

13. The composition of claim 12 wherein the second therapeutic agent comprises a chemotherapeutic agent useful in the treatment of cancer.

14. A pharmaceutical composition comprising a compound of claim 1 and a pharmaceutically acceptable carrier or vehicle.

15. A compound having a structure

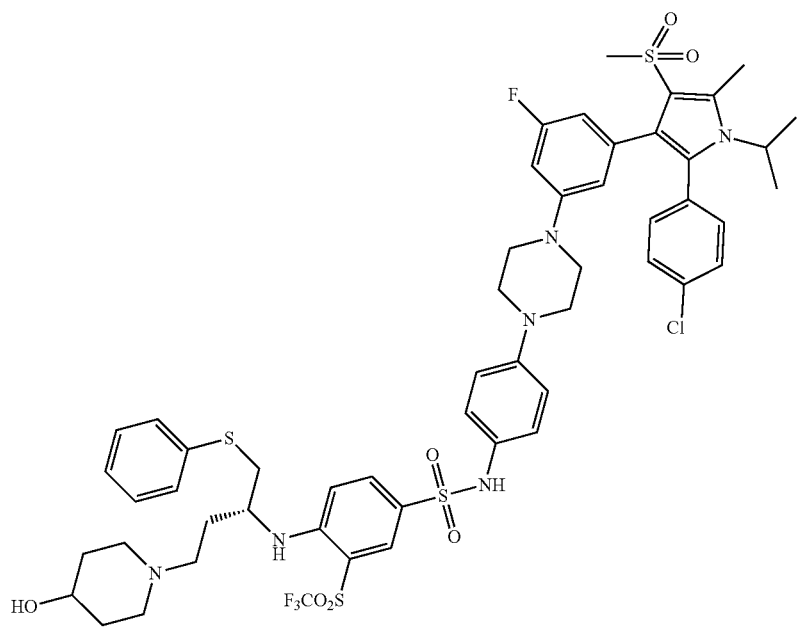

* * * * *